US009556245B2

(12) United States Patent
O'Brien et al.

(10) Patent No.: US 9,556,245 B2
(45) Date of Patent: Jan. 31, 2017

(54) CA125 GENE AND ITS USE FOR DIAGNOSTIC AND THERAPEUTIC INTERVENTIONS

(75) Inventors: Timothy O'Brien, Little Rock, AR (US); John Beard, Little Rock, AR (US); Lowell Underwood, Fayetteville, AR (US)

(73) Assignee: The Board of Trustees of the University of Arkansas, Little Rock, AR (US)

(*) Notice: Subject to any disclaimer, the term of this patent is extended or adjusted under 35 U.S.C. 154(b) by 918 days.

(21) Appl. No.: 12/455,366

(22) Filed: Jun. 1, 2009

(65) Prior Publication Data
US 2010/0331536 A1 Dec. 30, 2010

Related U.S. Application Data

(63) Continuation of application No. 10/715,066, filed on Nov. 17, 2003, now abandoned, which is a continuation-in-part of application No. 09/965,738, filed on Sep. 27, 2001, now Pat. No. 7,309,760, application No. 12/455,366, which is a continuation-in-part of application No. 10/475,117, filed on Oct. 17, 2003, now Pat. No. 8,124,728, which is a continuation-in-part of application No. PCT/US02/11734, filed on Apr. 12, 2002, and a continuation-in-part of application No. 09/965,738, filed on Sep. 27, 2001, now Pat. No. 7,309,760.

(60) Provisional application No. 60/427,045, filed on Nov. 15, 2002, provisional application No. 60/284,175, filed on Apr. 17, 2001, provisional application No. 60/299,380, filed on Jun. 19, 2001, provisional application No. 60/345,180, filed on Dec. 21, 2001.

(51) Int. Cl.
*C12Q 1/68* (2006.01)
*C07K 14/47* (2006.01)
*C07H 21/00* (2006.01)
*A61K 38/00* (2006.01)

(52) U.S. Cl.
CPC .......... *C07K 14/47* (2013.01); *C12Q 1/6886* (2013.01); *A61K 38/00* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,889,806 A | 12/1989 | Olson et al. | |
| 4,921,790 A * | 5/1990 | O'Brien | 435/7.94 |
| 5,688,690 A * | 11/1997 | Valiante et al. | 435/334 |
| 6,335,194 B1 | 1/2002 | Bennett et al. | |
| 6,451,602 B1 | 9/2002 | Popoff et al. | |
| 6,468,546 B1 | 10/2002 | Mitcham et al. | |
| 6,962,980 B2 | 11/2005 | Mitcham et al. | |
| 7,309,760 B2 * | 12/2007 | O'Brien et al. | 530/350 |
| 2002/0118158 A1 | 8/2002 | Yamamoto et al. | |
| 2003/0091580 A1 * | 5/2003 | Mitcham et al. | 424/185.1 |
| 2003/0096238 A1 * | 5/2003 | Salceda et al. | 435/6 |
| 2003/0143667 A1 | 7/2003 | O'Brien et al. | |
| 2003/0219741 A1 * | 11/2003 | Isogai | C07K 14/47 435/6.16 |
| 2004/0009474 A1 * | 1/2004 | Leach et al. | 435/6 |
| 2004/0127401 A1 * | 7/2004 | O'Brien et al. | 514/8 |
| 2007/0015907 A1 | 1/2007 | O'Brien et al. | |

FOREIGN PATENT DOCUMENTS

| | | | | |
|---|---|---|---|---|
| EP | 0288082 A | 10/1988 | | |
| EP | 1074617 A2 | 2/2001 | | |
| WO | WO 00/36107 A | 6/2000 | | |
| WO | WO 00/36107 A2 | 6/2000 | | |
| WO | WO 00/58473 A2 * | 10/2000 | | C12N 15/12 |
| WO | WO 01/51513 A2 | 7/2001 | | |
| WO | WO 01/60860 A2 * | 8/2001 | | C07K 14/47 |
| WO | WO 01/70804 | 9/2001 | | |
| WO | WO 01/70979 A2 * | 9/2001 | | C12N 15/12 |

(Continued)

OTHER PUBLICATIONS

Harlow and Lane (Antibodies: A Laboratory Manual, Cold Spring Harbor Laboratory, Cold Spring Harbor, NY, 1988, p. 76).*
Sambrook et al. (Molecular Cloning a laboratory Manual, 2nd edition, Cold Spring Harbor, N.Y. 1989, pp. 2.43-2.84 and pp. 16.3-36).*
Aruffo et al. (Pro. Natl. Aced. Sci. USA, 1987 vol. 84, No. 23, pp. 8573-8577).*
Bressan et al. (Disease Markers 2013 34:257-26).*
GenBank: AK056791.1 (Ishibashi, T. et al. *Homo sapiens* cDNA FLJ32229 fis, clone PLACE6004454, weakly similar to Glucoamylase S1/S2 Precursor (EC 3.2.1.3) Oct. 31, 2001).*
Bon GC et al. Am. J. Obstet. Gynecol. 174:107-114, 1996.
Clemons-Miller A et al. Clincal Cancer Research 7:917s-924s, Mar. 2001 (Suppl.).
Fendrick JL et al. Tumor Biol. 14:310-318, 1993.

(Continued)

*Primary Examiner* — Peter J Reddig
(74) *Attorney, Agent, or Firm* — Hugh McTavish

(57) ABSTRACT

The CA125 gene has been cloned and multiple repeat sequences as well as the carboxy terminus have been identified. The CA125 molecule comprises three major domains: an extracellular amino terminal domain (Domain 1); a large multiple repeat domain (Domain 2); and a carboxy terminal domain (Domain 3) which includes a transmembrane anchor with a short cytoplasmic domain. The amino terminal domain is dominated by its capacity for O-glycosylation and its resultant richness in serine and threonine residues. An amino terminal extension is presented, which comprises four genomic exons. The molecular structure is dominated by a repeat domain comprising 156 amino acid repeat units, which encompass the epitope binding sites. More than 60 repeat units have been identified, sequenced, and contiguously placed in the CA125 domain structure. More specifically, this invention is directed to a CA125 cDNA sequence which can be introduced into animal or human cells to achieve transcription or expression of the cDNA.

7 Claims, No Drawings

(56) References Cited

FOREIGN PATENT DOCUMENTS

| WO | WO 01/75067 A2 | * | 10/2001 | |
|----|----------------|---|---------|---|
| WO | WO 02/06317 A2 |   | 1/2002  | |
| WO | WO 02/68579 A2 |   | 6/2002  | |
| WO | WO 02/092836 A |   | 11/2002 | |
| WO | WO 03/025148 A2 | * | 3/2003 | |
| WO | WO 03/029271 A2 | * | 4/2003 | C07K 14/47 |

OTHER PUBLICATIONS

Fendrick JL et al. Tmuor Biol. 18:278-289, 1997.
Foon KA et al., Clin. Cancer Research 7:1112-1115, 2001.
Gendler SJ et al., Annu. Rev. Physiol. 57:607-634, 1995.
Gum Jr., JR Am. J. Respir Cell Mol. Biol. 7:557-564, 1992.
Gum Jr. Biochemical Society Transactions 23:795-599, 1995.
Hardardottir H et al., Am. J. Obstet.-Gynecol. 163:1925-1931, 1990.
Konish I et al., J. Soc. Gynecol. Invest. 1:89-96, 1994.
O'Brien TJ et al., More than 15 years of CA125: what is known about the antigen, its structure and its function. International J. of Biological Markers 13:188-195, 1998.
Lloyd Ko et al. Isolation and characterization of ovarian cancer antigen CA125 using a new . . . International J. Cancer 71:842-850, 1997.
Nap M et al. Immunohistochemical characterization of 22 monoclonal antibodies . . . Tumor Biol.: 17:325-331, 1996.
Desseyn J-L et al. J. Biol. Chem. 272:3168-78, 1997.
Chambers J et al., Genomics 38:305-313, 1996.
Genbank Accession No. AA640762.
Yin BWT et al. J. Biol. Chem. 276:27371-75, 2001.
O'Brien TJ et al., Tumor Biology 22:348-366, 2001.
O'Brien TJ et al. Tumor Biology 23:154-169, 2002.
Bast RC et al. New England J. Med. 309:883-887, 1993.
Lloyd Ko et al., Tumor Biol. 22:77-82, 2001.
Marshall E Science 292:1982-1980, 2001.
Nustad K et al., Int. J. Biol. Markers 13:196-199, 1998.
Nustad K et al. Tumor Biology 17:196-219, 1996.
O'Brien TJ et al., Am. J. Obstet. Gynecol. 155:50-55, 1986.
O'Brien TJ et al., Am. J. Obstet. Gynecol. 165:1857-1864, 1991.
Quirk JG et al. Am. J. Obstet. Gynecol. 159:644-649, 1988.
Santin Ad et al. Am. J. Obstet. Gynecol. 183:601-609, 2000.
Shigesmasa K et al. International J. of Gynecologic Cancer 7:296-303, 1997.
Shigesmasa K et al., J. Soc. Gynecol. Investigation 4:95-102 (1997).
Verma M et al., Glycoconjugate J. 11:172-179, 1994.
Wagner, U. et al. Hybridoma 16:33-40 (1997).
Wagner U et al., Clin. Cancer Res. 7:1112-1115, 2001.
Williams, SJ et al., J. Biol. Chem. 276:18327-18336, 2001.
Yin, TWT et al., J. Biol. Chem. 276:27371-27375, 2001.
Argueso et al.MUC16 mucin is expressed by the human ocular . . . Invest. Ophthalmol Vis. Sci 44:2487-95, 2003.
Coleman et al., Research in Immunology 145:33-36, 1994.
Abaza et al., J. Protein Chem. 1:433-444, 1992.
Rudikoff et al., Proc. Nat'l Acad. Sci. USA 79:1979-1983, 1982.
Burgess et al., J. Cell Biol. 111:2129-2138, 1990.
Ping Fu et al., J. Biochem. Biophys. Methods 40:101-112, 1999.
Ma NS et al. Owl monkey gene map: evidence for a homologous human chromosome 7q region near cystic fibrosis locus. Genomics 5:389-396, 1989.
Tanaka T et al. Efficient generation of antibodies to oncoproteins by usnig synthetic peptide antigens. Proc. Natl. Acad. Sci. USA 82:3400-3404, 1985.
Rudikoff et al. Proc. Natl. Acad. Sci. USA 79:1979-1983, 1982.
Genbank Accession No. AC016584, May 29, 2002.
Genbank Accession No. AF414442, Oct. 29, 2002.
Genbank Accession No. AF361486, Jul. 20, 2001.
Roitt et al., 1998, Immunology, 4th ed. Mosby, section titled "The Structure of Antigens."
Holmes, 2001, Exp. Opin. Invest. Drugs 10(3):511-519.
Greenspan et al., 1999, Nature Biotechnology 7:936-937.
Herbert et al., The Dictionary of Immunology, Academic Press, 4th edition, 1995, p. 58-59, "Epitope".
Bowie JU et al. Science 247:1306-1310, 1990.
Sequence Revision History for GenBank accession No. AF361486, Jul. 20, 2001.
Genbank Accession No. AF361486.1, Version GI:14971109, Jul. 20, 2001.
Rudd, P.M. et al., 2001, Glycosylation and the immune system. Science 291:2370-2376.
Modrak, D.E., et al., 2005, Identification of Mu-9 . . . , Intl. J. Oncology 26:1591-1596.

* cited by examiner

CA125 GENE AND ITS USE FOR DIAGNOSTIC AND THERAPEUTIC INTERVENTIONS

This application is a continuation of U.S. patent application Ser. No. 10/715,066, filed Nov. 17, 2003, now abandoned which claims priority from U.S. Provisional Application Ser. No. 60/427,045, filed Nov. 15, 2002, and which is a continuation-in-part of U.S. patent application Ser. No. 09/965,738, filed Sep. 27, 2001, now U.S. Pat. No. 7,309,760, which in turn claims priority from U.S. Provisional Patent Application Ser. No. 60/284,175, filed Apr. 17, 2001, and U.S. Provisional Patent Application Ser. No. 60/299,380, filed Jun. 19, 2001. This application is also a continuation-in-part of U.S. patent application Ser. No. 10/475,117, filed Oct. 17, 2003, now U.S. Pat. No. 8,124,728, which claims priority from provisional patent application No. 60/427,045, filed Nov. 15, 2002, and is a continuation in part of International Application No. PCT/US02/11734, filed Apr. 12, 2002, which claims priority from provisional application No. 60/345,180, filed Dec. 21, 2001. International Application No. PCT/US02/11734 is also a continuation-in-part of U.S. patent application Ser. No. 09/965,738, filed Sep. 27, 2001, now U.S. Pat. No. 7,309,760, which in turn claims priority from Provisional Application No. 60/284,175, filed Apr. 17, 2001, and 60/299,380, filed Jun. 19, 2001. All of these applications are hereby specifically incorporated by reference. Applicants hereby specifically claim the benefit of these prior-filed applications under 35 U.S.C. §§119 (e) and 120.

BACKGROUND OF THE INVENTION

Included with this application and hereby incorporated by reference into this specification is a sequence listing submitted as a text file named 110-018US5-seq.txt, which is 535 kb in size and was created on May 29, 2009.

The present invention relates generally to the cloning, identification, and expression of the CA125 gene's glycosylated amino terminal domain, the multiple repeat domain, and the carboxy terminal domain in vitro and, more specifically, to the use of recombinant CA125 with epitope binding sites for diagnostic and therapeutic purposes. Additionally, the genomic DNA, a molecule encoding a 5' upstream region of CA125 and a genomic DNA sequence for the amino terminal, extra cellular repeats and carboxy terminal of CA125 has been determined.

CA125 is an antigenic determinant located on the surface of ovarian carcinoma cells with essentially no expression in normal adult ovarian tissue. Elevated in the sera of patients with ovarian adenocarcinoma, CA125 has played a critical role for more than 15 years in the management of these patients relative to their response to therapy and also as an indicator of recurrent disease.

It is well established that CA125 is not uniquely expressed in ovarian carcinoma, but is also found in both normal secretory tissues and other carcinomas (i.e., pancreas, liver, colon) [Hardardottir H et al., Distribution of CA125 in embryonic tissue and adult derivatives of the fetal periderm, Am J Obstet. Gynecol. 163; 6(1):1925-1931 (1990); Zurawski V R et al., Tissue distribution and characteristics of the CA125 antigen, Cancer Rev. 11-12:102-108 (1988); and O'Brien T J et al., CA125 antigen in human amniotic fluid and fetal membranes, Am J Obstet Gynecol. 155:50-55, (1986); Nap M et al., Immunohistochemical characterization of 22 monoclonal antibodies against the CA125 antigen: 2nd report from the ISOBM TD-1 workshop, Tumor Biology 17:325-332 (1996)]. Notwithstanding, CA125 correlates directly with the disease status of affected patients (i.e., progression, regression, and no change), and has become the "gold standard" for monitoring patients with ovarian carcinoma [Bast R C et al., A radioimmunoassay using a monoclonal antibody to monitor the course of epithelial ovarian cancer, N Engl J Med. 309:883-887 (1983); and Bon G C et al., Serum tumor marker immunoassays in gynecologic oncology: Establishment of reference values, Am J. Obstet. Gynecol. 174:107-114 (1996)]. CA125 is especially useful in post-menopausal patients where endometrial tissue has become atrophic and, as a result, is not a major source of normal circulating CA125.

During the mid 1980's, the inventor of the present invention and others developed M11, a monoclonal antibody to CA125. M11 binds to a dominant epitope on the repeat structure of the CA125 molecule [O'Brien T J et al., New monoclonal antibodies identify the glycoprotein carrying the CA125 epitope, Am J Obstet Gynecol 165:1857-64 (1991)]. More recently, the inventor and others developed a purification and stabilization scheme for CA125, which allows for the accumulation of highly purified high molecular weight CA125 [O'Brien T J et al., More than 15 years of CA125: What is known about the antigen, its structure and its function, Int J Biological Markers 13(4):188-195 (1998)].

Considerable progress has been made over the years to further characterize the CA125 molecule, its structure and its function. The CA125 molecule is a high molecular weight glycoprotein with a predominance of O-linked sugar side chains. The native molecule exists as a very large complex (~2-5 million daltons). The complex appears to be composed of an epitope containing CA125 molecule and binding proteins which carry no CA125 epitopes. The CA125 molecule is heterogenous in both size and charge, most likely due to continuous deglycosylation of the side chains during its life-span in bodily fluids. The core CA125 subunit is in excess of 200,000 daltons, and retains the capacity to bind both OC125 and M11 class antibodies.

Despite the advances in detection and quantitation of serum tumor markers like CA125, the majority of ovarian cancer patients are still diagnosed at an advanced stage of the disease—Stage III or IV. Further, the management of patients' responses to treatment and the detection of disease recurrence remain major problems. There, thus, remains a need to significantly improve and standardize current CA125 assay systems. Further, the development of an early indicator of risk of ovarian cancer will provide a useful tool for early diagnosis and improved prognosis.

SUMMARY OF THE INVENTION

Thus, it is an object of the present invention to provide a recombinant CA125 cDNA molecule which can be introduced into animals or human cells to achieve transcription or expression of the cDNA. The utility of knowing the DNA sequence of a specific gene is that a recombinant protein can be produced which can be used as an easily renewable source of that gene or a portion of the gene. Producing and purifying recombinant protein is easier and can produce greater quantities of protein than purifying native protein from patients. The recombinant protein can then be used to produce antibodies to the gene, both polyclonal and monoclonal. The recombinant protein can also be used as a positive control in test kits and experiments.

The genomic sequence for CA125 and a 5' upstream region has been determined. A DNA sequence showing the 5' upstream region and the amino terminal portion of the CA125 molecule is set out in Table 1 and SEQ ID NO: 1. The extracellular amino terminal domain is made of exons: Exon 1 from 2205-11679; Exon 2 from 13464-13570; Exon 3 from 16177-34419; Exon 4 from 34575-38024; Exon 5 from 38689-38800; Exon 6 from 40578-45257; Exon 7 from 47360-47395; Exon 8 from 52407-52442; Exon 9 from 52686-52744 as set out in SEQ ID NO: 1. A DNA sequence showing the extracellular repeat portion of the CA125 molecule is set out in Table 2 and SEQ ID NO: 2. The genomic repeats are made of exons: Exon R1 from 1-130; Exon R2 from 442-510; Exon R3 from 5479-5652; Exon R4 from 6301-6334; Exon R5 from 6593-6657; Exon R1 from 7558-7683; Exon R2 from 8216-8284; Exon R3 from 8877-9050; Exon R4 from 9380-9413; Exon R5 from 9675-9739; Exon R1 from 10201-10291; Exon R2 from 10524-10592; Exon R3 from 11200-11373; Exon R4 from 11722-11755; Exon R5 from 12016-12036; Exon R1 from 12169-12295; Exon R2 from 12532-12600; Exon R3 from 13219-13392; Exon R4 from 13723-13756; Exon R5 from 14016-14077; Exon R1 from 15001-15126; Exon R2 from 15367-15435; Exon R1 from 15648-15773; Exon R2 from 16002-16070; Exon R3 from 16653-16826; Exon R4 from 17158-17191; Exon R5 from 17453-17517; Exon R1 from 18532-18657; Exon R2 from 18888-18956; Exon R3 from 19633-19806; Exon R4 from 20141-20176; Exon R5 from 20387-20449; Exon R1 from 21609-21731; Exon R2 from 21940-22008; Exon R3 from 22605-22778; Exon R4 from 23109-23142; Exon R1 from 29046-29168; Exon R2 from 29266-29334; Exon R3 from 33917-34090; Exon R4 from 36702-36734; Exon R5 from 38270-38320; Exon R1 from 39104-39224; Exon R2 from 39315-39383; Exon R3 from 39532-39705; Exon R4 from 41862-41992. A DNA sequence showing the carboxy terminal domain of the CA125 molecule is set out in Table 3 and SEQ ID NO: 3. The carboxy terminal portion is made of exons: Exon C1 from 1-66; Exon C2 from 1802-1947; Exon C3 from 4198-4350; Exon C4, from 4679-4747; Exon C5 from 6811-6978; Exon C6 from 11232-11270; Exon C7 from 11594-11677; Exon C8 from 14095-14187 as set out in SEQ ID NO: 3. A full length cDNA molecule for CA125 is set out in Table 4 and SEQ ID NO: 4. A CA125 protein is set out in Table 5 and SEQ ID NO: 5.

Now that the DNA sequence which encodes CA125 has been discovered known synthetic methods can be employed to prepare DNA molecules containing portions of the sequence. Conventional cloning vehicles, such as plasmids, viruses, or bacteria phages can be modified using known methods so as to produce novel cloning vehicles which contain cDNA encoding, CA125, analogs or mutants thereof. Similarly, such cloning vehicles can be modified or engineered so that they contain DNA molecules from Table 4 and SEQ ID NO: 4 or segments substantially similar thereto. The DNA molecule inserted may be made by various methods including enzymatic or chemical synthesis.

The CA125 gene has been cloned and multiple repeat sequences as well as the glycosylated amino terminal and the carboxy terminus have been identified. CA125 requires a transcript of more than 35,000 bases and occupies approximately 150,000 bp on chromosome 19p 13.2. The CA125 molecule comprises three major domains: an extracellular amino terminal domain (Domain 1); a large multiple repeat domain (Domain 2); and a carboxy terminal domain (Domain 3) which includes a transmembrane anchor with a short cytoplasmic domain. The amino terminal domain is assembled by combining five genomic exons, four very short amino terminal sequences and one extraordinarily large exon. This domain is dominated by its capacity for O-glycosylation and its resultant richness in serine and threonine residues. Additionally, an amino terminal extension is present, which comprises four genomic exons. Analysis of the amino terminal extension revealed that its amino acid composition is consistent with the amino acid composition of the amino terminal domain.

Perhaps even more significantly, the multiple repeat domains of CA125 or other domains could also be used for the development of a potential vaccine for patients with ovarian cancer. In order to induce cellular and humoral immunity in humans to CA125, murine antibodies specific for CA125 were utilized in anticipation of patient production of anti-ideotypic antibodies, thus indirectly allowing the induction of an immune response to the CA125 molecule. With the availability of recombinant CA125, especially domains which encompass epitope binding sites for known murine antibodies, it will be feasible to more directly stimulate patients' immune systems to CA125 and, as a result, extend the life of ovarian carcinoma patients.

The recombinant CA125 of the present invention may also be used to develop therapeutic targets. Molecules like CA125, which are expressed on the surface of tumor cells, provide potential targets for immune stimulation, drug delivery, biological modifier delivery or any agent which can be specifically delivered to ultimately kill the tumor cells. Humanized or human antibodies to CA125 epitopes could be used to deliver all drug or toxic agents including radioactive agents to mediate direct killing of tumor cells. Natural ligands having a natural binding affinity for domains on the CA125 molecule could also be utilized to deliver therapeutic agents to tumor cells.

CA125 expression may further provide a survival or metastatic advantage to ovarian tumor cells. Antisense oligonucleotides derived from the CA125 repeat sequences could be used to down-regulate the expression of CA125. Further, antisense therapy could be used in association with a tumor cell delivery system of the type described above.

Recombinant domains of the CA125 molecule also have the potential to identify small molecules, which bind to individual domains of the CA125 molecule. These small molecules could also be used as delivery agents or as biological modifiers.

In another aspect of the present invention, an isolated nucleic acid of the CA125 gene is disclosed, which comprises a nucleotide sequence selected from the group consisting of: (a) the nucleotide sequences set forth in SEQ ID NOS: 1, 2, 3 and 4; (b) a nucleotide sequence having at least 70% sequence identity to any one of the sequences in (a); (c) a degenerate variant of any one of (a) to (b); and (d) a fragment of any one of (a) to (c).

In another aspect of the present invention, an isolated nucleic acid of the CA125 gene, comprising a sequence that encodes a polypeptide with the amino acid sequence selected from the group consisting of: (a) the amino acid sequences set forth in SEQ ID NO: 5; (b) an amino acid sequence having at least 50% sequence identity to any one of the sequences in (a); (c) a conservative variant of any one of (a) to (b); and (d) a fragment of any one of (a) to (c).

The vector may be a cloning vector, a shuttle vector, or an expression vector. A cultured cell comprising the vector is also contemplated.

More specifically, this invention relates to a purified antibody that selectively binds to an epitope in the CA125 protein of SEQ ID NO: 5. Similarly, the purified antibody selectively binds to an amino acid sequence having at least 50% sequence identity to said sequence; the purified antibody selectively binds to an amino acid sequence having at least 60% sequence identity to said sequence; the purified antibody selectively binds to an amino acid sequence having at least 70% sequence identity to said sequence; the purified antibody selectively binds to an amino acid sequence having at least 80% sequence identity to said sequence; and the purified antibody selectively binds to an amino acid sequence having at least 90% sequence identity to said sequence. Additionally, purified antibody can be a conservative variant of the amino acid sequence set forth in SEQ ID NO: 5 or a fragment thereof.

DETAILED DESCRIPTION OF THE INVENTION

In accordance with the present invention, conventional molecular biology, microbiology, and recombinant DNA techniques may be used that will be apparent to those skilled in the relevant art. Such techniques are explained fully in the literature (see, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells And Enzymes" (IRL Press, (1986)); and B. Perbal, "A Practical Guide To Molecular Cloning" (1984)).

Therefore, if appearing herein, the following terms shall have the definitions set out below.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

As used herein, the term "gene" shall mean a region of DNA encoding a polypeptide chain.

"Messenger RNA" or "mRNA" shall mean an RNA molecule that encodes for one or more polypeptides.

"DNA polymerase" shall mean an enzyme which catalyzes the polymerization of deoxyribonucleotide triphosphates to make DNA chains using a DNA template.

"Reverse transcriptase" shall mean an enzyme which catalyzes the polymerization of deoxy- or ribonucleotide triphosphates to make DNA or RNA chains using an RNA or DNA template.

"Complementary DNA" or "cDNA" shall mean the DNA molecule synthesized by polymerization of deoxyribonucleotides by an enzyme with reverse transcriptase activity.

An "isolated nucleic acid" is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

"Oligonucleotide", as used herein in referring to the probes or primers of the present invention, is defined as a molecule comprised of two or more deoxy- or ribonucleotides, preferably more than ten. Its exact size will depend upon many factors which, in turn, depend upon the ultimate function and use of the oligonucleotide.

"DNA fragment" includes polynucleotides and/or oligonucleotides and refers to a plurality of joined nucleotide units formed from naturally-occurring bases and cyclofuranosyl groups joined by native phosphodiester bonds. This term effectively refers to naturally-occurring species or synthetic species formed from naturally-occurring subunits. "DNA fragment" also refers to purine and pyrimidine groups and moieties which function similarly but which have non naturally-occurring portions. Thus, DNA fragments may have altered sugar moieties or inter-sugar linkages. Exemplary among these are the phosphorothioate and other sulfur containing species. They may also contain altered base units or other modifications, provided that biological activity is retained. DNA fragments may also include species which include at least some modified base forms. Thus, purines and pyrimidines other than those normally found in nature may be so employed. Similarly, modifications on the cyclofuranose portions of the nucleotide subunits may also occur as long as biological function is not eliminated by such modifications.

"Primer" shall refer to an oligonucleotide, whether occurring naturally or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, the source of primer and the method used. For example, for diagnostic applications, depending on the complexity of the target sequence, the oligonucleotide primer typically contains 10-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the term "hybridization" refers generally to a technique wherein denatured RNA or DNA is combined with complementary nucleic acid sequence which is either free in solution or bound to a solid phase. As recognized by one skilled in the art, complete complementarity between the two nucleic acid sequences is not a pre-requisite for hybridization to occur. The technique is ubiquitous in molecular genetics and its use centers around the identification of particular DNA or RNA sequences within complex mixtures of nucleic acids.

As used herein, "restriction endonucleases" and "restriction enzymes" shall refer to bacterial enzymes which cut double-stranded DNA at or near a specific nucleotide sequence.

"Purified polypeptide" refers to any peptide generated from CA125 either by proteolytic cleavage or chemical cleavage.

"Degenerate variant" refers to any amino acid variation in the repeat sequence, which fulfills the homology exon structure and conserved sequences and is recognized by the M11, OC125 and ISOBM series of antibodies.

"Fragment" refers to any part of the CA125 molecule identified in a purification scheme.

"Conservative variant antibody" shall mean any antibody that fulfills the criteria of M11, OC125 or any of the ISOBM antibody series.

"Homology" refers to similarity based on identical base matches in alignment. When two sequences are identical there is a 100% homology, as base matches differ in alignment the homology between two sequences is reduced.

The CA125 gene has been cloned and multiple repeat sequences as well as the carboxy terminus have been identified. The cDNA for the CA125. gene is set out in SEQ ID NO: 4. The CA125 molecule comprises three major domains: an extracellular amino terminal domain (Domain 1); a large multiple repeat domain (Domain 2); and a carboxy terminal domain (Domain 3) which includes a transmembrane anchor with a short cytoplasmic domain. The amino terminal domain is assembled by combining five genomic exons, four very short amino terminal sequences and one extraordinarily large exon. This domain is dominated by its capacity for O-glycosylation and its resultant richness in serine and threonine residues. Additionally, an amino terminal extension is present, which comprises four genomic exons. The amino acid composition of the amino terminal extension was found to be consistent with the amino acid composition of the amino terminal domain. The molecular structure is dominated by a repeat domain comprising 156 amino acid repeat units, which encompass the epitope binding sites. More than 60 repeat units have been identified, sequenced, and contiguously placed in the CA125 domain structure. The repeat units encompass an interactive disulfide bridged C-enclosure and the site of OC125 and M11 binding. The repeat sequences demonstrated 70-85% homology to each other. Expression of the repeats was demonstrated in E. coli. The CA125 molecule is anchored at its carboxy terminal through a transmembrane domain and a short cytoplasmic tail. The carboxy terminal also contains a proteolytic cleavage site approximately 50 amino acids upstream from the transmembrane domain, which allows for proteolytic cleavage and release of the CA125 molecule. Any one of the repeat domains has the potential for use as a new gold standard for detecting and monitoring the presence of the CA125 antigen. Further, the repeat domains or other domains, especially the c-terminal to the repeat domain also provide a basis for the development of a vaccine, which would be useful for the treatment of ovarian cancer and other carcinomas where CA125 is elevated.

The DNA sequences of the present invention can also be characterized as encoding the amino acid sequence equivalents of the amino acid sequence, equivalents, as used in this context, include peptides of substantially similar length and amino acid identity to those disclosed, but having conservative amino acid substitution at a non-critical residue position. A conservative amino acid substitution is a substitution in which an amino acid residue is replaced with an amino acid residue of differing identity, but whose R group can be characterized by chemically similar. Four common categories include: polor but uncharged R groups; positively charged R groups; negatively charged R groups; and, hydrophobic R groups. A preferred conservative substitution involves the substitution of a second hydrophobic residue for a fir hydrophobic residue, the first and second hydrophobic residues differing primarily in the size of the R group. The hydrophobic residue would be predicted to be located internally in the folded peptide structure and the mild pertubatim caused only by a change in the size of an R group at an internally located which would not alter the antigenecity of R protein. More specifically, two nucleic acid molecules are substantially equivalent if they have at least about 70% homology.

The isolated cDNA sequences (Table 4 and SEQ ID NO: 4) of the present invention can be inserted into an expression vector. Such vectors contain all necessary regulatory signals to promote the expression of a DNA sequence of interest. Expression vectors are typically either prokaryote or eukaryote specific. Expression vectors can be introduced into either prokaryote or eukaryote cells to produce CA125 proteins or portions thereof. The isolated cDNA sequence as shown in Table 4 was expressed to provide the CA125 molecule set out in Table 5 and SEQ ID NO: 5. The expressed CA125 is a polypeptide with the amino acid sequence set forth in SEQ ID NO: 5; an amino acid sequence having at least 50% sequence identity to the sequence, a conservative for variant or a fragment of any of the above. Two polypeptide sequences are substantially equivalent if there is at least 50% sequence homology and substantial similar physical characteristics. However, in practice, a portion of an isolated nucleic acid molecule set out in SEQ ID NO: 4 is expressed to obtain a fragment of the CA125 molecule. This fragment is then purified to obtain an isolated CA125 fragment.

In certain embodiments, "purified" refers to a polypeptide composition which has been subjected to fractionation to remove various nonprotein components such as other cellular components. Various techniques suitable for use in protein purification are known to those skilled in the relevant art. These techniques include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combination of such techniques. Similarly, a "purification scheme" is a technique or system to remove various nonprotein components such as other cellular components from the expressed protein. Various techniques suitable for use in protein purification are known to those skilled in the relevant art. These techniques include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combination of such techniques.

The genomic DNA and a full-length cDNA sequence of human CA125 has been determined. Additionally, a nucleic acid molecule encoding a 5' upstream region of the CA125 gene has been determined. cDNA is expressed with the use of an expression vector. An expression vector is a carrying vector that has an inducer for expression built into the vector. Different vectors use different inducers. The cDNA is ligased into the expression vector using restriction digest sites designed in the vector. The cDNA must be ligased in the sense direction and in the correct reading frame for expression to occur. Once the cDNA is ligased into the expression vector, the construct is transformed into a cell. In the preferred embodiment, we use *E-Coli* bacteria, but the transformation can be done with yeast, mammalian cells, plants cells, etc. The transformed cells are then grown in culture and protein production is induced with the an inducing agent for the expression vector. In the preferred embodiment, we use the pQE-30 expression vector and induce with IPTG. Once induction has occurred, the cells are harvested and the protein is purified. It should be noted that some expression vectors add tags to the recombinant protein to aid in purification. For example, pQE-30 adds a His-Tag which binds to nickel to aid in purification. Once cells have been successfully transformed, a small aliquot can be frozen and stored for future use.

With a cDNA sequence, one skilled in the art has an easily renewable source of purified CA125. Portions of this cDNA sequence can be expressed to make CA125 polypeptides and these polypeptides can be used to make monoclonal antibodies. These monoclonal antibodies can be made by one skilled in the art to portions of the protein which heretofore do not have any monoclonal antibodies, such as the amino terminal sequence.

More specifically, the purified antibodies are made by the following process: the recombinant protein is injected into an animal (usually a mouse, but other animals can be used). The animal's B-lymphocytes produce antibodies to the protein. Each activated B lymphocyte forms a clone of cells in spleen or lymph nodes, with each cell of the clone producing identical antibody. These spleen cells are then harvested and fused with myeloma cells to produce hybridomas. These hybridomas are immortal and produce only one type of antibody. The hybridomas are selected from cells that did not fuse by selective media. The hybidomas can then be grown in large quantities to produce large quantities of monoclonal antibodies.

Therapeutic Targets: Molecules, which are expressed on the surface of tumor cells as CA125 is, offer potential targets for immune stimulation, drug delivery, biological modifier delivery or any agent which can be specifically delivered to ultimately kill the tumor cells. CA125 offers such potential as a target: 1) Antibodies to CA125 epitopes or newly described potential epitopes: Most especially humanized or human antibodies to CA125 which could directly activate the patients' immune system to attack and kill tumor cells. Antibodies could be used to deliver all drug or toxic agents, including radioactive agents to mediate direct killing of tumor cells. 2) Natural ligands: Under normal circumstances, molecules are bound to the CA125 molecule e.g. a 50 k dalton protein which does not contain CA125 epitopes co-purifies with CA125. Such a molecule, which might have a natural binding affinity for domains on the CA125 molecule, could also be utilized to deliver therapeutic agents to tumor cells.

Anti-sense therapy: CA125 expression may provide a survival or metastatic advantage to ovarian tumor cells as such antisense oligonucleotide derived from the CA125 sequence could be used to down-regulate the expression of CA125. Antisense therapy could be used in association with a tumor cell delivery system such as described above.

Small Molecules: Recombinant domains of CA125 also offer the potential to identify small molecules which bind to individual domains of the molecule. Small molecules either from combinatorial chemical libraries or small peptides can also be used as delivery agents or as biological modifiers.

Transgenic Animals/Transformed: CA125 and genomic DNA can be used to develop transgenic animal models and can be used under low stringency conditions, to clone CA125 cDNAs and genomic DNAs of other animal species. The CA125 cDNA can be used to prepare stable transformants. The bacterial cells could be transformed with CA125 cDNA to include these genes.

Example 1

Expression of 6×His-tagged CA125 repeat in *E. coli*: The open reading frame of the CA125 repeat was amplified by PCR with the 5' sense primer 1 (5'-ACCGGATC-CATGGGCCACACAGAGCCTGGCCC-3') (SEQ ID NO: 6) and the 3' antisense primer 2 (5'-TGTAAGCTTAGGCA-GGGAGGATGGAGTCC-3') (SEQ ID NO: 7). The open reading frame of the CA125 repeat constitutes a portion of the isolated nucleic acid molecule set out in SEQ ID NO: 4. PCR was performed in a reaction mixture consisting of ovarian tumor cDNA derived from 50 ng of mRNA, 5 µmol each of sense and antisense primers for the CA125 repeat, 0.2 mmol of dNTPs, and 0.625 U of Taq polymerase in 1× buffer in a final volume of 25 µl. This mixture was subjected to 1 minute of denaturation at 95° C. followed by 30 cycles of PCR consisting of the following: denaturation for 30 seconds at 95° C., 30 seconds of annealing at 62° C., and 1 minute of extension at 72° C. with an additional 7 minutes of extension on the last cycle. The product was electrophoresed through a 2% agarose gel for separation, the PCR product was purified and digested with the restriction enzymes BamHI and HindIII. This digested PCR product was ligated into the expression vector pQE-30, which had also been digested with BamHI and HindIII. The ligation reaction consisted of 1 ul of 10× ligation buffer, 1 ul of 10× bovine serum albumin (BSA), 1 ul of T4 ligase enzyme, and 7 ul of digested PCR product. The reaction went overnight at 15° C. This clone would allow for expression of recombinant amino-terminal 6×His-tagged CA125 repeat. The construct was then transformed into JM109 *E. coli* cells. The transformation reaction consisted of 5 ul of ligation reaction and 50 ul of cells. The reaction was mixed gently and then incubated on ice for 30 minutes. The reaction was then heat shocked at 42° C. for 45 seconds in a water bath before being returned to ice for 2 minutes. 500 ul of LB broth media were added and the mixture was incubated at 37° C. for 1 hour. At the end of 1 hour the cells were spun down in a microfuge at 4,000×g for 5 minutes and approximately 450 ul of media was removed. The cells were resuspended in the remaining 100 ul of media, transferred to a LAIX plate, and incubated overnight at 37° C. White colonies were picked from the plate and cultured in 5 ml LB broth media to determine if the transformation was successful. Transformed *E. coli* were grown in 1 L cultures to an $OD_{600}$ of 1.5-2.0 at 37° C. and were induced with IPTG (0.1 mM) for 4-6 hours at 25° C. to produce recombinant protein. Whole *E. coli* lysate was electrophoresed through a denaturing 12% polyacrylamide gel and Coomassie stained to detect highly expressed proteins. His-tagged proteins were purified under denaturing conditions using Ni-NTA agarose metal chelating affinity chromatography available from Qiagen according to the manufacturer's instructions. Cells are spun down to remove liquid LB broth media. The cells are then resuspended in 40 ml of 8M Urea lysis buffer (pH 8.0) and incubated with agitation overnight at room temperature. The mixture is then spun down and the lysate is removed. The lysate is then incubated with Ni-NTA agarose beads with agitation overnight at room temperature. The beads are pelleted and the supernatant is removed. The beads are then washed twice in lysis buffer pH 8.0 plus Triton X, three times with lysis buffer pH 6.3 plus Triton X, and four times with lysis buffer pH 6.3 without Triton X. The protein is then eluted from the beads with lysis buffer pH4.2 plus 25 mM EDTA incubated overnight with agitation at room temperature. The beads are pelleted and the supernatant containing the recombinant protein is removed. The supernatant is then dialyzed twice in 0.2×PBS to remove the urea and freeze dried for storage. 1 L of culture produced 2.4 mg of recombinant protein.

It should be understood that various changes and modifications to the presently preferred embodiments described herein will be apparent to those skilled in the art. Such changes and modifications can be made without departing from the spirit and scope of the present invention and without diminishing its attendant advantages.

TABLE 1

Genomic CA125 Amino Terminal Sequence
(SEQ ID NO: 1)

```
   1 GGTGCGCACC ACTATGTCTG GCTAATTTTT GTATTTTTTT GTAGAGACAT
  51 GGTTTCACCA TGTTGGCCAG GCTGGTCTCG AATTCCTGAC TTCAAGTAAT
 101 CCACCCACCT CAGCCTCCCA AAGTGCTGGG ATTACAAGCA TGAGCCACCA
 151 TGCATGGCCT AAAGCTTCTT TTAAAGCCAC CAAGTCCCTT CCCATGTTAG
 201 CCCACTAATC CATGGGTTAG TCATGAATGG ATTAATCTAT TCATACGGAC
 251 AGAGCCCTCA TCACCCAATC ACCTCTTAAA GGCCCCACCT CTCAATACTG
 301 CCACACTGGG GATTAAGTTT CAACAGAGTT TTGGAGGGGA CATTCAAATC
 351 ATAGTAATGC CCAAAGTGAA AAATCTTCCC TGCACTTTTC CCTCAACAAA
 401 AACAGCCAGA GATAGTGAGC TGCCAGGAAA TTCTTTTTTT TTTCCTCTTC
 451 TGTCCTAAAT CAGCATCGCT AGACCTTTAC ATGATTCAAC CTCATCTTCT
 501 TCACCCTCTG GGTCATGAAA TTTTATTTAT TTATTTATTA TTTTCTTGGG
 551 ACAGACTCTG GCTCTGTCGC CCAGGCTGAA GTGCAGTGGT GTGATCTTGG
 601 CTCACTGCAA CCTCCGCCTC CCGGGTTCAA GCGATTCTCC TGCCTCAGCC
 651 TCCTGAGTAG CTGGGATTAC AGGTGGGCGC CACCACACCC AGCTAATTTT
 701 TTGTATTTTT AGTAGAGATG GGGTTTCACC ATATTAGCCA GGATGGTCTC
 751 CATCTCTTGA CCTCGTGATC TGCCCACCTC AGCCTCCCAA AATGCTGGGA
 801 TTACAGGCAT GAGACACCAC GCCCAGCAGG CCAGGGTCAT GAGATTTTAA
 851 TCAAGAGCAA CTTCCACTGA TTCCTGAGAG TGCATCTGTG GGCCCCTGCT
 901 CTGATCTGAA CAGAAGTGCC GTGTCTTCTC TGACCTCCAC TTCTCAATTC
 951 AAGAGCCTTA GTATCTGCCA GTATCACACA CTGAGCATTA GCTCCATCTC
1001 ATGGGGGTGT AGGTAGGGGC TCTATCTGCA TCTTTCTTTC TTTTTTTCTT
1051 TCTTTCCCTT CCTCCCTTCC TCACTCCCTC GGTCCTCTCT TTCTTTCCTT
1101 TTCTTTCTTC CTTCCTCCCT TCCTCCCTCC CTCCCTCTCT CTTTCTCTCT
1151 TTCTTTCTTT CCTTCTTTCT TTCTTTCTCT CTTCCTTCCC TCCCTCCCTC
1201 CTTCCTTCCT TTCTCTTTCT TTCTCTTTCT TTCTTTTTTT CCTTCCTTCC
1251 TTCCTTCTTT CTCTTTCTCT CCCTCCCTTC CTTCCTTCCT TCCTTCCTTC
1301 CTTCCTTTCT TTCTTTCTTT CTTTCTTTCT TTCTTTCTTT CTTTCTTTCT
1351 TTCTTTCTTC CTTCCTTCCT TCCTTCCTTC CTTCCTTCCT TCCTTCCTTT
1401 CTTTTCTTTC TTTCTCTTTC TTTTTGAGAC AGAGCTCTTA TTACCCATGC
1451 TGGAGTGCAG TGGTGTGACC TTGGCTTACT GCAACATCTG CCTCCTAGGG
1501 TCAAGTGATT CTCCTGCCTC AGCCTCCTAA GTAGCTGGGA TTACAGACAC
1551 ATGCCACCAC ACCCAATATT TATTTTTATT AAAATTTTTT TTAAAATTAT
```

TABLE 1-continued

Genomic CA125 Amino Terminal Sequence
(SEQ ID NO: 1)

1601 TTTTAAAAAA TTAAAAATAA TTTTGTATTT TTAGTAGAGA CGGGGTTTCT

1651 CCATGTTGGT CAGGCTGATC TCAAACTCCC AACCTCAGGT GATCCTCCCA

1701 CCTCACCTCC CAAAGTGCTG GGATTACAGG CATGAGCCAC CGTGCCCAGC

1751 CTGGTTCCTG GTTTCTAAGA CATCACACAC ACACACACAC ACACACACAC

1801 ACACTCACAC ACTCAGAGAG AGAGAGAGAG AGAGGATCAT TAAGACATGA

1851 TACACTAAGA AATTCTATTC TGCAGACACT GAGAATCCGT TAAAAAGTTT

1901 GAAGGGAAGA ATTGAGATCA TCAGGTGTTT ATTTGAGGAA ATTGTCTGTG

1951 GTTGAACTAT CCTTTCCTTT CTCTCCCTGA GATTTGGTCT TCTCAATTAG

2001 AAGCGTTGCA CAATTCCCCC AACCTCCATA CATACGGCAG CTCTTCTAGA

2051 CACAGGTTTT CCCAGGTCAA ATGCGGGGAC CCCAGCCATA TCTCCCACCC

2101 TGAGAAATTT TGGAGTTTCA GGGAGCTCAG AAGCTCTGCA GAGGCCACCC

2151 TCTCTGAGGG GATTCTTCTT AGACCTCCAT CCAGAGGCAA ATGTTGACCT

Exon 1

2201 GTCCATGCTG AAACCCTCAG GCCTTCCTGG GTCATCTTCT CCCACCCGCT

2251 CCTTGATGAC AGGGAGCAGG AGCACTAAAG CCACACCAGA AATGGATTCA

2301 GGACTGACAG GAGCCACCTT GTCACCTAAG ACATCTACAG GTGCAATCGT

2351 GGTGACAGAA CATACTCTGC CCTTTACTTC CCCAGATAAG ACCTTGGCCA

2401 GTCCTACATC TTCGGTTGTG GGAAGAACCA CCCAGTCTTT GGGGGTGATG

2451 TCCTCTGCTC TCCCTGAGTC AACCTCTAGA GGAATGCACA CTCCGAGCA

2501 AAGAACCAGC CCATCGCTGA GTCCCCAGGT CAATGGAACT CCCTCTAGGA

2551 ACTACCCTGC TACAAGCATG GTTTCAGGAT TGAGTTCCCC AAGGACCAGG

2601 ACCAGTTCCA CAGAAGGAAA TTTTACCAAA GAAGCATCTA CATACACACT

2651 CACTGTAGAG ACCACAAGTG GCCCAGTCAC TGAGAAGTAC ACAGTCCCCA

2701 CTGAGACCTC AACAACTGAA GGTGACAGCA CAGAGACCCC CTGGGACACA

2751 AGATATATTC CTGTAAAAAT CACATCTCCA ATGAAAACAT TTGCAGATTC

2801 AACTGCATCC AAGGAAAATG CCCCAGTGTC TATGACTCCA GCTGAGACCA

2851 CAGTTACTGA CTCACATACT CCAGGAAGGA CAAACCCATC ATTTGGGACA

2901 CTTTATTCTT CCTTCCTTGA CCTATCACCT AAAGGGACCC CAAATTCCAG

2951 AGGTGAAACA AGCCTGGAAC TGATTCTATC AACCACTGGA TATCCCTTCT

3001 CCTCTCCTGA ACCTGGCTCT GCAGGACACA GCAGAATAAG TACCAGTGCG

3051 CCTTTGTCAT CATCTGCTTC AGTTCTCGAT AATAAAATAT CAGAGACCAG

3101 CATATTCTCA GGCCAGAGTC TCACCTCCCC TCTGTCTCCT GGGGTGCCCG

3151 AGGCCAGAGC CAGCACAATG CCCAACTCAG CTATCCCTTT TTCCATGACA

3201 CTAAGCAATG CAGAAACAAG TGCCGAAAGG GTCAGAAGCA CAATTTCCTC

3251 TCTGGGGACT CCATCAATAT CCACAAAGCA GACAGCAGAG ACTATCCTTA

3301 CCTTCCATGC CTTCGCTGAG ACCATGGATA TACCCAGCAC CCACATAGCC

3351 AAGACTTTGG CTTCAGAATG GTTGGGAAGT CCAGGTACCC TTGGTGGCAC

3401 CAGCACTTCA GCGCTGACAA CCACATCTCC ATCTACCACT TTAGTCTCAG

3451 AGGAGACCAA CACCCATCAC TCCACGAGTG GAAAGGAAAC AGAAGGAACT

TABLE 1-continued

Genomic CA125 Amino Terminal Sequence
(SEQ ID NO: 1)

```
3501 TTGAATACAT CTATGACTCC ACTTGAGACC TCTGCTCCTG GAGAAGAGTC
3551 CGAAATGACT GCCACCTTGG TCCCCACTCT AGGTTTTACA ACTCTTGACA
3601 GCAAGATCAG AAGTCCATCT CAGGTCTCTT CATCCCACCC AACAAGAGAG
3651 CTCAGAACCA CAGGCAGCAC CTCTGGGAGG CAGAGTTCCA GCACAGCTGC
3701 CCACGGGAGC TCTGACATCC TGAGGGCAAC CACTTCCAGC ACCTCAAAAG
3751 CATCATCATG GACCAGTGAA AGCACAGCTC AGCAATTTAG TGAACCCCAG
3801 CACACACAGT GGGTGGAGAC AAGTCCTAGC ATGAAAACAG AGAGACCCCC
3851 AGCATCAACC AGTGTGGCAG CCCCTATCAC CACTTCTGTT CCCTCAGTGG
3901 TCTCTGGCTT CACCACCCTG AAGACCAGCT CCACAAAAGG GATTTGGCTT
3951 GAAGAAACAT CTGCAGACAC ACTCATCGGA GAATCCACAG CTGGCCCAAC
4001 CACCCATCAG TTTGCTGTTC CCACTGGGAT TCAATGACA GGAGGCAGCA
4051 GCACCAGGGG AAGCCAGGGC ACAACCCACC TACTCACCAG AGCCACAGCA
4101 TCATCTGAGA CATCCGCAGA TTTGACTCTG CCACGAACG GTGTCCCAGT
4151 CTCCGTGTCT CCAGCAGTGA GCAAGACGGC TGCTGGCTCA AGTCCTCCAG
4201 GAGGGACAAA GCCATCATAT ACAATGGTTT CTTCTGTCAT CCCTGAGACA
4251 TCATCTCTAC AGTCCTCAGC TTTCAGGGAA GGAACCAGCC TGGGACTGAC
4301 TCCATTAAAC ACTAGACATC CCTTCTCTTC CCCTGAACCA GACTCTGCAG
4351 GACACACCAA GATAAGCACC AGCATTCCTC TGTTGTCATC TGCTTCAGTT
4401 CTTGAGGATA AAGTGTCAGC GACCAGCACA TTCTCACACC ACAAAGCCAC
4451 CTCATCTATT ACCACAGGGA CTCCTGAAAT CTCAACAAAG ACAAAGCCCA
4501 GCTCAGCCGT TCTTTCCTCC ATGACCCTAA GCAATGCAGC AACAAGTCCT
4551 GAAAGAGTCA GAAATGCAAC TTCCCCTCTG ACTCATCCAT CTCCATCAGG
4601 GGAAGAGACA GCAGGGAGTG TCCTCACTCT CAGCACCTCT GCTGAGACTA
4651 CAGACTCACC TAACATCCAC CCAACTGGGA CACTGACTTC AGAATCGTCA
4701 GAGAGTCCTA GCACTCTCAG CCTCCCAAGT GTCTCTGGAG TCAAAACCAC
4751 ATTTTCTTCA TCTACTCCTT CCACTCATCT ATTTACTAGT GGAGAAGAAA
4801 CAGAGGAAAC TTCGAATCCA TCTGTGTCTC AACCTGAGAC TTCTGTTTCC
4851 AGAGTAAGGA CCACCTTGGC CAGCACCTCT GTCCCTACCC CAGTATTCCC
4901 CACCATGGAC ACCTGGCCTA CACGTTCAGC TCAGTTCTCT TCATCCCACC
4951 TAGTGAGTGA GCTCAGAGCT ACGAGCAGTA CCTCAGTTAC AAACTCAACT
5001 GGTTCAGCTC TTCCTAAAAT ATCTCACCTC ACTGGGACGG CAACAATGTC
5051 ACAGACCAAT AGAGACACGT TTAATGACTC TGCTGCACCC CAAAGCACAA
5101 CTTGGCCAGA GACTAGTCCC AGATTCAAGA CAGGGTTACC TTCAGCAACA
5151 ACCACTGTTT CAACCTCTGC CACTTCTCTC TCTGCTACTG TAATGGTCTC
5201 TAAATTCACT TCTCCAGCAA CTAGTTCCAT GGAAGCAACT TCTATCAGGG
5251 AACCATCAAC AACCATCCTC ACAACAGAGA CCACGAATGG CCCAGGCTCT
5301 ATGGCTGTGG CTTCTACCAA CATCCCAATT GGAAAGGGCT ACATTACTGA
5351 AGGAAGATTG GACACAAGCC ATCTGCCCAT TGGAACCACA GCTTCCTCTG
```

TABLE 1-continued

Genomic CA125 Amino Terminal Sequence
(SEQ ID NO: 1)

```
5401 AGACATCTAT GGATTTTACC ATGGCCAAAG AAAGTGTCTC AATGTCAGTA
5451 TCTCCATCTC AGTCCATGGA TGCTGCTGGC TCAAGCACTC CAGGAAGGAC
5501 AAGCCAATTC GTTGACACAT TTTCTGATGA TGTCTATCAT TTAACATCCA
5551 GAGAAATTAC AATACCTAGA GATGGAACAA GCTCAGCTCT GACTCCACAA
5601 ATGACTGCAA CTCACCCTCC ATCTCCTGAT CCTGGCTCTG CTAGAAGCAC
5651 CTGGCTTGGC ATCTTGTCCT CATCTCCTTC TTCTCCTACT CCCAAAGTCA
5701 CAATGAGCTC CACATTTTCA ACTCAGAGAG TCACCACAAG CATGATAATG
5751 GACACAGTTG AAACTAGTCG GTGGAACATG CCCAACTTAC CTTCCACGAC
5801 TTCCTTGACA CCAAGTAATA TTCCAACAAG TGGTGCCATA GGAAAAAGCA
5851 CCCTGGTTCC CTTGGACACT CCATCTCCAG CCACATCATT GGAGGCATCA
5901 GAAGGGGGAC TTCCAACCCT CAGCACCTAC CCTGAATCAA CAAACACACC
5951 CAGCATCCAC CTCGGAGCAC ACGCTAGTTC AGAAAGTCCA AGCACCATCA
6001 AACTTACCAT GGCTTCAGTA GTAAAACCTG GCTCTTACAC ACCTCTCACC
6051 TTCCCCTCAA TAGAGACCCA CATTCATGTA TCAACAGCCA GAATGGCTTA
6101 CTCTTCTGGG TCTTCACCTG AGATGACAGC TCCTGGAGAG ACTAACACTG
6151 GTAGTACCTG GGACCCCACC ACCTACATCA CCACTACGGA TCCTAAGGAT
6201 ACAAGTTCAG CTCAGGTCTC TACACCCCAC TCAGTGAGGA CACTCAGAAC
6251 CACAGAAAAC CATCCAAAGA CAGAGTCCGC CACCCCAGCT GCTTACTCTG
6301 GAAGTCCTAA AATCTCAAGT TCACCCAATC TCACCAGTCC GGCCACAAAA
6351 GCATGGACCA TCACAGACAC AACTGAACAC TCCACTCAAT TACATTACAC
6401 AAAATTGGCA GAAAAATCAT CTGGATTTGA GACACAGTCA GCTCCAGGAC
6451 CTGTCTCTGT AGTAATCCCT ACCTCCCCTA CCATTGGAAG CAGCACATTG
6501 GAACTAACTT CTGATGTCCC AGGGGAACCC CTGGTCCTTG CTCCCAGTGA
6551 GCAGACCACA ATCACTCTCC CCATGGCAAC ATGGCTGAGT ACCAGTTTGA
6601 CAGAGGAAAT GGCTTCAACA GACCTTGATA TTTCAAGTCC AAGTTCACCC
6651 ATGAGTACAT TTGCTATTTT TCCACCTATG TCCACACCTT CTCATGAACT
6701 TTCAAAGTCA GAGGCAGATA CCAGTGCCAT TAGAAATACA GATTCAACAA
6751 CGTTGGATCA GCACCTAGGA ATCAGGAGTT TGGGCAGAAC TGGGGACTTA
6801 ACAACTGTTC CTATCACCCC ACTGACAACC ACGTGGACCA GTGTGATTGA
6851 ACACTCAACA CAAGCACAGG ACACCCTTTC TGCAACGATG AGTCCTACTC
6901 ACGTGACACA GTCACTCAAA GATCAAACAT CTATACCAGC CTCAGCATCC
6951 CCTTCCCATC TTACTGAAGT CTACCCTGAG CTCGGGACAC AAGGGAGAAG
7001 CTCCTCTGAG GCAACCACTT TTTGGAAACC ATCTACAGAC ACACTGTCCA
7051 GAGAGATTGA GACTGGCCCA ACAAACATTC AATCCACTCC ACCCATGGAC
7101 AACACAACAA CAGGGAGCAG TAGTAGTGGA GTCACCCTGG GCATAGCCCA
7151 CCTTCCCATA GGAACATCCT CCCCAGCTGA GACATCCACA AACATGGCAC
7201 TGGAAAGAAG AAGTTCTACA GCCACTGTCT CTATGGCTGG GACAATGGGA
7251 CTCCTTGTTA CTAGTGCTCC AGGAAGAAGC ATCAGCCAGT CATTAGGAAG
7301 AGTTTCCTCT GTCCTTTCTG AGTCAACTAC TGAAGGAGTC ACAGATTCTA
```

TABLE 1-continued

Genomic CA125 Amino Terminal Sequence
(SEQ ID NO: 1)

```
7351 GTAAGGGAAG CAGCCCAAGG CTGAACACAC AGGGAAATAC AGCTCTCTCC
7401 TCCTCTCTTG AACCCAGCTA TGCTGAAGGA AGCCAGATGA GCACAAGCAT
7451 CCCTCTAACC TCATCTCCTA CAACTCCTGA TGTGGAATTC ATAGGGGGCA
7501 GCACATTTTG GACCAAGGAG GTCACCACAG TTATGACCTC AGACATCTCC
7551 AAGTCTTCAG CAAGGACAGA GTCCAGCTCA GCTACCCTTA TGTCCACAGC
7601 TTTGGGAAGC ACTGAAAATA CAGGAAAAGA AAAACTCAGA ACTGCCTCTA
7651 TGGATCTTCC ATCTCCAACT CCATCAATGG AGGTGACACC ATGGATTTCT
7701 CTCACTCTCA GTAATGCCCC CAATACCACA GATTCACTTG ACCTCAGCCA
7751 TGGGGTGCAC ACCAGCTCTG CAGGGACTTT GGCCACTGAC AGGTCATTGA
7801 ATACTGGTGT CACTAGAGCC TCCAGATTGG AAAACGGCTC TGATACCTCT
7851 TCTAAGTCCC TGTCTATGGG AAACAGCACT CACACTTCCA TGACTTACAC
7901 AGAGAAGAGT GAAGTGTCTT CTTCAATCCA TCCCCGACCT GAGACCTCAG
7951 CTCCTGGAGC AGAGACCACT TTGACTTCCA CTCCTGGAAA CAGGGCCATA
8001 AGCTTAACAT TGCCTTTTTC ATCCATTCCA GTGGAAGAAG TCATTTCTAC
8051 AGGCATAACC TCAGGACCAG ACATCAACTC AGCACCCATG ACACATTCTC
8101 CCATCACCCC ACCAACAATT GTATGGACCA GTACAGGCAC AATTGAACAG
8151 TCCACTCAAC CACTACATGC AGTTTCTTCA GAAAAAGTTT CTGTGCAGAC
8201 ACAGTCAACT CCATATGTCA ACTCTGTGGC AGTGTCTGCT TCCCCTACCC
8251 ATGAGAATTC AGTCTCTTCT GGAAGCAGCA CATCCTCTCC ATATTCCTCA
8301 GCCTCACTTG AATCCTTGGA TTCCACAATC AGTAGGAGGA ATGCAATCAC
8351 TTCCTGGCTA TGGGACCTCA CTACATCTCT CCCCACTACA ACTTGGCCAA
8401 GTACTAGTTT ATCTGAGGCA CTGTCCTCAG GCCATTCTGG GGTTTCAAAC
8451 CCAAGTTCAA CTACGACTGA ATTTCCACTC TTTTCAGCTG CATCCACATC
8501 TGCTGCTAAG CAAAGAAATC CAGAAACAGA GACCCATGGT CCCCAGAATA
8551 CAGCCGCGAG TACTTTGAAC ACTGATGCAT CCTCGGTCAC AGGTCTTTCT
8601 GAGACTCCTG TGGGGCAAG TATCAGCTCT GAAGTCCCTC TTCCAATGGC
8651 CATAACTTCT AGATCAGATG TTTCTGGCCT TACATCTGAG AGTACTGCTA
8701 ACCCGAGTTT AGGCACAGCC TCTTCAGCAG GGACCAAATT AACTAGGACA
8751 ATATCCCTGC CCACTTCAGA GTCTTTGGTT TCCTTTAGAA TGAACAAGGA
8801 TCCATGGACA GTGTCAATCC CTTTGGGGTC CCATCCAACT ACTAATACAG
8851 AAACAAGCAT CCCAGTAAAC AGCGCAGGTC CACCTGGCTT GTCCACAGTA
8901 GCATCAGATG TAATTGACAC ACCTTCAGAT GGGGCTGAGA GTATTCCCAC
8951 TGTCTCCTTT TCCCCCTCCC CTGATACTGA AGTGACAACT ATCTCACATT
9001 TCCCAGAAAA GACAACTCAT TCATTTAGAA CCATTTCATC TCTCACTCAT
9051 GAGTTGACTT CAAGAGTGAC ACCTATTCCT GGGGATTGGA TGAGTTCAGC
9101 TATGTCTACA AAGCCCACAG GAGCCAGTCC CTCCATTACA CTGGGAGAGA
9151 GAAGGACAAT CACCTCTGCT GCTCCAACCA CTTCCCCCAT AGTTCTCACT
9201 GCTAGTTTCA CAGAGACCAG CACAGTTTCA CTGGATAATG AAACTACAGT
```

TABLE 1-continued

Genomic CA125 Amino Terminal Sequence
(SEQ ID NO: 1)

```
 9251 AAAAACCTCA GATATCCTTG ACGCACGGAA AACAAATGAG CTCCCCTCAG
 9301 ATAGCAGTTC TTCTTCTGAT CTGATCAACA CCTCCATAGC TTCTTCAACT
 9351 ATGGATGTCA CTAAAACAGC CTCCATCAGT CCCACTAGCA TCTCAGGAAT
 9401 GACAGCAAGT TCCTCCCCAT CTCTCTTCTC TTCAGATAGA CCCCAGGTTC
 9451 CCACATCTAC AACAGAGACA AATACAGCCA CCTCTCCATC TGTTTCCAGT
 9501 AACACCTATT CTCTTGATGG GGGCTCCAAT GTGGGTGGCA CTCCATCCAC
 9551 TTTACCACCC TTTACAATCA CCCACCCTGT CGAGACAAGC TCGGCCCTAT
 9601 TAGCCTGGTC TAGACCAGTA AGAACTTTCA GCACCATGGT CAGCACTGAC
 9651 ACTGCCTCCG GAGAAAATCC TACCTCTAGC AATTCTGTGG TGACTTCTGT
 9701 TCCAGCACCA GGTACATGGA CCAGTGTAGG CAGTACTACT GACTTACCTG
 9751 CCATGGGCTT TCTCAAGACA AGTCCTGCAG GAGAGGCACA CTCACTTCTA
 9801 GCATCAACTA TTGAACCAGC CACTGCCTTC ACTCCCCATC TCTCAGCAGC
 9851 AGTGGTCACT GGATCCAGTG CTACATCAGA AGCCAGTCTT CTCACTACGA
 9901 GTGAAAGCAA AGCCATTCAT TCTTCACCAC AGACCCCAAC TACACCCACC
 9951 TCTGGAGCAA ACTGGGAAAC TTCAGCTACT CCTGAGAGCC TTTTGGTAGT
10001 CACTGAGACT TCAGACACAA CACTTACCTC AAAGATTTTG GTCACAGATA
10051 CCATCTTGTT TTCAACTGTG TCCACGCCAC CTTCTAAATT TCCAAGTACG
10101 GGGACTCTGT CTGGAGCTTC CTTCCCTACT TTACTCCCGG ACACTCCAGC
10151 CATCCCTCTC ACTGCCACTG AGCCAACAAG TTCATTAGCT ACATCCTTTG
10201 ATTCCACCCC ACTGGTGACT ATAGCTTCGG ATAGTCTTGG CACAGTCCCA
10251 GAGACTACCC TGACCATGTC AGAGACCTCA AATGGTGATG CACTGGTTCT
10301 TAAGACAGTA AGTAACCCAG ATAGGAGCAT CCCTGGAATC ACTATCCAAG
10351 GAGTAACAGA AAGTCCACTC CATCCTTCTT CCACTTCCCC CTCTAAGATT
10401 GTTGCTCCAC GGAATACAAC CTATGAAGGT TCGATCACAG TGGCACTTTC
10451 TACTTTGCCT GCGGGAACTA CTGGTTCCCT TGTATTCAGT CAGAGTTCTG
10501 AAAACTCAGA GACAACGGCT TTGGTAGACT CATCAGCTGG GCTTGAGAGG
10551 GCATCTGTGA TGCCACTAAC CACAGGAAGC CAGGGTATGG CTAGCTCTGG
10601 AGGAATCAGA AGTGGGTCCA CTCACTCAAC TGGAACCAAA ACATTTTCTT
10651 CTCTCCCTCT GACCATGAAC CCAGGTGAGG TTACAGCCAT GTCTGAAATC
10701 ACCACGAACA GACTGACAGC TACTCAATCA ACAGCACCCA AAGGGATACC
10751 TGTGAAGCCC ACCAGTGCTG AGTCAGGCCT CCTAACACCT GTCTCTGCCT
10801 CCTCAAGCCC ATCAAAGGCC TTTGCCTCAC TGACTACAGC TCCCCCAACT
10851 TGGGGGATCC CACAGTCTAC CTTGACATTT GAGTTTTCTG AGGTCCCAAG
10901 TTTGGATACT AAGTCCGCTT CTTTACCAAC TCCTGGACAG TCCCTGAACA
10951 CCATTCCAGA CTCAGATGCA AGCACAGCAT CTTCCTCACT GTCCAAGTCT
11001 CCAGAAAAAA ACCCAAGGGC AAGGATGATG ACTTCCACAA AGGCCATAAG
11051 TGCAAGCTCA TTTCAATCAA CAGGTTTTAC TGAAACCCCT GAGGGATCTG
11101 CCTCCCCTTC TATGGCAGGG CATGAACCCA GAGTCCCCAC TTCAGGAACA
11151 GGGGACCCTA GATATGCCTC AGAGAGCATG TCTTATCCAG ACCCAAGCAA
```

TABLE 1-continued

Genomic CA125 Amino Terminal Sequence
(SEQ ID NO: 1)

```
11201 GGCATCATCA GCTATGACAT CGACCTCTCT TGCATCAAAA CTCACAACTC

11251 TCTTCAGCAC AGGTCAAGCA GCAAGGTCTG GTTCTAGTTC CTCTCCCATA

11301 AGCCTATCCA CTGAGAAAGA AACAAGCTTC CTTTCCCCCA CTGCATCCAC

11351 CTCCAGAAAG ACTTCACTAT TTCTTGGGCC TTCCATGGCA AGGCAGCCCA

11401 ACATATTGGT GCATCTTCAG ACTTCAGCTC TGACACTTTC TCCAACATCC

11451 ACTCTAAATA TGTCCCAGGA GGAGCCTCCT GAGTTAACCT CAAGCCAGAC

11501 CATTGCAGAA GAAGAGGGAA CAACAGCTGA ACACAGACG TTAACCTTCA

11551 CACCATCTGA GACCCCAACA TCCTTGTTAC CTGTCTCTTC TCCCACAGAA

11601 CCCACAGCCA GAAGAAAGAG TTCTCCAGAA ACATGGGCAA GCTCTATTTC

11651 AGTTCCTGCC AAGACCTCCT TGGTTGAAAG TAAGAATGCC CTGCTCCTTC

11701 CCCAAGTGTG CTGGGATGA ATCTGGAAAT AAACTACATC TTTTTTATTT

11751 TTTAAACTTT TATATTTGAA AATATAAATA TTTTAGGTTC AGGGAACATG

11801 TGCAGGTTTG TTATATAGGT AAATTGCATG TCATGGGGGC TTGGGGTACA

11851 GATTACATCA TCAGCCAGGT AATAAGCCTA GTACCTGATC AGTAGATTTT

11901 TTTTAATCCT CTCCCTCCTC CCAGCCTCCA CCCTCAATTC ACATGTCTCC

11951 ATGTGTACTC AAGGTTTAAT TCCCACTTAT GAGTGAGAAC ATGCGGTATT

12001 TGTAAACTAC ATCTTTATTT TTGCTAACCT CGAACTGAAA TTTAGCATTT

12051 GTTTTATTGA TGAATAGAGG TAACAAAACA AACCACATTA ATCCTAGCAG

12101 TGCCTGTGCC TTTGCCAACA ACAGAAATTC CGGACACTTT CATATCCTAT

12151 GACAATTGTT GCAAGCACTT TTAAAAATCA TGTACGACTT TATTCATAAT

12201 TATAGTGGTT ATTAGGCTTT TCAATAGATC TTATTTTATG AGTTAGTAAA

12251 ATAAGTGCCT GTATTATTGT ATTACATTTG TTTATTAAGA TCTTGATAAC

12301 AACATTTCAA TATAATCATT TCCTTTGTTT TTTAAATTTT AGATTCAGGG

12351 GTATATGTGC AGGTTTGTTA CGTGGATATA CTGCATAATG ATGAGGTTTG

12401 GCTTCTAGTG AACCCATCAG CCAAATAGTG AATGTTGTGC CAATAAGTA

12451 GTTTTTCAAT CCTCACTTCA CTCCCAGCCT CCTCTATTTT GGAGTCCCAG

12501 TGTCTATTAT TTCTATCTTT ATGTCCACAT GTACCCATTG GTTAGCTCCC

12551 ACTTATAAGT GAGAATGTGC AGTATTTAAT TTTCTGTTTT TGAGTTATTT

12601 TGCTTAGGTT GATGGCCTTC AGCTCCAGCC ACGTTGCTTT AAAGAACATG

12651 ATTTCATTCT TTTTTATGGC TGCATAGTAC TCCGAGGTGT ATGTGTACCA

12701 GATTTTCTTT ATCCACAATG ATTTCCTTTG TAATCTAATA TTTTATATTG

12751 TTATTTTATG TTTTATTCTA TATTTTTATT TTAATTTATA AAGGAATTCA

12801 TATGGTTCAC AAGCCTGTCA AAGGGACCTA AATAAAAAG AGGTTAAGAA

12851 TCCATGCTCT AAACAGAATA TTACTCCATT TTATTTCATT TATTTTTAAA

12901 GAGACAGTCT CACTCTGTCA TCCAGGCTGG AGTACAGTGG AGTGATCATA

12951 GCTCATTGCA ACCCTGAACT CTTGGGCACA AGCAATTCTC CTGCTTCATC

13001 CTCCAGAGGA GCTGGGACTA CAGGTGCACA TCACCATGCC CAGCTAGTTT

13051 TAAAAATTAT TTTGTAGAGA TGGTGTCTCA CTATCCTACC CAGGCTGGTC
```

TABLE 1-continued

Genomic CA125 Amino Terminal Sequence
(SEQ ID NO: 1)

```
13101 TCAAACTCCT GGGCTCAGGC AATCCTCCCA CTTTGACCTC CCAAAGTGTT

13151 GAGATTACAG GGGCAAGCCA CTGTGCCTGG CCACTTGTCA CATTTTAATT

13201 TGTGATTACT TATAAAATGA ACCCCTTCCC ATCTGAGATC TGTCAGTCTT

13251 TCTGGTGACG GTGCCTGGTG TCTGCTTTCT ACCATGTCCT GTTAGACTAG

13301 TGTTTGATGG GAGGTCACCT GGGCAGCTGT CCAGCTCACT CACTGGGCTC

13351 TAGAGCCTCT GAGTTGAAGC AAAATAGAAA GATCAGTCAA TGTAAAGAAA

13401 GCTCAAAAAC TGACATTCTG AAGTAATGGA TAGCTAAACC TTCCTATTGC
```

Exon 2

```
13451 CCTTTTCTTT CAGCAACTGA TGGAACGCTA GTGACCACCA TAAAGATGTC

13501 AAGCCAGGCA GCACAAGGAA ATTCCACGTG GCCTGCCCCA GCAGAGGAGA

13551 CGGGGACCAG TCCAGCAGGT AAATATAGAC CTTGTTTCCA TTTCTGCTCT

13601 GCTAATGCCA CCCAAGCCTT TCTTTTCTTT TCTTTTCTTT TCTTTTCTTT

13651 TCTTTTCTTT TCTTTTCTTT CTCTCCCTTT CTTTCTTTCT TTCTTTCTTT

13701 CTTTCTTTCT TTCTTTCTTT CTTTCTTTCT CTTTCTTTCT TTCTTTCTTT

13751 CTTTCTTTCT TTCTTTCTTT CTTTCTTTCT CTTTCTTTCT TCTTTCTCTC

13801 TCTCTCTTTC TTTCTTTCTC TTGTTCTTTT TAAATTTTTT ATTTTTTTAC

13851 TTAATTTTTT TCACCCAAGC CTTAAGGCCA GTTTGGACCA GATAGTGAGA

13901 CCCCACCTCT ATAAAAAAAA TTTTTAAAAA AAAAATAAGT TGGGCATCGT

13951 GCAGGCCTGT AGTCCCTGCT ACTCGAGAGG CCAAGGTGGG AGGACAGCTT

14001 GCTGCTGACT AAAAGTGCTG CTTATTGATT CTGGGAAGAA AAAATATACA

14051 AGGCTTCAGT TTCATTATTT TATAAGTAAA TGCTAGCAAC TTTTCCTTTC

14101 TTTCTCTCTT TCTCTCTTCC TCTCTTTCTC TCCTCTCCTT CTCTTCTCTC

14151 TCTCTCTCTC TCTCTCTCTC TTTTCTCTCTC CTCTCCTTCT CTTCTCTTCT

14201 TTCTCTCTCT CTCTCTTTCA TTTATTTTTG AGACATGGTC TCATTCTGTC

14251 ACCCAGGCTG GAGTACAGTG GTGTATATTT ACTGCAGTAC TCACTGTACT

14301 CACTGCAGCC TCAAATTCCT GGGCTCAAGC TATCCTCTCA CCTCAGCCTC

14351 CTGAGTAGCT GGGCAGCAGT CCAGCTCACT CACTGGGCTC TAGAGCCTCT

14401 GTGCTATGCC CAGCTTATTG TTGTTGTTTT TTTAAATTTT TTTTTTTGTA

14451 CAGATGGGGT CTCACTATGT GGCCCAAGGT GGTCTTAAAC TCCTGGCTCC

14501 AAGAGATCCT CCCACCTCAG CCTCCCAAAG TGCAGGGATT ACAGGTGTGA

14551 GCCACTGTGC CCAGCCTAGA CAGCATTTTT TTTTTTTGAA ACAGGGTCTC

14601 CCTCTGTTGC CCAGGCTGGA GTGCAATGGC GTGTTCATGG TTCACTGCAG

14651 CCTCAGCCTC CTCAGTCTCA AGCAATCCTC CAACTTCAGC CTCCCCCAAC

14701 AGCTAGAACT GCAGGTGATC ATCACCAATT AGCCTGGTTA ATTGTGTGTG

14751 TATTTCTTAA ATTTTTTGTA GAGATAGTTC TCACTATATT GCTTGGGCTG

14801 GTCTCAAACT CCTGGACTCA AGTGATTCAC CTACCTCGGC CTCCCTAAGC

14851 ACTGGGATTA CAGGCTTGAG CCACCACACC CGGCAAGGAC TAGGTTTTAA

14901 AATAGGTTCC TAGGCTGGGT GTGGTGGCTT ACGCCCGTAA TCCCAGCACT

14951 TTGGGAGGCT GAGGTGGGCG GATCACGAGG TCAGGAGTTT GAGACCAGCC
```

TABLE 1-continued

Genomic CA125 Amino Terminal Sequence
(SEQ ID NO: 1)

15001 TGGCCAACAT AGTGAAACCC TGTCTCTACT AAAAATACAA AAAATTAGCT

15051 GGGCATAGTG CACACACCT GTAATCCCAG CTACTCGGGA GGCTGAGGAA

15101 GGAGAATCAC TTGAACCTGG GAGGCGGAGG TTGCAGTGAG CCGAGATCAT

15151 GCCATTGCTC TCCAGCCTGG GTGACAGAGC AAGACTCCAT CTAAAAAAAA

15201 AAAAAAAGT TCCTTTGACT TCTTGACACT CTTCTCTGAG GATATTGATC

15251 ATTTTTCCCC AATAGATGTT ACTAATTGAA CACTTCTGTT GCTTCAACTT

15301 ACTAATTTAC ATGATCAATA GCCAATTAAT TCAGCAGGAG AGAATGCTAC

15351 AGAGTCGATT CTTTCTGTAC TTTCTTCTGC TCCAGAGTGA AGGATCTTTC

15401 TAAATCAGAG ACCATCACTG TGTTCACAGG GAGGGCCTAG GTGAACCTGA

15451 GATGGCAAAT GTTGCGTTTG TTCTACGGAA GAAGGGATTA TGGGTTGAAG

15501 TCCTTGGCAG TGCCAAATTG CTTAGAAAAA TGTGAAATAT GGTCCCTAGG

15551 AGTGCTCTTG GGATGTCACA TTTTTCTCAC TCCTTTGACA GGTAGATGTT

15601 ATTTTCCTGA AGGCCAGGGA AAGGATTCAG AGGGAGGAAT GAATTTGAAA

15651 GAAAATGAAG GTGACGAGAA AGAATGAGCT CATCTCCCTT ATCCTCTTTC

15701 TTCTCAAATC CTTAAGTAGC TTTGCAGTGA ACTAAGATTT GGGGGAACCT

15751 AGAGGAGGCT GAAAGTTGGA AGCTGAAATT GGCTTAGCAA GGGCAAGCTC

15801 CAAAGACAAA AGTGGAAATA GTTTGGGGGT AGCCTTTTGC ATGGGTGAAA

15851 TCCTGGTTCA TCACATCCTC CCTTATGCAA AGAGCCCTTT TATATGGGGC

15901 ATGGGAAAAA ACTGAGCTAA AGGTGATAAT TTCTCCTGAG CAAGCCAGAT

15951 GGTCAAAGCT CTAACTTCAC CATCTCCCTT GGAATGTTTA ATGTGTTCCC

16001 TGGTGTCCAG AGGCTTAACG TGTGAGAATT AAAAGCTCAA CATTTTCTTT

16051 CCCAGGGAAG GAGGAAATAG TTTTAATTGA AATCCCGGGA GGAAATGAAT

16101 GATAGTGTCA AACCAAAAAA CTTCATCTTC TGTACCACTT GCATATACTC

Exon 3

16151 CACTGACTTA CTTTCTAATC ACAGGC<u>ACAT CCCCAGGAAG CCCAGAAATG</u>

16201 <u>TCTACCACTC TCAAAATCAT GAGCTCCAAG GAACCCGGCA TCAGCCCAGA</u>

16251 <u>GATCAGGTCC ACTGTGAGAA ATTCTCCTTG GAAGACTCCA GAAACAACTG</u>

16301 <u>TTCCCATGGA GACCACAGTG GAACCAGTCA CCCTTCAGTC CACAGCCCTA</u>

16351 <u>GGAAGTGGCA GCACCAGCAT CTCTCACCTG CCCACAGGAA CCACATCACC</u>

16401 <u>AACCAAGTCA CCAACAGAAA ATATGTTGGC TACAGAAAGG GTCTCCCTCT</u>

16451 <u>CCCCATCCCC ACCTGAGGCT TGGACCAACC TTTATTCTGG AACTCCAGGA</u>

16501 <u>GGGACCAGGC AGTCACTGGC ACAATGTCC TCTGTCTCCC TAGAGTCACC</u>

16551 <u>AACTGCTAGA AGCATCACAG GGACTGGTCA GCAAAGCAGT CCAGAACTGG</u>

16601 <u>TTTTAAAGAC AACTGGAATG GAATTCTCTA TGTGGCATGG CTCTACTGGA</u>

16651 <u>GGGACCACAG GGACACACA TGTCTCTCTG AGCACATCTT CCAATATCCT</u>

16701 <u>TGAAGACCCT GTAACCAGCC CAAACTCTGT GAGCTCATTG ACAGATAAAT</u>

16751 <u>CCAAACATAA AACCGAGACA TGGGTCAGCA CCACAGCCAT TCCCTCCACT</u>

16801 <u>GTCCTGAATA ATAAGATAAT GGCAGCTGAA CAACAGACAA GTCGATCTGT</u>

TABLE 1-continued

Genomic CA125 Amino Terminal Sequence
(SEQ ID NO: 1)

```
16851 GGATGAGGCT TATTCATCAA CTAGTTCTTG GTCAGATCAG ACATCTGGGA
16901 GTGACATCAC CCTTGGTGCA TCTCCTGATG TCACAAACAC ATTATACATC
16951 ACCTCCACAG CACAAACCAC CTCACTAGTA TCTCTGCCCT CTGGAGACCA
17001 AGGCATTACA AGCCTCACCA ATCCCTCAGG AGGAAAAACA AGCTCTGCAT
17051 CATCTGTCAC ATCTCCTTCA ATAGGGCTTG AGACTCTGAT GGCCAATGTA
17101 AGTGCAGTGA CAAGTGACAT TGCCCCTACT GCTGGGCATC TATCTCAGAC
17151 TTCATCTCCT GCGGAAGTGA GCATCCTGGA CATAACCACA GCTCCTACTC
17201 CAGGTATCTC CACCACCATC ACCACCATGG GAACCAACTC AATCTCAACT
17251 ACCACACCCA ACCCAGAAGT GGGTATGAGT ACCATGGACA GCACCCCGGC
17301 CACAGAGAGG CACACAACTT CTACAGAACA CCCTTCCACC TGGTCTTCCA
17351 CAGCTGCATC AGATTCCTGG ACTGTCACAG ACATGACTTC AAACTTGAAA
17401 GTTGCAAGAT CTCCTGGAAC AATTTCCACA ATGCATACAA CTTCATTCTT
17451 AGCCTCAAGC ACTGAATTAG ACTCCATGTC TACTCCCCAT GGCCGTATAA
17501 CTGTCATTGG AACCAGCCTG GTCACTCCAT CCTCTGATGC TTCAGCTGTA
17551 AAGACAGAGA CCAGTACAAG TGAAAGAACA TTGAGTCCTT CAGACACAAC
17601 TGCATCTACT CCCATCTCAA CTTTTTCTCG TGTCCAGAGG ATGAGCATCT
17651 CAGTTCCTGA CATTTTAAGT ACAAGTTGGA CTCCCAGTAG TACAGAAGCA
17701 GAAGATGTGC CTGTTTCAAT GGTTTCTACA GATCATGCTA GTACAAAGAC
17751 TGACCCAAAT ATGCCCCTGT CCACTTTTCT GTTTGATTCT CTGTCCACTC
17801 TTGACTGGGA CACTGGGAGA TCTCTGTCAT CAGCCACAGC CACTACCTCA
17851 GCTCCTCAGG GGGCCACAAC TCCCCAAGAA CTCACTTTGG AAACCATGAT
17901 CAGCCCAGCT ACCTCACAGT TGCCCTTCTC TATAGGGCAC ATTACAAGTG
17951 CAGTCATACC AGCTGCAATG GCAAGGAGCT CTGGAGTTAC TTTTTCAAGA
18001 CCAGATCCCA CAAGCAAAAA GGCAGAGCAG ACTTCCACTC AGCTTCCCAC
18051 CACCACTTCT GCACATCCAG AGCAGGTGCC CAGATCAGCA GCAACAACTC
18101 TGGATGTGAT CCCACACACA GCAAAAACTC CAGATGCAAC TTTTCAGAGA
18151 CAAGGGCAGA CAGCTCTTAC AACAGAGGCA AGAGCTACAT CTGACTCCTG
18201 GAATGAGAAA GAAAAATCAA CCCCAAGTGC ACCTTGGATC ACTGAGATGA
18251 TGAATTCTGT CTCAGAAGAT ACCATCAAGG AGGTTACCAG CTCCTCCAGT
18301 GTGTTAAGGA CCCTGAATAC GCTGGACATA AACTTGGAAT CTGGGACGAC
18351 TTCATCCCCA AGTTGGAAAA GCAGCCCATA TGAGAGAATT GCCCCTTCTG
18401 AGTCTACCAC AGACAAAGAG GCAATTCACC CTTCTACAAA CACAGTAGAG
18451 ACCACTGGCT GGGTCACAAG TTCCGAACAT GCTTCTCATT CCACTATCCC
18501 AGCCCACTCA GCGTCATCCA AACTCACATC TCCAGTGGTT ACAACCTCCA
18551 CCAGGGAACA AGCAATAGTT TCTATGTCAA CAACCACATG GCCAGAGTCT
18601 ACAAGGGCTA GAACAGAGCC TAATTCCTTC TTGACTATTG AACTGAGGGA
18651 CGTCAGCCCT TACATGGACA CCAGCTCAAC CACACAAACA AGTTTTATCT
18701 CTTCCCCAGG TTCCACTGCG ATCACCAAGG GGCCTAGAAC AGAAATTACC
18751 TCCTCTAAGA GAATATCCAG CTCATTCCTT GCCCAGTCTA TGAGGTCGTC
```

TABLE 1-continued

Genomic CA125 Amino Terminal Sequence
(SEQ ID NO: 1)

```
18801 AGACAGCCCC TCAGAAGCCA TCTCCAGGCT GTCTAACTTT CCTGCCATGA
18851 CAGAATCTGG AGGAATGATC CTTGCTATGC AAACAAGTCC ACCTGGCGCT
18901 ACATCACTAA GTGCACCTAC TTTGGATACA TCAGCCACAG CCTCCTGGAC
18951 AGGGACTCCA CTGGCTACGA CTCAGAGATT TACATACTCA GAGAAGACCA
19001 CTCTCTTTAG CAAAGGTCCT GAGGATACAT CACAGCCAAG CCCTCCCTCT
19051 GTGGAAGAAA CCAGCTCTTC CTCTTCCCTG GTACCTATCA ATGCTACAAC
19101 CTCGCCTTCC AATATTTTGT TGACATCACA AGGGCACAGT CCCTCCTCTA
19151 CTCCACCTGT GACCTCAGTT TTCTTGTCTG AGACCTCTGG CCTGGGGAAG
19201 ACCACAGACA TGTCGAGGAT AAGCTTGGAA CCTGGCACAA GTTTACCTCC
19251 CAATTTGAGC AGTACAGCAG GTGAGGCGTT ATCCACTTAT GAAGCCTCCA
19301 GAGATACAAA GGCAATTCAT CATTCTGCAG ACACAGCAGT GACGAATATG
19351 GAGGCAACCA GTTCTGAATA TTCTCCTATC CCAGGCCATA CAAAGCCATC
19401 CAAAGCCACA TCTCCATTGG TTACCTCCCA CATCATGGGG GACATCACTT
19451 CTTCCACATC AGTATTTGGC TCCTCCGAGA CCACAGAGAT TGAGACAGTG
19501 TCCTCTGTGA ACCAGGGACT TCAGGAGAGA AGCACATCCC AGGTGGCCAG
19551 CTCTGCTACA GAGACAAGCA CTGTCATTAC CCATGTGTCT AGTGGTGATG
19601 CTACTACTCA TGTCACCAAG ACACAAGCCA CTTTCTCTAG CGGAACATCC
19651 ATCTCAAGCC CTCATCAGTT TATAACTTCT ACCAACACAT TTACAGATGT
19701 GAGCACCAAC CCCTCCACCT CTCTGATAAT GACAGAATCT TCAGGAGTGA
19751 CCATCACCAC CCAAACAGGT CCTACTGGAG CTGCAACACA GGGTCCATAT
19801 CTCTTGGACA CATCAACCAT GCCTTACTTG ACAGAGACTC CATTAGCTGT
19851 GACTCCAGAT TTTATGCAAT CAGAGAAGAC CACTCTCATA AGCAAAGGTC
19901 CCAAGGATGT GTCCTGGACA AGCCCTCCCT CTGTGGCAGA AACCAGCTAT
19951 CCCTCTTCCC TGACACCTTT CTTGGTCACA ACCATACCTC CTGCCACTTC
20001 CACGTTACAA GGGCAACATA CATCCTCTCC TGTTTCTGCG ACTTCAGTTC
20051 TTACCTCTGG ACTGGTGAAG ACCACAGATA TGTTGAACAC AAGCATGGAA
20101 CCTGTGACCA ATTCACCTCA AAATTTGAAC AATCCATCAA ATGAGATACT
20151 GGCCACTTTG GCAGCCACCA CAGATATAGA GACTATTCAT CCTTCCATAA
20201 ACAAAGCAGT GACCAATATG GGGACTGCCA GTTCAGCACA TGTACTGCAT
20251 TCCACTCTCC CAGTCAGCTC AGAACCATCT ACAGCCACAT CTCCAATGGT
20301 TCCTGCCTCC AGCATGGGGG ACGCTCTTGC TTCTATATCA ATACCTGGTT
20351 CTGAGACCAC AGACATTGAG GGAGAGCCAA CATCCTCCCT GACTGCTGGA
20401 CGAAAAGAGA ACAGCACCCT CCAGGAGATG AACTCAACTA CAGAGTCAAA
20451 CATCATCCTC TCCAATGTGT CTGTGGGGGC TATTACTGAA GCCACAAAAA
20501 TGGAAGTCCC CTCTTTTGAT GCAACATTCA TACCAACTCC TGCTCAGTCA
20551 ACAAAGTTCC CAGATATTTT CTCAGTAGCC AGCAGTAGAC TTTCAAACTC
20601 TCCTCCCATG ACAATATCTA CCCACATGAC CACCACCCAG ACAGGGTCTT
20651 CTGGAGCTAC ATCAAAGATT CCACTTGCCT TAGACACATC AACCTTGGAA
```

TABLE 1-continued

Genomic CA125 Amino Terminal Sequence
(SEQ ID NO: 1)

```
20701 ACCTCAGCAG GGACTCCATC AGTGGTGACT GAGGGGTTTG CCCACTCAAA
20751 AATAACCACT GCAATGAACA ATGATGTCAA GGACGTGTCA CAGACAAACC
20801 CTCCCTTTCA GGATGAAGCC AGCTCTCCCT CTTCTCAAGC ACCTGTCCTT
20851 GTCACAACCT TACCTTCTTC TGTTGCTTTC ACACCGCAAT GGCACAGTAC
20901 CTCCTCTCCT GTTTCTATGT CCTCAGTTCT TACTTCTTCA CTGGTAAAGA
20951 CCGCAGGCAA GGTGGATACA AGCTTAGAAA CAGTGACCAG TTCACCTCAA
21051 AGATATAGAG ACAACGCATC CTTCCATAAA CACAGTAGTT ACCAATGTGG
21101 GGACCACCGG TTCAGCATTT GAATCACATT CTACTGTCTC AGCTTACCCA
21151 GAGCCATCTA AAGTCACATC TCCAAATGTT ACCACCTCCA CCATGGAAGA
21201 CACCACAATT TCCAGATCAA TACCTAAATC CTCTAAGACT ACAAGAACTG
21251 AGACTGAGAC AACTTCCTCC CTGACTCCTA AACTGAGGGA GACCAGCGTC
21301 TCCCAGGAGA TCACCTCGTC CACAGAGACA AGCACTGTTC CTTACAAAGA
21351 GCTCACTGGT GCCACTACCG AGGTATCCAG GACAGATGTC ACTTCCTCTA
21401 GCAGTACATC CTTCCCTGGC CCTGATCAGT CCACAGTGTC ACTAGACATC
21451 TCCACAGAAA CCAACACCAG GCTGTCTACC TCCCAATAA TGACAGAATC
21501 TGCAGAAATA ACCATCACCA CCCAAACAGG TCCTCATGGG GCTACATCAC
21551 AGGATACTTT TACCATGGAC CCATCAAATA CAACCCCCCA GGCAGGGATC
21601 CACTCAGCTA TGACTCATGG ATTTTCACAA TTGGATGTGA CCACTCTTAT
21651 GAGCAGAATT CCACAGGATG TATCATGGAC AAGTCCTCCC TCTGTGGATA
21701 AAACCAGCTC CCCCTCTTCC TTTCTGCCCT CACCTGCAAT GACCACACCT
21751 TCCCTGATTT CTTCTACCTT ACCAGAGGAT AAGCTCTCCT CTCCTATGAC
21801 TTCACTTCTC ACCTCTGGCC TAGTGAAGAT TACAGACATA TTACGTACAC
21851 GCTTGGAACC TGTGACCAGC TCACTTCCAA ATTTCAGCAG CACCTCAGAT
21901 AAGATACTGG CCACTTCTAA AGACAGTAAA GACACAAAGG AAATTTTTCC
21951 TTCTATAAAC ACAGAAGAGA CCAATGTGAA AGCCAACAAC TCTGGACATG
22001 AATCCCATTC CCCTGCACTG GCTGACTCAG AGACACCCAA AGCCACAACT
22051 CAAATGGTTA TCACCACCAC TGTGGGAGAT CCAGCTCCTT CCACATCAAT
22101 GCCAGTGCAT GGTTCCTCTG AGACTACAAA CATTAAGAGA GAGCCAACAT
22151 ATTTCTTGAC TCCTAGACTG AGAGAGACCA GTACCTCTCA GGAGTCCAGC
22201 TTTCCCACGG ACACAAGTTT TCTACTTTCC AAAGTCCCCA CTGGTACTAT
22251 TACTGAGGTC TCCAGTACAG GGTCATCTC TTCTAGCAAA ATTTCCACCC
22301 CAGACCATGA TAAGTCCACA GTGCCACCTG ACACCTTCAC AGGAGAGATC
22351 CCCAGGGTCT TCACCTCCTC TATTAAGACA AAATCTGCAG AAATGACGAT
22401 CACCACCCAA GCAAGTCCTC CTGAGTCTGC ATCGCACAGT ACCCTTCCCT
22451 TGGACACATC AACCACACTT TCCCAGGGAG GGACTCATTC AACTGTGACT
22501 CAGGGATTCC CATACTCAGA GGTGACCACT CTCATGGGCA TGGGTCCTGG
22551 GAATGTGTCA TGGATGACAA CTCCCCCTGT GGAAGAAACC AGCTCTGTGT
22601 CTTCCCTGAT GTCTTCACCT GCCATGACAT CCCCTTCTCC TGTTTCCTCC
22651 ACATCACCAC AGAGCATCCC CTCCTCTCCT CTTCCTGTGA CTGCACTTCC
```

TABLE 1-continued

Genomic CA125 Amino Terminal Sequence
(SEQ ID NO: 1)

```
22701 TACTTCTGTT CTGGTGACAA CCACAGATGT GTTGGGCACA ACAAGCCCAG
22751 AGTCTGTAAC CAGTTCACCT CCAAATTTGA GCAGCATCAC TCATGAGAGA
22801 CCGGCCACTT ACAAAGACAC TGCACACACA GAAGCCGCCA TGCATCATTC
22851 CACAAACACC GCAGTGACCA ATGTAGGGAC TTCCGGGTCT GGACATAAAT
22901 CACAATCCTC TGTCCTAGCT GACTCAGAGA CATCGAAAGC CACACCTCTG
22951 ATGAGTACCA CCTCCACCCT GGGGGACACA AGTGTTTCCA CATCAACTCC
23001 TAATATCTCT CAGACTAACC AAATTCAAAC AGAGCCAACA GCATCCCTGA
23051 GCCCTAGACT GAGGGAGAGC AGCACGTCTG AGAAGACCAG CTCAACAACA
23101 GAGACAAATA CTGCCTTTTC TTATGTGCCC ACAGGTGCTA TTACTCAGGC
23151 CTCCAGAACA GAAATCTCCT CTAGCAGAAC ATCCATCTCA GACCTTGATC
23201 GGTCCACAAT AGCACCCGAC ATCTCCACAG GAATGATCAC CAGGCTCTTC
23251 ACCTCCCCCA TCATGACAAA ATCTGCAGAA ATGACCGTCA CCACTCAAAC
23301 AACTACTCCT GGGGCTACAT CACAGGGTAT CCTTCCCTGG GACACATCAA
23351 CCACACTTTT CCAGGGAGGG ACTCATTCAA CCGTGTCTCA GGGATTCCCA
23401 CACTCAGAGA TAACCACTCT TCGGAGCAGA ACCCCTGGAG ATGTGTCATG
23451 GATGACAACT CCCCCTGTGG AAGAAACCAG CTCTGGGTTT TCCCTGATGT
23501 CACCTTCCAT GACATCCCCT TCTCCTGTTT CCTCCACATC ACCAGAGAGC
23551 ATCCCCTCCT CTCCTCTCCC TGTGACTGCA CTTCTTACTT CTGTTCTGGT
23601 GACAACCACA AATGTATTGG GCACAACAAG CCCAGAGCCC GTAACGAGTT
23651 CACCTCCAAA TTTAAGCAGC CCCACACAGG AGAGACTGAC CACTTACAAA
23701 GACACTGCGC ACACAGAAGC CATGCATGCT TCCATGCATA CAAACACTGC
23751 AGTGGCCAAC GTGGGGACCT CCATTTCTGG ACATGAATCA CAATCTTCTG
23801 TCCCAGCTGA TTCAGACACA TCCAAAGCCA CATCTCCAAT GGGTACCACC
23851 TTCGCCATGG GGGATACAAG TGTTTCTACA TCAACTCCTG CCTTCTTTGA
23901 GACTAGAATT CAGACTGAAT CAACATCCTC TTTGATTCCT GGATTAAGGG
23951 ACACCAGGAC GTCTGAGGAG ATCAACACTG TGACAGAGAC CAGCACTGTC
24001 CTTTCAGAAG TGCCCACTAC TACTACTACT GAGGTCTCCA GGACAGAAGT
24051 TATCACTTCC AGCAGAACAA CCATCTCAGG GCCTGATCAT TCCAAAATGT
24101 CACCCTACAT CTCCACAGAA ACCATCACCA GGCTCTCCAC TTTTCCTTTT
24151 GTAACAGGAT CCACAGAAAT GGCCATCACC AACCAAACAG GTCCTATAGG
24201 GACTATCTCA CAGGCTACCC TTACCCTGGA CACATCAAGC ACAGCTTCCT
24251 GGGAAGGGAC TCACTCACCT GTGACTCAGA GATTCCACA CTCAGAGGAG
24301 ACCACTACTA TGAGCAGAAG TACTAAGGGC GTGTCATGGC AAAGCCCTCC
24351 CTCTGTGGAA GAAACCAGTT CTCCTTCTTC CCCAGTGCCT TTACCTGCAA
24401 TAACCTCACA TTCATCTCTT TATTCCGCAG TATCAGGAAG TAGCCCCACT
24451 TCTGCTCTCC CTGTGACTTC CCTTCTCACC TCTGGCAGGA GGAAGACCAT
24501 AGACATGTTG GACACACACT CAGAACTTGT GACCAGCTCC TTACCAAGTG
24551 CAAGTAGCTT CTCAGGTGAG ATACTCACTT CTGAAGCCTC CACAAATACA
```

TABLE 1-continued

Genomic CA125 Amino Terminal Sequence
(SEQ ID NO: 1)

```
24601 GAGACAATTC ACTTTTCAGA GAACACAGCA GAAACCAATA TGGGGACCAC
24651 CAATTCTATG CATAAACTAC ATTCCTCTGT CTCAATCCAC TCCCAGCCAT
24701 CCGGACACAC ACCTCCAAAG GTTACTGGAT CTATGATGGA GGACGCTATT
24751 GTTTCCACAT CAACACCTGG TTCTCCTGAG ACTAAAAATG TTGACAGAGA
24801 CTCAACATCC CCTCTGACTC CTGAACTGAA AGAGGACAGC ACCGCCCTGG
24851 TGATGAACTC AACTACAGAG TCAAACACTG TTTTCTCCAG TGTGTCCCTG
24901 GATGCTGCTA CTGAGGTCTC CAGGGCAGAA GTCACCTACT ATGATCCTAC
24951 ATTCATGCCA GCTTCTGCTC AGTCAACAAA GTCCCCAGAC ATTTCACCTG
25001 AAGCCAGCAG CAGTCATTCT AACTCTCCTC CCTTGACAAT ATCTACACAC
25051 AAGACCATCG CCACACAAAC AGGTCCTTCT GGGGTGACAT CTCTTGGCCA
25101 ACTGACCCTG GACACATCAA CCATAGCCAC CTCAGCAGGA ACTCCATCAG
25151 CCAGAACTCA GGATTTTGTA GATTCAGAAA CAACCAGTGT CATGAACAAT
25201 GATCTCAATG ATGTGTTGAA GACAAGCCCT TTCTCTGCAG AAGAAGCCAA
25251 CTCTCTCTCT TCTCAGGCAC CTCTCCTTGT GACAACCTCA CCTTCTCCTG
25301 TAACTTCCAC ATTGCAAGAG CACAGTACCT CCTCTCTTGT TTCTGTGACC
25351 TCAGTACCCA CCCCTACACT GGCGAAGATC ACAGACATGG ACACAAACTT
25401 AGAACCTGTG ACTCGTTCAC CTCAAAATTT AAGGAACACC TTGGCCACTT
25451 CAGAAGCCAC CACAGATACA CACACAATGC ATCCTTCTAT AAACACAGCA
25501 GTGGCCAATG TGGGACCCAC CAGTTCACCA AATGAATTCT ATTTTACTGT
25551 CTCACCTGAC TCAGACCCAT ATAAAGCCAC ATCCGCAGTA GTTATCACTT
25601 CCACCTCGGG GGACTCAATA GTTTCCACAT CAATGCCTAG ATCCTCTGCG
25651 ATGAAAAAGA TTGAGTCTGA GACAACTTTC TCCCTGATAT TTAGACTGAG
25701 GGAGACTAGC ACCTCCCAGA AAATTGGCTC ATCCTCAGAC ACAAGCACGG
25751 TCTTTGACAA AGCATTCACT GCTGCTACTA CTGAGGTCTC CAGAACAGAA
25801 CTCACCTCCT CTAGCAGAAC ATCCATCCAA GGCACTGAAA AGCCCACAAT
25851 GTCACCGGAC ACCTCCACAA GATCTGTCAC CATGCTTTCT ACTTTTGCTG
25901 GCCTGACAAA ATCCGAAGAA AGGACCATTG CCACCCAAAC AGGTCCTCAT
25951 AGGGCGACAT CACAGGGTAC CCTTACCTGG GACACATCAA TCACAACCTC
26001 ACAGGCAGGG ACCCACTCAG CTATGACTCA TGGATTTTCA CAATTAGATT
26051 TGTCCACTCT TACGAGTAGA GTTCCTGAGT ACATATCAGG GACAAGCCCA
26101 CCCTCTGTGG AAAAAACCAG CTCTTCCTCT TCCCTTCTGT CTTTACCAGC
26151 AATAACCTCA CCGTCCCCTG TACCTACTAC ATTACCAGAA AGTAGGCCGT
26201 CTTCTCCTGT TCATCTGACT TCACTCCCCA CCTCTGGCCT AGTGAAGACC
26251 ACAGATATGC TGGCATCTGT GGCCAGTTTA CCTCCAAACT TGGGCAGCAC
26301 CTCACATAAG ATACCGACTA CTTCAGAAGA CATTAAAGAT ACAGAGAAAA
26351 TGTATCCTTC CACAAACATA GCAGTAACCA ATGTGGGGAC CACCACTTCT
26401 GAAAAGGAAT CTTATTCGTC TGTCCCAGCC TACTCAGAAC CACCCAAAGT
26451 CACCTCTCCA ATGGTTACCT CTTTCAACAT AAGGGACACC ATTGTTTCCA
26501 CATCCATGCC TGGCTCCTCT GAGATTACAA GGATTGAGAT GGAGTCAACA
```

TABLE 1-continued

Genomic CA125 Amino Terminal Sequence
(SEQ ID NO: 1)

```
26551 TTCTCCCTGG CTCATGGGCT GAAGGGAACC AGCACCTCCC AGGACCCCAT
26601 CGTATCCACA GAGAAAAGTG CTGTCCTTCA CAAGTTGACC ACTGGTGCTA
26651 CTGAGACCTC TAGGACAGAA GTTGCCTCTT CTAGAAGAAC ATCCATTCCA
26701 GGCCCTGATC ATTCCACAGA GTCACCAGAC ATCTCCACTG AAGTGATCCC
26751 CAGCCTGCCT ATCTCCCTTG GCATTACAGA ATCTTCAAAT ATGACCATCA
26801 TCACTCGAAC AGGTCCTCCT CTTGGCTCTA CATCACAGGG CACATTTACC
26851 TTGGACACAC CAACTACATC CTCCAGGGCA GGAACACACT CGATGGCGAC
26901 TCAGGAATTT CCACACTCAG AAATGACCAC TGTCATGAAC AAGGACCCTG
26951 AGATTCTATC ATGGACAATC CCTCCTTCTA TAGAGAAAAC CAGCTTCTCC
27001 TCTTCCCTGA TGCCTTCACC AGCCATGACT TCACCTCCTG TTTCCTCAAC
27051 ATTACCAAAG ACCATTCACA CCACTCCTTC TCCTATGACC TCACTGCTCA
27101 CCCCTAGCCT AGTGATGACC ACAGACACAT TGGGCACAAG CCCAGAACCT
27151 ACAACCAGTT CACCTCCAAA TTTGAGCAGT ACCTCACATG AGATACTGAC
27201 AACAGATGAA GACACCACAG CTATAGAAGC CATGCATCCT TCCACAAGCA
27251 CAGCAGCGAC TAATGTGGAA ACCACCAGTT CTGGACATGG GTCACAATCC
27301 TCTGTCCTAG CTGACTCAGA AAAAACCAAG GCCACAGCTC AATGGATAC
27351 CACCTCCACC ATGGGGCATA CAACTGTTTC CACATCAATG TCTGTTTCCT
27401 CTGAGACTAC AAAAATTAAG AGAGAGTCAA CATATTCCTT GACTCCTGGA
27451 CTGAGAGAGA CCAGCATTTC CCAAAATGCC AGCTTTTCCA CTGACACAAG
27501 TATTGTTCTT TCAGAAGTCC CCACTGGTAC TACTGCTGAG GTCTCCAGGA
27551 CAGAAGTCAC CTCCTCTGGT AGAACATCCA TCCCTGGCCC TTCTCAGTCC
27601 ACAGTTTTGC CAGAAATATC CACAAGAACA ATGACAAGGC TCTTTGCCTC
27651 GCCCACCATG ACAGAATCAG CAGAAATGAC CATCCCCACT CAAACAGGTC
27701 CTTCTGGGTC TACCTCACAG GATACCCTTA CCTTGGACAC ATCCACCACA
27751 AAGTCCCAGG CAAAGACTCA TTCAACTTTG ACTCAGAGAT TTCCACACTC
27801 AGAGATGACC ACTCTCATGA GCAGAGGTCC TGGAGATATG TCATGGCAAA
27851 GCTCTCCCTC TCTGGAAAAT CCCAGCTCTC TCCCTTCCCT GCTGTCTTTA
27901 CCTGCCACAA CCTCACCTCC TCCCATTTCC TCCACATTAC CAGTGACTAT
27951 CTCCTCCTCT CCTCTTCCTG TGACTTCACT TCTCACCTCT AGCCCGGTAA
28001 CGACCACAGA CATGTTACAC ACAAGCCCAG AACTTGTAAC CAGTTCACCT
28051 CCAAAGCTGA GCCACACTTC AGATGAGAGA CTGACCACTG GCAAGGACAC
28101 CACAAATACA GAAGCTGTGC ATCCTTCCAC AAACACAGCA GCGTCCAATG
28151 TGGAGATTCC CAGCTCTGGA CATGAATCCC CTTCCTCTGC CTTAGCTGAC
28201 TCAGAGACAT CCAAAGCCAC ATCACCAATG TTTATTACCT CCACCCAGGA
28251 GGATACAACT GTTGCCATAT CAACCCCTCA CTTCTTGGAG ACTAGCAGAA
28301 TTCAGAAAGA GTCAATTTCC TCCCTGAGCC CTAAATTGAG GGAGACAGGC
28351 AGTTCTGTGG AGACAAGCTC AGCCATAGAG ACAAGTCTG TCCTTTCTGA
28401 AGTGTCCGTT GGTGCTACTA CTGAGATCTC CAGGACAGAA GTCACCTCCT
```

TABLE 1-continued

Genomic CA125 Amino Terminal Sequence
(SEQ ID NO: 1)

```
28451 CTAGCAGAAC ATCCATCTCT GGTTCTGCTG AGTCCACAAT GTTGCCAGAA
28501 ATATCCACCA CAAGAAAAAT CATTAAGTTC CCTACTTCCC CCATCCTGGC
28551 AGAATCATCA GAAATGACCA TCAAGACCCA AACAAGTCCT CCTGGGTCTA
28601 CATCAGAGAG TACCTTTACA TTAGACACAT CAACCACTCC CTCCTTGGTA
28651 ATAACCCATT CGACTATGAC TCAGAGATTG CCACACTCAG AGATAACCAC
28701 TCTTGTGAGT AGAGGTGCTG GGGATGTGCC ACGGCCCAGC TCTCTCCCTG
28751 TGGAAGAAAC AAGCCCTCCA TCTTCCCAGC TGTCTTTATC TGCCATGATC
28801 TCACCTTCTC CTGTTTCTTC CACATTACCA GCAAGTAGCC ACTCCTCTTC
28851 TGCTTCTGTG ACTTCACTTC TCACACCAGG CCAAGTGAAG ACTACTGAGG
28901 TGTTGGACGC AAGTGCAGAA CCTGAAACCA GTTCACCTCC AAGTTTGAGC
28951 AGCACCTCAG TTGAAATACT GGCCACCTCT GAAGTCACCA CAGATACGGA
29001 GAAAATTCAT CCTTTCTCAA ACACGGCAGT AACCAAAGTT GGAACTTCCA
29051 GTTCTGGACA TGAATCCCCT TCCTCTGTCC TACCTGACTC AGAGACAACC
29101 AAAGCCACAT CGGCAATGGG TACCATCTCC ATTATGGGGG ATACAAGTGT
29151 TTCTACATTA ACTCCTGCCT TATCTAACAC TAGGAAAATT CAGTCAGAGC
29201 CAGCTTCCTC ACTGACCACC AGATTGAGGG AGACCAGCAC CTCTGAAGAG
29251 ACCAGCTTAG CCACAGAAGC AAACACTGTT CTTTCTAAAG TGTCCACTGG
29301 TGCTACTACT GAGGTCTCCA GGACAGAAGC CATCTCCTTT AGCAGAACAT
29351 CCATGTCAGG CCCTGAGCAG TCCACAATGT CACAAGACAT CTCCATAGGA
29401 ACCATCCCCA GGATTTCTGC CTCCTCTGTC CTGACAGAAT CTGCAAAAAT
29451 GACCATCACA ACCCAAACAG TCCTTCGGA GTCTACACTA GAAAGTACCC
29501 TTAATTTGAA CACAGCAACC ACACCCTCTT GGGTGGAAAC CCACTCTATA
29551 GTAATTCAGG GATTTCCACA CCCAGAGATG ACCACTTCCA TGGGCAGAGG
29601 TCCTGGAGGT GTGTCATGGC CTAGCCCTCC CTTTGTGAAA GAAACCAGCC
29651 CTCCATCCTC CCCGCTGTCT TTACCTGCCG TGACCTCACC TCATCCTGTT
29701 TCCACCACAT TCCTAGCACA TATCCCCCCC TCTCCCCTTC CTGTGACTTC
29751 ACTTCTCACC TCTGGCCCGG CGACAACCAC AGATATCTTG GGTACAAGCA
29801 CAGAACCTGG AACCAGTTCA TCTTCAAGTT TGAGCACCAC CTCCCATGAG
29851 AGACTGACCA CTTACAAAGA CACTGCACAT ACAGAAGCCG TGCATCCTTC
29901 CACAAACACA GGAGGGACCA ATGTGGCAAC CACCAGCTCT GGATATAAAT
29951 CACAGTCCTC TGTCCTAGCT GACTCATCTC CAATGTGTAC CACCTCCACC
30001 ATGGGGGATA CAAGTGTTCT CACATCAACT CCTGCCTTCC TTGAGACTAG
30051 GAGGATTCAG ACAGAGCTAG CTTCCTCCCT GACCCCTGGA TTGAGGGAGT
30101 CCAGTGGCTC TGAAGGGACC AGCTCAGGCA CCAAGATGAG CACTGTCCTC
30151 TCTAAAGTGC CCACTGGTGC TACTACTGAG ATCTCCAAGG AAGACGTCAC
30201 CTCCATCCCA GGTCCCGCTC AATCCACAAT ATCACCAGAC ATCTCCACAA
30251 GAACCGTCAG CTGGTTCTCT ACATCCCCTG TCATGACAGA ATCAGCAGAA
30301 ATAACCATGA ACACCCATAC AAGTCCTTTA GGGGCCACAA CACAAGGCAC
30351 CAGTACTTTG GCCACGTCAA GCACAACCTC TTTGACAATG ACACACTCAA
```

TABLE 1-continued

Genomic CA125 Amino Terminal Sequence
(SEQ ID NO: 1)

```
30401 CTATATCTCA AGGATTTTCA CACTCACAGA TGAGCACTCT TATGAGGAGG
30451 GGTCCTGAGG ATGTATCATG GATGAGCCCT CCCCTTCTGG AAAAAACTAG
30501 ACCTTCCTTT TCTCTGATGT CTTCACCAGC CACAACTTCA CCTTCTCCTG
30551 TTTCCTCCAC ATTACCAGAG AGCATCTCTT CCTCTCCTCT TCCTGTGACT
30601 TCACTCCTCA CGTCTGGCTT GGCAAAAACT ACAGATATGT TGCACAAAAG
30651 CTCAGAACCT GTAACCAACT CACCTGCAAA TTTGAGCAGC ACCTCAGTTG
30701 AAATACTGGC CACCTCTGAA GTCACCACAG ATACAGAGAA AACTCATCCT
30751 TCTTCAAACA GAACAGTGAC CGATGTGGGG ACCTCCAGTT CTGGACATGA
30801 ATCCACTTCC TTTGTCCTAG CTGACTCACA GACATCCAAA GTCACATCTC
30851 CAATGGTTAT TACCTCCACC ATGGAGGATA CGAGTGTCTC CACATCAACT
30901 CCTGGCTTTT TTGAGACTAG CAGAATTCAG ACAGAACCAA CATCCTCCCT
30951 GACCCTTGGA CTGAGAAAGA CCAGCAGCTC TGAGGGGACC AGCTTAGCCA
31001 CAGAGATGAG CACTGTCCTT TCTGGAGTGC CCACTGGTGC CACTGCTGAA
31051 GTCTCCAGGA CAGAAGTCAC CTCCTCTAGC AGAACATCCA TCTCAGGCTT
31101 TGCTCAGCTC ACAGTGTCAC CAGAGACTTC CACAGAAACC ATCACCAGAC
31151 TCCCTACCTC CAGCATAATG ACAGAATCAG CAGAAATGAT GATCAAGACA
31201 CAAACAGATC CTCCTGGGTC TACACCAGAG AGTACTCATA CTGTGGACAT
31251 ATCAACAACA CCCAACTGGG TAGAAACCCA CTCGACTGTG ACTCAGAGAT
31301 TTTCACACTC AGAGATGACC ACTCTTGTGA GCAGAAGCCC TGGTGATATG
31351 TTATGGCCTA GTCAATCCTC TGTGGAAGAA ACCAGCTCTG CCTCTTCCCT
31401 GCTGTCTCTG CCTGCCACGA CCTCACCTTC TCCTGTTTCC TCTACATTAG
31451 TAGAGGATTT CCCTTCCGCT TCTCTTCCTG TGACTTCTCT TCTCACCCCT
31501 GGCCTGGTGA TAACCACAGA CAGGATGGGC ATAAGCAGAG AACCTGGAAC
31551 CAGTTCCACT TCAAATTTGA GCAGCACCTC CCATGAGAGA CTGACCACTT
31601 TGGAAGACAC TGTAGATACA GAAGACATGC AGCCTTCCAC ACACACAGCA
31651 GTGACCAACG TGAGGACCTC CATTTCTGGA CATGAATCAC AATCTTCTGT
31701 CCTATCTGAC TCAGAGACAC CCAAAGCCAC ATCTCCAATG GGTACCACCT
31751 ACACCATGGG GGAAACGAGT GTTTCCATAT CCACTTCTGA CTTCTTTGAG
31801 ACCAGCAGAA TTCAGATAGA ACCAACATCC TCCCTGACTT CTGGATTGAG
31851 GGAGACCAGC AGCTCTGAGA GGATCAGCTC AGCCACAGAG GGAAGCACTG
31901 TCCTTTCTGA AGTGCCCAGT GGTGCTACCA CTGAGGTCTC CAGGACAGAA
31951 GTGATATCCT CTAGGGGAAC ATCCATGTCA GGGCCTGATC AGTTCACCAT
32001 ATCACCAGAC ATCTCTACTG AAGCGATCAC CAGGCTTTCT ACTTCCCCCA
32051 TTATGACAGA ATCAGCAGAA AGTGCCATCA CTATTGAGAC AGGTTCTCCT
32101 GGGGCTACAT CAGAGGGTAC CCTCACCTTG GACACCTCAA CAACAACCTT
32151 TTGGTCAGGG ACCCACTCAA CTGCATCTCC AGGATTTTCA CACTCAGAGA
32201 TGACCACTCT TATGAGTAGA ACTCCTGGAG ATGTGCCATG GCCGAGCCTT
32251 CCCTCTGTGG AAGAAGCCAG CTCTGTCTCT TCCTCACTGT CTTCACCTGC
```

TABLE 1-continued

Genomic CA125 Amino Terminal Sequence
(SEQ ID NO: 1)

```
32301 CATGACCTCA ACTTCTTTTT TCTCCACATT ACCAGAGAGC ATCTCCTCCT

32351 CTCCTCATCC TGTGACTGCA CTTCTCACCC TTGGCCCAGT GAAGACCACA

32401 GACATGTTGC GCACAAGCTC AGAACCTGAA ACCAGTTCAC CTCCAAATTT

32451 GAGCAGCACC TCAGCTGAAA TATTAGCCAC GTCTGAAGTC ACCAAAGATA

32501 GAGAGAAAAT TCATCCCTCC TCAAACACAC CTGTAGTCAA TGTAGGGACT

32551 GTGATTTATA AACATCTATC CCCTTCCTCT GTTTTGGCTG ACTTAGTGAC

32601 AACAAAACCC ACATCTCCAA TGGCTACCAC CTCCACTCTG GGAATACAA

32651 GTGTTTCCAC ATCAACTCCT GCCTTCCCAG AAACTATGAT GACACAGCCA

32701 ACTTCCTCCC TGACTTCTGG ATTAAGGGAG ATCAGTACCT CTCAAGAGAC

32751 CAGCTCAGCA ACAGAGAGAA GTGCTTCTCT TTCTGGAATG CCCACTGGTG

32801 CTACTACTAA GGTCTCCAGA ACAGAAGCCC TCTCCTTAGG CAGAACATCC

32851 ACCCCAGGTC CTGCTCAATC CACAATATCA CCAGAAATCT CCACGGAAAC

32901 CATCACTAGA ATTTCTACTC CCCTCACCAC GACAGGATCA GCAGAAATGA

32951 CCATCACCCC CAAAACAGGT CATTCTGGGG CATCCTCACA AGGTACCTTT

33001 ACCTTGGACA CATCAAGCAG AGCCTCCTGG CCAGGAACTC ACTCAGCTGC

33051 AACTCACAGA TCTCCACACT CAGGGATGAC CACTCCTATG AGCAGAGGTC

33101 CTGAGGATGT GTCATGGCCA AGCCGCCCAT CAGTGGAAAA AACTAGCCCT

33151 CCATCTTCCC TGGTGTCTTT ATCTGCAGTA ACCTCACCTT CGCCACTTTA

33201 TTCCACACCA TCTGAGAGTA GCCACTCATC TCCTCTCCGG GTGACTTCTC

33251 TTTTCACCCC TGTCATGATG AAGACCACAG ACATGTTGGA CACAAGCTTG

33301 GAACCTGTGA CCACTTCACC TCCCAGTATG AATATCACCT CAGATGAGAG

33351 TCTGGCCACT TCTAAAGCCA CCATGGAGAC AGAGGCAATT CAGCTTTCAG

33401 AAAACACAGC TGTGACTCAG ATGGGCACCA TCAGCGCTAG ACAAGAATTC

33451 TATTCCTCTT ATCCAGGCCT CCCAGAGCCA TCCAAAGTGA CATCTCCAGT

33501 GGTCACCTCT TCCACCATAA AAGACATTGT TTCTACAACC ATACCTGCTT

33551 CCTCTGAGAT AACAAGAATT GAGATGGAGT CAACATCCAC CCTGACCCCC

33601 ACACCAAGGG AGACCAGCAC CTCCCAGGAG ATCCACTCAG CCACAAAGCC

33651 AAGCACTGTT CCTTACAAGG CACTCACTAG TGCCACGATT GAGGACTCCA

33701 TGACACAAGT CATGTCCTCT AGCAGAGGAC CTAGCCCTGA TCAGTCCACA

33751 ATGTCACAAG ACATATCCAG TGAAGTGATC ACCAGGCTCT CTACCTCCCC

33801 CATCAAGGCA GAATCTACAG AAATGACCAT TACCACCCAA ACAGGTTCTC

33851 CTGGGGCTAC ATCAAGGGGT ACCCTTACCT TGGACACTTC AACAACTTTT

33901 ATGTCAGGGA CCCACTCAAC TGCATCTCAA GGATTTTCAC ACTCACAGAT

33951 GACCGCTCTT ATGAGTAGAA CTCCTGGAGA TGTGCCATGG CTAAGCCATC

34001 CCTCTGTGGA AGAAGCCAGC TCTGCCTCTT TCTCACTGTC TTCACCTGTC

34051 ATGACCTCAT CTTCTCCCGT TTCTTCCACA TTACCAGACA GCATCCACTC

34101 TTCTTCGCTT CCTGTGACAT CACTTCTCAC CTCAGGGCTG GTGAAGACCA

34151 CAGAGCTGTT GGGCACAAGC TCAGAACCTG AAACCAGTTC ACCCCCAAAT

34201 TTGAGCAGCA CCTCAGCTGA AATACTGGCC ACCACTGAAG TCACTACAGA
```

TABLE 1-continued

Genomic CA125 Amino Terminal Sequence
(SEQ ID NO: 1)

34251 TACAGAGAAA CTGGAGATGA CCAATGTGGT AACCTCAGGT TATACACATG

34301 AATCTCCTTC CTCTGTCCTA GCTGACTCAG TGACAACAAA GGCCACATCT

34351 TCAATGGGTA TCACCTACCC CACAGGAGAT ACAAATGTTC TCACATCAAC

34401 CCCTGCCTTC TCTGACACCN NNNNNNNNNN NNNNNNNNNN NNNNNNNNNN

34451 NNNNNNNNNN NNNNNNNNNN NNNNNNNNNN NNNNNNNNNN NNNNNNNNNN

34501 NNNNNNNNNN NNNNNNNNNN NNNNNNNNNN NNNNCGGAAA CCAAGTTTCT

Exon 4

34551 AACCAACCCC TCCTTTTTGA CCCCAGTAGG ATTCAAACAA AGTCAAAGCT

34601 CTCACTGACT CCTGGGTTGA TGGAGACCAG CATCTCTGAA GAGACCAGCT

34651 CTGCCACAGA AAAAGCACT GTCCTTTCTA GTGTGCCCAC TGGTGCTACT

34701 ACTGAGGTCT CCAGGACAGA AGCCATCTCT TCTAGCAGAA CATCCATCCC

34751 AGGCCCTGCT CAATCCACAA TGTCATCAGA CACCTCCATG GAAACCATCA

34801 CTAGAATTTC TACCCCCCTC ACAAGGAAAG AATCAACAGA CATGGCCATC

34851 ACCCCCAAAA CAGGTCCTTC TGGGGCTACC TCGCAGGGTA CCTTTACCTT

34901 GGACTCATCA AGCACAGCCT CCTGGCCAGG AACTCACTCA GCTACAACTC

34951 AGAGATTTCC ACAGTCAGTG GTGACAACTC CTATGAGCAG AGGTCCTGAG

35001 GATGTGTCAT GGCCAAGCCC GCTGTCTGTG GAAAAAAACA GCCCTCCATC

35051 TTCCCTGGTA TCTTCATCTT CAGTAACCTC ACCTTCGCCA CTTTATTCCA

35101 CACCATCTGG GAGTAGCCAC TCCTCTCCTG TCCCTGTCAC TTCTCTTTTC

35151 ACCTCTATCA TGATGAAGGC CACAGACATG TTGGATGCAA GTTTGGAACC

35201 TGAGACCACT TCAGCTCCCA ATATGAATAT CACCTCAGAT GAGAGTCTGG

35251 CCACTTCTAA AGCCACCACG GAGACAGAGG CAATTCACGT TTTTGAAAAT

35301 ACAGCAGCGT CCCATGTGGA AACCACCAGT GCTACAGAGG AACTCTATTC

35351 CTCTTCCCCA GGCTTCTCAG AGCCAACAAA AGTGATATCT CCAGTGGTCA

35401 CCTCTTCCTC TATAAGAGAC AACATGGTTT CCACAACAAT GCCTGGCTCC

35451 TCTGGCATTA CAAGGATTGA GATAGAGTCA ATGTCATCTC TGACCCCTGG

35501 ACTGAGGGAG ACCAGAACCT CCCAGGACAT CACCTCATCC ACAGAGACAA

35551 GCACTGTCCT TTACAAGATG TCCTCTGGTG CCACTCCTGA GGTCTCCAGG

35601 ACAGAAGTTA TGCCCTCTAG CAGAACATCC ATTCCTGGCC CTGCTCAGTC

35651 CACAATGTCA CTAGACATCT CCGATGAAGT TGTCACCAGG CTGTCTACCT

35701 CTCCCATCAT GACAGAATCT GCAGAAATAA CCATCACCAC CCAAACAGGT

35751 TATTCTCTGG CTACATCCCA GGTTACCCTT CCCTTGGGCA CCTCAATGAC

35801 CTTTTTGTCA GGGACCCACT CAACTATGTC TCAAGGACTT TCACACTCAG

35851 AGATGACCAA TCTTATGAGC AGGGGTCCTG AAAGTCTGTC ATGGACGAGC

35901 CCTCGCTTTG TGGAAACAAC TAGATCTTCC TCTTCTCTGA CATCATTACC

35951 TCTCACGACC TCACTTTCTC CTGTGTCCTC CACATTACTA GACAGTAGCC

36001 CCTCCTCTCC TCTTCCTGTG ACTTCACTTA TCCTCCCAGG CCTGGTGAAG

36051 ACTACAGAAG TGTTGGATAC AAGCTCAGAG CCTAAAACCA GTTCATCTCC

TABLE 1-continued

Genomic CA125 Amino Terminal Sequence
(SEQ ID NO: 1)

```
36101 AAATTTGAGC AGCACCTCAG TTGAAATACC GGCCACCTCT GAAATCATGA
36151 CAGATACAGA GAAAATTCAT CCTTCCTCAA ACACAGCGGT GGCCAAAGTG
36201 AGGACCTCCA GTTCTGTTCA TGAATCTCAT TCCTCTGTCC TAGCTGACTC
36251 AGAAACAACC ATAACCATAC CTTCAATGGG TATCACCTCC GCTGTGGACG
36301 ATACCACTGT TTTCACATCA AATCCTGCCT TCTCTGAGAC TAGGAGGATT
36351 CCGACAGAGC CAACATTCTC ATTGACTCCT GGATTCAGGG AGACTAGCAC
36401 CTCTGAAGAG ACCACCTCAA TCACAGAAAC AAGTGCAGTC CTTTATGGAG
36451 TGCCCACTAG TGCTACTACT GAAGTCTCCA TGACAGAAAT CATGTCCTCT
36501 AATAGAACAC ACATCCCTGA CTCTGATCAG TCCACGATGT CTCCAGACAT
36551 CATCACTGAA GTGATCACCA GGCTCTCTTC CTCATCCATG ATGTCAGAAT
36601 CAACACAAAT GACCATCACC ACCCAAAAAA GTTCTCCTGG GGCTACAGCA
36651 CAGAGTACTC TTACCTTGGC CACAACAACA GCCCCCTTGG CAAGGACCCA
36701 CTCAACTGTT CCTCCTAGAT TTTTACACTC AGAGATGACA ACTCTTATGA
36751 GTAGGAGTCC TGAAAATCCA TCATGGAAGA GCTCTCCCTT TGTGGAAAAA
36801 ACTAGCTCTT CATCTTCTCT GTTGTCCTTA CCTGTCACGA CCTCACCTTC
36851 TGTTTCTTCC ACATTACCGC AGAGTATCCC TTCCTCCTCT TTTTCTGTGA
36901 CTTCACTCCT CACCCCAGGC ATGGTGAAGA CTACAGACAC AAGCACAGAA
36951 CCTGGAACCA GTTTATCTCC AAATCTGAGT GGCACCTCAG TTGAAATACT
37001 GGCTGCCTCT GAAGTCACCA CAGATACAGA GAAAATTCAT CCTTCTTCAA
37051 GCATGGCAGT GACCAATGTG GGAACCACCA GTTCTGGACA TGAACTATAT
37101 TCCTCTGTTT CAATCCACTC GGAGCCATCC AAGGCTACAT ACCCAGTGGG
37151 TACTCCCTCT TCCATGGCTG AAACCTCTAT TTCCACATCA ATGCCTGCTA
37201 ATTTTGAGAC CACAGGATTT GAGGCTGAGC CATTTTCTCA TTTGACTTCT
37251 GGATTTAGGA AGACAAACAT GTCCCTGGAC ACCAGCTCAG TCACACCAAC
37301 AAATACACCT TCTTCTCCTG GGTCCACTCA CCTTTTACAG AGTTCCAAGA
37351 CTGATTTCAC CTCTTCTGCA AAAACATCAT CCCCAGACTG GCCTCCAGCC
37401 TCACAGTATA CTGAAATTCC AGTGGACATA ATCACCCCCT TTAATGCTTC
37451 TCCATCTATT ACGGAGTCCA CTGGGATAAC CTCCTTCCCA GAATCCAGGT
37501 TTACTATGTC TGTAACAGAA AGTACTCATC ATCTGAGTAC AGATTTGCTG
37551 CCTTCAGCTG AGACTATTTC CACTGGCACA GTGATGCCTT CTCTATCAGA
37601 GGCCATGACT TCATTTGCCA CCACTGGAGT TCCACGAGCC ATCTCAGGTT
37651 CAGGTAGTCC ATTCTCTAGG ACAGAGTCAG GCCCTGGGGA TGCTACTCTG
37701 TCCACCATTG CAGAGAGCCT GCCTTCATCC ACTCCTGTGC CATTCTCCTC
37751 TTCAACCTTC ACTACCACTG ATTCTTCAAC CATCCCAGCC TCCATGAGA
37801 TAACTTCCTC TTCAGCTACC CCATATAGAG TGGACACCAG TCTTGGGACA
37851 GAGAGCAGCA CTACTGAAGG ACGCTTGGTT ATGGTCAGTA CTTTGGACAC
37901 TTCAAGCCAA CCAGGCAGGA CATCTTCAAC ACCCATTTTG GATACCAGAA
37951 TGACAGAGAG CGTTGAGCTG GGAACAGTGA CAAGTGCTTA TCAAGTTCCT
38001 TCACTCTCAA CACGGTTGAC AAGAGAATGC GCATGGCGAG AAGGGAGAAG
```

TABLE 1-continued

Genomic CA125 Amino Terminal Sequence
(SEQ ID NO: 1)

```
38051 TGTAGTTGGA TGGATAAAAG GAAGAATGGA GAGAAGAGTG AATGGAAGGA

38101 AGCAAAGATG AAGCGGAGGA AGGATAGATG CACAGAAGGA AGGATGAAAA

38151 GAAAGAAAGA TGATGGAAGA CAGGATTGAA GGGGATATAG ATTGAAGGAA

38201 AGAAAGGTAG AAGGATGAAA TGAAGTAAAG ATTGAAGAAA AGATGGATGG

38251 AAAGAAGAAA GGAGGGTGCA CAAAAAATCT CACACTTCAC CACATATGAT

38301 TCATCCATAT AAGAAAAAAC CACTTGTACC CTCAAAGCTA TTGAAATACA

38351 AACTTTTAAA TTAAAATTTT AAAAAGCAAG AGAAAGGAAA GAAGGGAGGA

38401 AAGACAAAAG GAAGAATGGG TGATAGAAGG AAAGAATAAA AGGAAGAAAA

38451 AATGGAAGAA TAGATGATCA GATCTAGGGA TGAATGAAAG GAAGGATGGA

38501 CAAATCTATA GGTAGGTGGA TGGATCTATG GACAGGTGTG GCCACTTATG

38551 GCACATAGTC CCAGCTCCAG TTCATACTGA TGGACTTGAG GAGTGTTTGT

38601 GGCCAATGAA GTGGATCCAT TTAGACAGTG CTCTTCTTCT GAATGAGATG
```

Exon 5

```
38651 AGTTACCCCA GTTTTTCTCC CCACCTTCAT CTTCAGGAAC TGATGGCATT

38701 ATGGAACACA TCACAAAAAT ACCCAATGAA GCAGCACACA GAGGTACCAT

38751 AAGACCAGTC AAAGGCCCTC AGACATCCAC TTCGCCTGCC AGTCCTAAAG

38801 GTAGGTTAA CTTTGCTTAC CTCCCAGTAA TGCCACTCGT GACCATATTT

38851 CCTCCTCCAG AGAGACAAAA TGTTTGTATT CTTTAGAGAG AGAATTGTGT

38901 GTGGTTGTCA TAGGTTTCCC TGTCTGAACT GAGTCTTTAT CTAATGGTTA

38951 CCAGGCAGAT GTTACCACTG TCTCTTTCTC CTCATGGCAT GCTGAGTGAG

39001 TTTTGTCCAA CATCAAATAT TCACAAATTT GTCCATATTA ACCAAATTTT

39051 AAAAATGCTC ATTAAAAACT TACTATGAGC TGGGCGCAGT GGCTCATGCC

39101 TGTAATCCCA ATACTTTGGG AGGCTGAGCT GGGTGGATCA CCAGAGGTCA

39151 AAAATTCGAG ACCAGTCTGA CCAAAATGGT GAAACTCCAT CTCTACTGAA

39201 AATATAAAAA TTAGCCGGGC ATGGTGGCAC ACACCGTAAT CACAGCTACT

39251 CAGGAGGCTG AGGCAAGAGA GTCACTTGAA CCACAGGAGG TAGAGGCTGC

39301 AGTGAGCTGA GCATTGTGCC AATGCACTCC AGCCTGGGTG CAGAGCAAG

39351 ACTCCAGCTC AGAAATAAAT AATATATTAT ATATATATAT ATATGTTTTA

39401 TTTAGATGGA ATATACTATA TATATATGTA TATATATATG TATGTATATA

39451 TATATATGTA TGTATATATA TATATATATA TATATATATA TATATAGAGA

39501 GAGAGAGAGA GAGAGAGAGA GAGAGAGACA GAGTATGTCT GAGAATGCAT

39551 CCCGATAGTT CTAGCAAGGT AGGAAAAGGA AGTATCATAA CAGCCTTGAA

39601 GTAGCCTGTT GAAACAGACA GACTCTCTTG TAAGAGAACT CACAAAATCT

39651 AGGATTATAT CTCCCATGAT GAAAAATTTG GAACTGTACA TTTTTGTTTA

39701 ACTGTCACTT AAATNNNNNN NNNNNNNNNN NNNNNNNNNN NNNNNNNNNN

39751 NNNNNNNNNN NNNNNNNNNN NCCAGGAGGC ACTGTGCTTG GCGCCTTTTT

39801 ACCACACACTT TGAGATGGCC ATTGTACTTA TCCCCACTTT ATAGACGGGA

39851 AAATGGAGGT CCAGCAATAT TTTTTAACTT AAAGAGCCAC CCATCTCTTT
```

TABLE 1-continued

Genomic CA125 Amino Terminal Sequence
(SEQ ID NO: 1)

39901 AGAGAAAGAG CCAGAATCCC AGGCAGGGGC TATCTTATTC CAGAGCCCAA
39951 GCTCTCAAAC ACATGATACA CAATACTTAA TCTCTCTCAA GTCAGAGGAG
40001 ATCCACTTAA GTATACATCC ATCCACATAT TCATTCATTC AATCATTCAA
40051 CAAATATTAG TTGAGCACTT ACCGTATGCC AAACAGTCAA ACGTGAATAG
40101 CTGTTACAAA TGAGACTGTG AAGGATGGTA CAACGCAGAT TCAGACAGTG
40151 TGATAAGGAA ATATTGAGAA GCAAAGATGA GTTCTGGAGT GAATTTGTAA
40201 AGGTGGATGT GGGCTTGGAT TTCAATAATG GCAGAACTTA AGGAATCTGA
40251 TGAGAAGTGG GCACTTCAGG CAGAGAGAAG AGCTTGAACA AGGCTCAGAG
40301 GCTGACAGTG CAGGAAACAC ATGGGAAGAG GGAATAGAGT AGCGGTCAAG
40351 AATTCACAGA GGAGTTATAG GTGAAGATGC AACCAAGTTA CAGACCAAGG
40401 TAAGATAGGG GAATACCAAT CACAATCTCT TTTCCCATTC CAGAAGCATC
40451 CCAGACACAT CCTAGTAACC GAGAGACATT TCTCTCCCTT TCCTCCTGTG
40501 GAGAATAAAT AAGCTATTGC AAGTCCAGTA AGTGTAATCA TTTTGTTCAA

Exon 6

40551 ATTGTGTGCC CATTCCCCAA TTTACAGGAC TACACACAGG AGGGACAAAA
40601 AGAATGGAGA CCACAACCAC AGCTCTGAAG ACCACCACCA CAGCTCTGAA
40651 GACCACTTCC AGAGCCACCT TGACCACCAG TGTCTATACT CCCACTTTGG
40701 GAACACTGAC TCCCCTCAAT GCATCAATGC AAATGGCCAG CACAATCCCC
40751 ACAGAAATGA TGATCACAAC CCCATATGTT TTCCCTGATG TTCCAGAAAC
40801 GACATCCTCA TTGGCTACCA GCCTGGGAGC AGAAACCAGC ACAGCTCTTC
40851 CCAGGACAAC CCCATCTGTT TTCAATAGAG AATCAGAGAC CACAGCCTCA
40901 CTGGTCTCTC GTTCTGGGGC AGAGAGAAGT CCGGTTATTC AAACTCTAGA
40951 TGTTTCTTCT AGTGAGCCAG ATACAACAGC TTCATGGGTT ATCCATCCTG
41001 CAGAGACCAT CCCAACTGTT TCCAAGACAA CCCCCAATTT TTTCCACAGT
41051 GAATTAGACA CTGTATCTTC CACAGCCACC AGTCATGGGG CAGACGTCAG
41101 CTCAGCCATT CCAACAAATA TCTCACCTAG TGAACTAGAT GCACTGACCC
41151 CACTGGTCAC TATTTCGGGG ACAGATACTA GTACAACATT CCCAACACTG
41201 ACTAAGTCCC CACATGAAAC AGAGACAAGA ACCACATGGC TCACTCATCC
41251 TGCAGAGACC AGCTCAACTA TTCCCAGAAC AATCCCCAAT TTTTCTCATC
41301 ATGAATCAGA TGCCACACCT TCAATAGCCA CCAGTCCTGG GGCAGAAACC
41351 AGTTCAGCTA TTCCAATTAT GACTGTCTCA CCTGGTGCAG AAGATCTGGT
41401 GACCTCACAG GTCACTAGTT CTGGGACAGA CAGAAATATG ACTATTCCAA
41451 CTTTGACTCT TTCTCCTGGT GAACCAAAGA CGATAGCCTC ATTAGTCACC
41501 CATCCTGAAG CACAGACAAG TTCGGCCATT CCAACTTCAA CTATCTCGCC
41551 TGCTGTATCA CGGTTGGTGA CCTCAATGGT CACCAGTTTG GCGGCAAAGA
41601 CAAGTACAAC TAATCGAGCT CTGACAAACT CCCCTGGTGA ACCAGCTACA
41651 ACAGTTTCAT TGGTCACGCA TCCTGCACAG ACCAGCCCAA CAGTTCCCTG
41701 GACAACTTCC ATTTTTTTCC ATAGTAAATC AGACACCACA CCTTCAATGA
41751 CCACCAGTCA TGGGGCAGAA TCCAGTTCAG CTGTTCCAAC TCCAACTGTT

TABLE 1-continued

Genomic CA125 Amino Terminal Sequence
(SEQ ID NO: 1)

```
41801 TCAACTGAGG TACCAGGAGT AGTGACCCCT TTGGTCACCA GTTCTAGGGC

41851 AGTGATCAGT ACAACTATTC CAATTCTGAC TCTTTCTCCT GGTGAACCAG

41901 AGACCACACC TTCAATGGCC ACCAGTCATG GGGAAGAAGC CAGTTCTGCT

41951 ATTCCAACTC CAACTGTTTC ACCTGGGGTA CCAGGAGTGG TGACCTCTCT

42001 GGTCACTAGT TCTAGGGCAG TGACTAGTAC AACTATTCCA ATTCTGACTT

42051 TTTCTCTTGG TGAACCAGAG ACCACACCTT CAATGGCCAC CAGTCATGGG

42101 ACAGAAGCTG GCTCAGCTGT TCCAACTGTT TTACCTGAGG TACCAGGAAT

42151 GGTGACCTCT CTGGTTGCTA GTTCTAGGGC AGTAACCAGT ACAACTCTTC

42201 CAACTCTGAC TCTTTCTCCT GGTGAACCAG AGACCACACC TTCAATGGCC

42251 ACCAGTCATG GGGCAGAAGC CAGCTCAACT GTTCCAACTG TTTCACCTGA

42301 GGTACCAGGA GTGGTGACCT CTCTGGTCAC TAGTTCTAGT GGAGTAAACA

42351 GTACAAGTAT TCCAACTCTG ATTCTTTCTC CTGGTGAACT AGAAACCACA

42401 CCTTCAATGG CCACCAGTCA TGGGGCAGAA GCCAGCTCAG CTGTTCCAAC

42451 TCCAACTGTT TCACCTGGGG TATCAGGAGT GGTGACCCCT CTGGTCACTA

42501 GTTCCAGGGC AGTGACCAGT ACAACTATTC CAATTCTAAC TCTTTCTTCT

42551 AGTGAGCCAG AGACCACACC TTCAATGGCC ACCAGTCATG GGGTAGAAGC

42601 CAGCTCAGCT GTTCTAACTG TTTCACCTGA GGTACCAGGA ATGGTGACCT

42651 CTCTGGTCAC TAGTTCTAGA GCAGTAACCA GTACAACTAT TCCAACTCTG

42701 ACTATTTCTT CTGATGAACC AGAGACCACA ACTTCATTGG TCACCCATTC

42751 TGAGGCAAAG ATGATTTCAG CCATTCCAAC TTTAGCTGTC TCCCCTACTG

42801 TACAAGGGCT GGTGACTTCA CTGGTCACTA GTTCTGGGTC AGAGACCAGT

42851 GCGTTTTCAA ATCTAACTGT TGCCTCAAGT CAACCAGAGA CCATAGACTC

42901 ATGGGTCGCT CATCCTGGGA CAGAAGCAAG TTCTGTTGTT CCAACTTTGA

42951 CTGTCTCCAC TGGTGAGCCG TTTACAAATA TCTCATTGGT CACCCATCCT

43001 GCAGAGAGTA GCTCAACTCT TCCCAGGACA ACCTCAAGGT TTTCCCACAG

43051 TGAATTAGAC ACTATGCCTT CTACAGTCAC CAGTCCTGAG GCAGAATCCA

43101 GCTCAGCCAT TTCAACAACT ATTTCACCTG GTATACCAGG TGTGCTGACA

43151 TCACTGGTCA CTAGCTCTGG GAGAGACATC AGTGCAACTT TTCCAACAGT

43201 GCCTGAGTCC CCACATGAAT CAGAGGCAAC AGCCTCATGG GTTACTCATC

43251 CTGCAGTCAC CAGCACAACA GTTCCCAGGA CAACCCCTAA TTATTCTCAT

43301 AGTGAACCAG ACACCACACC ATCAATAGCC ACCAGTCCTG GGGCAGAAGC

43351 CACTTCAGAT TTTCCAACAA TAACTGTCTC ACCTGATGTA CCAGATATGG

43401 TAACCTCACA GGTCACTAGT TCTGGGACAG ACACCAGTAT AACTATTCCA

43451 ACTCTGACTC TTTCTTCTGG TGAGCCAGAG ACCACAACCT CATTTATCAC

43501 CTATTCTGAG ACACACACAA GTTCAGCCAT TCCAACTCTC CCTGTCTCCC

43551 CTGGTGCATC AAAGATGCTG ACCTCACTGG TCATCAGTTC TGGGACAGAC

43601 AGCACTACAA CTTTCCCAAC ACTGACGGAG ACCCCATATG AACCAGAGAC

43651 AACAGCCATA CAGCTCATTC ATCCTGCAGA GACCAACACA ATGGTTCCCA
```

TABLE 1-continued

Genomic CA125 Amino Terminal Sequence
(SEQ ID NO: 1)

| | |
|---|---|
| 43701 | GGACAACTCC CAAGTTTTCC CATAGTAAGT CAGACACCAC ACTCCCAGTA |
| 43751 | GCCATCACCA GTCCTGGGCC AGAAGCCAGT TCAGCTGTTT CAACGACAAC |
| 43801 | TATCTCACCT GATATGTCAG ATCTGGTGAC CTCACTGGTC CCTAGTTCTG |
| 43851 | GGACAGACAC CAGTACAACC TTCCCAACAT TGAGTGAGAC CCCATATGAA |
| 43901 | CCAGAGACTA CAGCCACGTG GCTCACTCAT CCTGCAGAAA CCAGCACAAC |
| 43951 | GGTTTCTGGG ACAATTCCCA ACTTTTCCCA TAGGGGATCA GACACTGCAC |
| 44001 | CCTCAATGGT CACCAGTCCT GGAGTAGACA CGAGGTCAGG TGTTCCAACT |
| 44051 | ACAACCATCC CACCCAGTAT ACCAGGGGTA GTGACCTCAC AGGTCACTAG |
| 44101 | TTCTGCAACA GACACTAGTA CAGCTATTCC AACTTTGACT CCTTCTCCTG |
| 44151 | GTGAACCAGA GACCACAGCC TCATCAGCTA CCCATCCTGG GACACAGACT |
| 44201 | GGCTTCACTG TTCCAATTCG GACTGTTCCC TCTAGTGAGC CAGATACAAT |
| 44251 | GGCTTCCTGG GTCACTCATC CTCCACAGAC CAGCACACCT GTTTCCAGAA |
| 44301 | CAACCTCCAG TTTTTCCCAT AGTAGTCCAG ATGCCACACC TGTAATGGCC |
| 44351 | ACCAGTCCTA GGACAGAAGC CAGTTCAGCT GTACTGACAA CAATCTCACC |
| 44401 | TGGTGCACCA GAGATGGTGA CTTCACAGAT CACTAGTTCT GGGGCAGCAA |
| 44451 | CCAGTACAAC TGTTCCAACT TTGACTCATT CTCCTGGTAT GCCAGAGACC |
| 44501 | ACAGCCTTAT TGAGCACCCA TCCAGAACA GAGACAAGTA AAACATTTCC |
| 44551 | TGCTTCAACT GTGTTTCCTC AAGTATCAGA GACCACAGCC TCACTCACCA |
| 44601 | TTAGACCTGG TGCAGAGACT AGCACAGCTC TCCCAACTCA GACAACATCC |
| 44651 | TCTCTCTTCA CCCTACTTGT AACTGGAACC AGCAGAGTTG ATCTAAGTCC |
| 44701 | AACTGCTTCA CCTGGTGTTT CTGCAAAAAC AGCCCCACTT TCCACCCATC |
| 44751 | CAGGGACAGA AACCAGCACA ATGATTCCAA CTTCAACTCT TTCCCTTGGT |
| 44801 | TTACTAGAGA CTACAGGCTT ACTGGCCACC AGCTCTTCAG CAGAGACCAG |
| 44851 | CACGAGTACT CTAACTCTGA CTGTTTCCCC TGCTGTCTCT GGGCTTTCCA |
| 44901 | GTGCCTCTAT AACAACTGAT AAGCCCCAAA CTGTGACCTC CTGGAACACA |
| 44951 | GAAACCTCAC CATCTGTAAC TTCAGTTGGA CCCCCAGAAT TTTCCAGGAC |
| 45001 | TGTCACAGGC ACCACTATGA CCTTGATACC ATCAGAGATG CCAACACCAC |
| 45051 | CTAAAACCAG TCATGGAGAA GGAGTGAGTC CAACCACTAT CTTGAGAACT |
| 45101 | ACAATGGTTG AAGCCACTAA TTTAGCTACC ACAGGTTCCA GTCCCACTGT |
| 45151 | GGCCAAGACA CAACCACCT TCAATACACT GGCTGGAAGC CTCTTTACTC |
| 45201 | CTCTGACCAC ACCTGGGATG TCCACCTTGG CCTCTGAGAG TGTGACCTCA |
| 45251 | AGAACAAGTA AGAATAACTT TTTTATTGTG GTAAAATATA AATACTATAA |
| 45301 | AAATTGCCAT TCTAAACATT TTAATTGTAC AACTCAGCAG TACTAATACA |
| 45351 | TTCACATTGT TGTGCAACCC TCACCACTAT CTGTTTTCAA AACTTTTTTT |
| 45401 | ATCACCCCAA ACAGGACTGA AGGAATAATT TCCCATTCCC CATTCTCCCT |
| 45451 | AGTGCAGTGG TGCAATCTCG GCTCACCACA ACCTCTGAAC CTCTGTCTCC |
| 45501 | TGGGTTCAAG CAATTCTCCT GCATCAGCCT CCTGAGTAGT TGGGACTACA |
| 45551 | GGTGCACGCC ACCGTGCCTG GCTAATTTTT GTATTTTTAG TACAGACAGG |
| 45601 | GTTTTACCAT GTTGGTCAGG CTGGTCTCAA ACTCCTGACC TCAGGTGGTC |

TABLE 1-continued

Genomic CA125 Amino Terminal Sequence
(SEQ ID NO: 1)

```
45651 CACACGCCTT GGCCTCCCAA AGTGCTGGGA TTACAAGTGT GAGACACTGT

45701 GCCCGGCCAT ATCTGTTAGA TCTTACTAAT CCTGTCAAGA GGATTCAGTG

45751 TCCTTTTTTT TTTTTCTTTC TTTTTTTTGA TAGAGTCTCC CTCTGGCACC

45801 CAGGCTGGAG TGCAGTGGTA CGGTCTTGGC TCACTGCAGC CTCCACCTCC

45851 CAGACTGAAG CGATTCTCCT GCCTCAGCCT CCCGAATAGC TGGGACTACA

45901 GGCGCGTGCC ACCACGCCCA GCTAATTTTT GCATTTTTAG TAGAGATGGG

45951 ATTTCACTAT GTTGGCCAGG CTGGTCTCAA ACTCCTGATC TCAAGTGATC

46001 CGCCCAAGGG CCTCCCAAAG TACTGGGATT ACAGGTAGGA GCCACCTCAC

46051 CTGGCCCTAT TTTCGGAATG GATTTTTTTT TAATGTTTAA AATGTCACCT

46101 AAGATTATTG TGAAGATCAA ATAAGATAAA ATCCTAATAA CCCAAGTAAA

46151 CCACAGGGCT CCACTTGGAC CAGTCTCAGA AGTTTCAAGA AAATCAGTCA

46201 GACCATCAAA TGTAAAATAA GTCTAAATTT CTTTGCACT ATTCACAGAG

46251 TGCCAAAGAG GATCTAATTC ATGTTTCAGA ACATACCCTA CTTACTAAAA

46301 TCCCCTTTTC CTCATTTCTT CTCATTCTGC AACTTTATCA TCTCCTGCGG

46351 ACCCCCTAGC CTCTCCCCTC CCCATAGTCA GTCTCTCTCT CTCTCTTTCC

46401 CTCCCCTCTT ATTATCTCAA TTTCACACGA AAGAATTCCA GAAACTATAC

46451 TGCCAAAAGT CTTTCCTGTC TTTGAAAAGT TGGGAAAGAG GAGAAACTCA

46501 GACAGCAATG ACAAAATTAT ACGTAATGGA TGAAGGAAAC ACAAATAAGG

46551 CTGGAAACAG AAAATTTTGT CCCCATCATT TATTTAATGA AGGTGGCAGT

46601 ATTCCAGCCA CATAGTGAAC CCCCACAATA AGAAGGGGCC TCTGGCGATT

46651 GATTATTGTC ATTGTTGTTA ATGATAATGA GGGTGAGGAT ATCATGAGCA

46701 TCAGTGTAGG AGGCAGTTAA CTAATAAGAC CAAGCTGTTG GCTGGGCGTG

46751 CTGGTTCACA CCTGCAGTCC CAGCACTTTG GGAGGCCAAA GTGGGTGGAT

46801 CACTTGAGGT CAGGAGTTCA AGACTAGCCT GGCCAACATG GTGAAACCTG

46851 GTCTCTACCA AAAATACAAA AATTAGTCAG GTGTGGTGGC GTGTGCCTGT

46901 AATGACAACT ACTTGGGAGG CTGAGGCAGG AGAATCACTT GAACCTGGGA

46951 GGCGGAGGCT GCAGTGAGAT GAGCTTGAAC CACTGCACTC CAGCCCGGGC

47001 AACAGAGAGA GACTCTTGTC TCAAAAAACA AAACAAACAA ACAAAAACTA

47051 AACCAAACAA AAAAAGACTA GCTGTTATTC ATTTATTTAT TTATTTATTT

47101 AGAGACGGAG TCTCGCTCTG TCACCCAGGC TGGAGTGCAG CGGCACAATC

47151 TTGGCTCACT GCAACCTCTG CCTCCCAGGT TCATGTGATT CTCCCGCCTC

47201 AGCCTCCCCA GCTGTTGTTA TTCATGAATG AACCTCAGAG AAAGCACACA

47251 GGAGGGTTGG TGCACCTGTG TTTTGAGTTC TACCCCTCCT TCCTCTCTTA

47301 ACTTCCTCCT GTCTTCTCAC TCTGATTCGT TCTTCCTTCC TCTCCCTCTC
```

Exon 7

```
47351 TCTCTGCAGG TTATAACCAT CGGTCCTGGA TCTCCACCAC CAGCAGTGAG

47401 TAAACATGGC CCTGAAGTCC CTATGCCCTG GGAATTCTTC CTCCCTAAGC

47451 CTGCCTTCCA GGAGGAAAGT ATCCCCCATT CCCTAGGTTC TCATCCCCAC
```

TABLE 1-continued

Genomic CA125 Amino Terminal Sequence
(SEQ ID NO: 1)

```
47501 AGAAACTCCA GAATAGCAAA AGTCTCAGGC TGAGCCAAGG CACAGATGCC
47551 AGTGCTCACC AAGAGTCCTA TTCTCCCTC GCTAAATGAT AGGACCCAAC
47601 AAACCCGATT CACGCTGCGT TTTCTTTCAG CTCCGATGAC CTCCATGTTC
47651 TCTCCAAGGC CTCTCGTATC TGTGAGCCCC ACCCCCAGCG CTACAGGTAG
47701 GAATCTGGCT TCCAGCTCCC ATGAAACGTC GGCTGCCATT CAGTGGCTGA
47751 TTAATTGCTG TGTGGTCTGA GTCCTGATGC CCACCAAGTC TCAGCGTGTT
47801 CCCCTCTGTC CAATCTCATC CAACAATTTA AGCTAATGCT TGTTTAATGA
47851 TGTCCTCACT ATACCACCTT GGACACTTTC TTTTTGCCTG GATTTAAAGC
47901 TTCCATTTCT TTCCTTCCTT CCTTCTTTTC TTCCTTCCTT CCTTCCTTCC
47951 TTCCTTCCTT CCTTCCTTCC TTCCTTCCTT CCTTCCTTCC TCCTTCCTTC
48001 CTTCCTTTCT TCCTTTCTTC CTGTCTTTTT CTTTCTTTCC TTCTTTTGGC
48051 AGAGTCTCAC TCTGTCGCCC AGGCTGGAGT GCAATGGTGC AATCTCGGTT
48101 CACTGCAACC TCTGCCTCCC AGGTTCAAGC GATTCTCATG CCACATGCCA
48151 CTATGCCTGG CTAATTTTTG TTTTTTTGTT TTTGGGGGG TTTTTTGAGA
48201 CAGAGTCTCA GTCTGTTGCC CAAGCTGGAG TGCAGTGGCA TGATCTCGGG
48251 TCACTGCAAC CTCCTTCTCC CAGGTTCAAG CGATTTTCCT GCCTCAGCCT
48301 CCTGAGTAGC TGGAACTACA GGCACGCACC ATCACACCGG CTAATTTTTT
48351 GTGTTTTTAG TAGAGACGAC GGTTTTGCAA TGTGGGCCAG GCTTGTCTCG
48401 AACTCCTGAC CTCAAGTGAT CCTCCAGCCT CGGCCTCTCA AGTGCTGGG
48451 ATTACAAGTG TGAGCCACTG CACCAGGCCA AAAACTTGTA TTTCAATAGT
48501 CATTGAGGCT GGGTGCAGTG GCTCACGCCT GTAATCCCAG CACTTTGGGA
48551 GGCTGAGGCC AGTGGATCAT GAGGTCAGGA GATCAAGACC ACCCTGGCTA
48601 ACACAGTGAA ACCCCATCTC TACTAAAAAT ACACACAAAA ATTAGCCGGG
48651 CATGGTGGCA AGATGCCTGT AGTCCCAGCT ACTCAGGAGG CTGAGGCAGG
48701 AGAATGGCGT GAACCTGGGA GGCAGAGCTT GCAGTGAGCG GAGATCGCAC
48751 CGCTGCACTC CAGCCTGGGC AACAGAGAGC GACTCTGTCT CAAAAAAAA
48801 AATATATATA TATATATATA TATATTCATT GAGACCGACT CTGACTTAAA
48851 AGCAGTAATG AATGGTGTAG GTTTTGGTAA ATTACAGGTC TTGCTTTAAG
48901 TCCTGGTCCT CTCTTTTGCT CACTGTGTGG CCCCGGAAGA GCCATGTAAC
48951 CTCTCCAGGC TTCAGTGTCC ATTTTTAGAA CGGAGTAAGT GAATAAGCTG
49001 TGTCCAATCA TCTCTGGCCA TATCAGCTTC ATTTTTTTTT TCCTCCAGGG
49051 TCCAAACATC CCTCCACCCT CAGAGTCTTT GCACCTGGTG TTCTTGTCCT
49101 TCAAATCTCA GCTTGGATCA CCCTTTATAA AGTAGCATTT CCCCCGTATA
49151 CGCATCTTGC ACACAGCCAA TCTCTATTCT ACCTCTATGC TCACTTCCTT
49201 CCTGGCAATT ATTACTACAG CTGGGCCCTT GAACAGCATG AGGGTTCAGG
49251 GTGCTGACCC CTATGCATTC AAAAATCCAC ATATAACTTT TTTTTTTTG
49301 AGATGGAGTT TCACACTTGT TGCCCAGGCT GGAGTGCAGT GGCGCCATCT
49351 TGGCTCACTG CAAACTCTGC CTCCTGGGTT CAAGTGATTC TCCTGCCTCA
49401 GCCTCCTGAG TAGCTGGGAT TACAGGCATG TGCCACCATG CCCAGCTAAT
```

TABLE 1-continued

Genomic CA125 Amino Terminal Sequence
(SEQ ID NO: 1)

```
49451 TTTGTATTTT TAGTAGAGAT GAGGTTTCTC CATGTTCGCC AGGCTGCTCT

49501 TGAACTCCTG ACTTCAGGTG ATCCGCCTGC CTTGGCCTCC CAAAGTGCTG

49551 GGATTACAGG CATGAGCCAT GATGCCCGGC CATTTGCTAA TGGCATCTAG

49601 TAAGTAGAGG CCAGAGATGT TGCAAAACAT CCAACAATGC ACAAAGCAGC

49651 CTCCTATCAA AACACATTAT CCAGACCAAA ATGTCAATAG GGCTGAGGTT

49701 GAGCATCTGC TGTACACAGA TTCCAAGTTC TGGTACAAAT CTCGTAGTTC

49751 TCTGAGGGCT CATCTTTCAA TGCCTAGCAC ATCAAAGGAG GCCAATTTCC

49801 TCTTCCCTTT CACCTCCTGG TATGAAATGT TTCCTCCTCC ACCTTGATCC

49851 TGTAAGAGCC CAGCTGGAGT TTGCAGACGA CGGGGAAAGA AATGGGTGAG

49901 GGAGGGTCCT ATGGTTGAGT CTCCGCAGTG GGCCCTGGGT GCCCAGTTCA

49951 CCCTCCTCCC CTTCATTTTC TCCATCATGA CAACTCAAGG CAAATTCTCA

50001 GTTTCCATGG GCCAGTGGAA TCCACTGACT TCATGAAATA ACCCCACCCT

50051 GAGCAAATAC CCCTCAAATA ATAACTGTTT ACACAACATC AGTGGCAACA

50101 ATGACCCAAG CAGCAATGCC ACCACCAGAA TAGCAACCAT AACAGCAGCT

50151 CATTTTCATC AAAAGGAAAC TGTAGGGCCA GGCACAGTGG CTCACACCTA

50201 TATTCCCAGC ATTTTGGGAG GCTGAGGCAG GCAGATCACC TGAGGTCAGG

50251 AGTTCAAGAC CAGCCCAGCC AACATGGTGA AACCCCATCT CTACTAAAAA

50301 TACAAAAACT AGCCAGGCTT GGTGGCATGT GCCTGTAATC CTAGCTACTC

50351 GGGAGGCTGA GGCAGGAGAA TTGCTTGAAC CTGGGAGGCA GAGGTTGCAG

50401 TGAGCTGAGA TTGTGCCACT GCACTCCAGC CTGGGCGACA GAGCAAGACT

50451 CCGTCTGAAA AAAAAAAAA AAGGAATTGT GCCAGGAATT GTGATGAGAA

50501 CTTTATATGC ATTATCTCCT ATTAATATTA CCCAAACCTC CGTGAGTTAG

50551 TATACTCATT TCTACAGAGA GCATTTATGC ATCCAGGGAG GAAGTAATTA

50601 GCCCAGAATT ACTCAGTTAT GACACAGGAC AGTATGAAAA CTCCAACCGA

50651 AGATTGGAGA CTCATGAAAA CTCCAGGCTC CTAACTACAA GACATCACTG

50701 TGGATCGTCC AAATAGAGCA AGCCCCAATC TCAGGACAGG AATGAGGCAT

50751 GAATGGCCTC TATGCTAATG ATCTAACCTA ATGCTGAATT TGTTACTTCC

50801 CTTCTGAATC CACTTGGAGA TTTCCTTTAT ATCTGACTTG AAATAGAGGA

50851 TATATACTCC TCTATCCTTG ACATAGGAGA TAATACACAG AAAGTATTTC

50901 ATTGTAGTAT CAAGTACACA TCCTGTTCTG TGTCCATAGG ATTATGACTA

50951 ATTTAGGGCA TGGCTTAACA GTGTGGTACT ATTGAATGAC AGACAGATGT

51001 CTGTTTTGTT GGATGCAGGA CAAGCCATGT AACCTCCCCA GACTTTAGTG

51051 TCCCCTCTGT GGAATGGAAT AAAAATACTA CGTGGGATTG TTCTGATAAT

51101 CAAATGAGAT AATTCAGGAA CAACCCAGAT AAATAACAGG GCTGCCCTGG

51151 GTTCTGTCTT TCCTTGTATC TCTCACAGAG CCTCAAAGGA GATGCAATCC

51201 ATGACCTAGA GAAACACTCA GGACAAATTC TCTTTTCCCC AGTTCCTTTC

51251 TTGCTCCAAT GGCAACACCA CCCCTCTCAT CCTGAAGTCT CTTGTTTTA

51301 CCACCACACC TATTTTGCCA AATTTTCTCC AATATTCCAA ACCATATGAA
```

TABLE 1-continued

Genomic CA125 Amino Terminal Sequence
(SEQ ID NO: 1)

```
51351 ACCTTTCTTT CTTTCTTTTC TTTCCTTCCT TTCCTTCTTT CTTTCTTTTT
51401 TCTCTTCTTT TCTTTTCTTT TTGAGACATG GTCTCACTCT GTTGCACAGG
51451 CTGGAGTGCA ATGGCACGAT CTTTGCTCAC TGCAACCTCC GCCTCCCAGG
51501 TTCAAGAGAT TCTCTTGCCT CAGCCTCCTG AGTAGCTGGG ATTACAGGCG
51551 CCCACCGCCA CGCCACGCTA ATTTTGTGT TCTTAGTGGA GACGGGGTTT
51601 CGCCATGTTG GCCAGGCTGG TCTTGAACTC CTGACCTCAA GTGATTTGCC
51651 CATCTCGGTC TCCCAAAGTG CTAGGATTAC AGGCGTGAGC CACCAAGCCC
51701 GGCCCCATAT GAACCGTTTC TATCCCTCAT TTCTCTGTAC TTTTACCTAA
51751 AAACACCACT CCCTTCACCC ATCACATTTT TGTCAATTCT ACATCACACA
51801 CACACACACA CACACACACA CACACACAGA GAAAGTAAGT TGGAAAAAAA
51851 TTATACTATC ATGAAATTTT GTGAAAGGAG GTAAGCTGAG AGAGTAAGAA
51901 TCAAACTAAA TTATCTTTAT GGGTAGAAAG CACACTCATC CATACATGTG
51951 TCTTTCCACC CTTGTAATGT ATTTATTATT ATTGTTTGTA TATACTAGAT
52001 TCCCAATAAA TAGGGACAGC TATTATGGTA TTTTTATTTC AGGAATAATA
52051 ATAGTGATGA TTTCCACCAT TATTGTCAAA GGACAAAGCA CAAAATATGT
52101 ACCAAATAAA ATATAGCCAT TATCCTTTAT TCACAAAAGA TCTTGGCCCC
52151 ACCTCTTCTC AATGAAATGT CCATGACTTG TTCAACTTTG GCCACTCTGG
52201 GCTGAGAGAT GGAGGTTCCC TTGCGAGCTG AAGTCACACA TCGAAGGTGG
52251 AAGCCCCTCC CCTCCCTCTG GCTGGCTGAG GGATAGCCCA GATGGGCTCA
52301 TCATGAAAGT TTCCCATTAT TTCCATTTCT GGATCTACCA TCTTCCCCTC
52351 CCCTACCTCT CACCCATCAT AATTGTCCTT CTTTACTCTT TCCTCCCTAT
```

Exon 8

```
52401 CTGCAGGTTA TAACCGTCGG TACTGGACCC CTGCCACCAG CAGTGAGTAT
52451 TCAAACCTGT GATATTCCAA TGCCCTTGGG ACCCTTCCTC CCCAAGGTGC
52501 ATTCCTCAGA AGAGAAACTG ATCATTCTCC CTCCCTACGT GCCCAGCCAC
52551 AGCCTCAGAG CAGCCCCTAA CCCGTCAAGG TCTTGGTGTG AGTCAAGATA
52601 GAAGTCCAAA TTCCAATGAG CAGTTCCTGT CCCATATTCC TTTAGGAAGA
```

Exon 9

```
52651 CACCCAATCA TTTCTCCATG TTCTTTTTTT CTCAGCTCCA GTGACTTCTA
52701 CATTCTCCCC AGGGATTTCC ACATCCTCCA TCCCCAGCTC CACAGGTAGG
52751 AAGCTCCTCT CTGGCATCTA TGAAATTTAA CACTGCATGG TCTGTTCCCT
52801 GCTGACCACC CAGACTCAGC CTGTTCCACT CGCCCTCTCA CTCTCTCTCT
52851 CTCTCTTTTT TTTTTTTTT TTTTTTTTT TTTACGGAGT CTTGCTCTGT
52901 CACCCAGGCT GGAGTGGAAT GGTGTGATCT CGGCTCACTG CAACCTTCGC
52951 CTCCCAGGTT CACGTGATTC TCCTGCCTCA GCCTCCGGAG TAGCTGGGAT
53001 TACAGGTGCA CACCACCATG CCTGGCTAAT TTTTTGTATT TTTAGTAGAG
53051 ACGGGGTTTC ACCATGTTGG CCAGGCTGGT CTTGAACTCC TGACCTCAAG
53101 TGATCTACCC ACCTTGGCCT CCCAAAGTGC TGGGATTATA GGCATGAGCC
53151 ACCACGCCAG GCCCACTCTC TAAATTTTGA CCACCCTGCC TTGAGTGGTC
```

TABLE 1-continued

Genomic CA125 Amino Terminal Sequence
(SEQ ID NO: 1)

```
53201 TTCTAGCACC CTAACCTCTG TCTAACCTCG AGAGCTTTGC ACTAGCGATT

53251 CCTGGGGACC AGCTATGGTT GGTATCTTCT CAACTTTCTA ATTTTTTTAA

53301 AATTATTATT ATTATTATTA TTATTTTAAA TGGAGTCTCG CTCTGTCACC

53351 CAGGCTGGAG TGCAGTGGCA CCATCTCGGC TCATTGCAAC CTCTACCTCC

53401 CGGGTTCATG CAATTTTCCT GCCTCAGCCA GAAATTTTCT CAGTGGTCGA

53451 GATTGTGCCA CTGCACTCCA GCCTGGGCAA TGGAGCTAGG CTCCATCTCA

53501 AAAAAAAAAA AAAAAGACG GAGGTCGGGC ATTCCTAACC CTTAACCCTG

53551 CCTTGTGATT CTGGAGTTAT GAGATAGAAC CTGGTGTCCC GTAATTAAAA

53601 TTCCGCCTTC AGGCCTTATG TTTTGTGAGT CACAACACTG CAAACTTTTT

53651 ACATGCTGTA GACAGGATGT TCACTCTCCA CTTCCTCACT GCTCTGCTCT

53701 AATCAATTCA ACCATTTATG TGACATGCCT AACCCCTCTG GGCTTGTACG

53751 TATGTAACAT GTATTACAAA GCAAGTCATT CCATGATCAA TGCTGTCACT

53801 TTTTCTAGGT GCTTTCAAAA TTTGTTCTTC ATCATTGATT TTCAGTAGTT

53851 TGATTACGAT GTGTCTGGGC ATGGTTTTCT TTGAGTTTAT CCTGCTTAAA

53901 GTGTTCTCAG CTTCTTGAGT CTCAAAGTGT TTATTTTCTG CTCTGATTCT

53951 TTCTCCCCTT CGGACCTCCA ATGAAATGAT GTTGCCCGAA GAGACCCTGA

54001 GGTTCTGTTC ATTTTGTTAT TTATCAATCT TTTTTCCTCT CCGAATTTCA

54051 GGTTTAATAA TTTTTTTTTT TTTTTGAGA CGGAGTCTCG CTCTGTCGCC

54101 CAGGCTGGAG TGCAGTGGCG CGATCTCGGC TCACCGCAAG CTCCGCCCCC

54151 TGGGTTCACG CCATTCTCCT GCCTCAGCCT CCGGAGTAGC TGGGATTACA

54201 GGCACCCGCC ACCATGCCCG GCTAATTTTT TGTATTTTTT AGTAGAGACG

54251 GGGTTTCACC GTATTAGCCA GGATGGTCTC AATCTCCTGA CCTCGTGATC

54301 CGCCCGCCTC AGCCTCCTAA AGAGCTGGGA TTACAGGCGT GAGCCACTGC

54351 GCCCGGCCCA GGTTTAATAA TTTTTATAGA ATATTTTCAC AATCACCAAG

54401 CCTTTTCTCT ACCAGCTCCA TTCTGCCCAT CCATTGAATT CTTTTTATCT

54451 CAGTTACTTT ATGTTTCAGT TCGAAAGTTT CTACTTGGTT AGATAGATAG

54501 ATGTTATATC ATATATTATA TGTTATATAA AAATATATTT ATGGTTATAC

54551 ATATAACATA TATGTTATAT ATAGTTATTT ATATAGCCAT AACTATATAT

54601 AGCCATATAT ATAGTTATAT ATAACCATAT ATATAGTTAC CATATAGTAA

54651 CCACATATAT AAAACATATA TATATAGTGT CTCTCTATAT ATAGTTATAT

54701 ATATAGTTTC TATATCTGTA ACTATATATA GTTATATATG TATGTTTCTC

54751 TGTATATAAA TATATATATT TCTATATATA TAGTTATACA CATTATATAT

54801 ATAACTGGGA GATGTTGGTA AAGGATGGCG TGAGGAAACC TGGAGCAGTC

54851 ATGGTAATCC TCGCTCTGCT CCGAACTCCT CAAGAGCAGG AGAAGGGTCC

54901 TCCTCATTCT CCAGCCATGT TGACTTTGAG CAATTACTC ATCCTCTCAG

54951 TACCTCAGTT TCCTCACCTG CCAATTGAGG ATAATAATAT TTCATAAATT

55001 GTTTGCAAAT GTTATATGCA ACTCTACGTA AGAACACCTA GCACAGGGGC

55051 TACCAGGGAA TTTGGTTTAA CAAATATTTA TCAGGCACCT ATTCTGGGCT
```

TABLE 1-continued

Genomic CA125 Amino Terminal Sequence
(SEQ ID NO: 1)

```
55101 GGGCAGGGGG GATAAGATGT TGACTAAGTC AAATGCAGTC CCTCCCCTCA
55151 CCAAGTTTAC AGTGTATTGG GCAAGACTGA AATGGAACAA GCAATTACAA
55201 TTGACAATAA AAGACAACCA AGTTATTGAG CACTTACTAT ATGGCATGCC
55251 ATATGCTATG TATTTTTTTT ATTTTTAACT TTTCATTTTG AAATAAATAA
55301 TAAATATAAA GTAAATAATA ATATAAATAA ATAATAAATA ACTTTTCATT
55351 TTGAAATAAA TAATAAATAA ATTCAGGAGA TGTTGCGAAA ATAGTGTAGC
55401 ATTCCCCTGT ATCCTTCACC CAGTTTCTCC CCAATGGCTA CATCTTACAT
55451 AACTCTAATA CAATATCAAA AGCAGGAAAC TGACATTGTT AAAATCCATT
55501 TTACTGGTTT TACACGCGTG TGTGCATATG TGAGCTTGTG TATGTGCGTG
55551 TGTGTGCAGG CATGTGTGTG CATGCACGCC TGTGTGTGCA TATGTGCATG
55601 TGTGCATGCG TGTGTGCATG TGTGCATGTG TGTGTGCATG CGTGCGTGCG
55651 TGCGTGCATC TGTGTGCATG TATGCACATG TGTGTGTGTC TGTGCACGTG
55701 TGTGCATGCA TGTGTGTGTG CGTGTGTGTT GGTAGCCCTA TGCAATTTTT
55751 ATCACATGGG CATAGCCCTA TAATCACCAC CACCATCAAG ATTCAGAACT
55801 GTTCCATTCC CCCAAAGATT CCCCTCATGC TAGCCTTCGT AATCATGCCC
55851 ACTGAGCCCA ACACTATTGC ATAGAATAGC TATTCTACTC TCCATCTCCA
55901 TCTCTGTCTC TACAATTTTC TTTTGAAGAT GTTATATAAA TGGAAATGTA
55951 CAACATGTCA CCTTTGAAAT TGGCTTCTTT TCCACTCAGT GTAATGCCCT
56001 GGAGATGTGC TCTTTTTAAC AGTCATGTAA CCTTCCTAAT TTCCCTCCAA
56051 AATATCATTA TGCCCCTCGC CGCCTTTTTT TTTTTTTTT TTTTTTGAGA
56101 CAGAGTCTCG CTCTGTTGCC CAGGCTGGAG TGCAGTGGTA TAATCTCAGC
56151 TCACTGCAGC CTCCGTCTCC CGGGTTCAAG GGATTCCCCT GCCTCAGCCT
56201 CCCAAGTAGC CAGGATTACA AGTGCATGCC ACCACGCCTG GCTAATTTTT
56251 GTATTTTTAG TCGAGACGGG GTTTCATTGT GTTGGCCAGG CTGGTCTCGA
56301 ATTCCTGACC TCAAGTGATC TGCCCGCCTT GGCCTCCCAA AGTGCTGGGA
56351 TTACAGGTGT GAGCCACCGC GCCCGACCCA TATTGCCCAT TGTATTACAG
56401 CGGAAGAAAC TGAGGTATGG ACAGGTAACA TGTCCATGGT CACTTGGCTG
56451 GTGAGGGGCA GAGAGGAGAT TTGAAACCAA ATCTGACTCA CTAGTGTGGC
56501 CGTAACCATG GTAACTATGT CTCTCTACCA TGTGGTCTCC TCTTTATTAA
56551 AGGAAGGGCA AGTTCTGGGA GTTTTGGGAG TTTTGGGCTT GAGTGGGGAA
56601 GGGTAGCCAA GTAAAGCAGG TGAGAGAAGG TCTGCTTTAA GGACTGCTGT
56651 TTGATTTTTA TTGTTGTTGT TCAGTGTTCA ATGGGATTGA GTTGACTCTT
56701 TTTTCCCTTC TTGTTCCCCA AAGCATGAGA CTGTTCCGGT CCTTTTCCCT
56751 TTTAACTTCT CAGCTAGAGT TTGTTAGGGC GGGTATGGGC ACCTGGCAGA
56801 GTCTGAGACC TCAGCTTCCA GTAGGCACAC GTTCTGACCC AATACACCTA
56851 CCCTGGTCCC CTAACCTGCT TCTGGTCCCC TAACCTGCTT CTGGGCCCAG
56901 GTAATGCATT TTAGGAACAT CCCACTTTTC TCCTTACCTG GCTTTCCATT
```

TABLE 1-continued

Genomic CA125 Amino Terminal Sequence
(SEQ ID NO: 1)

```
56951 ATCCGTCCAA ACTAAAGCAC CCACCTGTCT GCTTCAGACT CTTGCTTCAA
57001 GCACTCCGTC TGGGTCCTCA GAAATTGACT TACAGTCAGT TCAGATCTGA
57051 CTCAGGCGTG GCCTTCTTTT CTCCTTCCTT GC
```

TABLE 2

Genomic Repeats
(SEQ ID NO: 2)

ExonR1

```
   1 AGCAGCCACA GTCCCATTCA TGGTGCCATT CACCCTCAAC TTCACCATCA
  51 CCAACCTGCA GTACGAGGAG GACATGCGGC ACCCTGGTTC CAGGAAGTTC
 101 AACGCCACAG AGAGAGAACT GCAGGGTCTG GTGAGAGCCC CGCCCACCGT
 151 ACTCCTCCCT CGCCCACTTA GACAAACCAG CCCACCTCAC ACTGCCTCGC
 201 CCACTGATGC CAGCCACGCC CACCTCATCC AACCCCAGAC ACCTTTCCCT
 251 GCCCCACCCA CTGATTTTAG CCAAGCCCAC CTCACCCCAC CCAGCCTACT
 301 GATGCCAGCC ACGCCCACCT TTCCCTGCCC CGCCCACTGA TTTCAGCCAC
 351 GCCCACCTCA CCCTGGTCCA CCCCTCCAAT GCCCCACTCT TCCTGGCTTC
```

Exon R2

```
 401 CCGCAGCTGT TGTTTCTCAC CTCCCCTCTC CTTCCTTGCA GCTCAAACCC
 451 TTGTTCAGGA ATAGCAGTCT GGAATACCTC TATTCAGGCT GCAGACTAGC
 501 CTCACTCAGG TGAGACGCTC CTTAAGAAAA ACACAGCCCA ACAGGTGAAT
 551 ATGACCCTAG TCTCTGGGCT CCCTGACTCT GTTCATACTT GGAACAACTA
 601 TTGCCCATGG ATACTAAGCA TCACCACCAG CAGCAGCAGA TAACTATTCC
 651 TAAGACCCAA GGCACTGCAT TATGTACTTT ATATTTAATG CCTCATCAGT
 701 GCTTGCAACA GCCTCATGAA GCAGGAGCAG AAGGGGAAAC TGAGGCCCAG
 751 ATTAAGTGGC TTGTGCCAGG ACACACAAAG CAACTGCAGC ACTTCAGGTT
 801 CTATATCCAA ACTCCTATCC CTTAGGTGGC ACTTCCTCCT CTGCCCCCAT
 851 TATGAACTTG CAGCATGTGG AAAACCCCAA TCTGACTTCC CTCTAAGGGA
 901 ACTTGCCCAG AGAATCTAAG AGGGGAGGAA AGGAAGGCGT TCAGCCCTTA
 951 CAGGCAGGAG GTCAGCTCCT GAGTGGCTCA GATGCAGCCA CAGAGGGCCT
1001 GGCCGGTCTG AGGGTGACTG AGAGGCACCG AGGGCACTGT CCCTGAGTGC
1051 TGGAAAGGGC AGGTCTTTTA GGGTAGACAG CGGTTGATAT CATTTCCTGC
1101 CTGGCATTCT CACCTTCCAC ACCTCTCTCA CAGAATCTCC AAGTGTGGCT
1151 CTCCCAAGAG AGAGTGTCAG TCATCTACCT CCAGCTTCCT TTCCTTCCCA
1201 GGGGGAAGAG GGGACAGGGG GGCCCTAGTG GCTAAGAGCA TTGGTGAACT
1251 CAGGCAGACC TCAGTTCTGA ACCAACCCAG CTCTGCCATT TACTATCTGT
1301 GACTCTGAGC AAGTGCCTGA AGCCTTCTGT GCCCTATTTC CTGACATATT
1351 ATATATATAA AATACATATA TTATATATAG ACATATTTTA TATACATATT
1401 GAGGCATATT TTATAAACAT GTTTATAGAC ACATTTTTAT ATGCATATGT
1451 TATATACGTA TATAACATAT GTTATATATA ATGTATATAT TATACATATT
```

TABLE 2-continued

Genomic Repeats
(SEQ ID NO: 2)

```
1501 GTTATATTGT ATACATGTTA TATATGTTAT AGCATATATA GTACAAGTTA
1551 TATATAACAC ATACATTATG TTACATATAA TGTATATGTT ATATATGATA
1601 TATTATATAT AATTATATAT TATATAAAAC TGTTATATAT AATTATATAT
1651 AATATATAGT TGTTATATAT AATTATATAA TTGTTATATA TTATATACAA
1701 CATATAACAT ACATTATATA TTGTTATATA TAATATAATA TATACATATA
1751 TAACATATGT ATAACTTTTA TGTTATACAT AATGTATATA ACATATATGT
1801 GTATGTGTGA TGTACATAAC ATATCTGACA TTAACATATA ACATATGATA
1851 TAACAATATT ATATGTTATA ACATAATATA TGTTATAATA TAACAATATT
1901 ATATGTTATA ACTTATACTG TCATATGTAA CATATACATA ATATTTTATA
1951 AATCAGTTTA ATATACATTA TGTTACATAT AATGTATGTT ATATATGATA
2001 TATTATATAT AATTATATTA TACATAATTG TTATATATAA TGCATACATT
2051 GTATTTGTTA CGTATTATAT GCAACATATG GGGATCCTCT AGAGTCGGAC
2101 CAGCGGCAGC AGCTGCCTGC CTTTTNNNNN NNNNNNNNNN NNNNNNNNNN
2151 NNNNNNNNNN NNNNNNNNNN NNNNNNNNNN NNNNNNNNNN NNNNNNNNNN
2201 NNNNNNNNNN NNNNNNNNNN NNNNNNNNNN NNNNNNNNNN NNNNNNNNNN
2251 ATATACATAC ATAACATATG TATAACTTAT ATGTTATATA TAAGTATATA
2301 ACATATATGT GTATGTGATG TATATAACAT ATCTGACATT AACATATAAC
2351 ATATGTTATA ATATGACATA TTATATATAT TACATATAAC GTATATCATG
2401 TATAATATAA TGTGTATATA TAATATATTA AAGTATATAA GTATAAATAC
2451 ATGTAATATT TAAATATATA TTATATATAG TATACATGTG GATACATACA
2501 ACTTCTACAT ATACCTAGTA TATATTCTAT ATATAAACAG TCCATGAATT
2551 ACAATGATTC AACTTATGAT TTTTCAAACT TTGTGATAAT GCCATAGCAA
2601 TATGCATTCA GTAGAAAGCA TACCTTCAAC ACCCATGCAA CCATTCTGTC
2651 ATTCACTTTC AGTACAATAT TCAATAAATT ATATGAGATA TTCAACAGTT
2701 TATTATAAAA TAGGCTTTGT GTTAGGTGAT TTTGCCCACA TGTAGGCTAA
2751 TGTAAGGGTT CAGAGCATGT TTAAGGTAGG ATAGGCTAAC CTATCATGTT
2801 CTGTAGGTTA GGTATAGTCG ATTTTTATTT TTATTTTTAT TTTTGAGACA
2851 GAGTCTTGCT CTGTCACCCA GACTGGAATG CACTGGTGCG ATCATAGCTC
2901 ACTGCAGCCT TGAACTCCTG GGCTCAAGTG ATCCTCCTAC CTCAGCCTCC
2951 TGAGTAGCTG GGACTACAGG TGTGTGCCAC CACACCTGGC TATTTTTTTT
3001 TTAATTTTTT TTTTTTGTG GAGAGGAGGG TCTTGCCATG TTGCCCAGGT
3051 GGCCTTGAAC TCCTGGGCTC AAGGAATCCT CCCACCTTGG CCTCCCAAAA
3101 TCCTGGGATT ACAGGTGTGA GCCATCACGC CCGGCTACAG GGCATTTTTG
3151 ACTTATGACA TTTTCAGTTC ACAATGGATT TGTCAGGGCT GGGCATGATG
3201 GCTCACACCT GTCATCCCAG CACTTTGGGA GGCTGAGGCA GGTGGATCAC
3251 TTGAGGCCAG GAGTTTGAGA CCAGGCTGTC CAAATGGCAA AATCTTGTCT
3301 CTACTAAAAA TACAAAAATT AGCCAGGCGT GGTGTGACAA CTGTAGTTCC
3351 AGCTACTCGG GAGACTGAAG CGTGAGAATC ACTTGAACTT AGGAGATGGA
```

TABLE 2-continued

Genomic Repeats
(SEQ ID NO: 2)

```
3401 AGTTACAGTG AGTCAAGATC ACACCACCGC ACTCCAGCCT GGATGACAGA
3451 GCAAGACTCT TGTCTCCAAA AAACAAAAAA CAGGCTGGGT GCATGGCTCA
3501 TGCCTGTAAT CCCAGCAGTT TGGGAAGCTG AGGCAGGTTT ATCACCTGAG
3551 GTCAGTAGTT CACGATCAGC TTGGCAAACA TGGAGAAAAC CCATCTCTAC
3601 TAAAAATACA AAAATTAGCT GGATGTGGTG GTGGGTACCT GTAGTCCCAG
3651 CTACTCGGGA GGCTGAGGCA GGAGAATGGA TTGAACCTGG GAGGCAGAGG
3701 TTGCAGTGAG CCAAGATCAC ACCATTGAAC TCCAGCCTGG GCAACAGAGT
3751 GAGACTCCAT CTCCAAAAAC AAAAGAAAGC AAAAACAAAA AATAAAATA
3801 AAAAACCTGT GTTTATCAGG ACATAATACC ATCATGAGTC AAGAAGCATC
3851 TAAATGTACA TGGTAGTTAT ATAAAAATAG TTATATAGTT ATATACAATA
3901 GTTATATATA AACCAGTTTA ATATATGTTA AGTAGAGGTA TATGGTAGTT
3951 ATATAAAAAA TAGTTATATA ATAGTTATAG AGTTATATAA TTATATAAAA
4001 TAGTTATATA TAAACCAGTT TAATATATGT TAGGTAGAGG TATAATAATA
4051 TATATTGTAT ATACTATATA ATATAGTAAT GTATAAAATG CAAAACGATA
4101 TCATATATTT CTATATTAAG TTTATATTTA CAGATCTACA TTTTATATAT
4151 TTTATGTTAT ATACAATTGT GTTATACATA ATATAATTAG TATAGTACTG
4201 ACTTGGGGAA TTGAGCAGTA CCAACCCATA GGGATGTTTG AGGATGAAAA
4251 TATGTGATTA TGAATACAAA ATGCTGGGCC TGCTGCATAG GAAGTATTTA
4301 ATAAATGGTA GTTGTTACTA TAAAGTCGTT CCTACTATAG AGCTACTCAC
4351 AACCTGGGAC ATAGGGAAAG AGCCCGTTTC CCTCTAATCA CTCAATAGTG
4401 GGTGGCTAGG TAGGTGAGTC CACATCCTGT GGCCGGGAAC AGGTGCTGAG
4451 ACATGAAGAC CTTCTGACTG CATGTTGGAC CAGCCACAGT TTCAGACGGA
4501 CCAGCCAAAA AGGGCATTTT CCCCAAGCCA TTTAGCTCCC TTGAGTCTCA
4551 TAACAAATCT CCTAGACCCT GCTGGTCCAT AGGATCTAGA GAGGATGACT
4601 TGAACCTTCT GATCCCACCA TTTGAAAACG CCATGCCATG GGCACCAGTA
4651 GGAGGGCCAC TGCTACGTGC ACCAGTACAA GGGCCACTGC CATGGATTAC
4701 AGATTAACCC TAAGTATAGC TGTCGCACAC CTAGTACTTC AGGAGGCTTA
4751 TTCGGGGCCA TGCAGATCCC TGGCATTATT ATCCTAGGAT CCTACACCAA
4801 GCAAAGCAGG AGCTGCCCCT CCTCATAAAC CCATAAGCCC TCCTCTTGAG
4851 CAAAGCAGCT GGGAAGGCCA GAAGTTATTC AAGCTCCCCT CTGCCCCGGT
4901 TCCAAAGACA GACAGCTCAA GCCTACATGC AGCAAACCCT ATAAAAGTGT
4951 CACCTCTTGG CATTTCTGCC ATGGTAATGC TTTCTGCTTC CACTAATAAT
5001 CCTAGTAATT TGTTTATGGT GGGCATCTCT CTGATGAGAA CCACATTCTT
5051 TTTTTTTTT TTTTTTTTT TTGAGATAGA GTCTCACTCT GTTGCCCAGA
5101 CTGGAGTGCA GTGGCGCGAT CTCGGCTCAC TGTAACCTTT GGCTCCTAGG
5151 TTCAAGCAAT TCTCCTGCCT CAGCCTCCCA AGTAGCTGGG ACTGCAGGCA
5201 CGTACCACCA TGCCCAGCTA ATTTTTGTAT TTTTAGTTGA GACGGGGTTT
5251 CACCATGTTA GCCAGGATGG TCTCAATCTC TTGACCTCAT GATCCACCTG
5301 CCTTGGCCTC CCAAAGTGTT GGGATTACAG GCATGAGCCA CCATGCCTAG
```

TABLE 2-continued

Genomic Repeats
(SEQ ID NO: 2)

5351 CCTGAGAGCC ACATTCTTGT TAACCACAAT TTTCTCAGAG TCTGCATTAG

5401 GGGTTGACAA AGAGTGGAAA GGAAGGACAA AAGGATGGAG AGGTGGATGG

Exon R3

5451 ACTAAGCATA TGTAGGTTCT TACCCAGGCC AGAGAAGGAT AGCTCAGCCA

5501 CGGCAGTGGA TGCCATCTGC ACACATCGCC CTGACCCTGA AGACCTCGGA

5551 CTGGACAGAG AGCGACTGTA CTGGGAGCTG AGCAATCTGA CAAATGGCAT

5601 CCAGGAGCTG GGCCCCTACA CCCTGGACCG GAACAGTCTC TATGTCAATG

5651 GTGAGCAGCT GTGATGTGGT TGGAGGCTCT TCCTCCTTGC TGAGCAGCCT

5701 GTAATCACTG GCTTGAGGTC ACACTCACTG TCAGGCAATT GAAAATTTGG

5751 TCCTGTGCTC TACATGGGAT GACTAATTTC CGGACTTCAT GGTATCTTTT

5801 TTTTTTTTTT TTTTTTTTTG AGATGGAGTC TCGCTCTGTC ACCAGGCTGA

5851 GGTGCAGTGG CATGATCTCA GCTCACTGCA ACCTCCGCCT CCCGGATTCA

5901 AGCAATTCTC CTGCCTCAGC CTCCTGAGTA GCTGGGACTA CAGGTGCATG

5951 CCACCACACC CAGCTAATTT TTGTATTTTT AGTAGAGACA GGGTTTCACC

6001 ATGTTGGTCA GGATGGTCTC AATCTCTTGA CCTTCTACTC CACCTTGCCT

6051 TGGCCTCCCA AAGTACTGGG ATTACAGGCT TGAGCCACCA CACCTGGCCA

6101 GGACTTCATG GTTTCTTCAT CATCATGGAA TGAATTCCAT CAGGGCATTC

6151 TTCCCTGATG TGAGGGCACT GATAGGAAAT CTTTAATGGT CCCTGCTGCA

6201 TGAAACTGCT TCCATTGCAC CAGGGTAGCC CTGACCCCTA TTTGGTCCCC

6251 CACATCTCCT TGTAACTTAC CCACACTCCT CCCTCCTTCT CTGTGCAGGT

Exon R4

6301 TTCACCCATC GAAGCTCTAT GCCCACCACC AGCAGTGAGT ATTCAACTCA

6351 TGTCCACATG CCCATGATCC TACACCAAGC AAAGCAGGAG CTGCCCCTCC

6401 TCATAAACCC ATAAGTCCTC CTCTTGAGCA AAGTAGCTGG GAAGGCAGAA

6451 GTTATTCAAG CTCCCCTCTG CCCCAGTTTC AAAGACAGAC TCAGCTCAAG

6501 CCCACATGCA GCAAACCCTA TAAAAGTCTC ACCTCTTGGC ATTTCTGCCA

6551 TGGTAATGCT TTCTGCTCTC ACTAATGAGG ACTTCTCCTC AGCTCCTGGG

Exon R5

6601 ACCTCCACAG TGGATGTGGG AACCTCAGGG ACTCCATCCT CCAGCCCCAG

6651 CCCCACGAGT AAGTACCAGT CAATGGCATC TCTATTAGAG CATGCTATCT

6701 CTGTCATTTT TACTCAGATG AAGATGGAAA ATCATAGCAA ATCTACTGAT

6751 AGTGAGTGGA CCAACGAAAT TTGTTGGCCA CCTAGTGTGT ACCAGATCCT

6801 AGAGATACAG GAGGGAAAAC AAAACCAATA CAAAATTTCT GCTCTCAGTG

6851 AGCTTGTATT CTTGTCATGA TGATGATGTT GGTGGTGGTG CTGTTGATGA

6901 CGATGATGAT GATGATGATG ATGATGATGC TGGTGATACT GTTGATGGTG

6951 ATAGTGATGT TGATGACAAT GATGATGATG ATGATGTTGA AGAAAATGAT

7001 GCTGGTGATG GTGGTGGGGG TTATTATGGT AATAATGATA TGTTGAGTGT

7051 GACGATGATG GTGGTGGTGT TGATGATGAT GATGATTATT ATGCTAGTGA

TABLE 2-continued

| Genomic Repeats (SEQ ID NO: 2) |
|---|

| | | | | |
|---|---|---|---|---|
| 7101 CATTGATGAT | GGTAATGGTG | ATATCAACGA | CAGTGACAAT | GATGGTGATG |
| 7151 AGGATGATGT | CGGTGATGGT | GGTGGGGTTA | TGATGGTAAT | GATATGTTGA |
| 7201 ATGTGATGAT | GGTGATGATG | ATATTTGTGG | TTCATGATGG | GGATTGTCAT |
| 7251 GGTGGTGCTG | GTGGTACTTG | TGATGACAAT | AATGATAATA | ATGATGACAA |
| 7301 TGATAGTGAT | GATGGTGATG | GTGATAATAA | AGATAACAGA | TATCACCTTA |
| 7351 CAATATTGAG | CACTAAATAT | GTACCAAGAG | CTATGCTCAG | TATCTAACTA |
| 7401 CTATTATATA | ATCTACTTTA | GAAAATGAAT | TGTATCATAG | ATAAGAAAGG |
| 7451 CGTGGAAAAT | ATTTATTATG | TCACTCAATT | TAATTGCTGC | ATATGGTTAT |
| 7501 TACAAAGTGC | TATTCTCTCT | ACTTTGAACA | TAATGTTTAT | TTCACACTCC |

| Exon R1 |
|---|

| | | | | |
|---|---|---|---|---|
| 7551 CACTATAGCT | GCTGGCCCTC | TCCTGATGCC | GTTCACCCTC | AACTTCACCA |
| 7601 TCACCAACCT | GCAGTACGAG | GAGGACATGC | GTCGCACTGG | CTCCAGGAAG |
| 7651 TTCAACACCA | TGGAGAGTGT | CCTGCAGGGT | CTGGTTAGTG | TCCTGCCCTC |
| 7701 CACACTCTGC | CCTGCTCATG | ATACCCAGTC | CCTCTTACAT | CATCCATGCC |
| 7751 AGGGCAATGG | AAGAATATCA | AACCCAACTC | ACTTTTGCCC | CAAGAGATGC |
| 7801 AAGCCTCAGC | CAGGAGCGGT | GGCTCACGCC | TGTAATACCA | GCATTTGGGA |
| 7851 GGCCAAGGCG | GGTGGATCAC | CTGAGGTCAG | GAGTTTGTGA | CCAGCCTGGC |
| 7901 CAACATAGTG | AAACCTCATC | CCTACTAAAA | TACAAAAATT | AGCCAAGCAT |
| 7951 GGTGGTGCAT | GCCTGTAATC | CCAGCTACTT | GGGAGGGTGA | GGCAAGAGAA |
| 8001 TCACTTGAAT | CAAGGAGGCA | GAGGTTGCAG | TGAGTCAAGA | TCATGCCACT |
| 8051 TTACTCCAGC | CTAGGCAAAA | AGCGAAACT | CCATCTCACA | AAAAAAGAA |
| 8101 AAAAGAGAG | AGATGCAAGC | CTCCCCCACC | AAGGCCAGCC | CTGCCCACCT |
| 8151 CACTTCTGCC | TGGCTCTTAC | ATAAAACTTA | GCCCTCCTAC | TCACTGCCCT |

| Exon R2 |
|---|

| | | | | |
|---|---|---|---|---|
| 8201 CTCCCTCCTC | CACAGCTCAA | GCCCTTGTTC | AAGAACACCA | GTGTTGGCCC |
| 8251 TCTGTACTCT | GGCTGCAGAT | TGACCTTGCT | CAGGTGAGAA | CTTAGAATTT |
| 8301 CCAGCCTGGC | TGCCCCACTT | GTACTCACTC | CAAAAGACTT | TGCACTGCTT |
| 8351 CCTTGCTGCA | CTTCCTAGGG | ATATCCTCAC | CAAAGGTGGA | ATTCAGGAGT |
| 8401 CACAGGCTTC | AGGATCAGTG | TGTTTCCTGA | CAGTAACACC | CCTACACTCC |
| 8451 ACCTCAACAG | AGAGAATCTG | CATGGCCCAT | CATCAGGATT | GAGCCTCTCC |
| 8501 CTTTATCATC | CCTCTGAATT | CCCTCCATTC | CCTGTGCCTC | CCTTTCCTTT |
| 8551 ACATGTTAAA | TTCTGTCCCC | AGGATTTCTT | TCAGGACAAT | CATGCCTTAT |
| 8601 CCACGTGATT | TCATCCTCAT | TTCGAGCTCT | TCACTGGGCT | CAAGTCCGGC |
| 8651 TCCCCGTCCC | GTCCATGAAA | GTGTCAGTTT | CATCTTGTCA | CTGTATCCGT |
| 8701 GACTCCACTC | ACAGTCCTCA | GCAAGCCAAT | AGTCCATGCA | CTAAGAGTCG |
| 8751 ATGTGGCTTC | TCACCTCTTT | CCCAGGTTTC | TCATTTCTCT | GGTCCTTGCT |
| 8801 GTCCTTCCCT | CAGCAATCGC | AAGACCCTTC | CTAGATAAAC | TTTTCATTGT |

TABLE 2-continued

Genomic Repeats
(SEQ ID NO: 2)

Exon R3

8851 GATTTTTCCC ACTGACCCTC CCCAGGCCCG AGAAAGATGG GGCAGCCACT

8901 GGAGTGGATG CCATCTGCAC CCACCGCCTT GACCCCAAAA GCCCTGGACT

8951 CAACAGGGAG CAGCTGTACT GGGAGCTAAG CAAACTGACC AATGACATTG

9001 AAGAGCTGGG CCCCTACACC CTGGACAGGA ACAGTCTCTA TGTCAATGGT

9051 GAGTGGCTGT GATGTGGTTG AAATCTCTTC CCCCTTGCTG GGCAGCCTCT

9101 AATCTCTAAC TAGAGATCAC ACTCCCTGCC TGGCCTTTGA AAATTCTGTC

9151 ATGTGCTCTA CATGGGATGA CTAAGGTCTG GACTTCATGG TTTCCTTACC

9201 ATCATGGACT GTGTTCCCTC AGGGCATTCT TTCCTGATGT GAGGATGCTG

9251 ATAGAAAATC TTCAATTGTC CCTGTACCAT GAAACTCGGT TCATTGCACC

9301 AGGGTAGCAT TGACCTCCAT TTGGTCCCCC ACCTCTCCTT GTCTCTTACC

Exon R4

9351 CACTCTCCTC CCTCCTTCTC TATGCAGGTT TCACCCATCA GAGCTCTGTG

9401 TCCACCACCA GCAGTGAGTA TTCAACTCAT ATCCACATGC CTCGGTTCCT

9451 ACACCAAGAG GAGCAGGAGC TGGCCCCTCC TCATAAACCC ATTAAGTCCT

9501 CTTCATAAGC AAAGGATTTA GGAGGGCAGA AGTTATTTAA GTGTCCCTCT

9551 GCCCAGCTCA AGAGACCGAC CCAGCTCAAG CTACACATGC AACAAACCCC

9601 ATAAATAGTC TCCCCTCTTG CCATTTCTGC CAAGAGAGTG CTTTATGCTT

Exon R5

9651 TCACTGATGA GAACTTTTCC TCAGCTCCTG GGACCTCCAC AGTGGATCTC

9701 AGAACCTCAG GGACTCCATC CTCCCTCTCC AGCCCCACAA GTAAGTATCA

9751 GTCAATGACA TCTCTATGAG AGCATACCTG ATTAGTGTAA ACATCTCTGT

9801 CATTTTCACT CAAATAAAGA TGGAAAATCA TAGTAAATCT AGTGATACTG

9851 AGTGGACAAA TTTGTTTGTT TGTTTTTTCT CATCCTTTTC ACTTTTTTTA

9901 TTATACTTTA AGTTTTAGGG TACATGTGCA CAATGTGCAG TTTAGTTACA

9951 CATGTATACA TGTGCCATGC TGGTGTGCTG CACCCATTTG CTCGTCATTT

10001 AGCATTAAGT ATATGTCCTA TGCGATCCAA GCCCACGCGC CGCACCACGT

10051 GCAACAGTTT CACAGATTGG ATGGTCCGAT ANNNNNNNNN NNNNNNNNNN

10101 NNNNNNNNNN NNNNNNNNNN NNNNNNNNNN NNNNNNNNNN NNNNNNNNNN

10151 NNNNNNNNNN NNNNNNNNNN NNNNNNNNNN NNNNNNNNNN NNNNNNNNNN

Exon R1

10201 CTTCACCATC ACCAACCTGC AGTATGAGGA GGACATGCAT CGCCCTGGAT

10251 CTAGGAAGTT CAACACCACA GAGAGGGTCC TGCAGGGTCT GGTTAGCACC

10301 CTGCCCTCTT CACTCTCCCC CGCCCTGGAT GCCGAGCCCC TCATACAACA

10351 TTCATGCCAG GGCAATGGAA GAATATCGCA CCAACCTTGC CCTCATCCCC

10401 AGAGATGCAA GCCTCACCCA CTGAGGCCAG CCACTCTCAT GGGTGTCTGC

10451 CCCACCCACC TCACTTTTGT CCCCACACAG GGACCTTAGC CCTCCTACTT

TABLE 2-continued

Genomic Repeats
(SEQ ID NO: 2)

Exon R2

10501 ACCTCTCTCT CCCTCCCCCA CAG<u>CTTAGTC CCATATTCAA GAACACCAGT</u>

10551 <u>GTTGGCCCTC TGTACTCTGG CTGCAGACTG ACCTCTCTCA GGTGAGACCT</u>

10601 TAGAAGATCC AGCCTGGCTG CCCCAGTTGT TCCCACTCCA GTAGATTTTG

10651 CTCTGCTTCC TTGCTGCACC TCCTAGGGAT ATCCTCACCA AAAGGGGAAT

10701 TCAGGAGTCA CTGGCTTCTG GACCAATGTG TTTCCTGATA GTAACACTCC

10751 CACACCTCAC CTCAACAGGG AGAATCTGCA TGGTCCATCA TCAGGATTGA

10801 GCCTCTATCC TGATCATCCC TCAGAATTCC CTGCCCCTCC CTTTCATTTA

10851 GGTGTTAAAT TCTGTCCCCA GAATTTCTCT CAAGACAATC ATGCCTCATC

10901 CAAGTGCTTT CATCCCTGTT TCTAGCTCTT CACTGGTCTC AAGTCTGGGC

10951 TCTCCTGTCC CCATGCTATG AGAATGCAGG TTTCACCTTG CACTTTTATA

11001 AGCATGGTTG TATCTGTGAC TCTGTGCACA GTCCCAAGCA AGCCAGTAGT

11051 CCATGCACTC AGAGAATCTA AGTGTAGCTT CTCACCTCTT TCCCAGGTTT

11101 CTCATTTCCT CTGGTTCTTT ACTGTCTTTC CATCAGCAGT CTCAGGACAC

Exon R3

11151 AACCTAAGTA ATCTTTTCAT AGTCATTCTC CCCACCTACC TTCCCCAGGT

11201 <u>CTGAGAAGGA TGGAGCAGCC ACTGGAGTGG ATGCCATCTG CATCCATCAT</u>

11251 <u>CTTGACCCCA AAAGCCCTGG ACTCAACAGA GAGCGGCTGT ACTGGGAGCT</u>

11301 <u>GAGCCGACTG ACCAATGGCA TCAAAGAGCT GGGCCCCTAC ACCCTGGACA</u>

11351 <u>GGAACAGTCT CTATGTCAAT</u> GGTGAGCAGC TGTGATGTGG TTGGAGTCTT

11401 TTCCTTCTAG AGTCTGGAAA GAATCTAATC TGTGGCTTGA AGTCACACTC

11451 CCTGCCTGGC CATTGAATAT TCTGTCATGT GGTGTAGATG GGATGACAAA

11501 GTTCTGGACT TCACAGTTTC TTCATTGTCG TGAACTGTGT TCCCTCAGGG

11551 CACTCTTCCC TGTTGTGAGG ATACTGATAG GAATTCTTTA ATGGCCCCAG

11601 TCCCATGAAA CTCATTGTCC CATGAAACTC ATTTAATTGC ATTGGGATTG

11651 CCATGACCTT ATTGTGTCCC TCGTATCTCC TTAACGCTTA CCAAGTCTCC

Exon R4

11701 TCCCTCCTTC TCTATGCAGG <u>TTTCACCCAT CGGACCTCTG TGCCCACCAC</u>

11751 <u>CAGC</u>AGTGAG TATTCAACTC ATGTCCACAT GCCCCTGATC CTACATTAAG

11801 TGGAGCAGGA GCTGGCCCCT CCTCTTAAAC CCATAAGTCC TCCTCTTGAG

11851 CAAAGGAGCT GGGAAGGCAG AAGTTATTGA AGCTCCCTTC CACCTAGCTC

11901 CAAAGACAGG CCCAGCTCAT GCCCGTATGC AGCAGACCTC ATAATAGTCT

11951 ACCTTCTTGC CATTTCTGCC ATGAGATTAT TTTCTGCTTT CACTGATGAG

Exon R5

12001 CACTTTTTCT CAGCT<u>CCTGG GACCTCCACA GTGGAC</u>NNNN NNNNNNNNNN

12051 NNNNNNNNNN NNNNNNNNNN NNNNNNNNNN NNNNNNNNNN NNNNNNNNNN

12101 NNNNNNNNNN NNNNNNNNNN NNNNNNNNNN NNNNNNNNNN NNNNNNNNNN

TABLE 2-continued

Genomic Repeats
(SEQ ID NO: 2)

Exon R1

12151 ATTTTCAATT CCCACTAC<u>AG CTGCTGGCCC TCTCCTGGTG CTGTTCACCC</u>

12201 <u>TCAACTTCAC CATCACCAAC CTGAAGTATG AGGAGGACAT GCATCGCCCT</u>

12251 <u>GGCTCCAGGA AGTTCAACAC CACTGAGAGG GTCCTGCAGA CTCTGGTTAG</u>

12301 TGCCCTTCCC TCCTCACTCT GCCCAGCCCC AGATATCCAG TCCCTTCTAC

12351 ATCATCCATG CCAGGGTGAT GAAAGAAGAT AGCAACAACT TCCCCCCTTC

12401 CCCCCAAGAG ATGCAAGCCC CACCCACAGA GACCAGTCCT GCTTATTGGT

12451 GCCTGCTCCA CCCACCTCAC ATCTGCCCCG ACACACACAC ACCTTAGCCC

Exon R2

12501 CACTACTCAC CTCCCTCTCC CTCCTCTACA G<u>CTTGGTCCTATGTTCAAGA</u>

12551 <u>ACACCAGTGT TGGCCTTCTG TACTCTGGCT GCAGACTGAC CTTGCTCAGG</u>

12601 TGAGACTTTA GAAGAGCCAG CCTGGGTGCC CAAACTTGTT CCCACTCTAA

12651 AAGACTTTGC ACTGCTTCCT TGCTGCACTT CCTAGGTATA TCTTCACCAC

12701 AAGGGGAATT CAGGAGTCAT TGGCTTGAGA ACCAGTTGTT TCCTGATAGT

12751 AACACCCCCA TGCCCCAACT CAACATGCAA ATCTTCATG GTTCATCATC

12801 AGGATTGAGA CACTACCCTG ATTACCCATC TGAATTCCCT CCTTTCCCTG

12851 ACCCCTCCCT TTCATTTAGG TGTTAAATTC TGTCCCCAGG ATTTCTCTCA

12901 AGATAACCAT GCCTCATCCA CATACATGCA TCCGCCTTTC AAGCTCATCA

12951 CTAGTCTGAA GCTCTGGGTT CTCCTGTTCC CATGCCATGA GAATGCAGGT

13001 TTCACCTTGC ACTTTTATAA AAATTATTAT ATCCATGACT CTGCTTGCAG

13051 TCCCAGACCA AGATAGTGGT CTATGTACTC AGATAATCTA AGTGCAGATT

13101 CTCACCTCTT TCCCAGATTT CTCATTTCCT CTGGTTCCTT GATATGTTTC

13151 CCTCAGCAAT CTCAAGACAA GTCCTAGGCA ATCTTTTCAT TGTCATTCCC

Exon R3

13201 CCTCCTACCT TCCTCAGGT<u>C CGAGAAGGAT GGAGCAGCCA CTGGAGTGGA</u>

13251 <u>TGCCATCTGC ACCCACCGTC TTGACCCCAA AAGCCCTGGA GTGGACAGGG</u>

13301 <u>AGCAGCTATA CTGGGAGCTG AGCCAGCTGA CCAATGGCAT CAAAGAGCTG</u>

13351 <u>GGCCCCTACA CCCTGGACAG GAACAGTCTC TATGTCAATG GT</u>GAGCAGCT

13401 GTGATATGGT AGGGGTCTCT TCCTCCTGGC TGTGCAACCA TCTAATCTCT

13451 GGCTTGGGGG CACACTCCCT GCCTGGCCAT TGAAAATTCT GTCACGTGCT

13501 CTACATGGGA TGACTAAGTT CTGGACTTCA TGGTTTCTTT GTTATCATGA

13551 GAGGCATTCC CTCTGGGCAC TCTTCCCTGT TGTGAGGATG CTGATAGGAA

13601 ATCTTTAATG ACCCCTGTCC CATGAAACTC ATTTAATTGC ACCAGGGTAG

13651 TCCTGAACTC TATCGCGTCC CCCACATCTC CTTAACCCTT ACCCAGTCTC

Exon R4

13701 CTCCCTCCTT CTCTATGCAG GT<u>TTCACCCA TTGGATCCCT GTGCCCACCA</u>

13751 <u>GCAGCA</u>GTGA GTATTCAACT CATGTCCATG ATGCCCCTGA TCCTACATCA

13801 AGTGGAGCAA GAGCTGGCCC CTCCTCTTTA ACCCATAAGT CCTCCTCTTG

13851 AGCAAATGAG CTGGGAAGGC AGAAGTTACT CAAGCTCCCC TCTGCCCCAG

TABLE 2-continued

Genomic Repeats
(SEQ ID NO: 2)

13901 CTCCAAAGAC AGACCCAGCT CAAGCCCACA TGCAGCAGAC CTCATAATAG

13951 TCTATCTTCT TGCCATTTCT GCCATGAGAG TGCTTTCTGC TTTCACTGAT

Exon R5

14001 GAGGACTTTT TTCAGCTCCT GGGACCTCCA CAGTGGACCT TGGGTCAGGG

14051 ACTCCATCCT CCCTCCCCAG CCCCACAAGT AAGTACCAGC CAATGGTATC

14101 TGTATTAGAT CATGCCTGAT GAATGCAAAC ATCTGTGCCA TTTTCAGTCA

14151 AATGAAAATG GAAAATCATA ATAAATCTAG TGATACTGAG TGAACCAAAA

14201 AAAATGTATT GGCCACCTAC AGTGTACCAG ACCCTAGGGA TATAGCAAGG

14251 AAAATAGAAC CAATAAAAAC ATCTCTGCCC TCAGTGAGCT TGTGTTCATG

14301 TGATGATATG ATGGTGGTGG TGGTGGTAAT AGTAATAATG ACATATTCAG

14351 TTTGATGATA ATTTATGATT ATGGTGTTGC TGTTGATGAT GGTGGTGGTG

14401 ATGTTACTGA CAATGATGGT GACGGATCTT TGAGGATATT GTCCGTGATG

14451 GTCGTGAAGA TTATGATGAT AATGATGATG TGTTAAGTGT GATGATGATG

14501 ATGATCTGTG GTGATGCTGT TTAGGATGCT GTTCCGTGGT ACCGATGATA

14551 TTGATGTTGG TCGTGGTTAT GTTGTATGAC AATGACAATG ATGGTGATGA

14601 GGATAATCGC CAGTGATGGT GTGGGTTTAT GATGATGATG ATGTGTTGAA

14651 TGTGGTGATG ATAATGTTCG TGGTGGTCGT GATGGGCATT ACTATGGCAG

14701 TGATGGTCAT AATAATGATG GTGATGGTGA CAATGATAGC AAGGATGATG

14751 ATGGCAATAA AGATAGTACA TAACATCAGA CAATATTGAG CTCTGAATAT

14801 GCACCACGAG GAGTGCTCAG CATCTAAATA CTATTATATA ATATATTTTT

14851 GTAAAAATAA ATTGTATTGT TTTAGGCAAG GGAAGCATGG TAAATATTTT

14901 GTCACTCAAT TTAAATTCTG CATATGTTTA AAGATAAGTC TATTGCAAAC

14951 TCCTATTTTC TCTACTTTGG ACATAGTGTT TGTTTCCCAC CTCCACTACA

Exon R1

15001 GCTGCTGGCC CTCTCCTGGT GCCATTCACC CTCAACTTCA CCATCACCAA

15051 CCTGCAGTAC GAGGAGGACA TGCATCACCC AGGCTCCAGG AAGTTCAACA

15101 CCACGGAGCG GGTCCTGCAG GGTCTGGTTA GTGCTCCACC CTCCTCACTC

15151 CGCCCCACCC CAGAGAGTCA GTACCTCCTA CATCATCCAT GCCAGGTGAT

15201 GGAACAAGAT CATACCCACC TCACCCTTGC CCCAAGAGAT GCAAGCCATG

15251 CCCATTGAAA CCAGCCCCAC TCACTGATGC CTGTTACTGC CCCACCTGAC

15301 TTCTGCCCTA CACACCCACA CACGCAACTT AGCCCTCCTA CTCATCTCCT

Exon R2

15351 TCTCCCTCCT CCACAGCTTG GTCCCATGTT CAAGAACACC AGTGTCGGCC

15401 TTCTGTACTC TGGCTGCAGA CTGACCTTGC TCAGGTGAGA CCTTAGAAGA

15451 TCAAGCTTGG CTGCCCCACT TGTTNNNNNN NNNNNNNNNN NNNNNNNNNN

15501 NNNNNNNNNN NNNNNNNNNN NNNNNNNNNN NNNNNNNNNN NNNNNNNNNN

15551 NNNNNNNNNN NNNNNNNNNN NNNNNNNNNN NNNNNNNNNN NNNNNNNNNN

TABLE 2-continued

Genomic Repeats
(SEQ ID NO: 2)

Exon R1

15601 NGTGTTAGTC TACTTTTGAA CACTGTTTAT TTCCCATCTT CACTATAGCC

15651 GCCAGCCCTC TCCTGGTGCT ATTCACAATT AACTTCACCA TCACTAACCT

15701 GCGGTATGAG GAGAACATGC ATCAGCCTGG CTCTAGAAAG TTTAACACCA

15751 CGGAGAGAGT CCTTCAGGGT CTGGTAAGAG CCCCACATAC CTCATTCTAC

15801 CGCCACTCAC CATGTTTAGT CCTGCCCACC TCACCTATTG CAGAGCATGG

15851 AAGATCTCAT CTACCTCATC TTGCCCCCAG ATATGCATAC CCCAACCACT

15901 GATGCCAGCC CCACCAACTG TTGCCAGCCC TGCCCACCTC CCTTCTACCA

15951 CACCCCTATG ACTTCAGTCC TCCCACTCAC CTCCCTCTCC CTCCTCCACA

Exon R2

16001 GCTCAGGCCT GTGTTCAAGA ACACCAGTGT TGGCCCTCTG TACTCTGGCT

16051 GCAGACTGAC CTTGCTCAGG TGAGAACTGA GAACAGCCAG TCTGACTGAT

16101 CTGAGCAGTT TGACCTGCTT CCCTTCTGCA CTCCCTGGAG ATGTCCGCAG

16151 CCAGGTGGAA TCCAGGAGGC AGTGGCTCTA AGACCAATGT GCTTCCTGTT

16201 CCCACCACCT CCCACCTCAA CTGAGAGATG CAGAGCCCAT CAGCAGGACT

16251 GAGCTTCTAC CTTGGTCATC CCTCTGAATT CCCTCCTTTC CCCTACCTGC

16301 CTTTCCACAA GTGGTTCAAT TCTGTTCCCA GGATTTCTCC CAAGAAAAAC

16351 ATGCCTCGTC CACTTGCTTT CATCCCCAAA CCTAGCTCTT CACCTGTCTC

16401 AAGTATGAGT TCTCCTTACC CCATGCTACA AGAATGCAGT TTCCACTTTG

16451 CAATTTTATA AAAATCCTTG CATCCATGAT TCTGCTCATA GTTGCTAAGA

16501 GTCAGTGCAC TCAGAGAATG GAAGTATGGC TTCTCACTTC TCTACCAGGC

16551 TTCTCATTTC CTCTGGCCCC CTCCTGTCCT GCCCTGTGGG ATCTCAGAAC

16601 CCCTCCCTAG GCAATCCGTG TATTGTCTTT CCCCAATCTT GCCCTCCCCA

Exon R3

16651 GGCCCAAGAA GGATGGGGCA GCCACCAAAG TGGATGCCAT CTGCACTTAC

16701 CGCCCTGATC CCAAAAGCCC TGGACTGGAC AGAGAGCAGC TATACTGGGA

16751 GCTGAGCCAG CTGACCCACA GCATCACTGA CTGGGCCCC TACACACTGG

16801 ACAGGGACAG TCTCTATGTC AATGGTGAGT AGTTGTGATG TGGTTGGAGT

16851 CTCTTCCTCC TTGCTGGGCA GCCTCTACTC TCTGCCTTGA GGTCACGCTC

16901 CCTGCCTGGC TATTGAATGC TCATCCATGT TGTCTGTATG TGATGGCTGA

16951 GGTTGGAACT TCATGGTTTC TATTTCATCT TGGACTGAGT TCATCCTCAG

17001 GATCTGCTTT CTGGATCTGA GGGTGCTGAT AGAGAATCTT CAATGGTTCG

17051 TGTTCTGGGA AATTCCTTCC ATTGCACCAG GGTACCCTGA CCCCTATATA

17101 GTTCCCCACC ACTCCCTTAA CCCTTACCCA CCCTCTTCCC TCCCTCTCTA

Exon R4

17151 TGCAGGTTTC ACACAGCGGA GCTCTGTGCC CACCACTAGC AGTGAGTATC

17201 CACTGATTTC CAGTGCTCCT GATCCTACAT CATGCAGGGC AAGAACTGAC

17251 CCCTCCTCAC ATGCCCTAT GTCCTCTATG AGCAAAGGAG CTGGGACAGC

17301 ACAAGTTACT CCCTTTCCCT TCTGGCCCAA GTCTCTTCAG AGAGAGACCC

TABLE 2-continued

Genomic Repeats
(SEQ ID NO: 2)

17351 AGCTCAAGCC CCACATGCAG CAAGGTCCAT AAATACTCCT ACCTGCTGGC

17401 ATTTCTGCCA TGAGAGGGTT CAACACTTTC ACTAATGAGG CCTTCTCCTC

Exon R5

17451 AG<u>TTCCTGGG ACCCCCACAG TGGACCTGGG AACATCTGGG ACTCCAGTTT</u>

17501 <u>CTAAACCTGG TCCCTCGGGT</u> AAGTACAAAT CAATCGCATC TCTGTTAGAG

17551 CATGCCTGAT GACTGTCAAC ATCTCTGCCA TTTTCACTTA AATAAAGATA

17601 AAAAATCCTA GTGAATCTAC GGATGAGGAG TCATCCAGCA AACTTAATTG

17651 AGTGCCTAGT TTCTGCAGGG CTCTAGGGAT AAGAAAGGGG ACACAAAACA

17701 GTTAAAAATA TCTGCTGCAA GAAAGCTTAT TTTATTGTGA GGGTGATGGG

17751 AGTTGGTGGT GGTGAAGTTA CTGGAGATGA TGACAATAAG AATGGTGATG

17801 CTAGTGATGA TGATGGTGAT AAGGATGATA ATTATGAAGA TGGTGGTGGT

17851 GATGATGATG ATGGTNNNNN NNNNNNNNNN NNNNNNNNNN NNNNNNNNNN

17901 NNNNNNNNNN NNNNNNNNNN NNNNNNNNNN NNNNNNNNNN NNNNNNNNNN

17951 NNNNNNNNNN NNNNNNNNNN NNNNNNNNNN NNNNNNNNNN NNNNNNNNNN

18001 NNNNNNNNNN NNNNNNNNNN NNNNNNNNNN NNNNNNNNNN NNNNNNNNNN

18051 NNNNNNNNNN NNNNNNNNNN NNNNNNNNNN NNNNNNNNNN NNNNNNNNNN

18101 NNNNNNNNNN NNNNNNNNNN NNNNNNNNNN NNNNNNNNNN NNNNNNNNNN

18151 NNNNNNNNNN NNNNNNNNNN NNNNNNNNNN NNNNNNNNNN NNNNNNNNNN

18201 NNNNNNNNNN NNNNNNNNNN NNNNNNNNNN NNNNNNNNNN NNNNNNNNNN

18251 NNNNNNNNNN NNNNNNNNNN NNNNNNNNNN NNNNNNNNNN NNNNNNNNNN

18301 NNNNNNNNNN NNNNNNNNNN NNNNNNNNNN NNNNNNNNNN NNNNNNNNNN

18351 NNNNNNNNNN NNNNNNNNNN NNNNNNNNNN NNNNNNNNNN NNNNNNNNNN

18401 NNNNNNNNNN NNNNNNNNNN NNNNNNNNNN NNNNNNNNNN NNNNNNNNNN

18451 NNNNNNNNNN NNNNNNNNNN NNNNNNNNNN NNNNNNNNNN NNNNNNNNNN

Exon R1

18501 NNNNNNNNNN NNNNNNNNNN NNNNNNNNNN N<u>GCTGCCAGC CCTCTCCTGG</u>

18551 <u>TGCTATTCAC TCTCAACTTC ACCATCACCA ACCTGCGGTA TGAGGAGAAC</u>

18601 <u>ATGCAGCACC CTGGCTCCAG GAAGTTCAAC ACCACGGAGA GGGTCCTTCA</u>

18651 <u>GGGCCTG</u>NNNN NNNNNNNNNN NNNNNNNNNN NNNNNNNNNN NNNNNNNNNN

18701 NNNNNNNNNN NNNNNNNNNN NNNNNNNNNN NNNNNNNNNN NNNNNNNNNN

18751 NNNNNNNNNN NNNNNNNNNN NNNNNNNNNN NNNNNNNNNN NNNNNNNNNN

18801 NNNNNNNNNN NNNNNNNNNN NNNNNNNNNN NNNNNNNNNN NNNNNNNNNN

Exon R2

18851 NNNNNNNNNN NNNNNNNNNN NNNNNNNNNN NNNNNNN<u>CTC AGGTCCCTGT</u>

18901 <u>TCAAGAGCAC CAGTGTTGGC CCTCTGTACT CTGGCTGCAG ACTGACTTTG</u>

18951 <u>CTCAGG</u>NNNN NNNNNNNNNN NNNNNNNNNN NNNNNNNNNN NNNNNAGAAT

19001 TCAGTCGACC TACCGGCTTT GATGATTGCT CAGTTGAACT TAGAAATGCA

19051 CTGTCTGCCC AATGGTCCAG TCTCATGAGT GTGACTCTTT TCTGCCTCTC

TABLE 2-continued

Genomic Repeats
(SEQ ID NO: 2)

19101 TTGGGTATCT GATCAAGATG GACTCAGGAA AAGTGCTCCA GATAACTGTC

19151 TCCAATATAA CACTGCCCCT GCCATCACAC CCAAATGACT GGAAGTTTCA

19201 CAGGGTCATC AGCAGGGATT GGACTTCCAC CCCGGCCATC CCTCTGAATT

19251 TTCCCTCTTT TCTCCCCACC TCCCTTGCCC TTAGGTGTTA AAATTCTCTA

19301 ACTAAGATTT CTCTCAAGAC AAATGTGCCT CATTCACTTG TTTAATTCCC

19351 AATTCCAGCT TGTCACCTGT CTCAAGTCTA GGCTGTCCTG TCCCCATGCC

19401 ATGAGAATGC AAGAACCACA CTGAAATGTT AGAAAAATTC TTTTATCCAC

19451 AAGTATGCTC ACCGTCCCAA GCTGGACAGT AGTCAGTGCA CTCAGAGAAT

19501 CTAAGTGTGG CTTCTCATCT GTGTACCAGG CTTCTCATTT CCTGTGGGCC

19551 CTTCTTGTCC TTCCCTCCGC AATCTTGGGA CTCCTCCCTA GACAAAACTT

Exon R3

19601 TATTATTATT CCCCTCACCT GCCCTCTCCA GG<u>CCTGAAAA GGATGGGACA</u>

19651 <u>GCCACTGGAG TGGATGCCAT CTGCACCCAC CACCCTGACC CCAAAAGCCC</u>

19701 <u>TAGGCTGGAC AGAGAGCAGC TGTATTGGGA GCTGAGCCAG CTGACCCACA</u>

19751 <u>ATATCACTGA GCTGGGCCCC TATGCCCTGG ACAACGACAG CCTCTTTGTC</u>

19801 <u>AATGGT</u>GAGC AATTGTGATG TGGTTGGAGT TTCTTCTTCC TTGCTGAGCA

19851 GGCCTCTACT CTCTGTCTTG AGGTCACTCT CCCTGCCTGG CCACTGGTCT

19901 TGGCCATGTT GTCTGTATTT GATGATTGAT ATGAACTTCA CCGTTTCTTC

19951 TTCATCTTGT ACTGGAGACC TTCATCCTCA GGACCTTCTT CCCTGATCTG

20001 AGTGTACTTG TATAGAATCC TCAAAGCCCA TGTTCCCTGA AACTCCTTCA

20051 ATTGCACCAT GGTAGCACTG ACCCCTTTTG GTCCCCCACC TTNNNNNNNN

Exon R4

20101 NNNNNNNNNN NNNNNNNNNN NNNNNNNNNN NNNNNNNNNN <u>TTCACTCATC</u>

20151 <u>GGAGCTCTGT GTCCACCACC AGCACT</u>NNNN NNNNNNNNNN NNNNNNNNNN

20201 NNNNNNNNNN NNNNNNNNNN NNNNNNNNNN NNNNNNNNNN NNNNNNNNNN

20251 NNNNNNNNNN NNNNNNNNNN NNNNNNNNNN NNNNNNNNNN NNNNNNNNNN

20301 NNNNNNNNNN NNNNNNNNNN NNNNNNNNNN NNNNNNNNNN NNNNNNNNNN

Exon R5

20351 NNNNNNNNNN NNNNNNNNNN NNNNNNNNNN NNNNNN<u>CCTG GACCCCCAC</u>

20401 <u>AGTGTATCTG GGAGCATCTA AGACTCCAGC CTCGATATTT GGCCCTTCA</u>N

20451 NNNNNNNNNN NNNNNNNNNN NNNNNNNNNN NNNGACTCCA GCCTCGATAT

20501 TTGGCCCTTC AGGTAAGTAC CAGTCAATGG CACCTCTATT AGAGTATGCA

20551 TGATGAGTGT CAACATCTCT GTCCTTTTCA CTCAAATAAG ATTAAAAATC

20601 ATAGCAAATT GTACGTGATG ATGAGTCACC CAACAAACTT CTTTGAGTAC

20651 CCACTCTCTG CCAGGCCCTA GAGATAAGGC AGGGAACACA AAAGAGGTAA

20701 AAATCTCTGC CCTCAGAGAG CTTCTTTTAT TTTGAGGATG ATGTGGGATA

20751 GTGGTGATGA TGATGTTGCT GGAGATGATT ACAATAATGA TGGTGATGCT

20801 TATGACCATG ATGTGATGAT GATGGTGATT ATGAAGATGA TGATGATGAT

20851 ATTGATGATG GTAGTGGTTT TGACAGTAAT GATGATGTGA TGATGATGAT

TABLE 2-continued

Genomic Repeats
(SEQ ID NO: 2)

```
20901 GATAGTGGTG GTGGTGATTA TGGGAAGGAT GACAGTGGTG GTGGTGATGG

20951 TGGTGGTTGT GGTGGTGATT GACAATGTGG TGGTGATATT GACAATGAGG

21001 ATGATGATGA TAGTGGTGGT GGTTATGATG GTTAAGGATG ATGTGATGAT

21051 GGTGTTGGTG ATCACGGTAC TAGTGGTGGT GATGTGGACC GTCATGGTTG

21101 TGGTTGTGGT GGTGATGGTG GTGATCATGA TGATAATGAG GATGATGGTG

21151 GTGATTGTCA TGATGGTAAG GATGAAACAG TGATGGTGTT GGTGACCATG

21201 TTCCTGGTGG TGATGGTGCA GGTGATGATG TGGATGATGA TGGTGATGGT

21251 GGTGGAGATG ATAGGGATTA TGAATATGGT TCGGGTCTCT GACTGGTGGT

21301 GGTGATGACA ATAATGAAAA TGATGGTCAC AGTGTTGGTG ATGATGATGG

21351 TGGTGATAAC AAAGGTAATA GATAGTGTCT AGTATTATGG AACACAGAAC

21401 ATCACCAAAG GTTATGCTCA GCATCTAACT ATTATTATTT AGCATGCTCT

21451 ATGAAAAACT TTGATCGTTA TAGTCAAGGG AGGCATGAAA ACCTTCTATT

21501 TTATCACTCT CTTTAAATCT GGTTGCATAT GTTTAGAAAT AAATCTATTA

21551 CAAACTCTTA AATGTTCTCT ACTTTGAAC ATAGTGTTTA TTTCCCACCT
```

Exon R1

```
21601 CCACTACAGC TGCCAGCCAT CTCCTGATAC TATTCACCCT CAACTTCACC

21651 ATCACTAACC TGCGGTATGA GGAGAACATG TGGCCTGGCT CCAGGAAGTT

21701 CAACACTACA GAGAGGGTCC TTCAGGGCCT GGTGAGAGCC CTGCCCACCT

21751 CACTCTGCCC TGCCCACCTT GTCTTGTTCC ACCTACGTCA CCCATTCCAA

21801 GGCATGGAAG AAGATCTCAC CCACCTCCCC TCACCTGAGA GATAGCCCCG

21851 CCCCCTGATT ACAGCCCCTT CCACCTTACA TCTTCCTCAC TTCTATGTCC
```

Exon R2

```
21901 TCAGCCATCT TACTCACCTC CCTCTTCCTC CTCCACAGGC TAAGGCCCTT

21951 GTTCAAGAAC ACCAGTGTTG GCCCTCTGTA CTCTGGCTGC AGGCTGACCT

22001 TGCTCAGGTG AGAACTGAGA ATAACCAGTC TGGCTACCCC AAGTGTTCCC

22051 AGGCCCAAGG AGTTTCATCA GCTTTCTTCC TTCCCTCCCT ATGGAAGTCC

22101 TCAGCACAAG TGGAATTCAG GCGTTGGTGG CTCCAGGATG AACATATCTG

22151 CTGATCCTAC CACCTCCCCC ATCAATCGAG AGAATTTGCA GGGCCCATCA

22201 GCCAGATCAG GCTTCTACTT TGGTCATCCT TCTGAATTTC TTACTTCTCC

22251 CTACCTCCCT CTCCTTCAGG TGTTAAATTC TCTTCCAAGG TTTCTCTCAA

22301 GATAAACATC CCCCATCCAC TTGCTTTCAT CCCCAATTCC AGCTCTTAAT

22351 ATTTCTCAAG TCTGGGCTCT CCTGTCCCCA TACCATGAGA ATGCAATTTT

22401 ATAAAATTCT TGTATTCCTG ACTCTACTCA CATTCCCAGG CTGCCTGGAA

22451 GTTGGTGCAT TCAGAGAATC TTAGTATGGC TTCTCACCTG TCTACCAGGA

22501 TTCTCATTTC CTCTGTCCCC TTCCTGTCCT GCCCCCAGGA ATCTCAGGAT

22551 GCCTCCCCAT AGGCAATCTA TTTAATGTCA TCCCCCTTAT CTGCCCTCCC
```

TABLE 2-continued

Genomic Repeats
(SEQ ID NO: 2)

Exon R3

22601 TAGGCCAGAG AAAGATGGGG AAGCCACCGG AGTGGATGCC ATCTGCACCC

22651 ACCGCCCTGA CCCCACAGGC CCTGGGCTGG ACAGAGAGCA GCTGTATTTG

22701 GAGCTGAGCC AGCTGACCCA CAGCATCACT GAGCTGGGCC CCTACACACT

22751 GGACAGGGAC AGTCTCTATG TCAATGGTGA GCGGCTGTGA TGTGGTTGGA

22801 GATTCTTCCT CTTTGCTGGA CAGCTTCTTA CTCTCTGACT TGAGGTCACA

22851 CTCCCTGACT GGCCATTGAC GTCTTGGCTA TGTTGTCTGT ATGTGATGAC

22901 TGATGTCTGA ACTTCATAGT TTCTTCATCT TGGACTGAGT TCATCCTCAG

22951 TACCTTCTTC CCTGATCTGA GGGTACTGAT AGAGAATCTT CAAAGGCCCC

23001 TGTTCCTTGA AACTTCTTCC ATTCCACTAG GGTATCTGTG ACCCCTATTT

23051 GATTCCCCAC CTCTCCCTTA ACCCTTACCC ACTCTCCTCC CTCCTTCTCT

Exon R4

23101 GTGCAGGTTT CACCCATCGG AGCTCTGTAC CCACCACCAG CAGTGAGTAT

23151 TCAACCGATG CTCCAGTAGC CCCAATTATA CACCAAGCAG GGCAGGAGCT

23201 GTCCTGTCTT CCTATGCCCC TATGTCCTCT TCATAAAGGA AGGGGCTGGG

23251 AGGGCACAAG TTATTCCCTT TCCCTTCTGG CCAGCTCCAG AGAGAGACCC

23301 AGCTCAGGCC CGATATGCAG CAAGGCCTGT AAATAGTTTT ATTTGCTGAC

23351 CTTTCTGCCA TGAGAGGCTT GGATGCTTCC CCTGAAGAGG GTTTCTCTGT

23401 AGCTCTTGGG ACTACCACAG TGGACCTGGG AAACTCTGGG GATCCACCCC

23451 TTCTACTGGT CCCTTGAATA AGTACCAGCC AATGGCACCT CTGTTAGAGC

23501 ATGGCTGATG AGTGTAAACA TCTCTTCCAT TATTCAGTCA AATAAAGATG

23551 GAAATTCTTT ATAAATCTAG TGATGATGAG CCAACCAACA AACTTTATTG

23601 AGCATTGTGA CAAGCCCTGG GGCTCTGCCA AATCCTGGGG ATATGGCATG

23651 GATCATGAAA CAATTAATAA TCTCTCCTCT CAGAGAGCTA TTTTTATGAT

23701 GATACTGATG GTGGCAATGA TGATGATGTT GATGGTGATT ATGACCATGA

23751 TGACAATGGT GATGGTGGTG GTGATGATGG TAATGATGAT GATGGTGATG

23801 TTGGTAATGA TGGTGGTGAT TATGACAATA ATGATGGTGA TGGTGACAGG

23851 GATGGTGATG ATTATGATGG TGGTGGTGAT AACAAAGTTA ATGGATAATA

23901 TATGAACTTA TTGGCTACTG AATATGCACC AAAGTGCTAT GCTCAGTGTT

23951 TAACTAGTAC TATTTAATAT GATTTCTAAA AAAAATCTTG AATTATTATA

24001 GGCAGAAGAA TCATGGGAAC CTTTTATTTT GTCACTCACT TTAAGTCCTA

24051 TTGCATATTT TTTAAGTCAA TTGCAAACAC AGTTTCTCTG CTTTGAACAT

24101 TGTGTTTATA TCCAGTCACC CCAATAGTGC ATAAACCTGC TGATTGGAGC

24151 AACTGTGTCT TACTCCCTTG TGCTTCCCTA GTATCTGCTT CAGGACCTTG

24201 TACATGGTAG ATCGACAGAT TTAGATCTAC AGGAAAATAT GGATTTTCCC

24251 AGGGAAGGAA GGAATGAAGT ATGCTTTCTT ATAATGTATG GAAACTTTCC

24301 TCTTCTGCCT TGGTTCAACT TTAGTGTCTG CCAGAGTTTA CACTGGAAAA

24351 CTATATGGCA TCTGCTCCAC TCCCTCATCC ATGACAGACA TCATTAATTG

24401 ATTGCAGCAT TCATGGCAGA CATCACCAAT TGATAATAGC ATTCATTTTC

TABLE 2-continued

Genomic Repeats
(SEQ ID NO: 2)

```
24451 TCTCAGTTCA AAACAGCTTC AGAATGGTTA CCAAAAAAAA AAAATTCAGT

24501 CGCTACCAAT TCAATTGGAG CTGACTCAGG ATTATGGGAC AGAATTCAAG

24551 AGAGTTAGGT TCCTTGATGA TGTGTAGTGG CTATTTGTTT TCCGGTCCAG

24601 GCTAATNNNN NNNNNNNNNN NNNNNNNNNN NNNNNNNNNN NNNNNNNNNN

24651 NNNNNNNNNN NNNNNNNNNN NNNNNNNNNN NNNNNNNNNN NNNNNNNNNN

24701 CTTTGTGCGG CAAAGTTCAG GGGCCCCAAA AATTTCTGTG CCCCAATCAT

24751 GGCGGACCTA GGTTTAGGCA CAAATTCCAG GGATTAAGTC CCTGGAGATG

24801 TTATGGCTTT TGGTTTTCCT AGAAAGGCTC AGCTCAGGCT CAGCTTGGTC

24851 ATGCTGATAT CCTTTCTTCC ACTTGGTCGA TTTGGCTGTT GATACTTATG

24901 TATGCTTCAC GAAGTTTTTG TGCTGTGTTT TTCAGCTCCA TCGGTTGGTT

24951 TATGTTCCTC TCTAAACTGG TTATTCTAGT TAGCAATTCC TTTAACCTTT

25001 CATCAAGGTG CTTAGCTTTG CATTGCATTA GAACATGCTC CTTTAGCTCA

25051 TCGTACTTTT TTATTGCCCA TCTTCTGAAG CCTACTTCTG TCAATTCATC

25101 CATCTGATCC TCCATCCAGT TCTGCACCCT TAATGGAGAG ATGTTGCGGT

25151 CATTTGGAGG AAAAGAGGCA CTCTGGCCTT TGGGTTTTC AGCATTTTTT

25201 TGTTGATTAT TTCCCATCTT CAGGAGTTTT AGTTTCAGGC TTTGAGGCTG

25251 CTGATCCTTG GATGGGGTTT TTATGGGGGT CTTTTGGTTG TTGTTGTTGA

25301 TGATGATGAT GTTATTGTCA CTTTCTGCTT GTTTTTCTTT CAATAGTCAG

25351 GTCCCTCTTC TGTAGGGCTG CTGCAGTTTG CTAGGGGTTC ACTTCAGGCC

25401 CTATTCATCT GATTCGCTCC CATGTCTGGA GGTGTCACTC AAGGAGGCTT

25451 GGAGAGCAGC GAACATAGGT GCCTGCTTCT TCTGGGACCT CTGACCTCGA

25501 GGGACACCAA CCTGATGCCA GTAGGATCGC TCCTGTGTAG GGTGTCTGAC

25551 AACTATTGTT GGAGGGTTTC GCCCAGTTGA CTGGCATGGA GAGCAGGACC

25601 CATTTAATGA AGCACTTTGT CCCCTGGTGG AGAGGGGGTT CTTCACTGGG

25651 GGGAAACCAC ATGTCTGGGC TGCTTGGATT CCTCAGAACT ACCAGAGGAG

25701 AGGCTAAGTC TGCTGGTCCA CAGAGACTAC AGCCATCCCT CCCACTAGGG

25751 GCCCAAGCCC AGGGAGTCCA AATTCTGTCT CTGAGCCTCT GGCTGGAGTC

25801 TTTGGAGATC CTGCAAGGAA GCTCTGCCCA CTGAGGAAGG ATGGGTCAGG

25851 GTTAGCCCTG AAGAGGCACT CTGGCTGCAG ACTGCCACAG CCGGTGTGTT

25901 GGGCTGTGGG GACAAGTCTT GGGACCAAGC CGTCCAGCCT ACCCGGCTCT

25951 AGCAGGGGAA AAGTACAGCC TGGAGCTATT GAAAGGGGTG CCGCCCTTCC

26001 CCCGCCCAGG GAGCTTAGCG TGTTAGGCAG TTGTGAGTCC AGTGCTGGCT

26051 GTCGCCCCTT CCCCAAGGAA CAAAAAAGAC TTAGCAGGCA GCCGCAGCCA

26101 GTGCTGGTCG CCCCTCCCCC GGGGAGTTCC GTAGGCTTAG GCAGATTCCA

26151 GCTGTAAGAA TCTGCGTGTT CTGGGGTTGG GACACTAGGT CCCAGTGGCA

26201 TGGGTTCGCG AGTGAGATCT TCCAATCTGT GAGTTGCACA GTTCCGTGGA

26251 AAAAGCACAG TTTCCCCCTC TTGGGTAGCC CGTCACTCA CCACCTCCCT

26301 TGGCTGGAAG GAGGGGGTTC CCCTTCCCCG TGTGTCTCTC AGGTGGGCCA
```

TABLE 2-continued

Genomic Repeats
(SEQ ID NO: 2)

```
26351 CCACACCACA CTGCTCTTCC TTCTCTCTGT GGGTCACTGC CAGCCTTCTA
26401 GTCAATTTTG ATGAGGGAAC CTGGACATTT TGGTTGCCAG GAAGGATCAC
26451 ACACTTATTA CAGTTTTTTT CAATGTGAGC CTCTGAGCGC TGCTGCTTAT
26501 AGTCGACCAT CTTGGCCCCC AGAGTCACAC ATCTGTTATT TTTTGATGTT
26551 TTGATTGTGG CAATTCTTGC AGAAGTAAGG TGGTATCACC TTATGGTTTT
26601 GATTTCCCTG GTCATTAGTG ATGTTGAACA TTTTTTTCAT ATGTTCATTA
26651 GCCATTTGTA TATATTCTTT CAACAACTGT CTATTTATGT CCTTAGCCCA
26701 CTTTTTGATG GGATTGTTTT TTTCTTGCCA ATTTGTTTGA GTTCGTTGTA
26751 GATTCTAGAT ATTAGTCCTT TGTTGGATAT ATAGATTGTG AAGATTTTCT
26801 CCCACTCTGT GGGTTGTCTG TTTACTCTAC TGACTGTGAA GGAAAAGTCA
26851 ATTTCTTATA CGAATTTGTC TCACTCCTAC TTCCAAATGA GATCCTGGGG
26901 TTTTTTTTTT CTGTTAATCC TTCACAATAC TTCTCCCACT TTTTTGAACT
26951 CATTTGTTTA TATTCTGTTG TCTGCTTCTC TTTTATAGGA ATGTGACTTC
27001 TTATGGGCTT TCTCTATTAT ACCACATATG GGTTTTTGTT TTGTTTTGTT
27051 TTGTTTTGTT TTGTTTTTGT CCTCGGATCC ATTCTCCAAC CTCCTCCAGC
27101 CTTCCCGTGC TCTGTGGGAT AGACGTCTGA CTCATGAAAA CTACATTTCC
27151 CAGGCTCCCA TGCTAACTAG CTTCCTGTTA GGTTCAGCCA ATAGGAGGCA
27201 TTGGTGGGAC AATGGTGGGC GGGGCTATGG AAGGGCCAGA GTATTTCTGT
27251 ACCCCGCCCC CCTGCTCCCC TTCCAATGTT CCTGGAGCGG TGTAGGACCA
27301 ATACTGTATA TATGGAAGGA AGGCAAGGTG GATAGATTGG AAGGAAGAAG
27351 TGACAGATGG AAAGAAGAAG TGATAAATGG CAAGCGAGGC AAGGGAGCAG
27401 AGGATGGATG AGTGGATTGC AAGAAAGAAA AAAATGGATG AAATATAAAA
27451 GGAGCAGGAC AGATGGATAA GTAGATGGAA GTAAGAAAAG ACTGGTGTAA
27501 GAAAGGAACG ATTGATGATG GATGATGAAT GGATCAGTGG TGATTGGGTG
27551 AAGGGATGAA TGGATGGATG GACAGATGGA TGAACAGATG GGTGGGTGGA
27601 TAGATGGATG GATGGATAAA ATGGGTAGGT GGATGGATGG ATGGATGGAC
27651 AGATGGGTGG GTAGGTGGAT GGATGGATAG ATGGATGGAT AAGTGAATGG
27701 ATGGATGGAT GGATGGATGG ATAAATGGAT GGATGGGTGA AAGGAAGGAA
27751 AGAAGTGAGA GAAGGAAGAG GAAGGATAGA CAGATGTTAG AAGGTACAAA
27801 TGAAAGGAAG GAAGCCAGCA AGAAAGAAAG GATGCATTAA TAGAATGAAA
27851 GATGGAAGGG AAGAAGAAAG GATGGAAAGA GAAGAGGAAG AATGAACAGA
27901 AGGAAGTTCA AGAGTGGTGA AAAGAAGAAA GGCAGGGAGA GAAGGAGAAG
27951 TAAACTTTTC TTCTAGAGAT TTGTCTTAAA CCTTAGCTTG GCTGGACACT
28001 GTGGTTCACG CCTGTAATCC CAGCACTTTG GGAGGCCGAG GCGGGTGGAT
28051 CATGAGGTCA GGAGATCAAG ACCATCCTGG CTAACACGGT GAAACCCTGT
28101 CTCTACTAAA AATACAAAAA AAATTTAGTC AGGTGTGGTG GTGCATGCCT
28151 GTGGTCCCAG CTACTCAGGA GGCTGAGGCA GGAGAATGGC ATAAAACCTG
28201 GGAGGCAGAG CTTGCAGTGA GCCAAGATCA CACCACTGCA CTCTAGCCTG
28251 GGCGACAAAG TGAGACTCTG TCTCAAACAA AAACAAAACA AAAAACAAA
```

TABLE 2-continued

Genomic Repeats
(SEQ ID NO: 2)

```
28301 AACAAAAAAC AAAACCAAAC CAAAACAAAA AAAAAAACCT TAACTCATAC
28351 TTTCATAAAG TTCCACACAC AGGGAGTGAT TAGAAAGCAT TTGCTGATAT
28401 ATTTTATATA ATAAACATGT ACACCATATT GACCTGTGTG CCCAGCAGTG
28451 CTTACATGAT TTACAATGAT TAACTTGTTT AAGCTTCATA ACAACGGTTG
28501 AGGCAGGAAA CATCATTGTG AACCATTGTC ATCTCATTTT ACAGATGAGT
28551 AAACTGAAGT GCTGAGAGGT TGGTTATGGC TGCAAAGATT GTTGGCCATG
28601 TTAACCAATG CATAGAAGAT TAGCATACCT GGTTGTGAGT GCAGGAGAGA
28651 GAGAGAAATG GGAGAAAGGC AGAGAAGGAT CGATGGGGAG AGAGGAAGAG
28701 AGAGAGAGAG AATAAATTTT TTAAAAATGT CTAGAGTCAT GACTTCCGCA
28751 TCAGTGTGGT AATATGCAGC CTTTACCCTG GGAAAGATCA GAACCATTGG
28801 TACTTTTTAC AGAATCTTCC CTTCCTGCAT TTGGGTAGAA GGACCCCATC
28851 TGGACATCCC AAATCATTAA GCACACCCTT ACTGGCTGCT GGAGTTGTCT
28901 CCATTAAAAG TCACCGTTGG GTTTATTAAG AGGCGGACAC AGGGTCCTTA
28951 GAACACACTG CCCCCACCTG TCCCACACCA CCCCCCACCC ACCCATCATC
```

Exon R1

```
29001 CTCCCCAAGA GCTTCATCTC TCTCTCTCTT CCCCCTGCCC TAGCCGGGGT
29051 GGTCAGCGAG GAGCCATTCA CACTGAACTT CACCATCAAC AACCTGCGCT
29101 ACATGGCGGA CATGGGCCAA CCCGGCTCCC TCAAGTTCAA CATCACAGAC
29151 AACGTCATGC AGCACCTGGT GAGAGGCCTG CCTCCCGCTG CAGCCCTGCC
29201 ATGCCCATCC TAGGGCTGTT GCCTGCCTGC CTCTGACCAA CCCAAGCTCC
```

Exon R2

```
29251 CTTCTCCCTC TGCAGCTCAG TCCTTTGTTC CAGAGGAGCA GCCTGGGTGC
29301 ACGGTACACA GGCTGCAGGG TCATCGCACT AAGGTGAGAA ACTCCCCCAC
29351 CCACAGCGCA CCACCAAGAA CTTAGAGTTC TGACTGGGAG GTCCCTCTTG
29401 GGTTGGGGTG GGCTACATAT TTTTTTAAAT CTTTTTATCT TTCCTTTTTT
29451 TTTTTTTGAG ATGAAGTTTC GCTCTCGTTG CCCAGGCTAG AGTGCAATGG
29501 CACGATCTTG GCTCACTGCA ACCTCTGCCT CCCGGGTTCA AGTGATTATC
29551 CTGCCTCAGC CTCCCCAGTA GCTGGGATTA CAGGCAGGCA CCACCATGCC
29601 TGGCTAATTG TTTTGTATTT TTAGTAGAGA TGGGGTGTCT CCATGTTGAT
29651 CAGGCTGGTC TTGAACTCCT GACTTCAGGT GATCCACCCT CCTCAGCCTC
29701 CCAAAGTGCT GGGATTACAG GCGTGAGCCA CCATATCTGG CCCCATTCTT
29751 TTTTTTTAAA TGAATTTAAG GAGTGCAAAT GCAGTTTTTG TTACATGCAT
29801 ATATTCCATA GTGAAGTCTG CAGACAGTAG ACTTCCAGAC AGTAGCTTCT
29851 GGTGTATCAC CCGAATAGTG TACATTGTAC TTATTAAGTG AGGTTCCCCA
29901 CCCTTCTCCC ACTCTCCCAC CTTTCTGAGT ATCCAGTGTC TATTATTCCA
29951 CACTCCAGGT CCATGCTCTC ACGTATAAGT GAGAACGTAT GGTATTCCAC
30001 CATGAGCTAA TGGACATGGA GTCCATTGGC TCCCACTTAT AAGTGAGAGC
30051 ATGCGGTATT TGACTATTTC TGAGTTTCAC TTAAGATAAT GGACTCCCAT
```

TABLE 2-continued

Genomic Repeats
(SEQ ID NO: 2)

```
30101 TCCATCCATG TTGCTGCAAA ATACATGATT TCACTCTTTT TATGGCTGAA
30151 TAGTATTTCG TGGTATATAT ATATACCACA TTTTCTTTAT CCAGTCTTCT
30201 ACTGATGGAC ACTTAGGTTG GGTCCATACC TTTGCTGTTG AAATAGTGCT
30251 GCAATAAACA TACACGTGCA GGTGTCTTTC TTATATAAAT GATTTCTTTT
30301 TTTCTTTCCT TTTTTTTGAT ATAACGAATT TCTTTTATTT GGGTTAAATC
30351 CCCCAATAGT GGGATTGNNN NNNNNNNNNN NNNNNNNNNN NNNNNNNNNN
30401 NNNNNNNNNN NNNNNNNNNN NNNNNNNNNN NNNNNNNNNN NNNNNNNNNN
30451 TGACCTGTCC GTATTGATAT ATAAAATGCT GCATTTAAAG TGTACAACTT
30501 GATATTTTGG TATACATTGT TAAATCATGG CCACATTTCA GCTAATTAAT
30551 ATATCTATTA TCTCTACATA GTTATCATGT TTGTACCCTT TGACCAGCAT
30601 CACCCCATTT GCTCCTCCTC CCAGCCCCTG GCAACCACCA TCCTACTCTC
30651 TGCTTCTATG AGTCTGACAA TTTTAGATTC CACCTATAAG TTAGATTATG
30701 CGGTATTTGT CTTTCTGTGC CTGGCTTATT TCACTTAGCC TAATGTCCTC
30751 CAGCTCCATC TATGTTATCC CAAGTGGCAG GATTTTCATC TTTCTTATAT
30801 ATTTCATTGT ATATGTGTAT GCCACATTTT CTTTACCCAT TCATCCATTG
30851 AAGGTCATTT AGCTTGTTTC CATATCTTGG CTATTTTGAA TAGTGCTGCA
30901 ATGAACATAG GAGTGCAGAT ATCTCTTTAA GATACTGGTT TCATTTCTTT
30951 CTTTCTTCTC TTTTTTTTTT TTCTGAGACA GAGTCTGACT CTGTCGCTCA
31001 AGCTGGAGTA CAGTGGTGCA ATCTTGGCTC ACTGCAAACT CTGCCTCCTG
31051 AGTTCAAGCG ATTCTCGTGC CTCAACCTCC CAGGGAGTTT TGCTCTTGCT
31101 GCCCAGGCTG AAGTGCAGTG GTGCAATCTT CACTCACCAC AACCTGTGCC
31151 TCCCGGGTTC AAGCGATTCT CGTGCCTCAG CCTCCCAGGT AGCAAGGATT
31201 ACAGGCGCCC AACACCACAC CAGGCTAAAT TTTTTTGCAT TTTTAGTAGA
31251 GACGGGGTTT TGCCATGTTG GCCAGGCTGG TCTCAAATTC CTGGCCTCAA
31301 GTGATCCACC TGCCTCAGCC TCCTGAAGTG CTGGGATTTT ACAGGCATGA
31351 ACCACCACAC ATGGCCTCAT TTCTTTTAGA TATATATGGG TTGAGCTATT
31401 CTCAGAGGGT CCTTTTCTGC ATCTATTTAA GATCACATTT TTTTTATATT
31451 GTGGCAAAAA TACATGTAAC ATAAAATCTG CCATTTTAAC CATTTTTAAA
31501 TGTACAATTC AGTGACATTG ATTATATTCA CAATGTCATA CAGCCATCAC
31551 CACTATTTAT TTCTAATACT TTTCCATTGG GTAGATCCCC AACAGTGGGA
31601 TTGCTGGGTC AAATGGTAGT TCTGATTTTT TTTTTTTGTT TTTTGAGAAA
31651 TCTCCATACT GTTTTTCATT TGAGGTTGTA CTAATTTACA TTCCCACCAA
31701 CAGTGTATAA GAGTTTCCTA GGCCGGGCAT GGTGGCTTAT GCCTGTAATC
31751 CCAGCACTTT GCGAGGCCCA GGTGGGTGGA TCATGAGGTC AGGAGATCGA
31801 GACCACCCTG GCTAACATGG TGAAACCCCG TCTCTACTAA AAATGCAAAA
31851 AATTAGCCGG GCGTGGTGGC GGGTGCCTGT AGTCCCAGCT ACTGGAGAGG
31901 CTGAGGCAGG AGAATGGCAT GAACCCTGAA GGCGGGGCTT GCAGTGAGCT
31951 GAGATCGCAC CACTGCACAC TTCAACCTAG GCGACAGAGC GAGACTCCAT
32001 CTCAAAAAAA AAAAAAAAAA AAAAGGTTTC CTTTCAGTGC ATCCTTGCCA
```

TABLE 2-continued

Genomic Repeats
(SEQ ID NO: 2)

```
32051 ACTTGAGTTT TCTGGGTTGG TTTGCACTCT CATGGTATTT ACTAGATACT

32101 TCTCCATTTA TATTTTTACT CAACCCATGC CCATAACACC ACTCCTCTAC

32151 CATTCCCACC AACCATGTAT AAGAGTTCCT TTTCTTGCAT CCTTGCCAAC

32201 TTGACTTCTT TGGGTCAGTT TGCACTCTCT TGGTATTTAC TATTTACTTC

32251 TCCATTTATA TTTTTAGTCA ACTGATGCCC ATGGCACCGC TCCTCTGAGG

32301 CAGGTGCTGG GTACTAGAGT GATAAGACAG ATGCTGTCCC TGCCCTCACC

32351 CAGTGGAGAA GAACAGATGC TAAACAGGAA CATAAATATC TAAGTAAAAT

32401 GGCTTCAAAT GGAGTAAAGT GATATGAAAC ATAAATAAAT AGCAAGTGAT

32451 GGGTAGAGCA ACTTTACCCA GGATGAATCT TGGGCTGTGT CCCAAATGGC

32501 CATGAAAACT GTTCCAGGCA GGGAGAACAG CATGAGAAAA GGTCTTGAGG

32551 TGCAAATGAG CTTGGCATGT TCTATGAACA GCAAAGAGGC CAGTGTGGCT

32601 GGAGCAGAGA GAGAGCAAGA AGAAAAGAGA GAAAGGATGA GACTCAAGAC

32651 ATCAGCAAGT TGAAGGGCC TTGGAGGACT TGGATTTTTT TTTTTAAGAC

32701 AGCTTTGTTC TTGTTGCCCA GGCATGATCT CGGCTCACCA CAACCTCCGC

32751 CTCCTGGGTT CAAACGATTC CTCTGCCTCA GCCTCCCGAG TAGCTGGGG

32801 TAACAGGCAT GTGCCCACCA CACCTGGCTA ATTTTGTATT TTTAGTAGAA

32851 ATGGGGCTTC TCCATGGTTG GTCAGGCTGG TCTCGAACTC CCGACCTCAG

32901 GTGATCCGAC CGCCTCGGCC TCCCAAAGTG CTGGGATTAT AGGTGTGAGC

32951 CACTGCACCT GGCTTGGATT TTTTTTGTTC TATATTGTGG TAACATACAC

33001 ATCACATTAA ATTGATCATT TTAGCTATAT TTCCCGTTCA GTGGCATCAA

33051 GCACATTCAC ATTATTGTGC AACCATCACC ACTATCATCC ATCTCCAGAA

33101 CTTTCTCATC TTCCCAAACT GAAACTCCAT CCCCATGAAA CACTCATTCC

33151 TCATCCCCCT CCTCAAGCCT CTGGCACCCA CCATTCTACT TTCTGTCTCT

33201 GTGAATCTGA TGATTCTGAG GACCTCCTAT GAATGGAGGA ATCATATGGT

33251 ATATGTCCTG GTTTATACTG TATGGCTGGC TTATTTCACC AAGCATAATG

33301 TCCTCAAAGT TCATCCATGT TGTAGCATGT GTCAGAATTC CCTTCCTTTT

33351 CCACTTGTAT GTAAATGCTG TATTGTGTTT CTCCATTCAT TAGGACTTTG

33401 ATTTTTGCAG GGAGTTGTCA AGGGGTGCTG GGTTCTGGGG CTTCAATATA

33451 ATAAGAGTAA GCTAAACTGG TTCATTTCCT CCTTCGTGGA GACCATGTTC

33501 TGGTAGGAAC AGGAACAAAT AATTTATGAT TACATAGAGG GTGACCAGGG

33551 CAGTGACAGG GGAAGAGTGG AGGATTGTGG GACCCAGAGG AGGCTCCTGA

33601 CCTTGCCTAG GAAGATAGGA GGAGGAAGAG GAGGAGGAAG AGGAGGAGGA

33651 AGAGGAGGAG GAGGAGGAGG AGGGAGTCCT CTAAGCTGAG ACCTGGAGGA

33701 TGACCAGGAA GTTATCCAGG TAAGGAGAAA TGGGGAGAAG CTTCCAGACA

33751 AAAGTAACAG CAATTGCAAA GATCCTGAGA TGATAGATAA GGTCAGGTGG

33801 AGAAAGTGCA AACTGTCAAT GAGACCAAAA TATGGACTGT GAGTTGTGCA

33851 GTGACCACAA GTGGAGAGGT GCTAGGTGGC CTTCATCCCC CAAAGCTGCA
```

TABLE 2-continued

Genomic Repeats
(SEQ ID NO: 2)

Exon R3

33901 CCTCTCCCTC CTCAGGTCTG TGAAGAACGG TGCTGAGACA CGGGTGGACC

33951 TCCTCTGCAC CTACCTGCAG CCCCTCAGCG GCCCAGGTCT GCCTATCAAG

34001 CAGGTGTTCC ATGAGCTGAG CCAGCAGACC CATGGCATCA CCCGGCTGGG

34051 CCCCTACTCT CTGGACAAAG ACAGCCTCTA CCTTAACGGT GAGCAGCTAT

34101 CAGCCCCATC TCCCTGCCCC ACCCCCAGC CCCCACTGCA GTCCAGGAGG

34151 GTGTCTGTTT GCCGGTTCTC TAGGGAAAGA CTTGGGGTTC AAGTCTTGGC

34201 ATTACCACTG GCCCTCCCAT AACCACAATG CAAGGTTGGA CTTTGATTAA

34251 TCCCATTTTA CAGATGAAGA AACTGAGGCT TAGACAGGCT AAGCAATTTA

34301 CCTTGACAGT GGTGGAACCA GGATATGAAC TCCACTTGTC AGCATTCGGT

34351 GCTATGATCC ACTCCACATG TTTAACTCAC AGAAGAGTCT TCCTGGTGGG

34401 GGCACTTGGG GGACAAAAAA CACATTTCCG GCTGTGAGCA GTGGCTCACA

34451 CCTGTAATCC CAGCACTTTG GGAGGCCAAG GCGGGCGGAT CACAAGGTCA

34501 AGAGATTGAG ACCACCCTGG ACAACATAGT GAAACCCTGT CTCTACTAAA

34551 AATACAAAAA TTAGCTGGGT GTGGTGGCGC ACGCCTGTAG TCCCACCTAC

34601 TCGGGAGGCT GAGGCAGGAG AATCGCTTGA ACTCGGGAGG CAGAGGTTGC

34651 AGTGAGCCAA GATTGCGCCA TTGCACTCCA GTCTGGGTGA CAAGAGTGAA

34701 ACTCTGTCTC AAAAAAAAA AAAACAATTT CCCCTCCCTG CTTTCTTCTC

34751 ACCATTGACG AGGGATGGGC TTCTCTCCTA CCTGAGGCCC CCTATACCAG

34801 GAAGATCTAT GGGATCTAAT CTTCAGCGCA CACTGGGCCT CAGCATTGGT

34851 CTAGAACTCA GGATAAGATA GCATTTAAGA AGGCATCCCC TAAATGGGGT

34901 TCTGAGAGGC AAAGCATGAC CGTGGAGAAT TGACAAAATA GCTCGCCTTT

34951 CATCCCCTCC ACCGCCAACC CAAGAACAGT GCTTATCATC ATGACCCCAT

35001 GAGGTGGGCA CCCCATATCA CTTATATGAG GTACCTTTAG GTAGGTACCG

35051 GGATGTGGAG AGACATCCTG GGCTTTCATT ACTCTTATTT TAGCAAAGAG

35101 GGAATCTGAG GCACAGAGAA GGGAAGGGAC TTGCCCATGC CCACAGCGAG

35151 TTTTTGGCTA GTATGGGTCT TGATGTTCTT TCTGGGTCCG TNNNNNNNNN

35201 NNNNNNNNNN NNNNNNNNNN NNNNNNNNNN NNNNNNNNNN NNNNNNNNNN

35251 NNNNNNNNNT TCCTGCGTGG GAGATGTGTG GATTTGATTT GTATCTGGAA

35301 AGATGATTTT TTATTGGTGA CAAAGCAGTT AAAGTTAATC TTCACAGTTG

35351 TGCGGAGAGT GACCACGCGA GTTAGTCTTA TCCTTATTTT TTTGATCATC

35401 CCGCTACACA AGACAAAGCG AACCGCACAG GCAACATCAG CAGGCCCCAT

35451 TGGTGTGTTC CCCTCTATGG GTCCATGTGT TCTCATCATT AGCTCCCACG

35501 TATAAAGTGA GAAGATGGCA GTATTGGTTT TCTGTTCCTG CATTAGTTTG

35551 GTAAGGATAA TGACCTCCAG CTCCAACCAT GTTCCTGCAA CGGACATGAT

35601 CTCATTCTTT TTTATAGCTG CATAGTATTC CATGGTGTAT ATGTTCCTCA

35651 TGTTCTTTAT CCAGTCTATC CTTGATGGGC ATTTAAGTAG ATTCCATGTC

35701 TTTGCTATTG TGAATAGTGC TTCAGTGAAC AGGTGTCTTT ATGATAGAAA

35751 AATTTATATG CCTTTGGGCA TATATGCAGT GATGAGATTG CTGGGTCAGA

TABLE 2-continued

Genomic Repeats
(SEQ ID NO: 2)

```
35801 CGGTAGTTCT GTTTTTAGCT CTTTGAGGAA TCATCCTGCT GCTTTCTACA
35851 GTGGATGAAC TAATTTACAC TCCCACCAAC AGTGTATAAA CACTCCTTTT
35901 TATCTGCAAC CTCAGCAGCA TGGTTTTATT TCTCTTTATG GCTGAATAGT
35951 GTTCCATTGT GCATATATAC CACACTTTCT TTATGGATTC ATCTGCTGAT
36001 GGACATATAG GTTGATTCCA CATCTCTGCT ATTGTGAATA GTGCTGTGAT
36051 AAACACACAG GTGCGGGTTG GGTCTTGATG ATCTCAGTTA ACATCCAGTC
36101 CCTTCAACTT GGCTATTGCA GGGAGCTGTT CCCCCTTGTA AACTGCACAG
36151 CTTATGTGCT TCATTTTGTT CCTTCATTTA GATTTACCAA GCAGCTACTA
36201 TTAACCAGGC CACAATGTGC CTCGCCCCCA GGAACAGAGA TAGGTTACAT
36251 GTGCATCCTG TCCTAATGTA ATCTCCAGGG GGGCGGAGAC TGTTTGTTC
36301 TACCCTATAT TCCCCAAATG TAAAGGGAGC CTTGCACATA CTAAGCCCTT
36351 AATAAACATT CATTGGGTGG AGGAATAGAT TGGAGGAGGC CTGGAAGGGG
36401 AGGCGGGGGT TATGGATGGA TAGGAGGATA GACTTGTGAA CACAAAGGTA
36451 GTGAGAGCCT CTCATTGGAG GCATGCTGGA GACGTGAGTA GGGAAGGGTC
36501 AGTGCTAATT GAAATATCAG GAAATTCTTT CTAGTGGTGA ACACATTTAA
36551 GTCAAATATT AGATGATACA TAAATGTATC CATAATCTCT AGATACACAA
36601 AGGGAAAGGC ATCCAGGCAG GGGCCCCATA TGGACAAAGG CATGGAGTAT
36651 CTGGGACGGT TCCACCACCT CCTCTTACGT GTGACTTCTT TGTTTCAAGG
```

Exon R4

```
36701 TTACAATGAA CCTGGTCTAG ATGAGCCTCC TACAAGTACG TGTCTTTGAA
36751 TCTAGTGCCC ATTTCAATCT CCATGGGTCT TGGTTCAAGC TTTTCTCCTC
36801 ATTCATGAAG GAAGGTTGCC CCAAATTCGG GCTGGTCCCC TAGGTGGTGA
36851 GGGGCATTGT CTCAGTGGGA GGAAGAATGC TGAGTCCTTG GCCCTGTTTT
36901 TAGACCTGCA GCCATAGTCT TGGCTTTGTG AATTTTCCAT GTCCCTCTGG
36951 GTTGGAGGAA GAAGTTTGAA CAAGCATTCC CTACACGGGA TAGAGGTTGA
37001 GGTCAGATGA TGACCTCTGT TAGTCTGTAC CCTCCTTGAT AAGAAAATCT
37051 CCTCCAAGTG CCCCAGCAGA GGCTTCATGG TCAAGCTGCA GACTCTGCTG
37101 GCTACTGGTT TTGGCTAAAT TTGCCCATTG CCTCATCCAG TGATCCACTC
37151 GTCTATCTTT CCAGCCATCC ATTTTTCTAT CCTTCCAGTC ATCTCTCAGA
37201 CACCACCTGT CCTTCCATCC ATCCATCCGT CCATCCATTT ACCCATCCAT
37251 CCATCCACCC CATTTTCCTG ACCATTTACC TCCTCGTCCT TCCTTCCATC
37301 TGTCCTTTTA TCCATCTATT CATCCATCAC CCATCCTCCT GCCCATTCAC
37351 CTGCTTGTCC CTCCTTTCTT CTGTCCTTCT ATACATCCAT CCATCCATCC
37401 ATCCATCCAT CCACCCATCC ACTCATCCAC CACCCACCCA TCCTTCTGCC
37451 CACTCACTCG CTAGCCCCTC CTTCCTTCTG TCCTTCCATC CATCCATCCA
37501 CCCATCTTCC TGCCCATTCA CCTGCTTGTC CTTCCTTCTA TCTGTCTTTT
37551 ATCCATCTCT CCATCCATTC TCACCATCCA TCCATCCATC CTTCTCCCTA
37601 TTCACTGGTT TGTCTTTCCT TCTGTCCTTC CAACCATCCA CCCATCTCTC
```

TABLE 2-continued

| Genomic Repeats (SEQ ID NO: 2) |
|---|
| 37651 CATTCATTCT CCTCTTCATT CACCATGTTT CCTTATTTCT GTCTCTTCCA |
| 37701 TCCATCCATC TATCCAGACA GACATCTCCT CCCCCCATTC TCCTCCCCAT |
| 37751 TCACTCAATT GTCCTTCCTT CCATCTGTCC TTTTATCCAT CCATCCACCC |
| 37801 ATCCATCCAT CCATCTATCC TTCTCCCCAT TCACCTGTTT GTCCTTCTTT |
| 37851 CTGTCCTTCC AACCATCCAT CCATCCATCA TCCATCCATC TATCCTTTTC |
| 37901 CCCATTCACC TGTTTTGTCC TTCCTTCTGT CCTTCCAACA TCCCTCCATC |
| 37951 TCTCCATCCA TCCTCCTGCC TATTCATCTG CTTGTCTTTC CTTCCTTCTG |
| 38001 TCCTTCCATC CATTCATCCA TCTGCCCATC CACCCACTCA TCCTCTTGCC |
| 38051 CATTCACCTG CTTGTCCTTC CTTCCACCTG TCCTTTTATC CATCCATCCA |
| 38101 TCCATCCATC TTGCTCACTC CTCCACTCAC ACAATCACTC CTTCCCTCAG |
| 38151 TCTCATTTAT GGCCCACCTG TGAATGGTTG TCCTGGCTTG GACCACTGAT |
| 38201 GAAGCCCAGG GGAGCTTCTC CCACTAGTGG TGGGCTTTTG TCCTCTCTGA |

| Exon R5 |
|---|
| 38251 TGGACTGTTC CTTCCACAGC TCCCAAGCCA GCCACCACAT TCCTGCCTCC |
| 38301 TCTGTCAGAA GCCACAACAG GTATTTGGGG CCATTTTTCC TCCTCGAAGA |
| 38351 TTAGAATAGC ATTTCAATCA GACACCTGCC CTCGTGGAGT CCCAGATTTT |
| 38401 ATGAAATAAA TAGACCATCA TAATGTCAGA TGTTTTGGGG TGAGATACCT |
| 38451 GGCATAGTTG GGAAGGAGGA GGGCTTTCTG GAGAAAGTTT CACCTGAACT |
| 38501 GAGTCTTTAA GGATGACTAA GAGTGATTCA GGCAAATAGG GCATGAATAG |
| 38551 TATAACTGAA AGAGGGGAAT CTGTGAGCAA AGCCTCAGTG GCCAGAAACA |
| 38601 GCATAGAGTA TAGGGAGAAG TGAGAGAAAT TTGGTTTGCA TGAAACATAA |
| 38651 AGCTTAACCC AGAGTGGATG GATAAGTGAG ACTGAAAGGT CAGCAGGAGC |
| 38701 CAGATTGGGA AGGGCCTTGA ATGCCAAGTC AAGAAATTTG AACTTAACAC |
| 38751 TGAAGGCCAT AGGGAGCTGT GGATGGTACT AGAGCAGGGG CAGCCATAGT |
| 38801 GAGATTGTCA TTTCAGAAAG ATTCTTCTTG TGTTCAGTAT AGAGAATGTC |
| 38851 CTTTAGACAG GGCATCCAGT GAGTCTGCCA GGTGCTAATC AGGGTGAGAG |
| 38901 AAAATAAGAC CTGAACTGGG ATAGGGGGAG GAGAGAGAGG ATATATGTGA |
| 38951 TGAATATTCA GTAAAGAGAA TTGGTGTTAC TTGGAGGGGA GAAGACACAT |
| 39001 AGCTTCTGAC TTGCGATGGC CACACTCAGT TTAATAATGA GCGCAGTCTG |
| 39051 ATCTAGTCTC AGACCAGCCC TCAGTTGCAG ACGTCTCTCC TCCCCTCCTG |

| Exon R1 |
|---|
| 39101 CAGCATGGGG TACCACCTGA AGACCCTCAC ACTCAACTTC ACCATCTCCA |
| 39151 ATCTCCAGTA TTCACCAGAT ATGGGCAAGG GCTCAGCTAC ATTCAACTCC |
| 39201 ACCGAGGGGG TCCTTCAGCA CCTGGTGAGA CCCTGGTCCC AGCAGTCCT |
| 39251 GGTGGGATAA ATCCTACCCC CAACCTCTGT TCCTCGGCTT ACCCTCTTCC |

| Exon R2 |
|---|
| 39301 TCCTTCCTCT CAAGCTCAGA CCCTTGTTCC AGAAGAGCAG CATGGGCCCC |
| 39351 TTCTACTTGG GTTGCCAACT GATCTCCCTC AGGTGAGACC ACTTCCTGGC |
| 39401 CATTTGCCAG TAACAACCAC CCCTTTTGTG ACCACCCCTT CCTCAGCTTT |

TABLE 2-continued

Genomic Repeats
(SEQ ID NO: 2)

39451 CCCCTGCTCC TCCCTCCACT GCTCTTTACC TGCAGAGGTC TCGGGACCTC

Exon R3

39501 TCTAGAGTCC TCAAATGCCT CTCTCCCCAG GCCTGAGAAG GATGGGGCAG
39551 CCACTGGTGT GGACACCACC TGCACCTACC ACCCTGACCC TGTGGGCCCC
39601 GGGCTGGACA TACAGCAGCT TTACTGGGAG CTGAGTCAGC TGACCCATGG
39651 TGTCACCCAA CTGGGCTTCT ATGTCCTGGA CAGGGATAGC CTCTTCATCA
39701 ATGGTGAGTG TCAGGCTGAA CTTGGATTTA CAGTGACTTT TGGGGAGTTG
39751 GTTTCTTTGT TTTTGAGATG GAGTCTCACT CTATCACCCA GGCTGGAGTG
39801 CAATGGTGCA ATCTTGGCTC TGCAACAGTG ATTCTCCTGC CTCAGCCTCC
39851 CAAGTAGCTG GGATTTACAG GTGCATGCCA CCACGCTCAG CTAATTTTTG
39901 TATTTTTAGT AGAGATGGGG TTTCACCATG TTGCCCAGGC TGGTCTCGAA
39951 CTCCTGACCT CAGGTGATCC ACCTGCCTTG GCCTCCCAAA GTGCCAGGAT
40001 TACAGGCATG AGCCACCATG CCCGGCCCAC CATGACTATT ATTTGTCCCT
40051 GTTGTATGCC CTTTCCTCTC TAAAAAAAAT AGCCCAAGGC CTGGCTGGGG
40101 GACACCCTTC CCCAAACCAC CAAGGGGAGG GTCTTTCCCA TTATTTTGAG
40151 TAAATAGCAT GAAATTCTTT GACCAAATTA ATGTCATAAA TTGTTTGTCT
40201 CTTTCTCCTT CACTTTTGTT TCCAACTTGG TTGCGGTATA ACTATCAAAT
40251 ACAATTGTAT GTATTTAAGA TGTATAATGC AGTGATTTAA TATATGTGTA
40301 GCTTATGAAA TGATTACCAT GATCAAATTA GTTAACACTG CTTTCATGTC
40351 ACATAGTTAC CGTGTGTCTG TGTGCGTCTG TGTGAGTTAG AGAGAAAGAG
40401 AACATTTAAG GTCTACCCTC ATAGAAAATT TCAGGTTTAC AATACAGTAT
40451 TATTAACTAT AATCATCAAG CTTTATACTC GATCCCCAGA ACTTATTCAT
40501 CTTGTAACTA AAAGTTTGTA TTTTGTGACC AACATCTCCC CATTTTCTCT
40551 ATCACCACCC CCATGCCCCC AGCCCCTGAT AACCATCATG CTACTCTCTG
40601 CTTCTGTAAG TTTGACTTCT GATCCCACAT ATAAGTGAGA TCATGCAGTA
40651 TTTGTTTCTC TCTATCTGGT ATATTTCACT TAGCATAATG AACCCCCCCC
40701 AGGTACATCC ATAATGAATT TCAATTCAAA ACCCAAGTGG CTGAGTCGTG
40751 GCATCCTTTG GGACAGGATA GCAGGTCCCT TCTATATAAG GATCCTCTGT
40801 GTCAGTGGTT ATTACCAGGG GACAATTCTG CACTTCTGCC CCACCCCACC
40851 CCCCAACTGG GAGACTCTAG GCAATATCCG AAATCATTTT TGGGTATCAC
40901 AACTCAGGGA GGGAAGGAGG GTGCAACTGG CACCTAGTGG GTCGGTAGCC
40951 CATTTTCCAG TGCACAGGAG ACAACCACCC CAGGGAATGA TCCAGCCCCA
41001 AATGCCAATA ATTTCAAGGG TGAGAAATCC TGTTGTACAT GGTCTCAAAG
41051 TTCTTAGGTG GGCACAAGGC TGACATTTAT CACACTTTAC TGTAATTACT
41101 TGTTAAATTT ATCTGATTCC CCCTTACCCT GTGAACTCAA CAAAATTACG
41151 GTCTATTATG AGTGCCACTG TACCCTCGGT TCGCAGTACA TCAGCACATC
41201 ATAGTATGGA AAGAATCATT GAATGAGTGA GCAAATTAAA GATTTGTGTC
41251 TCTGCTGTAA CTCACATTCA TTAATTCATT CATTCAGCAA ACATATATGG

TABLE 2-continued

| Genomic Repeats (SEQ ID NO: 2) | | | | |
|---|---|---|---|---|
| 41301 GTGGCTGTTC | TGCCCCAAGC | CTTGTACTGG | GTCTGGAGAT | AGAAGACACA |
| 41351 TTTTTCTGTC | TCTGAAAAAC | TCATACTCAA | GTTAACAACA | AATTACGGGC |
| 41401 ACAACAAAGA | CCCCACTGCT | GTTATTAACA | GGGTACTATG | GGAGCTGAGA |
| 41451 GGAGGAGTAA | ATTAAGGAGG | GCTTCCTGGA | GGAGGGTGTT | ATATACCCGG |
| 41501 CCCTGTGCCG | GGACACATAA | TGATAAGACA | GACTTGGGCC | TCTGCTGTCC |
| 41551 TGGAGCTCCC | TCTCACTGGG | CTCTTGAAGC | GTGAGCAGGA | GTTTTGCAGG |
| 41601 AAATGAAAAG | GATGCATTCC | TAGAAGTGGG | AACTGCATAG | CACATGCAGG |
| 41651 AAAGCTCAGC | TCAGAAGAAT | CTGTGTAATA | TTCCATTTTT | CCCTCTCTTT |
| 41701 GGGGCAACTT | TCTGTCTAAG | AGCTCCTGCA | ATGCCCAGCG | TGTGGACCTG |
| 41751 AAATTGATTC | TGACAGTAGG | CAGGGGACTG | CTGGGCAACT | TTGGCTCTGC |
| 41801 ATTTTGTGAT | CAACATTTCC | CCACCATATG | TTGCCTTTTC | TTCTTCTCTG |

| Exon R4 | | | | |
|---|---|---|---|---|
| 41851 TGGCTCCAGG | <u>CTATGCACCC</u> | <u>CAGAATTTAT</u> | <u>CAATCCGGGG</u> | <u>CGAGTACCAG</u> |
| 41901 <u>ATAAATTTCC</u> | <u>ACATTGTCAA</u> | <u>CTGGAACCTC</u> | <u>AGTAATCCAG</u> | <u>ACCCCACATC</u> |
| 41951 <u>CTCAGAGTAC</u> | <u>ATCACCCTGC</u> | <u>TGAGGGACAT</u> | <u>CCAGGACAAG</u> | GTGGGGCATC |
| 42001 TCTCACCCCT | CCCGTCTTCT | CTGTCCTGTG | TGCTTCTCTC | CCTCTTCTAC |
| 42051 CTGATTTCTC | TGTTAAGTGA | TCACTTTAAA | TGCTTCACTT | CACTATGTAT |
| 42101 TCTGGGTTCT | CTCTCAGTTT | CCAAAAGTAC | TCTCTTGACT | ACCATTCCCA |
| 42151 TTTCACAGAT | GGGCAAACTG | AGGCTCAGAA | AGGGGCGTGG | TGTGCCTAGG |
| 42201 GTCATACAGT | GCTTTAGGAA | CAGAGTTAGG | ATTTGAACTC | TGGTCCCCTT |
| 42251 TGCTCCAAGT | CCTGTGTTTT | TTTCCACTGG | CATCAGCGGC | CCCTCCACCC |
| 42301 CCAAGAGGCC | TCCATCTCAC | CCACTCTCCC | TACCCATCTT | TCTAGGTC |

TABLE 3

| Genomic Carboxy Terminal (SEQ ID NO: 3) | | | | |
|---|---|---|---|---|
| Exon C1 | | | | |
| 1 ACCACACTCT | ACAAAGGCAG | TCAACTACAT | GACACATTCC | GCTTCTGCCT |
| 51 <u>GGTCACCAAC</u> | <u>TTGACG</u>TAAG | TTCTGAAGGT | CATAAGCAGT | GACCAAGCTT |
| 101 GTGGCTGTGT | CTCTGAGCAC | CCTTGAGCTA | GACGTCCCCA | GTGGGGTACC |
| 151 CATTCTCCCC | TACATCCCTG | TCTAGCTAAT | CCTACCATCT | CCTCCCATAA |
| 201 ATCCTCAAGG | TAGGGAGTGA | GGATTAACCT | CATGGGGCCA | CCAACTCCCA |
| 251 GCATACACCT | TCTTTTTTTT | CTGGACACTT | GGGAAAATAT | AACTTTTTGA |
| 301 TGTAGAACTC | AAAATATTAG | CCCAATAATA | ATATTTAACA | TCAACCAGCC |
| 351 TCCTCTCATT | TAATTCTCAC | AACAGAATCT | ATGAGTTGAG | TGCAAAAATC |
| 401 ATCCCTATTG | TGCAGATGGG | AAAACTGAGG | GTCAGAAAAG | TGAACTTCCC |
| 451 AAGAACTGTC | AAAGTTGGGA | TTTGAACCCA | GGTCTCTGAT | GACTGGATGA |
| 501 AGGAATGAAG | ATACCTATAC | TTGGGAATGA | GGAGGGTCGA | CAGGACACGA |
| 551 GGGCTGACTT | TGTATATTTC | TAAACTTCAA | AGATTTTCTG | TATTTCAGCT |

TABLE 3-continued

Genomic Carboxy Terminal
(SEQ ID NO: 3)

```
 601 GGGAATATGG TAGAAGGTTA ATTGGAACAA AAAAATGCAA AGCAATGAAT
 651 AAGACCTCAG TATTTGCTAT GCACAACAGG GTGACTGTAG TCCCACAAAT
 701 AACTTCACTG TACATTGTTA AAATATAACT AAAGGTGTAT GCTTGGATTG
 751 TTTGCAACAC AAAGGATATA TGCTTGAGGG GATGGATACC CCATTTACCC
 801 TGATGATTAT TATGCATTAC ATGCTTGTAT CAAACATCT CATATACCCC
 851 ATAAATATAA AAACACCTAC TATGTACCCC AAAAAATTAA AACAAATAA
1051 AGGCATGGTG GCACACACCT GTAGTCCCAG CCACTCAGGA AGCTGAGGTG
1101 GGAGGATCGC CTGAGCCTAG GAGGCTGTAC TCCAGCCTGG GTGACAGAGC
1151 GAGACTCTAT CTCAAAAAAT AAAATAAAAT AATAAAAAGT AGAAATCAAG
1201 AGGGAAAATG TGGGAGAAAT TGGGATAATT TTAACAATAC CTTCCACCAG
1251 AGTGATGATG AAGAATGCAT AAGTCACTTC TTAGTGGTCT TGATCTATAA
1301 AAAGTGTTCA ATAAATATCG ATTATTGTTA CTGTTATTGC TTCTAGACGT
1351 AATTCCTGGA AGCATTTTTT TTTTTTTTT TTTTGAGATG GAGTCATGCT
1401 CTGTTGCTCA GGCTGGAGTG CAGTGGTATG ATCTCGGCTC ACTACAACTG
1451 CCTCCTGGGT TCAAGCAATT CTCCTGCCTC AGCCCCCCAT GTAGCAGGGA
1501 CTACAGGCAT GCGCCACCAC ACCCGGTGAA GTTTTGTATT TTTATTAGAG
1551 ACAGGGTTTT GCCATGTTGG TCAGGCTGGT CTCGAACTCC TGACCTCAGG
1601 CAATTTGCCT GCCTCGGCCT CCCAAAGTGC TGAGATTACA GGCTTGGGCC
1651 ACTGCATCCA GCCGAAGGCC TCCCATTTTG ATCAGAACCC TTCTCTAGAC
1701 TGAGGGTGGG TGCCTCTAGA TCTTTTGCTC TTTAAAGACA GCAACCGATG
1751 ACCCTGCTGA TGCTGAGTAC TGGCTGAATT CCTGTGGTCT CTGTCCCTAG
```

Exon C2

```
1801 GATGGACTCC GTGTTGGTCA CTGTCAAGGC ATTGTTCTCC TCCAATTTGG
1851 ACCCCAGCCT GGTGGAGCAA GTCTTTCTAG ATAAGACCCT GAATGCCTCA
1901 TTCCATTGGC TGGGCTCCAC CTACCAGTTG GTGGACATCC ATGTGACAGG
1951 TACAAGGTGG GGTGGCTGGT TTCCTAACTG GAAGAGGTGG GGTTATGAGG
2001 AAAGATGGGG CTTCTCGGTA CCAGTGGAAT TGGTGGAGGC TCTAGAGAGG
2051 GAAAGGGAGG CTTTCTGGAG ACCCATGTAG GTGACCTCTG GCAGTAGATC
2101 ATCCAACGAG GCAGGAACAG AACACCAGCC ATTGCATCTA AGAGAATAGC
2151 TATTTTTACA TGTAAAAAGA ATTGTGTTGA ATGAATGAAT CAATAGATCA
2201 TTTATTTTGA ATCAATTTAT TGATTCATTC ATTTAATTAA TGAATAATAA
2251 ATGATTCAGT ACATAATTGA TTAATTGATG TAATTGAGAA TTGATTTAAT
2301 TGATTAATTG ATCAATTAAA ATGATCAATT AAATGAATGA ATCAGTAAAT
2351 GAATAATTCA TTCATTCAAT AAACAATGGA AGTAGGCCGG GCATGGTGGC
2401 TCACGCCTGT AATACCAGTA CTTTGGGAGG CCCAGGCAGG CAGATCACGA
2451 GGTCAGGAGA TTGAGACCAT CCTGGCTAAC ACGGTGAAAC CCTGTCTCTA
2501 CTAAAAATAC AAAAAAAATT AGCCAGGCAT GGTGGTGGCC ACCTGTAGTC
2551 GCAGCTACTC GGGAGGCTGA GGCAGGAGAA TGGCGTGAAC CCGGGAGGCA
```

TABLE 3-continued

| Genomic Carboxy Terminal (SEQ ID NO: 3) |
| --- |
| 2601 GAGCTTGCAG TGAGCCGAGA TCGCGCCACT GCACTCCAGC CTGGGCGACA |
| 2651 GATGGAGACT CTGTCTCAAA AATAAATAAA TAAATAAAAA TAAAAAATAA |
| 2701 ATAAACAATG GAAGTAAACA CGTACTGATA ACACAGTGTG ATCATTGCTA |
| 2751 TGATAAGGGA ATTTCAGGGG CCTGTGGGAG CCCCAAGGAG GAACACACAA |
| 2801 CCTTGTCTTG GAAAGTTTTA TGTAGGAAGG GGTGAAGAAG CTGAGATCTG |
| 2851 ACAGAGAATG GGACCTAGCC AGGGGTAATA GATGGAGAAT TGTGCTCCAT |
| 2901 GCATCTATAA CCTAGAAGAT AGAAAGAATA TGGCATCTGG CCGGGTGCGG |
| 2951 TGGCTCACGC CTGTAGTCCC AGCACTTTCA GAGGCTGAGA TGGGTGGATC |
| 3001 ACCTGAGGTC AGGAGTTCAA GACCAGCCTG ACCAATATGA TGAAACCCCA |
| 3051 TCTCTGCTAA AAATACAAAA ATTAGCCAGG CATGGTGGTG CGTGCCTGTA |
| 3101 ATCCCAGCCA CTTGGGAGGC TGAGAGAGGA GAACTGCTTG AACTCGGGAG |
| 3151 GCGGAGGTTG CAGTGAGCCG AGATTGTGCC ATTGCACTCA AGCCTGGGCA |
| 3201 AAAAGAGCAA AACTGCATTT CAAAAAAAAA AAAAGTGGCA TTTTGGGGCA |
| 3251 AGTTTAAGAA GATTGGTGTA GCTGGAGCAT CCACTTTGAT ACTGGAGAGG |
| 3301 TGACAGTTGA AGCCAAAGAT GTGGGCAGAG ACTTTGTTGG GCACTGGAAT |
| 3351 GGCTTGGGGA GGAACATGAC ACACTCATGA GTTCTGCTTT AGAAAGAAAA |
| 3401 TGAAATGAAT TCTGCTCATC CTCTGGGTGC TGTGTGCAGA ATGGAGGGTG |
| 3451 GGGGGAGAGA AGAGCAAAGG CAAGAAGACC CTTTAGGAAC AATGATCATT |
| 3501 AGTTAGAAGA CTCTGGGTTT CTCAGCACCT GCAATTGCTG ACTACACCCC |
| 3551 CAGAGAAACC CAGTCTCTTT TCCCCCATGT TGTAGAGAAT TCTTACAATG |
| 3601 CTTGGTAGAA AGAGAATTGA ACAGGTAGAT GGGTGGATGG ATACAAGCTG |
| 3651 GACAGATGGA TGGAGGAAGA TCCTCCATCC AATATAGAGC TGTTACCTAA |
| 3701 AACCCTCCAT CCCACCTTTA AAATCCTAGC TCAGCCAGGC GCGGTGGCTC |
| 3751 ACACCTGTAA TCCCAGCACT TTGGGAGGCC AAGGCGGGTG GATCACTTGA |
| 3801 GGTCGGGGGT TCGAGACCAG TCTGACCAAC ATGGTGAAAC CCCCTTCTCC |
| 3851 ACTAAAAATA CAAAAAAAAA AAAAAGTTAG CCAGGCAGGG TGGCGCATGC |
| 3901 CTGTAATCCC GCTACTCGGG AGGCTGAGGC AGGAGAATGG CTTGCACCCA |
| 3951 GGAGGTGGAG GTTGTGGTGA GCCAAGATCA CGCCATTACA CTCCAGCCTG |
| 4001 GGCAAAGAGA GTGAAACTGT CTCAAAAAAC AAAACAAATG ACCCCCCTGC |
| 4051 CAAAAAAAAA AAAAAAAAAA AAGAAAAGAA AAAAAGAAAA GCCTAGCTCA |
| 4101 GCTCACACTG TCAGGAATAA GTAAGCTAGC TGGAATCATC TCTTTCTTAA |
| Exon C3 |
| 4151 AACCCTGCCT TGATAGTGGA TTTTTACATA CTTTTTTTTT AATTCTAGAA |
| 4201 ATGGAGTCAT CAGTTTATCA ACCAACAAGC AGCTCCAGCA CCCAGCACTT |
| 4251 CTACCTGAAT TCACCATCA CCAACCTACC ATATTCCCAG GACAAAGCCC |
| 4301 AGCCAGGCAC CACCAATTAC CAGAGGAACA AAAGGAATAT TGAGGATGCG |
| 4351 GTGAGAAGGG GGTGGTATGT CCACTCTGTT GCCATGCAGA AACTGACTTA |
| 4401 TGCATACTGG GTAGCCACAG GGTGACTTTT TATAACAATC CACAAAGACA |
| 4451 GGTTCTTATT CCCATTTAAT ACACAAGCAC AGAGAGGTTC AGTAGCTGAC |

TABLE 3-continued

Genomic Carboxy Terminal
(SEQ ID NO: 3)

| | |
|---|---|
| 4501 | CCAAGGTCAC ACAGCTAAGT CATACCCTAG AAGAGCATGT CCTTTGATAT |
| 4551 | ACATACCTGG GCAAGTGGTT GTCATGACAA GAAGCAAAAT AGACGGAGAA |
| 4601 | GTGTGCTCAG TGGCTGAAAA TTCTCTGATG CTACTGGGGC CAGGATTCTG |

Exon C4

| | |
|---|---|
| 4651 | ACCTAAGAAA CATCGCCCTG TCTTTCAGCT CAACCAACTC TTCCGAAACA |
| 4701 | GCAGCATCAA GAGTTATTTT TCTGACTGTC AAGTTTCAAC ATTCAGGTAA |
| 4751 | GTTCTAACTC AGGACCTAAT GACTCTAGGA ACTTCTGCTG TCCTTTAAAT |
| 4801 | AGAAGTGTCC CCAAGCCATA GCTTTGATGG AAGAGAGCCC TAGAAATAGA |
| 4851 | GAGCTGTTAA CTAAAAACTA GCTTTTTCCT AAAGCTGGAG CCCAACTGGC |
| 4901 | TTCAACACTC AAGAGAGCTG GTGTAAATCT CAGCAGACAT AAAGGTACCT |
| 4951 | GGTGCTGAGG CCATGGAGTC TAGAGTGTAG AATCTACTAC ATTAAGACAT |
| 5001 | CAGCTACTGA AATCAGGACC CATGGAAGAC GGGGAAGGA GGGGACTAAA |
| 5051 | ACCAGATTAC TTAGAATCTA GCAGCCTAAC TGTGCTTTTC AATGAGAGGT |
| 5101 | ATCATTTCCA ATGGTGGGGG GTACCAATGA TTTTTTTTTT TTGACAACTG |
| 5151 | CCTTGAGAAC AGGCTTTCCT CACTAAACAA ATTCTGAATC AGAACAAATA |
| 5201 | AAGATAAGCC CTGAGAATAG GCTTTTTCA AGGAGCTGCC AAACAGATCA |
| 5251 | AATAGTGACT ATGTTCTGCA GATTGATGTC TGGAGAACTC TACAGCTATT |
| 5301 | TTGACTGCTA GGCAGCTGGT TTTCACAGAT ATCATGATTC TGAGGCTGCC |
| 5351 | AGTTTTCAAA GTTACCGAGG ATCTTGCTGG ATGCAGTGGC TTGCGACTGT |
| 5401 | AATCCCAGCC CTTTGGGAGG CCAAGGTGGG TAGATCGCTT GAGCTCAGGA |
| 5451 | GTTTGAGACC AGCCTGGGCA ATATGGTGAA AACCCATCTC TACAAAAAAT |
| 5501 | ACAAAAATCA GCTGAGCATA GTGGCATGTG CTGTAGTCCC AGTTACTTAG |
| 5551 | GAGGCTGAGG TGGGAGGATG GCTTGAGCCC AGGAGGCAGA GGTTGCAGTG |
| 5601 | AGCTGACATT GTGCCATGCA CTCTAGCCTG GGCAACAGAG CCAAAGCCTG |
| 5651 | TCTCAAAAAA AAAAAAACAA ATAATAATAA TAATAAAATA CTGAGGATCT |
| 5701 | TGAAAGAGCA CTGTGGAAAT AATGCAAGTT AAAATGCCAC AAAGCTTGCT |
| 5751 | CTTTTTACTG AGATTTAACA CTTTCCTTAA CTAAACACCC CTCGAATTTT |
| 5801 | TGCAAGCCTT TGGTTCACTT CTAGACTTCT GGAAAAATTG ATTTGGACTA |
| 5851 | TTTTGGCCAA TGTTCTCATT GATTTTATGG GTATTCAGAA GTTGTTACCC |
| 5901 | CAACATTCCA GAAATGTTCT CCCTGTGGCT ATTACTTTAT TTATTTATTT |
| 5951 | ATTTATTTAT TTATTTATTT ATTTGAGACG GAGTCTCCCT CTGTTGCCCA |
| 6001 | GGCTGGAGTG CAGTGGCGCA ATCTCAGCTC ACTGCAACCT CCGCTTCCCA |
| 6051 | GGTTCAAGCG ATTCTCCTGC CTCAGCCTCC CAAGTAGCTG GGATTATGGA |
| 6101 | TGTGCACCAC CACACCGGCT AATTTTTGTG TTTTTAGTAG AGATGGGGTT |
| 6151 | TCACTGTGTT GGCCAGGCTG GTCTCGAACT CCTGATCTCA AGTGATCCAC |
| 6201 | CCGCCTTGGC CTCCCAAAGT GCTGGGATAA CAGGCATGAG CCACTGTGCC |
| 6251 | TGACCTCCCT GTGGCTATTT TTAAATGAAT TAAGTGGAAT AAAATTAGAA |
| 6301 | ATTCAGTTCT TCTCCCACGC TAGCTGCATT TTAAGCATTT AATAACAACA |

TABLE 3-continued

Genomic Carboxy Terminal
(SEQ ID NO: 3)

```
6351 TGAAGCTACT AATGGCTGCA TTGTGTAGTG CAGATGTAGA ATTTTTTTTT

6401 TGTTTTTTGT TTTGTTTTTG AGATGGAGTC TCGCTCTGTC ACCAGGCTAG

6451 AGTGCAGTGG CGTGATCTCG TCTCACTGCA ATCTCTACTC CCCGATTCAA

6501 GTGATTCTCC TGCCTCAGCC TCCCAAGTAG CTGGGATTAC AGGCACGTGC

6551 CACCACACCC AGCTAATATT TGTATGGATG GTCTCAATCT CCTGACCTCG

6601 TGATTTGTAT GGATGGTCTC GATCTGACCT CATGATCCGC CTGCCTGGGC

6651 CTCCCAAAGT GCTGGGATTA CAGGCGTGAG CCACTGTGCC CGGCCGACAT

6701 AGAATGTTTA CATCATTGCA GAAAGTTTCT GCAGGAAGAG CCTAGAAGGA

6751 GAAAGCCTAG AATCATGATA AAATTGCAGA TATCTTTGCT TATCCCTGTC
```

Exon C5

```
6801 CCCTTCCAGG TCTGTCCCCA ACAGGCACCA CACCGGGGTG GACTCCCTGT

6851 GTAACTTCTC GCCACTGGCT CGGAGAGTAG ACAGAGTTGC CATCTATGAG

6901 GAATTTCTGC GGATGACCCG GAATGGTACC CAGCTGCAGA ACTTCACCCT

6951 GGACAGGAGC AGTGTCCTTG TGGATGGTAA AGCTCCCTGG GTCATTGGGA

7001 CTGAGGTGGA AGCTCCCACT TCCTCACCTG GTCCTTCCC TGGGAATCTG

7051 AAGGCTTGGG GTTGATTCGT CATCGAGCTT TCTCAGACTG GGAGAAAGTG

7101 GCTTAGTTCT CCTAAGCTTT ACCCATCATT GAAGGAAAGA AAAGGACGCC

7151 CGAGGGATAT GGGAGGCATT TGCCCTCTTC TGGCCAGCTC TGTGACCTCA

7201 GGCTAGTCAC ATCTCCTTTC TGGACTTCTT ATCTCTCTGT ACTTAGCAAG

7251 CCACTTGGTT TTTGGTTCCC ATCTTGCCTG CCCTAGATGG TATTGCTCCT

7301 CCACCCCCAG GCAGCTGCAG TGTTAAACAA TTACCCTGAT TAGTTATTGT

7351 TGTTGTGTTG TTTGTTTGTT TTTGAGACAG GGTCTCACTC TGTCACCTAG

7401 GCTGGAGTGC AGTGACATGA TCTCAGCTCA CTGCAACCTC AACCCCTGGA

7451 CTCAAGCAAT CCACCCACTT CAGCCTCCCA AGTAACTGGG ACTACAGCCA

7501 TGCGCCACCA CACCCGGATA ATTTTTGTAT TTTTTCTAGA GATGGGGTTT

7551 TGCAACATTG CCCAGGCTGG TCTTGAACTC CTGAGCTCAA GCATGCCACC

7601 TGCTTCAGCC TCCCAAAGTG CTGGGATTAC AGGCAGGCAG CACCACTGC

7651 AGCTGGTTCT GGTTTTTTGT GTTTGTTTTT TTCTTTTAGA GGCAGGGTCT

7701 CGCTCTGTTA ACCAGAATGG AGTACAGTGG TGCAATCATA GCTCACTGCA

7751 GTCTTGAACT CCTGGGCTCA AGCGATCCTC CCACCTCAGC CTCCTGAGTA

7801 CCTGGAACTA CAGGCACGTG TCACCACGCC TTGCTAATTT CTAAATTTTT

7851 TGTAGAGACA GGGTCTCACT ATGTTGCCCA GACTGGTCTC TAATTCCTGG

7901 CCACAAGTGA TCCTCCTGCC TCAGCAGGTC AATGAGGGCT TCCAGTTTCA

7951 AGTTGTATGT GATTCATCCT CAACAAATGT GGTAGGATGG ACCTATTTTC

8001 CAACTCCAGA GATGGCTTCA AGGTGGCTCA ACTTTGCATA TCCAATTTTA

8051 CCCATTCAAA GAATAGTTAT ATACATTGTA CCATGTATCA GGAATATAAC

8101 AGAGAGTAAC TGTTTGCTCT TTCACCACTA TATTCCAAGA ACCCCATATT

8151 CTGCCTGGCA CATAATAAAC ACTCAAGTCA TATTTGCAGA AGGAATAACT

8201 AGATTTCATA CAAGGTTCTT TTCAAGTCAA ATGCGAATAA CGTTTTAGAC
```

TABLE 3-continued

Genomic Carboxy Terminal
(SEQ ID NO: 3)

```
 8251 GGGACCTTCC AATGCCTGTG TGCACTGTCC TTGATTCCGA ATTATTGTTG
 8301 TGCAAGAGAG CACTGTTGAT CCTTCAGAAT CAACAAGCCT TTCACATGCC
 8351 TGTCACAGGT TTTTCTTTTT CTTGTTTTAC CAATTTTGTT TGTTGTTTGT
 8401 TTGTTGTTAT TGTTTTGTTT TGTTTTTGTT TTTTATTTGT TTTTATTTTT
 8451 TCTTTTTTTT TGAGACAGAG TCTCGCTCTG TCACCCAGGC TGGAGTGCAG
 8501 TGGCACGATC TCCGCCCACT GCAAGCTCCG CCTCCTGGGT TCATGCCATT
 8551 TTCCTGCCTC AGCCTCCTGA GTAGCTGGGA CTACAGGCGC CTGCCACCAT
 8601 GTCTGGCTAA TTTTTTTTGT ATTTTTAGTA GAAACAGGGT TTCACCATGT
 8651 TGACCAGGAT GGTCTCGATC TCCTGACCTC GTGATCTGCC CACCTGGGCC
 8701 TCCCAAAGTG CTGGGATTAC AGGCGTGAGC CACCACACCC AGCCCCAATT
 8751 TTTTTTTTAA TTAAAATTGT TGTCAGCTCA CAAGCTTTCT AAAAACAGGC
 8801 CATGGACCCA GCATCGCTGT AGTTTGCCAA ACCCTTGCCT TGAATCAGTA
 8851 CCATCCAATA GAACTTTCTG CAGTGATAGA AAATGTTTCT ATCTGTGCTA
 8901 TTCAGCACAA AGCCATGTGT GATTACTAAG CTTGAAGTGT GGTTAATGTA
 8951 ACTGAGATAC CGAAGTTTTA ATTTTATTTA ATTTTAATTT AAAAAGCCAC
 9001 TTGTGGCTGC TCCATATTGC ACACTACTTT TTAAAATTAT TATTTGTATA
 9051 TATTTAAGGG GCACAAGTAC AATTTTGTTG CATGGATTTA TAGCCCAGTG
 9101 GGGAAGTCTG GGCTTTTAGG GTATCTATTA CCTGAATAAT GTACATTGTA
 9151 CCCATTGAGT AATTTCTCAT CATCCACTCT CCTCCACTCC CCAACCCTTC
 9201 CAAGTTTCCA CTGTCTATTA TTCCACTCTC TATGTCCATG CCTATGCATT
 9251 ATTTAGCATT GACATGTCTA TGCATTATTT AGTCAAATAC ATGTGCTATT
 9301 TGACTTCCTG TATCTGAGTT GTTTGACTTA AGATAATGAC CTTCACTTGC
 9351 ATCCATGTTG CTGCAAAAGA CATGATTTCA TTCTTTTTTA TGCCTGGGTG
 9401 GTATTGCATT GTGTGTGTGT GTGTGTGTGT GTGTGTAGAG AGAGAGAGAG
 9451 ATCACATTTT CTTTATACAG TCCTCCATTG ATGGGCACTT AGGTTGATTC
 9501 CATATCTTTG CTATTGTGAA TAGTTTTGTG ATAAACACAC AGGTTCAGGT
 9551 GTCTTTTTGA CAAAATTATT TATTTTCCTT TGTGTAGATA CCCAGTCGTG
 9601 GGATTCCTGG ATCAAATGGT AGTTTCATTT TTAGTTATTT GAGAAATCTC
 9651 CACGTTTTTC ATAGAGATTA TACTAAATTA CATTCCCACC AACAGTGTGT
 9701 AACGGTTCAC TTTTCTTGCA TCCTTTTTAA CATCTGTTAT TTTTGTCTTT
 9751 TTAGTAACAG CCATTCTGAC TGGCGTAAGG TGGTATCTCA TCATGGTTTT
 9801 AATCTGTATT TCTCTGATTA TTAGTAATGT CGAGCATTTT TTCATATGCT
 9851 TGTTAGCCAT TGGTATGTCT TCTACATCTT TAAGAAGCTG GCTATGGGCT
 9901 GGGCGCAGTG GCTCACACCT GTAATCCCAG CACTTTGGGA GGCCGAGGCA
 9951 GCGGATCAC GAGGTCAGGA GTTAAAAACC AGCCTGGCCA ACATGGTAAA
10001 ACCCTGCCTC TACTAAAAAT ACAAAAAATT ACCCAGGCAT GGTGGTGCGC
10051 CTGTAATCCC AGCTACTCAG GAAGCTGAGG CAGGAGAATC ACTTGAACCC
10101 AGGAGGCGGA GGTTGCAGTG AGACGAGATC ACATCATTGC ACTCCAGCCT
```

TABLE 3-continued

Genomic Carboxy Terminal
(SEQ ID NO: 3)

10151 GGGTGACAGA GTGAGACTCT ATCTTGAGAA AAAAAAAAG TTGGCTATAA

10201 CAGGGTTGTA AAGTAGAGG AACCAGTAAC CCTTCTCGCC ATGCCTGATG

10251 ATGGCTTTAC ATCCCTGTCT TCATGGAGTT TATGCTGTCG TGAGGAATAA

10301 CAAGAACAGG CAGTTGTCAA TTATAAATTA TTTGATGTGA ACCTATTCAT

10351 ACATGGGTGT GGTCATCAGG GAAGGCTTCC TGGAGGAAAT GACATTGAAG

10401 GTGAATTCTA AAAGATGACG ATAAACCACC AAGTGAAGGA GAGCTTAAAT

10451 GTGTTTTTAG GCAGAAGAAA AACCTTTTGG GTGAAAATTT TAAAACTTAG

10501 AGAGGTCCCA TCAGTTTCCA ACTGCGATGA TCCATTCTCT CCACCACTGC

10551 CCTTGGGCCC AGCCCAATTT AGGTCCACCA TGCCCAGAGG CATGAATTTA

10601 ACTTATGACA CTCTTGTGGT GGAATAATGG CTTTGGGCTT ATGTAGCCAT

10651 GTGTCATTTT TTTAGAGATA CAAATTGAAA TATTTGGGGT GAGATGTCAT

10701 GGTGTCTACT GGCCTCTAAA ACTTCAGTGA AAACATTTAC TTTCACTGAA

10751 ATGTCAATAA ATCATAAATT GGATGTATAT GTTTTAGTTG GAGGAAATAT

10801 AAACCACTAA ATCTAGGTGA TGCATATTTA TTATACTCTT CTCTCTGCTT

10851 TTTTGTACGC TTGTAAAATT GTATTTAAAA GAATAAGACA CACTTGGCCG

10901 GGCGCGGTGG CTCACGCCTG TAATCCCAGC ACTTTGGGAG ACCGAGGTGG

10951 GTGGATCATG AGGTCAGGAG TTCAAGACCA GCCTGGCCAA CATGGTAAAA

11001 CTCCATCACT ACATACAAAA ATTAGCCAGG CATTTTGGCG GGCACCTGTA

11051 ATCTCAGCTA CTTGGGAGGC TGAAGCAGGA GAATTGCTTG AACCCGGGAA

11101 GCAGAGGTTG CAGTGAGCCA AGATCACGCC ACTGCACTCT AGCCTGGGCA

11151 ACAGAGCAAG ACTCCATCTC CAGAAAAAAA AAAAAAAAA GACACACTCA

Exon C6

11201 CATGCACCCT CCATTTCTTT CATTTCTAGG G<u>TATTCTCCC AACAGAAATG</u>

11251 <u>AGCCCTTAAC TGGGAATTCT</u> GGTAAGTCTC AAAGAAGCCC CAGCCCAGGG

11301 TAGGGAGGGG GTAGCCTGAT GGTGCTTTGC CTTGTCCAAG AGCACCAGGC

11351 ACACAGAGTC TTGGATGAGG ATCAAAATTG CCAACCCATG GCAAAGACTA

11401 TTGAGGCATA GTAAAGGGAT AGCAGGGATC CTGGCTTTCT GGGGGCCCAG

11451 TTTTTGGGGG CATCAGAGGC ATGAGGTGTT GAGCCACTAA GCTCTCTTCC

11501 CCAGGGGCTG TGCCCATCCT CAGGCCACAT AGGGTCCAAG AAGGAGCCCT

Exon C7

11551 GGGACGTGGC AGGAGGTGGC TCACCCCAGC CCTTGTCTCC CCA<u>GACCTTC</u>

11601 <u>CCTTCTGGGC TGTCATCCTC ATCGGCTTGG CAGGACTCCT GGGAGTCATC</u>

11651 <u>ACATGCCTGA TCTGCGGTGT CCTGGTGAGC</u> AAGGAAGGGT TGCTTGTCTT

11701 CTTAACAATT GGGTTGTAAG AGTTCTTAAT ATATTATAAA ACCATACTAT

11751 ACTATACACA AGTCCTTTGC TGGATATATG TTTTGCAAAT ATTTTCTCCC

11801 AGTTCACGGA GTGGCTTTCC TATTTTCTTT TTATAATTTT ATTTTTAATT

11851 AATTGACAAA TAATGAATGC ATATATTTAG GGGATACAAT GTGATGCTTT

11901 GGTATATGTA CAATTATGGA ATGACTCAAT CAAGCTAATT AATATGTCCC

11951 TCACCTCTCA TACTTATTAT TTCTTTGTGG TGTGAACATT GGCAACCTAT

TABLE 3-continued

Genomic Carboxy Terminal
(SEQ ID NO: 3)

```
12001 ACTCTTAGCA ATTTTGAAAT CTACATTATT ATTAACTATA GTTACTATGT

12051 TATGCAGATC TCAAAAACTT CACAACCTAT ATGCTGATTA CAAGATATTG

12101 AGAGAAAAAG TGATTGCAAA GAGTGTAAAT AAAATAATGT AAGAGGGAAA

12151 AATGTAACAA AATTAGTCGT TAGGGAAATG TACACGGAAG TCACAATGAG

12201 AGGCCACTTT TCACAAGAAT GGATAAAATT GAAAAGATTG ACTATAACAA

12251 GTGTTGGTGA AAATGTGACA GAACTGGAAC TCTCATAAAG TGAAAGTGGA

12301 AAATAGCTTG GCCATTTCTT TGAAAATTAC ACACACCTAC CGTAAGACCT

12351 ACCATCCCAC TACTAGTAAT TTATCTAAGA GAATAAAAA CATATGTCTA

12401 TATGAAGACT TGTACACAAG TAAATGTTCA TAACAGCTTT GTTTGTAATA

12451 GCCAAACTCT GAAACAAGC CCCTAATGTC CATTAACAAA TATATCCTGA

12501 CAATGGAATA TTATTCAGCA ACAAAAAGGA ATTATTAATA CATTAATAAA

12551 TTATACAGCA ACATGTATAA ATTGCAAAAT AGTTATGCCT AGTGAAAGAA

12601 TCCAGATGAA GAAAAGAGTA CATGCCATAT GATTCCCTTA ATAGACAAAT

12651 TCTAGAAAAT ACAAACTAAT CTGTAAGGAC AGGAATCAGA TCAGCGGTTG

12701 CCTGGGAATG AAAATGTGTT TGCAGTGGCA GGGAAAAAGG AATTGTAAAA

12751 GAGCAGGAAG AAAGTTTTTT TGTTGTTTTT TTTTTGTTTT TTCTTGAGAC

12801 AGAGTCTTAG TCTATCGCCC AAGCTGGAGT GCAATGGCAC GATCTCAGCT

12851 CATTGCAACC TCTGCCTCTC GGGTTCAAGC GTTTTTCCTG CCCCAGCCTC

12901 CCAAGTAGCT GGGATTACAC ATGCGCACCA CCACACTCAG CTAATTTTTG

12951 TATTTTTAGT AGAGACGGGG TTTTACCATG TTGGCCAGGC TGGTCTCGAA

13001 CTCCTGACCT CAGGTGATCC ACCCGCCTTG GCCTCCCAAA GTGCTGGGAT

13051 TACAGGAGTG AGCCACCATG CCTGGCCAGG ACGAAAGTTT TGGGGATGAT

13101 GGATGGATGT TCCTTATGTT GATTGTGGTG ACGATTCAAT AAGTTATGAT

13151 CAGAACTTAT CAAAACATTC ACTTTAAATG TGTGCAGTTT ATTTTATGTC

13201 AGTTATGCCT CAGTTAAGCT GGACAGATGT AGAGGAGGAA GGGAGGGAGA

13251 GAGGGGGCTG AGATCAGGAC CAAAAGCCAG AGAGAAAGAG ACTGAGAATG

13301 AGATGAGAGA GAAATGGTAT TTAGACAGAA GACAGGCGAT AGATGATTGA

13351 TAGTTGACAG ATGATTGGTG GATANNNNNN NNNNNNNNNN NNNNNNNNNN

13401 NNNNNNNNNN NNNNNNNNNN NNNNNNNNNN NNNNNNNNNN NNNNNNNNNN

13451 NNNNNNNNNN NNNNNNNNNN NNNNNNNNNN NNNNNNNNNN NNNNNNNNNN

13501 AGGAGGTTTA AACAAAACGC AATTATGTTG AAATGACAAT GATTGTGGAT

13551 ATAAAGGTAG ATAGAAATAG ATATTTGTGA AGATAATGGT TAGATAAAAA

13601 TGATAGGTAA CAGATATTGA TAGATCTTGA TAAGTAGATG ATAAATACAT

13651 GATTGATGGA TGACAGGTGA TTGATAGATG ATTTGATGGA TTATAAATAG

13701 GAGATGATTG AGAGGTGAGA GATAATTGAT GGTTATTTGA TTGGTAGATA

13751 ATTGATTGAC AGGTTGATAA ATATTGATAG CTAGATGATA GATAAATAGA

13801 TCATTGGTAG ATATGTGATA TATTGATAAA GAATTCAGA GGCAAAAGGA

13851 GAGAGAAATG AAGGGGATAT CGGAGGGGGA AAAATTTTTT TAAACCGAGA
```

TABLE 3-continued

Genomic Carboxy Terminal
(SEQ ID NO: 3)

```
13901 GTGAAACAAG GAGACAGAAG AAAAGAAAGT GGTGAAAAGA GGAAAAGAAC
13951 TGAGGGAGAA ATTAAATGAA ACAATGAAGG GAGACAGAGG AAGCATAAGG
```

Exon C8

```
14001 CCTCTGGCTT TGGCCATATT CTCACCCCTG TGGTCTCCTC TCCCTGGACG
14051 GCTGACCAGT CCATTCTCAC GCCTCCTCCT CACCCTCATA GGTGACCACC
14101 CGCCGGCGGA AGAAGGAAGG AGAATACAAC GTCCAGCAAC AGTGCCCAGG
14151 CTACTACCAG TCACACCTAG ACCTGGAGGA TCTGCAATGA CTGGAACTTG
14201 CCGGTGCCTG GGGTGCCTTT CCCCCAGCCA GGGTCCAAAG AAGCTTGGCT
14251 GGGGCAGAAA TAAACCATAT TGGTCGG
```

TABLE 4

Human cDNA of CA125
(SEQ ID NO: 4)

```
   1 AAGCGTTGCA CAATTCCCCC AACCTCCATA CATACGGCAG CTCTTCTAGA
  51 CACAGGTTTT CCCAGGTCAA ATGCGGGGAC CCCAGCCATA TCTCCCACCC
 101 TGAGAAATTT TGGAGTTTCA GGGAGCTCAG AAGCTCTGCA GAGGCCACCC
 151 TCTCTGAGGG GATTCTTCTT AGACCTCCAT CCAGAGGCAA ATGTTGACCT
 201 GTCCATGCTG AAACCCTCAG GCCTTCCTGG GTCATCTTCT CCCACCCGCT
 251 CCTTGATGAC AGGGAGCAGG AGCACTAAAG CCACACCAGA AATGGATTCA
 301 GGACTGACAG GAGCCACCTT GTCACCTAAG ACATCTACAG GTGCAATCGT
 351 GGTGACAGAA CATACTCTGC CCTTTACTTC CCCAGATAAG ACCTTGGCCA
 401 GTCCTACATC TTCGGTTGTG GGAAGAACCA CCCAGTCTTT GGGGGTGATG
 451 TCCTCTGCTC TCCCTGAGTC AACCTCTAGA GGAATGACAC ACTCCGAGCA
 501 AGAACCAGC CCATCGCTGA GTCCCCAGGT CAATGGAACT CCCTCTAGGA
 551 ACTACCCTGC TACAAGCATG GTTTCAGGAT TGAGTTCCCC AAGGACCAGG
 601 ACCAGTTCCA CAGAAGGAAA TTTTACCAAA GAAGCATCTA CATACACACT
 651 CACTGTAGAG ACCACAAGTG GCCCAGTCAC TGAGAAGTAC ACAGTCCCCA
 701 CTGAGACCTC AACAACTGAA GGTGACAGCA CAGAGACCCC CTGGGACACA
 751 AGATATATTC CTGTAAAAAT CACATCTCCA ATGAAAACAT TTGCAGATTC
 801 AACTGCATCC AAGGAAAATG CCCCAGTGTC TATGACTCCA GCTGAGACCA
 851 CAGTTACTGA CTCACATACT CCAGGAAGGA CAAACCCATC ATTTGGGACA
 901 CTTTATTCTT CCTTCCTTGA CCTATCACCT AAAGGGACCC CAAATTCCAG
 951 AGGTGAAACA AGCCTGGAAC TGATTCTATC AACCACTGGA TATCCCTTCT
1001 CCTCTCCTGA ACCTGGCTCT GCAGGACACA GCAGAATAAG TACCAGTGCG
1051 CCTTTGTCAT CATCTGCTTC AGTTCTCGAT AATAAAATAT CAGAGACCAG
1101 CATATTCTCA GGCCAGAGTC TCACCTCCCC TCTGTCTCCT GGGGTGCCCG
1151 AGGCCAGAGC CAGCACAATG CCCAACTCAG CTATCCCTTT TTCCATGACA
1201 CTAAGCAATG CAGAAACAAG TGCCGAAAGG GTCAGAAGCA CAATTTCCTC
1251 TCTGGGGACT CCATCAATAT CCACAAAGCA GACAGCAGAG ACTATCCTTA
```

TABLE 4-continued

Human cDNA of CA125
(SEQ ID NO: 4)

```
1301 CCTTCCATGC CTTCGCTGAG ACCATGGATA TACCCAGCAC CCACATAGCC
1351 AAGACTTTGG CTTCAGAATG GTTGGGAAGT CCAGGTACCC TTGGTGGCAC
1401 CAGCACTTCA GCGCTGACAA CCACATCTCC ATCTACCACT TTAGTCTCAG
1451 AGGAGACCAA CACCCATCAC TCCACGAGTG GAAAGGAAAC AGAAGGAACT
1501 TTGAATACAT CTATGACTCC ACTTGAGACC TCTGCTCCTG GAGAAGAGTC
1551 CGAAATGACT GCCACCTTGG TCCCCACTCT AGGTTTTACA ACTCTTGACA
1601 GCAAGATCAG AAGTCCATCT CAGGTCTCTT CATCCCACCC AACAAGAGAG
1651 CTCAGAACCA CAGGCAGCAC CTCTGGGAGG CAGAGTTCCA GCACAGCTGC
1701 CCACGGGAGC TCTGACATCC TGAGGGCAAC CACTTCCAGC ACCTCAAAAG
1751 CATCATCATG GACCAGTGAA AGCACAGCTC AGCAATTTAG TGAACCCCAG
1801 CACACACAGT GGGTGGAGAC AAGTCCTAGC ATGAAAACAG AGAGACCCCC
1851 AGCATCAACC AGTGTGGCAG CCCCTATCAC CACTTCTGTT CCCTCAGTGG
1901 TCTCTGGCTT CACCACCCTG AAGACCAGCT CCACAAAAGG GATTTGGCTT
1951 GAAGAAACAT CTGCAGACAC ACTCATCGGA GAATCCACAG CTGGCCCAAC
2001 CACCCATCAG TTTGCTGTTC CCACTGGGAT TCAATGACA GGAGGCAGCA
2051 GCACCAGGGG AAGCCAGGGC ACAACCCACC TACTCACCAG AGCCACAGCA
2101 TCATCTGAGA CATCCGCAGA TTTGACTCTG GCCACGAACG GTGTCCCAGT
2151 CTCCGTGTCT CCAGCAGTGA GCAAGACGGC TGCTGGCTCA AGTCCTCCAG
2201 GAGGGACAAA GCCATCATAT ACAATGGTTT CTTCTGTCAT CCCTGAGACA
2251 TCATCTCTAC AGTCCTCAGC TTTCAGGGAA GGAACCAGCC TGGGACTGAC
2301 TCCATTAAAC ACTAGACATC CCTTCTCTTC CCCTGAACCA GACTCTGCAG
2351 GACACACCAA GATAAGCACC AGCATTCCTC TGTTGTCATC TGCTTCAGTT
2401 CTTGAGGATA AAGTGTCAGC GACCAGCACA TTCTCACACC ACAAAGCCAC
2451 CTCATCTATT ACCACAGGGA CTCCTGAAAT CTCAACAAAG ACAAAGCCCA
2501 GCTCAGCCGT TCTTTCCTCC ATGACCCTAA GCAATGCAGC AACAAGTCCT
2551 GAAAGAGTCA GAAATGCAAC TTCCCCTCTG ACTCATCCAT CTCCATCAGG
2601 GGAAGAGACA GCAGGGAGTG TCCTCACTCT CAGCACCTCT GCTGAGACTA
2651 CAGACTCACC TAACATCCAC CCAACTGGGA CACTGACTTC AGAATCGTCA
2701 GAGAGTCCTA GCACTCTCAG CCTCCCAAGT GTCTCTGGAG TCAAAACCAC
2751 ATTTTCTTCA TCTACTCCTT CCACTCATCT ATTTACTAGT GGAGAAGAAA
2801 CAGAGGAAAC TTCGAATCCA TCTGTGTCTC AACCTGAGAC TTCTGTTTCC
2851 AGAGTAAGGA CCACCTTGGC CAGCACCTCT GTCCCTACCC CAGTATTCCC
2901 CACCATGGAC ACCTGGCCTA CACGTTCAGC TCAGTTCTCT TCATCCCACC
2951 TAGTGAGTGA GCTCAGAGCT ACGAGCAGTA CCTCAGTTAC AAACTCAACT
3001 GGTTCAGCTC TTCCTAAAAT ATCTCACCTC ACTGGGACGG CAACAATGTC
3051 ACAGACCAAT AGAGACACGT TTAATGACTC TGCTGCACCC CAAAGCACAA
3101 CTTGGCCAGA GACTAGTCCC AGATTCAAGA CAGGGTTACC TTCAGCAACA
3151 ACCACTGTTT CAACCTCTGC CACTTCTCTC TCTGCTACTG TAATGGTCTC
```

TABLE 4-continued

| Human cDNA of CA125 (SEQ ID NO: 4) |
|---|

```
3201 TAAATTCACT TCTCCAGCAA CTAGTTCCAT GGAAGCAACT TCTATCAGGG

3251 AACCATCAAC AACCATCCTC ACAACAGAGA CCACGAATGG CCCAGGCTCT

3301 ATGGCTGTGG CTTCTACCAA CATCCCAATT GGAAAGGGCT ACATTACTGA

3351 AGGAAGATTG GACACAAGCC ATCTGCCCAT GGAACCACA GCTTCCTCTG

3401 AGACATCTAT GGATTTTACC ATGGCCAAAG AAAGTGTCTC AATGTCAGTA

3451 TCTCCATCTC AGTCCATGGA TGCTGCTGGC TCAAGCACTC CAGGAAGGAC

3501 AAGCCAATTC GTTGACACAT TTTCTGATGA TGTCTATCAT TTAACATCCA

3551 GAGAAATTAC AATACCTAGA GATGGAACAA GCTCAGCTCT GACTCCACAA

3601 ATGACTGCAA CTCACCCTCC ATCTCCTGAT CCTGGCTCTG CTAGAAGCAC

3651 CTGGCTTGGC ATCTTGTCCT CATCTCCTTC TTCTCCTACT CCCAAAGTCA

3701 CAATGAGCTC ACATTTTCA ACTCAGAGAG TCACCACAAG CATGATAATG

3751 GACACAGTTG AAACTAGTCG GTGGAACATG CCCAACTTAC CTTCCACGAC

3801 TTCCCTGACA CCAAGTAATA TTCCAACAAG TGGTGCCATA GGAAAAAGCA

3851 CCCTGGTTCC CTTGGACACT CCATCTCCAG CCACATCATT GGAGGCATCA

3901 GAAGGGGGAC TTCCAACCCT CAGCACCTAC CCTGAATCAA CAAACACACC

3951 CAGCATCCAC CTCGGAGCAC ACGCTAGTTC AGAAAGTCCA AGCACCATCA

4001 AACTTACCAT GGCTTCAGTA GTAAAACCTG GCTCTTACAC ACCTCTCACC

4051 TTCCCCTCAA TAGAGACCCA CATTCATGTA TCAACAGCCA GAATGGCTTA

4101 CTCTTCTGGG TCTTCACCTG AGATGACAGC TCCTGGAGAG ACTAACACTG

4151 GTAGTACCTG GGACCCCACC ACCTACATCA CCACTACGGA TCCTAAGGAT

4201 ACAAGTTCAG CTCAGGTCTC TACACCCCAC TCAGTGAGGA CACTCAGAAC

4251 CACAGAAAAC CATCCAAAGA CAGAGTCCGC CACCCCAGCT GCTTACTCTG

4301 GAAGTCCTAA AATCTCAAGT TCACCCAATC TCACCAGTCC GGCCACAAAA

4351 GCATGGACCA TCACAGACAC AACTGAACAC TCCACTCAAT TACATTACAC

4401 AAAATTGGCA GAAAAATCAT CTGGATTTGA GACACAGTCA GCTCCAGGAC

4451 CTGTCTCTGT AGTAATCCCT ACCTCCCCTA CCATTGGAAG CAGCACATTG

4501 GAACTAACTT CTGATGTCCC AGGGGAACCC CTGGTCCTTG CTCCCAGTGA

4551 GCAGACCACA ATCACTCTCC CCATGGCAAC ATGGCTGAGT ACCAGTTTGA

4601 CAGAGGAAAT GGCTTCAACA GACCTTGATA TTTCAAGTCC AAGTTCACCC

4651 ATGAGTACAT TTGCTATTTT TCCACCTATG TCCACACCTT CTCATGAACT

4701 TTCAAAGTCA GAGGCAGATA CCAGTGCCAT TAGAAATACA GATTCAACAA

4751 CGTTGGATCA GCACCTAGGA ATCAGGAGTT TGGGCAGAAC TGGGGACTTA

4801 ACAACTGTTC CTATCACCCC ACTGACAACC ACGTGGACCA GTGTGATTGA

4851 ACACTCAACA CAAGCACAGG ACACCCTTTC TGCAACGATG AGTCCTACTC

4901 ACGTGACACA GTCACTCAAA GATCAAACAT CTATACCAGC CTCAGCATCC

4951 CCTTCCCATC TTACTGAAGT CTACCCTGAG CTCGGGACAC AAGGGAGAAG

5001 CTCCTCTGAG GCAACCACTT TTTGGAAACC ATCTACAGAC ACACTGTCCA

5051 GAGAGATTGA GACTGGCCCA ACAAACATTC AATCCACTCC ACCCATGGAC

5101 AACACAACAA CAGGGAGCAG TAGTAGTGGA GTCACCCTGG GCATAGCCCA
```

TABLE 4-continued

Human cDNA of CA125
(SEQ ID NO: 4)

```
5151 CCTTCCCATA GGAACATCCT CCCCAGCTGA GACATCCACA AACATGGCAC

5201 TGGAAAGAAG AAGTTCTACA GCCACTGTCT CTATGGCTGG ACAATGGGA

5251 CTCCTTGTTA CTAGTGCTCC AGGAAGAAGC ATCAGCCAGT CATTAGGAAG

5301 AGTTTCCTCT GTCCTTTCTG AGTCAACTAC TGAAGGAGTC ACAGATTCTA

5351 GTAAGGGAAG CAGCCCAAGG CTGAACACAC AGGGAAATAC AGCTCTCTCC

5401 TCCTCTCTTG AACCCAGCTA TGCTGAAGGA AGCCAGATGA GCACAAGCAT

5451 CCCTCTAACC TCATCTCCTA CAACTCCTGA TGTGGAATTC ATAGGGGCA

5501 GCACATTTTG GACCAAGGAG GTCACCACAG TTATGACCTC AGACATCTCC

5551 AAGTCTTCAG CAAGGACAGA GTCCAGCTCA GCTACCCTTA TGTCCACAGC

5601 TTTGGGAAGC ACTGAAAATA CAGGAAAAGA AAAACTCAGA ACTGCCTCTA

5651 TGGATCTTCC ATCTCCAACT CCATCAATGG AGGTGACACC ATGGATTTCT

5701 CTCACTCTCA GTAATGCCCC CAATACCACA GATTCACTTG ACCTCAGCCA

5751 TGGGGTGCAC ACCAGCTCTG CAGGGACTTT GGCCACTGAC AGGTCATTGA

5801 ATACTGGTGT CACTAGAGCC TCCAGATTGG AAAACGGCTC TGATACCTCT

5851 TCTAAGTCCC TGTCTATGGG AAACAGCACT CACACTTCCA TGACTGACAC

5901 AGAGAAGAGT GAAGTGTCTT CTTCAATCCA TCCCCGACCT GAGACCTCAG

5951 CTCCTGGAGC AGAGACCACT TTGACTTCCA CTCCTGGAAA CAGGGCCATA

6001 AGCTTAACAT GCCTTTTTC ATCCATTCCA GTGGAAGAAG TCATTTCTAC

6051 AGGCATAACC TCAGGACCAG ACATCAACTC AGCACCCATG ACACATTCTC

6101 CCATCACCCC ACCAACAATT GTATGGACCA GTACAGGCAC AATTGAACAG

6151 TCCACTCAAC CACTACATGC AGTTTCTTCA GAAAAAGTTT CTGTGCAGAC

6201 ACAGTCAACT CCATATGTCA ACTCTGTGGC AGTGTCTGCT TCCCCTACCC

6251 ATGAGAATTC AGTCTCTTCT GGAAGCAGCA CATCCTCTCC ATATTCCTCA

6301 GCCTCACTTG AATCCTTGGA TTCCACAATC AGTAGGAGGA ATGCAATCAC

6351 TTCCTGGCTA TGGGACCTCA CTACATCTCT CCCCACTACA ACTTGGCCAA

6401 GTACTAGTTT ATCTGAGGCA CTGTCCTCAG GCCATTCTGG GGTTTCAAAC

6451 CCAAGTTCAA CTACGACTGA ATTTCCACTC TTTTCAGCTG CATCCACATC

6501 TGCTGCTAAG CAAAGAAATC CAGAAACAGA GACCCATGGT CCCCAGAATA

6551 CAGCCGCGAG TACTTTGAAC ACTGATGCAT CCTCGGTCAC AGGTCTTTCT

6601 GAGACTCCTG TGGGGCAAG TATCAGCTCT GAAGTCCCTC TTCCAATGGC

6651 CATAACTTCT AGATCAGATG TTTCTGGCCT ACATCTGAG AGTACTGCTA

6701 ACCCGAGTTT AGGCACAGCC TCTTCAGCAG GGACCAAATT AACTAGGACA

6751 ATATCCCTGC CCACTTCAGA GTCTTTGGTT TCCTTTAGAA TGAACAAGGA

6801 TCCATGGACA GTGTCAATCC CTTTGGGGTC CCATCCAACT ACTAATACAG

6851 AAACAAGCAT CCCAGTAAAC AGCGCAGGTC CACCTGGCTT GTCCACAGTA

6901 GCATCAGATG TAATTGACAC ACCTTCAGAT GGGGCTGAGA GTATTCCCAC

6951 TGTCTCCTTT TCCCCCTCCC CTGATACTGA AGTGACAACT ATCTCACATT

7001 TCCCAGAAAA GACAACTCAT TCATTTAGAA CCATTTCATC TCTCACTCAT
```

TABLE 4-continued

Human cDNA of CA125
(SEQ ID NO: 4)

```
7051 GAGTTGACTT CAAGAGTGAC ACCTATTCCT GGGGATTGGA TGAGTTCAGC

7101 TATGTCTACA AAGCCCACAG GAGCCAGTCC CTCCATTACA CTGGGAGAGA

7151 GAAGGACAAT CACCTCTGCT GCTCCAACCA CTTCCCCCAT AGTTCTCACT

7201 GCTAGTTTCA CAGAGACCAG CACAGTTTCA CTGGATAATG AAACTACAGT

7251 AAAAACCTCA GATATCCTTG ACGCACGGAA AACAAATGAG CTCCCCTCAG

7301 ATAGCAGTTC TTCTTCTGAT CTGATCAACA CCTCCATAGC TTCTTCAACT

7351 ATGGATGTCA CTAAAACAGC CTCCATCAGT CCCACTAGCA TCTCAGGAAT

7401 GACAGCAAGT TCCTCCCCAT CTCTCTTCTC TTCAGATAGA CCCCAGGTTC

7451 CCACATCTAC AACAGAGACA AATACAGCCA CCTCTCCATC TGTTTCCAGT

7501 AACACCTATT CTCTTGATGG GGGCTCCAAT GTGGGTGGCA CTCCATCCAC

7551 TTTACCACCC TTTACAATCA CCCACCCTGT CGAGACAAGC TCGGCCCTAT

7601 TAGCCTGGTC TAGACCAGTA AGAACTTTCA GCACCATGGT CAGCACTGAC

7651 ACTGCCTCCG GAGAAAATCC TACCTCTAGC AATTCTGTGG TGACTTCTGT

7701 TCCAGCACCA GGTACATGGG CCAGTGTAGG CAGTACTACT GACTTACCTG

7751 CCATGGGCTT TCTCAAGACA AGTCCTGCAG GAGAGGCACA CTCACTTCTA

7801 GCATCAACTA TTGAACCAGC CACTGCCTTC ACTCCCCATC TCTCAGCAGC

7851 AGTGGTCACT GGATCCAGTG CTACATCAGA AGCCAGTCTT CTCACTACGA

7901 GTGAAAGCAA AGCCATTCAT TCTTCACCAC AGACCCCAAC TACACCCACC

7951 TCTGGAGCAA ACTGGGAAAC TTCAGCTACT CCTGAGAGCC TTTTGGTAGT

8001 CACTGAGACT TCAGACACAA CACTTACCTC AAAGATTTTG GTCACAGATA

8051 CCATCTTGTT TTCAACTGTG TCCACGCCAC CTTCTAAATT TCCAAGTACG

8101 GGGACTCTGT CTGGAGCTTC CTTCCCTACT TTACTCCCGG ACACTCCAGC

8151 CATCCCTCTC ACTGCCACTG AGCCAACAAG TTCATTAGCT ACATCCTTTG

8201 ATTCCACCCC ACTGGTGACT ATAGCTTCGG ATAGTCTTGG CACAGTCCCA

8251 GAGACTACCC TGACCATGTC AGAGACCTCA AATGGTGATG CACTGGTTCT

8301 TAAGACAGTA AGTAACCCAG ATAGGAGCAT CCCTGGAATC ACTATCCAAG

8351 GAGTAACAGA AAGTCCACTC CATCCTTCTT CCACTTCCCC CTCTAAGATT

8401 GTTGCTCCAC GGAATACAAC CTATGAAGGT TCGATCACAG TGGCACTTTC

8451 TACTTTGCCT GCGGGAACTA CTGGTTCCCT TGTATTCAGT CAGAGTTCTG

8501 AAAACTCAGA GACAACGGCT TTGGTAGACT CATCAGCTGG GCTTGAGAGG

8551 GCATCTGTGA TGCCACTAAC CACAGGAAGC CAGGGTATGG CTAGCTCTGG

8601 AGGAATCAGA AGTGGGTCCA CTCACTCAAC TGGAACCAAA ACATTTTCTT

8651 CTCTCCCTCT GACCATGAAC CCAGGTGAGG TTACAGCCAT GTCTGAAATC

8701 ACCACGAACA GACTGACAGC TACTCAATCA ACAGCACCCA AAGGGATACC

8751 TGTGAAGCCC ACCAGTGCTG AGTCAGGCCT CCTAACACCT GTCTCTGCCT

8801 CCTCAAGCCC ATCAAAGGCC TTTGCCTCAC TGACTACAGC TCCCCCATCA

8851 ACTTGGGGGA TCCCACAGTC TACCTTGACA TTTGAGTTTT CTGAGGTCCC

8901 AAGTTTGGAT ACTAAGTCCG CTTCTTTACC AACTCCTGGA CAGTCCCTGA

8951 ACACCATTCC AGACTCAGAT GCAAGCACAG CATCTTCCTC ACTGTCCAAG
```

TABLE 4-continued

Human cDNA of CA125
(SEQ ID NO: 4)

```
 9001 TCTCCAGAAA AAAACCCAAG GGCAAGGATG ATGACTTCCA CAAAGGCCAT
 9051 AAGTGCAAGC TCATTTCAAT CAACAGGTTT TACTGAAACC CCTGAGGGAT
 9101 CTGCCTCCCC TTCTATGGCA GGGCATGAAC CCAGAGTCCC CACTTCAGGA
 9151 ACAGGGGACC CTAGATATGC CTCAGAGAGC ATGTCTTATC CAGACCCAAG
 9201 CAAGGCATCA TCAGCTATGA CATCGACCTC TCTTGCATCA AAACTCACAA
 9251 CTCTCTTCAG CACAGGTCAA GCAGCAAGGT CTGGTTCTAG TTCCTCTCCC
 9301 ATAAGCCTAT CCACTGAGAA AGAAACAAGC TTCCTTTCCC CCACTGCATC
 9351 CACCTCCAGA AAGACTTCAC TATTTCTTGG GCCTTCCATG GCAAGGCAGC
 9401 CCAACATATT GGTGCATCTT CAGACTTCAG CTCTGACACT TTCTCCAACA
 9451 TCCACTCTAA ATATGTCCCA GGAGGAGCCT CCTGAGTTAA CCTCAAGCCA
 9501 GACCATTGCA GAAGAAGAGG GAACAACAGC TGAAACACAG ACGTTAACCT
 9551 TCACACCATC TGAGACCCCA ACATCCTTGT TACCTGTCTC TTCTCCCACA
 9601 GAACCCACAG CCAGAAGAAA GAGTTCTCCA GAAACATGGG CAAGCTCTAT
 9651 TTCAGTTCCT GCCAAGACCT CCTTGGTTGA ACAACTGAT GGAACGCTAG
 9701 TGACCACCAT AAAGATGTCA AGCCAGGCAG CACAAGGAAA TTCCACGTGG
 9751 CCTGCCCCAG CAGAGGAGAC GGGGACCAGT CCAGCAGGCA CATCCCCAGG
 9801 AAGCCCAGAA GTGTCTACCA CTCTCAAAAT CATGAGCTCC AAGGAACCCA
 9851 GCATCAGCCC AGAGATCAGG TCCACTGTGC GAAATTCTCC TTGGAAGACT
 9901 CCAGAAACAA CTGTTCCCAT GGAGACCACA GTGGAACCAG TCACCCTTCA
 9951 GTCCACAGCC CTAGGAAGTG GCAGCACCAG CATCTCTCAC CTGCCCACAG
10001 GAACCACATC ACCAACCAAG TCACCAACAG AAAATATGTT GGCTACAGAA
10051 AGGGTCTCCC TCTCCCCATC CCCACCTGAG GCTTGGACCA ACCTTTATTC
10101 TGGAACTCCA GGAGGGACCA GGCAGTCACT GGCCACAATG TCCTCTGTCT
10151 CCCTAGAGTC ACCAACTGCT AGAAGCATCA CAGGGACTGG TCAGCAAAGC
10201 AGTCCAGAAC TGGTTTCAAA GACAACTGGA ATGGAATTCT CTATGTGGCA
10251 TGGCTCTACT GGAGGGACCA CAGGGGACAC ACATGTCTCT CTGAGCACAT
10301 CTTCCAATAT CCTTGAAGAC CCTGTAACCA GCCCAAACTC TGTGAGCTCA
10351 TTGACAGATA AATCCAAACA TAAAACCGAG ACATGGGTAA GCACCACAGC
10401 CATTCCCTCC ACTGTCCTGA ATAATAAGAT AATGGCAGCT GAACAACAGA
10451 CAAGTCGATC TGTGGATGAG GCTTATTCAT CAACTAGTTC TTGGTCAGAT
10501 CAGACATCTG GGAGTGACAT CACCCTTGGT GCATCTCCTG ATGTCACAAA
10551 CACATTATAC ATCACCTCCA CAGCACAAAC CACCTCACTA GTGTCTCTGC
10601 CCTCTGGAGA CCAAGGCATT ACAAGCCTCA CCAATCCCTC AGGAGGAAAA
10651 ACAAGCTCTG CGTCATCTGT CACATCTCCT TCAATAGGGC TTGAGACTCT
10701 GAGGGCCAAT GTAAGTGCAG TGAAAAGTGA CATTGCCCCT ACTGCTGGGC
10751 ATCTATCTCA GACTTCATCT CCTGCGGAAG TGAGCATCCT GGACGTAACC
10801 ACAGCTCCTA CTCCAGGTAT CTCCACCACC ATCACCACCA TGGGAACCAA
10851 CTCAATCTCA ACTACCACAC CCAACCCAGA AGTGGGTATG AGTACCATGG
```

TABLE 4-continued

Human cDNA of CA125
(SEQ ID NO: 4)

```
10901 ACAGCACCCC GGCCACAGAG AGGCGCACAA CTTCTACAGA ACACCCTTCC
10951 ACCTGGTCTT CCACAGCTGC ATCAGATTCC TGGACTGTCA CAGACATGAC
11001 TTCAAACTTG AAAGTTGCAA GATCTCCTGG AACAATTTCC ACAATGCATA
11051 CAACTTCATT CTTAGCCTCA AGCACTGAAT TAGACTCCAT GTCTACTCCC
11101 CATGGCCGTA TAACTGTCAT TGGAACCAGC CTGGTCACTC CATCCTCTGA
11151 TGCTTCAGCT GTAAAGACAG AGACCAGTAC AAGTGAAAGA ACATTGAGTC
11201 CTTCAGACAC AACTGCATCT ACTCCCATCT CAACTTTTTC TCGTGTCCAG
11251 AGGATGAGCA TCTCAGTTCC TGACATTTTA AGTACAAGTT GGACTCCCAG
11301 TAGTACAGAA GCAGAAGATG TGCCTGTTTC AATGGTTTCT ACAGATCATG
11351 CTAGTACAAA GACTGACCCA AATACGCCCC TGTCCACTTT TCTGTTTGAT
11401 TCTCTGTCCA CTCTTGACTG GGACACTGGG AGATCTCTGT CATCAGCCAC
11451 AGCCACTACC TCAGCTCCTC AGGGGCCAC AACTCCCCAG GAACTCACTT
11501 TGGAAACCAT GATCAGCCCA GCTACCTCAC AGTTGCCCTT CTCTATAGGG
11551 CACATTACAA GTGCAGTCAC ACCAGCTGCA ATGGCAAGGA GCTCTGGAGT
11601 TACTTTTTCA AGACCAGATC CCACAAGCAA AAGGCAGAG CAGACTTCCA
11651 CTCAGCTTCC CACCACCACT TCTGCACATC CAGGGCAGGT GCCCAGATCA
11701 GCAGCAACAA CTCTGGATGT GATCCCACAC ACAGCAAAAA CTCCAGATGC
11751 AACTTTTCAG AGACAAGGGC AGACAGCTCT TACAACAGAG GCAAGAGCTA
11801 CATCTGACTC CTGGAATGAG AAAGAAAAAT CAACCCCAAG TGCACCTTGG
11851 ATCACTGAGA TGATGAATTC TGTCTCAGAA GATACCATCA AGGAGGTTAC
11901 CAGCTCCTCC AGTGTATTAA AGGACCCTGA ATACGCTGGA CATAAACTTG
11951 GAATCTGGGA CGACTTCATC CCCAAGTTTG AAAAGCAGC CCATATGAGA
12001 GAGTTGCCCC TTCTGAGTCC ACCACAGGAC AAAGAGGCAA TTCACCCTTC
12051 TACAAACACA GTAGAGACCA CAGGCTGGGT CACAAGTTCC GAACATGCTT
12101 CTCATTCCAC TATCCCAGCC CACTCAGCGT CATCCAAACT CACATCTCCA
12151 GTGGTTACAA CCTCCACCAG GGAACAAGCA ATAGTTTCTA TGTCAACAAC
12201 CACATGGCCA GAGTCTACAA GGGCTAGAAC AGAGCCTAAT TCCTTCTTGA
12251 CTATTGAACT GAGGGACGTC AGCCCTTACA TGGACACCAG CTCAACCACA
12301 CAAACAAGTA TTATCTCTTC CCCAGGTTCC ACTGCGATCA CCAAGGGGCC
12351 TAGAACAGAA ATTACCTCCT CTAAGAGAAT ATCCAGCTCA TTCCTTGCCC
12401 AGTCTATGAG GTCGTCAGAC AGCCCCTCAG AAGCCATCAC CAGGCTGTCT
12451 AACTTTCCTG CCATGACAGA ATCTGGAGGA ATGATCCTTG CTATGCAAAC
12501 AAGTCCACCT GGCGCTACAT CACTAAGTGC ACCTACTTTG GATACATCAG
12551 CCACAGCCTC CTGGACAGGG ACTCCACTGG CTACGACTCA GAGATTTACA
12601 TACTCAGAGA AGACCACTCT CTTTAGCAAA GGTCCTGAGG ATACATCACA
12651 GCCAAGCCCT CCCTCTGTGG AAGAAACCAG CTCTTCCTCT TCCCTGGTAC
12701 CTATCCATGC TACAACCTCG CCTTCCAATA TTTTGTTGAC ATCACAAGGG
12751 CACAGTCCCT CCTCTACTCC ACCTGTGACC TCAGTTTTCT TGTCTGAGAC
12801 CTCTGGCCTG GGGAAGACCA CAGACATGTC GAGGATAAGC TTGGAACCTG
```

TABLE 4-continued

Human cDNA of CA125
(SEQ ID NO: 4)

```
12851 GCACAAGTTT ACCTCCCAAT TGAGCAGTA CAGCAGGTGA GGCGTTATCC

12901 ACTTATGAAG CCTCCAGAGA TACAAAGGCA ATTCATCATT CTGCAGACAC

12951 AGCAGTGACG AATATGGAGG CAACCAGTTC TGAATATTCT CCTATCCCAG

13001 GCCATACAAA GCCATCCAAA GCCACATCTC CATTGGTTAC CTCCCACATC

13051 ATGGGGGACA TCACTTCTTC CACATCAGTA TTTGGCTCCT CCGAGACCAC

13101 AGAGATTGAG ACAGTGTCCT CTGTGAACCA GGGACTTCAG GAGAGAAGCA

13151 CATCCCAGGT GGCCAGCTCT GCTACAGAGA CAAGCACTGT CATTACCCAT

13201 GTGTCTAGTG GTGATGCTAC TACTCATGTC ACCAAGACAC AAGCCACTTT

13251 CTCTAGCGGA ACATCCATCT CAAGCCCTCA TCAGTTTATA ACTTCTACCA

13301 ACACATTTAC AGATGTGAGC ACCAACCCCT CCACCTCTCT GATAATGACA

13351 GAATCTTCAG GAGTGACCAT CACCACCCAA ACAGGTCCTA CTGGAGCTGC

13401 AACACAGGGT CCATATCTCT TGGACACATC AACCATGCCT TACTTGACAG

13451 AGACTCCATT AGCTGTGACT CCAGATTTTA TGCAATCAGA GAAGACCACT

13501 CTCATAAGCA AAGGTCCCAA GGATGTGACC TGGACAAGCC CTCCCTCTGT

13551 GGCAGAAACC AGCTATCCCT CTTCCCTGAC ACCTTTCTTG GTCACAACCA

13601 TACCTCCTGC CACTTCCACG TTACAAGGGC AACATACATC CTCTCCTGTT

13651 TCTGCGACTT CAGTTCTTAC CTCTGGACTG GTGAAGACCA CAGATATGTT

13701 GAACACAAGC ATGGAACCTG TGACCAATTC ACCTCAAAAT TTGAACAATC

13751 CATCAAATGA GATACTGGCC ACTTTGGCAG CCACCACAGA TATAGAGACT

13801 ATTCATCCTT CCATAAACAA AGCAGTGACC AATATGGGGA CTGCCAGTTC

13851 AGCACATGTA CTGCATTCCA CTCTCCCAGT CAGCTCAGAA CCATCTACAG

13901 CCACATCTCC AATGGTTCCT GCCTCCAGCA TGGGGACGC TCTTGCTTCT

13951 ATATCAATAC CTGGTTCTGA GACCACAGAC ATTGAGGGAG AGCCAACATC

14001 CTCCCTGACT GCTGGACGAA AAGAGAACAG CACCCTCCAG GAGATGAACT

14051 CAACTACAGA GTCAAACATC ATCCTCTCCA ATGTGTCTGT GGGGGCTATT

14101 ACTGAAGCCA CAAAAATGGA AGTCCCCTCT TTTGATGCAA CATTCATACC

14151 AACTCCTGCT CAGTCAACAA AGTTCCCAGA TATTTTCTCA GTAGCCAGCA

14201 GTAGACTTTC AAACTCTCCT CCCATGACAA TATCTACCCA CATGACCACC

14251 ACCCAGACAG GGTCTTCTGG AGCTACATCA AAGATTCCAC TTGCCTTAGA

14301 CACATCAACC TTGGAAACCT CAGCAGGGAC TCCATCAGTG GTGACTGAGG

14351 GGTTTGCCCA CTCAAAAATA ACCACTGCAA TGAACAATGA TGTCAAGGAC

14401 GTGTCACAGA CAAACCCTCC CTTTCAGGAT GAAGCCAGCT CTCCCTCTTC

14451 TCAAGCACCT GTCCTTGTCA CAACCTTACC TTCTTCTGTT GCTTTCACAC

14501 CGCAATGGCA CAGTACCTCC TCTCCTGTTT CTATGTCCTC AGTTCTTACT

14551 TCTTCACTGG TAAAGACCGC AGGCAAGGTG GATACAAGCT TAGAAACAGT

14601 GACCAGTTCA CCTCAAAGTA TGAGCAACAC TTTGGATGAC ATATCGGTCA

14651 CTTCAGCAGC CACCACAGAT ATAGAGACAA CGCATCCTTC CATAAACACA

14701 GTAGTTACCA ATGTGGGGAC CACCGGTTCA GCATTTGAAT CACATTCTAC
```

TABLE 4-continued

Human cDNA of CA125
(SEQ ID NO: 4)

```
14751 TGTCTCAGCT TACCCAGAGC CATCTAAAGT CACATCTCCA AATGTTACCA

14801 CCTCCACCAT GGAAGACACC ACAATTTCCC GATCAATACC TAAATCCTCT

14851 AAGACTACAA GAACTGAGAC TGAGACAACT TCCTCCCTGA CTCCTAAACT

14901 GAGGGAGACC AGCATCTCCC AGGAGATCAC CTCGTCCACA GAGACAAGCA

14951 CTGTTCCTTA CAAAGAGCTC ACTGGTGCCA CTACCGAGGT ATCCAGGACA

15001 GATGTCACTT CCTCTAGCAG TACATCCTTC CCTGGCCCTG ATCAGTCCAC

15051 AGTGTCACTA GACATCTCCA CAGAAACCAA CACCAGGCTG TCTACCTCCC

15101 CAATAATGAC AGAATCTGCA GAAATAACCA TCACCACCCA AACAGGTCCT

15151 CATGGGGCTA CATCACAGGA TACTTTTACC ATGGACCCAT CAAATACAAC

15201 CCCCCAGGCA GGGATCCACT CAGCTATGAC TCATGGATTT TCACAATTGG

15251 ATGTGACCAC TCTTATGAGC AGAATTCCAC AGGATGTATC ATGGACAAGT

15301 CCTCCCTCTG TGGATAAAAC CAGCTCCCCC TCTTCCTTTC TGTCCTCACC

15351 TGCAATGACC ACACCTTCCC TGATTTCTTC TACCTTACCA GAGGATAAGC

15401 TCTCCTCTCC TATGACTTCA CTTCTCACCT CTGGCCTAGT GAAGATTACA

15451 GACATATTAC GTACACGCTT GGAACCTGTG ACCAGCTCAC TTCCAAATTT

15501 CAGCAGCACC TCAGATAAGA TACTGGCCAC TTCTAAAGAC AGTAAAGACA

15551 CAAAGGAAAT TTTTCCTTCT ATAAACACAG AAGAGACCAA TGTGAAAGCC

15601 AACAACTCTG GACATGAATC CCATTCCCCT GCACTGGCTG ACTCAGAGAC

15651 ACCCAAAGCC ACAACTCAAA TGGTTATCAC CACCACTGTG GGAGATCCAG

15701 CTCCTTCCAC ATCAATGCCA GTGCATGGTT CCTCTGAGAC TACAAACATT

15751 AAGAGAGAGC CAACATATTT CTTGACTCCT AGACTGAGAG AGACCAGTAC

15801 CTCTCAGGAG TCCAGCTTTC CCACGGACAC AAGTTTTCTA CTTTCCAAAG

15851 TCCCCACTGG TACTATTACT GAGGTCTCCA GTACAGGGGT CAACTCTTCT

15901 AGCAAAATTT CCACCCCAGA CCATGATAAG TCCACAGTGC CACCTGACAC

15951 CTTCACAGGA GAGATCCCCA GGGTCTTCAC CTCCTCTATT AAGACAAAAT

16001 CTGCAGAAAT GACGATCACC ACCCAAGCAA GTCCTCCTGA GTCTGCATCG

16051 CACAGTACCC TTCCCTTGGA CACATCAACC ACACTTTCCC AGGGAGGGAC

16101 TCATTCAACT GTGACTCAGG GATTCCCATA CTCAGAGGTG ACCACTCTCA

16151 TGGGCATGGG TCCTGGGAAT GTGTCATGGA TGACAACTCC CCCTGTGGAA

16201 GAAACCAGCT CTGTGTCTTC CCTGATGTCT TCACCTGCCA TGACATCCCC

16251 TTCTCCTGTT TCCTCCACAT CACCACAGAG CATCCCCTCC TCTCCTCTTC

16301 CTGTGACTGC ACTTCCTACT TCTGTTCTGG TGACAACCAC AGATGTGTTG

16351 GGCACAACAA GCCCAGAGTC TGTAACCAGT TCACCTCCAA ATTTGAGCAG

16401 CATCACTCAT GAGAGACCGG CCACTTACAA AGACACTGCA CACACAGAAG

16451 CCGCCATGCA TCATTCCACA AACACCGCAG TGACCAATGT AGGGACTTCC

16501 GGGTCTGGAC ATAAATCACA ATCCTCTGTC CTAGCTGACT CAGAGACATC

16551 GAAAGCCACA CCTCTGATGA GTACCACCTC CACCCTGGGG ACACAAGTG

16601 TTTCCACATC AACTCCTAAT ATCTCTCAGA CTAACCAAAT TCAAACAGAG

16651 CCAACAGCAT CCCTGAGCCC TAGACTGAGG GAGAGCAGCA CGTCTGAGAA
```

TABLE 4-continued

Human cDNA of CA125
(SEQ ID NO: 4)

```
16701 GACCAGCTCA ACAACAGAGA CAAATACTGC CTTTTCTTAT GTGCCCACAG
16751 GTGCTATTAC TCAGGCCTCC AGAACAGAAA TCTCCTCTAG CAGAACATCC
16801 ATCTCAGACC TTGATCGGCC CACAATAGCA CCCGACATCT CCACAGGAAT
16851 GATCACCAGG CTCTTCACCT CCCCCATCAT GACAAATCT GCAGAAATGA
16901 CCGTCACCAC TCAAACAACT ACTCCTGGGG CTACATCACA GGGTATCCTT
16951 CCTTGGGACA CATCAACCAC ACTTTTCCAG GGAGGGACTC ATTCAACCGT
17001 GTCTCAGGGA TTCCCACACT CAGAGATAAC CACTCTTCGG AGCAGAACCC
17051 CTGGAGATGT GTCATGGATG ACAACTCCCC CTGTGGAAGA AACCAGCTCT
17101 GGGTTTTCCC TGATGTCACC TTCCATGACA TCCCCTTCTC CTGTTTCCTC
17151 CACATCACCA GAGAGCATCC CCTCCTCTCC TCTCCCTGTG ACTGCACTTC
17201 TTACTTCTGT TCTGGTGACA ACCACCAATG TATTGGGCAC AACAAGCCCA
17251 GAGACCGTAA CGAGTTCACC TCCAAATTTA AGCAGCCCCA CACAGGAGAG
17301 ACTGACCACT TACAAAGACA CTGCGCACAC AGAAGCCATG CATGCTTCCA
17351 TGCATACAAA CACTGCAGTG GCCAACGTCG GGACCTCCAT TTCTGGACAT
17401 GAATCACAAT CTTCTGTCCC AGCTGATTCA CACACATCCA AAGCCACATC
17451 TCCAATGGGT ATCACCTTCG CCATGGGGGA TACAAGTGTT TCTACATCAA
17501 CTCCTGCCTT CTTTGAGACT AGAATTCAGA CTGAATCAAC ATCCTCTTTG
17551 ATTCCTGGAT TAAGGGACAC CAGGACGTCT GAGGAGATCA ACACTGTGAC
17601 AGAGACCAGC ACTGTCCTTT CAGAAGTGCC CACTACTACT ACTACTGAGG
17651 TCTCCAGGAC AGAAGTTATC ACTTCCAGCA GAACAACCAT CTCAGGGCCT
17701 GATCATTCCA AAATGTCACC CTACATCTCC ACAGAAACCA TCACCAGGCT
17751 CTCCACTTTT CCTTTTGTAA CAGGATCCAC AGAAATGGCC ATCACCAACC
17801 AAACAGGTCC TATAGGGACT ATCTCACAGG CTACCCTTAC CCTGGACACA
17851 TCAAGCACAG CTTCCTGGGA AGGGACTCAC TCACCTGTGA CTCAGAGATT
17901 TCCACACTCA GAGGAGACCA CTACTATGAG CAGAAGTACT AAGGGCGTGT
17951 CATGGCAAAG CCCTCCCTCT GTGGAAGAAA CCAGTTCTCC TTCTTCCCCA
18001 GTGCCTTTAC CTGCAATAAC CTCACATTCA TCTCTTTATT CCGCAGTATC
18051 AGGAAGTAGC CCCACTTCTG CTCTCCCTGT GACTTCCCTT CTCACCTCTG
18101 GCAGGAGGAA GACCATAGAC ATGTTGGACA CACACTCAGA ACTTGTGACC
18151 AGCTCCTTAC CAAGTGCAAG TAGCTTCTCA GGTGAGATAC TCACTTCTGA
18201 AGCCTCCACA AATACAGAGA CAATTCACTT TTCAGAGAAC ACAGCAGAAA
18251 CCAATATGGG GACCACCAAT TCTATGCATA AACTACATTC CTCTGTCTCA
18301 ATCCACTCCC AGCCATCCGG ACACACACCT CCAAAGGTTA CTGGATCTAT
18351 GATGGAGGAC GCTATTGTTT CCACATCAAC ACCTGGTTCT CCTGAGACTA
18401 AAAATGTTGA CAGAGACTCA ACATCCCCTC TGACTCCTGA ACTGAAAGAG
18451 GACAGCACCG CCCTGGTGAT GAACTCAACT ACAGAGTCAA ACACTGTTTT
18501 CTCCAGTGTG TCCCTGGATG CTGCTACTGA GGTCTCCAGG GCAGAAGTCA
18551 CCTACTATGA TCCTACATTC ATGCCAGCTT CTGCTCAGTC AACAAAGTCC
```

TABLE 4-continued

Human cDNA of CA125
(SEQ ID NO: 4)

```
18601 CCAGACATTT CACCTGAAGC CAGCAGCAGT CATTCTAACT CTCCTCCCTT
18651 GACAATATCT ACACACAAGA CCATCGCCAC ACAAACAGGT CCTTCTGGGG
18701 TGACATCTCT TGGCCAACTG ACCCTGGACA CATCAACCAT AGCCACCTCA
18751 GCAGGAACTC CATCAGCCAG AACTCAGGAT TTTGTAGATT CAGAAACAAC
18801 CAGTGTCATG AACAATGATC TCAATGATGT GTTGAAGACA AGCCCTTTCT
18851 CTGCAGAAGA AGCCAACTCT CTCTCTTCTC AGGCACCTCT CCTTGTGACA
18901 ACCTCACCTT CTCCTGTAAC TTCCACATTG CAAGAGCACA GTACCTCCTC
18951 TCTTGTTTCT GTGACCTCAG TACCCACCCC TACACTGGCG AAGATCACAG
19001 ACATGGACAC AAACTTAGAA CCTGTGACTC GTTCACCTCA AAATTTAAGG
19051 AACACCTTGG CCACTTCAGA AGCCACCACA GATACACACA CAATGCATCC
19101 TTCTATAAAC ACAGCAATGG CCAATGTGGG GACCACCAGT TCACCAAATG
19151 AATTCTATTT TACTGTCTCA CCTGACTCAG ACCCATATAA AGCCACATCC
19201 GCAGTAGTTA TCACTTCCAC CTCGGGGGAC TCAATAGTTT CCACATCAAT
19251 GCCTAGATCC TCTGCGATGA AAAAGATTGA GTCTGAGACA ACTTTCTCCC
19301 TGATATTTAG ACTGAGGGAG ACTAGCACCT CCCAGAAAAT TGGCTCATCC
19351 TCAGACACAA GCACGGTCTT TGACAAAGCA TTCACTGCTG CTACTACTGA
19401 GGTCTCCAGA ACAGAACTCA CCTCCTCTAG CAGAACATCC ATCCAAGGCA
19451 CTGAAAAGCC CACAATGTCA CCGGACACCT CCACAAGATC TGTCACCATG
19501 CTTTCTACTT TTGCTGGCCT GACAAAATCC GAAGAAAGGA CCATTGCCAC
19551 CCAAACAGGT CCTCATAGGG CGACATCACA GGGTACCCTT ACCTGGGACA
19601 CATCAATCAC AACCTCACAG GCAGGGACCC ACTCAGCTAT GACTCATGGA
19651 TTTTCACAAT TAGATTTGTC CACTCTTACG AGTAGAGTTC CTGAGTACAT
19701 ATCAGGGACA AGCCCACCCT CTGTGGAAAA AACCAGCTCT TCCTCTTCCC
19751 TTCTGTCTTT ACCAGCAATA ACCTCACCGT CCCCTGTACC TACTACATTA
19801 CCAGAAAGTA GGCCGTCTTC TCCTGTTCAT CTGACTTCAC TCCCCACCTC
19851 TGGCCTAGTG AAGACCACAG ATATGCTGGC ATCTGTGGCC AGTTTACCTC
19901 CAAACTTGGG CAGCACCTCA CATAAGATAC CGACTACTTC AGAAGACATT
19951 AAAGATACAG AGAAAATGTA TCCTTCCACA AACATAGCAG TAACCAATGT
20001 GGGGACCACC ACTTCTGAAA AGGAATCTTA TTCGTCTGTC CCAGCCTACT
20051 CAGAACCACC CAAAGTCACC TCTCCAATGG TTACCTCTTT CAACATAAGG
20101 GACACCATTG TTTCCACATC CATGCCTGGC TCCTCTGAGA TTACAAGGAT
20151 TGAGATGGAG TCAACATTCT CCGTGGCTCA TGGGCTGAAG GGAACCAGCA
20201 CCTCCCAGGA CCCCATCGTA TCCACAGAGA AAAGTGCTGT CCTTCACAAG
20251 TTGACCACTG GTGCTACTGA GACCTCTAGG ACAGAAGTTG CCTCTTCTAG
20301 AAGAACATCC ATTCCAGGCC CTGATCATTC CACAGAGTCA CCAGACATCT
20351 CCACTGAAGT GATCCCCAGC CTGCCTATCT CCCTTGGCAT TACAGAATCT
20401 TCAAATATGA CCATCATCAC TCGAACAGGT CCTCCTCTTG GCTCTACATC
20451 ACAGGGCACA TTTACCTTGG ACACACCAAC TACATCCTCC AGGGCAGGAA
20501 CACACTCGAT GGCGACTCAG GAATTTCCAC ACTCAGAAAT GACCACTGTC
```

TABLE 4-continued

Human cDNA of CA125
(SEQ ID NO: 4)

```
20551 ATGAACAAGG ACCCTGAGAT TCTATCATGG ACAATCCCTC CTTCTATAGA

20601 GAAAACCAGC TTCTCCTCTT CCCTGATGCC TTCACCAGCC ATGACTTCAC

20651 CTCCTGTTTC CTCAACATTA CCAAAGACCA TTCACACCAC TCCTTCTCCT

20701 ATGACCTCAC TGCTCACCCC TAGCCAGTG ATGACCACAG ACACATTGGG

20751 CACAAGCCCA GAACCTACAA CCAGTTCACC TCCAAATTTG AGCAGTACCT

20801 CACATGTGAT ACTGACAACA GATGAAGACA CCACAGCTAT AGAAGCCATG

20851 CATCCTTCCA CAAGCACAGC AGCGACTAAT GTGGAAACCA CCTGTTCTGG

20901 ACATGGGTCA CAATCCTCTG TCCTAACTGA CTCAGAAAAA ACCAAGGCCA

20951 CAGCTCCAAT GGATACCACC TCCACCATGG GCATACAAC TGTTTCCACA

21001 TCAATGTCTG TTTCCTCTGA CTACAAAA ATTAAGAGAG AGTCAACATA

21051 TTCCTTGACT CCTGGACTGA GAGAGACCAG CATTTCCCAA AATGCCAGCT

21101 TTTCCACTGA CACAAGTATT GTTCTTTCAG AAGTCCCCAC TGGTACTACT

21151 GCTGAGGTCT CCAGGACAGA AGTCACCTCC TCTGGTAGAA CATCCATCCC

21201 TGGCCCTTCT CAGTCCACAG TTTTGCCAGA AATATCCACA GAACAATGA

21251 CAAGGCTCTT TGCCTCGCCC ACCATGACAG AATCAGCAGA AATGACCATC

21301 CCCACTCAAA CAGGTCCTTC TGGGTCTACC TCACAGGATA CCCTTACCTT

21351 GGACACATCC ACCACAAAGT CCCAGGCAAA GACTCATTCA ACTTTGACTC

21401 AGAGATTTCC ACACTCAGAG ATGACCACTC TCATGAGCAG AGGTCCTGGA

21451 GATATGTCAT GGCAAAGCTC TCCCTCTCTG GAAAATCCCA GCTCTCTCCC

21501 TTCCCTGCTG TCTTTACCTG CCACAACCTC ACCTCCTCCC ATTTCCTCCA

21551 CATTACCAGT GACTATCTCC TCCTCTCCTC TTCCTGTGAC TTCACTTCTC

21601 ACCTCTAGCC CGGTAACGAC CACAGACATG TTACACACAA GCCCAGAACT

21651 TGTAACCAGT TCACCTCCAA AGCTGAGCCA CACTTCAGAT GAGAGACTGA

21701 CCACTGGCAA GGACACCACA AATACAGAAG CTGTGCATCC TTCCACAAAC

21751 ACAGCAGCGT CCAATGTGGA GATTCCCAGC TTTGGACATG AATCCCCTTC

21801 CTCTGCCTTA GCTGACTCAG AGACATCCAA AGCCACATCA CCAATGTTTA

21851 TTACCTCCAC CCAGGAGGAT ACAACTGTTG CCATATCAAC CCCTCACTTC

21901 TTGGAGACTA GCAGAATTCA GAAAGAGTCA ATTTCCTCCC TGAGCCCTAA

21951 ATTGAGGGAG ACAGGCAGTT CTGTGGAGAC AAGCTCAGCC ATAGAGACAA

22001 GTGCTGTCCT TTCTGAAGTG TCCATTGGTG CTACTACTGA GATCTCCAGG

22051 ACAGAAGTCA CCTCCTCTAG CAGAACATCC ATCTCTGGTT CTGCTGAGTC

22101 CACAATGTTG CCAGAAATAT CCACCACAAG AAAAATCATT AAGTTCCCTA

22151 CTTCCCCCAT CCTGGCAGAA TCATCAGAAA TGACCATCAA GACCCAAACA

22201 AGTCCTCCTG GGTCTACATC AGAGAGTACC TTTACATTAG ACACATCAAC

22251 CACTCCCTCC TTGGTAATAA CCCATTCGAC TATGACTCAG AGATTGCCAC

22301 ACTCAGAGAT AACCACTCTT GTGAGTAGAG GTGCTGGGGA TGTGCCACGG

22351 CCCAGCTCTC TCCCTGTGGA AGAAACAAGC CCTCCATCTT CCCAGCTGTC

22401 TTTATCTGCC ATGATCTCAC CTTCTCCTGT TTCTTCCACA TTACCAGCAA
```

TABLE 4-continued

Human cDNA of CA125
(SEQ ID NO: 4)

```
22451 GTAGCCACTC CTCTTCTGCT TCTGTGACTT CACCTCTCAC ACCAGGCCAA
22501 GTGAAGACTA CTGAGGTGTT GGACGCAAGT GCAGAACCTG AAACCAGTTC
22551 ACCTCCAAGT TTGAGCAGCA CCTCAGTTGA AATACTGGCC ACCTCTGAAG
22601 TCACCACAGA TACGGAGAAA ATTCATCCTT TCCCAAACAC GGCAGTAACC
22651 AAAGTTGGAA CTTCCAGTTC TGGACATGAA TCCCCTTCCT CTGTCCTACC
22701 TGACTCAGAG ACAACCAAAG CCACATCGGC AATGGGTACC ATCTCCATTA
22751 TGGGGGATAC AAGTGTTTCT ACATTAACTC CTGCCTTATC TAACACTAGG
22801 AAAATTCAGT CAGAGCCAGC TTCCTCACTG ACCACCAGAT TGAGGGAGAC
22851 CAGCACCTCT GAAGAGACCA GCTTAGCCAC AGAAGCAAAC ACTGTTCTTT
22901 CTAAAGTGTC CACTGGTGCT ACTACTGAGG TCTCCAGGAC AGAAGCCATC
22951 TCCTTTAGCA GAACATCCAT GTCAGGCCCT GAGCAGTCCA CAATGTCACA
23001 AGACATCTCC ATAGGAACCA TCCCCAGGAT TTCTGCCTCC TCTGTCCTGA
23051 CAGAATCTGC AAAAATGACC ATCACAACCC AAACAGGTCC TTCGGAGTCT
23101 ACACTAGAAA GTACCCTTAA TTTGAACACA GCAACCACAC CCTCTTGGGT
23151 GGAAACCCAC TCTATAGTAA TTCAGGGATT TCCACACCCA GAGATGACCA
23201 CTTCCATGGG CAGAGGTCCT GGAGGTGTGT CATGGCCTAG CCCTCCCTTT
23251 GTGAAAGAAA CCAGCCCTCC ATCCTCCCCG CTGTCTTTAC CTGCCGTGAC
23301 CTCACCTCAT CCTGTTTCCA CCACATTCCT AGCACATATC CCCCCCTCTC
23351 CCCTTCCTGT GACTTCACTT CTCACCTCTG GCCCGGCGAC AACCACAGAT
23401 ATCTTGGGTA CAAGCACAGA ACCTGGAACC AGTTCATCTT CAAGTTTGAG
23451 CACCACCTCC CATGAGAGAC TGACCACTTA CAAAGACACT GCACATACAG
23501 AAGCCGTGCA TCCTTCCACA AACACAGGAG GGACCAATGT GGCAACCACC
23551 AGCTCTGGAT ATAAATCACA GTCCTCTGTC CTAGCTGACT CATCTCCAAT
23601 GTGTACCACC TCCACCATGG GGGATACAAG TGTTCTCACA TCAACTCCTG
23651 CCTTCCTTGA GACTAGGAGG ATTCAGACAG AGCTAGCTTC CTCCCTGACC
23701 CCTGGATTGA GGGAGTCCAG TGGCTCTGAA GGGACCAGCT CAGGCACCAA
23751 GATGAGCACT GTCCTCTCTA AAGTGCCCAC TGGTGCTACT ACTGAGATCT
23801 CCAAGGAAGA CGTCACCTCC ATCCCAGGTC CCGCTCAATC CACAATATCA
23851 CCAGACATCT CCACAAGAAC CGTCAGCTGG TTCTCTACAT CCCCTGTCAT
23901 GACAGAATCA GCAGAAATAA CCATGAACAC CCATACAAGT CCTTTAGGGG
23951 CCACAACACA AGGCACCAGT ACTTTGGCCA CGTCAAGCAC AACCTCTTTG
24001 ACAATGACAC ACTCAACTAT ATCTCAAGGA TTTTCACACT CACAGATGAG
24051 CACTCTTATG AGGAGGGGTC CTGAGGATGT ATCATGGATG AGCCCTCCCC
24101 TTCTGGAAAA AACTAGACCT TCCTTTTCTC TGATGTCTTC ACCAGCCACA
24151 ACTTCACCTT CTCCTGTTTC CTCCACATTA CCAGAGAGCA TCTCTTCCTC
24201 TCCTCTTCCT GTGACTTCAC TCCTCACGTC TGGCTTGGCA AAAACTACAG
24251 ATATGTTGCA CAAAAGCTCA GAACCTGTAA CCAACTCACC TGCAAATTTG
24301 AGCAGCACCT CAGTTGAAAT ACTGGCCACC TCTGAAGTCA CCACAGATAC
24351 AGAGAAAACT CATCCTTCTT CAAACAGAAC AGTGACCGAT GTGGGGACCT
```

TABLE 4-continued

Human cDNA of CA125
(SEQ ID NO: 4)

```
24401 CCAGTTCTGG ACATGAATCC ACTTCCTTTG TCCTAGCTGA CTCACAGACA
24451 TCCAAAGTCA CATCTCCAAT GGTTATTACC TCCACCATGG AGGATACGAG
24501 TGTCTCCACA TCAACTCCTG GCTTTTTTGA GACTAGCAGA ATTCAGACAG
24551 AACCAACATC CTCCCTGACC CTTGGACTGA GAAAGACCAG CAGCTCTGAG
24601 GGGACCAGCT TAGCCACAGA GATGAGCACT GTCCTTTCTG GAGTGCCCAC
24651 TGGTGCCACT GCTGAAGTCT CCAGGACAGA AGTCACCTCC TCTAGCAGAA
24701 CATCCATCTC AGGCTTTGCT CAGCTCACAG TGTCACCAGA GACTTCCACA
24751 GAAACCATCA CCAGACTCCC TACCTCCAGC ATAATGACAG AATCAGCAGA
24801 AATGATGATC AAGACACAAA CAGATCCTCC TGGGTCTACA CCAGAGAGTA
24851 CTCATACTGT GGACATATCA ACAACACCCA ACTGGGTAGA ACCCACTCG
24901 ACTGTGACTC AGAGATTTTC ACACTCAGAG ATGACCACTC TTGTGAGCAG
24951 AAGCCCTGGT GATATGTTAT GGCCTAGTCA ATCCTCTGTG GAAGAAACCA
25001 GCTCTGCCTC TTCCCTGCTG TCTCTGCCTG CCACGACCTC ACCTTCTCCT
25051 GTTTCCTCTA CATTAGTAGA GGATTTCCCT TCCGCTTCTC TTCCTGTGAC
25101 TTCTCTTCTC ACCCCTGGCC TGGTGATAAC CACAGACAGG ATGGGCATAA
25151 GCAGAGAACC TGGAACCAGT TCCACTTCAA ATTTGAGCAG CACCTCCCAT
25201 GAGAGACTGA CCACTTTGGA AGACACTGTA GATACAGAAG ACATGCAGCC
25251 TTCCACACAC ACAGCAGTGA CCAACGTGAG GACCTCCATT TCTGGACATG
25301 AATCACAATC TTCTGTCCTA TCTGACTCAG AGACACCCAA AGCCACATCT
25351 CCAATGGGTA CCACCTACAC CATGGGGGAA ACGAGTGTTT CCATATCCAC
25401 TTCTGACTTC TTTGAGACCA GCAGAATTCA GATAGAACCA ACATCCTCCC
25451 TGACTTCTGG ATTGAGGGAG ACCAGCAGCT CTGAGAGGAT CAGCTCAGCC
25501 ACAGAGGGAA GCACTGTCCT TTCTGAAGTG CCCAGTGGTG CTACCACTGA
25551 GGTCTCCAGG ACAGAAGTGA TATCCTCTAG GGAACATCC ATGTCAGGGC
25601 CTGATCAGTT CACCATATCA CCAGACATCT CTACTGAAGC GATCACCAGG
25651 CTTTCTACTT CCCCCATTAT GACAGAATCA GCAGAAAGTG CCATCACTAT
25701 TGAGACAGGT TCTCCTGGGG CTACATCAGA GGGTACCCTC ACCTTGGACA
25751 CCTCAACAAC AACCTTTTGG TCAGGGACCC ACTCAACTGC ATCTCCAGGA
25801 TTTTCACACT CAGAGATGAC CACTCTTATG AGTAGAACTC TGGAGATGT
25851 GCCATGGCCG AGCCTTCCCT CTGTGGAAGA AGCCAGCTCT GTCTCTTCCT
25901 CACTGTCTTC ACCTGCCATG ACCTCAACTT CTTTTTTCTC CGCATTACCA
25951 GAGAGCATCT CCTCCTCTCC TCATCCTGTG ACTGCACTTC TCACCCTTGG
26001 CCCAGTGAAG ACCACAGACA TGTTGCGCAC AAGCTCAGAA CCTGAAACCA
26051 GTTCACCTCC AAATTTGAGC AGCACCTCAG CTGAAATATT AGCCACGTCT
26101 GAAGTCACCA AAGATAGAGA GAAATTCAT CCCTCCTCAA ACACACCTGT
26151 AGTCAATGTA GGGACTGTGA TTTATAAACA TCTATCCCCT TCCTCTGTTT
26201 TGGCTGACTT AGTGACAACA AAACCCACAT CTCCAATGGC TACCACCTCC
26251 ACTCTGGGGA ATACAAGTGT TTCCACATCA ACTCCTGCCT TCCCAGAAAC
```

TABLE 4-continued

Human cDNA of CA125
(SEQ ID NO: 4)

```
26301 TATGATGACA CAGCCAACTT CCTCCCTGAC TTCTGGATTA AGGGAGATCA
26351 GTACCTCTCA AGAGACCAGC TCAGCAACAG AGAGAAGTGC TTCTCTTTCT
26401 GGAATGCCCA CTGGTGCTAC TACTAAGGTC TCCAGAACAG AAGCCCTCTC
26451 CTTAGGCAGA ACATCCACCC CAGGTCCTGC TCAATCCACA ATATCACCAG
26501 AAATCTCCAC GGAAACCATC ACTAGAATTT CTACTCCCCT CACCACGACA
26551 GGATCAGCAG AAATGACCAT CACCCCCAAA ACAGGTCATT CTGGGGCATC
26601 CTCACAAGGT ACCTTTACCT TGGACACATC AAGCAGAGCC TCCTGGCCAG
26651 GAACTCACTC AGCTGCAACT CACAGATCTC CACACTCAGG GATGACCACT
26701 CCTATGAGCA GAGGTCCTGA GGATGTGTCA TGGCCAAGCC GCCCATCAGT
26751 GGAAAAAACT AGCCCTCCAT CTTCCCTGGT GTCTTTATCT GCAGTAACCT
26801 CACCTTCGCC ACTTTATTCC ACACCATCTG AGAGTAGCCA CTCATCTCCT
26851 CTCCGGGTGA CTTCTCTTTT CACCCCTGTC ATGATGAAGA CCACAGACAT
26901 GTTGGACACA AGCTTGGAAC CTGTGACCAC TTCACCTCCC AGTATGAATA
26951 TCACCTCAGA TGAGAGTCTG GCCACTTCTA AAGCCACCAT GGAGACAGAG
27001 GCAATTCAGC TTTCAGAAAA CACAGCTGTG ACTCAGATGG CACCATCAG
27051 CGCTAGACAA GAATTCTATT CCTCTTATCC AGGCCTCCCA GAGCCATCCA
27101 AAGTGACATC TCCAGTGGTC ACCTCTTCCA CCATAAAAGA CATTGTTTCT
27151 ACAACCATAC CTGCTTCCTC TGAGATAACA AGAATTGAGA TGGAGTCAAC
27201 ATCCACCCTG ACCCCCACAC CAAGGGAGAC CAGCACCTCC CAGGAGATCC
27251 ACTCAGCCAC AAAGCCAAGC ACTGTTCCTT ACAAGGCACT CACTAGTGCC
27301 ACGATTGAGG ACTCCATGAC ACAAGTCATG TCCTCTAGCA GAGGACCTAG
27351 CCCTGATCAG TCCACAATGT CACAAGACAT ATCCAGTGAA GTGATCACCA
27401 GGCTCTCTAC CTCCCCCATC AAGGCAGAAT CTACAGAAAT GACCATTACC
27451 ACCCAAACAG GTTCTCCTGG GGCTACATCA AGGGGTACCC TTACCTTGGA
27501 CACTTCAACA ACTTTTATGT CAGGGACCCA CTCAACTGCA TCTCAAGGAT
27551 TTTCACACTC ACAGATGACC GCTCTTATGA GTAGAACTCC TGGAGATGTG
27601 CCATGGCTAA GCCATCCCTC TGTGGAAGAA GCCAGCTCTG CCTCTTTCTC
27651 ACTGTCTTCA CCTGTCATGA CCTCATCTTC TCCCGTTTCT TCCACATTAC
27701 CAGACAGCAT CCACTCTTCT TCGCTTCCTG TGACATCACT TCTCACCTCA
27751 GGGCTGGTGA AGACCACAGA GCTGTTGGGC ACAAGCTCAG AACCTGAAAC
27801 CAGTTCACCC CCAAATTTGA GCAGCACCTC AGCTGAAATA CTGGCCACCA
27851 CTGAAGTCAC TACAGATACA GAGAAACTGG AGATGACCAA TGTGGTAACC
27901 TCAGGTTATA CACATGAATC TCCTTCCTCT GTCCTAGCTG ACTCAGTGAC
27951 AACAAAGGCC ACATCTTCAA TGGGTATCAC CTACCCCACA GGAGATACAA
28001 ATGTTCTCAC ATCAACCCCT GCCTTCTCTG ACACCAGTAG GATTCAAACA
28051 AAGTCAAAGC TCTCACTGAC TCCTGGGTTG ATGGAGACCA GCATCTCTGA
28101 AGAGACCAGC TCTGCCACAG AAAAAAGCAC TGTCCTTTCT AGTGTGCCCA
28151 CTGGTGCTAC TACTGAGGTC TCCAGGACAG AAGCCATCTC TTCTAGCAGA
28201 ACATCCATCC CAGGCCCTGC TCAATCCACA ATGTCATCAG ACACCTCCAT
```

TABLE 4-continued

Human cDNA of CA125
(SEQ ID NO: 4)

```
28251 GGAAACCATC ACTAGAATTT CTACCCCCCT CACAAGGAAA GAATCAACAG

28301 ACATGGCCAT CACCCCCAAA ACAGGTCCTT CTGGGGCTAC CTCGCAGGGT

28351 ACCTTTACCT TGGACTCATC AAGCACAGCC TCCTGGCCAG GAACTCACTC

28401 AGCTACAACT CAGAGATTTC CACAGTCAGT GGTGACAACT CCTATGAGCA

28451 GAGGTCCTGA GGATGTGTCA TGGCCAAGCC CGCTGTCTGT GGAAAAAAAC

28501 AGCCCTCCAT CTTCCCTGGT ATCTTCATCT TCAGTAACCT CACCTTCGCC

28551 ACTTTATTCC ACACCATCTG GGAGTAGCCA CTCCTCTCCT GTCCCTGTCA

28601 CTTCTCTTTT CACCTCTATC ATGATGAAGG CCACAGACAT GTTGGATGCA

28651 AGTTTGGAAC CTGAGACCAC TTCAGCTCCC AATATGAATA TCACCTCAGA

28701 TGAGAGTCTG GCCACTTCTA AAGCCACCAC GGAGACAGAG GCAATTCACG

28751 TTTTTGAAAA TACAGCAGCG TCCCATGTGG AAACCACCAG TGCTACAGAG

28801 GAACTCTATT CCTCTTCCCC AGGCTTCTCA GAGCCAACAA AAGTGATATC

28851 TCCAGTGGTC ACCTCTTCCT CTATAAGAGA CAACATGGTT TCCACAACAA

28901 TGCCTGGCTC CTCTGGCATT ACAAGGATTG AGATAGAGTC AATGTCATCT

28951 CTGACCCCTG GACTGAGGGA GACCAGAACC TCCCAGGACA TCACCTCATC

29001 CACAGAGACA AGCACTGTCC TTTACAAGAT GTCCTCTGGT GCCACTCCTG

29051 AGGTCTCCAG GACAGAAGTT ATGCCCTCTA GCAGAACATC CATTCCTGGC

29101 CCTGCTCAGT CCACAATGTC ACTAGACATC TCCGATGAAG TTGTCACCAG

29151 GCTGTCTACC TCTCCCATCA TGACAGAATC TGCAGAAATA ACCATCACCA

29201 CCCAAACAGG TTATTCTCTG CTACATCCC AGGTTACCCT TCCCTTGGGC

29251 ACCTCAATGA CCTTTTTGTC AGGGACCCAC TCAACTATGT CTCAAGGACT

29301 TTCACACTCA GAGATGACCA ATCTTATGAG CAGGGGTCCT GAAAGTCTGT

29351 CATGGACGAG CCCTCGCTTT GTGGAAACAA CTAGATCTTC CTCTTCTCTG

29401 ACATCATTAC CTCTCACGAC CTCACTTTCT CCTGTGTCCT CCACATTACT

29451 AGACAGTAGC CCCTCCTCTC CTCTTCCTGT GACTTCACTT ATCCTCCCAG

29501 GCCTGGTGAA GACTACAGAA GTGTTGGATA CAAGCTCAGA GCCTAAAACC

29551 AGTTCATCTC CAAATTTGAG CAGCACCTCA GTTGAAATAC CGGCCACCTC

29601 TGAAATCATG ACAGATACAG AGAAAATTCA TCCTTCCTCA ACACAGCGG

29651 TGGCCAAAGT GAGGACCTCC AGTTCTGTTC ATGAATCTCA TTCCTCTGTC

29701 CTAGCTGACT CAGAAACAAC CATAACCATA CCTTCAATGG GTATCACCTC

29751 CGCTGTGGAC GATACCACTG TTTTCACATC AAATCCTGCC TTCTCTGAGA

29801 CTAGGAGGAT TCCGACAGAG CCAACATTCT CATTGACTCC TGGATTCAGG

29851 GAGACTAGCA CCTCTGAAGA GACCACCTCA ATCACAGAAA CAAGTGCAGT

29901 CCTTTATGGA GTGCCCACTA GTGCTACTAC TGAAGTCTCC ATGACAGAAA

29951 TCATGTCCTC TAATAGAACA CACATCCCTG ACTCTGATCA GTCCACGATG

30001 TCTCCAGACA TCATCACTGA AGTGATCACC AGGCTCTCTT CCTCATCCAT

30051 GATGTCAGAA TCAACACAAA TGACCATCAC CACCCAAAAA AGTTCTCCTG

30101 GGGCTACAGC ACAGAGTACT CTTACCTTGG CCACAACAAC AGCCCCCTTG
```

TABLE 4-continued

Human cDNA of CA125
(SEQ ID NO: 4)

```
30151 GCAAGGACCC ACTCAACTGT TCCTCCTAGA TTTTTACACT CAGAGATGAC
30201 AACTCTTATG AGTAGGAGTC CTGAAAATCC ATCATGGAAG AGCTCTCCCT
30251 TTGTGGAAAA AACTAGCTCT TCATCTTCTC TGTTGTCCTT ACCTGTCACG
30301 ACCTCACCTT CTGTTTCTTC CACATTACCG CAGAGTATCC CTTCCTCCTC
30351 TTTTTCTGTG ACTTCACTCC TCACCCCAGG CATGGTGAAG ACTACAGACA
30401 CAAGCACAGA ACCTGGAACC AGTTTATCTC CAAATCTGAG TGGCACCTCA
30451 GTTGAAATAC TGGCTGCCTC TGAAGTCACC ACAGATACAG AGAAAATTCA
30501 TCCTTCTTCA AGCATGGCAG TGACCAATGT GGGAACCACC AGTTCTGGAC
30551 ATGAACTATA TTCCTCTGTT TCAATCCACT CGGAGCCATC CAAGGCTACA
30601 TACCCAGTGG GTACTCCCTC TTCCATGGCT GAAACCTCTA TTTCCACATC
30651 AATGCCTGCT AATTTTGAGA CCACAGGATT TGAGGCTGAG CCATTTTCTC
30701 ATTTGACTTC TGGATTTAGG AAGACAAACA TGTCCCTGGA CACCAGCTCA
30751 GTCACACCAA CAAATACACC TTCTTCTCCT GGGTCCACTC ACCTTTTACA
30801 GAGTTCCAAG ACTGATTTCA CCTCTTCTGC AAAAACATCA TCCCCAGACT
30851 GGCCTCCAGC CTCACAGTAT ACTGAAATTC CAGTGGACAT AATCACCCCC
30901 TTTAATGCTT CTCCATCTAT TACGGAGTCC ACTGGGATAA CCTCCTTCCC
30951 AGAATCCAGG TTTACTATGT CTGTAACAGA AAGTACTCAT CATCTGAGTA
31001 CAGATTTGCT GCCTTCAGCT GAGACTATTT CCACTGGCAC AGTGATGCCT
31051 TCTCTATCAG AGGCCATGAC TTCATTTGCC ACCACTGGAG TTCCACGAGC
31101 CATCTCAGGT TCAGGTAGTC CATTCTCTAG ACAGAGTCA GGCCCTGGGG
31151 ATGCTACTCT GTCCACCATT GCAGAGAGCC TGCCTTCATC CACTCCTGTG
31201 CCATTCTCCT CTTCAACCTT CACTACCACT GATTCTTCAA CCATCCCAGC
31251 CCTCCATGAG ATAACTTCCT CTTCAGCTAC CCCATATAGA GTGGACACCA
31301 GTCTTGGGAC AGAGAGCAGC ACTACTGAAG GACGCTTGGT TATGGTCAGT
31351 ACTTTGGACA CTTCAAGCCA ACCAGGCAGG ACATCTTCAA CACCCATTTT
31401 GGATACCAGA ATGACAGAGA GCGTTGAGCT GGGAACAGTG ACAAGTGCTT
31451 ATCAAGTTCC TTCACTCTCA ACACGGTTGA CAAGAACTGA TGGCATTATG
31501 GAACACATCA CAAAAATACC CAATGAAGCA GCACACAGAG GTACCATAAG
31551 ACCAGTCAAA GGCCCTCAGA CATCCACTTC GCCTGCCAGT CCTAAAGGAC
31601 TACACACAGG AGGGACAAAA AGAATGGAGA CCACCACCAC AGCTTTGAAG
31651 ACCACCACCA CAGCTTTGAA GACCACTTCC AGAGCCACCT TGACCACCAG
31701 TGTCTATACT CCCACTTTGG GAACACTGAC TCCCCTCAAT GCATCAAGGC
31751 AAATGGCCAG CACAATCCTC ACAGAAATGA TGATCACAAC CCCATATGTT
31801 TTCCCTGATG TTCCAGAAAC GACATCCTCA TTGGCTACCA GCCTGGGAGC
31851 AGAAACCAGC ACAGCTCTTC CCAGGACAAC CCCATCTGTT CTCAATAGAG
31901 AATCAGAGAC CACAGCCTCA CTGGTCTCTC GTTCTGGGGC AGAGAGAAGT
31951 CCGGTTATTC AAACTCTAGA TGTTTCTTCT AGTGAGCCAG ATACAACAGC
32001 TTCATGGGTT ATCCATCCTG CAGAGACCAT CCCAACTGTT TCCAAGACAA
32051 CCCCCAATTT TTTCCACAGT GAATTAGACA CTGTATCTTC CACAGCCACC
```

TABLE 4-continued

Human cDNA of CA125
(SEQ ID NO: 4)

```
32101 AGTCATGGGG CAGACGTCAG CTCAGCCATT CCAACAAATA TCTCACCTAG

32151 TGAACTAGAT GCACTGACCC CACTGGTCAC TATTTCGGGG ACAGATACTA

32201 GTACAACATT CCCAACACTG ACTAAGTCCC CACATGAAAC AGAGACAAGA

32251 ACCACATGGC TCACTCATCC TGCAGAGACC AGCTCAACTA TTCCCAGAAC

32301 AATCCCCAAT TTTTCTCATC ATGAATCAGA TGCCACACCT TCAATAGCCA

32351 CCAGTCCTGG GGCAGAAACC AGTTCAGCTA TTCCAATTAT GACTGTCTCA

32401 CCTGGTGCAG AAGATCTGGT GACCTCACAG GTCACTAGTT CTGGGACAGA

32451 CAGAAATATG ACTATTCCAA CTTTGACTCT TTCTCCTGGT GAACCAAAGA

32501 CGATAGCCTC ATTAGTCACC CATCCTGAAG CACAGACAAG TTCGGCCATT

32551 CCAACTTCAA CTATCTCGCC TGCTGTATCA CGGTTGGTGA CCTCAATGGT

32601 CACCAGTTTG GCGGCAAAGA CAAGTACAAC TAATCGAGCT CTGACAAACT

32651 CCCCTGGTGA ACCAGCTACA CAGTTTCAT TGGTCACGCA TCCTGCACAG

32701 ACCAGCCCAA CAGTTCCCTG GACAACTTCC ATTTTTTTCC ATAGTAAATC

32751 AGACACCACA CCTTCAATGA CCACCAGTCA TGGGGCAGAA TCCAGTTCAG

32801 CTGTTCCAAC TCCAACTGTT TCAACTGAGG TACCAGGAGT AGTGACCCCT

32851 TTGGTCACCA GTTCTAGGGC AGTGATCAGT ACAACTATTC CAATTCTGAC

32901 TCTTTCTCCT GGTGAACCAG AGACCACACC TTCAATGGCC ACCAGTCATG

32951 GGGAAGAAGC CAGTTCTGCT ATTCCAACTC CAACTGTTTC ACCTGGGGTA

33001 CCAGGAGTGG TGACCTCTCT GGTCACTAGT TCTAGGGCAG TGACTAGTAC

33051 AACTATTCCA ATTCTGACTT TTTCTCTTGG TGAACCAGAG ACCACACCTT

33101 CAATGGCCAC CAGTCATGGG ACAGAAGCTG GCTCAGCTGT TCCAACTGTT

33151 TTACCTGAGG TACCAGGAAT GGTGACCTCT CTGGTTGCTA GTTCTAGGGC

33201 AGTAACCAGT ACAACTCTTC CAACTCTGAC TCTTTCTCCT GGTGAACCAG

33251 AGACCACACC TTCAATGGCC ACCAGTCATG GGCAGAAGC CAGCTCAACT

33301 GTTCCAACTG TTTCACCTGA GGTACCAGGA GTGGTGACCT CTCTGGTCAC

33351 TAGTTCTAGT GGAGTAAACA GTACAAGTAT TCCAACTCTG ATTCTTTCTC

33401 CTGGTGAACT AGAAACCACA CCTTCAATGG CCACCAGTCA TGGGGCAGAA

33451 GCCAGCTCAG CTGTTCCAAC TCCAACTGTT TCACCTGGGG TATCAGGAGT

33501 GGTGACCCCT CTGGTCACTA GTTCCAGGGC AGTGACCAGT ACAACTATTC

33551 CAATTCTAAC TCTTTCTTCT AGTGAGCCAG AGACCACACC TTCAATGCC

33601 ACCAGTCATG GGGTAGAAGC CAGCTCAGCT GTTCTAACTG TTTCACCTGA

33651 GGTACCAGGA ATGGTGACCT CTCTGGTCAC TAGTTCTAGA GCAGTAACCA

33701 GTACAACTAT TCCAACTCTG ACTATTTCTT CTGATGAACC AGAGACCACA

33751 ACTTCATTGG TCACCCATTC TGAGGCAAAG ATGATTTCAG CCATTCCAAC

33801 TTTAGCTGTC TCCCCTACTG TACAAGGGCT GGTGACTTCA CTGGTCACTA

33851 GTTCTGGGTC AGAGACCAGT GCGTTTTCAA ATCTAACTGT TGCCTCAAGT

33901 CAACCAGAGA CCATAGACTC ATGGGTCGCT CATCCTGGGA CAGAAGCAAG

33951 TTCTGTTGTT CCAACTTTGA CTGTCTCCAC TGGTGAGCCG TTTACAAATA
```

TABLE 4-continued

| Human cDNA of CA125 (SEQ ID NO: 4) |
| --- |

```
34001 TCTCATTGGT CACCCATCCT GCAGAGAGTA GCTCAACTCT TCCCAGGACA
34051 ACCTCAAGGT TTTCCCACAG TGAATTAGAC ACTATGCCTT CTACAGTCAC
34101 CAGTCCTGAG GCAGAATCCA GCTCAGCCAT TTCAACTACT ATTTCACCTG
34151 GTATACCAGG TGTGCTGACA TCACTGGTCA CTAGCTCTGG GAGAGACATC
34201 AGTGCAACTT TTCCAACAGT GCCTGAGTCC CCACATGAAT CAGAGGCAAC
34251 AGCCTCATGG GTTACTCATC CTGCAGTCAC CAGCACAACA GTTCCCAGGA
34301 CAACCCCTAA TTATTCTCAT AGTGAACCAG ACACCACACC ATCAATAGCC
34351 ACCAGTCCTG GGGCAGAAGC CACTTCAGAT TTTCCAACAA TAACTGTCTC
34401 ACCTGATGTA CCAGATATGG TAACCTCACA GGTCACTAGT TCTGGGACAG
34451 ACACCAGTAT AACTATTCCA ACTCTGACTC TTTCTTCTGG TGAGCCAGAG
34501 ACCACAACCT CATTTATCAC CTATTCTGAG ACACACACAA GTTCAGCCAT
34551 TCCAACTCTC CCTGTCTCCC CTGGTGCATC AAAGATGCTG ACCTCACTGG
34601 TCATCAGTTC TGGGACAGAC AGCACTACAA CTTTCCCAAC ACTGACGGAG
34651 ACCCCATATG AACCAGAGAC AACAGCCATA CAGCTCATTC ATCCTGCAGA
34701 GACCAACACA ATGGTTCCCA AGACAACTCC CAAGTTTTCC CATAGTAAGT
34751 CAGACACCAC ACTCCCAGTA GCCATCACCA GTCCTGGGCC AGAAGCCAGT
34801 TCAGCTGTTT CAACGACAAC TATCTCACCT GATATGTCAG ATCTGGTGAC
34851 CTCACTGGTC CCTAGTTCTG GACAGACACC CAGTACAACC TTCCCAACAT
34901 TGAGTGAGAC CCCATATGAA CCAGAGACTA CAGTCACGTG GCTCACTCAT
34951 CCTGCAGAAA CCAGCACAAC GGTTTCTGGG ACAATTCCCA ACTTTTCCCA
35001 TAGGGGATCA GACACTGCAC CCTCAATGGT CACCAGTCCT GGAGTAGACA
35051 CGAGGTCAGG TGTTCCAACT ACAACCATCC CACCCAGTAT ACCAGGGGTA
35101 GTGACCTCAC AGGTCACTAG TTCTGCAACA GACACTAGTA CAGCTATTCC
35151 AACTTTGACT CCTTCTCCTG GTGAACCAGA GACCACAGCC TCATCAGCTA
35201 CCCATCCTGG GACACAGACT GGCTTCACTG TTCCAATTCG GACTGTTCCC
35251 TCTAGTGAGC CAGATACAAT GGCTTCCTGG GTCACTCATC CTCCACAGAC
35301 CAGCACACCT GTTTCCAGAA CAACCTCCAG TTTTTCCCAT AGTAGTCCAG
35351 ATGCCACACC TGTAATGGCC ACCAGTCCTA GGACAGAAGC CAGTTCAGCT
35401 GTACTGACAA CAATCTCACC TGGTGCACCA GAGATGGTGA CTTCACAGAT
35451 CACTAGTTCT GGGGCAGCAA CCAGTACAAC TGTTCCAACT TTGACTCATT
35501 CTCCTGGTAT GCCAGAGACC ACAGCCTTAT TGAGCACCCA TCCCAGAACA
35551 GGGACAAGTA AAACATTTCC TGCTTCAACT GTGTTTCCTC AAGTATCAGA
35601 GACCACAGCC TCACTCACCA TTAGACCTGG TGCAGAGACT AGCACAGCTC
35651 TCCCAACTCA GACAACATCC TCTCTCTTCA CCCTACTTGT AACTGGAACC
35701 AGCAGAGTTG ATCTAAGTCC AACTGCTTCA CCTGGTGTTT CTGCAAAAAC
35751 AGCCCCACTT TCCACCCATC CAGGGACAGA GACCAGCACA ATGATTCCAA
35801 CTTCAACTCT TTCCCTTGGT TTACTAGAGA CTACAGGCTT ACTGGCCACC
35851 AGCTCTTCAG CAGAGACCAG CACGAGTACT CTAACTCTGA CTGTTTCCCC
35901 TGCTGTCTCT GGGCTTTCCA GTGCCTCTAT AACAACTGAT AAGCCCCAAA
```

TABLE 4-continued

Human cDNA of CA125
(SEQ ID NO: 4)

```
35951 CTGTGACCTC CTGGAACACA GAAACCTCAC CATCTGTAAC TTCAGTTGGA
36001 CCCCCAGAAT TTTCCAGGAC TGTCACAGGC ACCACTATGA CCTTGATACC
36051 ATCAGAGATG CCAACACCAC CTAAAACCAG TCATGGAGAA GGAGTGAGTC
36101 CAACCACTAT CTTGAGAACT ACAATGGTTG AAGCCACTAA TTTAGCTACC
36151 ACAGGTTCCA GTCCCACTGT GGCCAAGACA CAACCACCT TCAATACACT
36201 GGCTGGAAGC CTCTTTACTC CTCTGACCAC ACCTGGGATG TCCACCTTGG
36251 CCTCTGAGAG TGTGACCTCA AGAACAAGTT ATAACCATCG GTCCTGGATC
36301 TCCACCACCA GCAGTTATAA CCGTCGGTAC TGGACCCCTG CCACCAGCAC
36351 TCCAGTGACT TCTACATTCT CCCCAGGGAT TTCCACATCC TCCATCCCCA
36401 GCTCCACAGC AGCCACAGTC CCATTCATGG TGCCATTCAC CCTCAACTTC
36451 ACCATCACCA ACCTGCAGTA CGAGGAGGAC ATGCGGCACC CTGGTTCCAG
36501 GAAGTTCAAC GCCACAGAGA GAGAACTGCA GGGTCTGCTC AAACCCTTGT
36551 TCAGGAATAG CAGTCTGGAA TACCTCTATT CAGGCTGCAG ACTAGCCTCA
36601 CTCAGGCCAG AGAAGGATAG CTCAGCCATG GCAGTGGATG CCATCTGCAC
36651 ACATCGCCCT GACCCTGAAG ACCTCGGACT GGACAGAGAG CGACTGTACT
36701 GGGAGCTGAG CAATCTGACA AATGGCATCC AGGAGCTGGG CCCCTACACC
36751 CTGGACCGGA ACAGTCTCTA TGTCAATGGT TTCACCCATC GAAGCTCTAT
36801 GCCCACCACC AGCACTCCTG GACCTCCAC AGTGGATGTG GAACCTCAG
36851 GGACTCCATC CTCCAGCCCC AGCCCCACGG CTGCTGGCCC TCTCCTGATG
36901 CCGTTCACCC TCAACTTCAC CATCACCAAC CTGCAGTACG AGGAGGACAT
36951 GCGTCGCACT GGCTCCAGGA AGTTCAACAC CATGGAGAGT GTCCTGCAGG
37001 GTCTGCTCAA GCCCTTGTTC AAGAACACCA GTGTTGGCCC TCTGTACTCT
37051 GGCTGCAGAT TGACCTTGCT CAGGCCCGAG AAAGATGGGG CAGCCACTGG
37101 AGTGGATGCC ATCTGCACCC ACCGCCTTGA CCCCAAAAGC CCTGGACTCA
37151 ACAGGGAGCA GCTGTACTGG GAGCTAAGCA AACTGACCAA TGACATTGAA
37201 GAGCTGGGCC CCTACACCCT GGACAGGAAC AGTCTCTATG TCAATGGTTT
37251 CACCCATCAG AGCTCTGTGT CCACCACCAG CACTCCTGGG ACCTCCACAG
37301 TGGATCTCAG AACCTCAGGG ACTCCATCCT CCCTCTCCAG CCCCACAATT
37351 ATGGCTGCTG GCCCTCTCCT GGTACCATTC ACCCTCAACT TCACCATCAC
37401 CAACCTGCAG TATGGGGAGG ACATGGGTCA CCCTGGCTCC AGGAAGTTCA
37451 ACACCACAGA GAGGGTCCTG CAGGGTCTGC TTGGTCCCAT ATTCAAGAAC
37501 ACCAGTGTTG GCCCTCTGTA CTCTGGCTGC AGACTGACCT CTCTCAGGTC
37551 TGAGAAGGAT GGAGCAGCCA CTGAGTGGA TGCCATCTGC ATCCATCATC
37601 TTGACCCCAA AGCCCTGGA CTCAACAGAG AGCGGCTGTA CTGGGAGCTG
37651 AGCCAACTGA CCAATGGCAT CAAAGAGCTG GGCCCCTACA CCCTGGACAG
37701 GAACAGTCTC TATGTCAATG GTTTCACCCA TCGGACCTCT GTGCCCACCA
37751 CCAGCACTCC TGGGACCTCC ACAGTGGACC TTGGAACCTC AGGGACTCCA
37801 TTCTCCCTCC CAAGCCCCGC AACTGCTGGC CCTCTCCTGG TGCTGTTCAC
```

TABLE 4-continued

| Human cDNA of CA125 (SEQ ID NO: 4) |
|---|

```
37851 CCTCAACTTC ACCATCACCA ACCTGAAGTA TGAGGAGGAC ATGCATCGCC

37901 CTGGCTCCAG GAAGTTCAAC ACCACTGAGA GGGTCCTGCA GACTCTGCTT

37951 GGTCCTATGT TCAAGAACAC CAGTGTTGGC CTTCTGTACT CTGGCTGCAG

38001 ACTGACCTTG CTCAGGTCCG AGAAGGATGG AGCAGCCACT GGAGTGGATG

38051 CCATCTGCAC CCACCGTCTT GACCCCAAAA GCCCTGGACT GGACAGAGAG

38101 CAGCTATACT GGGAGCTGAG CCAGCTGACC AATGGCATCA AAGAGCTGGG

38151 CCCCTACACC CTGGACAGGA ACAGTCTCTA TGTCAATGGT TTCACCCATT

38201 GGATCCCTGT GCCCACCAGC AGCACTCCTG GGACCTCCAC AGTGGACCTT

38251 GGGTCAGGGA CTCCATCCTC CCTCCCCAGC CCCACAGCTG CTGGCCCTCT

38301 CCTGGTGCCA TTCACCCTCA ACTTCACCAT CACCAACCTG CAGTACGAGG

38351 AGGACATGCA TCACCCAGGC TCCAGGAAGT TCAACACCAC GGAGCGGGTC

38401 CTGCAGGGTC TGCTTGGTCC CATGTTCAAG AACACCAGTG TCGGCCTTCT

38451 GTACTCTGGC TGCAGACTGA CCTTGCTCAG GTCCGAGAAG GATGGAGCAG

38501 CCACTGGAGT GGATGCCATC TGCACCCACC GTCTTGACCC CAAAAGCCCT

38551 GGAGTGGACA GGGAGCAGCT ATACTGGGAG CTGAGCCAGC TGACCAATGG

38601 CATCAAAGAG CTGGGTCCCT ACACCCTGGA CAGAAACAGT CTCTATGTCA

38651 ATGGTTTCAC CCATCAGACC TCTGCGCCCA ACACCAGCAC TCCTGGGACC

38701 TCCACAGTGG ACCTTGGGAC CTCAGGGACT CCATCCTCCC TCCCCAGCCC

38751 TACATCNGCT GGCCCTCTCC TGGTNCCNTT CACCCTCAAC TTCACCATCA

38801 CCAACCTGCA GTACGAGGAG GACATGCGGC ACCCNGGNTC CAGGAAGTTC

38851 AACACCACNG AGAGGGTNCT GCAGGGTCTG CTNAAGCCCC TNTTCAAGAG

38901 CACCAGTGTT GGCCCTCTGT ACTCTGGCTG CAGACTGACC TTGCTCAGGT

38951 CCGAGAAGGA TGGAGCAGCC ACTGGAGTGG ATGCCATCTG CACCCACCGT

39001 CTTGACCCCA AAAGCCCTGG AGTGGACAGG GAGCAGCTAT ACTGGGAGCT

39051 GAGCCAGCTG ACCAATGGCA TCAAAGAGCT GGGTCCCTAC ACCCTGGACA

39101 GAAACAGTCT CTATGTCAAT GGTTTCACCC ATCAGACCTC TGCGCCCAAC

39151 ACCAGCACTC TGGGACCTC CACAGTGGAC CTTGGGACCT CAGGGACTCC

39201 ATCCTCCCTC CCCAGCCCTA CATCTGCTGG CCCTCTCCTG GTGCCATTCA

39251 CCCTCAACTT CACCATCACC AACCTGCAGT ACGAGGAGGA CATGCATCAC

39301 CCAGGCTCCA GGAAGTTCAA CACCACGGAG CGGGTCCTGC AGGGTCTGCT

39351 TGGTCCCATG TTCAAGAACA CCAGTGTCGG CCTTCTGTAC TCTGGCTGCA

39401 GACTGACCTT GCTCAGGCCT GAGAAGAATG GGCAGCCAC TGGAATGGAT

39451 GCCATCTGCA GCCACCGTCT TGACCCCAAA AGCCCTGGAC TCAACAGAGA

39501 GCAGCTGTAC TGGGAGCTGA GCCAGCTGAC CCATGGCATC AAAGAGCTGG

39551 GCCCCTACAC CCTGGACAGG AACAGTCTCT ATGTCAATGG TTTCACCCAT

39601 CGGAGCTCTG TGGCCCCCAC CAGCACTCCT GGGACCTCCA CAGTGGACCT

39651 TGGGACCTCA GGGACTCCAT CCTCCCTCCC CAGCCCCACA ACAGCTGTTC

39701 CTCTCCTGGT GCCGTTCACC CTCAACTTTA CCATCACCAA TCTGCAGTAT

39751 GGGGAGGACA TGCGTCACCC TGGCTCCAGG AAGTTCAACA CCACAGAGAG
```

TABLE 4-continued

Human cDNA of CA125
(SEQ ID NO: 4)

```
39801 GGTCCTGCAG GGTCTGCTTG GTCCCTTGTT CAAGAACTCC AGTGTCGGCC

39851 CTCTGTACTC TGGCTGCAGA CTGATCTCTC TCAGGTCTGA GAAGGATGGG

39901 GCAGCCACTG GAGTGGATGC CATCTGCACC CACCACCTTA ACCCTCAAAG

39951 CCCTGGACTG GACAGGGAGC AGCTGTACTG GCAGCTGAGC CAGATGACCA

40001 ATGGCATCAA AGAGCTGGGC CCCTACACCC TGGACCGGAA CAGTCTCTAC

40051 GTCAATGGTT TCACCCATCG GAGCTCTGGG CTCACCACCA GCACTCCTTG

40101 GACTTCCACA GTTGACCTTG GAACCTCAGG GACTCCATCC CCCGTCCCCA

40151 GCCCCACAAC TGCTGGCCCT CTCCTGGTGC CATTCACCCT CAACTTCACC

40201 ATCACCAACC TGCAGTATGA GGAGGACATG CATCGCCCTG GATCTAGGAA

40251 GTTCAACACC ACAGAGAGGG TCCTGCAGGG TCTGCTTAGT CCCATTTTCA

40301 AGAACTCCAG TGTTGGCCCT CTGTACTCTG GCTGCAGACT GACCTCTCTC

40351 AGGCCCGAGA AGGATGGGGC AGCAACTGGA ATGGATGCTG TCTGCCTCTA

40401 CCACCCTAAT CCCAAAAGAC CTGGACTGGA CAGAGAGCAG CTGTACTGGG

40451 AGCTAAGCCA GCTGACCCAC AACATCACTG AGCTGGGCCC CTACAGCCTG

40501 GACAGGGACA GTCTCTATGT CAATGGTTTC ACCCATCAGA ACTCTGTGCC

40551 CACCACCAGT ACTCCTGGGA CCTCCACAGT GTACTGGGCA ACCACTGGGA

40601 CTCCATCCTC CTTCCCCGGC CACACAGAGC CTGGCCCTCT CCTGATACCA

40651 TTCACTTTCA ACTTTACCAT CACCAACCTG CATTATGAGG AAAACATGCA

40701 ACACCCTGGT TCCAGGAAGT TCAACACCAC GGAGAGGGTT CTGCAGGGTC

40751 TGCTCAAGCC CTTGTTCAAG AACACCAGTG TTGGCCCTCT GTACTCTGGC

40801 TGCAGACTGA CCTCTCTCAG GCCCGAGAAG GATGGGCAG CAACTGGAAT

40851 GGATGCTGTC TGCCTCTACC ACCCTAATCC CAAAAGACCT GGGCTGGACA

40901 GAGAGCAGCT GTACTGGGAG CTAAGCCAGC TGACCCACAA CATCACTGAG

40951 CTGGGCCCCT ACAGCCTGGA CAGGGACAGT CTCTATGTCA ATGGTTTCAC

41001 CCATCAGAAC TCTGTGCCCA CCACCAGTAC TCCTGGGACC TCCACAGTGT

41051 ACTGGGCAAC CACTGGGACT CCATCCTCCT TCCCCGGCCA CACAGAGCCT

41101 GGCCCTCTCC TGATACCATT CACTTTCAAC TTTACCATCA CCAACCTGCA

41151 TTATGAGGAA AACATGCAAC ACCCTGGTTC CAGGAAGTTC AACACCACGG

41201 AGAGGGTTCT GCAGGGTCTG CTCAAGCCCT TGTTCAAGAA CACCAGTGTT

41251 GGCCCTCTGT ACTCTGGCTG CAGACTGACC TTGCTCAGAC TGAGAAGCA

41301 TGAGGCAGCC ACTGGAGTGG ACACCATCTG TACCCACCGC GTTGATCCCA

41351 TCGGACCTGG ACTGGACAGG GAGCGGCTAT ACTGGGAGCT GAGCCAGCTG

41401 ACCAACAGCA TTACCGAACT GGGACCCTAC ACCCTGGACA GGGACAGTCT

41451 CTATGTCAAT GGCTTCAACC CTCGGAGCTC TGTGCCAACC ACCAGCACTC

41501 CTGGGACCTC ACAGTGCAC CTGGCAACCT CTGGGACTCC ATCCTCCCTG

41551 CCTGGCCACA CAGCCCCTGT CCCTCTCTTG ATACCATTCA CCCTCAACTT

41601 TACCATCACC AACCTGCATT ATGAGGAAAA CATGCAACAC CCTGGTTCCA

41651 GGAAGTTCAA CACCACGGAG AGGGTTCTGC AGGGTCTGCT CAAGCCCTTG
```

TABLE 4-continued

Human cDNA of CA125
(SEQ ID NO: 4)

```
41701 TTCAAGAACA CCAGTGTTGG CCCTCTGTAC TCTGGCTGCA GACTGACCTT
41751 GCTCAGACCT GAGAAGCATG AGGCAGCCAC TGGAGTGGAC ACCATCTGTA
41801 CCCACCGCGT TGATCCCATC GGACCTGGAC TGNACAGNGA GCNGCTNTAC
41851 TGGGAGCTNA GCCANCTGAC CAANNNCATC NNNGAGCTGG GNCCCTACAC
41901 CCTGGACAGG NACAGTCTCT ATGTCAATGG TTTCACCCAT CNGANCTCTG
41951 NGCCCACCAC CAGCACTCCT GGGACCTCCA CAGTGNACNT NGGNACCTCN
42001 GGGACTCCAT CCTCCNTCCC CNGCCNCACA TCTGCTGGCC CTCTCCTGGT
42051 GCCATTCACC CTCAACTTCA CCATCACCAA CCTGCAGTAC GAGGAGGACA
42101 TGCATCACCC AGGCTCCAGG AAGTTCAACA CCACGGAGCG GGTCCTGCAG
42151 GGTCTGCTTG GTCCCATGTT CAAGAACACC AGTGTCGGCC TTCTGTACTC
42201 TGGCTGCAGA CTGACCTTGC TCAGGCCTGA GAAGAATGGG GCAGCCACTG
42251 GAATGGATGC CATCTGCAGC CACCGTCTTG ACCCCAAAAG CCCTGGACTC
42301 GACAGAGAGC AGCTGTACTG GGAGCTGAGC CAGCTGACCC ATGGCATCAA
42351 AGAGCTGGGC CCCTACACCC TGGACAGGAA CAGTCTCTAT GTCAATGGTT
42401 TCACCCATCG GAGCTCTGTG GCCCCCACCA GCACTCCTGG GACCTCCACA
42451 GTGGACCTTG GACCTCAGG GACTCCATCC TCCCTCCCCA GCCCCACAAC
42501 AGCTGTTCCT CTCCTGGTGC CGTTCACCCT CAACTTTACC ATCACCAATC
42551 TGCAGTATGG GGAGGACATG CGTCACCCTG GCTCCAGGAA GTTCAACACC
42601 ACAGAGAGGG TCCTGCAGGG TCTGCTTGGT CCCTTGTTCA AGAACTCCAG
42651 TGTCGGCCCT CTGTACTCTG GCTGCAGACT GATCTCTCTC AGGTCTGAGA
42701 AGGATGGGGC AGCCACTGGA GTGGATGCCA TCTGCACCCA CCACCTTAAC
42751 CCTCAAAGCC CTGGACTGGA CAGGGAGCAG CTGTACTGGC AGCTGAGCCA
42801 GATGACCAAT GGCATCAAAG AGCTGGGCCC CTACACCCTG GACCGGAACA
42851 GTCTCTACGT CAATGGTTTC ACCCATCGGA GCTCTGGGCT CACCACCAGC
42901 ACTCCTTGGA CTTCCACAGT TGACCTTGGA ACCTCAGGGA CTCCATCCCC
42951 CGTCCCCAGC CCCACAACTG CTGGCCCTCT CCTGGTGCCA TTCACCCTAA
43001 ACTTCACCAT CACCAACCTG CAGTATGAGG AGGACATGCA TCGCCCTGGA
43051 TCTAGGAAGT TCAACGCCAC AGAGAGGGTC CTGCAGGGTC TGCTTAGTCC
43101 CATATTCAAG AACTCCAGTG TTGGCCCTCT GTACTCTGGC TGCAGACTGA
43151 CCTCTCTCAG GCCCGAGAAG GATGGGCAG CAACTGGAAT GGATGCTGTC
43201 TGCCTCTACC ACCCTAATCC CAAAAGACCT GGACTGGACA GAGAGCAGCT
43251 GTACTGGGAG CTAAGCCAGC TGACCCACAA CATCACTGAG CTGGGCCCCT
43301 ACAGCCTGGA CAGGGACAGT CTCTATGTCA ATGGTTTCAC CCATCAGAGC
43351 TCTATGACGA CCACCAGAAC TCCTGATACC TCCACAATGC ACCTGGCAAC
43401 CTCGAGAACT CCAGCCTCCC TGTCTGGACC TACGACGCC AGCCCTCTCC
43451 TGGTGCTATT CACAATCAAC TGCACCATCA CCAACCTGCA GTACGAGGAG
43501 GACATGCGTC GCACTGGCTC CAGGAAGTTC AACACCATGG AGAGTGTCCT
43551 GCAGGGTCTG CTCAAGCCCT TGTTCAAGAA CACCAGTGTT GGCCCTCTGT
43601 ACTCTGGCTG CAGATTGACC TTGCTCAGGC CCAAGAAAGA TGGGGCAGCC
```

TABLE 4-continued

Human cDNA of CA125
(SEQ ID NO: 4)

```
43651 ACTGGAGTGG ATGCCATCTG CACCCACCGC CTTGACCCCA AAAGCCCTGG

43701 ACTCAACAGG GAGCAGCTGT ACTGGGAGCT AAGCAAACTG ACCAATGACA

43751 TTGAAGAGCT GGGCCCCTAC ACCCTGGACA GGAACAGTCT CTATGTCAAT

43801 GGTTTCACCC ATCAGAGCTC TGTGTCCACC ACCAGCACTC CTGGGACCTC

43851 CACAGTGGAT CTCAGAACCT CAGGGACTCC ATCCTCCCTC TCCAGCCCCA

43901 CAATTATGNC NNCTGNCCCT CTCCTGNTNC CNTTCACCNT CAACTTNACC

43951 ATCACCAACC TGCANTANGN GGANNACATG CNNCNCCCNG GNTCCAGGAA

44001 GTTCAACACC ACNGAGAGGG TCCTACAGGG TCTGCTCAGG CCCTTGTTCA

44051 AGAACACCAG TGTCAGCTCT CTGTACTCTG GTTGCAGACT GACCTTGCTC

44101 AGGCCTGAGA AGGATGGGGC AGCCACCAGA GTGGATGCTG CCTGCACCTA

44151 CCGCCCTGAT CCCAAAAGCC CTGGACTGGA CAGAGAGCAA CTATACTGGG

44201 AGCTGAGCCA GCTAACCCAC AGCATCACTG AGCTGGGACC CTACACCCTG

44251 GACAGGGTCA GTCTCTATGT CAATGGCTTC AACCCTCGGA GCTCTGTGCC

44301 AACCACCAGC ACTCCTGGGA CCTCCACAGT GCACCTGGCA ACCTCTGGGA

44351 CTCCATCCTC CCTGCCTGGC CACACANCNN CTGNCCCTCT CCTGNTNCCN

44401 TTCACCNTCA ACTTNACCAT CACCAACCTG CANTANGNGG ANNACATGCN

44451 NCNCCCNGGN TCCAGGAAGT TCAACACCAC NGAGAGGGTT CTGCAGGGTC

44501 TGCTCAAACC CTTGTTCAGG AATAGCAGTC TGGAATACCT CTATTCAGGC

44551 TGCAGACTAG CCTCACTCAG GCCAGAGAAG GATAGCTCAG CCATGGCAGT

44601 GGATGCCATC TGCACACATC GCCCTGACCC TGAAGACCTC GGACTGGACA

44651 GAGAGCGACT GTACTGGGAG CTGAGCAATC TGACAAATGG CATCCAGGAG

44701 CTGGGCCCCT ACACCCTGGA CCGGAACAGT CTCTACGTCA ATGGTTTCAC

44751 CCATCGGAGC TCTGGGCTCA CCACCAGCAC TCCTTGGACT TCCACAGTTG

44801 ACCTTGGAAC CTCAGGGACT CCATCCCCCG TCCCCAGCCC CACAACTGCT

44851 GGCCCTCTCC TGGTGCCATT CACCCTCAAC TTCACCATCA CCAACCTGCA

44901 GTATGAGGAG GACATGCATC GCCCTGGTTC CAGGAGGTTC AACACCACGG

44951 AGAGGGTTCT GCAGGGTCTG CTCACGCCCT TGTTCAAGAA CACCAGTGTT

45001 GGCCCTCTGT ACTCTGGCTG CAGACTGACC TTGCTCAGAC CTGAGAAGCA

45051 AGAGGCAGCC ACTGGAGTGG ACACCATCTG TACCCACCGC GTTGATCCCA

45101 TCGGACCTGG ACTGGACAGA GAGCGGCTAT ACTGGAGCT GAGCCAGCTG

45151 ACCAACAGCA TCACAGAGCT GGGACCCTAC ACCCTGGATA GGGACAGTCT

45201 CTATGTCAAT GGCTTCAACC CTTGGAGCTC TGTGCCAACC ACCAGCACTC

45251 CTGGGACCTC CACAGTGCAC CTGGCAACCT CTGGGACTCC ATCCTCCCTG

45301 CCTGGCCACA CAGCCCCTGT CCCTCTCTTG ATACCATTCA CCCTCAACTT

45351 TACCATCACC GACCTGCATT ATGAAGAAAA CATGCAACAC CCTGGTTCCA

45401 GGAAGTTCAA CACCACGGAG AGGGTTCTGC AGGGTCTGCT CAAGCCCTTG

45451 TTCAAGAGCA CCAGCGTTGG CCCTCTGTAC TCTGGCTGCA GACTGACCTT

45501 GCTCAGACCT GAGAAACATG GGGCAGCCAC TGGAGTGGAC GCCATCTGCA
```

TABLE 4-continued

Human cDNA of CA125
(SEQ ID NO: 4)

```
45551 CCCTCCGCCT TGATCCCACT GGTCCTGGAC TGGACAGAGA GCGGCTATAC
45601 TGGGAGCTGA GCCAGCTGAC CAACAGCGTT ACAGAGCTGG GCCCCTACAC
45651 CCTGGACAGG GACAGTCTCT ATGTCAATGG CTTCACCCAT CGGAGCTCTG
45701 TGCCAACCAC CAGTATTCCT GGGACCTCTG CAGTGCACCT GGAAACCTCT
45751 GGGACTCCAG CCTCCCTCCC TGGCCACACA GCCCCTGGCC CTCTCCTGGT
45801 GCCATTCACC CTCAACTTCA CTATCACCAA CCTGCAGTAT GAGGAGGACA
45851 TGCGTCACCC TGGTTCCAGG AAGTTCAGCA CCACGGAGAG AGTCCTGCAG
45901 GGTCTGCTCA AGCCCTTGTT CAAGAACACC AGTGTCAGCT CTCTGTACTC
45951 TGGTTGCAGA CTGACCTTGC TCAGGCCTGA GAAGGATGGG GCAGCCACCA
46001 GAGTGGATGC TGTCTGCACC CATCGTCCTG ACCCCAAAAG CCCTGGACTG
46051 GACAGAGAGC GGCTGTACTG GAAGCTGAGC CAGCTGACCC ACGGCATCAC
46101 TGAGCTGGGC CCCTACACCC TGGACAGGCA CAGTCTCTAT GTCAATGGTT
46151 TCACCCATCA GAGCTCTATG ACGACCACCA GAACTCCTGA TACCTCCACA
46201 ATGCACCTGG CAACCTCGAG AACTCCAGCC TCCCTGTCTG ACCTACGAC
46251 CGCCAGCCCT CTCCTGGTGC TATTCACAAT TAACTTCACC ATCACTAACC
46301 TGCGGTATGA GGAGAACATG CATCACCCTG GCTCTAGAAA GTTTAACACC
46351 ACGGAGAGAG TCCTTCAGGG TCTGCTCAGG CCTGTGTTCA AGAACACCAG
46401 TGTTGGCCCT CTGTACTCTG GCTGCAGACT GACCACGCTC AGGCCCAAGA
46451 AGGATGGGGC AGCCACCAAA GTGGATGCCA TCTGCACCTA CCGCCCTGAT
46501 CCCAAAAGCC CTGGACTGGA CAGAGAGCAG CTATACTGGG AGCTGAGCCA
46551 GCTAACCCAC AGCATCACTG AGCTGGGCCC CTACACCCAG GACAGGGACA
46601 GTCTCTATGT CAATGGCTTC ACCCATCGGA GCTCTGTGCC AACCACCAGT
46651 ATTCCTGGGA CCTCTGCAGT GCACCTGGAA ACCTCTGGGA CTCCAGCCTC
46701 CCTCCCTGGC CACACAGCCC CTGGCCCTCT CCTGGTGCCA TTCACCCTCA
46751 ACTTCACTAT CACCAACCTG CAGTATGAGG AGGACATGCG TCACCCTGGT
46801 TCCAGGAAGT TCAACACCAC GGAGAGAGTC CTGCAGGGTC TGCTCAAGCC
46851 CTTGTTCAAG AGCACCAGTG TTGGCCCTCT GTACTCTGGC TGCAGACTGA
46901 CCTTGCTCAG GCCTGAAAAA CGTGGGGCAG CCACCGGCGT GGACACCATC
46951 TGCACTCACC GCCTTGACCC TCTAAACCCA GGACTGGACA GAGAGCAGCT
47001 ATACTGGGAG CTGAGCAAAC TGACCCGTGG CATCATCGAG CTGGGCCCCT
47051 ACCTCCTGGA CAGAGGCAGT CTCTATGTCA ATGGTTTCAC CCATCGGACC
47101 TCTGTGCCCA CCACCAGCAC TCCTGGGACC TCCACAGTGG ACCTTGGAAC
47151 CTCAGGGACT CCATTCTCCC TCCCAAGCCC CGCANCNNCT GNCCCTCTCC
47201 TGNTCCNTT CACCNTCAAC TTNACCATCA CCAACCTGCA NTANGNGGAN
47251 NACATGCNNC NCCCNGGNTC CAGGAAGTTC AACACCACNG AGAGGGTCCT
47301 GCAGACTCTG CTTGGTCCTA TGTTCAAGAA CACCAGTGTT GGCCTTCTGT
47351 ACTCTGGCTG CAGACTGACC TTGCTCAGGT CCGAGAAGGA TGGAGCAGCC
47401 ACTGGAGTGG ATGCCATCTG CACCCACCGT CTTGACCCCA AAAGCCCTGG
47451 AGTGGACAGG GAGCAACTAT ACTGGGAGCT GAGCCAGCTG ACCAATGGCA
```

TABLE 4-continued

Human cDNA of CA125
(SEQ ID NO: 4)

```
47501 TTAAAGAACT GGGCCCCTAC ACCCTGGACA GGAACAGTCT CTATGTCAAT
47551 GGGTTCACCC ATTGGATCCC TGTGCCCACC AGCAGCACTC CTGGGACCTC
47601 CACAGTGGAC CTTGGGTCAG GGACTCCATC CTCCCTCCCC AGCCCCACAA
47651 CTGCTGGCCC TCTCCTGGTG CCGTTCACCC TCAACTTCAC CATCACCAAC
47701 CTGAAGTACG AGGAGGACAT GCATTGCCCT GGCTCCAGGA AGTTCAACAC
47751 CACAGAGAGA GTCCTGCAGA GTCTGCTTGG TCCCATGTTC AAGAACACCA
47801 GTGTTGGCCC TCTGTACTCT GGCTGCAGAC TGACCTTGCT CAGGTCCGAG
47851 AAGGATGGAG CAGCCACTGG AGTGGATGCC ATCTGCACCC ACCGTCTTGA
47901 CCCCAAAAGC CCTGGAGTGG ACAGGGAGCA GCTATACTGG GAGCTGAGCC
47951 AGCTGACCAA TGGCATCAAA GAGCTGGGTC CCTACACCCT GGACAGAAAC
48001 AGTCTCTATG TCAATGGTTT CACCCATCAG ACCTCTGCGC CAACACCAG
48051 CACTCCTGGG ACCTCCACAG TGGACCTTGG GACCTCAGGG ACTCCATCCT
48101 CCCTCCCCAG CCCTACANCN NCTGNCCCTC TCCTGNTNCC NTTCACCNTC
48151 AACTTNACCA TCACCAACCT GCANTANGNG GANNACATGC NNCNCCCNGG
48201 NTCCAGGAAG TTCAACACCA CNGAGNGNGT NCTGCAGGGT CTGCTNNNNC
48251 CCNTNTTCAA GAACNCCAGT GTNGGCCNTC TGTACTCTGG CTGCAGACTG
48301 ACCTNNCTCA GGNCNGAGAA GNATGGNGCA GCCACTGGAN TGGATGCCAT
48351 CTGCANCCAC CNNCNTNANC CCAAAAGNCC TGGACTGNAC AGNGAGCNGC
48401 TNTACTGGGA GCTNAGCCAN CTGACCAANN NCATCNNNGA GCTGGGNCCC
48451 TACACCCTGG ACAGGNACAG TCTCTATGTC AATGGTTTCA CCCATTGGAT
48501 CCCTGTGCCC ACCAGCAGCA CTCCTGGGAC CTCCACAGTG GACCTTGGGT
48551 CAGGGACTCC ATCCTCCCTC CCCAGCCCCA CAACTGCTGG CCCTCTCCTG
48601 GTGCCGTTCA CCCTCAACTT CACCATCACC AACCTGAAGT ACGAGGAGGA
48651 CATGCATTGC CCTGGCTCCA GGAAGTTCAA CACCACAGAG AGAGTCCTGC
48701 AGAGTCTGCT TGGTCCCATG TTCAAGAACA CCAGTGTTGG CCCTCTGTAC
48751 TCTGGCTGCA GACTGACCTC GCTCAGGTCC GAGAAGGATG GAGCAGCCAC
48801 TGGAGTGGAT GCCATCTGCA CCCACCGTGT TGACCCCAAA AGCCCTGGAG
48851 TGGACAGGGA GCAGCTATAC TGGGAGCTGA GCCAGCTGAC CAATGGCATC
48901 AAAGAGCTGG GTCCCTACAC CCTGGACAGA AACAGTCTCT ATGTCAATGG
48951 TTTCACCCAT CAGACCTCTG CGCCCAACAC CAGCACTCCT GGGACCTCCA
49001 CAGTGNACNT NGGNACCTCN GGGACTCCAT CCTCCNTCCC CNGCCNCACA
49051 TCTGCTGGCC CTCTCCTGGT GCCATTCACC CTCAACTTCA CCATCACCAA
49101 CCTGCAGTAC GAGGAGGACA TGCATCACCC AGGCTCCAGG AAGTTCAACA
49151 CCACGGAGCG GGTCCTGCAG GTCTGCTTG GTCCCATGTT CAAGAACACC
49201 AGTGTCGGCC TTCTGTACTC TGGCTGCAGA CTGACCTTGC TCAGGCCTGA
49251 GAAGAATGGG GCAACCACTG GAATGGATGC CATCTGCACC CACCGTCTTG
49301 ACCCCAAAAG CCCTGGACTG NACAGNGAGC NGCTNTACTG GGAGCTNAGC
49351 CANCTGACCA ANNNCATCNN NGAGCTGGGN CCCTACACCC TGGACAGGNA
```

TABLE 4-continued

Human cDNA of CA125
(SEQ ID NO: 4)

```
49401 CAGTCTCTAT GTCAATGGTT TCACCCATCN GANCTCTGNG CCCACCACCA
49451 GCACTCCTGG GACCTCCACA GTGNACNTNG GNACCTCNGG GACTCCATCC
49501 TCCNTCCCCN GCCNCACANC NNCTGNCCCT CTCCTGNTNC CNTTCACCNT
49551 CAACTTNACC ATCACCAACC TGCANTANGN GGANNACATG CNNCNCCCNG
49601 GNTCCAGGAA GTTCAACACC ACNGAGAGGG TTCTGCAGGG TCTGCTCAAA
49651 CCCTTGTTCA GGAATAGCAG TCTGGAATAC CTCTATTCAG GCTGCAGACT
49701 AGCCTCACTC AGGCCAGAGA AGGATAGCTC AGCCATGGCA GTGGATGCCA
49751 TCTGCACACA TCGCCCTGAC CCTGAAGACC TCGGACTGGA CAGAGAGCGA
49801 CTGTACTGGG AGCTGAGCAA TCTGACAAAT GGCATCCAGG AGCTGGGCCC
49851 CTACACCCTG GACCGGAACA GTCTCTATGT CAATGGTTTC ACCCATCGAA
49901 GCTCTATGCC CACCACCAGC ACTCCTGGGA CCTCCACAGT GGATGTGGGA
49951 ACCTCAGGGA CTCCATCCTC CAGCCCCAGC CCACGACTG CTGGCCCTCT
50001 CCTGATACCA TTCACCCTCA ACTTCACCAT CACCAACCTG CAGTATGGGG
50051 AGGACATGGG TCACCCTGGC TCCAGGAAGT TCAACACCAC AGAGAGGGTC
50101 CTGCAGGGTC TGCTTGGTCC CATATTCAAG AACACCAGTG TTGGCCCTCT
50151 GTACTCTGGC TGCAGACTGA CCTCTCTCAG GTCTGAGAAG GATGGAGCAG
50201 CCACTGGAGT GGATGCCATC TGCATCCATC ATCTTGACCC CAAAAGCCCT
50251 GGACTCAACA GAGAGCGGCT GTACTGGGAG CTGAGCCAAC TGACCAATGG
50301 CATCAAAGAG CTGGGCCCCT ACACCCTGGA CAGGAACAGT CTCTATGTCA
50351 ATGGTTTCAC CCATCGGACC TCTGTGCCCA CCACCAGCAC TCCTGGGACC
50401 TCCACAGTGG ACCTTGGAAC CTCAGGGACT CCATTCTCCC TCCCAAGCCC
50451 CGCAACTGCT GGCCCTCTCC TGGTGCTGTT CACCCTCAAC TTCACCATCA
50501 CCAACCTGAA GTATGAGGAG GACATGCATC GCCCTGGCTC CAGGAAGTTC
50551 AACACCACTG AGAGGGTCCT GCAGACTCTG CTTGGTCCTA TGTTCAAGAA
50601 CACCAGTGTT GGCCTTCTGT ACTCTGGCTG CAGACTGACC TTGCTCAGGT
50651 CCGAGAAGGA TGGAGCAGCC ACTGGAGTGG ATGCCATCTG CACCCACCGT
50701 CTTGACCCCA AAAGCCCTGG ACTGNACAGN GAGCNGCTNT ACTGGGAGCT
50751 NAGCCANCTG ACCAANNNCA TCNNNGAGCT GGGNCCCTAC ACCCTGGACA
50801 GGNACAGTCT CTATGTCAAT GGTTTCACCC ATCNGANCTC TGNGCCCACC
50851 ACCAGCACTC CTGGGACCTC CACAGTGNAC NTNGGNACCT CNGGGACTCC
50901 ATCCTCCNTC CCCNGCCNCA CANCNNCTGN CCCTCTCCTG NTNCCNTTCA
50951 CCNTCAACTT NACCATCACC AACCTGCANT ANGNGGANNA CATGCNNCNC
51001 CCNGGNTCCA GGAAGTTCAA CACCACNGAG AGAGTCCTTC AGGGTCTGCT
51051 CAGGCCTGTG TTCAAGAACA CCAGTGTTGG CCCTCTGTAC TCTGGCTGCA
51101 GACTGACCTT GCTCAGGCCC AAGAAGGATG GGCAGCCAC CAAAGTGGAT
51151 GCCATCTGCA CCTACCGCCC TGATCCCAAA AGCCCTGGAC TGGACAGAGA
51201 GCAGCTATAC TGGGAGCTGA GCCAGCTAAC CCACAGCATC ACTGAGCTGG
51251 GCCCCTACAC CCAGGACAGG GACAGTCTCT ATGTCAATGG CTTCACCCAT
51301 CGGAGCTCTG TGCCAACCAC CAGTATTCCT GGGACCTCTG CAGTGCACCT
```

TABLE 4-continued

Human cDNA of CA125
(SEQ ID NO: 4)

```
51351 GGAAACCACT GGGACTCCAT CCTCCTTCCC CGGCCACACA GAGCCTGGCC

51401 CTCTCCTGAT ACCATTCACT TTCAACTTTA CCATCACCAA CCTGCGTTAT

51451 GAGGAAAACA TGCAACACCC TGGTTCCAGG AAGTTCAACA CCACGGAGAG

51501 GGTTCTGCAG GGTCTGCTCA CGCCCTTGTT CAAGAACACC AGTGTTGGCC

51551 CTCTGTACTC TGGCTGCAGA CTGACCTTGC TCAGACCTGA GAAGCAGGAG

51601 GCAGCCACTG GAGTGGACAC CATCTGTACC CACCGCGTTG ATCCCATCGG

51651 ACCTGGACTG GACAGAGAGC GGCTATACTG GGAGCTGAGC CAGCTGACCA

51701 ACAGCATCAC AGAGCTGGGA CCCTACACCC TGGATAGGGA CAGTCTCTAT

51751 GTCGATGGCT TCAACCCTTG GAGCTCTGTG CCAACCACCA GCACTCCTGG

51801 GACCTCCACA GTGCACCTGG CAACCTCTGG GACTCCATCC CCCTGCCTG

51851 GCCACACAGC CCCTGTCCCT CTCTTGATAC CATTCACCCT CAACTTTACC

51901 ATCACCGACC TGCATTATGA AGAAAACATG CAACACCCTG GTTCCAGGAA

51951 GTTCAACACC ACGGAGAGGG TTCTGCAGGG TCTGCTCAAG CCCTTGTTCA

52001 AGAGCACCAG CGTTGGCCCT CTGTACTCTG GCTGCAGACT GACCTTGCTC

52051 AGACCTGAGA ACATGGGGC AGCCACTGGA GTGGACGCCA TCTGCACCCT

52101 CCGCCTTGAT CCCACTGGTC CTGGACTGGA CAGAGAGCGG CTATACTGGG

52151 AGCTGAGCCA GCTGACCAAC AGCATCACAG AGCTGGGACC CTACACCCTG

52201 GATAGGGACA GTCTCTATGT CAATGGCTTC AACCCTTGGA GCTCTGTGCC

52251 AACCACCAGC ACTCCTGGGA CCTCCACAGT GCACCTGGCA ACCTCTGGGA

52301 CTCCATCCTC CCTGCCTGGC CACACAACTG CTGGCCCTCT CCTGGTGCCG

52351 TTCACCCTCA ACTTCACCAT CACCAACCTG AAGTACGAGG AGGACATGCA

52401 TTGCCCTGGC TCCAGGAAGT TCAACACCAC AGAGAGAGTC CTGCAGAGTC

52451 TGCATGGTCC CATGTTCAAG AACACCAGTG TTGGCCCTCT GTACTCTGGC

52501 TGCAGACTGA CCTTGCTCAG GTCCGAGAAG GATGGAGCAG CCACTGGAGT

52551 GGATGCCATC TGCACCCACC GTCTTGACCC CAAAAGCCCT GGACTGNACA

52601 GNGAGCNGCT NTACTGGGAG CTNAGCCANC TGACCAANNN CATCNNNGAG

52651 CTGGGNCCCT ACACCCTGGA CAGGNACAGT CTCTATGTCA ATGGTTTCAC

52701 CCATCNGANC TCTGNGCCCA CCACCAGCAC TCCTGGGACC TCCACAGTGN

52751 ACNTGGGNAC CTCNGGGACT CCATCCTCCN TCCCCNGCCA CACANCNNCT

52801 GNCCCTCTCC TGNTNCCNTT CACCNTCAAC TTNACCATCA CCAACCTGCA

52851 NTANGNGGAN NACATGCNNC NCCCNGGNTC CAGGAAGTTC AACACCACNG

52901 AGNGNGTNCT GCAGGGTCTG CTNNNNCCCN TNTTCAAGAA CNCCAGTGTN

52951 GGCCNTCTGT ACTCTGGCTG CAGACTGACC TNNCTCAGGN CNGAGAAGNA

53001 TGGNGCAGCC ACTGGANTGG ATGCCATCTG CANCCACCNN CNTNANCCCA

53051 AAAGNCCTGG ACTGNACAGN GAGCNGCTNT ACTGGGAGCT NAGCCANCTG

53101 ACCAACAGCA TCACAGAGCT GGGACCCTAC ACCCTGGATA GGGACAGTCT

53151 CTATGTCAAT GGTTTCACCC ATCGAAGCTC TATGCCCACC ACCAGTATTC

53201 CTGGGACCTC TGCAGTGCAC CTGGAAACCT CTGGGACTCC AGCCTCCCTC
```

TABLE 4-continued

Human cDNA of CA125
(SEQ ID NO: 4)

```
53251 CCTGGCCACA CAGCCCTGG  CCCTCTCCTG GTGCCATTCA CCCTCAACTT

53301 CACTATCACC AACCTGCAGT ATGAGGAGGA CATGCGTCAC CCTGGTTCCA

53351 GGAAGTTCAA CACCACGGAG AGAGTCCTGC AGGGTCTGCT CAAGCCCTTG

53401 TTCAAGAGCA CCAGTGTTGG CCCTCTGTAC TCTGGCTGCA GACTGACCTT

53451 GCTCAGGCCT GAAAAACGTG GGGCAGCCAC CGGCGTGGAC ACCATCTGCA

53501 CTCACCGCCT TGACCCTCTA AACCCTGGAC TGNACAGNGA GCNGCTNTAC

53551 TGGGAGCTNA GCCANCTGAC CAANNNCATC NNNGAGCTGG GNCCCTACAC

53601 CCTGGACAGG NACAGTCTCT ATGTCAATGG TTTCACCCAT CNGANCTCTG

53651 NGCCCACCAC CAGCACTCCT GGGACCTCCA CAGTGNACNT NGGNACCTCN

53701 GGGACTCCAT CCTCCNTCCC CNGCCNCACA NCNNCTGNCC CTCTCCTGNT

53751 NCCNTTCACC NTCAACTTNA CCATCACCAA CCTGCANTAN GNGGANNACA

53801 TGCNNCNCCC NGGNTCCAGG AAGTTCAACA CCACNGAGNG NGTNCTGCAG

53851 GGTCTGCTNN NNCCCNTNTT CAAGAACNCC AGTGTNGGCC NTCTGTACTC

53901 TGGCTGCAGA CTGACCTNNC TCAGGNCNGA GAAGNATGGN GCAGCCACTG

53951 GANTGGATGC CATCTGCANC CACCNNCNTN ANCCCAAAAG NCCTGGACTG

54001 NACAGNGAGC NGCTNTACTG GGAGCTNAGC CANCTGACCA ANNNCATCNN

54051 NGAGCTGGGN CCCTACACCC TGGACAGGNA CAGTCTCTAT GTCAATGGTT

54101 TTCACCCTCG GAGCTCTGTG CCAACCACCA GCACTCCTGG GACCTCCACA

54151 GTGCACCTGG CAACCTCTGG GACTCCATCC TCCCTGCCTG GCCACACAGC

54201 CCCTGTCCCT CTCTTGATAC CATTCACCCT CAACTTTACC ATCACCAACC

54251 TGCATTATGA AGAAAACATG CAACACCCTG GTTCCAGGAA GTTCAACACC

54301 ACGGAGCGGG TCCTGCAGGG TCTGCTTGGT CCCATGTTCA AGAACACAAG

54351 TGTCGGCCTT CTGTACTCTG GCTGCAGACT GACCTTGCTC AGGCCTGAGA

54401 AGAATGGGGC AGCCACTGGA ATGGATGCCA TCTGCAGCCA CCGTCTTGAC

54451 CCCAAAAGCC CTGGACTGNA CAGNGAGCNG CTNTACTGGG AGCTNAGCCA

54501 NCTGACCAAN NNCATCNNNG AGCTGGGNCC CTACACCCTG GACAGGNACA

54551 GTCTCTATGT CAATGGTTTC ACCCATCNGA NCTCTGNGCC CACCACCAGC

54601 ACTCCTGGGA CCTCCACAGT GNACNTGGN  ACCTCNGGGA CTCCATCCTC

54651 CNTCCCCNGC CNCACANCNN CTGNCCCTCT CCTGNTNCCN TTCACCNTCA

54701 ACTTNACCAT CACCAACCTG CANTANGNGG ANNACATGCN NCNCCCNGGN

54751 TCCAGGAAGT TCAACACCAC NGAGNGNGTN CTGCAGGGTC TGCTNNNNCC

54801 CNTNTTCAAG AACNCCAGTG TNGGCCNTCT GTACTCTGGC TGCAGACTGA

54851 CCTNNCTCAG GNCNGAGAAG NATGGNGCAG CCACTGGANT GGATGCCATC

54901 TGCANCCACC NNCNTNANCC CAAAAGNCCT GGACTGNACA GNGAGCNGCT

54951 NTACTGGGAG CTNAGCCANC TGACCAANNN CATCNNNGAG CTGGGNCCCT

55001 ACACCCTGGA CAGGNACAGT CTCTATGTCA ATGGTTTCAC CCATCAGAAC

55051 TCTGTGCCCA CCACCAGTAC TCCTGGGACC TCCACAGTGT ACTGGGCAAC

55101 CACTGGGACT CCATCCTCCT TCCCCGGCCA CACAGAGCCT GGCCCTCTCC

55151 TGATACCATT CACTTTCAAC TTTACCATCA CCAACCTGCA TTATGAGGAA
```

TABLE 4-continued

Human cDNA of CA125
(SEQ ID NO: 4)

```
55201 AACATGCAAC ACCCTGGTTC CAGGAAGTTC AACACCACGG AGAGGGTTCT

55251 GCAGGGTCTG CTCACGCCCT TGTTCAAGAA CACCAGTGTT GGCCCTCTGT

55301 ACTCTGGCTG CAGACTGACC TTGCTCAGAC CTGAGAAGCA GGAGGCAGCC

55351 ACTGGAGTGG ACACCATCTG TACCCACCGC GTTGATCCCA TCGGACCTGG

55401 ACTGNACAGN GAGCNGCTNT ACTGGGAGCT NAGCCANCTG ACCAANNNCA

55451 TCNNNGAGCT GGGNCCCTAC ACCCTGGACA GGNACAGTCT CTATGTCAAT

55501 GGTTTCACCC ATCNGANCTC TGNGCCCACC ACCAGCACTC CTGGGACCTC

55551 CACAGTGNAC NTNGGNACCT CNGGGACTCC ATCCTCCNTC CCCNGCCNCA

55601 CANCNNCTGN CCCTCTCCTG NTNCCNTTCA CCNTCAACTT NACCATCACC

55651 AACCTGCANT ANGNGGANNA CATGCNNCNC CCNGGNTCCA GGAAGTTCAA

55701 CACCACNGAG NGNGTNCTGC AGGGTCTGCT NNNNCCCNTN TTCAAGAACN

55751 CCAGTGTNGG CCNTCTGTAC TCTGGCTGCA GACTGACCTN NCTCAGGNCN

55801 GAGAAGNATG GNGCAGCCAC TGGANTGGAT GCCATCTGCA NCCACCNNCN

55851 TNANCCCAAA AGNCCTGGAC TGNACAGNGA GCNGCTNTAC TGGGAGCTNA

55901 GCCANCTGAC CAANNNCATC NNNGAGCTGG GNCCCTACAC CCTGGACAGG

55951 NACAGTCTCT ATGTCAATGG TTTCACCCAT CGGAGCTCTG TGCCAACCAC

56001 CAGCAGTCCT GGGACCTCCA CAGTGCACCT GGCAACCTCT GGGACTCCAT

56051 CCTCCCTGCC TGGCCACACA GCCCCTGTCC CTCTCTTGAT ACCATTCACC

56101 CTCAACTTTA CCATCACCAA CCTGCATTAT GAAGAAAACA TGCAACACCC

56151 TGGTTCCAGG AAGTTCAACA CCACGGAGAG GGTTCTGCAG GGTCTGCTCA

56201 AGCCCTTGTT CAAGAGCACC AGTGTTGGCC CTCTGTACTC TGGCTGCAGA

56251 CTGACCTTGC TCAGACCTGA GAAACATGGG GCAGCCACTG GAGTGGACGC

56301 CATCTGCACC CTCCGCCTTG ATCCCACTGG TCCTGGACTG NACAGNGAGC

56351 NGCTNTACTG GGAGCTNAGC CANCTGACCA ANNNCATCNN NGAGCTGGGN

56401 CCCTACACCC TGGACAGGNA CAGTCTCTAT GTCAATGGTT TCACCCATCN

56451 GANCTCTGNG CCCACCACCA GCACTCCTGG GACCTCCACA GTGNACNTNG

56501 GNACCTCNGG GACTCCATCC TCCNTCCCCN GCCNCACANC NNCTGNCCCT

56551 CTCCTGNTNC CNTTCACCNT CAACTTNACC ATCACCAACC TGCANTANGN

56601 GGANNACATG CNNCNCCCNG GNTCCAGGAA GTTCAACACC ACNGAGNGNG

56651 TNCTGCAGGG TCTGCTNNNN CCCNTNTTCA AGAACNCCAG TGTNGGCCNT

56701 CTGTACTCTG GCTGCAGACT GACCTNNCTC AGGNCNGAGA AGNATGGNGC

56751 AGCCACTGGA NTGGATGCCA TCTGCANCCA CCNNCNTNAN CCCAAAAGNC

56801 CTGGACTGNA CAGNGAGCNG CTNTACTGGG AGCTNAGCCA NCTGACCAAN

56851 NNCATCNNNG AGCTGGGNCC CTACACCCTG ACAGGNACA GTCTCTATGT

56901 CAATGGTTTC ACCCATCGGA CCTCTGTGCC CACCACCAGC ACTCCTGGGA

56951 CCTCCACAGT GCACCTGGCA ACCTCTGGGA CTCCATCCTC CCTGCCTGGC

57001 CACACAGCCC CTGTCCCTCT CTTGATACCA TTCACCCTCA ACTTTACCAT

57051 CACCAACCTG CAGTATGAGG AGGACATGCA TCGCCCTGGA TCTAGGAAGT
```

TABLE 4-continued

| Human cDNA of CA125 (SEQ ID NO: 4) |
|---|

```
57101 TCAACACCAC AGAGAGGGTC CTGCAGGGTC TGCTTAGTCC CATTTTCAAG
57151 AACTCCAGTG TTGGCCCTCT GTACTCTGGC TGCAGACTGA CCTCTCTCAG
57201 GCCCGAGAAG GATGGGGCAG CAACTGGAAT GGATGCTGTC TGCCTCTACC
57251 ACCCTAATCC CAAAAGACCT GGGCTGGACA GAGAGCAGCT GTACTGCGAG
57301 CTAAGCCAGC TGACCCACAA CATCACTGAG CTGGGCCCCT ACAGCCTGGA
57351 CAGGGACAGT CTCTATGTCA ATGGTTTCAC CCATCAGAAC TCTGTGCCCA
57401 CCACCAGTAC TCCTGGGACC TCCACAGTGT ACTGGGCAAC CACTGGGACT
57451 CCATCCTCCT TCCCCGGCCA CACANCNNCT GNCCCTCTCC TGNTNCCNTT
57501 CACCNTCAAC TTNACCATCA CCAACCTGCA NTANGNGGAN NACATGCNNC
57551 NCCCNGGNTC CAGGAAGTTC AACACCACNG AGNGNGTNCT GCAGGGTCTG
57601 CTNNNNCCCN TNTTCAAGAA CNCCAGTGTN GGCCNTCTGT ACTCTGGCTG
57651 CAGACTGACC TNNCTCAGGN CNGAGAAGNA TGGNGCAGCC ACTGGANTGG
57701 ATGCCATCTG CANCCACCNN CNTNANCCCA AAAGNCCTGG ACTGNACAGN
57751 GAGCNGCTNT ACTGGGAGCT NAGCCANCTG ACCAANNNCA TCNNNGAGCT
57801 GGGNCCCTAC ACCCTGGACA GGNACAGTCT CTATGTCAAT GGTTTCACCC
57851 ATTGGAGCTC TGGGCTCACC ACCAGCACTC CTTGGACTTC CACAGTTGAC
57901 CTTGGAACCT CAGGGACTCC ATCCCCGTC CCCAGCCCCA CAACTGCTGG
57951 CCCTCTCCTG GTGCCATTCA CCCTAAACTT CACCATCACC AACCTGCAGT
58001 ATGAGGAGGA CATGCATCGC CCTGGATCTA GGAAGTTCAA CGCCACAGAG
58051 AGGGTCCTGC AGGGTCTGCT TAGTCCCATA TTCAAGAACA CCAGTGTTGG
58101 CCCTCTGTAC TCTGGCTGCA GACTGACCTT GCTCAGACCT GAGAAGCAGG
58151 AGGCAGCCAC TGGAGTGGAC ACCATCTGTA CCCACCGCGT TGATCCCATC
58201 GGACCTGGAC TGNACAGNGA GCNGCTNTAC TGGGAGCTNA GCCANCTGAC
58251 CAANNNCATC NNNGAGCTGG GNCCCTACAC CCTGGACAGG NACAGTCTCT
58301 ATGTCAATGG TTTCACCCAT CNGANCTCTG NGCCCACCAC CAGCACTCCT
58351 GGGACCTCCA CAGTGNACNT NGGNACCTCN GGGACTCCAT CCTCCNTCCC
58401 CNGCCNCACA NCNNCTGNCC CTCTCCTGNT NCCNTTCACC NTCAACTTNA
58451 CCATCACCAA CCTGCANTAN GNGGANNACA TGCNNCNCCC NGGNTCCAGG
58501 AAGTTCAACA CCACNGAGNG NGTNCTGCAG GGTCTGCTNN NNCCCNTNTT
58551 CAAGAACNCC AGTGTNGGCC NTCTGTACTC TGGCTGCAGA CTGACCTNNC
58601 TCAGGNCNGA GAAGNATGGN GCAGCCACTG GANTGGATGC CATCTGCANC
58651 CACCNNCNTN ANCCCAAAAG NCCTGGACTG NACAGNGAGC NGCTNTACTG
58701 GGAGCTNAGC CANCTGACCA ANNNCATCNN NGAGCTGGGN CCCTACACCC
58751 TGGACAGGNA CAGTCTCTAT GTCAATGGTT TCACCCATCG GAGCTTTGGG
58801 CTCACCACCA GCACTCCTTG GACTTCCACA GTTGACCTTG AACCTCAGG
58851 GACTCCATCC CCCGTCCCCA GCCCCACAAC TGCTGGCCCT CCTGGTGC
58901 CATTCACCCT AAACTTCACC ATCACCAACC TGCAGTATGA GGAGGACATG
58951 CATCGCCCTG GCTCCAGGAA GTTCAACACC ACGGAGAGGG TCCTTCAGGG
59001 TCTGCTTACG CCCTTGTTCA GGAACACCAG TGTCAGCTCT CTGTACTCTG
```

TABLE 4-continued

Human cDNA of CA125
(SEQ ID NO: 4)

```
59051 GTTGCAGACT GACCTTGCTC AGGCCTGAGA AGGATGGGGC AGCCACCAGA

59101 GTGGATGCTG TCTGCACCCA TCGTCCTGAC CCCAAAAGCC CTGGACTGNA

59151 CAGNGAGCNG CTNTACTGGG AGCTNAGCCA NCTGACCAAN NNCATCNNNG

59201 AGCTGGGNCC CTACACCCTG GACAGGNACA GTCTCTATGT CAATGGTTTC

59251 ACCCATCNGA NCTCTGNGCC CACCACCAGC ACTCCTGGGA CCTCCACAGT

59301 GNACNTNGGN ACCTCNGGGA CTCCATCCTC CNTCCCCNGC CNCACANCNN

59351 CTGNCCCTCT CCTGNTNCCN TTCACCNTCA ACTTNACCAT CACCAACCTG

59401 CANTANGNGG ANNACATGCN NCNCCCNGGN TCCAGGAAGT TCAACACCAC

59451 NGAGNGNGTN CTGCAGGGTC TGCTNNNNCC CNTNTTCAAG AACNCCAGTG

59501 TNGGCCNTCT GTACTCTGGC TGCAGACTGA CCTNNCTCAG GNCNGAGAAG

59551 NATGGNGCAG CCACTGGANT GGATGCCATC TGCANCCACC NNCNTNANCC

59601 CAAAAGNCCT GGACTGNACA GNGAGCNGCT NTACTGGGAG CTNAGCCANC

59651 TGACCAANNN CATCNNNGAG CTGGGNCCCT ACACCCTGGA CAGGNACAGT

59701 CTCTATGTCA ATGGTTTCAC CCATTGGATC CCTGTGCCCA CCAGCAGCAC

59751 TCCTGGGACC TCCACAGTGG ACCTTGGGTC AGGGACTCCA TCCTCCCTCC

59801 CCAGCCCCAC AACTGCTGGC CCTCTCCTGG TACCATTCAC CCTCAACTTC

59851 ACCATCACCA ACCTGCAGTA TGGGGAGGAC ATGGGTCACC CTGGCTCCAG

59901 GAAGTTCAAC ACCACAGAGA GGGTCCTGCA GGGTCTGCTT GGTCCCATAT

59951 TCAAGAACAC CAGTGTTGGC CCTCTGTACT CTGGCTGCAG ACTGACCTCT

60001 CTCAGGTCCG AGAAGGATGG AGCAGCCACT GGAGTGGATG CCATCTGCAT

60051 CCATCATCTT GACCCCAAAA GCCCTGGACT GNACAGNGAG CNGCTNTACT

60101 GGGAGCTNAG CCANCTGACC AANNNCATCN NNGAGCTGGG NCCCTACACC

60151 CTGGACAGGN ACAGTCTCTA TGTCAATGGT TTCACCCATC NGANCTCTGN

60201 GCCCACCACC AGCACTCCTG GGACCTCCAC AGTGNACNTN GGNACCTCNG

60251 GGACTCCATC CTCCNTCCCC NGCCNCACAN CNNCTGNCCC TCTCCTGNTN

60301 CCNTTCACCN TCAACTTNAC CATCACCAAC CTGCANTANG NGGANNACAT

60351 GCNNCNCCCN GGNTCCAGGA AGTTCAACAC CACNGAGNGN GTNCTGCAGG

60401 GTCTGCTNNN NCCCNTNTTC AAGAACNCCA GTGTNGGCCN TCTGTACTCT

60451 GGCTGCAGAC TGACCTNNCT CAGGNCNGAG AAGNATGGNG CAGCCACTGG

60501 ANTGGATGCC ATCTGCANCC ACCNNCNTNA NCCCAAAAGN CCTGGACTGN

60551 ACAGNGAGCN GCTNTACTGG GAGCTNAGCC ANCTGACCAA NNNCATCNNN

60601 GAGCTGGGNC CCTACACCCT GGACAGGNAC AGTCTCTATG TCAATGGTTT

60651 CACCCATCAG ACCTTTGCGC CAACACCAG CACTCCTGGG ACCTCCACAG

60701 TGGACCTTGG GACCTCAGGG ACTCCATCCT CCCTCCCCAG CCCTACATCT

60751 GCTGGCCCTC TCCTGGTGCC ATTCACCCTC AACTTCACCA TCACCAACCT

60801 GCAGTACGAG GAGGACATGC ATCACCCAGG CTCCAGGAAG TTCAACACCA

60851 CGGAGCGGGT CCTGCAGGGT CTGCTTGGTC CCATGTTCAA GAACACCAGT

60901 GTCGGCCTTC TGTACTCTGG CTGCAGACTG ACCTTGCTCA GGCCTGAGAA
```

TABLE 4-continued

Human cDNA of CA125
(SEQ ID NO: 4)

```
60951 GAATGGGGCA GCCACCAGAG TGGATGCTGT CTGCACCCAT CGTCCTGACC

61001 CCAAAAGCCC TGGACTGNAC AGNGAGCNGC TNTACTGGGA GCTNAGCCAN

61051 CTGACCAANN NCATCNNNGA GCTGGGNCCC TACACCCTGG ACAGGNACAG

61101 TCTCTATGTC AATGGTTTCA CCCATCNGAN CTCTGNGCCC ACCACCAGCA

61151 CTCCTGGGAC CTCCACAGTG NACNTNGGNA CCTCNGGGAC TCCATCCTCC

61201 NTCCCCNGCC NCACAGCCCC TGTCCCTCTC TTGATACCAT TCACCCTCAA

61251 CTTTACCATC ACCAACCTGC ATTATGAAGA AAACATGCAA CACCCTGGTT

61301 CCAGGAAGTT CAACACCACG GAGAGGGTTC TGCAGGGTCT GCTCAAGCCC

61351 TTGTTCAAGA GCACCAGCGT TGGCCCTCTG TACTCTGGCT GCAGACTGAC

61401 CTTGCTCAGA CCTGAGAAAC ATGGGCAGC CACTGGAGTG GACGCCATCT

61451 GCACCCTCCG CCTTGATCCC ACTGGTCCTG GACTGGACAG AGAGCGGCTA

61501 TACTGGGAGC TGAGCCAGCT GACCAACAGC GTTACAGAGC TGGGCCCCTA

61551 CACCCTGGAC AGGGACAGTC TCTATGTCAA TGGCTTCACC CAGCGGAGCT

61601 CTGTGCCAAC CACCAGTATT CCTGGGACCT CTGCAGTGCA CCTGGAAACC

61651 TCTGGGACTC CAGCCTCCCT CCCTGGCCAC ACAGCCCCTG GCCCTCTCCT

61701 GGTGCCATTC ACCCTCAACT TCACTATCAC CAACCTGCAG TATGAGGTGG

61751 ACATGCGTCA CCCTGGTTCC AGGAAGTTCA ACACCACGGA GAGAGTCCTG

61801 CAGGGTCTGC TCAAGCCCTT GTTCAAGAGC ACCAGTGTTG CCCTCTGTA

61851 CTCTGGCTGC AGACTGACCT TGCTCAGGCC TGAAAAACGT GGGGCAGCCA

61901 CCGGCGTGGA CACCATCTGC ACTCACCGCC TTGACCCTCT AAACCCTGGA

61951 CTGGACAGAG AGCAGCTATA CTGGGAGCTG AGCAAACTGA CCCGTGGCAT

62001 CATCGAGCTG GGCCCCTACC TCCTGGACAG AGGCAGTCTC TATGTCAATG

62051 GTTTCACCCA TCGGAACTTT GTGCCCATCA CCAGCACTCC TGGGACCTCC

62101 ACAGTACACC TAGGAACCTC TGAAACTCCA TCCTCCCTAC CTAGACCCAT

62151 AGTGCCTGGC CCTCTCCTGG TGCCATTCAC CCTCAACTTC ACCATCACCA

62201 ACTTGCAGTA TGAGGAGGCC ATGCGACACC CTGGCTCCAG GAAGTTCAAT

62251 ACCACGGAGA GGGTCCTACA GGGTCTGCTC AGGCCCTTGT TCAAGAATAC

62301 CAGTATCGGC CCTCTGTACT CCAGCTGCAG ACTGACCTTG CTCAGGCCAG

62351 AGAAGGACAA GGCAGCCACC AGAGTGGATG CCATCTGTAC CCACCACCCT

62401 GACCCTCAAA GCCCTGGACT GAACAGAGAG CAGCTGTACT GGGAGCTGAG

62451 CCAGCTGACC ACGGCATCA CTGAGCTGGG CCCCTACACC CTGGACAGGG

62501 ACAGTCTCTA TGTCGATGGT TTCACTCATT GGAGCCCCAT ACCGACCACC

62551 AGCACTCCTG GGACCTCCAT AGTGAACCTG GGAACCTCTG GGATCCCACC

62601 TTCCCTCCCT GAAACTACAN CNNCTGNCCC TCTCCTGNTN CCNTTCACCN

62651 TCAACTTNAC CATCACCAAC CTGCANTANG NGGANNACAT GCNNCNCCCN

62701 GGNTCCAGGA AGTTCAACAC CACNGAGAGG GTTCTGCAGG GTCTGCTCAA

62751 GCCCTTGTTC AAGAGCACCA GTGTTGGCCC TCTGTATTCT GGCTGCAGAC

62801 TGACCTTGCT CAGGCCTGAG AAGGACGGAG TAGCCACCAG AGTGGACGCC

62851 ATCTGCACCC ACCGCCCTGA CCCCAAAATC CCTGGGCTAG ACAGACAGCA
```

TABLE 4-continued

Human cDNA of CA125
(SEQ ID NO: 4)

```
62901 GCTATACTGG GAGCTGAGCC AGCTGACCCA CAGCATCACT GAGCTGGGAC
62951 CCTACACCCT GGATAGGGAC AGTCTCTATG TCAATGGTTT CACCCAGCGG
63001 AGCTCTGTGC CCACCACCAG CACTCCTGGG ACTTTCACAG TACAGCCGGA
63051 AACCTCTGAG ACTCCATCAT CCCTCCCTGG CCCCACAGCC ACTGGCCCTG
63101 TCCTGCTGCC ATTCACCCTC AATTTTACCA TCACTAACCT GCAGTATGAG
63151 GAGGACATGC ATCGCCCTGG CTCCAGGAAG TTCAACACCA CGGAGAGGGT
63201 CCTTCAGGGT CTGCTTATGC CCTTGTTCAA GAACACCAGT GTCAGCTCTC
63251 TGTACTCTGG TTGCAGACTG ACCTTGCTCA GGCCTGAGAA GGATGGGGCA
63301 GCCACCAGAG TGGATGCTGT CTGCACCCAT CGTCCTGACC CCAAAAGCCC
63351 TGGACTGGAC AGAGAGCGGC TGTACTGGAA GCTGAGCCAG CTGACCCACG
63401 GCATCACTGA GCTGGGCCCC TACACCCTGG ACAGGCACAG TCTCTATGTC
63451 AATGGTTTCA CCCATCAGAG CTCTATGACG ACCACCGAAA CTCCTGATAC
63501 CTCCACAATG CACCTGGCAA CCTCGAGAAC TCCAGCCTCC CTGTCTGGAC
63551 CTACGACCGC CAGCCCTCTC CTGGTGCTAT TCACAATTAA CTTCACCATC
63601 ACTAACCTGC GGTATGAGGA GAACATGCAT CACCCTGGCT CTAGAAAGTT
63651 TAACACCACG GAGAGAGTCC TTCAGGGTCT GCTCAGGCCT GTGTTCAAGA
63701 ACACCAGTGT TGGCCCTCTG TACTCTGGCT GCAGACTGAC CTTGCTCAGG
63751 CCCAAGAAGG ATGGGGCAGC CACCAAAGTG GATGCCATCT GCACCTACCG
63801 CCCTGATCCC AAAAGCCCTG GACTGGACAG AGAGCAGCTA TACTGGGAGC
63851 TGAGCCAGCT AACCCACAGC ATCACTGAGC TGGGCCCCTA CACCCTGGAC
63901 AGGGACAGTC TCTATGTCAA TGGTTTCACA CAGCGGAGCT CTGTGCCCAC
63951 CACTAGCATT CCTGGGACCC CCACAGTGGA CCTGGGAACA TCTGGGACTC
64001 CAGTTTCTAA ACCTGGTCCC TCGGCTGCCA GCCCTCTCCT GGTGCTATTC
64051 ACTCTCAACT TCACCATCAC CAACCTGCGG TATGAGGAGA ACATGCAGCA
64101 CCCTGGCTCC AGGAAGTTCA ACACCACGGA GAGGGTCCTT CAGGGCCTGC
64151 TCAGGTCCCT GTTCAAGAGC ACCAGTGTTG GCCCTCTGTA CTCTGGCTGC
64201 AGACTGACTT TGCTCAGGCC TGAAAAGGAT GGGACAGCCA CTGGAGTGGA
64251 TGCCATCTGC ACCCACCACC CTGACCCCAA AGCCCTAGG CTGGACAGAG
64301 AGCAGCTGTA TTGGGAGCTG AGCCAGCTGA CCCACAATAT CACTGAGCTG
64351 GGCCACTATG CCCTGGACAA CGACAGCCTC TTTGTCAATG GTTTCACTCA
64401 TCGGAGCTCT GTGTCCACCA CCAGCACTCC TGGGACCCCC ACAGTGTATC
64451 TGGGAGCATC TAAGACTCCA GCCTCGATAT TTGGCCCTTC AGCTGCCAGC
64501 CATCTCCTGA TACTATTCAC CCTCAACTTC ACCATCACTA ACCTGCGGTA
64551 TGAGGAGAAC ATGTGGCCTG GCTCCAGGAA GTTCAACACT ACAGAGAGGG
64601 TCCTTCAGGG CCTGCTAAGG CCCTTGTTCA AGAACACCAG TGTTGGCCCT
64651 CTGTACTCTG GCTCCAGGCT GACCTTGCTC AGGCCAGAGA AGATGGGGA
64701 AGCCACCGGA GTGGATGCCA TCTGCACCCA CCGCCCTGAC CCCACAGGCC
64751 CTGGGCTGGA CAGAGAGCAG CTGTATTTGG AGCTGAGCCA GCTGACCCAC
```

TABLE 4-continued

| Human cDNA of CA125 (SEQ ID NO: 4) |
|---|

```
64801 AGCATCACTG AGCTGGGCCC CTACACACTG GACAGGGACA GTCTCTATGT

64851 CAATGGTTTC ACCCATCGGA GCTCTGTACC CACCACCAGC ACCGGGGTGG

64901 TCAGCGAGGA GCCATTCACA CTGAACTTCA CCATCAACAA CCTGCGCTAC

64951 ATGGCGGACA TGGGCCAACC CGGCTCCCTC AAGTTCAACA TCACAGACAA

65001 CGTCATGAAG CACCTGCTCA GTCCTTTGTT CCAGAGGAGC AGCCTGGGTG

65051 CACGGTACAC AGGCTGCAGG GTCATCGCAC TAAGGTCTGT GAAGAACGGT

65101 GCTGAGACAC GGGTGGACCT CCTCTGCACC TACCTGCAGC CCCTCAGCGG

65151 CCCAGGTCTG CCTATCAAGC AGGTGTTCCA TGAGCTGAGC CAGCAGACCC

65201 ATGGCATCAC CCGGCTGGGC CCCTACTCTC TGGACAAAGA CAGCCTCTAC

65251 CTTAACGGTT ACAATGAACC TGGTCTAGAT GAGCCTCCTA CAACTCCCAA

65301 GCCAGCCACC ACATTCCTGC CTCCTCTGTC AGAAGCCACA ACAGCCATGG

65351 GGTACCACCT GAAGACCCTC ACACTCAACT TCACCATCTC CAATCTCCAG

65401 TATTCACCAG ATATGGGCAA GGGCTCAGCT ACATTCAACT CCACCGAGGG

65451 GGTCCTTCAG CACCTGCTCA GACCCTTGTT CCAGAAGAGC AGCATGGGCC

65501 CCTTCTACTT GGGTTGCCAA CTGATCTCCC TCAGGCCTGA GAAGGATGGG

65551 GCAGCCACTG GTGTGGACAC CACCTGCACC TACCACCCTG ACCCTGTGGG

65601 CCCCGGGCTG GACATACAGC AGCTTTACTG GGAGCTGAGT CAGCTGACCC

65651 ATGGTGTCAC CCAACTGGGC TTCTATGTCC TGGACAGGGA TAGCCTCTTC

65701 ATCAATGGCT ATGCACCCCA GAATTTATCA ATCCGGGGCG AGTACCAGAT

65751 AAATTTCCAC ATTGTCAACT GGAACCTCAG TAATCCAGAC CCCACATCCT

65801 CAGAGTACAT CACCCTGCTG AGGGACATCC AGGACAAGGT CACCACACTC

65851 TACAAAGGCA GTCAACTACA TGACACATTC CGCTTCTGCC TGGTCACCAA

65901 CTTGACGATG GACTCCGTGT TGGTCACTGT CAAGGCATTG TTCTCCTCCA

65951 ATTTGGACCC CAGCCTGGTG GAGCAAGTCT TTCTAGATAA GACCCTGAAT

66001 GCCTCATTCC ATTGGCTGGG CTCCACCTAC CAGTTGGTGG ACATCCATGT

66051 GACAGAAATG GAGTCATCAG TTTATCAACC AACAAGCAGC TCCAGCACCC

66101 AGCACTTCTA CCTGAATTTC ACCATCACCA ACTACCATA TTCCCAGGAC

66151 AAAGCCCAGC CAGGCACCAC CAATTACCAG AGGAACAAAA GGAATATTGA

66201 GGATGCGCTC AACCAACTCT TCCGAAACAG CAGCATCAAG AGTTATTTTT

66251 CTGACTGTCA AGTTTCAACA TTCAGGTCTG TCCCCAACAG GCACCACACC

66301 GGGGTGGACT CCCTGTGTAA CTTCTCGCCA CTGGCTCGGA GAGTAGACAG

66351 AGTTGCCATC TATGAGGAAT TTCTGCGGAT GACCCGGAAT GGTACCCAGC

66401 TGCAGAACTT CACCCTGGAC AGGAGCAGTG TCCTTGTGGA TGGGTATTCT

66451 CCCAACAGAA ATGAGCCCTT AACTGGGAAT TCTGACCTTC CCTTCTGGGC

66501 TGTCATCCTC ATCGGCTTGG CAGGACTCCT GGGACTCATC ACATGCCTGA

66551 TCTGCGGTGT CCTGGTGACC ACCCGCCGGC GGAAGAAGGA AGGAGAATAC

66601 AACGTCCAGC AACAGTGCCC AGGCTACTAC CAGTCACACC TAGACCTGGA
```

TABLE 4-continued

Human cDNA of CA125
(SEQ ID NO: 4)

```
66651 GGATCTGCAA TGACTGGAAC TTGCCGGTGC CTGGGGTGCC TTTCCCCCAG
66701 CCAGGGTCCA AGAAGCTTG GCTGGGGCAG AAATAAACCA TATTGGTCGG
66751 AAAAAAAAAA AAAAA
```

TABLE 5

Human Protein of CA125 Molecule
(SEQ ID NO: 5)

```
   1 MLKPSGLPGS SSPTRSLMTG SRSTKATPEM DSGLTGATLS PKTSTGAIVV
  51 TEHTLPFTSP DKTLASPTSS VVGRTTQSLG VMSSALPEST SRGMTHSEQR
 101 TSPSLSPQVN GTPSRNYPAT SMVSGLSSPR TRTSSTEGNF TKEASTYTLT
 151 VETTSGPVTE KYTVPTETST TEGDSTETPW DTRYIPVKIT SPMKTFADST
 201 ASKENAPVSM TPAETTVTDS HTPGRTNPSF GTLYSSFLDL SPKGTPNSRG
 251 ETSLELILST TGYPFSSPEP GSAGHSRIST SAPLSSSASV LDNKISETSI
 301 FSGQSLTSPL SPGVPEARAS TMPNSAIPFS MTLSNAETSA ERVRSTISSL
 351 GTPSISTKQT AETILTPFHAF AETMDIPSTH IAKTLASEWL GSPGTLGGTS
 401 TSALTTTSPS TTLVSEETNT HHSTSGKETE GTLNTSMTPL ETSAPGEESE
 451 MTATLVPTLG FTTLDSKIRS PSQVSSSHPT RELRTTGSTS GRQSSSTAAH
 501 GSSDILRATT SSTSKASSWT SESTAQQFSE PQHTQWVETS PSMKTERPPA
 551 STSVAAPITT SVPSVVSGFT TLKTSSTKGI WLEETSADTL IGESTAGPTT
 601 HQFAVPTGIS MTGGSSTRGS QGTTHLLTRA TASSETSADL TLATNGVPVS
 651 VSPAVSKTAA GSSPPGGTKP SYTMVSSVIP ETSSLQSSAF REGTSLGLTP
 701 LNTRHPFSSP EPDSAGHTKI STSIPLLSSA SVLEDKVSAT STFSHHKATS
 751 SITTGTPEIS TKTKPSSAVL SSMTLSNAAT SPERVRNATS PLTHPSPSGE
 801 ETAGSVLTLS TSAETTDSPN IHPTGTLTSE SSESPSTLSL PSVSGVKTTF
 851 SSSTPSTHLF TSGEETEETS NPSVSQPETS VSRVRTTLAS TSVPTPVFPT
 901 MDTWPTRSAQ FSSSHLVSEL RATSSTSVTN STGSALPKIS HLTGTATMSQ
 951 TNRDTFNDSA APQSTTWPET SPRFKTGLPS ATTTVSTSAT SLSATVMVSK
1001 FTSPATSSME ATSIREPSTT ILTTETTNGP GSMAVASTNI PIGKGYITEG
1051 RLDTSHLPIG TTASSETSMD FTMAKESVSM SVSPSQSMDA AGSSTPGRTS
1101 QFVDTFSDDV YHLTSREITI PRDGTSSALT PQMTATHPPS PDPGSARSTW
1151 LGILSSSPSS PTPKVTMSST FSTQRVTTSM IMDTVETSRW NMPNLPSTTS
1201 LTPSNIPTSG AIGKSTLVPL DTPSPATSLE ASEGGLPTLS TYPESTNTPS
1251 IHLGAHASSE SPSTINLTMA SVVKPGSYTP LTFPSIETHI HVSTARMAYS
1301 SGSSPEMTAP GETNTGSTWD PTTYITTTDP KDTSSAQVST PHSVRTLRTT
1351 ENHPKTESAT PAAYSGSPKI SSSPNLTSPA TKAWTITDTT EHSTQLHYTK
1401 LAEKSSGFET QSAPGPVSVV IPTSPTIGSS TLELTSDVPG EPLVLAPSEQ
1451 TTITLPMATW LSTSLTEEMA STDLDISSPS SPMSTFAIFP PMSTPSHELS
1501 KSEADTSAIR NTDSTTLDQH LGIRSLGRTG DLTTVPITPL TTTWTSVIEH
1551 STQAQDTLSA TMSPTHVTQS LKDQTSIPAS ASPSHLTEVY PELGTQGRSS
```

TABLE 5-continued

Human Protein of CA125 Molecule
(SEQ ID NO: 5)

```
1601  SEATTFWKPS TDTLSREIET GPTNIQSTPP MDNTTTGSSS SGVTLGIAHL

1651  PIGTSSPAET STNMALERRS STATVSMAGT MGLLVTSAPG RSISQSLGRV

1701  SSVLSESTTE GVTDSSKGSS PRLNTQGNTA LSSSLEPSYA EGSQMSTSIP

1751  LTSSPTTPDV EFIGGSTFWT KEVTTVMTSD ISKSSARTES SSATLMSTAL

1801  GSTENTGKEK LRTASMDLPS PTPSMEVTPW ISLTLSNAPN TTDSLDLSHG

1851  VHTSSAGTLA TDRSLNTGVT RASRLENGSD TSSKSLSMGN STHTSMTDTE

1901  KSEVSSSIHP RPETSAPGAE TTLTSTPGNR AISLTLPFSS IPVEEVISTG

1951  ITSGPDINSA PMTHSPITPP TIVWTSTGTI EQSTQPLHAV SSEKVSVQTQ

2001  STPYVNSVAV SASPTHENSV SSGSSTSSPY SSASLESLDS TISRRNAITS

2051  WLWDLTTSLP TTTWPSTSLS EALSSGHSGV SNPSSTTTEF PLFSAASTSA

2101  AKQRNPETET HGPQNTAAST LNTDASSVTG LSETPVGASI SSEVPLPMAI

2151  TSRSDVSGLT SESTANPSLG TASSAGTKLT RTISLPTSES LVSFRMNKDP

2201  WTVSIPLGSH PTTNTETSIP VNSAGPPGLS TVASDVIDTP SDGAESIPTV

2251  SFSPSPDTEV TTISHFPEKT THSFRTISSL THELTSRVTP IPGDWMSSAM

2301  STKPTGASPS ITLGERRTIT SAAPTTSPIV LTASFTETST VSLDNETTVK

2351  TSDILDARKT NELPSDSSSS SDLINTSIAS STMDVTKTAS ISPTSISGMT

2401  ASSSPSLFSS DRPQVPTSTT ETNTATSPSV SSNTYSLDGG SNVGGTPSTL

2451  PPPFTITHPVE TSSALLAWSR PVRTFSTMVS TDTASGENPT SSNSVVTSVP

2501  APGTWASVGS TTDLPAMGFL KTSPAGEAHS LLASTIEPAT AFTPHLSAAV

2551  VTGSSATSEA SLLTTSESKA IHSSPQTPTT PTSGANWETS ATPESLLVVT

2601  ETSDTTLTSK ILVTDTILFS TVSTPPSKFP STGTLSGASF PTLLPDTPAI

2651  PLTATEPTSS LATSFDSTPL VTIASDSLGT VPETTLTMSE TSNGDALVLK

2701  TVSNPDRSIP GITIQGVTES PLHPSSTSPS KIVAPRNTTY EGSITVALST

2751  LPAGTTGSLV FSQSSENSET TALVDSSAGL ERASVMPLTT GSQGMASSGG

2801  IRSGSTHSTG TKTFSSLPLT MNPGEVTAMS EITTNRLTAT QSTAPKGIPV

2851  KPTSAESGLL TPVSASSSPS KAFASLTTAP PSTWGIPQST LTFEFSEVPS

2901  LDTKSASLPT PGQSLNTIPD SDASTASSSL SKSPEKNPRA RMMTSTKAIS

2951  ASSFQSTGFT ETPEGSASPS MAGHEPRVPT SGTGDPRYAS ESMSYPDPSK

3001  ASSAMTSTSL ASKLTTLFST GQAARSGSSS SPISLSTEKE TSFLSPTAST

3051  SRKTSLFLGP SMARQPNILV HLQTSALTLS PTSTLNMSQE EPPELTSSQT

3101  IAEEEGTTAE TQTLTFTPSE TPTSLLPVSS PTEPTARRKS SPETWASSIS

3151  VPAKTSLVET TDGTLVTTIK MSSQAAQGNS TWPAPAEETG TSPAGTSPGS

3201  PEVSTTLKIM SSKEPSISPE IRSTVRNSPW KTPETTVPME TTVEPVTLQS

3251  TALGSGSTSI SHLPTGTTSP TKSPTENMLA TERVSLSPSP PEAWTNLYSG

3301  TPGGTRQSLA TMSSVSLESP TARSITGTGQ QSSPELVSKT TGMEFSMWHG

3351  STGGTTGDTH VSLSTSSNIL EDPVTSPNSV SSLTDKSKHK TETWVSTTAI

3401  PSTVLNNKIM AAEQQTSRSV DEAYSSTSSW SDQTSGSDIT LGASPDVTNT

3451  LYITSTAQTT SLVSLPSGDQ GITSLTNPSG GKTSSASSVT SPSIGLETLR
```

TABLE 5-continued

Human Protein of CA125 Molecule
(SEQ ID NO: 5)

```
3501 ANVSAVKSDI APTAGHLSQT SSPAEVSILD VTTAPTPGIS TTITTMGTNS

3551 ISTTTPNPEV GMSTMDSTPA TERRTTSTEH PSTWSSTAAS DSWTVTDMTS

3601 NLKVARSPGT ISTMHTTSFL ASSTELDSMS TPHGRITVIG TSLVTPSSDA

3651 SAVKTETSTS ERTLSPSDTT ASTPISTFSR VQRMSISVPD ILSTSWTPSS

3701 TEAEDVPVSM VPTDHASTKT DPNTPLSTFL FDSLSTLDWD TGRSLSSATA

3751 TTSAPQGATT PQELTLETMI SPATSQLPFS IGHITSAVTP AAMARSSGVT

3801 FSRPDPTSKK AEQTSTQLPT TTSAHPGQVP RSAATTLDVI PHTAKTPDAT

3851 FQRQGQTALT TEARATSDSW NEKEKSTPSA PWITEMMNSV SEDTIKEVTS

3901 SSSVLKDPEY AGHKLGIWDD FIPKFGKAAH MRELPLLSPP QDKEAIHPST

3951 NTVETTGWVT SSEHASHSTI PAHSASSKLT SPVVTTSTRE QAIVSMSTTT

4001 WPESTRARTE PNSFLTIELR DVSPYMDTSS TTQTSIISSP GSTAITKGHR

4051 TEITSYKRIS SSFLAQSMRS SDSPSEAITR LSNFPAMTES GGMILAMQTS

4101 PPGATSISAP TLDTSATASW TGTPLATTQR FTYSEKTTLF SKGREDTSQP

4151 SPPCVEETSS SSSVVPIHAT TSPSNILLTS QGHSPSSTPP VTSVFLSETS

4201 GLGKTTDMSR ISLEPGTSLP PNLSSTAGEA LSTYEASRDT KAIHHSADTA

4251 VTNMEATSSE YSPIPGHTKP SKATSPLVTS HIMGDITSST SVFGSSETTE

4301 IETVSSVNQG LQERSTSQVA SSATETSTVI THVSSGDATT HVTKTQATFS

4351 SGTSISSPHQ FITSTNTFTD VSTNPSTSLI MTESSGVTIT TQTGPTGAAT

4401 QGPYLLDTST MPYLTETPLA VTPDFMQSEK TTLISKGPKD VTWTSPPSVA

4451 ETSYPSSLTP FLVTTIPPAT STLQGQHTSS PVSATSVLTS GLVKTTDMLN

4501 TSMEPVTNSP QNLNNPSNEI LATLAATTDI ETIHPSINKA VTNMGTASSA

4551 HVLHSTLPVS SEPSTATSPM VPASSMGDAL ASISIPGSET TDIEGEPTSS

4601 LTAGRKENST LQEMNSTTES NIILSNVSVG AITEATKMEV PSFDATFIPT

4651 PAQSTKFPDI FSVASSRLSN SPPMTISTHM TTTQTGSSGA TSKIPLALDT

4701 STLETSAGTP SVVTEGFAHS KITTAMNNDV KDVSQTNPPF QDEASSPSSQ

4751 APVLVTTLPS SVAFTPQWHS TSSPVSMSSV LTSSLVKTAG KVDTSLETVT

4801 SSPQSMSNTL DDISVTSAAT TDIETTHPSI NTVVTNVGTT GSAFESHSTV

4851 SAYPEPSKVT SPNVTTSTME DTTISRSIPK SSKTTRTETE TTSSLTPKLR

4901 ETSISQEITS STETSTVPYK ELTGATTEVS RTDVTSSSST SFPGPDQSTV

4951 SLDISTETNT RLSTSPIMTE SAEITITTQT GPHGATSQDT FTMDPSNTTP

5001 QAGIHSAMTH GFSQLDVTTL MSRIPQDVSW TSPPSVDKTS SPSSFLSSPA

5051 MTTPSLISST LPEDKLSSPM TSLLTSGLVK ITDILRTRLE PVTSSLPNFS

5101 STSDKILATS KDSKDTKEIF PSINTEETNV KANNSGHESH SPALADSETP

5151 KATTQMVITT TVGDPAPSTS MPVHGSSETT NIKREPTYFL TPRLRETSTS

5201 QESSFPTDTS FLLSKVPTGT ITEVSSTGVI SSSKISTPDH DKSTVPPDTF

5251 TGEIPRVFTS SIKTKSAEMT ITTQASPPES ASHSTLPLDT STTLSQGGTH

5301 STVSQGFPYS EVTTLMGMGP GNVSWMTTPP VEETSSVSSL MSSPAMTSPS

5351 PVSSTSPQSI PSSPLPVTAL PTSVLVTTTD VLGTTSPESV TSSPPNLSSI

5401 THERPATYKD TAHTEAAMHH STNTAVTNVG TSGSGHKSQS SVLADSETSK
```

TABLE 5-continued

Human Protein of CA125 Molecule
(SEQ ID NO: 5)

```
5451  ATPLMSTAST LGDTSVSTST PNISQTNQIQ TEPTASLSPR LRESSTSEKT

5501  SSTTETNTAF SYVPTGAITQ ASRTEISSSR TSISDLDRST IAPDISTGMI

5551  TRLFTSPIMT KSAEMTVTTQ TTTPGATSQG ILPWDTSTTL FQGGTHSTVS

5601  QGFPHSEITT LRSRTPGDVS WMTTPPVEET SSGFSLMSPS MTSPSPVSST

5651  SPESIPSSPL PVTALLTSVL VTTTNVLGTT SPEPVTSSPP NLSSPTQERL

5701  TTYKDTAHTE AMHASMHTNT AVANVGTSIS GHESQSSVPA DSHTSKATSP

5751  MGITFAMGDT SVYTSTPAFF ETRIQSESTS SLIPGLRDTR TSEEINTVTE

5801  TSTVLSEVPT TTTTEVSRTE VITSSRTTIS GPDHSKMSPY ISTETITRLS

5851  TFPFVTGSTE MAITNQTGPI GTISQATLTL DTSSTASWEG THSPVTQRFP

5901  HSEETTTMSR STKGVSWQSP PSVEETSSPS SPVPLPAITS HSSLYSAVSG

5951  SSPTSALPVT SLLTSGRRKT IDMLDTHSEL VTSSLPSASS FSGEILTSEA

6001  STNTETIHFS ENTAETNMGT TNSMHKLHSS VSIHSQPSGH TPPKVTGSMM

6051  EDAIVSTSTP GSPETKNVDR DSTSPLTPEL KEDSTALVMN STTESNTVFS

6101  SVSLDAATEV SRAEVTYYDP TFMPASAQST KSPDISPEAS SSHSNSPPLT

6151  ISTHKTIATQ TGPSGVTSLG QLTLDTSTIA TSAGTPSART QDFVDSETTS

6201  VMNNDLNDVL KTSPFSAEEA NSLSSQAPLL VTTSPSPVTS TLQEHSTSSL

6251  VSVTSVPTPT LAKITDMDTN LEPVTRSPQN LRNTLATSEA TTDTHTMHPS

6301  INTAMANVGT TSSPNEFYFT VSPDSDPYKA TSAVVITSTS GDSIVSTSMP

6351  RSSAMKKIES ETTFSLIFRL RETSTSQKIG SSSDTSTVFD KAFTAATTEV

6401  SRTELTSSSR TSIQGTEKPT MSPDTSTRSV TMLSTFAGLT KSEERTIATQ

6451  TGPHRATSQG TLTWDTSITT SQAGTHSAMT HGFSQLDLST LTSRVPEYIS

6501  GTSPPSVEKT SSSSSLLSLP AITSPSPVPT TLPESRPSSP VHLTSLPTSG

6551  LVKTTDMLAS VASLPPNLGS TSHKIPTTSE DIKDTEKMYP STNIAVTNVG

6601  TTTSEKESYS SVPAYSEPPK VTSPMVTSFN IRDTIVSTSM PGSSEITRIE

6651  MESTFSLAHG LKGTSTSQDP IVSTEKSAVL HKLTTGATET SRTEVASSRR

6701  TSIPGPDHST ESPDISTEVI PSLPISLGIT ESSNMTIITR TGPPLGSTSQ

6751  GTFTLDTPTT SSRAGTHSMA TQEFPHSEMT TVMNKDPEIL SWTIPPSIEK

6801  TSFSSSLMPS PAMTSPPVSS TLPKTIHTTP SPMTSLLTPS LVMTTDTLGT

6851  SPEPTTSSPP NLSSTSHVIL TTDEDTTAIE AMHPSTSTAA TNVETTCSGH

6901  GSQSSVLTDS EKTKATAPMD TTSTMGHTTV STSMSVSSET TKIKRESTYS

6951  LTPGLRETSI SQNASFSTDT SIVLSEVPTG TTAEVSRTEV TSSGRTSIPG

7001  PSQSTVLPEI STRTMTRLFA SPTMTESAEM TIPTQTGPSG STSQDTLTLD

7051  TSTTKSQAKT HSTLTQRFPH SEMTTLMSRG PGDMSWQSSP SLENPSSLPS

7101  LLSLPATTSP PPISSTLPVT ISSSPLPVTS LLTSSPVTTT DMLHTSPELV

7151  TSSPPKLSHT SDERLTTGKD TTNTEAVHPS TNTAASNVEI PSFGHESPSS

7201  ALADSETSKA TSPMFITSTQ EDTTVAISTP HFLETSRIQK ESISSLSPKL

7251  RETGSSVETS SAIETSAVLS EVSIGATTEI SRTEVTSSSR TSISGSAEST

7301  MLPEISTTRK IIKFPTSPIL AESSEMTIKT QTSPPGSTSE STFTLDTSTT
```

TABLE 5-continued

Human Protein of CA125 Molecule
(SEQ ID NO: 5)

```
7351  PSLVITHSTM  TQRLPHSEIT  TLVSRGAGDV  PRPSSLPVEE  TSPPSSQLSL

7401  SAMISPSPVS  STLPASSHSS  SASVTSPLTP  GQVKTTEVLD  ASAEPETSSP

7451  PSLSSTSVEI  LATSEVTTDT  EKIHPFPNTA  VTKVGTSSSG  HESPSSVLPD

7501  SETTKATSAM  GTISIMGDTS  VSTLTPALSN  TRKIQSEPAS  SLTTRLRETS

7551  TSEETSLATE  ANTVLSKVST  GATTEVSRTE  AISFSRTSMS  GPEQSTMSQD

7601  ISIGTIPRIS  ASSVLTESAK  MTITTQTGPS  ESTLESTLNL  NTATTPSWVE

7651  THSIVIQGFP  HPEMTTSMGR  GPGGVSWPSP  PFVKETSPPS  SPLSLPAVTS

7701  PHPVSTTFLA  HIPPSPLPVT  SLLTSGPATT  TDILGTSTEP  GTSSSSSLST

7751  TSHERLTTYK  DTAHTEAVHP  STNTGGTNVA  TTSSGYKSQS  SVLADSSPMC

7801  TTSTMGDTSV  LTSTPAFLET  RRIQTELASS  LTPGLRESSG  SEGTSSGTKM

7851  STVLSKVPTG  ATTEISKEDV  TSIPGPAQST  ISPDTSTRTV  SWFSTSPVMT

7901  ESAEITMNTH  TSPLGATTQG  TSTLDTSSTT  SLTMTHSTIS  QGFSHSQMST

7951  LMRRGPEDVS  WMSPPLLEKT  RPSFSLMSSP  ATTSPSPVSS  TLPESISSSP

8001  LPVTSLLTSG  LAKTTDMLHK  SSEPVTNSPA  NLSSTSVEIL  ATSEVTTDTE

8051  KTHPSSNRTV  TDVGTSSSGH  ESTSFVLADS  QTSKVTSPMV  ITSTMEDTSV

8101  STSTPGFFET  SRIQTEPTSS  LTLGLRKTSS  SEGTSLATEM  STVLSGVPTG

8151  ATAEVSRTEV  TSSSRTSISG  FAQLTVSPET  STETITRLPT  SSIMTESAEM

8201  MIKTQTDPPG  STPESTHTVD  ISTTPNWVET  HSTVTQRFSH  SEMTTLVSRS

8251  PGDMLWPSQS  SVEETSSASS  LLSLPATTSP  SPVSSTLVED  FPSASLPVTS

8301  LLTPGLVITT  DRMGISREPG  TSSTSNLSST  SHERLTTLED  TVDTEAMQPS

8351  THTAVTNVRT  SISGHESQSS  VLSDSETPKA  TSSMGTTYTM  GETSVSISTS

8401  DFFETSRVQI  EPTSSLTSGL  RETSSSERIS  SATEGSTVLS  EVPSGATTEV

8451  SRTEVISSRG  TSMSGPDQFT  ISPDISTEAI  TRLSTSPIMT  ESAESAITIE

8501  TGSPGATSEG  TLTLDTSTTT  FWSGTHSTAS  PGFSHSEMTT  LMSRTPGDVP

8551  WPSLPSVEEA  SSVSSSLSSP  AMTSTSFFSA  LPESISSSPH  PVTALLTLGP

8601  VKTTDMLRTS  SEPETSSPPN  LSSTSAEILA  TSEVTKDREK  IHPSSNTPVV

8651  NVGTVIYKHL  SPSSVLADLV  TTKPTSPMAT  TSTLGNTSVS  TSTPAFPETM

8701  MTQPTSSLTS  GLREISTSQE  TSSATERSAS  LSGMPTGATT  KVSRTEALSL

8751  GRTSTPGPAQ  STISPEISTE  TITRISTPLT  TTGSAEMTIT  PKTGHSGASS

8801  QGTFTLDTSS  RASWPGTHSA  ATHRSPHSGM  TTPMSRGPED  VSWPSRPSVE

8851  KTSPPSSLVS  LSAVTSPSPL  YSTPSESSHS  SPLRVTSLFT  PVMMKTTDML

8901  DTSLEPVTTS  PPSMNITSDE  SLATSKATME  TEAIQLSENT  AVTQMGTISA

8951  RQEFYSSYPG  LPEPSKVTSP  VVTSSTIKDI  VSTTIPASSE  ITRIEMESTS

9001  TLTPTPRETS  TSQEIHSATK  PSTVPYKALT  SATIEDSMTQ  VMSSSRGPSP

9051  DQSTMSQDIS  TEVITRLSTS  PIKAESTEMT  ITTQTGSPGA  TSRGTLTLDT

9101  STTFMSGTHS  TASQGFSHSQ  MTALMSRTPG  DVPWLSHPSV  EEASSASFSL

9151  SSPVMTSSSP  VSSTLPDSIH  SSSLPVTSLL  TSGLVKTTEL  LGTSSEPETS

9201  SPPNLSSTSA  EILATTEVTT  DTEKLEMTNV  VTSGYTHESP  SSVLADSVTT

9251  KATSSMGITY  PTGDTNVLTS  TPAFSDTSRI  QTKSKLSLTP  GLMETSISEE
```

TABLE 5-continued

Human Protein of CA125 Molecule
(SEQ ID NO: 5)

```
 9301 TSSATEKSTV LSSVPTGATT EVSRTEAISS SRTSIPGPAQ STMSSDTSME
 9351 TITRISTPLT RKESTDMAIT PKTGPSGATS QGTFTLDSSS TASWPGTHSA
 9401 TTQRFPQSVV TTPMSRGPED VSWPSPLSVE KNSPPSSLVS SSSVTSPSPL
 9451 YSTPSGSSHS SPVPVTSLFT SIMMKATDML DASLEPETTS APNMNITSDE
 9501 SLATSKATTE TEAIHVFENT AASHVETTSA TEELYSSSPG FSEPTKVISP
 9551 VVTSSSIRDN MVSTTMPGSS GITRIEIESM SSLTPGLRET RTSQDITSST
 9601 ETSTVLYKMS SGATPEVSRT EVMPSSRTSI PGPAQSTMSL DISDEVVTRL
 9651 STSPIMTESA EITITTQTGY SLATSQVTLP LGTSMTFLSG THSTMSQGLS
 9701 HSEMTNLMSR GPESLSWTSP RFVETTRSSS SLTSLPLTTS LSPVSSTLLD
 9751 SSPSSPLPVT SLILPGLVKT TEVLDTSSEP KTSSSPNLSS TSVEIPATSE
 9801 IMTDTEKIHP SSNTAVAKVR TSSSVHESHS SVLADSETTI TIPSMGITSA
 9851 VDDTTVFTSN PAFSETRRIP TEPTFSLTPG FRETSTSEET TSITETSAVL
 9901 YGVPTSATTE VSMTEIMSSN RTHIPDSDQS TMSPDIITEV ITRLSSSSMM
 9951 SESTQMTITT QKSSPGATAQ STLTLATTTA PLARTHSTVP PRFLHSEMTT
10001 LMSRSPENPS WKSSPFVEKT SSSSSLLSLP VTTSPSVSST LPQSIPSSSF
10051 SVTSLLTPGM VKTTDTSTEP GTSLSPNLSG TSVEILAASE VTTDTEKIHP
10101 SSSMAVTNVG TTSSGHELYS SVSIHSEPSK ATYPVGTPSS MAETSISTSM
10151 PANFETTGFE AEPFSHLTSG FRKTNMSLDT SSVTPTNTPS SPGSTHLLQS
10201 SKTDFTSSAK TSSPDWPPAS QYTEIPVDII TPFNASPSIT ESTGITSFPE
10251 SRFTMSVTES THHLSTDLLP SAETISTGTV MPSLSEAMTS FATTGVPRAI
10301 SGSGSPFSRT ESGPGDATLS TIAESLPSST PVPFSSSTFT TTDSSTIPAL
10351 HEITSSSATP YRVDTSLGTE SSTTEGRLVM VSTLDTSSQP GRTSSTPILD
10401 TRMTESVELG TVTSAYQVPS LSTRLTRTDG IMEHITKIPN EAAHRGTIRP
10451 VKGPQTSTSP ASPKGLHTGG TKRMETTTTA LKTTTTALKT TSRATLTTSV
10501 YTPTLGTLTP LNASRQMAST ILTEMMITTP YVFPDVPETT SSLATSLGAE
10551 TSTALPRTTP SVLNRESETT ASLVSRSGAE RSPVIQTLDV SSSEPDTTAS
10601 WVIHPAETIP TVSKTTPNFF HSELDTVSST ATSHGADVSS AIPTNISPSE
10651 LDALTPLVTI SGTDTSTTFP TLTKSPHETE TRTTWLTHPA ETSSTIPRTI
10701 PNFSHHESDA TPSIATSPGA ETSSAIPIMT VSPGAEDLVT SQVTSSGTDR
10751 NMTIPTLTLS PGEPKTIASL VTHPEAQTSS AIPTSTISPA VSRLVTSMVT
10801 SLAAKTSTTN RALTNSPGEP ATTVSLVTHP AQTSPTVPWT TSIFFHSKSD
10851 TTPSMTTSHG AESSSAVPTP TVSTEVPGVV TPLVTSSRAV ISTTIPILTL
10901 SPGEPETTPS MATSHGEEAS SAIPTPTVSP GVPGVVTSLV TSSRAVTSTT
10951 IPILTFSLGE PETTPSMATS HGTEAGSAVP TVLPEVPGMV TSLVASSRAV
11001 TSTTLPTLTL SPGEPETTPS MATSHGAEAS STVPTVSPEV PGVVTSLVTS
11051 SSGVNSTSIP TLILSPGELE TTPSMATSHG AEASSAVPTP TVSPGVSGVV
11101 TPLVTSSRAV TSTTIPILTL SSSEPETTPS MATSHGVEAS SAVLTVSPEV
11151 PGMVTSLVTS SRAVTSTTIP TLTISSDEPE TTTSLVTHSE AKMISAIPTL
```

TABLE 5-continued

Human Protein of CA125 Molecule
(SEQ ID NO: 5)

```
11201 AVSPTVQGLV TSLVTSSGSE TSAFSNLTVA SSQPETIDSW VAHPGTEASS

11251 VVPTLTVSTG EPFTNISLVT HPAESSSTLP RTTSRFSHSE LDTMPSTVTS

11301 PEAESSSAIS TTISPGIPGV LTSLVTSSGR DISATFPTVP ESPHESEATA

11351 SWVTHPAVTS TTVPRTTPNY SHSEPDTTPS IATSPGAEAT SDFPTITVSP

11401 DVPDMVTSQV TSSGTDTSIT IPTLTLSSGE PETTTSFITY SETHTSSAIP

11451 TLPVSPGASK MLTSLVISSG TDSTTTFPTL TETPYEPETT AIQLIHPAET

11501 NTMVPRTTPK FSHSKSDTTL PVAITSPGPE ASSAVSTTTI SPDMSDLVTS

11551 LVPSSGTDTS TTFPTLSETP YEPETTATWL THPAETSTTV SGTIPNFSHR

11601 GSDTAPSMVT SPGVDTRSGV PTTTIPPSIP GVVTSQVTSS ATDTSTAIPT

11651 LTPSPGEPET TASSATHPGT QTGFTVPIRT VPSSEPDTMA SWVTHPPQTS

11701 TPVSRTTSSF SHSSPDATPV MATSPRTEAS SAVLTTISPG APEMVTSQIT

11751 SSGAATSTTV PTLTHSPGMP ETTALLSTHP RTETSKTFPA STVFPQVSET

11801 TASLTIRPGA ETSTALPTQT TSSLFTLLVT GTSRVDLSPT ASPGVSAKTA

11851 PLSTHPGTET STMIPTSTLS LGLLETTGLL ATSSSAETST STLTLTVSPA

11901 VSGLSSASIT TDKPQTVTSW NTETSPSVTS VGPPEFSRTV TGTTMTLIPS

11951 EMPTPPKTSH GEGVSPTTIL RTTMVEATNL ATTGSSPTVA KTTTTFNTLA

12001 GSLFTPLTTP GMSTLASESV TSRTSYNHRS WISTTSSYNR RYWTPATSTP

12051 VTSTFSPGIS TSSIPSSTAA TVPFMVPFTL NFTITNLQYE EDMRHPGSRK

12101 FNATERELQG LLKPLFRNSS LEYLYSGCRL ASLRPEKDSS AMAVDAICTH

12151 RPDPEDLGLD RERLYWELSN LTNGIQELGP YTLDRNSLYV NGFTHRSSMP

12201 TTSTPGTSTV DVGTSGTPSS SPSPTAAGPL LMPFTLNFTI TNLQYEEDMR

12251 RTGSRKFNTM ESVLQGLLKP LFKNTSVGPL YSGCRLTLLR PEKDGAATGV

12301 DAICTHRLDP KSPGLNREQL YWELSKLTND IEELGPYTLD RNSLYVNGFT

12351 HQSSVSTTST PGTSTVDLRT SGTPSSLSSP TIMAAGPLLV PFTLNFTITN

12401 LQYGEDMGHP GSRKFNTTER VLQGLLGPIF KNTSVGPLYS GCRLTSLRSE

12451 KDGAATGVDA ICIHHLDPKS PGLNRERLYW ELSQLTNGIK ELGPYTLDRN

12501 SLYVNGFTHR TSVPTSSTPG TSTVDLGTSG TPFSLPSPAT AGPLLVLFTL

12551 NFTITNLKYE EDMHRPGSRK FNTTERVLQT LLGPMFKNTS VGLLYSGCRL

12601 TLLRSEKDGA ATGVDAICTH RLDPKSPGLD REQLYWELSQ LTNGIKELGP

12651 YTLDRNSLYV NGFTHWIPVP TSSTPGTSTV DLGSGTPSSL PSPTAAGPLL

12701 VPFTLNFTIT NLQYEEDMHH PGSRKFNTTE RVLQGLLGPM FKNTSVGLLY

12751 SGCRLTLLRS EKDGAATGVD AICTHRLDPK SPGVDREQLY WELSQLTNGI

12801 KELGPYTLDR NSLYVNGFTH QTSAPNTSTP GTSTVDLGTS GTPSSLPSPT

12851 SAGPLLVPFT LNFTITNLQY EEDMRHPGSR KFNTTERVLQ GLLKPLFKST

12901 SVGPLYSGCR LTLLRSEKDG AATGVDAICT HRLDPKSPGV DREQLYWELS

12951 QLTNGIKELG PYTLDRNSLY VNGFTHQTSA PNTSTPGTST VDLGTSGTPS

13001 SLPSPTSAGP LLVPFTLNFT ITNLQYEEDM HHPGSRKFNT TERVLQGLLG

13051 PMFKNTSVGL LYSGCRLTLL RPEKNGAATG MDAICSHRLD PKSPGLNREQ

13101 LYWELSQLTH GIKELGPYTL DRNSLYVNGF THRSSVAPTS TPGTSTVDLG
```

TABLE 5-continued

Human Protein of CA125 Molecule
(SEQ ID NO: 5)

```
13151 TSGTPSSLPS PTTAVPLLVP FTLNFTITNL QYGEDMRHPG SRKFNTTERV

13201 LQGLLGPLFK NSSVGPLYSG CRLISLRSEK DGAATGVDAI CTHHLNPQSP

13251 GLDREQLYWQ LSQMTNGIKE LGPYTLDRNS LYVNGFTHRS SGLTTSTPWT

13301 STVDLGTSGT PSPVPSPTTA GPLLVPFTLN FTITNLQYEE DMHRPGSRKF

13351 NATERVLQGL LSPIFKNSSV GPLYSGCRLT SLRPEKDGAA TGMDAVCLYH

13401 PNPKRPGLDR EQLYWELSQL THNITELGPY SLDRDSLYVN GFTHQNSVPT

13451 TSTPGTSTVY WATTGTPSSF PGHTEPGPLL IPFTFNFTIT NLHYEENMQH

13501 PGSRKFNTTE RVLQGLLKPL FKNTSVGPLY SGCRLTSLRP EKDGAATGMD

13551 AVCLYHPNPK RPGLDREQLY CELSQLTHNI TELGPYSLDR DSLYVNGFTH

13601 QNSVPTTSTP GTSTVYWATT GTPSSFPGHT EPGPLLIPFT FNFTITNLHY

13651 EENMQHPGSR KFNTTERVLQ GLLKPLFKNT SVGPLYSGCR LTLLRPEKHE

13701 AATGVDTICT HRVDPIGPGL DRERLYWELS QLTNSITELG PYTLDRDSLY

13751 VNGFNPRSSV PTTSTPGTST VHLATSGTPS SLPGHTAPVP LLIPFTLNFT

13801 ITNLHYEENM QHPGSRKFNT TERVLQGLLK PLFKNTSVGP LYSGCRLTLL

13851 RPEKHEAATG VDTICTHRVD PIGPGLDREX LYWELSXLTX XIXELGPYXL

13901 DRXSLYVNGF XXXXXXXXTS TPGTSXVXLX TSGTPXXXPX XTSAGPLLVP

13951 FTLNFTITNL QYEEDMHHPG SRKFNTTERV LQGLLGPMFK NTSVGLLYSG

14001 CRLTLLRPEK NGAATGMDAI CSHRLDPKSP GLDREQLYWE LSQLTHGIKE

14051 LGPYTLDRNS LYVNGFTHRS SVAPTSTPGT STVDLGTSGT PSSLPSPTTA

14101 VPLLVPFTLN FTITNLQYGE DMRHPGSRKF NTTERVLQGL LGPLFKNSSV

14151 GPLYSGCRLI SLRSEKDGAA TGVDAICTHH LNPQSPGLDR EQLYWQLSQM

14201 TNGIKELGPY TLDRNSLYVN GFTHRSSGLT TSTPWTSTVD LGTSGTPSPV

14251 PSPTTAGPLL VPFTLNFTIT NLQYEEDMHR PGSRKFNATE RVLQGLLSPI

14301 FKNSSVGPLY SGCRLTSLRP EKDGAATGMD AVCLYHPNPK RPGLDREQLY

14351 WELSQLTHNI TELGPYSLDR DSLYVNGFTH QSSMTTTRTP DTSTMHLATS

14401 RTPASLSGPT TASPLLVLFT INCTITNLQY EEDMRRTGSR KFNTMESVLQ

14451 GLLKPLFKNT SVGPLYSGCR LTLLRPKKDG AATGVDAICT HRLDPKSPGL

14501 NREQLYWELS KLTNDIEELG PYTLDRNSLY VNGFTHQSSV STTSTPGTST

14551 VDLRTSGTPS SLSSPTIMXX XPLLXPFTLN FTITNLXYEE XMXXPGSRKF

14601 NTTERVLQGL LRPLFKNTSV SSLYSGCRLT LLRPEKDGAA TRVDAACTYR

14651 PDPKSPGLDR EQLYWELSQL THSITELGPY TLDRVSLYVN GFNPRSSVPT

14701 TSTPGTSTVH LATSGTPSSL PGHTXXXPLL XPFTLNFTIT NLXYEEXMXX

14751 PGSRKFNTTE RVLQGLLKPL FRNSSLEYLY SGCRLASLRP EKDSSAMAVD

14801 AICTHRPDPE DLGLDRERLY WELSNLTNGI QELGPYTLDR NSLYVNGFTH

14851 RSSFLTTSTP WTSTVDLGTS GTPSPVPSPT TAGPLLVPFT LNFTITNLQY

14901 EEDMHRPGSR RFNTTERVLQ GLLTPLFKNT SVGPLYSGCR LTLLRPEKQE

14951 AATGVDTICT HRVDPIGPGL DRERLYWELS QLTNSITELG PYTLDRDSLY

15001 VNGFNPWSSV PTTSTPGTST VHLATSGTPS SLPGHTAPVP LLIPFTLNFT
```

TABLE 5-continued

Human Protein of CA125 Molecule
(SEQ ID NO: 5)

```
15051 ITDLHYEENM QHPGSRKFNT TERVLQGLLK PLFKSTSVGP LYSGCRLTLL

15101 RPEKHGAATG VDAICTLRLD PTGPGLDRER LYWELSQLTN SVTELGPYTL

15151 DRDSLYVNGF THRSSVPTTS IPGTSAVHLE TSGTPASLPG HTAPGPLLVP

15201 FTLNFTITNL QYEEDMRHPG SRKFSTTERV LQGLLKPLFK NTSVSSLYSG

15251 CRLTLLRPEK DGAATRVDAV CTHRPDPKSP GLDRERLYWK LSQLTHGITE

15301 LGPYTLDRHS LYVNGFTHQS SMTTTRTPDT STMHLATSRT PASLSGPTTA

15351 SPLLVLFTIN FTITNQRYEE NMHHPGSRKF NTTERVLQGL LRPVFKNTSV

15401 GPLYSGCRLT LLRPKKDGAA TKVDAICTYR PDPKSPGLDR EQLYWELSQL

15451 THSITELGPY TQDRDSLYVN GFTHRSSVPT TSIPGTSAVH LETSGTPASL

15501 PGHTAPGPLL VPFTLNFTIT NLQYEEDMRH PGSRKFNTTE RVLQGLLKPL

15551 FKSTSVGPLY SGCRLTLLRP EKRGAATGVD TICTHRLDPL NPGLDREQLY

15601 WELSKLTRGI IELGPYLLDR GSLYVNGFTH RTSVPTTSTP GTSTVDLGTS

15651 GTPFSLPSPA XXXPLLXPFT LNFTITNLXY EEXMXXPGSR KFNTTERVLQ

15701 TLLGPMFKNT SVGLLYSGCR LTLLRSEKDG AATGVDAICT HRLDPKSPGV

15751 DREQLYWELS QLTNGIKELG PYTLDRNSLY VNGFTHWIPV PTSSTPGTST

15801 VDLGSGTPSL PSSPTTAGPL LVPFTLNFTI TNLKYEEDMH CPGSRKFNTT

15851 ERVLQSLLGP MFKNTSVGPL YSGCRLTLLR SEKDGAATGV DAICTHRLDP

15901 KSPGVDREQL YWELSQLTNG IKELGPYTLD RNSLYVNGFT HQTSAPNTST

15951 PGTSTVDLGT SGTPSSLPSP TXXXPLLXPF TLNFTITNLX YEEXMXXPGS

16001 RKFNTTERVL QGLLXPXFKX TSVGXLYSGC RLTLLRXEKX XAATXVDXXC

16051 XXXXDPXXPG LDREXLYWEL SXLTXXIXEL GPYXLDRXSL YVNGFTHWIP

16101 VPTSSTPGTS TVDLGSGTPS SLPSPTTAGP LLVPFTLNFT ITNLKYEEDM

16151 HCPGSRKFNT TERVLQSLLG PMFKNTSVGP LYSGCRLTSL RSEKDGAATG

16201 VDAICTHRVD PKSPGVDREQ LYWELSQLTN GIKELGPYTL DRNSLYVNGF

16251 THQTSAPNTS TPGTSTVDLG TSGTPSSLPS PTSAGPLLVP FTLNFTITNL

16301 QYEEDMHHPG SRKFNTTERV LQGLLGPMFK NTSVGLLYSG CRLTLLRPEK

16351 NGAATGMDAI CTHRLDPKSP GLDREXLYWE LSXLTXXIXE LGPYXLDRXS

16401 LYVNGFXXXX XXXXTSTPGT SXVXLXTSGT PXXXPXXTXX XPLLXPFTLN

16451 FTITNLXYEE XMXXPGSRKF NTTERVLQGL LKPLFRNSSL EYLYSGCRLA

16501 SLRPEKDSSA MAVDAICTHR PDPEDLGLDR ERLYWELSNL TNGIQELGPY

16551 TLDRNSLYVN GFTHRSSMPT TSTPGTSTVD VGTSGTPSSS PSPTTAGPLL

16601 IPFTLNFTIT NLQYGEDMGH PGSRKFNTTE RVLQGLLGPI FKNTSVGPLY

16651 SGCRLTSLRS EKDGAATGVD AICIHHLDPK SPGLNRERLY WELSQLTNGI

16701 KELGPYTLDR NSLYVNGFTH RTSVPTTSTP GTSTVDLGTS GTPFSLPSPA

16751 TAGPLLVLFT LNFTITNLKY EEDMHRPGSR KFNTTERVLQ TLLGPMFKNT

16801 SVGLLYSGCR LTLLRSEKDG AATGVDAICT HRLDPKSPGL DREXLYWELS

16851 XLTXXIXELG PYXLDRXSLY VNGFXXXXXX XXTSTPGTSX VXLXTSGTPX

16901 XXPXXTXXXP LLXPFTLNFT ITNLXYEEXM XXPGSRKFNT TERVLQGLLR

16951 PVFKNTSVGP LYSGCRLTLL RPKKDGAATK VDAICTYRPD PKSPGLDREQ
```

TABLE 5-continued

Human Protein of CA125 Molecule
(SEQ ID NO: 5)

```
17001 LYWELSQLTH SITELGPYTQ DRDSLYVNGF THRSSVPTTS IPGTSAVHLE

17051 TTGTPSSFPG HTEPGPLLIP FTFNFTITNL RYEENMQHPG SRKFNTTERV

17101 LQGLLTPLFK NTSVGPLYSG CRLTLLRPEK QEAATGVDTI CTHRVDPIGP

17151 GLDRERLYWE LSQLTNSITE LGPYTLDRDS LYVDGFNPWS SVPTTSTPGT

17201 STVHLATSGT PSPLPGHTAP VPLLIPFTLN FTITDLHYEE NMQHPGSRKF

17251 NTTERVLQGL LKPLFKSTSV GPLYSGCRLT LLRPEKHGAA TGVDAICTLR

17301 LDPTGPGLDR ERLYWELSQL TNSITELGPY TLDRDSLYVN GFNPWSSVPT

17351 TSTPGTSTVH LATSGTPSSL PGHTTAGPLL VPFTLNFTIT NLKYEEDMHC

17401 PGSRKFNTTE RVLQSLHGPM FKNTSVGPLY SGCRLTLLRS EKDGAATGVD

17451 AICTHRLDPK SPGLDREXLY WELSXLTXXI XELGPYXLDR XSLYVNGFXX

17501 XXXXXXTSTP GTSXVXLXTS GTPXXXPXXT XXXPLLXPFT LNFTITNLXY

17551 EEXMXXPGSR KFNTTERVLQ GLLXPXFKXT SVGXLYSGCR LTLLRXEKXX

17601 AATXVDXXCX XXXDPXXPGL DREXLYWELS XLTNSITELG PYTLDRDSLY

17651 VNGFTHRSSM PTTSIPGTSA VHLETSGTPA SLPGHTAPGP LLVPFTLNFT

17701 ITNLQYEEDM RHPGSRKFNT TERVLQGLLK PLFKSTSVGP LYSGCRLTLL

17751 RPEKRGAATG VDTICTHRLD PLNPGLDREX LYWELSXLTX XIXELGPYXL

17801 DRXSLYVNGF XXXXXXXXTS TPGTSXVXLX TSGTPXXXPX XTXXXPLLXP

17851 FTLNFTITNL XYEEXMXXPG SRKFNTTERV LQGLLXPXFK XTSVGXLYSG

17901 CRLTLLRXEK XXAATXVDXX CXXXXDPXXP GLDREXLYWE LSXLTXXIXE

17951 LGPYXLDRXS LYVNGFHPRS SVPTTSTPGT STVHLATSGT PSSLPGHTAP

18001 VPLLIPFTLN FTITNLHYEE NMQHPGSRKF NTTERVLQGL LGPMFKNTSV

18051 GLLYSGCRLT LLRPEKNGAA TGMDAICSHR LDPKSPGLDR EXLYWELSXL

18101 TXXIXELGPY XLDRXSLYVN GFXXXXXXXX TSTPGTSXVX LXTSGTPXXX

18151 PXXTXXXPLL XPFTLNFTIT NLXYEEXMXX PGSRKFNTTE RVLQGLLXPX

18201 FKXTSVGXLY SGCRLTLLRX EKXXAATXVD XXCXXXXDPX XPGLDREXLY

18251 WELSXLTXXI XELGPYXLDR XSLYVNGFTH QNSVPTTSTP GTSTVYWATT

18301 GTPSSFPGHT EPGPLLIPFT FNFTITNLHY EENMQHPGSR KFNTTERVLQ

18351 GLLTPLFKNT SVGPLYSGCR LTLLRPEKQE AATGVDTICT HRVDPIGPGL

18401 DREXLYWELS XLTXXIXELG PYXLDRXSLY VNGFXXXXXX XXTSTPGTSX

18451 VXLXTSGTPX XXPXXTXXXP LLXPFTLNFT ITNLXYEEXM XXPGSRKFNT

18501 TERVLQGLLX PXFKXTSVGX LYSGCRLTLL RXEKXXAATX VDXXCXXXXD

18551 PXXPGLDREX LYWELSXLTX XIXELGPYXL DRXSLYVNGF THRSSVPTTS

18601 SPGTSTVHLA TSGTPSSLPG HTAPVPLLIP FTLNFTITNL HYEENMQHPG

18651 SRKFNTTERV LQGLLKPLFK STSVGPLYSG CRLTLLRPEK HGAATGVDAI

18701 CTLRLDPTGP GLDREXLYWE LSXLTXXIXE LGPYXLDRXS LYVNGFXXXX

18751 XXXXTSTPGT SXVXLXTSGT PXXXPXXTXX XPLLXPFTLN FTITNLXYEE

18801 XMXXPGSRKF NTTERVLQGL LXPXFKXTSV GXLYSGCRLT LLREKXXAA

18851 TXVDXXCXXX XDPXXPGLDR EXLYWELSXL TXXIXELGPY XLDRXSLYVN
```

TABLE 5-continued

Human Protein of CA125 Molecule
(SEQ ID NO: 5)

```
18901 GFTHRTSVPT TSTPGTSTVH LATSGTPSSL PGHTAPVPLL IPFTLNFTIT

18951 NLQYEEDMHR PGSRKFNTTE RVLQGLLSPI FKNSSVGPLY SGCRLTSLRP

19001 EKDGAATGMD AVCLYHPNPK RPGLDREQLY CELSQLTHNI TELGPYSLDR

19051 DSLYVNGFTH QNSVPTTSTP GTSTVYWATT GTPSSFPGHT XXXPLLXPFT

19101 LNFTITNLXY EEXMXXPGSR KFNTTERVLQ GLLXPXFKXT SVGXLYSGCR

19151 LTLLRXEKXX AATXVDXXCX XXXDPXXPGL DREXLYWELS XLTXXIXELG

19201 PYXLDRXSLY VNGFTHWSSG LTTSTPWTST VDLGTSGTPS PVPSPTTAGP

19251 LLVPFTLNFT ITNLQYEEDM HRPGSRKFNA TERVLQGLLS PIFKNTSVGP

19301 LYSGCRLTLL RPEKQEAATG VDTICTHRVD PIGPGLDREX LYWELSXLTX

19351 XIXELGPYXL DRXSLYVNGF XXXXXXXXTS TPGTSXVXLX TSGTPXXXPX

19401 XTXXXPLLXP FTLNFTITNL XYEEXMXXPG SRKFNTTERV LQGLLXPXFK

19451 XTSVGXLYSG CRLTLLRXEK XXAATXVDXX CXXXXDPXXP GLDREXLYWE

19501 LSXLTXXIXE LGPYXLDRXS LYVNGFTHRS FGLTTSTPWT STVDLGTSGT

19551 PSPVPSPTTA GPLLVPFTLN FTITNLQYEE DMHRPGSRKF NTTERVLQGL

19601 LTPLFRNTSV SSLYSGCRLT LLRPEKDGAA TRVDAVCTHR PDPKSPGLDR

19651 EXLYWELSXL TXXIXELGPY XLDRXSLYVN GFXXXXXXXX TSTPGTSXVX

19701 LXTSGTPXXX PXXTXXXPLL XPFTLNFTIT NLXYEEXMXX PGSRKFNTTE

19751 RVLQGLLXPX FKXTSVGXLY SGCRLTLLRX EKXXAATXVD XXCXXXXDPX

19801 XPGLDREXLY WELSXLTXXI XELGPYXLDR XSLYVNGFTH WIPVPTSSTP

19851 GTSTVDLGSG TPSSLPSPTT AGPLLVPFTL NFTITNLQYG EDMGHPGSRK

19901 FNTTERVLQG LLGPIFKNTS VGPLYSGCRL TSLRSEKDGA ATGVDAICIH

19951 HLDPKSPGLD REXLYWELSX LTXXIXELGP YXLDRXSLYV NGFXXXXXXX

20001 XTSTPGTSXV XLXTSGTPXX XPXXTXXXPL LXPFTLNFTI TNLXYEEXMX

20051 XPGSRKFNTT ERVLQGLLXP XFKXTSVGXL YSGCRLTLLR XEKXXAATXV

20101 DXXCXXXXDP XXPGLDREXL YWELSXLTXX IXELGPYXLD RXSLYVNGFT

20151 HQTFAPNTST PGTSTVDLGT SGTPSSLPSP TSAGPLLVPF TLNFTITNLQ

20201 YEEDMHHPGS RKFNTTERVL QGLLGPMFKN TSVGLLYSGC RLTLLRPEKN

20251 GAATRVDAVC THRPDPKSPG LDREXLYWEL SXLTXXIXEL GPYXLDRXSL

20301 YVNGFXXXXX XXXTSTPGTS XVXLXTSGTP XXXPXXTAPV PLLIPFTLNF

20351 TITNLHYEEN MQHPGSRKFN TTERVLQGLL RPLFKSTSVG PLYSGCRLTL

20401 LRPEKHGAAT GVDAICTLRL DPTGPGLDRE RLYWELSQLT NSVTELGPYT

20451 LDRDSLYVNG FTQRSSVPTT SIPGTSAVHL ETSGTPASLP GHTAPGPLLV

20501 PFTLNFTITN LQYEVDMRHP GSRKFNTTER VLQGLLKPLF KSTSVGPLYS

20551 GCRLTLLRPE KRGAATGVDT ICTHRLDPLN PGLDREQLYW ELSKLTRGII

20601 ELGPYLLDRG SLYVNGFTHR NFVPITSTPG TSTVHLGTSE TPSSLPRPIV

20651 PGPLLVPFTL NFTITNLQYE EAMRHPGSRK FNTTERVLQG LLRPLFKNTS

20701 IGPLYSSCRL TLLRPEKDKA ATRVDAICTH HPDPQSPGLN REQLYWELSQ

20751 LTHGITELGP YTLDRDSLYV DGFTHWSPIP TTSTPGTSIV NLGTSGIPPS

20801 LPETTXXXPL LXPFTLNFTI TNLXYEEXMX XPGSRKFNTT ERVLQGLLKP
```

TABLE 5-continued

Human Protein of CA125 Molecule
(SEQ ID NO: 5)

```
20851 LFKSTSVGPL YSGCRLTLLR PEKDGVATRV DAICTHRPDP KIPGLDRQQL

20901 YWELSQLTHS ITELGPYTLD RDSLYVNGFT QRSSVPTTST PGTFTVQPET

20951 SETPSSLPGP TATGPVLLPF TLNFTITNLQ YEEDMHRPGS RKFNTTERVL

21001 QGLLMPLFKN TSVSSLYSGC RLTLLRPEKD GAATRVDAVC THRPDPKSPG

21051 LDRERLYWKL SQLTHGITEL GPYTLDRHSL YVNGFTHQSS MTTTRTPDTS

21101 TMHLATSRTP ASLSGPTTAS PLLVLFTINF TITNLRYEEN MHHPGSRKFN

21151 TTERVLQGLL RPVFKNTSVG PLYSGCRLTL LRPKKDGAAT KVDAICTYRP

21201 DPKSPGLDRE QLYWELSQLT HSITELGPYT QDRDSLYNVG FTQRSSVPTT

21251 SVPGTPTVDL GTSGTPVSKP GPSAASPLLV LFTLNGTITN LRYEENMQHP

21301 GSRKFNTTER VLQGLLRSLF KSTSVGPLYS GCRLTLLRPE KDGTATGVDA

21351 ICTHHPDPKS PRLDREQLYW ELSQLTHNIT ELGHYALDND SLFVNGFTHR

21401 SSVSTTSTPG TPTVYLGASK TPASIFGPSA ASHLLILFTL NFTITNLRYE

21451 ENMWPGSRKF NTTERVLQGL LRPLFKNTSV GPLYSGSRLT LLRPEKDGEA

21501 TGVDAICTHR PDPTGPGLDR EQLYLELSQL THSITELGPY TLDRDSLYVN

21551 GFTHRSSVPT TSTGVVSEEP FTLNFTINNL RYMADMGQPG SLKFNITDNV

21601 MKHLLSPLFQ RSSLGARYTG CRVIALRSVK NGAETRVDLL CTYLQPLSGP

21651 GLPIKQVFHE LSQQTHGITR LGPYSLDKDS LYLNGYNEPG LDEPPTTPKP

21701 ATTFLPPLSE ATTAMGYHLK TLTLNFTISN LQYSPDMGKG SATFNSTEGV

21751 LQHLLRPLFQ KSSMGPFYLG CQLISLRPEK DGAATGVDTT CTYHPDPVGP

21801 GLDIQQLYWE LSQLTHGVTQ LGFYVLDRDS LFINGYAPQN LSIRGEYQIN

21851 FHIVNWNLSN PDPTSSEYIT LLRDIQDKVT TLYKGSQLHD TFRFCLVTNL

21901 TMDSVLVTVK ALFSSNLDPS LVEQVFLDKT LNASFHWLGS TYQLVDIHVT

21951 EMESSVYQPT SSSSTQHFYL NFTITNLPYS QDKAQPGTTN YQRNKRNIED

22001 ALNQLFRNSS IKSYFSDCQV STFRSVPNRH HTGVDSLCNF SPLARRVDRV

22051 AIYEEFLRMT RNGTQLQNFT LDRSSVLVDG YSPNRNEPLT GNSDLPFWAV

22101 ILIGLAGLLG LITCLICGVL VTTRRRKKEG EYNVQQQCPG YYQSHLDLED

22151 LQ
```

The sequence listing submitted with this application via EFS-WEB is an ASCII text file, named 110-018US5-seq.txt, created on May 25, 2009, with a file size of 536 kb. It is hereby incorporated by reference.

We claim:

1. An isolated nucleic acid molecule encoding residues 10,432 to 22,152 of SEQ ID NO:5 or a fragment of residues 10,432 to 22,152 of SEQ ID NO:5;

wherein the isolated nucleic acid molecule is an expression vector and is adapted to express in a cell residues 10,432 to 22,152 of SEQ ID NO:5 or a fragment of residues 10,432 to 22,152 of SEQ ID NO:5;

wherein the fragment of residues 10,432 to 22,152 of SEQ ID NO:5 is:

(a) a fragment of residues 12,070-22,152 of SEQ ID NO:5 at least 300 consecutive residues in length and comprising an antigenic fragment of one or more sequences selected from the group consisting of:

residues 12128-12148, 12284-12304, 12384-12539, 12540-12694, 12695-12850, 12851-13006, 13537-13630, 13689-13709, 13845-13865, 14001-14021, 14157-14177, 14313-14333, 14469-14489, 14627-14647, 14783-14803, 14939-14959, 15037-15192, 15193-15348, 15349-15504, 15505-15659, 15650-15815, 15816-15971, 16030-16050, 16127-16282, 16341-16361, 16497-16517, 16595-16750, 16751-16906, 16907-17062, 17121-17141, 17219-17374, 17375-17530, 17589-17609, 17687-17842, 17901-17921, 18057-18077, 18213-18233, 18369-18389, 18525-18545, 18623-18778, 18837-18857, 18993-19013, 19149-19169, 19305-19325, 19461-19481, 19560-19714, 19773-19793, 19870-20025, 20084-20104, 20240-20260, 20338-20493, and 20806-20961 of SEQ ID NO:5; or is (b) an antigenic fragment of residues 10,432-22,152 of SEQ ID NO:5 at least 150 consecutive residues in length and comprising an antigenic fragment of either residues 10,432-10563 or residues 11219-12069-of SEQ ID NO:5.

2. The isolated nucleic acid of claim 1 wherein the fragment of residues 10,432-22,152 is an antigenic fragment of residues 10,432-22,152 of SEQ ID NO:5 at least 150 consecutive residues in length and comprising an antigenic fragment of either residues 10,432-10563 or residues 11219-12069-of SEQ ID NO:5.

3. The isolated nucleic acid of claim 1 wherein the fragment of residues 10,432-22,152 is a fragment of residues 12,070-22,152 of SEQ ID NO:5 at least 300 consecutive residues in length and comprising an antigenic fragment of one or more sequences selected from the group consisting of:

(a) residues 12128-12148, 12284-12304, 12384-12539, 12540-12694, 12695-12850, 12851-13006, 13537-13630, 13689-13709, 13845-13865, 14001-14021, 14157-14177, 14313-14333, 14469-14489, 14627-14647, 14783-14803, 14939-14959, 15037-15192, 15193-15348, 15349-15504, 15505-15659, 15650-15815, 15816-15971, 16030-16050, 16127-16282, 16341-16361, 16497-16517, 16595-16750, 16751-16906, 16907-17062, 17121-17141, 17219-17374, 17375-17530, 17589-17609, 17687-17842, 17901-17921, 18057-18077, 18213-18233, 18369-18389, 18525-18545, 18623-18778, 18837-18857, 18993-19013, 19149-19169, 19305-19325, 19461-19481, 19560-19714, 19773-19793, 19870-20025, 20084-20104, 20240-20260, 20338-20493, and 20806-20961 of SEQ ID NO:5.

4. The isolated nucleic acid molecule of claim 3 wherein the fragment of residues 10,432-22,152 of SEQ ID NO:5 is a fragment of residues 12,070-22,152 of SEQ ID NO:5 at least 450 consecutive residues in length.

5. The isolated nucleic acid molecule of claim 3 wherein the fragment of residues 10,432-22,152 of SEQ ID NO:5 is a fragment of residues 12,070-21,720 of SEQ ID NO:5 at least 300 consecutive residues in length.

6. An isolated nucleic acid molecule encoding CA125 (SEQ ID NO:5) or a fragment thereof;
   wherein the isolated nucleic acid molecule is an expression vector and is adapted to express in a cell CA125 (SEQ ID NO:5) or a fragment thereof;
   wherein the fragment thereof is an antigenic fragment of a sequence selected from the group consisting of residues 1-563, 654-1317, 1803-2095, 3846-6980, 7053-7531, and 7629-8408 of SEQ ID NO:5.

7. The isolated nucleic acid of claim 6 wherein the fragment thereof is an antigenic fragment of residues 312-399 of SEQ ID NO:5.

* * * * *

SEQUENCE LISTING

```
<160> NUMBER OF SEQ ID NOS: 7

<210> SEQ ID NO 1
<211> LENGTH: 57082
<212> TYPE: DNA
<213> ORGANISM: Homo sapiens
<220> FEATURE:
<221> NAME/KEY: misc_feature
<222> LOCATION: (2205)..(11679)
<223> OTHER INFORMATION: Exon 1
<220> FEATURE:
<221> NAME/KEY: misc_feature
```

```
<222> LOCATION: (13464)..(13570)
<223> OTHER INFORMATION: Exon 2
<220> FEATURE:
<221> NAME/KEY: misc_feature
<222> LOCATION: (16177)..(34419)
<223> OTHER INFORMATION: Exon 3
<220> FEATURE:
<221> NAME/KEY: misc_feature
<222> LOCATION: (34420)..(34534)
<223> OTHER INFORMATION: n is a, c, g, or t
<220> FEATURE:
<221> NAME/KEY: misc_feature
<222> LOCATION: (34575)..(38024)
<223> OTHER INFORMATION: Exon 4
<220> FEATURE:
<221> NAME/KEY: misc_feature
<222> LOCATION: (38689)..(38800)
<223> OTHER INFORMATION: Exon 5
<220> FEATURE:
<221> NAME/KEY: misc_feature
<222> LOCATION: (39715)..(39771)
<223> OTHER INFORMATION: n is a, c, g, or t
<220> FEATURE:
<221> NAME/KEY: misc_feature
<222> LOCATION: (40578)..(45257)
<223> OTHER INFORMATION: Exon 6
<220> FEATURE:
<221> NAME/KEY: misc_feature
<222> LOCATION: (47360)..(47395)
<223> OTHER INFORMATION: Exon 7
<220> FEATURE:
<221> NAME/KEY: misc_feature
<222> LOCATION: (52407)..(52442)
<223> OTHER INFORMATION: Exon 8
<220> FEATURE:
<221> NAME/KEY: misc_feature
<222> LOCATION: (52686)..(52744)
<223> OTHER INFORMATION: Exon 9

<400> SEQUENCE: 1
ggtgcgcacc actatgtctg gctaattttt gtattttttt gtagagacat ggtttcacca      60
tgttggccag gctggtctcg aattcctgac ttcaagtaat ccaccccacct cagcctccca    120 aagtgctggg attacaagca tgagccacca tgcatggcct aaagcttctt ttaaagccac    180
caagtccctt cccatgttag cccactaatc catgggttag tcatgaatgg attaatctat    240
tcatacggac agagccctca tcacccaatc acctcttaaa ggcccaccct ctcaatactg    300
ccacactggg gattaagttt caacagagtt ttggagggga cattcaaatc atagtaatgc    360
ccaaagtgaa aaatcttccc tgcactttc cctcaacaaa aacagccaga gatagtgagc      420
tgccaggaaa ttcttttttt tttcctcttc tgtcctaaat cagcatcgct agacctttac    480
atgattcaac ctcatcttct tcaccctctg ggtcatgaaa ttttatttat ttatttatta    540
ttttcttggg acagactctg gctctgtcgc ccaggctgaa gtgcagtggt gtgatcttgg    600
ctcactgcaa cctccgcctc ccgggttcaa gcgattctcc tgcctcagcc tcctgagtag    660
ctgggattac aggtgggcgc caccacaccc agctaatttt ttgtattttt agtagagatg    720
gggtttcacc atattagcca ggatggtctc catctcttga cctcgtgatc tgcccacctc    780
agcctcccaa aatgctggga ttacaggcat gagacaccac gcccagcagg ccagggtcat    840
gagattttaa tcaagagcaa cttccactga ttcctgagag tgcatctgtg ggcccctgct    900
ctgatctgaa cagaagtgcc gtgtcttctc tgacctccac ttctcaattc aagagcctta    960
gtatctgcca gtatcacaca ctgagcatta gctccatctc atggggtgt aggtaggggc    1020 tctatctgca tctttctttc ttttttttctt tctttccctt cctcccttcc tcactccctc    1080
ggtcctctct ttctttcctt ttctttcttc cttcctccct tcctcccctcc ctccctctct    1140
```

```
ctttctctct ttctttcttt ccttctttct ttcttctct cttccttccc tccctccctc  1200
cttccttcct ttctctttct ttctctttct ttcttttttt ccttccttcc ttccttcttt  1260
ctctttctct ccctcccttc cttccttcct tccttccttc cttcctttct ttctttcttt  1320
ctttctttct ttctttcttt ctttctttct ttctttcttc cttccttcct tccttccttc  1380
cttccttcct tccttccttt cttttctttc tttctctttc tttttgagac agagctctta  1440
ttacccatgc tggagtgcag tggtgtgacc ttggcttact gcaacatctg cctcctaggg  1500
tcaagtgatt ctcctgcctc agcctcctaa gtagctggga ttacagacac atgccaccac  1560
acccaatatt tatttttatt aaattttttt ttaaaattat ttttaaaaaa ttaaaaataa  1620
ttttgtattt ttagtagaga cggggtttct ccatgttggt caggctgatc tcaaactccc  1680
aacctcaggt gatcctccca cctcacctcc caaagtgctg ggattacagg catgagccac  1740
cgtgcccagc ctggttcctg gtttctaaga catcacacac acacacacac acacacacac  1800
acactcacac actcagagag agagagagag agaggatcat taagacatga tacactaaga  1860
aattctattc tgcagacact gagaatccgt taaaagtttt gaagggaaga attgagatca  1920
tcaggtgttt atttgaggaa attgtctgtg gttgaactat cctttccttt ctctccctga  1980
gatttggtct tctcaattag aagcgttgca caattccccc aacctccata catacggcag  2040
ctcttctaga cacaggtttt cccaggtcaa atgcggggac cccagccata tctcccaccc  2100
tgagaaattt tggagtttca gggagctcag aagctctgca gaggccaccc tctctgaggg  2160
gattcttctt agacctccat ccagaggcaa atgttgacct gtccatgctg aaaccctcag  2220
gccttcctgg gtcatcttct cccacccgct ccttgatgac agggagcagg agcactaaag  2280
ccacaccaga aatggattca ggactgacag gagccacctt gtcacctaag acatctacag  2340
gtgcaatcgt ggtgacagaa catactctgc cctttacttc cccagataag accttggcca  2400
gtcctacatc ttcggttgtg ggaagaacca cccagtcttt gggggtgatg tcctctgctc  2460
tccctgagtc aacctctaga ggaatgcaca actccgagca agaaccagc ccatcgctga  2520
gtccccaggt caatggaact ccctctagga actaccctgc tacaagcatg gtttcaggat  2580
tgagttcccc aaggaccagg accagttcca cagaaggaaa ttttaccaaa gaagcatcta  2640
catacacact cactgtagag accacaagtg gcccagtcac tgagaagtac acagtcccca  2700
ctgagacctc aacaactgaa ggtgacagca cagagacccc ctgggacaca agatatattc  2760
ctgtaaaaat cacatctcca atgaaaacat ttgcagattc aactgcatcc aaggaaaatg  2820
ccccagtgtc tatgactcca gctgagacca cagttactga ctcacatact ccaggaagga  2880
caaacccatc atttgggaca ctttattctt ccttccttga cctatcacct aaagggaccc  2940
caaattccag aggtgaaaca agcctggaac tgattctatc aaccactgga tatcccttct  3000
cctctcctga acctggctct gcaggacaca gcagaataag taccagtgcg cctttgtcat  3060
catctgcttc agttctcgat aataaaatat cagagaccag catattctca ggccagagtc  3120
tcacctcccc tctgtctcct gggtgcccg aggccagagc cagcacaatg cccaactcag  3180
ctatcccttt ttccatgaca ctaagcaatg cagaaacaag tgccgaaagg gtcagaagca  3240
caatttcctc tctggggact ccatcaatat ccacaaagca gacagcagag actatcctta  3300
ccttccatgc cttcgctgag accatggata tacccagcac ccacatagcc aagactttgg  3360
cttcagaatg gttgggaagt ccaggtaccc ttggtggcac cagcacttca gcgctgacaa  3420
ccacatctcc atctaccact ttagtctcag aggagaccaa cacccatcac tccacgagtg  3480
gaaaggaaac agaaggaact ttgaatacat ctatgactcc acttgagacc tctgctcctg  3540
```

```
gagaagagtc cgaaatgact gccaccttgg tccccactct aggttttaca actcttgaca   3600
gcaagatcag aagtccatct caggtctctt catcccaccc aacaagagag ctcagaacca   3660
caggcagcac ctctgggagg cagagttcca gcacagctgc ccacgggagc tctgacatcc   3720
tgagggcaac cacttccagc acctcaaaag catcatcatg gaccagtgaa agcacagctc   3780
agcaatttag tgaaccccag cacacacagt gggtggagac aagtcctagc atgaaaacag   3840
agagaccccc agcatcaacc agtgtggcag cccctatcac cacttctgtt ccctcagtgg   3900
tctctggctt caccaccctg aagaccagct ccacaaaagg gatttggctt gaagaaacat   3960
ctgcagacac actcatcgga gaatccacag ctggcccaac cacccatcag tttgctgttc   4020
ccactgggat ttcaatgaca ggaggcagca gcaccagggg aagccagggc acaacccacc   4080
tactcaccag agccacagca tcatctgaga catccgcaga tttgactctg gccacgaacg   4140
gtgtcccagt ctccgtgtct ccagcagtga gcaagacggc tgctggctca agtcctccag   4200
gagggacaaa gccatcatat acaatggttt cttctgtcat ccctgagaca tcatctctac   4260
agtcctcagc tttcagggaa ggaaccagcc tgggactgac tccattaaac actagacatc   4320
ccttctcttc ccctgaacca gactctgcag gacacaccaa gataagcacc agcattcctc   4380
tgttgtcatc tgcttcagtt cttgaggata aagtgtcagc gaccagcaca ttctcacacc   4440
acaaagccac ctcatctatt accacaggga ctcctgaaat ctcaacaaag acaaagccca   4500
gctcagccgt tctttcctcc atgaccctaa gcaatgcagc aacaagtcct gaaagagtca   4560
gaaatgcaac ttcccctctg actcatccat ctccatcagg ggaagagaca gcagggagtg   4620
tcctcactct cagcacctct gctgagacta cagactcacc taacatccac ccaactggga   4680
cactgacttc agaatcgtca gagagtccta gcactctcag cctcccaagt gtctctggag   4740
tcaaaaccac attttcttca tctactcctt ccactcatct atttactagt ggagaagaaa   4800
cagaggaaac ttcgaatcca tctgtgtctc aacctgagac ttctgtttcc agagtaagga   4860
ccaccttggc cagcacctct gtccctaccc cagtattccc caccatggac acctggccta   4920
cacgttcagc tcagttctct tcatcccacc tagtgagtga gctcagagct acgagcagta   4980
cctcagttac aaactcaact ggttcagctc ttcctaaaat atctcacctc actgggacgg   5040
caacaatgtc acagaccaat agagacacgt taatgactc tgctgcaccc caaagcacaa   5100
cttggccaga gactagtccc agattcaaga cagggttacc ttcagcaaca accactgttt   5160
caacctctgc cacttctctc tctgctactg taatggtctc taaattcact tctccagcaa   5220
ctagttccat ggaagcaact tctatcaggg aaccatcaac aaccatcctc acaacagaga   5280
ccacgaatgg cccaggctct atggctgtgg cttctaccaa catcccaatt ggaaagggct   5340
acattactga aggaagattg gacacaagcc atctgcccat tggaaccaca gcttcctctg   5400
agacatctat ggatttttacc atggccaaag aaagtgtctc aatgtcagta tctccatctc   5460
agtccatgga tgctgctggc tcaagcactc aggaaggac aagccaattc gttgacacat   5520
tttctgatga tgtctatcat ttaacatcca gagaaattac aatacctaga gatggaacaa   5580
gctcagctct gactccacaa atgactgcaa ctcaccctcc atctcctgat cctggctctg   5640
ctagaagcac ctggcttggc atcttgtcct catctccttc ttctcctact cccaaagtca   5700
caatgagctc cacattttca actcagagag tcaccacaag catgataatg gacacagttg   5760
aaactagtcg gtggaacatg cccaacttac cttccacgac ttccttgaca ccaagtaata   5820
ttccaacaag tggtgccata ggaaaaagca ccctggttcc cttggacact ccatctccag   5880
```

```
ccacatcatt ggaggcatca gaaggggac ttccacccct cagcacctac cctgaatcaa      5940
caaacacacc cagcatccac ctcggagcac acgctagttc agaaagtcca agcaccatca      6000
aacttaccat ggcttcagta gtaaaacctg gctcttacac acctctcacc ttcccctcaa      6060
tagagaccca cattcatgta tcaacagcca gaatggctta ctcttctggg tcttcacctg      6120
agatgacagc tcctggagag actaacactg gtagtacctg ggaccccacc acctacatca      6180
ccactacgga tcctaaggat acaagttcag ctcaggtctc tacacccac tcagtgagga       6240 cactcagaac cacagaaaac catccaaaga cagagtccgc caccccagct gcttactctg      6300
gaagtcctaa aatctcaagt tcacccaatc tcaccagtcc ggccacaaaa gcatggacca     6360
tcacagacac aactgaacac tccactcaat tacattacac aaaattggca gaaaaatcat     6420
ctggatttga gacacagtca gctccaggac ctgtctctgt agtaatccct acctccccta     6480
ccattggaag cagcacattg gaactaactt ctgatgtccc aggggaaccc ctggtccttg      6540
ctcccagtga gcagaccaca atcactctcc ccatggcaac atggctgagt accagtttga     6600
cagaggaaat ggcttcaaca gaccttgata tttcaagtcc aagttcaccc atgagtacat     6660
ttgctatttt tccacctatg tccacacctt ctcatgaact ttcaaagtca gaggcagata    6720
ccagtgccat tagaaataca gattcaacaa cgttggatca gcacctagga atcaggagtt    6780
tgggcagaac tggggactta acaactgttc ctatcaccc actgacaacc acgtggacca    6840
gtgtgattga acactcaaca caagcacagg acacccttc tgcaacgatg agtcctactc     6900
acgtgacaca gtcactcaaa gatcaaacat ctataccagc ctcagcatcc ccttcccatc    6960
ttactgaagt ctaccctgag ctcgggacac aagggagaag ctcctctgag gcaaccactt    7020
tttggaaacc atctacagac acactgtcca gagagattga gactggccca acaaacattc    7080
aatccactcc acccatggac aacacaacaa cagggagcag tagtagtgga gtcaccctgg    7140
gcatagccca ccttcccata ggaacatcct ccccagctga gacatccaca aacatggcac    7200
tggaaagaag aagttctaca gccactgtct ctatggctgg acaatggga ctccttgtta     7260 ctagtgctcc aggaagaagc atcagccagt cattaggaag agtttcctct gtcctttctg    7320
agtcaactac tgaaggagtc acagattcta gtaaggaag cagcccaagg ctgaacacac     7380
agggaaatac agctctctcc tcctctcttg aacccagcta tgctgaagga agccagatga    7440
gcacaagcat ccctctaacc tcatctccta caactcctga tgtggaattc ataggggca     7500 gcacattttg gaccaaggag gtcaccacag ttatgacctc agacatctcc aagtcttcag    7560
caaggacaga gtccagctca gctaccctta tgtccacagc tttgggaagc actgaaaata    7620
caggaaaaga aaaactcaga actgcctcta tggatcttcc atctccaact ccatcaatgg    7680
aggtgacacc atggatttct ctcactctca gtaatgcccc caataccaca gattcacttg    7740
acctcagcca tggggtgcac accagctctg cagggacttt ggccactgac aggtcattga    7800
atactggtgt cactagagcc tccagattgg aaaacggctc tgatacctct tctaagtccc    7860
tgtctatggg aaacagcact cacacttcca tgacttacac agagaagagt gaagtgtctt    7920
cttcaatcca tccccgacct gagacctcag ctcctggagc agagaccact ttgacttcca    7980
ctcctggaaa cagggccata agcttaacat tgccttttc atccattcca gtggaagaag    8040
tcatttctac aggcataacc tcaggaccag acatcaactc agcacccatg acacattctc     8100
ccatcacccc accaacaatt gtatggacca gtacaggcac aattgaacag tccactcaac     8160
cactacatgc agtttcttca gaaaagttt ctgtgcagac acagtcaact ccatatgtca      8220
actctgtggc agtgtctgct tcccctaccc atgagaattc agtctcttct ggaagcagca    8280
```

```
catcctctcc atattcctca gcctcacttg aatccttgga ttccacaatc agtaggagga   8340
atgcaatcac ttcctggcta tgggacctca ctacatctct ccccactaca acttggccaa   8400
gtactagttt atctgaggca ctgtcctcag gccattctgg ggtttcaaac ccaagttcaa   8460
ctacgactga atttccactc ttttcagctg catccacatc tgctgctaag caaagaaatc   8520
cagaaacaga gacccatggt ccccagaata cagccgcgag tactttgaac actgatgcat   8580
cctcggtcac aggtctttct gagactcctg tgggggcaag tatcagctct gaagtccctc   8640
ttccaatggc cataacttct agatcagatg tttctggcct tacatctgag agtactgcta   8700
acccgagttt aggcacagcc tcttcagcag ggaccaaatt aactaggaca atatccctgc   8760
ccacttcaga gtctttggtt tcctttagaa tgaacaagga tccatggaca gtgtcaatcc   8820
ctttggggtc ccatccaact actaatacag aaacaagcat cccagtaaac agcgcaggtc   8880
cacctggctt gtccacagta gcatcagatg taattgacac accttcagat ggggctgaga   8940
gtattcccac tgtctccttt tcccctcccc tgatactga agtgacaact atctcacatt   9000
tcccagaaaa gacaactcat tcatttagaa ccatttcatc tctcactcat gagttgactt   9060
caagagtgac acctattcct ggggattgga tgagttcagc tatgtctaca aagcccacag   9120
gagccagtcc ctccattaca ctgggagaga aaggacaat cacctctgct gctccaacca   9180
cttcccccat agttctcact gctagtttca cagagaccag cacagtttca ctggataatg   9240
aaactacagt aaaaacctca gatatccttg acgcacggaa aacaaatgag ctcccctcag   9300
atagcagttc ttcttctgat ctgatcaaca cctccatagc ttcttcaact atggatgtca   9360
ctaaaacagc ctccatcagt cccactagca tctcaggaat gacagcaagt tcctcccat   9420 ctctcttctc ttcagataga ccccaggttc ccacatctac aacagagaca aatacagcca   9480
cctctccatc tgtttccagt aacacctatt ctcttgatgg gggctccaat gtgggtggca   9540
ctccatccac tttaccaccc tttacaatca cccaccctgt cgagacaagc tcggccctat   9600
tagcctggtc tagaccagta agaactttca gcaccatggt cagcactgac actgcctccg   9660
gagaaaatcc tacctctagc aattctgtgg tgacttctgt tccagcacca ggtacatgga   9720
ccagtgtagg cagtactact gacttacctg ccatgggctt tctcaagaca agtcctgcag   9780
gagaggcaca ctcacttcta gcatcaacta ttgaaccagc cactgccttc actccccatc   9840
tctcagcagc agtggtcact ggatccagtg ctacatcaga agccagtctt ctcactacga   9900
gtgaaagcaa agccattcat tcttccaccac agaccccaac tacacccacc tctggagcaa   9960
actgggaaac ttcagctact cctgagagcc ttttggtagt cactgagact tcagacacaa  10020
cacttacctc aaagatttgg gtcacagata ccatcttgtt ttcaactgtg tccacgccac  10080
cttctaaatt tccaagtacg gggactctgt ctggagcttc cttccctact ttactcccgg  10140
acactccagc catccctctc actgccactg agccaacaag ttcattagct acatccttg  10200 attccacccc actggtgact atagcttcgg atagtcttgg cacagtccca gagactaccc  10260
tgaccatgtc agagacctca aatggtgatg cactggttct taagacagta agtaacccag  10320
ataggagcat ccctggaatc actatccaag gagtaacaga aagtccactc catccttctt  10380
ccacttcccc ctctaagatt gttgctccac ggaatacaac ctatgaaggt tcgatcacag  10440
tggcactttc tactttgcct gcgggaacta ctggttccct tgtattcagt cagagttctg  10500
aaaactcaga gacaacggct ttggtagact catcagctgg gcttgagagg gcatctgtga  10560
tgccactaac cacaggaagc cagggtatgg ctagctctgg aggaatcaga agtgggtcca  10620
```

```
ctcactcaac tggaaccaaa acattttctt ctctccctct gaccatgaac ccaggtgagg   10680
ttacagccat gtctgaaatc accacgaaca gactgacagc tactcaatca acagcaccca   10740
aagggatacc tgtgaagccc accagtgctg agtcaggcct cctaacacct gtctctgcct   10800
cctcaagccc atcaaaggcc tttgcctcac tgactacagc tcccccaact tgggggatcc   10860
cacagtctac cttgacattt gagttttctg aggtcccaag tttggatact aagtccgctt   10920
ctttaccaac tcctggacag tccctgaaca ccattccaga ctcagatgca agcacagcat   10980
cttcctcact gtccaagtct ccagaaaaaa acccaagggc aaggatgatg acttccacaa   11040
aggccataag tgcaagctca tttcaatcaa caggttttac tgaaacccct gagggatctg   11100 cctcccttc tatggcaggg catgaaccca gagtccccac ttcaggaaca ggggacccta   11160
gatatgcctc agagagcatg tcttatccag acccaagcaa ggcatcatca gctatgacat   11220
cgacctctct tgcatcaaaa ctcacaactc tcttcagcac aggtcaagca gcaaggtctg   11280
gttctagttc ctctcccata agcctatcca ctgagaaaga aacaagcttc ctttccccca   11340
ctgcatccac ctcagaaaag acttcactat ttcttgggcc ttccatggca aggcagccca   11400
acatattggt gcatcttcag acttcagctc tgacactttc tccaacatcc actctaaata   11460
tgtcccagga ggagcctcct gagttaacct caagccagac cattgcagaa gaagagggaa   11520
caacagctga aacacagacg ttaaccttca caccatctga accccaaca tccttgttac   11580 ctgtctcttc tcccacagaa cccacagcca gaagaaagag ttctccagaa acatgggcaa   11640
gctctatttc agttcctgcc aagacctcct tggttgaaag taagaatgcc ctgctccttc   11700
cccaagtgtg ctggggatga atctggaaat aaactacatc tttttattt tttaaacttt   11760 tatatttgaa aatataaata ttttaggttc agggaacatg tgcaggtttg ttatataggt   11820
aaattgcatg tcatgggggc ttggggtaca gattacatca tcagccaggt aataagccta   11880
gtacctgatc agtagatttt ttttaatcct ctccctcctc ccagcctcca ccctcaattc   11940
acatgtctcc atgtgtactc aaggtttaat tcccacttat gagtgagaac atgcggtatt   12000
tgtaaactac atctttattt ttgctaacct cgaactgaaa tttagcattt gttttattga   12060
tgaatagagg taacaaaaca aaccacatta atcctagcag tgcctgtgcc tttgccaaca   12120
acagaaattc cggacacttt catatcctat gacaattgtt gcaagcactt ttaaaaatca   12180
tgtacgactt tattcataat tatagtggtt attaggcttt tcaatagatc ttatttaatg   12240
agttagtaaa ataagtgcct gtattattgt attacatttg tttattaaga tcttgataac   12300
aacatttcaa tataatcatt tcctttgttt tttaaatttt agattcaggg gtatatgtgc   12360
aggtttgtta cgtggatata ctgcataatg atgaggtttg gcttctagtg aacccatcag   12420
ccaaatagtg aatgttgtgc ccaataagta gttttcaat cctcacttca ctcccagcct   12480
cctctatttt ggagtcccag tgtctattat ttctatcttt atgtccacat gtacccattg   12540
gttagctccc acttataagt gagaatgtgc agtatttaat tttctgtttt tgagttattt   12600
tgcttaggtt gatggcctc agctccagcc acgttgcttt aaagaacatg atttcattct   12660
tttttatggc tgcatagtac tccgaggtgt atgtgtacca gattttcttt atccacaatg   12720
atttcctttg taatctaata ttttatattg ttatttatg ttttattcta tatttttatt   12780
ttaatttata aaggaattca tatggttcac aagcctgtca aagggaccta taataaaaag   12840
aggttaagaa tccatgctct aaacagaata ttactccatt ttatttcatt tatttttaaa   12900
gagacagtct cactctgtca tccaggctgg agtacagtgg agtgatcata gctcattgca   12960
accctgaact cttgggcaca agcaattctc ctgcttcatc ctccagagga gctgggacta   13020
```

```
caggtgcaca tcaccatgcc cagctagttt taaaaattat tttgtagaga tggtgtctca   13080
ctatcctacc caggctggtc tcaaactcct gggctcaggc aatcctccca ctttgacctc   13140
ccaaagtgtt gagattacag gggcaagcca ctgtgcctgg ccacttgtca cattttaatt   13200
tgtgattact tataaaatga acccctccc  atctgagatc tgtcagtctt tctggtgacg   13260
gtgcctggtg tctgctttct accatgtcct gttagactag tgtttgatgg gaggtcacct   13320
gggcagctgt ccagctcact cactgggctc tagagcctct gagttgaagc aaaatagaaa   13380
gatcagtcaa tgtaaagaaa gctcaaaaac tgacattctg aagtaatgga tagctaaacc   13440
ttcctattgc cctttctttt cagcaactga tggaacgcta gtgaccacca taagatgtc    13500 aagccaggca gcacaaggaa attccacgtg gcctgcccca gcagaggaga cggggaccag   13560
tccagcaggt aaatatagac cttgttccca tttctgctct gctaatgcca cccaagcctt   13620
tcttttcttt tcttttcttt tcttttcttt tcttttcttt tcttttcttt ctctcccttt   13680
ctttctttct ttctttcttt ctttctttct ttcttctttt cttcttttct ctttctttct   13740 ttcttcttt  ctttctttct ttcttctttt ctttctttct ctttctttct tctttctctc   13800
tctctctttc tttctttctc ttgttctttt taaatttttt atttttttac ttaatttttt   13860
tcacccaagc cttaaggcca gtttggacca gatagtgaga ccccacctct ataaaaaaaa   13920
tttttaaaaa aaaaataagt tgggcatcgt gcaggcctgt agtccctgct actcgagagg   13980
ccaaggtggg aggacagctt gctgctgact aaaagtgctg cttattgatt ctgggaagaa   14040
aaaatataca aggcttcagt ttcattattt tataagtaaa tgctagcaac ttttcctttc   14100
tttctctctt tctctcttcc tctctttctc tcctctcctt ctcttctctc tctctctctc   14160
tctctctctc tttctctctc ctctccttct cttctcttct ttctctctct ctctctttca   14220 tttattttg  agacatggtc tcattctgtc acccaggctg gagtacagtg gtgtatattt   14280
actgcagtac tcactgtact cactgcagcc tcaaattcct gggctcaagc tatcctctca   14340
cctcagcctc ctgagtagct gggcagcagt ccagctcact cactgggctc tagagcctct   14400
gtgctatgcc cagcttattg ttgttgtttt tttaaatttt ttttttttgta cagatggggt   14460 ctcactatgt ggcccaaggt ggtcttaaac tcctggctcc aagagatcct cccacctcag   14520
cctcccaaag tgcagggatt acaggtgtga gccactgtgc ccagcctaga cagcattttt   14580
tttttttgaa acagggtctc cctctgttgc ccaggctgga gtgcaatggc gtgttcatgg   14640
ttcactgcag cctcagcctc ctcagtctca agcaatcctc caacttcagc ctcccccaac   14700
agctagaact gcaggtgatc atcaccaatt agcctggtta attgtgtgtg tatttcttaa   14760 atttttgta  gagatagttc tcactatatt gcttgggctg gtctcaaact cctggactca   14820
agtgattcac ctacctcggc ctccctaagc actgggatta caggcttgag ccaccacacc   14880
cggcaaggac taggttttaa aataggttcc taggctgggt gtggtggctt acgcccgtaa   14940
tcccagcact ttgggaggct gaggtgggcg gatcacgagg tcaggagttt gagaccagcc   15000
tggccaacat agtgaaaccc tgtctctact aaaaatacaa aaaattagct gggcatagtg   15060
gcacacacct gtaatcccag ctactcggga ggctgaggaa ggagaatcac ttgaacctgg   15120
gaggcggagg ttgcagtgag ccgagatcat gccattgctc tccagcctgg gtgacagagc   15180
aagactccat ctaaaaaaaa aaaaaaagt  tcctttgact tcttgacact cttctctgag   15240
gatattgatc atttttcccc aatagatgtt actaattgaa cacttctgtt gcttcaactt   15300
actaatttac atgatcaata gccaattaat tcagcaggag agaatgctac agagtcgatt   15360
```

```
ctttctgtac tttcttctgc tccagagtga aggatctttc taaatcagag accatcactg    15420
tgttcacagg gagggcctag gtgaacctga gatggcaaat gttgcgtttg ttctacggaa    15480
gaagggatta tgggttgaag tccttggcag tgccaaattg cttagaaaaa tgtgaaatat    15540
ggtccctagg agtgctcttg ggatgtcaca ttttctcac tcctttgaca ggtagatgtt     15600
attttcctga aggccaggga aaggattcag agggaggaat gaatttgaaa gaaaatgaag    15660
gtgacgagaa agaatgagct catctccctt atcctctttc ttctcaaatc cttaagtagc    15720
tttgcagtga actaagattt ggggaacct agaggaggct gaaagttgga agctgaaatt     15780
ggcttagcaa gggcaagctc caaagacaaa agtggaaata gtttgggggt agccttttgc    15840
atgggtgaaa tcctggttca tcacatcctc ccttatgcaa agagcccttt tatatgggc    15900 atggggaaaa actgagctaa aagtgataat ttctcctgag caagccagat ggtcaaagct    15960
ctaacttcac catctcccctt ggaatgttta atgtgttccc tggtgtccag aggcttaacg   16020
tgtgagaatt aaaagctcaa cattttcttt cccagggaag gaggaaatag ttttaattga    16080
aatcccggga ggaaatgaat gatagtgtca aaccaaaaaa cttcatcttc tgtaccactt    16140
gcatatactc cactgactta ctttctaatc acaggcacat ccccaggaag cccagaaatg    16200
tctaccactc tcaaaatcat gagctccaag gaacccggca tcagcccaga gatcaggtcc    16260
actgtgagaa attctccttg gaagactcca gaaacaactg ttcccatgga gaccacagtg    16320
gaaccagtca cccttcagtc cacagcccta ggaagtggca gcaccagcat ctctcacctg    16380
cccacaggaa ccacatcacc aaccaagtca ccaacagaaa atatgttggc tacagaaagg    16440
gtctccctct ccccatcccc acctgaggct tggaccaacc tttattctgg aactccagga    16500
gggaccaggc agtcactggc cacaatgtcc tctgtctccc tagagtcacc aactgctaga    16560
agcatcacag ggactggtca gcaaagcagt ccagaactgg tttaaagac aactggaatg     16620 gaattctcta tgtggcatgg ctctactgga gggaccacag gggacacaca tgtctctctg    16680
agcacatctt ccaatatcct tgaagaccct gtaaccagcc caaactctgt gagctcattg    16740
acagataaat ccaaacataa aaccgagaca tgggtcagca ccacagccat tccctccact    16800
gtcctgaata taagataat ggcagctgaa caacagacaa gtcgatctgt ggatgaggct     16860
tattcatcaa ctagttcttg gtcagatcag acatctggga gtgacatcac ccttggtgca    16920
tctcctgatg tcacaaacac attatacatc acctccacag cacaaaccac ctcactagta    16980
tctctgccct ctggagacca aggcattaca agcctcacca atccctcagg aggaaaaaca    17040
agctctgcat catctgtcac atctccttca atagggcttg agactctgat ggccaatgta    17100
agtgcagtga caagtgacat tgcccctact gctgggcatc tatctcagac ttcatctcct    17160
gcggaagtga gcatcctgga cataaccaca gctcctactc caggtatctc caccaccatc    17220
accaccatgg gaaccaactc aatctcaact accacaccca acccagaagt gggtatgagt    17280
accatggaca gcaccccggc cacagagagg cacacaactt ctacagaaca cccttccacc    17340
tggtcttcca cagctgcatc agattcctgg actgtcacag acatgacttc aaacttgaaa    17400
gttgcaagat ctcctggaac aatttccaca atgcatacaa cttcattctt agcctcaagc    17460
actgaattag actccatgtc tactccccat ggccgtataa ctgtcattgg aaccagcctg    17520
gtcactccat cctctgatgc ttcagctgta aagacagaga ccagtacaag tgaaagaaca    17580
ttgagtcctt cagacacaac tgcatctact cccatctcaa cttttctcg tgtccgagg     17640 atgagcatct cagttcctga cattttaagt acaagttgga ctcccagtag tacagaagca    17700
gaagatgtgc ctgtttcaat ggtttctaca gatcatgcta gtacaaagac tgacccaaat    17760
```

```
atgccctgt ccactttct gtttgattct ctgtccactc ttgactggga cactgggaga   17820
tctctgtcat cagccacagc cactacctca gctcctcagg gggccacaac tccccaagaa   17880
ctcactttgg aaaccatgat cagcccagct acctcacagt tgcccttctc tatagggcac   17940
attacaagtg cagtcatacc agctgcaatg caaggagct ctggagttac tttttcaaga   18000
ccagatccca caagcaaaaa ggcagagcag acttccactc agcttcccac caccacttct   18060
gcacatccag agcaggtgcc cagatcagca gcaacaactc tggatgtgat cccacacaca   18120
gcaaaaactc cagatgcaac ttttcagaga caagggcaga cagctcttac aacagaggca   18180
agagctacat ctgactcctg gaatgagaaa gaaaaatcaa ccccaagtgc accttggatc   18240
actgagatga tgaattctgt ctcagaagat accatcaagg aggttaccag ctcctccagt   18300
gtgttaagga ccctgaatac gctggacata aacttggaat ctgggacgac ttcatcccca   18360
agttggaaaa gcagcccata tgagagaatt gccccttctg agtctaccac agacaaagag   18420
gcaattcacc cttctacaaa cacagtagag accactggct gggtcacaag ttccgaacat   18480
gcttctcatt ccactatccc agcccactca gcgtcatcca aactcacatc tccagtggtt   18540
acaacctcca ccagggaaca agcaatagtt tctatgtcaa caaccacatg gccagagtct   18600
acaagggcta gaacagagcc taattccttc ttgactattg aactgaggga cgtcagccct   18660
tacatggaca ccagctcaac cacacaaaca agttttatct cttccccagg ttccactgcg   18720
atcaccaagg ggcctagaac agaaattacc tcctctaaga gaatatccag ctcattcctt   18780
gcccagtcta tgaggtcgtc agacagcccc tcagaagcca tctccaggct gtctaacttt   18840
cctgccatga cagaatctgg aggaatgatc cttgctatgc aaacaagtcc acctggcgct   18900
acatcactaa gtgcacctac tttggataca tcagccacag cctcctggac agggactcca   18960
ctggctacga ctcagagatt tacatactca gagaagacca ctctctttag caaaggtcct   19020
gaggatacat cacagccaag ccctccctct gtggaagaaa ccagctcttc ctcttccctg   19080
gtacctatca atgctacaac ctcgccttcc aatattttgt tgacatcaca agggcacagt   19140
ccctcctcta ctccacctgt gacctcagtt ttcttgtctg agacctctgg cctggggaag   19200
accacagaca tgtcgaggat aagcttggaa cctggcacaa gttacctcc caatttgagc   19260 agtacagcag gtgaggcgtt atccacttat gaagcctcca gagatacaaa ggcaattcat   19320
cattctgcag acacagcagt gacgaatatg gaggcaacca gttctgaata ttctcctatc   19380
ccaggccata caaagccatc caaagccaca tctccattgg ttacctccca catcatgggg   19440
gacatcactt cttccacatc agtatttggc tcctccgaga ccacagagat tgagacagtg   19500
tcctctgtga accagggact tcaggagaga agcacatccc aggtggccag ctctgctaca   19560
gagacaagca ctgtcattac ccatgtgtct agtggtgatg ctactactca tgtcaccaag   19620
acacaagcca ctttctctag cggaacatcc atctcaagcc ctcatcagtt tataacttct   19680
accaacacat ttacagatgt gagcaccaac ccctccacct ctctgataat gacagaatct   19740
tcaggagtga ccatcaccac ccaaacaggt cctactggag ctgcaacaca gggtccatat   19800
ctcttggaca catcaaccat gccttacttg acagagactc cattagctgt gactccagat   19860
tttatgcaat cagagaagac cactctcata agcaaaggtc ccaaggatgt gtcctggaca   19920
agccctccct ctgtggcaga aaccagctat ccctcttccc tgacaccttt cttggtcaca   19980
accatacctc ctgccactcc cacgttacaa gggcaacata catcctctcc tgtttctgcg   20040
acttcagttc ttacctctgg actggtgaag accacagata tgttgaacac aagcatggaa   20100
```

```
cctgtgacca attcacctca aaatttgaac aatccatcaa atgagatact ggccactttg    20160
gcagccacca cagatataga gactattcat ccttccataa acaaagcagt gaccaatatg    20220
gggactgcca gttcagcaca tgtactgcat tccactctcc cagtcagctc agaaccatct    20280
acagccacat ctccaatggt tcctgcctcc agcatggggg acgctcttgc ttctatatca    20340
atacctggtt ctgagaccac agacattgag ggagagccaa catcctccct gactgctgga    20400
cgaaaagaga acagcaccct ccaggagatg aactcaacta cagagtcaaa catcatcctc    20460
tccaatgtgt ctgtgggggc tattactgaa gccacaaaaa tggaagtccc ctcttttgat    20520
gcaacattca taccaactcc tgctcagtca acaaagttcc cagatatttt ctcagtagcc    20580
agcagtagac tttcaaactc tcctcccatg acaatatcta cccacatgac caccacccag    20640
acagggtctt ctggagctac atcaaagatt ccacttgcct tagacacatc aaccttggaa    20700
acctcagcag ggactccatc agtggtgact gaggggtttg cccactcaaa ataaccact     20760 gcaatgaaca atgatgtcaa ggacgtgtca cagacaaacc ctcccttttca ggatgaagcc    20820 agctctccct cttctcaagc acctgtcctt gtcacaacct taccttcttc tgttgctttc    20880
acaccgcaat ggcacagtac ctcctctcct gtttctatgt cctcagttct tacttcttca    20940
ctggtaaaga ccgcaggcaa ggtggataca agcttagaaa cagtgaccag ttcacctcaa    21000
agtatgagca acactttgga tgacatatcg gtcacttcag cagccaccac agatatagag    21060
acaacgcatc cttccataaa cacagtagtt accaatgtgg ggaccaccgg ttcagcattt    21120
gaatcacatt ctactgtctc agcttaccca gagccatcta agtcacatc tccaaatgtt     21180 accacctcca ccatggaaga caccacaatt tccagatcaa tacctaaatc ctctaagact    21240
acaagaactg agactgagac aacttcctcc ctgactccta aactgaggga gaccagcgtc    21300
tcccaggaga tcacctcgtc cacagagaca agcactgttc cttacaaaga gctcactggt    21360
gccactaccg aggtatccag gacagatgtc acttcctcta gcagtacatc cttccctggc    21420
cctgatcagt ccacagtgtc actagacatc tccacagaaa ccaacaccag gctgtctacc    21480
tccccaataa tgacagaatc tgcagaaata accatcacca cccaaacagg tcctcatggg    21540
gctacatcac aggatacttt taccatggac ccatcaaata caacccccca ggcagggatc    21600
cactcagcta tgactcatgg attttcacaa ttggatgtga ccactcttat gagcagaatt    21660
ccacaggatg tatcatggac aagtcctccc tctgtggata aaaccagctc cccctcttcc    21720
tttctgccct cacctgcaat gaccacacct tccctgattt cttctacctt accagaggat    21780
aagctctcct ctcctatgac ttcacttctc acctctggcc tagtgaagat tacagacata    21840
ttacgtacac gcttggaacc tgtgaccagc tcacttccaa atttcagcag cacctcagat    21900
aagatactgg ccacttctaa agacagtaaa gacacaaagg aaattttttcc ttctataaac    21960 acagaagaga ccaatgtgaa agccaacaac tctggacatg aatcccattc ccctgcactg    22020
gctgactcag agacacccaa agccacaact caaatggtta tcaccaccac tgtgggagat    22080
ccagctcctt ccacatcaat gccagtgcat ggttcctctg agactacaaa cattaagaga    22140
gagccaacat atttcttgac tcctagactg agagagacca gtacctctca ggagtccagc    22200
tttcccacgg acacaagttt tctacttttcc aaagtcccca ctggtactat tactgaggtc    22260
tccagtacag gggtcatctc ttctagcaaa atttccaccc cagaccatga taagtccaca    22320
gtgccacctg acaccttcac aggagagatc cccagggtct tcacctcctc tattaagaca    22380
aaatctgcag aaatgacgat caccacccaa gcaagtcctc ctgagtctgc atcgcacagt    22440 accctttccct tggacacatc aaccacactt tcccagggag ggactcattc aactgtgact    22500
```

```
cagggattcc catactcaga ggtgaccact ctcatgggca tgggtcctgg gaatgtgtca   22560
tggatgacaa ctcccctgt ggaagaaacc agctctgtgt cttccctgat gtcttcacct    22620
gccatgacat ccccttctcc tgtttcctcc acatcaccac agagcatccc ctcctctcct   22680
cttcctgtga ctgcacttcc tacttctgtt ctggtgacaa ccacagatgt gttgggcaca   22740
acaagcccag agtctgtaac cagttcacct ccaaatttga gcagcatcac tcatgagaga   22800
ccggccactt acaaagacac tgcacacaca gaagccgcca tgcatcattc cacaaacacc   22860
gcagtgacca atgtagggac ttccgggtct ggacataaat cacaatcctc tgtcctagct   22920
gactcagaga catcgaaagc cacacctctg atgagtacca cctccaccct ggggacaca    22980 agtgtttcca catcaactcc taatatctct cagactaacc aaattcaaac agagccaaca   23040
gcatccctga gccctagact gagggagagc agcacgtctg agaagaccag ctcaacaaca   23100
gagacaaata ctgcctttc ttatgtgccc acaggtgcta ttactcaggc tccagaaca    23160 gaaatctcct ctagcagaac atccatctca gaccttgatc ggtccacaat agcacccgac   23220
atctccacag gaatgatcac caggctcttc acctccccca tcatgacaaa atctgcagaa   23280
atgaccgtca ccactcaaac aactactcct ggggctacat cacagggtat ccttccctgg   23340
gacacatcaa ccacactttt ccagggaggg actcattcaa ccgtgtctca gggattccca   23400
cactcagaga taaccactct tcggagcaga accctggag atgtgtcatg gatgacaact    23460 cccctgtgg aagaaaccag ctctgggttt tccctgatgt caccttccat gacatcccct    23520
tctcctgttt cctccacatc accagagagc atccctcct ctcctctccc tgtgactgca   23580
cttcttactt ctgttctggt gacaaccaca aatgtattgg gcacaacaag cccagagccc   23640
gtaacgagtt cacctccaaa tttaagcagc cccacacagg agagactgac cacttacaaa   23700
gacactgcgc acacagaagc catgcatgct tccatgcata caaacactgc agtggccaac   23760
gtggggacct ccatttctgg acatgaatca caatcttctg tcccagctga ttcagacaca   23820
tccaaagcca catctccaat gggtaccacc ttcgccatgg gggatacaag tgtttctaca   23880
tcaactcctg ccttctttga gactagaatt cagactgaat caacatcctc tttgattcct   23940
ggattaaggg acaccaggac gtctgaggag atcaacactg tgacagagac cagcactgtc   24000
ctttcagaag tgcccactac tactactact gaggtctcca ggacagaagt tatcacttcc   24060
agcagaacaa ccatctcagg gcctgatcat tccaaaatgt caccctacat ctccacagaa   24120
accatcacca ggctctccac ttttccttt gtaacaggat ccacagaaat ggccatcacc    24180
aaccaaacag gtcctatagg gactatctca caggctaccc ttaccctgga cacatcaagc   24240
acagcttcct gggaagggac tcactcacct gtgactcaga gatttccaca ctcagaggag   24300
accactacta tgagcagaag tactaagggc gtgtcatggc aaagccctcc ctctgtggaa   24360
gaaaccagtt ctccttcttc cccagtgcct ttacctgcaa taacctcaca ttcatctctt   24420
tattccgcag tatcaggaag tagccccact tctgctctcc ctgtgacttc ccttctcacc   24480
tctggcagga ggaagaccat agacatgttg gacacacact cagaacttgt gaccagctcc   24540
ttaccaagtg caagtagctt ctcaggtgag atactcactt ctgaagcctc cacaaataca   24600
gagacaattc acttttcaga gaacacagca gaaaccaata tggggaccac caattctatg   24660
cataaactac attcctctgt ctcaatccac tcccagccat ccggacacac acctccaaag   24720
gttactggat ctatgatgga ggcgctatt gtttccacat caacacctgg ttctcctgag    24780
actaaaaatg ttgacagaga ctcaacatcc cctctgactc ctgaactgaa agaggacagc   24840
```

```
accgccctgg tgatgaactc aactacagag tcaaacactg ttttctccag tgtgtccctg   24900
gatgctgcta ctgaggtctc cagggcagaa gtcacctact atgatcctac attcatgcca   24960
gcttctgctc agtcaacaaa gtccccagac atttcacctg aagccagcag cagtcattct   25020
aactctcctc ccttgacaat atctacacac aagaccatcg ccacacaaac aggtccttct   25080
ggggtgacat ctcttggcca actgaccctg acacatcaa ccatagccac ctcagcagga    25140
actccatcag ccagaactca ggattttgta gattcagaaa caaccagtgt catgaacaat   25200
gatctcaatg atgtgttgaa gacaagccct ttctctgcag aagaagccaa ctctctctct   25260
tctcaggcac ctctccttgt gacaacctca ccttctcctg taacttccac attgcaagag   25320
cacagtacct cctctcttgt ttctgtgacc tcagtaccca ccctacact ggcgaagatc    25380 acagacatgg acacaaactt agaacctgtg actcgttcac ctcaaaattt aaggaacacc   25440
ttggccactt cagaagccac cacagataca cacacaatgc atccttctat aaacacagca   25500
gtggccaatg tggggaccac cagttcacca aatgaattct attttactgt ctcacctgac   25560
tcagacccat ataaagccac atccgcagta gttatcactt ccacctcggg ggactcaata   25620
gtttccacat caatgcctag atcctctgcg atgaaaaaga ttgagtctga gacaactttc   25680
tccctgatat ttagactgag ggagactagc acctcccaga aaattggctc atcctcagac   25740
acaagcacgg tctttgacaa agcattcact gctgctacta ctgaggtctc cagaacagaa   25800
ctcacctcct ctagcagaac atccatccaa ggcactgaaa agcccacaat gtcaccggac   25860
acctccacaa gatctgtcac catgctttct acttttgctg gcctgacaaa tccgaagaa    25920 aggaccattg ccacccaaac aggtcctcat agggcgacat cacagggtac ccttacctgg   25980
gacacatcaa tcacaacctc acaggcaggg acccactcag ctatgactca tggattttca   26040
caattagatt tgtccactct tacgagtaga gttcctgagt acatatcagg acaagccca    26100 ccctctgtgg aaaaaaccag ctcttcctct tcccttctgt cttaccagc aataacctca    26160 ccgtcccctg tacctactac attaccagaa agtaggccgt tttctcctgt tcatctgact   26220
tcactcccca cctctggcct agtgaagacc acagatatgc tggcatctgt ggccagttta   26280 cctccaaaact tgggcagcac ctcacataag ataccgacta cttcagaaga cattaaagat   26340
acagagaaaa tgtatccttc cacaaacata gcagtaacca atgtgggac caccacttct    26400 gaaaaggaat cttattcgtc tgtcccagcc tactcagaac cacccaaagt cacctctcca   26460
atggttacct cttcaacat aagggacacc attgtttcca catccatgcc tggctcctct    26520
gagattacaa ggattgagat ggagtcaaca ttctccctgg ctcatgggct gaagggaacc   26580
agcacctccc aggaccccat cgtatccaca gagaaaagtg ctgtccttca caagttgacc   26640
actggtgcta ctgagacctc taggacagaa gttgcctctt ctagaagaac atccattcca   26700
ggccctgatc attccacaga gtcaccagac atctccactg aagtgatccc cagcctgcct   26760 atctccttg gcattacaga atcttcaaat atgaccatca tcactcgaac aggtcctcct    26820
cttggctcta catcacaggg cacatttacc ttgacacac caactacatc ctccagggca   26880
ggaacacact cgatggcgac tcaggaattt ccacactcag aaatgaccac tgtcatgaac   26940
aaggaccctg agattctatc atggacaatc cctccttcta tagagaaaac cagcttctcc   27000
tcttccctga tgccttcacc agccatgact tcacctcctg tttcctcaac attaccaaag   27060
accattcaca ccactccttc tcctatgacc tcactgctca cccctagcct agtgatgacc   27120
acagacacat tgggcacaag cccagaacct acaaccagtt cacctccaaa tttgagcagt   27180
acctcacatg agatactgac aacagatgaa gacaccacag ctatagaagc catgcatcct   27240
```

```
tccacaagca cagcagcgac taatgtggaa accaccagtt ctggacatgg gtcacaatcc    27300
tctgtcctag ctgactcaga aaaaccaag gccacagctc caatggatac cacctccacc    27360
atggggcata caactgtttc cacatcaatg tctgtttcct ctgagactac aaaaattaag    27420
agagagtcaa catattcctt gactcctgga ctgagagaga ccagcatttc ccaaaatgcc    27480
agcttttcca ctgacacaag tattgttctt tcagaagtcc ccactggtac tactgctgag    27540
gtctccagga cagaagtcac ctcctctggt agaacatcca tccctggccc ttctcagtcc    27600
acagttttgc cagaaatatc cacaagaaca atgacaaggc tctttgcctc gcccaccatg    27660
acagaatcag cagaaatgac catccccact caaacaggtc cttctgggtc tacctcacag    27720
gataccctta ccttggacac atccaccaca aagtcccagg caaagactca ttcaactttg    27780
actcagagat ttccacactc agagatgacc actctcatga gcagaggtcc tggagatatg    27840
tcatggcaaa gctctccctc tctggaaaat cccagctctc tcccttccct gctgtcttta    27900
cctgccacaa cctcacctcc tcccatttcc tccacattac cagtgactat ctcctcctct    27960
cctcttcctg tgacttcact tctcacctct agcccggtaa cgaccacaga catgttacac    28020
acaagcccag aacttgtaac cagttcacct ccaaagctga gccacacttc agatgagaga    28080
ctgaccactg gcaaggacac cacaaataca gaagctgtgc atccttccac aaacacagca    28140
gcgtccaatg tggagattcc cagctctgga catgaatccc cttcctctgc cttagctgac    28200
tcagagacat ccaaagccac atcaccaatg tttattacct ccacccagga ggatacaact    28260
gttgccatat caaccccctca cttcttggag actagcagaa ttcagaaaga gtcaatttcc    28320
tccctgagcc ctaaattgag ggagacaggc agttctgtgg agacaagctc agccatagag    28380
acaagtgctg tccttttctga agtgtccgtt ggtgctacta ctgagatctc caggacagaa    28440
gtcacctcct ctagcagaac atccatctct ggttctgctg agtccacaat gttgccagaa    28500
atatccacca caagaaaaat cattaagttc cctacttccc ccatcctggc agaatcatca    28560
gaaatgacca tcaagaccca aacaagtcct cctgggtcta catcagagag tacctttaca    28620
ttagacacat caaccactcc ctccttggta ataaccccatt cgactatgac tcagagattg    28680
ccacactcag agataaccac tcttgtgagt agaggtgctg gggatgtgcc acggcccagc    28740
tctctccctg tggaagaaac aagccctcca tcttcccagc tgtctttatc tgccatgatc    28800
tcaccttctc ctgtttcttc cacattacca gcaagtagcc actcctcttc tgcttctgtg    28860
acttcacttc tcacaccagg ccaagtgaag actactgagg tgttggacgc aagtgcagaa    28920
cctgaaacca gttcacctcc aagtttgagc agcacctcag ttgaaatact ggccacctct    28980
gaagtcacca cagatacgga gaaaattcat cctttctcaa acacggcagt aaccaaagtt    29040
ggaacttcca gttctggaca tgaatcccct tcctctgtcc tacctgactc agagacaacc    29100
aaagccacat cggcaatggg taccatctcc attatggggg atacaagtgt ttctacatta    29160
actcctgcct tatctaacac taggaaaatt cagtcagagc cagcttcctc actgaccacc    29220
agattgaggg agaccagcac ctctgaagag accagcttag ccacagaagc aaacactgtt    29280
ctttctaaag tgtccactgg tgctactact gaggtctcca ggacagaagc catctccttt    29340
agcagaacat ccatgtcagg ccctgagcag tccacaatgt cacaagacat ctccatagga    29400
accatcccca ggatttctgc ctcctctgtc ctgacagaat ctgcaaaaat gaccatcaca    29460
acccaaacag gtccttcgga gtctacacta gaaagtaccc ttaatttgaa cacagcaacc    29520
acaccctctt gggtggaaac ccactctata gtaattcagg gatttccaca cccagagatg    29580
```

```
accacttcca tgggcagagg tcctggaggt gtgtcatggc ctagccctcc ctttgtgaaa    29640
gaaaccagcc ctccatcctc cccgctgtct ttacctgccg tgacctcacc tcatcctgtt    29700
tccaccacat tcctagcaca tatccccccc tctccccttc ctgtgacttc acttctcacc    29760
tctggcccgg cgacaaccac agatatcttg ggtacaagca cagaacctgg aaccagttca    29820
tcttcaagtt tgagcaccac ctcccatgag agactgacca cttacaaaga cactgcacat    29880
acagaagccg tgcatccttc cacaaacaca ggagggacca atgtggcaac caccagctct    29940
ggatataaat cacagtcctc tgtcctagct gactcatctc caatgtgtac cacctccacc    30000
atggggata caagtgttct cacatcaact cctgccttcc ttgagactag gaggattcag    30060
acagagctag cttcctccct gaccctgga ttgagggagt ccagtggctc tgaagggacc    30120
agctcaggca ccaagatgag cactgtcctc tctaaagtgc ccactggtgc tactactgag    30180
atctccaagg aagacgtcac ctccatccca ggtcccgctc aatccacaat atcaccagac    30240
atctccacaa gaaccgtcag ctggttctct acatcccctg tcatgacaga atcagcagaa    30300
ataaccatga acacccatac aagtccttta ggggccacaa cacaaggcac cagtactttg    30360
gccacgtcaa gcacaacctc tttgacaatg acacactcaa ctatatctca aggattttca    30420
cactcacaga tgagcactct tatgaggagg ggtcctgagg atgtatcatg gatgagccct    30480
cccctttctgg aaaaaactag accttccttt tctctgatgt cttcaccagc cacaacttca    30540
ccttctcctg tttcctccac attaccgagag agcatctctt cctctcctct tcctgtgact    30600
tcactcctca cgtctggctt ggcaaaaact acagatatgt tgcacaaaag ctcagaacct    30660
gtaaccaact cacctgcaaa tttgagcagc acctcagttg aaatactggc cacctctgaa    30720
gtcaccacag atacagagaa aactcatcct tcttcaaaca gaacagtgac cgatgtgggg    30780
acctccagtt ctggacatga atccacttcc tttgtcctag ctgactcaca gacatccaaa    30840
gtcacatctc caatggttat tacctccacc atggaggata cgagtgtctc cacatcaact    30900
cctggctttt ttgagactag cagaattcag acagaaccaa catcctccct gacccttgga    30960
ctgagaaaga ccagcagctc tgaggggacc agcttagcca cagagatgag cactgtcctt    31020
tctggagtgc ccactggtgc cactgctgaa gtctccagga cagaagtcac ctcctctagc    31080
agaacatcca tctcaggctt tgctcagctc acagtgtcac cagagacttc cacagaaacc    31140
atcaccagac tccctacctc cagcataatg acagaatcag cagaaatgat gatcaagaca    31200
caaacagatc ctcctgggtc tacaccagag agtactcata ctgtggacat atcaacaaca    31260
cccaactggg tagaaaccca ctcgactgtg actcagagat tttcacactc agagatgacc    31320
actcttgtga gcagaagccc tggtgatatg ttatggccta gtcaatcctc tgtggaagaa    31380
accagctctg cctcttccct gctgtctctg cctgccacga cctcaccttc tcctgtttcc    31440
tctacattag tagaggattt cccttccgct tctcttcctg tgacttctct tctcacccct    31500
ggcctggtga taaccacaga caggatgggc ataagcagag aacctggaac cagttccact    31560
tcaaatttga gcagcacctc ccatgagaga ctgaccactt tggaagacac tgtagataca    31620
gaagacatgc agccttccac acacacagca gtgaccaacg tgaggacctc catttctgga    31680
catgaatcac aatcttctgt cctatctgac tcagagacac ccaaagccac atctccaatg    31740
ggtaccacct acaccatggg ggaaacgagt gtttccatat ccacttctga cttctttgag    31800
accagcagaa ttcagataga accaacatcc tccctgactt ctggattgag ggagaccagc    31860
agctctgaga ggatcagctc agccacagag ggaagcactg tcctttctga agtgcccagt    31920
ggtgctacca ctgaggtctc caggacagaa gtgatatcct ctaggggaac atccatgtca    31980
```

```
gggcctgatc agttcaccat atcaccagac atctctactg aagcgatcac caggctttct   32040
acttccccca ttatgacaga atcagcagaa agtgccatca ctattgagac aggttctcct   32100
ggggctacat cagagggtac cctcaccttg gacacctcaa caacaacctt ttggtcaggg   32160
acccactcaa ctgcatctcc aggattttca cactcagaga tgaccactct tatgagtaga   32220
actcctggag atgtgccatg gccgagcctt ccctctgtgg aagaagccag ctctgtctct   32280
tcctcactgt cttcacctgc catgacctca acttcttttt tctccacatt accagagagc   32340
atctcctcct ctcctcatcc tgtgactgca cttctcaccc ttggcccagt gaagaccaca   32400
gacatgttgc gcacaagctc agaacctgaa accagttcac ctccaaattt gagcagcacc   32460
tcagctgaaa tattagccac gtctgaagtc accaaagata gagagaaaat tcatccctcc   32520
tcaaacacac ctgtagtcaa tgtagggact gtgatttata acatctatc ccttcctct    32580
gttttggctg acttagtgac aacaaaaccc acatctccaa tggctaccac ctccactctg   32640
gggaatacaa gtgtttccac atcaactcct gccttcccag aaactatgat gacacagcca   32700
acttcctccc tgacttctgg attaagggag atcagtacct ctcaagagac cagctcagca   32760
acagagagaa gtgcttctct ttctggaatg cccactggtg ctactactaa ggtctccaga   32820
acagaagccc tctccttagg cagaacatcc accccaggtc ctgctcaatc cacaatatca   32880
ccagaaatct ccacggaaac catcactaga atttctactc ccctcaccac gacaggatca   32940
gcagaaatga ccatcacccc caaaacaggt cattctgggg catcctcaca aggtaccttt   33000
accttggaca catcaagcag agcctcctgg ccaggaactc actcagctgc aactcacaga   33060
tctccacact cagggatgac cactcctatg agcagaggtc ctgaggatgt gtcatggcca   33120
agccgcccat cagtggaaaa aactagcct ccatcttccc tggtgtcttt atctgcagta    33180
acctcacctt cgccacttta ttccacacca tctgagagta gccactcatc tcctctccgg   33240
gtgacttctc ttttcacccc tgtcatgatg aagaccacag acatgttgga cacaagcttg   33300
gaacctgtga ccacttcacc tcccagtatg aatatcacct cagatgagag tctggccact   33360
tctaaagcca ccatggagac agaggcaatt cagctttcag aaaacacagc tgtgactcag   33420
atgggcacca tcagcgctag acaagaattc tattcctctt atccaggcct cccagagcca   33480
tccaaagtga catctccagt ggtcacctct tccaccataa aagacattgt ttctacaacc   33540
atacctgctt cctctgagat aacaagaatt gagatggagt caacatccac cctgaccccc   33600
acaccaaggg agaccagcac ctcccaggag atccactcag ccacaaagcc aagcactgtt   33660
ccttacaagg cactcactag tgccacgatt gaggactcca tgacacaagt catgtcctct   33720
agcagaggac ctagccctga tcagtccaca atgtcacaag acatatccag tgaagtgatc   33780
accaggctct ctacctcccc catcaaggca gaatctacag aaatgaccat taccacccaa   33840
acaggttctc ctggggctac atcaaggggt acccttacct tggacacttc aacaactttt   33900
atgtcaggga cccactcaac tgcatctcaa ggattttcac actcacagat gaccgctctt   33960
atgagtagaa ctcctggaga tgtgccatgg ctaagccatc cctctgtgga agaagccagc   34020
tctgcctctt tctcactgtc ttcacctgtc atgacctcat cttctcccgt ttcttccaca   34080
ttaccagaca gcatccactc ttcttcgctt cctgtgacat cacttctcac ctcagggctg   34140
gtgaagacca cagagctgtt gggcacaagc tcagaacctg aaaccagttc accccccaaat  34200
ttgagcagca cctcagctga atatactggcc accactgaag tcactacaga tacagagaaa   34260
ctggagatga ccaatgtggt aacctcaggt tatacacatg aatctccttc ctctgtccta   34320
```

```
gctgactcag tgacaacaaa ggccacatct tcaatgggta tcacctaccc cacaggagat   34380
acaaatgttc tcacatcaac ccctgccttc tctgacaccn nnnnnnnnnn nnnnnnnnnn   34440
nnnnnnnnnn nnnnnnnnnn nnnnnnnnnn nnnnnnnnnn nnnnnnnnnn nnnnnnnnnn   34500
nnnnnnnnnn nnnnnnnnnn nnnnnnnnnn nnnncggaaa ccaagtttct aaccaacccc   34560 tccttttga ccccagtagg attcaaacaa agtcaaagct ctcactgact cctgggttga   34620
tggagaccag catctctgaa gagaccagct ctgccacaga aaaagcact gtcctttcta   34680 gtgtgcccac tggtgctact actgaggtct ccaggacaga agccatctct tctagcagaa   34740
catccatccc aggccctgct caatccacaa tgtcatcaga cacctccatg gaaaccatca   34800
ctagaatttc tacccccctc acaaggaaag aatcaacaga catggccatc accccccaaaa  34860 caggtccttc tggggctacc tcgcagggta cctttacctt ggactcatca agcacagcct   34920
cctggccagg aactcactca gctacaactc agagatttcc acagtcagtg gtgacaactc   34980
ctatgagcag aggtcctgag gatgtgtcat ggccaagccc gctgtctgtg gaaaaaaaca   35040
gccctccatc ttccctggta tcttcatctt cagtaacctc accttcgcca ctttattcca   35100
caccatctgg gagtagccac tcctctcctg tccctgtcac ttctcttttc acctctatca   35160
tgatgaaggc cacagacatg ttggatgcaa gtttggaacc tgagaccact tcagctccca   35220
atatgaatat cacctcagat gagagtctgg ccacttctaa agccaccacg gagacagagg   35280
caattcacgt ttttgaaaat acagcagcgt cccatgtgga aaccaccagt gctacagagg   35340
aactctattc ctcttcccca ggcttctcag agccaacaaa agtgatatct ccagtggtca   35400
cctcttcctc tataagagac aacatggttt ccacaacaat gcctggctcc tctggcatta   35460
caaggattga atagagtcaa atgtcatctc tgaccctgg actgagggag accagaacct   35520
cccaggacat caccctcatcc acagagacaa gcactgtcct ttacaagatg tcctctggtg   35580
ccactcctga ggtctccagg acagaagtta tgccctctag cagaacatcc attcctggcc   35640
ctgctcagtc cacaatgtca ctagacatct ccgatgaagt tgtcaccagg ctgtctacct   35700
ctcccatcat gacagaatct gcagaaataa ccatcaccac ccaaacaggt tattctctgg   35760
ctacatccca ggttacccct cccttgggca cctcaatgac cttttttgtca gggacccact   35820 caactatgtc tcaaggactt tcacactcag agatgaccaa tcttatgagc aggggtcctg   35880
aaagtctgtc atggacgagc cctcgctttg tggaaacaac tagatcttcc tcttctctga   35940
catcattacc tctcacgacc tcactttctc ctgtgtcctc cacattacta gacagtagcc   36000
cctcctctcc tcttcctgtg acttcactta tcctcccagg cctggtgaag actacagaag   36060
tgttggatac aagctcagag cctaaaacca gttcatctcc aaatttgagc agcacctcag   36120
ttgaaatacc ggccacctct gaaatcatga cagatacaga gaaaattcat ccttcctcaa   36180
acacagcggt ggccaaagtg aggacctcca gttctgttca tgaatctcat tcctctgtcc   36240
tagctgactc agaaacaacc ataaccatac cttcaatggg tatcacctcc gctgtggacg   36300
ataccactgt tttcacatca aatcctgcct tctctgagac taggaggatt ccgacagagc   36360
caacattctc attgactcct ggattcaggg agactagcac ctctgaagag accacctcaa   36420
tcacagaaac aagtgcagtc ctttatggag tgcccactag tgctactact gaagtctcca   36480
tgacagaaat catgtcctct aatagaacac acatccctga ctctgatcag tccacgatgt   36540
ctccagacat catcactgaa gtgatcacca ggctctcttc ctcatccatg atgtcagaat   36600
caacacaaat gaccatcacc acccaaaaaa gttctcctgg ggctacagca cagagtactc   36660
ttaccttggc cacaacaaca gccccccttgg caaggaccca ctcaactgtt cctcctagat   36720
```

```
ttttacactc agagatgaca actcttatga gtaggagtcc tgaaaatcca tcatggaaga   36780
gctctcccct tgtggaaaaa actagctctt catcttctct gttgtcctta cctgtcacga   36840
cctcaccttc tgtttcttcc acattaccgc agagtatccc ttcctcctct ttttctgtga   36900
cttcactcct cacccagge atggtgaaga ctacagacac aagcacagaa cctggaacca    36960
gtttatctcc aaatctgagt ggcacctcag ttgaaatact ggctgcctct gaagtcacca   37020
cagatacaga gaaaattcat ccttcttcaa gcatggcagt gaccaatgtg ggaaccacca   37080
gttctggaca tgaactatat tcctctgttt caatccactc ggagccatcc aaggctacat   37140
acccagtggg tactccctct tccatggctg aaacctctat ttccacatca atgcctgcta   37200
attttgagac cacaggattt gaggctgagc cattttctca tttgacttct ggatttagga   37260
agacaaacat gtccctggac accagctcag tcacaccaac aaatacacct tcttctcctg   37320
ggtccactca ccttttacag agttccaaga ctgatttcac ctcttctgca aaacatcat    37380
ccccagactg gcctccagcc tcacagtata ctgaaattcc agtggacata atcaccccct   37440
ttaatgcttc tccatctatt acggagtcca ctgggataac ctccttccca gaatccaggt   37500
ttactatgtc tgtaacagaa agtactcatc atctgagtac agatttgctg ccttcagctg   37560
agactatttc cactggcaca gtgatgcctt ctctatcaga ggccatgact tcatttgcca   37620
ccactggagt tccacgagcc atctcaggtt caggtagtcc attctctagg acagagtcag   37680
gccctgggga tgctactctg tccaccattg cagagagcct gccttcatcc actcctgtgc   37740
cattctcctc ttcaacctte actaccactg attcttcaac catcccagcc ctccatgaga   37800
taacttcctc ttcagctacc ccatatagag tggacaccag tcttgggaca gagagcagca   37860
ctactgaagg acgcttggtt atggtcagta ctttggacac ttcaagccaa ccaggcagga   37920
catcttcaac acccatttt gataccagaa tgacagagag cgttgagctg ggaacagtga   37980
caagtgctta tcaagttcct tcactctcaa cacggttgac aagagaatgc gcatggcgag   38040
aagggagaag tgtagttgga tggataaaag gaagaatgga gagaagagtg aatggaagga   38100
agcaaagatg aagcggagga aggatagatg cacagaagga aggatgaaaa gaagaaaga    38160
tgatggaaga caggattgaa ggggatatag attgaaggaa agaaaggtag aaggatgaaa   38220
tgaagtaaag attgaagaaa agatggatgg aaagaagaaa ggagggtgca caaaaaatct   38280
cacacttcac cacatatgat tcatccatat aagaaaaaac cacttgtacc ctcaaagcta   38340
ttgaaataca aactttaaaa ttaaaatttt aaaaagcaag agaaaggaaa gaagggagga   38400
aagacaaaag gaagaatggg tgatagaagg aagaataaa aggaagaaa aatgaagaa     38460
tagatgatca gatctaggga tgaatgaaag gaaggatgga caaatctata ggtaggtgga   38520
tggatctatg gacaggtgtg gccacttatg gcacatagtc ccagctccag ttcatactga   38580
tggacttgag gagtgtttgt ggccaatgaa gtggatccat ttagacagtg ctcttcttct   38640
gaatgagatg agttacccca gttttctcc ccaccttcat cttcaggaac tgatggcatt    38700
atggaacaca tcacaaaaat acccaatgaa gcagcacaca gaggtaccat aagaccagtc   38760
aaaggccctc agacatccac ttcgcctgcc agtcctaaag gtaggtttaa ctttgcttac   38820
ctcccagtaa tgccactcgt gaccatattt cctcctccag agagacaaaa tgtttgtatt   38880
ctttagagag agaattgtgt gtggttgtca taggtttccc tgtctgaact gagtctttat   38940
ctaatggtta ccaggcagat gttaccactg tctcttctc ctcatggcat gctgagtgag   39000
ttttgtccaa catcaaatat tcacaaattt gtccatatta accaaatttt aaaaatgctc   39060
```

```
attaaaaact tactatgagc tgggcgcagt ggctcatgcc tgtaatccca atactttggg   39120
aggctgagct gggtggatca ccagaggtca aaaattcgag accagtctga ccaaaatggt   39180
gaaactccat ctctactgaa aatataaaaa ttagccgggc atggtggcac acaccgtaat   39240
cacagctact caggaggctg aggcaagaga gtcacttgaa ccacaggagg tagaggctgc   39300
agtgagctga gcattgtgcc aatgcactcc agcctgggtg gcagagcaag actccagctc   39360
agaaataaat aatatattat atatatatat atatgtttta tttagatgga atatactata   39420
tatatatgta tatatatatg tatgtatata tatatatgta tgtatatata tatatatata   39480
tatatatata tatatagaga gagagagaga gagagagaga gagagagaca gagtatgtct   39540
gagaatgcat cccgatagtt ctagcaaggt aggaaaagga agtatcataa cagccttgaa   39600
gtagcctgtt gaaacagaca gactctcttg taagagaact cacaaaatct aggattatat   39660
ctcccatgat gaaaaatttg gaactgtaca tttttgttta actgtcactt aaatnnnnnn   39720
nnnnnnnnnn nnnnnnnnnn nnnnnnnnnn nnnnnnnnnn nnnnnnnnnn nccaggaggc   39780
actgtgcttg gcgccttttt accaacactt tgagatggcc attgtactta tccccacttt   39840
atagacggga aaatggaggt ccagcaatat ttttttaactt aaagagccac ccatctcttt   39900
agagaaagag ccagaatccc aggcaggggc tatcttattc cagagcccaa gctctcaaac   39960
acatgataca caatacttaa tctctctcaa gtcagaggag atccacttaa gtatacatcc   40020
atccacatat tcattcattc aatcattcaa caaatattag ttgagcactt accgtatgcc   40080
aaacagtcaa acgtgaatag ctgttacaaa tgagactgtg aaggatggta caacgcagat   40140
tcagacagtg tgataaggaa atattgagaa gcaaagatga gttctggagt gaatttgtaa   40200
aggtggatgt gggcttggat ttcaataatg gcagaactta aggaatctga tgagaagtgg   40260
gcacttcagg cagagagaag agcttgaaca aggctcagag gctgacagtg caggaaacac   40320
atgggaagag ggaatagagt agcggtcaag aattcacaga ggagttatag gtgaagatgc   40380
aaccaagtta cagaccaagg taagataggg gaataccaat cacaatctct tttcccattc   40440
cagaagcatc ccagacacat cctagtaacc gagagacatt tctctccctt tcctcctgtg   40500
gagaataaat aagctattgc aagtccagta agtgtaatca ttttgttcaa attgtgtgcc   40560
cattccccaa tttacaggac tacacacagg agggacaaaa agaatggaga ccacaaccac   40620
agctctgaag accaccacca cagctctgaa gaccacttcc agagccacct tgaccaccag   40680
tgtctatact cccactttgg gaacactgac tcccctcaat gcatcaatgc aaatggccag   40740
cacaatcccc acagaaatga tgatcacaac cccatatgtt ttccctgatg ttccagaaac   40800
gacatcctca ttggctacca gcctgggagc agaaaccagc acagctcttc ccaggacaac   40860
cccatctgtt ttcaatagag aatcagagac cacagcctca ctggtctctc gttctggggc   40920
agagagaagt ccggttattc aaactctaga tgtttcttct agtgagccag atacaacagc   40980
ttcatgggtt atccatcctg cagagaccat cccaactgtt tccaagacaa ccccaatttt   41040
tttccacagt gaattagaca ctgtatcttc cacagccacc agtcatgggg cagacgtcag   41100
ctcagccatt ccaacaaata tctcacctag tgaactagat gcactgaccc cactggtcac   41160
tatttcgggg acagatacta gtacaacatt cccaacactg actaagtccc cacatgaaac   41220
agagacaaga accacatggc tcactcatcc tgcagagacc agctcaacta ttcccagaac   41280
aatccccaat ttttctcatc atgaatcaga tgccacacct tcaatagcca ccagtcctgg   41340
ggcagaaacc agttcagcta ttccaattat gactgtctca cctggtgcag aagatctggt   41400
gacctcacag gtcactagtt ctgggacaga cagaaatatg actattccaa ctttgactct   41460
```

```
ttctcctggt gaaccaaaga cgatagcctc attagtcacc catcctgaag cacagacaag    41520
ttcggccatt ccaacttcaa ctatctcgcc tgctgtatca cggttggtga cctcaatggt    41580
caccagtttg gcggcaaaga caagtacaac taatcgagct ctgacaaact cccctggtga    41640
accagctaca acagtttcat tggtcacgca tcctgcacag accagcccaa cagttccctg    41700
gacaacttcc atttttttcc atagtaaatc agacaccaca ccttcaatga ccaccagtca    41760
tggggcagaa tccagttcag ctgttccaac tccaactgtt tcaactgagg taccaggagt    41820
agtgacccct ttggtcacca gttctagggc agtgatcagt acaactattc caattctgac    41880
tctttctcct ggtgaaccag agaccacacc ttcaatggcc accagtcatg ggaagaagc    41940 cagttctgct attccaactc caactgtttc acctggggta ccaggagtgg tgacctctct    42000
ggtcactagt tctagggcag tgactagtac aactattcca attctgactt tttctcttgg    42060
tgaaccagag accacacctt caatggccac cagtcatggg acagaagctg gctcagctgt    42120
tccaactgtt ttacctgagg taccaggaat ggtgacctct ctggttgcta gttctagggc    42180
agtaaccagt acaactcttc caactctgac tctttctcct ggtgaaccag agaccacacc    42240
ttcaatggcc accagtcatg ggcagaagc cagctcaact gttccaactg tttcacctga    42300
ggtaccagga gtggtgacct ctctggtcac tagttctagt ggagtaaaca gtacaagtat    42360
tccaactctg attcttctc tggtgaact agaaaccaca ccttcaatgg ccaccagtca    42420
tggggcagaa gccagctcag ctgttccaac tccaactgtt tcacctgggg tatcaggagt    42480 ggtgaccct ctggtcacta gttccagggc agtgaccagt acaactattc caattctaac    42540
tctttcttct agtgagccag agaccacacc ttcaatggcc accagtcatg gggtagaagc    42600
cagctcagct gttctaactg tttcacctga ggtaccagga atggtgacct ctctggtcac    42660
tagttctaga gcagtaacca gtacaactat tccaactctg actatttctt ctgatgaacc    42720
agagaccaca acttcattgg tcacccattc tgaggcaaag atgatttcag ccattccaac    42780
tttagctgtc tcccctactg tacaagggct ggtgacttca ctggtcacta gttctgggtc    42840
agagaccagt gcgttttcaa atctaactgt tgcctcaagt caaccagaga ccatagactc    42900
atgggtcgct catcctggga cagaagcaag ttctgttgtt ccaactttga ctgtctccac    42960
tggtgagccg tttacaaata tctcattggt cacccatcct gcagagagta gctcaactct    43020
tcccaggaca acctcaaggt tttcccacag tgaattagac actatgcctt ctacagtcac    43080
cagtcctgag gcagaatcca gctcagccat ttcaacaact atttcacctg gtataccagg    43140
tgtgctgaca tcactggtca ctagctctgg gagagacatc agtgcaactt ttccaacagt    43200
gcctgagtcc ccacatgaat cagaggcaac agcctcatgg gttactcatc ctgcagtcac    43260
cagcacaaca gttcccagga caaccctaa ttattctcat agtgaaccag acaccacacc    43320
atcaatagcc accagtcctg gggcagaagc cacttcagat tttccaacaa taactgtctc    43380
acctgatgta ccagatatgg taacctcaca ggtcactagt tctgggacag acaccagtat    43440
aactattcca actctgactc tttcttctgg tgagccagag accacaacct catttatcac    43500
ctattctgag acacacacaa gttcagccat tccaactctc cctgtctccc ctggtgcatc    43560
aaagatgctg acctcactgg tcatcagttc tgggacagac agcactacaa ctttcccaac    43620
actgacggag accccatatg aaccagagac aacagccata cagctcattc atcctgcaga    43680
gaccaacaca atggttccca ggacaactcc caagtttccc catagtaagt cagacaccac    43740
actcccagta gccatcacca gtcctgggcc agaagccagt tcagctgttt caacgacaac    43800
```

```
tatctcacct gatatgtcag atctggtgac ctcactggtc cctagttctg ggacagacac   43860
cagtacaacc ttcccaacat tgagtgagac cccatatgaa ccagagacta cagccacgtg   43920
gctcactcat cctgcagaaa ccagcacaac ggtttctggg acaattccca acttttccca   43980
taggggatca gacactgcac cctcaatggt caccagtcct ggagtagaca cgaggtcagg   44040
tgttccaact acaaccatcc cacccagtat accagtggta gtgacctcac aggtcactag   44100
ttctgcaaca gacactagta cagctattcc aactttgact ccttctcctg gtgaaccaga   44160
gaccacagcc tcatcagcta cccatcctgg gacacagact ggcttcactg ttccaattcg   44220
gactgttccc tctagtgagc cagatacaat ggcttcctgg gtcactcatc ctccacagac   44280
cagcacacct gtttccagaa caacctccag ttttttccat agtagtccag atgccacacc   44340
tgtaatggcc accagtccta ggacagaagc cagttcagct gtactgacaa caatctcacc   44400
tggtgcacca gagatggtga cttcacagat cactagttct ggggcagcaa ccagtacaac   44460
tgttccaact ttgactcatt ctcctggtat gccagagacc acagcctttat tgagcaccca   44520 tcccagaaca gagacaagta aaacatttcc tgcttcaact gtgtttcctc aagtatcaga   44580
gaccacagcc tcactcacca ttagacctgg tgcagagact agcacagctc tcccaactca   44640
gacaacatcc tctctcttca ccctacttgt aactggaacc agcagagttg atctaagtcc   44700
aactgcttca cctggtgttt ctgcaaaaac agccccactt tccacccatc cagggacaga   44760
aaccagcaca atgattccaa cttcaactct ttcccttggt ttactagaga ctacaggctt   44820
actggccacc agctcttcag cagagaccag cacgagtact ctaactctga ctgttttcccc   44880 tgctgtctct gggcttttcca gtgcctctat aacaactgat aagccccaaa ctgtgacctc   44940
ctggaacaca gaaacctcac catctgtaac ttcagttgga cccccagaat tttccaggac   45000
tgtcacaggc accactatga ccttgatacc atcagagatg ccaacaccac ctaaaaccag   45060
tcatggagaa ggagtgagtc caaccactat cttgagaact acaatggttg aagccactaa   45120
tttagctacc acaggttcca gtcccactgt ggccaagaca caaccaccct tcaatacact   45180
ggctggaagc ctcttttactc ctctgaccac acctgggatg tccaccttgg cctctgagag   45240
tgtgacctca agaacaagta agaataactt ttttattgtg gtaaaatata aatactataa   45300
aaattgccat tctaaacatt ttaattgtac aactcagcag tactaataca ttcacattgt   45360
tgtgcaaccc tcaccactat ctgttttcaa aacttttttt atcacccaa acaggactga   45420 aggaataatt tcccattccc cattctccct agtgcagtgg tgcaatctcg gctcaccaca   45480
acctctgaac ctctgtctcc tgggttcaag caattctcct gcatcagcct cctgagtagt   45540
tgggactaca ggtgcacgcc accgtgcctg gctaattttt gtatttttag tacagacagg   45600
gttttaccat gttggtcagg ctggtctcaa actcctgacc tcaggtggtc cacacgcctt   45660
ggcctcccaa agtgctggga ttacaagtgt gagacactgt gcccggccat atctgttaga   45720
tcttactaat cctgtcaaga ggattcagtg tccttttttt ttttctttc ttttttttga   45780 tagagtctcc ctctggcacc caggctggag tgcagtggta cggtcttggc tcactgcagc   45840
ctccacctcc cagactgaag cgattctcct gcctcagcct cccgaatagc tgggactaca   45900
ggcgcgtgcc accacgccca gctaattttt gcatttttag tagagatggg atttcactat   45960
gttggccagg ctggtctcaa actcctgatc tcaagtgatc cgcccaaggg cctcccaaag   46020
tactgggatt acaggtagga gccacctcac ctggccctat tttcggaatg gatttttttt   46080
taatgtttaa aatgtcacct aagattattg tgaaagatcaa ataagataaa atcctaataa   46140
cccaagtaaa ccacagggct ccacttggac cagtctcaga agtttcaaga aaatcagtca   46200
```

```
gaccatcaaa tgtaaaataa gtctaaattt tctttgcact attcacagag tgccaaagag    46260
gatctaattc atgtttcaga acatacccta cttactaaaa tcccctttc ctcatttctt    46320 ctcattctgc aactttatca tctcctgcgg acccctagc ctctcccctc cccatagtca    46380
gtctctctct ctctctttcc ctcccctctt attatctcaa tttcacacga aagaattcca    46440
gaaactatac tgccaaaagt ctttcctgtc tttgaaaagt tgggaaagag gagaaactca    46500
gacagcaatg acaaaattat acgtaatgga tgaaggaaac acaaataagg ctggaaacag    46560
aaaattttgt ccccatcatt tatttaatga aggtggcagt attccagcca catagtgaac    46620
ccccacaata agaaggggcc tctggcgatt gattattgtc attgttgtta atgataatga    46680
gggtgaggat atcatgagca tcagtgtagg aggcagttaa ctaataagac caagctgttg    46740
gctgggcgtg ctggttcaca cctgcagtcc cagcactttg ggaggccaaa gtgggtggat    46800
cacttgaggt caggagttca agactagcct ggccaacatg gtgaaacctg gtctctacca    46860
aaaatacaaa aattagtcag gtgtggtggc gtgtgcctgt aatgacaact acttgggagg    46920
ctgaggcagg agaatcactt gaacctggga ggcggaggct gcagtgagat gagcttgaac    46980
cactgcactc cagcccgggc aacagagaga gactcttgtc tcaaaaaaca aaacaaacaa    47040
acaaaaacta aaccaaacaa aaaaagacta gctgttattc atttatttat ttatttattt    47100
agagacggag tctcgctctg tcacccaggc tggagtgcag cggcacaatc ttggctcact    47160
gcaacctctg cctcccaggt tcatgtgatt ctcccgcctc agcctcccca gctgttgtta    47220
ttcatgaatg aacctcagag aaagcacaca ggagggttgg tgcacctgtg ttttgagttc    47280 taccctcct tcctctctta acttcctcct gtcttctcac tctgattcgt tcttccttcc    47340
tctccctctc tctctgcagg ttataaccat cggtcctgga tctccaccac cagcagtgag    47400
taaacatggc cctgaagtcc ctatgccctg ggaattcttc ctccctaagc ctgccttcca    47460
ggaggaaagt atcccccatt ccctaggttc tcatccccac agaaactcca gaatagcaaa    47520
agtctcaggc tgagccaagg cacagatgcc agtgctcacc aagagtccta ttctcccctc    47580
gctaaatgat aggacccaac aaacccgatt cacgctgcgt tttcttcag ctccgatgac    47640 ctccatgttc tctccaaggc ctctcgtatc tgtgagcccc accccagcg ctacaggtag    47700 gaatctggct tccagctccc atgaaacgtc ggctgccatt cagtggctga ttaattgctg    47760
tgtggtctga gtcctgatgc ccaccaagtc tcagcgtgtt cccctctgtc caatctcatc    47820
caacaattta agctaatgct tgtttaatga tgtcctcact ataccacctt ggacactttc    47880
tttttgcctg gatttaaagc ttccatttct ttccttcctt ccttcttttc ttccttcctt    47940
ccttccttcc ttccttcctt ccttccttcc ttccttcctt ccttccttcc tccttccttc    48000
cttcttttct tcctttcttc ctgtcttttt ctttctttcc ttcttttggc agagtctcac    48060
tctgtcgccc aggctggagt gcaatggtgc aatctcggtt cactgcaacc tctgcctccc    48120
aggttcaagc gattctcatg ccacatgcca ctatgcctgg ctaattttttg ttttttttgtt    48180 ttttgggggg tttttttgaga cagagtctca gtctgttgcc caagctggag tgcagtggca    48240
tgatctcggg tcactgcaac ctccttctcc caggttcaag cgattttcct gcctcagcct    48300
cctgagtagc tggaactaca ggcacgcacc atcacaccgg ctaattttttt gtgttttttag    48360 tagagacgac ggttttgcaa tgtgggccag gcttgtctcg aactcctgac ctcaagtgat    48420
cctccagcct cggcctctca aagtgctggg attacaagtg tgagccactg caccaggcca    48480
aaaacttgta tttcaatagt cattgaggct gggtgcagtg gctcacgcct gtaatcccag    48540
```

```
cactttggga ggctgaggcc agtggatcat gaggtcagga gatcaagacc accctggcta    48600
acacagtgaa accccatctc tactaaaaat acacacaaaa attagccggg catggtggca    48660
agatgcctgt agtcccagct actcaggagg ctgaggcagg agaatggcgt gaacctggga    48720
ggcagagctt gcagtgagcg gagatcgcac cgctgcactc cagccgggc aacagagagc     48780 gactctgtct caaaaaaaaa aatatatata tatatatata tatattcatt gagaccgact    48840
ctgacttaaa agcagtaatg aatggtgtag gttttggtaa attacaggtc ttgctttaag    48900
tcctggtcct ctcttttgct cactgtgtgg ccccggaaga gccatgtaac ctctccaggc    48960
ttcagtgtcc attttagaa cggagtaagt gaataagctg tgtccaatca tctctggcca     49020
tatcagcttc attttttttt tcctccaggg tccaaacatc cctccaccct cagagtcttt    49080
gcacctggtg ttcttgtcct tcaaatctca gcttggatca cctttataa agtagcattt     49140 cccccgtata cgcatcttgc acacagccaa tctctattct acctctatgc tcacttcctt    49200
cctggcaatt attactacag ctgggcccctt gaacagcatg agggttcagg gtgctgaccc    49260
ctatgcattc aaaaatccac ataaacttt ttttttttg agatggagtt tcacacttgt      49320
tgcccaggct ggagtgcagt ggcgccatct tggctcactg caaactctgc ctcctgggtt    49380
caagtgattc tcctgcctca gcctcctgag tagctgggat tacaggcatg tgccaccatg    49440
cccagctaat tttgtatttt tagtagagat gaggtttctc catgttcgcc aggctgctct    49500
tgaactcctg acttcaggtg atccgcctgc cttggcctcc caaagtgctg ggattacagg    49560
catgagccat gatgcccggc catttgctaa tggcatctag taagtagagg ccagagatgt    49620
tgcaaaacat ccaacaatgc acaaagcagc ctcctatcaa aacacattat ccagaccaaa    49680
atgtcaatag gctgaggtt gagcatctgc tgtacacaga ttccaagttc tggtacaaat      49740
ctcgtagttc tctgagggct catctttcaa tgcctagcac atcaaaggag gccaatttcc    49800
tcttcccttt cacctcctgg tatgaaatgt ttcctcctcc accttgatcc tgtaagagcc    49860
cagctggagt ttgcagacga cggggaaaga aatgggtgag ggagggtcct atggttgagt    49920
ctccgcagtg ggccctgggt gccagttca ccctcctccc cttcattttc tccatcatga      49980
caactcaagg caaattctca gtttccatgg gccagtggaa tccactgact tcatgaaata    50040
accccaccct gagcaaatac ccctcaaata ataactgttt acacaacatc agtggcaaca    50100
atgacccaag cagcaatgcc accaccagaa tagcaaccat aacagcagct catttcatc     50160 aaaaggaaac tgtagggcca ggcacagtgg ctcacaccta tattcccagc attttgggag    50220
gctgaggcag gcagatcacc tgaggtcagg agttcaagac cagcccagcc aacatggtga    50280
aaccccatct ctactaaaaa tacaaaaact agccaggctt ggtggcatgt gcctgtaatc    50340
ctagctactc gggaggctga ggcaggagaa ttgcttgaac ctgggaggca gaggttgcag    50400
tgagctgaga ttgtgccact gcactccagc ctgggcgaca gagcaagact ccgtctgaaa    50460
aaaaaaaaaa aaggaattgt gccaggaatt gtgatgagaa ctttatatgc attatctcct    50520
attaatatta cccaaacctc cgtgagttac tatactcatt tctacagaga gcatttatgc    50580
atccagggag gaagtaatta gcccagaatt actcagttat gacacaggac agtatgaaaa    50640
ctccaaccga agattggaga ctcatgaaaa ctccaggctc ctaactacaa gacatcactg    50700
tggatcgtcc aaatagagca agccccaatc tcaggacagg aatgaggcat gaatggcctc    50760
tatgctaatg atctaaccta atgctgaatt tgttacttcc cttctgaatc cacttggaga    50820
tttcctttat atctgacttg aaatagagga tatatactcc tctatccttg acataggaga    50880
taatacacag aaagtatttc attgtagtat caagtacaca tcctgttctg tgtccatagg    50940
```

```
attatgacta atttagggca tggcttaaca gtgtggtact attgaatgac agacagatgt   51000
ctgttttgtt ggatgcagga caagccatgt aacctcccca gactttagtg tcccctctgt   51060
ggaatggaat aaaaatacta cgtgggattg ttctgataat caaatgagat aattcaggaa   51120
caacccagat aaataacagg gctgccctgg gttctgtctt tccttgtatc tctcacagag   51180
cctcaaagga gatgcaatcc atgacctaga gaaacactca ggacaaattc tcttttcccc   51240
agttcctttc ttgctccaat ggcaacacca cccctctcat cctgaagtct cttgttttta   51300
ccaccacacc tattttgcca aattttctcc aatattccaa accatatgaa acctttcttt   51360
cttcttttc tttccttcct ttccttcttt cttctttttt tctcttcttt tcttttcttt   51420
ttgagacatg gtctcactct gttgcacagg ctggagtgca atggcacgat ctttgctcac   51480
tgcaacctcc gcctcccagg ttcaagagat tctcttgcct cagcctcctg agtagctggg   51540
attacaggcg cccaccgcca cgccacgcta attttgtgt tcttagtgga gacggggttt   51600
cgccatgttg gccaggctgg tcttgaactc ctgacctcaa gtgatttgcc catctcggtc   51660
tcccaaagtg ctaggattac aggcgtgagc caccaagccc ggccccatat gaaccgtttc   51720
tatccctcat ttctctgtac ttttacctaa aaacaccact cccttcaccc atcacatttt   51780
tgtcaattct acatcacaca cacacacaca cacacacaga gaaagtaagt   51840
tggaaaaaaa ttatactatc atgaaatttt gtgaaaggag gtaagctgag agagtaagaa   51900
tcaaactaaa ttatctttat gggtagaaag cacactcatc catacatgtg tctttccacc   51960
cttgtaatgt atttattatt attgtttgta tatactagat tcccaataaa tagggacagc   52020
tattatggta ttttttatttc aggaataata atagtgatga tttccaccat tattgtcaaa   52080
ggacaaagca caaatatgt accaaataaa atatagccat tatcctttat tcacaaaaga   52140
tcttggcccc acctcttctc aatgaaatgt ccatgacttg ttcaactttg gccactctgg   52200
gctgagagat ggaggttccc ttgcgagctg aagtcacaca tcgaaggtgg aagcccctcc   52260
cctccctctg gctggctgag ggatagccca gatgggctca tcatgaaagt ttcccattat   52320
ttccatttct ggatctacca tcttcccctc ccctacctct cacccatcat aattgtcctt   52380
ctttactctt tcctccctat ctgcaggtta taaccgtcgg tactgaccc ctgccaccag   52440
cagtgagtat tcaaacctgt gatattccaa tgcccttggg acccttcctc cccaaggtgc   52500
attcctcaga agagaaactg atcattctcc ctccctacgt gcccagccac agcctcagag   52560
cagcccctaa cccgtcaagg tcttggtgtg agtcaagata gaagtccaaa ttccaatgag   52620
cagttcctgt cccatattcc tttaggaaga cacccaatca tttctccatg ttcttttttt   52680
ctcagctcca gtgacttcta cattctcccc agggatttcc acatcctcca tccccagctc   52740
cacaggtagg aagctcctct ctggcatcta tgaaatttaa cactgcatgg tctgttccct   52800
gctgaccacc cagactcagc ctgttccact cgccctctca ctctctctct ctctcttttt   52860
ttttttttt ttttttttt tttacggagt cttgctctgt cacccaggct ggagtggaat   52920
ggtgtgatct cggctcactg caaccttcgc ctcccaggtt cacgtgattc tcctgcctca   52980
gcctccggag tagctgggat tacaggtgca caccaccatg cctggctaat tttttgtatt   53040
tttagtagag acggggtttc accatgttgg ccaggctgg cttgaactcc tgacctcaag   53100
tgatctaccc accttggcct cccaaagtgc tgggattata ggcatgagcc accacgccag   53160
gcccactctc taaattttga ccaccctgcc ttgagtggtc ttctagcacc ctaacctctg   53220
tctaacctcg agagctttgc actagcgatt cctggggacc agctatggtt ggtatcttct   53280
```

```
caactttcta attttttaa aattattatt attattatta ttattttaaa tggagtctcg   53340
ctctgtcacc caggctggag tgcagtggca ccatctcggc tcattgcaac ctctacctcc   53400
cgggttcatg caattttcct gcctcagcca gaaattttct cagtggtcga gattgtgcca   53460
ctgcactcca gcctgggcaa tggagctagg ctccatctca aaaaaaaaaa aaaaaagacg   53520
gaggtcgggc attcctaacc cttaaccctg ccttgtgatt ctggagttat gagatagaac   53580
ctggtgtccc gtaattaaaa ttccgccttc aggccttatg ttttgtgagt cacaacactg   53640
caaactttt acatgctgta gacaggatgt tcactctcca cttcctcact gctctgctct   53700
aatcaattca accatttatg tgacatgcct aaccctctg ggcttgtacg tatgtaacat   53760
gtattacaaa gcaagtcatt ccatgatcaa tgctgtcact ttttctaggt gctttcaaaa   53820
tttgttcttc atcattgatt ttcagtagtt tgattacgat gtgtctgggc atggttttct   53880
ttgagtttat cctgcttaaa gtgttctcag cttcttgagt ctcaaagtgt ttattttctg   53940
ctctgattct ttctccctt cggacctcca atgaaatgat gttgcccgaa gagaccctga   54000
ggttctgttc attttgttat ttatcaatct tttttcctct ccgaatttca ggtttaataa   54060
tttttttttt tttttgaga cggagtctcg ctctgtcgcc caggctggag tgcagtggcg   54120
cgatctcggc tcaccgcaag ctccgccccc tgggttcacg ccattctcct gcctcagcct   54180
ccggagtagc tgggattaca ggcacccgcc accatgcccg gctaatttt tgtatttttt   54240
agtagagacg gggtttcacc gtattagcca ggatggtctc aatctcctga cctcgtgatc   54300
cgcccgcctc agcctcctaa agagctggga ttacaggcgt gagccactgc gcccggccca   54360
ggtttaataa ttttttataga atattttcac aatcaccaag ccttttctct accagctcca   54420
ttctgcccat ccattgaatt cttttatct cagttacttt atgtttcagt tcgaaagttt   54480
ctacttggtt agatagatag atgttatatc atatattata tgttatataa aaatatattt   54540
atggttatac ataacata tatgttatat atagttattt atatagccat aactatatat   54600
agccatatat atagttatat ataaccatat atatagttac catatagtaa ccacatatat   54660
aaaacatata tatagtgt ctctctatat atagttatat atatagtttc tatatctgta   54720
actatatata gttatatatg tatgtttctc tgtatataaa tatatatatt tctatatata   54780
tagttataca cattatatat ataactggga gatgttggta aaggatggcg tgaggaaacc   54840
tggagcagtc atggtaatcc tcgctctgct ccgaactcct caagagcagg agaagggtcc   54900
tcctcattct ccagccatgt tgactttgag caatttactc atcctctcag tacctcagtt   54960
tcctcacctg ccaattgagg ataataatat ttcataaatt gtttgcaaat gttatatgca   55020
actctacgta agaacaccta gcacaggggc taccagggaa tttggtttaa caaatattta   55080
tcaggcacct attctgggct gggcaggggg gataagatgt tgactaagtc aaatgcagtc   55140
cctcccctca ccaagtttac agtgtattgg gcaagactga aatggaacaa gcaattacaa   55200
ttgacaataa aagacaacca agttattgag cacttactat atggcatgcc atatgctatg   55260
tattttttt attttaact tttcattttg aaataaataa taaatataaa gtaaataata   55320
atataaataa ataataaata acttttcatt ttgaaataaa taataaataa attcaggaga   55380
tgttgcgaaa atagtgtagc attccctgt atccttcacc cagtttctcc ccaatggcta   55440
catcttacat aactctaata caatatcaaa agcaggaaac tgacattgtt aaaatccatt   55500
ttactggttt tacacgcgtg tgtgcatatg tgagcttgtg tatgtgcgtg tgtgtgcagg   55560
catgtgtgtg catgcacgcc tgtgtgtgca tatgtgcatg tgtgcatgcg tgtgtgcatg   55620
tgtgcatgtg tgtgtgcatg cgtgcgtgcg tgcgtgcatc tgtgtgcatg tatgcacatg   55680
```

-continued

```
tgtgtgtgtc tgtgcacgtg tgtgcatgca tgtgtgtgtg cgtgtgtgtt ggtagcccta    55740
tgcaattttt atcacatggg catagcccta taatcaccac caccatcaag attcagaact    55800
gttccattcc cccaaagatt cccctcatgc tagccttcgt aatcatgccc actgagccca    55860
acactattgc atagaatagc tattctactc tccatctcca tctctgtctc tacaattttc    55920
ttttgaagat gttatataaa tggaaatgta caacatgtca cctttgaaat tggcttcttt    55980
tccactcagt gtaatgccct ggagatgtgc tcttttttaac agtcatgtaa ccttcctaat   56040
ttccctccaa aatatcatta tgcccctcgc cgccttttt tttttttttt tttttgaga     56100
cagagtctcg ctctgttgcc caggctggag tgcagtggta taatctcagc tcactgcagc    56160
ctccgtctcc cgggttcaag ggattcccct gcctcagcct cccaagtagc caggattaca    56220
agtgcatgcc accacgcctg gctaattttt gtattttag tcgagacggg gtttcattgt     56280
gttggccagg ctggtctcga attcctgacc tcaagtgatc tgcccgcctt ggcctcccaa    56340
agtgctggga ttacaggtgt gagccaccgc gcccgaccca tattgcccat tgtattacag    56400
cggaagaaac tgaggtatgg acaggtaaca tgtccatggt cacttggctg gtgaggggca    56460
gagaggagat ttgaaaccaa atctgactca ctagtgtggc cgtaaccatg gtaactatgt    56520
ctctctacca tgtggtctcc tctttattaa aggaagggca agttctggga gttttgggag    56580
ttttgggctt gagtggggaa gggtagccaa gtaaagcagg tgagagaagg tctgctttaa    56640
ggactgctgt ttgattttta ttgttgttgt tcagtgttca atgggattga gttgactctt    56700
ttttcccttc ttgttcccca aagcatgaga ctgttccggt cctttccct tttaacttct      56760
cagctagagt ttgttagggc gggtatgggc acctggcaga gtctgagacc tcagcttcca    56820
gtaggcacac gttctgaccc aatacaccta ccctggtccc ctaacctgct tctggtcccc    56880
taacctgctt ctgggcccag gtaatgcatt ttaggaacat cccactttc tccttacctg      56940
gctttccatt atccgtccaa actaaagcac ccacctgtct gcttcagact cttgcttcaa    57000
gcactccgtc tgggtcctca gaaattgact tacagtcagt tcagatctga ctcaggcgtg    57060
gccttctttt ctccttcctt gc                                             57082
```

```
<210> SEQ ID NO 2
<211> LENGTH: 42348
<212> TYPE: DNA
<213> ORGANISM: Homo sapiens
<220> FEATURE:
<221> NAME/KEY: misc_feature
<222> LOCATION: (1)..(130)
<223> OTHER INFORMATION: Exon R1
<220> FEATURE:
<221> NAME/KEY: misc_feature
<222> LOCATION: (442)..(510)
<223> OTHER INFORMATION: Exon R2
<220> FEATURE:
<221> NAME/KEY: misc_feature
<222> LOCATION: (2126)..(2250)
<223> OTHER INFORMATION: n is a, c, g, or t
<220> FEATURE:
<221> NAME/KEY: misc_feature
<222> LOCATION: (5479)..(5652)
<223> OTHER INFORMATION: Exon R3
<220> FEATURE:
<221> NAME/KEY: misc_feature
<222> LOCATION: (6301)..(6334)
<223> OTHER INFORMATION: Exon R4
<220> FEATURE:
<221> NAME/KEY: misc_feature
<222> LOCATION: (6593)..(6657)
<223> OTHER INFORMATION: Exon R5
<220> FEATURE:
```

```
<221> NAME/KEY: misc_feature
<222> LOCATION: (7558)..(7683)
<223> OTHER INFORMATION: Exon R1
<220> FEATURE:
<221> NAME/KEY: misc_feature
<222> LOCATION: (8216)..(8284)
<223> OTHER INFORMATION: Exon R2
<220> FEATURE:
<221> NAME/KEY: misc_feature
<222> LOCATION: (8877)..(9050)
<223> OTHER INFORMATION: Exon R3
<220> FEATURE:
<221> NAME/KEY: misc_feature
<222> LOCATION: (9380)..(9413)
<223> OTHER INFORMATION: Exon R4
<220> FEATURE:
<221> NAME/KEY: misc_feature
<222> LOCATION: (9675)..(9739)
<223> OTHER INFORMATION: Exon R5
<220> FEATURE:
<221> NAME/KEY: misc_feature
<222> LOCATION: (10082)..(10200)
<223> OTHER INFORMATION: n is a, c, g, or t
<220> FEATURE:
<221> NAME/KEY: misc_feature
<222> LOCATION: (10201)..(10291)
<223> OTHER INFORMATION: Exon R1
<220> FEATURE:
<221> NAME/KEY: misc_feature
<222> LOCATION: (10524)..(10592)
<223> OTHER INFORMATION: Exon R2
<220> FEATURE:
<221> NAME/KEY: misc_feature
<222> LOCATION: (11200)..(11373)
<223> OTHER INFORMATION: Exon R3
<220> FEATURE:
<221> NAME/KEY: misc_feature
<222> LOCATION: (11722)..(11755)
<223> OTHER INFORMATION: Exon R4
<220> FEATURE:
<221> NAME/KEY: misc_feature
<222> LOCATION: (12016)..(12036)
<223> OTHER INFORMATION: Exon R5
<220> FEATURE:
<221> NAME/KEY: misc_feature
<222> LOCATION: (12037)..(12150)
<223> OTHER INFORMATION: n is a, c, g, or t
<220> FEATURE:
<221> NAME/KEY: misc_feature
<222> LOCATION: (12169)..(12295)
<223> OTHER INFORMATION: Exon R1
<220> FEATURE:
<221> NAME/KEY: misc_feature
<222> LOCATION: (12532)..(12600)
<223> OTHER INFORMATION: Exon R2
<220> FEATURE:
<221> NAME/KEY: misc_feature
<222> LOCATION: (13219)..(13392)
<223> OTHER INFORMATION: Exon R3
<220> FEATURE:
<221> NAME/KEY: misc_feature
<222> LOCATION: (13723)..(13756)
<223> OTHER INFORMATION: Exon R4
<220> FEATURE:
<221> NAME/KEY: misc_feature
<222> LOCATION: (14016)..(14077)
<223> OTHER INFORMATION: Exon R5
<220> FEATURE:
<221> NAME/KEY: misc_feature
<222> LOCATION: (15001)..(15126)
<223> OTHER INFORMATION: Exon R1
<220> FEATURE:
<221> NAME/KEY: misc_feature
<222> LOCATION: (15367)..(15435)
<223> OTHER INFORMATION: Exon R2
<220> FEATURE:
<221> NAME/KEY: misc_feature
<222> LOCATION: (15475)..(15601)
<223> OTHER INFORMATION: n is a, c, g, or t
```

```
<220> FEATURE:
<221> NAME/KEY: misc_feature
<222> LOCATION: (15648)..(15773)
<223> OTHER INFORMATION: Exon R1
<220> FEATURE:
<221> NAME/KEY: misc_feature
<222> LOCATION: (16002)..(16070)
<223> OTHER INFORMATION: Exon R2
<220> FEATURE:
<221> NAME/KEY: misc_feature
<222> LOCATION: (16653)..(16826)
<223> OTHER INFORMATION: Exon R3
<220> FEATURE:
<221> NAME/KEY: misc_feature
<222> LOCATION: (17158)..(17191)
<223> OTHER INFORMATION: Exon R4
<220> FEATURE:
<221> NAME/KEY: misc_feature
<222> LOCATION: (17453)..(17517)
<223> OTHER INFORMATION: Exon R5
<220> FEATURE:
<221> NAME/KEY: misc_feature
<222> LOCATION: (17866)..(18531)
<223> OTHER INFORMATION: n is a, c, g, or t
<220> FEATURE:
<221> NAME/KEY: misc_feature
<222> LOCATION: (18532)..(18657)
<223> OTHER INFORMATION: Exon R1
<220> FEATURE:
<221> NAME/KEY: misc_feature
<222> LOCATION: (18658)..(18887)
<223> OTHER INFORMATION: n is a, c, g, or t
<220> FEATURE:
<221> NAME/KEY: misc_feature
<222> LOCATION: (18888)..(18956)
<223> OTHER INFORMATION: Exon R2
<220> FEATURE:
<221> NAME/KEY: misc_feature
<222> LOCATION: (18957)..(18995)
<223> OTHER INFORMATION: n is a, c, g, or t
<220> FEATURE:
<221> NAME/KEY: misc_feature
<222> LOCATION: (19633)..(19806)
<223> OTHER INFORMATION: Exon R3
<220> FEATURE:
<221> NAME/KEY: misc_feature
<222> LOCATION: (20093)..(20140)
<223> OTHER INFORMATION: n is a, c, g, or t
<220> FEATURE:
<221> NAME/KEY: misc_feature
<222> LOCATION: (20141)..(20176)
<223> OTHER INFORMATION: Exon R4
<220> FEATURE:
<221> NAME/KEY: misc_feature
<222> LOCATION: (20177)..(20386)
<223> OTHER INFORMATION: n is a, c, g, or t
<220> FEATURE:
<221> NAME/KEY: misc_feature
<222> LOCATION: (20387)..(20449)
<223> OTHER INFORMATION: Exon R5
<220> FEATURE:
<221> NAME/KEY: misc_feature
<222> LOCATION: (20450)..(20483)
<223> OTHER INFORMATION: n is a, c, g, or t
<220> FEATURE:
<221> NAME/KEY: misc_feature
<222> LOCATION: (21609)..(21731)
<223> OTHER INFORMATION: Exon R1
<220> FEATURE:
<221> NAME/KEY: misc_feature
<222> LOCATION: (21940)..(22008)
<223> OTHER INFORMATION: Exon R2
<220> FEATURE:
<221> NAME/KEY: misc_feature
<222> LOCATION: (22605)..(22778)
<223> OTHER INFORMATION: Exon R3
<220> FEATURE:
<221> NAME/KEY: misc_feature
<222> LOCATION: (23109)..(23142)
```

```
<223> OTHER INFORMATION: Exon R4
<220> FEATURE:
<221> NAME/KEY: misc_feature
<222> LOCATION: (24607)..(24700)
<223> OTHER INFORMATION: n is a, c, g, or t
<220> FEATURE:
<221> NAME/KEY: misc_feature
<222> LOCATION: (29046)..(29168)
<223> OTHER INFORMATION: Exon R1
<220> FEATURE:
<221> NAME/KEY: misc_feature
<222> LOCATION: (29266)..(29334)
<223> OTHER INFORMATION: Exon R2
<220> FEATURE:
<221> NAME/KEY: misc_feature
<222> LOCATION: (30368)..(30450)
<223> OTHER INFORMATION: n is a, c, g, or t
<220> FEATURE:
<221> NAME/KEY: misc_feature
<222> LOCATION: (33917)..(34090)
<223> OTHER INFORMATION: Exon R3
<220> FEATURE:
<221> NAME/KEY: misc_feature
<222> LOCATION: (35192)..(35259)
<223> OTHER INFORMATION: n is a, c, g, or t
<220> FEATURE:
<221> NAME/KEY: misc_feature
<222> LOCATION: (36702)..(36734)
<223> OTHER INFORMATION: Exon R4
<220> FEATURE:
<221> NAME/KEY: misc_feature
<222> LOCATION: (38270)..(38320)
<223> OTHER INFORMATION: Exon R5
<220> FEATURE:
<221> NAME/KEY: misc_feature
<222> LOCATION: (39104)..(39224)
<223> OTHER INFORMATION: Exon R1
<220> FEATURE:
<221> NAME/KEY: misc_feature
<222> LOCATION: (39315)..(39383)
<223> OTHER INFORMATION: Exon R2
<220> FEATURE:
<221> NAME/KEY: misc_feature
<222> LOCATION: (39532)..(39705)
<223> OTHER INFORMATION: Exon R3
<220> FEATURE:
<221> NAME/KEY: misc_feature
<222> LOCATION: (41862)..(41992)
<223> OTHER INFORMATION: Exon R4

<400> SEQUENCE: 2
agcagccaca gtcccattca tggtgccatt caccctcaac ttcaccatca ccaacctgca      60
gtacgaggag gacatgcggc accctggttc caggaagttc aacgccacag agagagaact     120
gcagggtctg gtgagagccc cgccaccgt actcctccct cgcccactta gacaaaccag      180
cccacctcac actgcctcgc ccactgatgc cagccacgcc cacctcatcc aaccccagac     240
acctttccct gccccaccca ctgattttag ccaagcccac ctcaccccac ccagcctact     300
gatgccagcc acgcccacct ttccctgccc cgcccactga tttcagccac gcccacctca     360
ccctggtcca cccctccaat gccccactct tcctggcttc ccgcagctgt tgtttctcac     420
ctcccctctc cttccttgca gctcaaaccc ttgttcagga atagcagtct ggaataccte     480 tattcaggct gcagactagc ctcactcagg tgagacgctc cttaagaaaa acacagccca     540
acaggtgaat atgaccctag tctctgggct ccctgactct gttcatactt ggaacaacta     600
ttgcccatgg atactaagca tcaccaccag cagcagcaga taactattcc taagacccaa     660
ggcactgcat tatgtacttt atatttaatg cctcatcagt gcttgcaaca gcctcatgaa     720
gcaggagcag aaggggaaac tgaggcccag attaagtggc ttgtgccagg acacacaaag     780
caactgcagc acttcaggtt ctatatccaa actcctatcc cttaggtggc acttcctcct     840
```

```
ctgcccccat tatgaacttg cagcatgtgg aaaaccccaa tctgacttcc ctctaaggga      900
acttgcccag agaatctaag aggggaggaa aggaaggcgt tcagcccctta caggcaggag     960 gtcagctcct gagtggctca gatgcagcca cagagggcct ggccggtctg agggtgactg    1020
agaggcaccg agggcactgt ccctgagtgc tggaaagggc aggtctttta gggtagacag    1080
cggttgatat catttcctgc ctggcattct caccttccac acctctctca cagaatctcc    1140
aagtgtggct ctcccaagag agagtgtcag tcatctacct ccagcttcct ttccttccca    1200
gggggaagag gggacagggg ggccctagtg gctaagagca ttggtgaact caggcagacc    1260
tcagttctga accaacccag ctctgccatt tactatctgt gactctgagc aagtgcctga    1320
agccttctgt gccctatttc ctgacatatt atatatataa aatacatata ttatatatag    1380
acatatttta tatacatatt gaggcatatt ttataaacat gtttatagac acattttat    1440 atgcatatgt tatatacgta tataacatat gttatatata atgtatatat tatacatatt    1500
gttatattgt atacatgtta tatatgttat agcatatata gtacaagtta tatataacac    1560
atacattatg ttacatataa tgtatatgtt atatatgata tattatatat aattatatat    1620
tatataaaac tgttatatat aattatatat aatatatagt tgttatatat aattatataa    1680
ttgttatata ttatatacaa catataacat acattatata ttgttatata taatataata    1740
tatacatata taacatatgt ataacttta tgttatacat aatgtatata acatatatgt    1800
gtatgtgtga tgtacataac atatctgaca ttaacatata acatatgata taacaatatt    1860
atatgttata acataatata tgttataata taacaatatt atatgttata acttatactg    1920
tcatatgtaa catatacata atattttata aatcagttta atatacatta tgttacatat    1980
aatgtatgtt atatatgata tattatatat aattatatta tacataattg ttatatataa    2040
tgcatacatt gtatttgtta cgtattatat gcaacatatg gggatcctct agagtcggac    2100
cagcggcagc agctgcctgc cttttnnnnn nnnnnnnnnn nnnnnnnnnn nnnnnnnnnn    2160
nnnnnnnnnn nnnnnnnnnn nnnnnnnnnn nnnnnnnnnn nnnnnnnnnn nnnnnnnnnn    2220
nnnnnnnnnn nnnnnnnnnn nnnnnnnnnn atatacatac ataacatatg tataacttat    2280
atgttatata taagtatata acatatatgt gtatgtgatg tatataacat atctgacatt    2340
aacatataac atatgttata atatgacata ttatatatat tacatataac gtatatcatg    2400
tataatataa tgtgtatata taatatatta aagtatataa gtataaatac atgtaatatt    2460
taaatatata ttatatatag tatacatgtg gatacataca acttctacat atacctagta    2520
tatattctat atataaacag tccatgaatt acaatgattc aacttatgat ttttcaaact    2580
ttgtgataat gccatagcaa tatgcattca gtagaaagca taccttcaac acccatgcaa    2640
ccattctgtc attcactttc agtacaatat tcaataaatt atatgagata ttcaacagtt    2700
tattataaaa taggctttgt gttaggtgat tttgcccaca tgtaggctaa tgtaagggtt    2760
cagagcatgt ttaaggtagg ataggctaac ctatcatgtt ctgtaggtta ggtatagtcg    2820
atttttattt ttatttttat ttttgagaca gagtcttgct ctgtcaccca gactggaatg    2880
cactggtgcg atcatagctc actgcagcct tgaactcctg ggctcaagtg atcctcctac    2940
ctcagcctcc tgagtagctg ggactacagg tgtgtgccac cacacctggc tatttttttt    3000 ttaattttt tttttttgtg gagaggaggg tcttgccatg ttgcccaggt ggccttgaac    3060
tcctgggctc aaggaatcct cccaccttgg cctcccaaaa tcctgggatt acaggtgtga    3120
gccatcacgc ccggctacag ggcattttg acttatgaca ttttcagttc acaatggatt    3180
```

```
tgtcagggct gggcatgatg gctcacacct gtcatcccag cactttggga ggctgaggca    3240
ggtggatcac ttgaggccag gagtttgaga ccaggctgtc caaatggcaa aatcttgtct    3300
ctactaaaaa tacaaaaatt agccaggcgt ggtgtgacaa ctgtagttcc agctactcgg    3360
gagactgaag cgtgagaatc acttgaactt aggagatgga agttacagtg agtcaagatc    3420
acaccaccgc actccagcct ggatgacaga gcaagactct tgtctccaaa aaacaaaaaa    3480
caggctgggt gcatggctca tgcctgtaat cccagcagtt tgggaagctg aggcaggttt    3540
atcacctgag gtcagtagtt cacgatcagc ttggcaaaca tggagaaaac ccatctctac    3600
taaaaataca aaaattagct ggatgtggtg tgggtacct gtagtcccag ctactcggga    3660
ggctgaggca ggagaatgga ttgaacctgg gaggcagagg ttgcagtgag ccaagatcac    3720
accattgaac tccagcctgg gcaacagagt gagactccat ctccaaaaac aaaagaaagc    3780
aaaaacaaaa aaataaaata aaaaacctgt gtttatcagg acataatacc atcatgagtc    3840
aagaagcatc taaatgtaca tggtagttat ataaaaatag ttatatagtt atatacaata    3900
gttatatata aaccagttta atatatgtta agtagaggta tatggtagtt atataaaaaa    3960
tagttatata atagttatag agttatataa ttatataaaa tagttatata taaaccagtt    4020
taatatatgt taggtagagg tataataata tatattgtat atactatata atatagtaat    4080
gtataaaatg caaaacgata tcatatattt ctatattaag tttatattta cagatctaca    4140
ttttatatat tttatgttat atacaattgt gttatacata atataattag tatagtactg    4200
acttggggaa ttgagcagta ccaacccata gggatgtttg aggatgaaaa tatgtgatta    4260
tgaatacaaa atgctgggcc tgctgcatag gaagtattta ataaatggta gttgttacta    4320
taaagtcgtt cctactatag agctactcac aacctgggac atagggaaag agcccgtttc    4380
cctctaatca ctcaatagtg ggtggctagg taggtgagtc cacatcctgt ggccgggaac    4440
aggtgctgag acatgaagac cttctgactg catgttggac cagccacagt ttcagacgga    4500
ccagccaaaa agggcatttt ccccaagcca tttagctccc ttgagtctca taacaaatct    4560
cctagaccct gctggtccat aggatctaga gaggatgact tgaaccttct gatcccacca    4620
tttgaaaacg ccatgccatg ggcaccagta ggagggccac tgctacgtgc accagtacaa    4680
gggccactgc catggattac agattaaccc taagtatagc tgtcgcacac ctagtacttc    4740
aggaggctta ttcggggcca tgcagatccc tggcattatt atcctaggat cctacaccaa    4800
gcaaagcagg agctgcccct cctcataaac ccataagccc tcctcttgag caaagcagct    4860
gggaaggcca gaagttattc aagctcccct ctgccccggt tccaaagaca gacagctcaa    4920
gcctacatgc agcaaaccct ataaagtgt cacctcttgg catttctgcc atggtaatgc    4980
tttctgcttc cactaataat cctagtaatt tgtttatggt gggcatctct ctgatgagaa    5040
ccacattctt ttttttttt ttttttttt ttgagataga gtctcactct gttgcccaga    5100
ctggagtgca gtggcgcgat ctcggctcac tgtaacctt ggctcctagg ttcaagcaat    5160
tctcctgcct cagcctccca gtagctggg actgcaggca cgtaccacca tgcccagcta    5220 attttttgtat ttttagttga cgggggtttt caccatgtta gccaggatgg tctcaatctc    5280
ttgacctcat gatccacctg ccttggcctc ccaaagtgtt gggattacag gcatgagcca    5340
ccatgcctag cctgagagcc acattcttgt taaccacaat tttctcagag tctgcattag    5400
gggttgacaa agagtggaaa ggaaggacaa aaggatggag aggtggatgg actaagcata    5460
tgtaggttct tacccaggcc agagaaggat agctcagcca cggcagtgga tgccatctgc    5520
acacatcgcc ctgaccctga agacctcgga ctggacagag agcgactgta ctgggagctg    5580
```

```
agcaatctga caaatggcat ccaggagctg ggcccctaca ccctggaccg aacagtctc     5640 tatgtcaatg gtgagcagct gtgatgtggt tggaggctct tcctccttgc tgagcagcct    5700
gtaatcactg gcttgaggtc acactcactg tcaggcaatt gaaaatttgg tcctgtgctc    5760
tacatgggat gactaatttc cggacttcat ggtatctttt tttttttttt ttttttttttg   5820 agatggagtc tcgctctgtc accaggctga ggtgcagtgg catgatctca gctcactgca    5880
acctccgcct cccggattca agcaattctc ctgcctcagc ctcctgagta gctgggacta    5940
caggtgcatg ccaccacacc cagctaattt ttgtatttt  agtagagaca gggtttcacc    6000
atgttggtca ggatggtctc aatctcttga ccttctactc caccttgcct tggcctccca    6060
aagtactggg attacaggct tgagccacca cacctggcca ggacttcatg gtttcttcat    6120
catcatggaa tgaattccat cagggcattc ttccctgatg tgagggcact gataggaaat    6180
ctttaatggt ccctgctgca tgaaactgct tccattgcac cagggtagcc ctgacccta    6240 tttggtcccc cacatctcct tgtaacttac ccacactcct ccctccttct ctgtgcaggt    6300
ttcacccatc gaagctctat gcccaccacc agcagtgagt attcaactca tgtccacatg    6360
cccatgatcc tacaccaagc aaagcaggag ctgcccctcc tcataaaccc ataagtcctc    6420
ctcttgagca aagtagctgg gaaggcagaa gttattcaag ctcccctctg ccccagtttc    6480
aaagacagac tcagctcaag cccacatgca gcaaaccca  taaaagtctc acctcttggc    6540
atttctgcca tggtaatgct ttctgctctc actaatgagg acttctcctc agctcctggg    6600
acctccacag tggatgtggg aacctcaggg actccatcct ccagcccag  ccccacgagt    6660 aagtaccagt caatggcatc tctattagag catgctatct ctgtcatttt tactcagatg    6720
aagatggaaa atcatagcaa atctactgat agtgagtgga ccaacgaaat tgttggcca    6780 cctagtgtgt accagatcct agagatacag gagggaaaac aaaaccaata caaaatttct    6840
gctctcagtg agcttgtatt cttgtcatga tgatgatgtt ggtggtggtg ctgttgatga    6900
cgatgatgat gatgatgatg atgatgatgc tggtgatact gttgatggtg atagtgatgt    6960
tgatgacaat gatgatgatg atgatgttga agaaaatgat gctggtgatg gtggtggggg    7020
ttattatggt aataatgata tgttgagtgt gacgatgatg gtggtggtgt tgatgatgat    7080
gatgattatt atgctagtga cattgatgat ggtaatggtg atatcaacga cagtgacaat    7140
gatggtgatg aggatgatgt cggtgatggt ggtgggtta  tgatggtaat gatatgttga    7200
atgtgatgat ggtgatgatg atatttgtgg ttcatgatgg ggattgtcat ggtggtgctg    7260
gtggtacttg tgatgacaat aatgataata atgatgacaa tgatagtgat gatggtgatg    7320
gtgataataa agataacaga tatcaccta  caatattgag cactaaatat gtaccaagag    7380
ctatgctcag tatctaacta ctattatata atctactta  gaaaatgaat tgtatcatag    7440
ataagaaagg cgtggaaaat atttattatg tcactcaatt taattgctgc atatggttat    7500
tacaaagtgc tattctctct actttgaaca taatgtttat ttcacactcc cactatagct    7560
gctggccctc tcctgatgcc gttcaccctc aacttcacca tcaccaacct gcagtacgag    7620
gaggacatgc gtcgcactgg ctccaggaag ttcaacacca tggagagtgt cctgcagggt    7680
ctggttagtg tcctgcctc  cacactctgc cctgctcatg tacccagtc  cctcttacat    7740 catccatgcc agggcaatgg aagaatatca aacccaactc acttttgccc caagagatgc    7800
aagcctcagc caggagcggt ggctcacgcc tgtaatacca gcatttggga ggccaaggcg    7860
ggtggatcac ctgaggtcag gagtttgtga ccagcctggc caacatagtg aaaccctcatc   7920
```

```
cctactaaaa tacaaaaatt agccaagcat ggtggtgcat gcctgtaatc ccagctactt    7980
gggagggtga ggcaagagaa tcacttgaat caaggaggca gaggttgcag tgagtcaaga    8040
tcatgccact ttactccagc ctaggcaaaa aagcgaaact ccatctcaca aaaaaagaa     8100
aaaaagagag agatgcaagc ctcccccacc aaggccagcc ctgcccacct cacttctgcc    8160
tggctcttac ataaaactta gccctcctac tcactgccct ctccctcctc cacagctcaa    8220
gcccttgttc aagaacacca gtgttggccc tctgtactct ggctgcagat tgaccttgct    8280
caggtgagaa cttagaattt ccagcctggc tgccccactt gtactcactc caaaagactt    8340
tgcactgctt ccttgctgca cttcctaggg atatcctcac caaaggtgga attcaggagt    8400
cacaggcttc aggatcagtg tgtttcctga cagtaacacc cctacactcc acctcaacag    8460
agagaatctg catggcccat catcaggatt gagcctctcc ctttatcatc cctctgaatt    8520
ccctccattc cctgtgcctc ccttttcttt acatgttaaa ttctgtcccc aggatttctt    8580
tcaggacaat catgccttat ccacgtgatt tcatcctcat ttcgagctct tcactgggct    8640
caagtccggc tccccgtccc gtccatgaaa gtgtcagttt catcttgtca ctgtatccgt    8700
gactccactc acagtcctca gcaagccaat agtccatgca ctaagagtcg atgtggcttc    8760
tcacctcttt cccaggtttc tcatttctct ggtccttgct gtccttccct cagcaatcgc    8820
aagacccttc ctagataaac ttttcattgt gattttttccc actgaccctc cccaggcccg    8880
agaaagatgg ggcagccact ggagtggatg ccatctgcac ccaccgcctt gaccccaaaa    8940
gccctggact caacagggag cagctgtact gggagctaag caaactgacc aatgacattg    9000
aagagctggg cccctacacc ctggacagga acagtctcta tgtcaatggt gagtggctgt    9060
gatgtggttg aaatctcttc ccccttgctg ggcagcctct aatctctaac tagagatcac    9120
actccctgcc tggcctttga aaattctgtc atgtgctcta catgggatga ctaaggtctg    9180
gacttcatgg tttccttacc atcatggact gtgttccctc agggcattct ttcctgatgt    9240
gaggatgctg atagaaaatc ttcaattgtc cctgtaccat gaaactcggt tcattgcacc    9300
agggtagcat tgacctccat ttggtccccc acctctcctt gtctcttacc cactctcctc    9360
cctccttctc tatgcaggtt tcacccatca gagctctgtg tccaccacca gcagtgagta    9420
ttcaactcat atccacatgc ctcggttcct acaccaagag gagcaggagc tggcccctcc    9480
tcataaaccc attaagtcct cttcataagc aaaggattta ggagggcaga agttatttaa    9540
gtgtccctct gcccagctca agagaccgac ccagctcaag ctacacatgc aacaaacccc    9600
ataaatagtc tcccctcttg ccatttctgc caagagagtg ctttatgctt tcactgatga    9660
gaacttttcc tcagctcctg ggacctccac agtggatctc agaacctcag ggactccatc    9720
ctccctctcc agcccacaa gtaagtatca gtcaatgaca tctctatgag agcatacctg     9780
attagtgtaa acatctctgt cattttcact caaataaaga tggaaaatca tagtaaatct    9840
agtgatactg agtggacaaa tttgtttgtt tgttttttct catccttttc acttttttta    9900
ttatacttta agttttaggg tacatgtgca caatgtgcag tttagttaca catgtataca    9960
tgtgccatgc tggtgtgctg cacccatttg ctcgtcattt agcattaagt atatgtccta   10020
tgcgatccaa gccacgcgc cgcaccacgt gcaacagttt cacagattgg atggtccgat    10080
annnnnnnnn nnnnnnnnnn nnnnnnnnnn nnnnnnnnnn nnnnnnnnnn nnnnnnnnnn    10140
nnnnnnnnnn nnnnnnnnnn nnnnnnnnnn nnnnnnnnnn nnnnnnnnnn nnnnnnnnnn    10200
cttcaccatc accaacctgc agtatgagga ggacatgcat cgccctggat ctaggaagtt    10260
caacaccaca gagagggtcc tgcagggtct ggttagcacc ctgccctctt cactctcccc    10320
```

```
cgccctggat gccgagcccc tcatacaaca ttcatgccag ggcaatggaa gaatatcgca    10380
ccaaccttgc cctcatcccc agagatgcaa gcctcaccca ctgaggccag ccactctcat    10440
gggtgtctgc cccacccacc tcacttttgt ccccacacag ggaccttagc cctcctactt    10500
acctctctct ccctccccca cagcttagtc ccatattcaa gaaccagt  gttggccctc    10560 tgtactctgg ctgcagactg acctctctca ggtgagacct tagaagatcc agcctggctg    10620
ccccagttgt tcccactcca gtagattttg ctctgcttcc ttgctgcacc tcctagggat    10680
atcctcacca aaggggaat  tcaggagtca ctggcttctg gaccaatgtg tttcctgata    10740
gtaacactcc cacacctcac ctcaacaggg agaatctgca tggtccatca tcaggattga    10800
gcctctatcc tgatcatccc tcagaattcc ctgcccctcc ctttcattta ggtgttaaat    10860
tctgtcccca gaatttctct caagacaatc atgcctcatc caagtgcttt catcctgtt    10920 tctagctctt cactggtctc aagtctgggc tctcctgtcc ccatgctatg agaatgcagg    10980
tttcaccttg cactttata  agcatggttg tatctgtgac tctgtgcaca gtcccaagca    11040
agccagtagt ccatgcactc agagaatcta agtgtagctt ctcacctctt tcccaggttt    11100
ctcatttcct ctggttcttt actgtctttc catcagcagt ctcaggacac aacctaagta    11160
atcttttcat agtcattctc cccacctacc ttccccaggt ctgagaagga tggagcagcc    11220
actggagtgg atgccatctg catccatcat cttgacccca aaagccctgg actcaacaga    11280
gagcggctgt actgggagct gagccgactg accaatggca tcaaagagct gggcccctac    11340
accctggaca ggaacagtct ctatgtcaat ggtgagcagc tgtgatgtgg ttggagtctt    11400
ttccttctag agtctggaaa gaatctaatc tgtggcttga agtcacactc cctgcctggc    11460
cattgaatat tctgtcatgt ggtgtagatg ggatgacaaa gttctggact tcacagtttc    11520
ttcattgtcg tgaactgtgt tccctcaggg cactcttccc tgttgtgagg atactgatag    11580
gaattcttta atggccccag tcccatgaaa tcattgtcc  catgaaactc atttaattgc    11640
attgggattg ccatgacctt attgtgtccc tcgtatctcc ttaacgctta ccaagtctcc    11700
tccctccttc tctatgcagg tttcacccat cggacctctg tgcccaccac cagcagtgag    11760
tattcaactc atgtccacat gcccctgatc ctacattaag tggagcagga gctggcccct    11820
cctcttaaac ccataagtcc tcctcttgag caaaggagct gggaaggcag aagttattga    11880
agctcccttc cacctagctc caaagacagg cccagctcat gcccgtatgc agcagacctc    11940
ataatagtct accttcttgc catttctgcc atgagattat tttctgcttt cactgatgag    12000 cacttttct  cagctcctgg gacctccaca gtggacnnnn nnnnnnnnnn nnnnnnnnn    12060 nnnnnnnnnn nnnnnnnnnn nnnnnnnnnn nnnnnnnnnn nnnnnnnnnn nnnnnnnnnn    12120
nnnnnnnnnn nnnnnnnnnn nnnnnnnnnn attttcaatt cccactacag ctgctggccc    12180
tctcctggtg ctgttcaccc tcaacttcac catcaccaac ctgaagtatg aggaggacat    12240
gcatcgccct ggctccagga agttcaacac cactgagagg gtcctgcaga ctctggttag    12300
tgcccttccc tcctcactct gcccagcccc agatatccag tccttctac  atcatccatg    12360 ccagggtgat gaaagaagat agcaacaact tccccccttc cccccaagag atgcaagccc    12420
cacccacaga gaccagtcct gcttattggt gcctgctcca cccacctcac atctgccccg    12480
acacacacac accttagccc cactactcac ctccctctcc ctcctctaca gcttggtcct    12540
atgttcaaga acaccagtgt tggccttctg tactctggct gcagactgac cttgctcagg    12600
tgagacttta gaagagccag cctgggtgcc caaacttgtt cccactctaa aagactttgc    12660
```

```
actgcttcct tgctgcactt cctaggtata tcttcaccac aaggggaatt caggagtcat   12720
tggcttgaga accagttgtt tcctgatagt aacacccca tgccccaact caacatgcaa    12780
aatcttcatg gttcatcatc aggattgaga cactaccctg attacccatc tgaattccct   12840
cctttccctg acccctccct ttcatttagg tgttaaattc tgtccccagg atttctctca   12900
agataaccat gcctcatcca catacatgca tccgcctttc aagctcatca ctagtctgaa   12960
gctctgggtt ctcctgttcc catgccatga gaatgcaggt ttcaccttgc acttttataa   13020
aaattattat atccatgact ctgcttgcag tcccagacca agatagtggt ctatgtactc   13080
agataatcta agtgcagatt ctcacctctt tcccagattt ctcatttcct ctggttcctt   13140
gatatgtttc cctcagcaat ctcaagacaa gtcctaggca atcttttcat tgtcattccc   13200
cctcctacct tcctcaggtc cgagaaggat ggagcagcca ctggagtgga tgccatctgc   13260
acccaccgtc ttgaccccaa agccctggga gtggacaggg agcagctata ctgggagctg   13320
agccagctga ccaatggcat caaagagctg ggccctaca ccctggacag gaacagtctc    13380
tatgtcaatg gtgagcagct gtgatatggt agggtctct tcctcctggc tgtgcaacca    13440
tctaatctct ggcttggggg cacactccct gcctggccat tgaaaattct gtcacgtgct   13500
ctacatggga tgactaagtt ctggacttca tggtttcttt gttatcatga gaggcattcc   13560
ctctgggcac tcttccctgt tgtgaggatg ctgataggaa atcttaatg accctgtcc     13620
catgaaactc atttaattgc accagggtag tcctgaactc tatcgcgtcc cccacatctc   13680
cttaacccctt acccagtctc ctccctcctt ctctatgcag gtttcaccca ttggatccct  13740
gtgcccacca gcagcagtga gtattcaact catgtccatg atgcccctga tcctacatca   13800
agtggagcaa gagctggccc ctcctcttta acccataagt cctcctcttg agcaaatgag   13860
ctgggaaggc agaagttact caagctcccc tctgccccag ctccaaagac agaccccagct  13920
caagcccaca tgcagcagac ctcataatag tctatcttct tgccatttct gccatgagag   13980
tgctttctgc tttcactgat gaggactttt ttcagctcct gggacctcca cagtggacct   14040
tgggtcaggg actccatcct ccctccccag ccccacaagt aagtaccagc caatggtatc   14100
tgtattagat catgcctgat gaatgcaaac atctgtgcca ttttcagtca atgaaaatg    14160
gaaaatcata ataaatctag tgatactgag tgaaccaaaa aaatgtatt ggccacctac    14220
agtgtaccag accctaggga tatagcaagg aaaatagaac caataaaaac atctctgccc   14280
tcagtgagct tgtgttcatg tgatgatatg atggtggtgg tggtggtaat agtaataatg   14340
acatattcag tttgatgata atttatgatt atggtgttgc tgttgatgat ggtggtggtg   14400
atgttactga caatgatggt gacggatctt tgaggatatt gtccgtgatg gtcgtgaaga   14460
ttatgatgat aatgatgatg tgttaagtgt gatgatgatg atgatctgtg gtgatgctgt   14520
ttaggatgct gttccgtggt accgatgata ttgatgttgg tcgtggttat gttgtatgac   14580
aatgacaatg atggtgatga ggataatcgc cagtgatggt gtgggtttat gatgatgatg   14640
atgtgttgaa tgtggtgatg ataatgttcg tggtggtcgt gatgggcatt actatggcag   14700
tgatggtcat aataatgatg gtgatggtga caatgatagc aaggatgatg atggcaataa   14760
agatagtaca taacatcaga caatattgag ctctgaatat gcaccacgag gagtgctcag   14820
catctaaata ctattatata atatattttt gtaaaaataa attgtattgt tttaggcaag   14880
ggaagcatgg taaatatttt gtcactcaat ttaaattctg catatgttta aagataagtc   14940
tattgcaaac tcctatttc tctactttgg acatagtgtt tgtttcccac ctccactaca    15000
gctgctggcc ctctcctggt gccattcacc ctcaacttca ccatcaccaa cctgcagtac   15060
```

```
gaggaggaca tgcatcaccc aggctccagg aagttcaaca ccacggagcg ggtcctgcag    15120
ggtctggtta gtgctccacc ctcctcactc cgccccaccc cagagagtca gtacctccta    15180
catcatccat gccaggtgat ggaacaagat catacccacc tcaccctTgc cccaagagat    15240
gcaagccatg cccattgaaa ccagcccCac tcactgatgc ctgttactgc cccacctgac    15300
ttctgcccta cacacccaca cacgcaactt agccctccta ctcatctcct tctccctcct    15360
ccacagcttg gtcccatgtt caagaacacc agtgtcggcc ttctgtactc tggctgcaga    15420
ctgaccttgc tcaggtgaga ccttagaaga tcaagcttgg ctgccccact tgttnnnnnn    15480
nnnnnnnnnn nnnnnnnnnn nnnnnnnnnn nnnnnnnnnn nnnnnnnnnn nnnnnnnnnn    15540
nnnnnnnnnn nnnnnnnnnn nnnnnnnnnn nnnnnnnnnn nnnnnnnnnn nnnnnnnnnn    15600
ngtgttagtc tactTTtgaa cactgtTtat ttcccatctt cactatagcc gccagccctc    15660
tcctggtgct attcacaatt aacttcacca tcactaacct gcggtatgag gagaacatgc    15720
atcagcctgg ctctagaaag tttaacacca cggagagagt ccttcagggt ctggtaagag    15780
ccccacatac ctcattctac cgccactcac catgtttagt cctgcccacc tcacctattg    15840
cagagcatgg aagatctcat ctacctcatc ttgcccccag atatgcatac cccaaccact    15900
gatgccagcc ccaccaactg ttgccagccc tgcccacctc ccttctacca caccCctatg    15960
acttcagtcc tcccactcac ctccctctcc ctcctccaca gctcaggcct gtgttcaaga    16020
acaccagtgt tggccctctg tactctggct gcagactgac cttgctcagg tgagaactga    16080
gaacagccag tctgactgat ctgagcagtt tgacctgctt cccttctgca ctccctggag    16140
atgtccgcag ccaggtggaa tccaggaggc agtggctcta agaccaatgt gcttcctgtt    16200
cccaccacct cccacctcaa ctgagagatg cagagcccat cagcaggact gagcttctac    16260
cttggtcatc cctctgaatt ccctccttTc ccctacctgc cttTcacaa gtggtTcaat     16320 tctgttccca ggatttctcc caagaaaaac atgcctcgtc cacttgcttt catccccaaa    16380
cctagctctt cacctgtctc aagtatgagt tctccttacc ccatgctaca agaatgcagt    16440
ttccactttg caattttata aaaatccttg catccatgat tctgctcata gttgctaaga    16500
gtcagtgcac tcagagaatg gaagtatggc ttctcacttc tctaccaggc ttctcatttc    16560
ctctggcccc ctcctgtcct gccctgtggg atctcagaac ccctccctag gcaatccgtg    16620
tattgtcttt ccccaatctt gccctcccca ggcccaagaa ggatggggca gccaccaaag    16680
tggatgccat ctgcacttac cgccctgatc ccaaaagccc tggactggac agagagcagc    16740
tatactggga gctgagccag ctgacccaca gcatcactga gctgggcccc tacacactgg    16800
acagggacag tctctatgtc aatggtgagt agttgtgatg tggttggagt ctcttcctcc    16860
ttgctgggca gcctctactc tctgccttga ggtcacgctc cctgcctggc tattgaatgc    16920
tcatccatgt tgtctgtatg tgatggctga ggttggaact tcatggtttc tatttcatct    16980
tggactgagt tcatcctcag gatctgcttt ctggatctga gggtgctgat agagaatctt    17040
caatggttcg tgttctggga aattccttcc attgcaccag ggtaccctga cccctatata    17100
gttccccacc actcccttaa cccttaccca ccctcttccc tccctctcta tgcaggtttc    17160
acacagcgga gctctgtgcc caccactagc agtgagtatc cactgatttc cagtgctcct    17220
gatcctacat catgcagggc aagaactgac ccctcctcac atgcccctat gtcctctatg    17280
agcaaaggag ctgggacagc acaagttact ccctttccct tctggcccaa gtctcttcag    17340
agagagaccc agctcaagcc ccacatgcag caaggtccat aaatactcct acctgctggc    17400
```

```
atttctgcca tgagagggtt caacactttc actaatgagg ccttctcctc agttcctggg   17460
acccccacag tggacctggg aacatctggg actccagttt ctaaacctgg tccctcgggt   17520
aagtacaaat caatcgcatc tctgttagag catgcctgat gactgtcaac atctctgcca   17580
ttttcactta aataaagata aaaaatccta gtgaatctac ggatgaggag tcatccagca   17640
aacttaattg agtgcctagt ttctgcaggg ctctagggat aagaaagggg acacaaaaca   17700
gttaaaaata tctgctgcaa gaaagcttat tttattgtga gggtgatggg agttggtggt   17760
ggtgaagtta ctggagatga tgacaataag aatggtgatg ctagtgatga tgatggtgat   17820
aaggatgata attatgaaga tggtggtggt gatgatgatg atggtnnnnn nnnnnnnnnn   17880
nnnnnnnnnn nnnnnnnnnn nnnnnnnnnn nnnnnnnnnn nnnnnnnnnn nnnnnnnnnn   17940
nnnnnnnnnn nnnnnnnnnn nnnnnnnnnn nnnnnnnnnn nnnnnnnnnn nnnnnnnnnn   18000
nnnnnnnnnn nnnnnnnnnn nnnnnnnnnn nnnnnnnnnn nnnnnnnnnn nnnnnnnnnn   18060
nnnnnnnnnn nnnnnnnnnn nnnnnnnnnn nnnnnnnnnn nnnnnnnnnn nnnnnnnnnn   18120
nnnnnnnnnn nnnnnnnnnn nnnnnnnnnn nnnnnnnnnn nnnnnnnnnn nnnnnnnnnn   18180
nnnnnnnnnn nnnnnnnnnn nnnnnnnnnn nnnnnnnnnn nnnnnnnnnn nnnnnnnnnn   18240
nnnnnnnnnn nnnnnnnnnn nnnnnnnnnn nnnnnnnnnn nnnnnnnnnn nnnnnnnnnn   18300
nnnnnnnnnn nnnnnnnnnn nnnnnnnnnn nnnnnnnnnn nnnnnnnnnn nnnnnnnnnn   18360
nnnnnnnnnn nnnnnnnnnn nnnnnnnnnn nnnnnnnnnn nnnnnnnnnn nnnnnnnnnn   18420
nnnnnnnnnn nnnnnnnnnn nnnnnnnnnn nnnnnnnnnn nnnnnnnnnn nnnnnnnnnn   18480
nnnnnnnnnn nnnnnnnnnn nnnnnnnnnn nnnnnnnnnn nnnnnnnnnn ngctgccagc   18540
cctctcctgg tgctattcac tctcaacttc accatcacca acctgcggta tgaggagaac   18600
atgcagcacc ctggctccag gaagttcaac accacggaga gggtccttca gggcctgnnn   18660
nnnnnnnnnn nnnnnnnnnn nnnnnnnnnn nnnnnnnnnn nnnnnnnnnn nnnnnnnnnn   18720
nnnnnnnnnn nnnnnnnnnn nnnnnnnnnn nnnnnnnnnn nnnnnnnnnn nnnnnnnnnn   18780
nnnnnnnnnn nnnnnnnnnn nnnnnnnnnn nnnnnnnnnn nnnnnnnnnn nnnnnnnnnn   18840
nnnnnnnnnn nnnnnnnnnn nnnnnnnnnn nnnnnnnnnn nnnnnnctc aggtccctgt   18900 tcaagagcac cagtgttggc cctctgtact ctggctgcag actgactttg ctcaggnnnn   18960
nnnnnnnnnn nnnnnnnnnn nnnnnnnnnn nnnnnagaat tcagtcgacc taccggcttt   19020
gatgattgct cagttgaact tagaaatgca ctgtctgccc aatggtccag tctcatgagt   19080
gtgactcttt tctgcctctc ttgggtatct gatcaagatg gactcaggaa aagtgctcca   19140
gataactgtc tccaatataa cactgcccct gccatcacac ccaaatgact ggaagtttca   19200
cagggtcatc agcagggatt ggacttccac cccggccatc cctctgaatt ttccctcttt   19260
tctccccacc tcccttgccc ttaggtgtta aaattctcta actaagattt ctctcaagac   19320
aaatgtgcct cattcacttg tttaattccc aattccagct tgtcacctgt ctcaagtcta   19380
ggctgtcctg tccccatgcc atgagaatgc aagaaccaca ctgaaatgtt agaaaaattc   19440
ttttatccac aagtatgctc accgtcccaa gctggacagt agtcagtgca ctcagagaat   19500
ctaagtgtgg cttctcatct gtgtaccagg cttctcattt cctgtgggcc cttcttgtcc   19560
ttccctccgc aatcttggga ctcctcccta gacaaaactt tattattatt ccctcacct   19620 gccctctcca ggcctgaaaa ggatgggaca gccactggag tggatgccat ctgcacccac   19680
caccctgacc ccaaaagccc taggctggac agagagcagc tgtattggga gctgagccag   19740
ctgacccaca atatcactga gctgggcccc tatgccctgg acaacgacag cctctttgtc   19800
```

```
aatggtgagc aattgtgatg tggttggagt ttcttcttcc ttgctgagca ggcctctact   19860
ctctgtcttg aggtcactct ccctgcctgg ccactggtct tggccatgtt gtctgtattt   19920
gatgattgat atgaacttca ccgtttcttc ttcatcttgt actggagacc ttcatcctca   19980
ggaccttctt ccctgatctg agtgtacttg tatagaatcc tcaaagccca tgttccctga   20040
aactccttca attgcaccat ggtagcactg acccctttg gtcccccacc ttnnnnnnnn    20100
nnnnnnnnnn nnnnnnnnnn nnnnnnnnnn nnnnnnnnnn ttcactcatc ggagctctgt   20160
gtccaccacc agcactnnnn nnnnnnnnnn nnnnnnnnnn nnnnnnnnnn nnnnnnnnnn   20220
nnnnnnnnnn nnnnnnnnnn nnnnnnnnnn nnnnnnnnnn nnnnnnnnnn nnnnnnnnnn   20280
nnnnnnnnnn nnnnnnnnnn nnnnnnnnnn nnnnnnnnnn nnnnnnnnnn nnnnnnnnnn   20340
nnnnnnnnnn nnnnnnnnnn nnnnnnnnnn nnnnnnnnnn nnnnnncctg ggaccccac    20400
agtgtatctg ggagcatcta agactccagc ctcgatattt ggcccttcan nnnnnnnnnn   20460
nnnnnnnnnn nnnnnnnnnn nnngactcca gcctcgatat ttggcccttc aggtaagtac   20520
cagtcaatgg cacctctatt agagtatgca tgatgagtgt caacatctct gtccttttca   20580
ctcaaataag attaaaaatc atagcaaatt gtacgtgatg atgagtcacc caacaaactt   20640
ctttgagtac ccactctctg ccaggcccta gagataaggc agggaacaca aagaggtaa    20700
aaatctctgc cctcagagag cttcttttat tttgaggatg atgtgggata gtggtgatga   20760
tgatgttgct ggagatgatt acaataatga tggtgatgct tatgaccatg atgtgatgat   20820
gatggtgatt atgaagatga tgatgatgat attgatgatg gtagtggttt tgacagtaat   20880
gatgatgtga tgatgatgat gatagtggtg gtggtgatta tgggaaggat gacagtggtg   20940
gtggtgatgg tggtggttgt ggtggtgatt gacaatgtgg tggtgatatt gacaatgagg   21000
atgatgatga tagtggtggt ggttatgatg gttaaggatg atgtgatgat ggtgttggtg   21060
atcacggtac tagtggtggt gatgtggacc gtcatggttg tggttgtggt ggtgatggtg   21120
gtgatcatga tgataatgag gatgatggtg gtgattgtca tgatggtaag gatgaaacag   21180
tgatggtgtt ggtgaccatg ttcctggtgg tgatggtgca ggtgatgatg tggatgatga   21240
tggtgatggt ggtggagatg atagggatta tgaatatggt tcgggtctct gactggtggt   21300
ggtgatgaca ataatgaaaa tgatggtcac agtgttggtg atgatgatgg tggtgataac   21360
aaaggtaata gatagtgtct agtattatgg aacacagaac atcaccaaag gttatgctca   21420
gcatctaact attattattt agcatgctct atgaaaaact ttgatcgtta tagtcaaggg   21480
aggcatgaaa accttctatt ttatcactct ctttaaatct ggttgcatat gtttagaaat   21540
aaatctatta caaactctta aatgttctct acttttgaac atagtgttta tttcccacct   21600
ccactacagc tgccagccat ctcctgatac tattcaccct caacttcacc atcactaacc   21660
tgcggtatga ggagaacatg tggcctggct ccaggaagtt caacactaca gagagggtcc   21720
ttcagggcct ggtgagagcc ctgcccacct cactctgccc tgcccacctt gtcttgttcc   21780
acctacgtca cccattccaa ggcatggaag aagatctcac ccacctcccc tcacctgaga   21840
gatagcccg ccccctgatt acagccccctt ccaccttaca tcttcctcac ttctatgtcc   21900
tcagccatct tactcacctc cctcttcctc ctccacaggc taaggccctt gttcaagaac   21960
accagtgttg gccctctgta ctctggctgc aggctgacct tgctcaggtg agaactgaga   22020
ataaccagtc tggctacccc aagtgttccc aggcccaagg agtttcatca gctttcttcc   22080
ttccctccct atggaagtcc tcagcacaag tggaattcag gcgttggtgg ctccaggatg   22140
```

```
aacatatctg ctgatcctac cacctccccc atcaatcgag agaatttgca gggcccatca   22200
gccagatcag gcttctactt tggtcatcct tctgaatttc ttacttctcc ctacctccct   22260
ctccttcagg tgttaaattc tcttccaagg tttctctcaa gataaacatc ccccatccac   22320
ttgctttcat ccccaattcc agctcttaat atttctcaag tctgggctct cctgtcccca   22380
taccatgaga atgcaatttt ataaaattct tgtattcctg actctactca cattcccagg   22440
ctgcctggaa gttggtgcat tcagagaatc ttagtatggc ttctcacctg tctaccagga   22500
ttctcatttc ctctgtcccc ttcctgtcct gcccccagga atctcaggat gcctccccat   22560
aggcaatcta tttaatgtca tcccccttat ctgccctccc taggccagag aaagatgggg   22620
aagccaccgg agtggatgcc atctgcaccc accgccctga ccccacaggc cctgggctgg   22680
acagagagca gctgtatttg gagctgagcc agctgaccca cagcatcact gagctgggcc   22740
cctacacact ggacagggac agtctctatg tcaatggtga gcggctgtga tgtggttgga   22800
gattcttcct ctttgctgga cagcttctta ctctctgact tgaggtcaca ctccctgact   22860
ggccattgac gtcttggcta tgttgtctgt atgtgatgac tgatgtctga acttcatagt   22920
ttcttcatct tggactgagt tcatcctcag taccttcttc cctgatctga gggtactgat   22980
agagaatctt caaaggcccc tgttccttga aacttcttcc attccactag ggtatctgtg   23040
acccctattt gattccccac ctctccctta acccttaccc actctcctcc ctccttctct   23100
gtgcaggttt cacccatcgg agctctgtac ccaccaccag cagtgagtat tcaaccgatg   23160
ctccagtagc cccaattata caccaagcag ggcaggagct gtcctgtctt cctatgcccc   23220
tatgtcctct tcataaagga aggggctggg agggcacaag ttattccctt tcccttctgg   23280
ccagctccag agagagaccc agctcaggcc cgatatgcag caaggcctgt aaatagtttt   23340
atttgctgac ctttctgcca tgagaggctt ggatgcttcc cctgaagagg gtttctctgt   23400
agctcttggg actaccacag tggacctggg aaactctggg gatccacccc ttctactggt   23460
cccttgaata agtaccagcc aatggcacct ctgttagagc atggctgatg agtgtaaaca   23520
tctcttccat tattcagtca aataaagatg gaaattcttt ataaatctag tgatgatgag   23580
ccaaccaaca aactttattg agcattgtga caagccctgg ggctctgcca aatcctgggg   23640
atatggcatg gatcatgaaa caattaataa tctctcctct cagagagcta tttttatgat   23700
gatactgatg gtggcaatga tgatgatgtt gatggtgatt atgaccatga tgacaatggt   23760
gatggtggtg gtgatgatgg taatgatgat gatggtgatg ttggtaatga tggtggtgat   23820
tatgacaata atgatggtga tggtgacagg gatggtgatg attatgatgg tggtggtgat   23880
aacaaagtta atggataata tatgaactta ttggctactg aatatgcacc aaagtgctat   23940
gctcagtgtt taactagtac tatttaatat gatttctaaa aaaaatcttg aattattata   24000
ggcagaagaa tcatgggaac cttttatttt gtcactcact ttaagtccta ttgcatattt   24060
tttaagtcaa ttgcaaacac agtttctctg ctttgaacat tgtgtttata tccagtcacc   24120
ccaatagtgc ataaacctgc tgattggagc aactgtgtct tactcccttg tgcttcccta   24180
gtatctgctt caggaccttg tacatggtag atcgacagat ttagatctac aggaaaatat   24240
ggatttcccc agggaaggaa ggaatgaagt atgctttctt ataatgtatg gaaactttcc   24300
tcttctgcct tggttcaact ttagtgtctg ccagagttta cactggaaaa ctatatggca   24360
tctgctccac tccctcatcc atgacagaca tcattaattg attgcagcat tcatggcaga   24420
catcaccaat tgataatagc attcatttc tctcagttca aaacagcttc agaatggtta   24480
ccaaaaaaaa aaaattcagt cgctaccaat tcaattggag ctgactcagg attatgggac   24540
```

```
agaattcaag agagttaggt tccttgatga tgtgtagtgg ctatttgttt tccggtccag   24600
gctaatnnnn nnnnnnnnnn nnnnnnnnnn nnnnnnnnnn nnnnnnnnnn nnnnnnnnnn   24660
nnnnnnnnnn nnnnnnnnnn nnnnnnnnnn nnnnnnnnnn ctttgtgcgg caaagttcag   24720 gggcccccaaa aatttctgtg ccccaatcat ggcggaccta ggtttaggca caaattccag   24780
ggattaagtc cctggagatg ttatggcttt tggttttcct agaaaggctc agctcaggct   24840
cagcttggtc atgctgatat cctttcttcc acttggtcga tttggctgtt gatacttatg   24900
tatgcttcac gaagttttg tgctgtgttt ttcagctcca tcggttggtt tatgttcctc    24960
tctaaactgg ttattctagt tagcaattcc tttaaccttt catcaaggtg cttagctttg   25020
cattgcatta gaacatgctc ctttagctca tcgtactttt ttattgccca tcttctgaag   25080
cctacttctg tcaattcatc catctgatcc tccatccagt tctgcaccct taatggagag   25140
atgttgcggt catttggagg aaaagaggca ctctggcctt tgggttttc agcattttt    25200 tgttgattat ttcccatctt caggagtttt agtttcaggc tttgaggctg ctgatccttg   25260
gatggggttt ttatgggggt cttttggttg ttgttgttga tgatgatgat gttattgtca   25320 cttttctgctt gttttttctt caatagtcag gtccctcttc tgtagggctg ctgcagtttg  25380
ctaggggttc acttcaggcc ctattcatct gattcgctcc catgtctgga ggtgtcactc   25440
aaggaggctt ggagagcagc gaacataggt gcctgcttct tctgggacct ctgacctcga   25500
gggacaccaa cctgatgcca gtaggatcgc tcctgtgtag ggtgtctgac aactattgtt   25560
ggagggtttc gcccagttga ctggcatgga gagcaggacc catttaatga agcactttgt   25620
cccctggtgg agaggggtt cttcactggg gggaaaccac atgtctgggc tgcttggatt    25680
cctcagaact accagaggag aggctaagtc tgctggtcca cagagactac agccatccct   25740
cccactaggg gcccaagccc agggagtcca aattctgtct ctgagcctct ggctggagtc   25800
tttggagatc ctgcaaggaa gctctgccca ctgaggaagg atgggtcagg gttagccctg   25860
aagaggcact ctggctgcag actgccacag ccggtgtgtt gggctgtggg gacaagtctt   25920
gggaccaagc cgtccagcct acccggctct agcaggggaa aagtacagcc tggagctatt   25980
gaaaggggtg ccgcccttcc cccgcccagg gagcttagcg tgttaggcag ttgtgagtcc   26040
agtgctggct gtcgcccctt ccccaaggaa caaaaaagac ttagcaggca gccgcagcca   26100
gtgctggtcg cccctccccc ggggagttcc gtaggcttag gcagattcca gctgtaagaa   26160
tctgcgtgtt ctggggttgg gacactaggt cccagtggca tgggttcgcg agtgagatct   26220
tccaatctgt gagttgcaca gttccgtgga aaaagcacag tttcccctc ttgggtagcc     26280 cgctcactca ccacctccct tggctggaag gaggggggttc cccttccccg tgtgtctctc   26340
aggtgggcca ccacaccaca ctgctcttcc ttctctctgt gggtcactgc cagccttcta   26400
gtcaattttg atgagggaac ctggacattt tggttgccag gaaggatcac acacttatta   26460
cagttttttt caatgtgagc ctctgagcgc tgctgcttat agtcgaccat cttggccccc   26520
agagtcacac atctgttatt ttttgatgtt ttgattgtgg caattcttgc agaagtaagg   26580
tggtatcacc ttatggtttt gatttccctg gtcattagtg atgttgaaca tttttttcat   26640
atgttcatta gccatttgta tatattcttt caacaactgt ctatttatgt ccttagccca   26700 cttttttgatg ggattgtttt tttcttgcca atttgtttga gttcgttgta gattctagat   26760
attagtcctt tgttggatat atagattgtg aagattttct cccactctgt gggttgtctg   26820
tttactctac tgactgtgaa ggaaaagtca atttcttata cgaatttgtc tcactcctac   26880
```

-continued

```
ttccaaatga gatcctgggg ttttttttttt ctgttaatcc ttcacaatac ttctcccact   26940
tttttgaact catttgttta tattctgttg tctgcttctc ttttatagga atgtgacttc   27000
ttatgggctt tctctattat accacatatg ggttttttgtt ttgttttgtt ttgttttgtt   27060 ttgttttttgt cctcggatcc attctccaac ctcctccagc cttcccgtgc tctgtgggat   27120
agacgtctga ctcatgaaaa ctacatttcc caggctccca tgctaactag cttcctgtta   27180
ggttcagcca ataggaggca ttggtgggac aatggtgggc ggggctatgg aagggccaga   27240
gtatttctgt acccccgcccc cctgctcccc ttccaatgtt cctggagcgg tgtaggacca   27300
atactgtata tatggaagga aggcaaggtg gatagattgg aaggaagaag tgacagatgg   27360
aaagaagaag tgataaatgg caagcgaggc aagggagcag aggatggatg agtggattgc   27420 aagaagaaa aaaatggatg aaatataaaa ggagcaggac agatggataa gtagatggaa   27480
gtaagaaaag actggtgtaa gaaaggaacg attgatgatg gatgatgaat ggatcagtgg   27540
tgattgggtg aagggatgaa tggatggatg gacagatgga tgaacagatg ggtgggtgga   27600
tagatggatg gatggataaa atgggtaggt ggatggatgg atggatggac agatgggtgg   27660
gtaggtggat ggatggatag atggatggat aagtgaatgg atggatggat ggatggatgg   27720
ataaatggat ggatgggtga aggaaggaa agaagtgaga gaaggaagag gaaggataga   27780
cagatgttag aaggtacaaa tgaaaggaag gaagccagca agaaagaaag gatgcattaa   27840
tagaatgaaa gatggaaggg aagaagaaag gatggaaaga gagaaggaag aatgaacaga   27900
aggaagttca agagtggtga aaagaagaaa ggcagggaga gaaggagaag taaactttttc   27960 ttctagagat ttgtcttaaa ccttagcttg gctggacact gtggttcacg cctgtaatcc   28020
cagcactttg ggaggccgag gcgggtggat catgaggtca ggagatcaag accatcctgg   28080
ctaacacggt gaaaccctgt ctctactaaa aatacaaaaa aaatttagtc aggtgtggtg   28140
gtgcatgcct gtggtcccag ctactcagga ggctgaggca ggagaatggc ataaaacctg   28200
ggaggcagag cttgcagtga gccaagatca caccactgca ctctagcctg ggcgacaaag   28260
tgagactctg tctcaaacaa aaacaaaaca aaaaacaaa aacaaaaaac aaaaccaaac   28320
caaaacaaaa aaaaaaaacct taactcatac tttcataaag ttccacacac agggagtgat   28380
tagaaagcat ttgctgatat attttatata ataaacatgt acaccatatt gacctgtgtg   28440
cccagcagtg cttacatgat ttacaatgat taacttgttt aagcttcata caacgttg    28500 aggcaggaaa catcattgtg aaccattgtc atctcatttt acagatgagt aaactgaagt   28560
gctgagaggt tggttatggc tgcaaagatt gttggccatg ttaaccaatg catagaagat   28620
tagcatacct ggttgtgagt gcaggagaga gagagaaatg ggagaaaggc agagaaggat   28680
cgatggggag agaggaagag agagagagag aataaatttt ttaaaaatgt ctagagtcat   28740
gacttccgca tcagtgtggt aatatgcagc ctttaccctg ggaaagatca gaaccattgg   28800 tacttttttac agaatcttcc cttcctgcat ttgggtagaa ggaccccatc tggacatccc   28860
aaatcattaa gcacacccttt actggctgct ggagttgtct ccattaaaag tcaccgttgg   28920
gtttattaag aggcggacac agggtcctta gaacacactg ccccccacctg tcccacacca   28980 ccccccaccc acccatcatc ctccccaaga gcttcatctc tctctctctt cccctgccc    29040 tagccggggt ggtcagcgag gagccattca cactgaactt caccatcaac aacctgcgct   29100
acatggcgga catgggccaa cccggctccc tcaagttcaa catcacagac aacgtcatgc   29160
agcacctggt gagaggcctg cctccgctg cagccctgcc atgcccatcc tagggctgtt   29220
gcctgcctgc ctctgaccaa cccaagctcc cttctccctc tgcagctcag tcctttgttc   29280
```

```
cagaggagca gcctgggtgc acggtacaca ggctgcaggg tcatcgcact aaggtgagaa   29340
actcccccac ccacagcgca ccaccaagaa cttagagttc tgactgggag gtccctcttg   29400
ggttggggtg ggctacatat ttttttaaat cttttatct ttccttttt tttttttgag    29460
atgaagtttc gctctcgttg cccaggctag agtgcaatgg cacgatcttg gctcactgca   29520
acctctgcct cccgggttca agtgattatc ctgcctcagc ctccccagta gctgggatta   29580
caggcaggca ccaccatgcc tggctaattg ttttgtattt ttagtagaga tggggtgtct   29640
ccatgttgat caggctggtc ttgaactcct gacttcaggt gatccaccct cctcagcctc   29700
ccaaagtgct gggattacag gcgtgagcca ccatatctgg ccccattctt tttttttaaa   29760
tgaatttaag gagtgcaaat gcagttttg ttacatgcat atattccata gtgaagtctg    29820
cagacagtag acttccagac agtagcttct ggtgtatcac ccgaatagtg tacattgtac   29880
ttattaagtg aggttcccca cccttctccc actctcccac ctttctgagt atccagtgtc   29940
tattattcca cactccaggt ccatgctctc acgtataagt gagaacgtat ggtattccac   30000
catgagctaa tggacatgga gtccattggc tcccacttat aagtgagagc atgcggtatt   30060
tgactatttc tgagtttcac ttaagataat ggactcccat tccatccatg ttgctgcaaa   30120
atacatgatt tcactctttt tatggctgaa tagtatttcg tggtatatat ataccaca    30180
tttctttat ccagtcttct actgatggac acttaggttg ggtccatacc tttgctgttg    30240
aaatagtgct gcaataaaca tacacgtgca ggtgtctttc ttatataaat gatttcttt    30300
tttctttcct ttttttgat ataacgaatt tcttttattt gggttaaatc ccccaatagt    30360
gggattgnnn nnnnnnnnn nnnnnnnnnn nnnnnnnnnn nnnnnnnnnn nnnnnnnnnn    30420
nnnnnnnnnn nnnnnnnnnn nnnnnnnnnn tgacctgtcc gtattgatat ataaaatgct   30480
gcatttaaag tgtacaactt gatattttgg tatacattgt taaatcatgg ccacatttca   30540
gctaattaat atatctatta tctctacata gttatcatgt ttgtacccct tgaccagcat   30600
caccccattt gctcctcctc ccagcccctg gcaaccacca tcctactctc tgcttctatg   30660
agtctgacaa ttttagattc cacctataag ttagattatg cggtatttgt ctttctgtgc   30720
ctggcttatt tcacttagcc taatgtcctc cagctccatc tatgttatcc caagtggcag   30780
gattttcatc tttcttatat atttcattgt atatgtgtat gccacatttt ctttacccat   30840
tcatccattg aaggtcattt agcttgtttc catatcttgg ctatttgaa tagtgctgca    30900
atgaacatag gagtgcagat atctctttaa gatactggtt tcatttcttt ctttcttctc   30960
ttttttttt ttctgagaca gagtctgact ctgtcgctca agctggagta cagtggtgca    31020
atcttggctc actgcaaact ctgcctcctg agttcaagcg attctcgtgc ctcaacctcc   31080
cagggagttt tgctcttgct gcccaggctg aagtgcagtg gtgcaatctt cactcaccac   31140
aacctgtgcc tcccgggttc aagcgattct cgtgcctcag cctcccaggt agcaaggatt   31200
acaggcgccc aacaccacac caggctaaat ttttttgcat tttagtaga dcggggtttc    31260
tgccatgttg gccaggctgg tctcaaattc ctggcctcaa gtgatccacc tgcctcagcc   31320
tcctgaagtg ctgggatttt acaggcatga accaccacac atggcctcat ttcttttaga   31380
tatatatggg ttgagctatt ctcagagggt ccttttctgc atctatttaa gatcacattt   31440
tttttatatt gtggcaaaaa tacatgtaac ataaaatctg ccattttaac cattttaaa   31500
tgtacaattc agtgacattg attatattca caatgtcata cagccatcac cactatttat   31560
ttctaatact tttccattgg gtagatcccc aacagtggga ttgctgggtc aaatggtagt   31620
```

-continued

```
tctgattttt ttttttttgtt ttttgagaaa tctccatact gttttttcatt tgaggttgta  31680
ctaatttaca ttcccaccaa cagtgtataa gagtttccta ggccgggcat ggtggcttat  31740
gcctgtaatc ccagcacttt gcgaggccca ggtgggtgga tcatgaggtc aggagatcga  31800
gaccaccctg gctaacatgg tgaaacccc tctctactaa aaatgcaaaa aattagccgg  31860
gcgtggtggc gggtgcctgt agtcccagct actggagagg ctgaggcagg agaatggcat  31920
gaaccctgaa ggcggggctt gcagtgagct gagatcgcac cactgcacac ttcaacctag  31980
gcgacagagc gagactccat ctcaaaaaaa aaaaaaaaaa aaaaggtttc ctttcagtgc  32040
atccttgcca acttgagttt ctgggttgg tttgcactct catggtattt actagatact  32100
tctccattta tattttact caacccatgc ccataacacc actcctctac cattcccacc  32160
aaccatgtat aagagttcct tttcttgcat ccttgccaac ttgacttctt tgggtcagtt  32220
tgcactctct tggtatttac tatttacttc tccatttata tttttagtca actgatgccc  32280
atggcaccgc tcctctgagg caggtgctgg gtactagagt gataagacag atgctgtccc  32340
tgccctcacc cagtggagaa gaacagatgc taaacaggaa cataaatatc taagtaaaat  32400
ggcttcaaat ggagtaaagt gatatgaaac ataaataaat agcaagtgat gggtagagca  32460
actttaccca ggatgaatct tgggctgtgt cccaaatggc catgaaaact gttccaggca  32520
gggagaacag catgagaaaa ggtcttgagg tgcaaatgag cttggcatgt tctatgaaca  32580
gcaaagaggc cagtgtggct ggagcagaga gagagcaaga agaaaagaga gaaggatga  32640
gactcaagac atcagcaagt ttgaagggcc ttggaggact tggattttt ttttttaagac  32700
agctttgttc ttgttgccca ggcatgatct cggctcacca caacctccgc ctcctgggtt  32760
caaacgattc ctctgcctca gcctcccgag tagctgggg taacaggcat gtgcccacca  32820
cacctggcta attttgtatt tttagtagaa atggggcttc tccatggttg gtcaggctgg  32880
tctcgaactc ccgacctcag gtgatccgac cgcctcggcc tcccaaagtg ctgggattat  32940
aggtgtgagc cactgcacct ggcttggatt ttttttgttc tatattgtgg taacatacac  33000
atcacattaa attgatcatt ttagctatat ttcccgttca gtggcatcaa gcacattcac  33060
attattgtgc aaccatcacc actatcatcc atctccagaa ctttctcatc ttcccaaact  33120
gaaactccat ccccatgaaa cactcattcc tcatcccct cctcaagcct ctggcaccca  33180
ccattctact ttctgtctct gtgaatctga tgattctgag gacctcctat gaatggagga  33240
atcatatggt atatgtcctg gtttatactg tatggctggc ttatttcacc aagcataatg  33300
tcctcaaagt tcatccatgt tgtagcatgt gtcagaattc ccttccttt ccacttgtat  33360
gtaaatgctg tattgtgttt ctccattcat taggactttg atttttgcag ggagttgtca  33420
aggggtgctg ggttctgggg cttcaatata ataagagtaa gctaaactgg ttcatttcct  33480
ccttcgtgga gaccatgttc tggtaggaac aggaacaaat aatttatgat tacatagagg  33540
gtgaccaggg cagtgacagg ggaagagtgg aggattgtgg gacccagagg aggctcctga  33600
ccttgcctag gaagatagga ggaggaagag gaggaggaag aggaggagga agaggaggag  33660
gaggaggagg agggagtcct ctaagctgag acctggagga tgaccaggaa gttatccagg  33720
taaggagaaa tggggagaag cttccagaca aaagtaacag caattgcaaa gatcctgaga  33780
tgatagataa ggtcaggtgg agaaagtgca aactgtcaat gagaccaaaa tatggactgt  33840
gagttgtgca gtgaccacaa gtggagaggt gctaggtggc cttcatcccc caaagctgca  33900
cctctcctc ctcaggtctg tgaagaacg tgctgagaca cgggtggacc tcctctgcac  33960
ctacctgcag cccctcagcg gcccaggtct gcctatcaag caggtgttcc atgagctgag  34020
```

```
ccagcagacc catggcatca cccggctggg cccctactct ctggacaaag acagcctcta    34080
ccttaacggt gagcagctat cagccccatc tccctgcccc accccccagc ccccactgca    34140
gtccaggagg gtgtctgttt gccggttctc tagggaaaga cttggggttc aagtcttggc    34200
attaccactg gccctcccat aaccacaatg caaggttgga ctttgattaa tcccatttta    34260
cagatgaaga aactgaggct tagacaggct aagcaattta ccttgacagt ggtggaacca    34320
ggatatgaac tccacttgtc agcattcggt gctatgatcc actccacatg tttaactcac    34380
agaagagtct tcctggtggg ggcacttggg ggacaaaaaa cacatttccg gctgtgagca    34440
gtggctcaca cctgtaatcc cagcactttg ggaggccaag gcgggcggat cacaaggtca    34500
agagattgag accaccctgg acaacatagt gaaaccctgt ctctactaaa aatacaaaaa    34560
ttagctgggt gtggtggcgc acgcctgtag tcccacctac tcgggaggct gaggcaggag    34620
aatcgcttga actcgggagg cagaggttgc agtgagccaa gattgcgcca ttgcactcca    34680
gtctgggtga caagagtgaa actctgtctc aaaaaaaaaa aaaacaattt cccctccctg    34740
cttttcttctc accattgacg agggatgggc ttctctccta cctgaggccc cctataccag    34800
gaagatctat gggatctaat cttcagcgca cactgggcct cagcattggt ctagaactca    34860
ggataagata gcatttaaga aggcatcccc taaatggggt tctgagaggc aaagcatgac    34920
cgtggagaat tgacaaaata gctcgccttt catcccctcc accgccaacc caagaacagt    34980
gcttatcatc atgaccccat gaggtgggca ccccatatca cttatatgag gtacctttag    35040
gtaggtaccg ggatgtggag agacatcctg ggctttcatt actcttattt tagcaaagag    35100
ggaatctgag gcacagagaa gggaagggac ttgcccatgc ccacagcgag ttttttggcta   35160
gtatgggtct tgatgttctt tctgggtccg tnnnnnnnnn nnnnnnnnnn nnnnnnnnnn    35220
nnnnnnnnnn nnnnnnnnnn nnnnnnnnnn nnnnnnnnnt tcctgcgtgg gagatgtgtg    35280
gatttgattt gtatctggaa agatgatttt ttattggtga caaagcagtt aaagttaatc    35340
ttcacagttg tgcggagagt gaccacgcga gttagtctta tccttatttt tttgatcatc    35400
ccgctacaca agacaaagcg aaccgcacag gcaacatcag caggcccat tggtgtgttc     35460
ccctctatgg gtccatgtgt tctcatcatt agctcccacg tataaagtga gaagatggca    35520
gtattggttt tctgttcctg cattagtttg gtaaggataa tgacctccag ctccaaccat    35580
gttcctgcaa cggacatgat ctcattcttt tttatagctg catagtattc catggtgtat    35640
atgttcctca tgttctttat ccagtctatc cttgatgggc atttaagtag attccatgtc    35700
tttgctattg tgaatagtgc ttcagtgaac aggtgtcttt atgatagaaa aatttatatg    35760
cctttgggca tatatgcagt gatgagattg ctgggtcaga cggtagttct gtttttagct    35820
ctttgaggaa tcatcctgct gctttctaca gtggatgaac taatttacac tcccaccaac    35880
agtgtataaa cactcctttt tatctgcaac ctcagcagca tggttttatt tctctttatg    35940
gctgaatagt gttccattgt gcatatatac cacactttct ttatggattc atctgctgat    36000
ggacatatag gttgattcca catctctgct attgtgaata gtgctgtgat aaacacacag    36060
gtgcgggttg ggtcttgatg atctcagtta acatccagtc ccttcaactt ggctattgca    36120
gggagctgtt ccccccttgta aactgcacag cttatgtgct tcatttttgtt ccttcattta    36180
gatttaccaa gcagctacta ttaaccaggc cacaatgtgc ctcgccccca ggaacagaga    36240
taggttacat gtgcatcctg tcctaatgta atctccaggg gggcggagac tgttttgttc    36300
tacccctatat tccccaaatg taagggagc cttgcacata ctaagcccct aataaacatt     36360
```

```
cattgggtgg aggaatagat tggaggaggc ctggaagggg aggcgggggt tatggatgga    36420
taggaggata gacttgtgaa cacaaaggta gtgagagcct ctcattggag gcatgctgga    36480
gacgtgagta gggaagggtc agtgctaatt gaaatatcag gaaattcttt ctagtggtga    36540
acacatttaa gtcaaatatt agatgataca taaatgtatc cataatctct agatacacaa    36600
agggaaaggc atccaggcag gggcccccata tggacaaagg catggagtat ctgggacggt    36660
tccaccacct cctcttacgt gtgacttctt tgtttcaagg ttacaatgaa cctggtctag    36720
atgagcctcc tacaagtacg tgtctttgaa tctagtgccc atttcaatct ccatgggtct    36780
tggttcaagc ttttctcctc attcatgaag gaaggttgcc ccaaattcgg gctggtcccc    36840
taggtggtga ggggcattgt ctcagtggga ggaagaatgc tgagtccttg gccctgtttt    36900
tagacctgca gccatagtct tggctttgtg aattttccat gtccctctgg gttggaggaa    36960
gaagtttgaa caagcattcc ctacacggga tagaggttga ggtcagatga tgacctctgt    37020
tagtctgtac cctccttgat aagaaaatct cctccaagtg ccccagcaga ggcttcatgg    37080
tcaagctgca gactctgctg gctactggtt ttggctaaat ttgcccattg cctcatccag    37140
tgatccactc gtctatcttt ccagccatcc attttctat ccttccagtc atctctcaga     37200
caccacctgt ccttccatcc atccatccgt ccatccattt acccatccat ccatccaccc    37260
cattttcctg accattacc tcctcgtcct tccttccatc tgtccttta tccatctatt     37320 catccatcac ccatcctcct gcccattcac ctgcttgtcc ctcctttctt ctgtccttct    37380
atacatccat ccatccatcc atccatccat ccacccatcc actcatccac cacccaccca    37440
tccttctgcc cactcactcg ctagccccctc cttccttctg tccttccatc catccatcca   37500
cccatcttcc tgcccattca cctgcttgtc cttccttcta tctgtctttt atccatctct    37560
ccatccattc tcaccatcca tccatccatc cttctccccta ttcactggtt tgtcttttcct  37620 tctgtccttc caaccatcca cccatctctc cattcattct cctcttcatt caccatgttt    37680
ccttatttct gtctcttcca tccatccatc tatccagaca gacatctcct cccccattc     37740 tcctccccat tcactcaatt gtccttcctt ccatctgtcc ttttatccat ccatccaccc    37800
atccatccat ccatctatcc ttctccccat tcacctgttt gtccttcttt ctgtccttcc    37860
aaccatccat ccatccatca tccatccatc tatcctttc cccattcacc tgttttgtcc    37920
ttccttctgt ccttccaaca tccctccatc tctccatcca tcctcctgcc tattcatctg    37980
cttgtctttc cttccttctg tccttccatc cattcatcca tctgcccatc cacccactca    38040
tcctcttgcc cattcacctg cttgtccttc cttccacctg tccttttatc catccatcca    38100
tccatccatc ttgctcactc ctccactcac acaatcactc cttccctcag tctcatttat    38160
ggcccacctg tgaatggttg tcctggcttg gaccactgat gaagcccagg ggagcttctc    38220
ccactagtgg tgggcttttg tcctctctga tggactgttc cttccacagc tcccaagcca    38280
gccaccacat tcctgcctcc tctgtcagaa gccacaacag gtatttgggg ccattttttcc   38340 tcctcgaaga ttagaatagc atttcaatca gacacctgcc ctcgtggagt cccagatttt    38400
atgaaataaa tagaccatca taatgtcaga tgttttgggg tgagatacct ggcatagttg    38460
ggaaggagga gggctttctg gagaaagttt caccctgaact gagtctttaa ggatgactaa    38520
gagtgattca ggcaaatagg gcatgaatag tataactgaa agaggggaat ctgtgagcaa    38580
agcctcagtg gccagaaaca gcatagagta tagggagaag tgagagaaat ttggtttgca    38640
tgaaacataa agcttaaccc agagtggatg gataagtgag actgaaaggt cagcaggagc    38700
cagattggga agggccttga atgccaagtc aagaaatttg aacttaacac tgaaggccat    38760
```

```
agggagctgt ggatggtact agagcagggg cagccatagt gagattgtca tttcagaaag   38820
attcttcttg tgttcagtat agagaatgtc ctttagacag ggcatccagt gagtctgcca   38880
ggtgctaatc agggtgagag aaaataagac ctgaactggg ataggggag gagagagagg    38940 atatatgtga tgaatattca gtaaagagaa ttggtgttac ttggagggga gaagacacat   39000
agcttctgac ttgcgatggc cacactcagt ttaataatga gcgcagtctg atctagtctc   39060
agaccagccc tcagttgcag acgtctctcc tccctcctg cagcatgggg taccacctga    39120
agaccctcac actcaacttc accatctcca atctccagta ttcaccagat atgggcaagg   39180
gctcagctac attcaactcc accgagggg tccttcagca cctggtgaga ccctggtccc    39240
agcagctcct ggtgggataa atcctacccc caacctctgt tcctcggctt accctcttcc   39300
tccttcctct caagctcaga cccttgttcc agaagagcag catgggcccc ttctacttgg   39360
gttgccaact gatctccctc aggtgagacc acttcctggc catttgccag taacaaccac   39420
cccttttgtg accacccctt cctcagcttt ccctgctcc tcctccact gctcttacc     39480 tgcagaggtc tcgggacctc tctagagtcc tcaaatgcct ctctcccag gcctgagaag    39540 gatgggcag ccactggtgt ggacaccacc tgcacctacc accctgaccc tgtgggcccc    39600
gggctggaca tacagcagct ttactgggag ctgagtcagc tgacccatgg tgtcacccaa   39660
ctgggcttct atgtcctgga cagggatagc ctcttcatca atggtgagtg tcaggctgaa   39720
cttggattta cagtgacttt tggggagttg gtttctttgt ttttgagatg gagtctcact   39780
ctatcaccca ggctggagtg caatggtgca atcttggctc tgcaacagtg attctcctgc   39840
ctcagcctcc caagtagctg ggatttacag gtgcatgcca ccacgctcag ctaattttttg  39900 tattttagt agagatgggg tttcaccatg ttgcccaggc tggtctcgaa ctcctgacct   39960
caggtgatcc acctgccttg gcctcccaaa gtgccaggat tacaggcatg agccaccatg   40020
cccggcccac catgactatt atttgtccct gttgtatgcc ctttcctctc taaaaaaaat   40080
agcccaaggc ctggctgggg gacacccttc cccaaaccac caaggggagg gtctttccca   40140
ttattttgag taaatagcat gaaattcttt gaccaaatta atgtcataaa ttgtttgtct   40200 cttttctcctt cacttttgtt tccaacttgg ttgcggtata actatcaaat acaattgtat  40260
gtatttaaga tgtataatgc agtgatttaa tatatgtgta gcttatgaaa tgattaccat   40320
gatcaaatta gttaacactg ctttcatgtc acatagttac cgtgtgtctg tgtgcgtctg   40380
tgtgagttag agagaaagag aacatttaag gtctaccctc atagaaaatt tcaggtttac   40440
aatacagtat tattaactat aatcatcaag ctttatactc gatccccaga acttattcat   40500
cttgtaacta aaagtttgta ttttgtgacc aacatctccc cattttctct atcaccaccc   40560
ccatgccccc agccctgat aaccatcatg ctactctctg cttctgtaag tttgacttct    40620
gatcccacat ataagtgaga tcatgcagta tttgtttctc tctatctggt atatttcact   40680
tagcataatg aaccccccc aggtacatcc ataatgaatt tcaattcaaa acccaagtgg    40740
ctgagtcgtg gcatcctttg ggacaggata gcaggtccct tctatataag gatcctctgt   40800
gtcagtggtt attaccaggg gacaattctg cacttctgcc ccaccccacc ccccaactgg   40860
gagactctag gcaatatccg aaatcatttt tgggtatcac aactcaggga gggaaggagg   40920
gtgcaactgg cacctagtgg gtcggtagcc catttccag tgcacaggag acaaccaccc    40980
cagggaatga tccagcccca aatgccaata atttcaaggg tgagaaatcc tgttgtacat   41040
ggtctcaaag ttcttaggtg ggcacaaggc tgacatttat cacactttac tgtaattact   41100
```

```
tgttaaattt atctgattcc cccttaccct gtgaactcaa caaaattacg gtctattatg    41160
agtgccactg taccctcggt tcgcagtaca tcagcacatc atagtatgga aagaatcatt    41220
gaatgagtga gcaaattaaa gatttgtgtc tctgctgtaa ctcacattca ttaattcatt    41280
cattcagcaa acatatatgg gtggctgttc tgcccaagc cttgtactgg gtctggagat     41340
agaagacaca ttttctgtc tctgaaaaac tcatactcaa gttaacaaca aattacgggc     41400
acaacaaaga ccccactgct gttattaaca gggtactatg ggagctgaga ggaggagtaa    41460
attaaggagg gcttcctgga ggagggtgtt atatacccgg ccctgtgccg ggacacataa    41520
tgataagaca gacttgggcc tctgctgtcc tggagctccc tctcactggg ctcttgaagc    41580
gtgagcagga gttttgcagg aaatgaaaag gatgcattcc tagaagtggg aactgcatag    41640
cacatgcagg aaagctcagc tcagaagaat ctgtgtaata ttccattttt ccctctcttt    41700
ggggcaactt tctgtctaag agctcctgca atgcccagcg tgtggacctg aaattgattc    41760
tgacagtagg caggggactg ctgggcaact ttggctctgc attttgtgat caacatttcc    41820
ccaccatatg ttgcctttc ttcttctctg tggctccagg ctatgcaccc cagaatttat    41880
caatccgggg cgagtaccag ataaatttcc acattgtcaa ctggaacctc agtaatccag    41940
accccacatc ctcagagtac atcaccctgc tgagggacat ccaggacaag gtggggcatc    42000
tctcacccct cccgtcttct ctgtcctgtg tgcttctctc cctcttctac ctgatttctc    42060
tgttaagtga tcactttaaa tgcttcactt cactatgtat tctgggttct ctctcagttt    42120
ccaaaagtac tctcttgact accattccca tttcacagat gggcaaactg aggctcagaa    42180
aggggcgtgg tgtgcctagg gtcatacagt gctttaggaa cagagttagg atttgaactc    42240 tggtccccctt tgctccaagt cctgtgtttt tttccactgg catcagcggc ccctccaccc    42300
ccaagaggcc tccatctcac ccactctccc tacccatctt tctaggtc                 42348
```

```
<210> SEQ ID NO 3
<211> LENGTH: 14277
<212> TYPE: DNA
<213> ORGANISM: Homo sapiens
<220> FEATURE:
<221> NAME/KEY: misc_feature
<222> LOCATION: (1)..(66)
<223> OTHER INFORMATION: Exon C1
<220> FEATURE:
<221> NAME/KEY: misc_feature
<222> LOCATION: (1802)..(1947)
<223> OTHER INFORMATION: Exon C2
<220> FEATURE:
<221> NAME/KEY: misc_feature
<222> LOCATION: (4198)..(4350)
<223> OTHER INFORMATION: Exon C3
<220> FEATURE:
<221> NAME/KEY: misc_feature
<222> LOCATION: (4679)..(4747)
<223> OTHER INFORMATION: Exon C4
<220> FEATURE:
<221> NAME/KEY: misc_feature
<222> LOCATION: (6811)..(6978)
<223> OTHER INFORMATION: Exon C5
<220> FEATURE:
<221> NAME/KEY: misc_feature
<222> LOCATION: (11232)..(11270)
<223> OTHER INFORMATION: Exon C6
<220> FEATURE:
<221> NAME/KEY: misc_feature
<222> LOCATION: (11594)..(11677)
<223> OTHER INFORMATION: Exon C7
<220> FEATURE:
<221> NAME/KEY: misc_feature
<222> LOCATION: (13375)..(13500)
<223> OTHER INFORMATION: n is a, c, g, or t
```

```
<220> FEATURE:
<221> NAME/KEY: misc_feature
<222> LOCATION: (14095)..(14187)
<223> OTHER INFORMATION: Exon C8

<400> SEQUENCE: 3
accacactct acaaaggcag tcaactacat gacacattcc gcttctgcct ggtcaccaac        60
ttgacgtaag ttctgaaggt cataagcagt gaccaagctt gtggctgtgt ctctgagcac       120
ccttgagcta gacgtcccca gtggggtacc cattctcccc tacatccctg tctagctaat       180
cctaccatct cctcccataa atcctcaagg tagggagtga ggattaacct catggggcca       240
ccaactccca gcatacacct tcttttttt ctggacactt gggaaaatat aacttttga        300 tgtagaactc aaaatattag cccaataata atatttaaca tcaaccagcc tcctctcatt       360
taattctcac aacagaatct atgagttgag tgcaaaaatc atccctattg tgcagatggg       420
aaaactgagg gtcagaaaag tgaacttccc aagaactgtc aaagttggga tttgaaccca       480
ggtctctgat gactggatga aggaatgaag atacctatac ttgggaatga ggagggtcga       540
caggacacga gggctgactt tgtatatttc taaacttcaa agattttctg tatttcagct       600
gggaatatgg tagaaggtta attggaacaa aaaaatgcaa agcaatgaat aagacctcag       660
tatttgctat gcacaacagg gtgactgtag tcccacaaat aacttcactg tacattgtta       720
aaatataact aaaggtgtat gcttggattg tttgcaacac aaaggatata tgcttgaggg       780
gatggatacc ccatttaccc tgatgattat tatgcattac atgcttgtat caaaacatct       840
catatacccc ataaatataa aaacacctac tatgtaccccc aaaaaattaa aaacaaataa       900
aatcaaaagt aggctgggca cagtggctca tgcctgtaat cccagcactt tgggaggcca       960
gggcaggtgg atctcttgag cccagaagtt caagaccagc gagggcaaca tagggagtcc      1020
tagtctctac aaaaaataca aaaattagcc aggcatggtg gcacacacct gtagtcccag      1080
ccactcagga agctgaggtg ggaggatcgc ctgagcctag gaggctgtac tccagcctgg      1140
gtgacagagc gagactctat ctcaaaaaat aaaataaaat aataaaaagt agaaatcaag      1200
agggaaaatg tgggagaaat tgggataatt ttaacaatac cttccaccag agtgatgatg      1260
aagaatgcat aagtcacttc ttagtggtct tgatctataa aaagtgttca ataaatatcg      1320
attattgtta ctgttattgc ttctagacgt aattcctgga agcatttttt tttttttt       1380 ttttgagatg gagtcatgct ctgttgctca ggctggagtg cagtggtatg atctcggctc      1440
actacaactg cctcctgggt tcaagcaatt ctcctgcctc agccccccat gtagcaggga      1500
ctacaggcat gcgccaccac acccggtgaa gttttgtatt tttattagag acagggtttt      1560
gccatgttgg tcaggctggt ctcgaactcc tgacctcagg caatttgcct gcctcggcct      1620
cccaaagtgc tgagattaca ggcttgggcc actgcatcca gccgaaggcc tcccattttg      1680
atcagaaccc ttctctagac tgagggtggg tgcctctaga tcttttgctc tttaaagaca      1740
gcaaccgatg accctgctga tgctgagtac tggctgaatt cctgtggtct ctgtccctag      1800
gatggactcc gtgttggtca ctgtcaaggc attgttctcc tccaatttgg accccagcct      1860
ggtggagcaa gtcttttctag ataagaccct gaatgcctca ttccattggc tgggctccac      1920
ctaccagttg gtggacatcc atgtgacagg tacaaggtgg ggtggctggt ttcctaactg      1980
gaagaggtgg ggttatgagg aaagatgggg cttctcggta ccagtggaat tggtggaggc      2040
tctagagagg gaaagggagg cttcctggag acccatgtag gtgacctctg gcagtagatc      2100
atccaacgag gcaggaacag aacaccagcc attgcatcta agagaatagc tatttttaca      2160
```

-continued

```
tgtaaaaaga attgtgttga atgaatgaat caatagatca tttattttga atcaatttat    2220
tgattcattc atttaattaa tgaataataa atgattcagt acataattga ttaattgatg    2280
taattgagaa ttgatttaat tgattaattg atcaattaaa atgatcaatt aaatgaatga    2340
atcagtaaat gaataattca ttcattcaat aaacaatgga agtaggccgg gcatggtggc    2400
tcacgcctgt aataccagta cttttgggagg cccaggcagg cagatcacga ggtcaggaga    2460
ttgagaccat cctggctaac acggtgaaac cctgtctcta ctaaaaatac aaaaaaaatt    2520
agccaggcat ggtggtggcc acctgtagtc gcagctactc gggaggctga ggcaggagaa    2580
tggcgtgaac ccgggaggca gagcttgcag tgagccgaga tcgcgccact gcactccagc    2640
ctgggcgaca gatggagact ctgtctcaaa aataaataaa taaataaaaa taaaaaataa    2700
ataaacaatg gaagtaaaca cgtactgata acacagtgtg atcattgcta tgataaggga    2760
atttcagggg cctgtgggag ccccaaggag gaacacacaa ccttgtcttg gaaagtttta    2820
tgtaggaagg ggtgaagaag ctgagatctg acagagaatg ggacctagcc aggggtaata    2880
gatggagaat tgtgctccat gcatctataa cctagaagat agaaagaata tggcatctgg    2940
ccgggtgcgg tggctcacgc ctgtagtccc agcactttca gaggctgaga tgggtggatc    3000
acctgaggtc aggagttcaa gaccagcctg accaatatga tgaaacccca tctctgctaa    3060
aaatacaaaa attagccagg catggtggtg cgtgcctgta atcccagcca cttgggaggc    3120
tgagagagga gaactgcttg aactcgggag gcggaggttg cagtgagccg agattgtgcc    3180
attgcactca agcctgggca aaaagagcaa aactgcattt caaaaaaaaa aaaagtggca    3240
ttttggggca agtttaagaa gattggtgta gctggagcat ccactttgat actggagagg    3300
tgacagttga agccaaagat gtgggcagag actttgttgg gcactggaat ggcttgggga    3360
ggaacatgac acactcatga gttctgcttt agaaagaaaa tgaaatgaat ctgctcatc    3420
ctctgggtgc tgtgtgcaga atggagggtg gggggagaga agagcaaagg caagaagacc    3480
ctttaggaac aatgatcatt agttagaaga ctctgggttt ctcagcacct gcaattgctg    3540
actacacccc cagagaaacc cagtctcttt tcccccatgt tgtagagaat tcttacaatg    3600
cttggtagaa agagaattga acaggtagat gggtggatgg atacaagctg gacagatgga    3660
tggaggaaga tcctccatcc aatatagagc tgttacctaa aaccctccat cccacccttta    3720
aaatcctagc tcagccaggc gcggtggctc acacctgtaa tcccagcact ttgggaggcc    3780
aaggcgggtg gatcacttga ggtcgggggt tcgagaccag tctgaccaac atggtgaaac    3840
ccccttctcc actaaaaata caaaaaaaaa aaaagttag ccaggcaggg tggcgcatgc    3900
ctgtaatccc gctactcggg aggctgaggc aggagaatgg cttgcaccca ggaggtggag    3960
gttgtggtga gccaagatca cgccattaca ctccagcctg gcaaagaga gtgaaactgt    4020
ctcaaaaaac aaaacaaatg acccccctgc caaaaaaaaa aaaaaaaaa aagaaaagaa    4080
aaaaagaaaa gcctagctca gctcacactg tcaggaataa gtaagctagc tggaatcatc    4140
tctttcttaa aaccctgcct tgatagtgga tttttacata cttttttttt aattctagaa    4200
atggagtcat cagtttatca accaacaagc agctccagca cccagcactt ctacctgaat    4260
ttcaccatca ccaacctacc atattcccag gacaaagccc agccaggcac caccaattac    4320
cagaggaaca aaaggaatat tgaggatgcg gtgagaaggg ggtggtatgt ccactctgtt    4380
gccatgcaga aactgactta tgcatactgg gtagccacag ggtgactttt tataacaatc    4440
cacaaagaca ggttcttatt cccatttaat acacaagcac agagaggttc agtagctgac    4500
ccaaggtcac acagctaagt catacccctag aagagcatgt cctttgatat acatacctgg    4560
```

```
gcaagtggtt gtcatgacaa gaagcaaaat agacggagaa gtgtgctcag tggctgaaaa      4620
ttctctgatg ctactggggc caggattctg acctaagaaa catcgccctg tctttcagct      4680
caaccaactc ttccgaaaca gcagcatcaa gagttatttt tctgactgtc aagtttcaac      4740
attcaggtaa gttctaactc aggacctaat gactctagga acttctgctg tcctttaaat      4800
agaagtgtcc ccaagccata gctttgatgg aagagagccc tagaaataga gagctgttaa      4860
ctaaaaacta gcttttttcct aaagctggag cccaactggc ttcaacactc aagagagctg     4920
gtgtaaatct cagcagacat aaaggtacct ggtgctgagg ccatggagtc tagagtgtag      4980
aatctactac attaagacat cagctactga aatcaggacc catggaagac gggggaagga      5040
ggggactaaa accagattac ttagaatcta gcagcctaac tgtgcttttc aatgagaggt      5100
atcatttcca atggtggggg gtaccaatga ttttttttt ttgacaactg ccttgagaac       5160
aggctttcct cactaaacaa attctgaatc agaacaaata aagataagcc ctgagaatag      5220 ggcttttca aggagctgcc aaacagatca aatagtgact atgttctgca gattgatgtc       5280
tggagaactc tacagctatt ttgactgcta ggcagctggt tttcacagat atcatgattc      5340
tgaggctgcc agttttcaaa gttaccgagg atcttgctgg atgcagtggc ttgcgactgt      5400
aatcccagcc ctttgggagg ccaaggtggg tagatcgctt gagctcagga gtttgagacc      5460
agcctgggca atatggtgaa aacccatctc tacaaaaaat acaaaaatca gctgagcata      5520
gtggcatgtg ctgtagtccc agttacttag gaggctgagg tgggaggatg gcttgagccc      5580
aggaggcaga ggttgcagtg agctgacatt gtgccatgca ctctagcctg gcaacagag      5640 ccaaagcctg tctcaaaaaa aaaaaaacaa ataataataa taataaaata ctgaggatct      5700
tgaaagagca ctgtggaaat aatgcaagtt aaaatgccac aaagcttgct cttttttactg    5760 agatttaaca ctttccttaa ctaaacaccc ctcgaatttt tgcaagcctt tggttcactt      5820
ctagacttct ggaaaaattg atttggacta ttttggccaa tgttctcatt gattttatgg      5880
gtattcagaa gttgttaccc caacattcca gaaatgttct ccctgtggct attactttat      5940
ttatttattt atttatttat ttatttattt atttgagacg gagtctccct ctgttgccca      6000
ggctggagtg cagtggcgca atctcagctc actgcaacct ccgcttccca ggttcaagcg      6060
attctcctgc ctcagcctcc caagtagctg ggattatgga tgtgcaccac cacaccggct      6120 aattttttgtg tttttagtag agatgggggtt tcactgtgtt ggccaggctg gtctcgaact    6180
cctgatctca gtgatccac ccgccttggc ctcccaaagt gctgggataa caggcatgag       6240
ccactgtgcc tgacctccct gtggctattt ttaaatgaat taagtggaat aaaattagaa      6300
attcagttct tctcccacgc tagctgcatt ttaagcattt aataacaaca tgaagctact      6360
aatggctgca ttgtgtagtg cagatgtaga attttttttt tgtttttgt tttgtttttg       6420 agatggagtc tcgctctgtc accaggctag agtgcagtgg cgtgatctcg tctcactgca      6480
atctctactc cccgattcaa gtgattctcc tgcctcagcc tcccaagtag ctgggattac      6540
aggcacgtgc caccacaccc agctaatatt tgtatggatg gtctcaatct cctgacctcg      6600
tgatttgtat ggatggtctc gatctgacct catgatccgc ctgcctgggc ctcccaaagt     6660
gctgggatta caggcgtgag ccactgtgcc cggccgacat agaatgttta catcattgca      6720
gaaagtttct gcaggaagag cctagaagga gaaagcctag aatcatgata aaattgcaga     6780
tatctttgct tatccctgtc cccttccagg tctgtcccca acaggcacca caccggggtg     6840
gactccctgt gtaacttctc gccactggct cggagagtag acagagttgc catctatgag      6900
```

```
gaatttctgc ggatgacccg gaatggtacc cagctgcaga acttcaccct ggacaggagc      6960
agtgtccttg tggatggtaa agctccctgg gtcattggga ctgaggtgga agctcccact      7020
tcctcacctg ggtccttccc tgggaatctg aaggcttggg gttgattcgt catcgagctt      7080
tctcagactg ggagaaagtg gcttagttct cctaagcttt acccatcatt gaaggaaaga      7140
aaaggacgcc cgagggatat gggaggcatt tgccctcttc tggccagctc tgtgacctca      7200
ggctagtcac atctcctttc tggacttctt atctctctgt acttagcaag ccacttggtt      7260
tttggttccc atcttgcctg ccctagatgg tattgctcct ccaccccag gcagctgcag       7320 tgttaaacaa ttaccctgat tagttattgt tgttgtgttg tttgtttgtt tttgagacag      7380
ggtctcactc tgtcacctag gctggagtgc agtgacatga tctcagctca ctgcaacctc      7440 aaccctgga ctcaagcaat ccacccactt cagcctccca gtaactggga actacagcca      7500
tgcgccacca cacccggata atttttgtat tttttctaga gatggggttt tgcaacattg      7560
cccaggctgg tcttgaactc ctgagctcaa gcatgccacc tgcttcagcc tcccaaagtg      7620
ctgggattac aggcaggcag gcaccactgc agctggttct ggttttttgt gtttgttttt      7680
ttcttttaga ggcagggtct cgctctgtta accagaatgg agtacagtgg tgcaatcata      7740
gctcactgca gtcttgaact cctgggctca agcgatcctc ccacctcagc ctcctgagta      7800
cctggaacta caggcacgtg tcaccacgcc ttgctaattt ctaatttttt tgtagagaca      7860
gggtctcact atgttgccca gactggtctc taattcctgg ccacaagtga tcctcctgcc      7920
tcagcaggtc aatgagggct tccagtttca agttgtatgt gattcatcct caacaaatgt      7980
ggtaggatgg acctattttc caactccaga gatggcttca aggtggctca actttgcata      8040 tccaattta cccattcaaa gaatagttat atacattgta ccatgtatca ggaatataac       8100
agagagtaac tgtttgctct ttcaccacta tattccaaga accccatatt ctgcctggca      8160
cataataaac actcaagtca tatttgcaga aggaataact agatttcata caaggttctt      8220
ttcaagtcaa atgcgaataa cgttttagac gggaccttcc aatgcctgtg tgcactgtcc      8280
ttgattccga attattgttg tgcaagagag cactgttgat ccttcagaat caacaagcct      8340
ttcacatgcc tgtcacaggt ttttcttttt cttgttttac caattttgtt tgttgtttgt      8400
ttgttgttat tgttttgttt tgttttgtt tttatttgt ttttattttt tcttttttt        8460 tgagacagag tctcgctctg tcacccaggc tggagtgcag tggcacgatc tcgcccact       8520 gcaagctccg cctcctgggt tcatgccatt ttcctgcctc agcctcctga gtagctggga      8580
ctacaggcgc ctgccaccat gtctggctaa ttttttttgt attttagta gaaacagggt       8640 ttcaccatgt tgaccaggat ggtctcgatc tcctgacctc gtgatctgcc cacctgggcc      8700
tcccaaagtg ctgggattac aggcgtgagc caccacaccc agcccaatt ttttttttaa       8760 ttaaaattgt tgtcagctca caagctttct aaaaacaggc catggaccca gcatcgctgt      8820
agtttgccaa acccttgcct tgaatcagta ccatccaata gaactttctg cagtgataga      8880
aaatgtttct atctgtgcta ttcagcacaa agccatgtgt gattactaag cttgaagtgt      8940
ggttaatgta actgagatac cgaagtttta attttattta attttaattt aaaaagccac      9000
ttgtggctgc tccatattgc acactacttt ttaaaattat tatttgtata tatttaaggg     9060
gcacaagtac aattttgttg catggattta tagcccagtg gggaagtctg gcttttagg       9120 gtatctatta cctgaataat gtacattgta cccattgagt aatttctcat catccactct      9180
cctccactcc ccaaccctc caagtttcca ctgtctatta ttccactctc tatgtccatg       9240
cctatgcatt atttagcatt gacatgtcta tgcattattt agtcaaatac atgtgctatt      9300
```

```
tgacttcctg tatctgagtt gtttgactta agataatgac cttcacttgc atccatgttg   9360
ctgcaaaaga catgatttca ttcttttta tgcctgggtg gtattgcatt gtgtgtgtgt    9420
gtgtgtgtgt gtgtgtagag agagagagag atcacatttt ctttatacag tcctccattg   9480
atgggcactt aggttgattc catatctttg ctattgtgaa tagttttgtg ataaacacac   9540
aggttcaggt gtcttttga caaaattatt tattttcctt tgtgtagata cccagtcgtg    9600
ggattcctgg atcaaatggt agtttcattt ttagttattt gagaaatctc cacgttttc    9660 atagagatta tactaaatta cattcccacc aacagtgtgt aacggttcac ttttcttgca   9720 tccttttaa catctgttat ttttgtcttt ttagtaacag ccattctgac tggcgtaagg    9780
tggtatctca tcatggtttt aatctgtatt tctctgatta ttagtaatgt cgagcatttt   9840
ttcatatgct tgttagccat tggtatgtct tctacatctt taagaagctg gctatgggct   9900
gggcgcagtg gctcacacct gtaatcccag cactttggga ggccgaggca ggcggatcac   9960
gaggtcagga gttaaaaacc agcctggcca acatggtaaa accctgcctc tactaaaaat  10020
acaaaaaatt acccaggcat ggtggtgcgc ctgtaatccc agctactcag gaagctgagg  10080
caggagaatc acttgaaccc aggaggcgga ggttgcagtg agacgagatc acatcattgc  10140
actccagcct gggtgacaga gtgagactct atcttgagaa aaaaaaaaag ttggctataa  10200
cagggttgta gaagtagagg aaccagtaac ccttctcgcc atgcctgatg atggctttac  10260
atccctgtct tcatggagtt tatgctgtcg tgaggaataa caagaacagg cagttgtcaa  10320
ttataaatta tttgatgtga acctattcat acatgggtgt ggtcatcagg gaaggcttcc  10380
tggaggaaat gacattgaag gtgaattcta aaagatgacg ataaaccacc aagtgaagga  10440
gagcttaaat gtgtttttag gcagaagaaa aaccttttgg gtgaaaattt taaaacttag  10500
agaggtccca tcagtttcca actgcgatga tccattctct ccaccactgc ccttgggccc  10560
agcccaattt aggtccacca tgcccagagg catgaattta acttatgaca ctcttgtggt  10620
ggaataatgg ctttgggctt atgtagccat gtgtcatttt tttagagata caaattgaaa  10680 tatttgggt gagatgtcat ggtgtctact ggcctctaaa acttcagtga aaacatttac   10740
tttcactgaa atgtcaataa atcataaatt ggatgtatat gttttagttg gaggaaatat  10800
aaaccactaa atctaggtga tgcatattta ttatactctt ctctctgctt ttttgtacgc  10860
ttgtaaaatt gtatttaaaa gaataagaca cacttggccg ggcgcggtgg ctcacgcctg  10920
taatcccagc actttgggag accgaggtgg gtggatcatg aggtcaggag ttcaagacca  10980
gcctggccaa catggtaaaa ctccatcact acatacaaaa attagccagg catttggcg   11040 ggcacctgta atctcagcta cttgggaggc tgaagcagga gaattgcttg aacccgggaa  11100
gcagaggttg cagtgagcca agatcacgcc actgcactct agcctgggca acagagcaag  11160
actccatctc cagaaaaaaa aaaaaaaaa gacacactca catgcaccct ccatttcttt   11220
catttctagg gtattctccc aacagaaatg agcccttaac tgggaattct ggtaagtctc  11280
aaagaagccc cagcccaggg tagggagggg gtagcctgat ggtgctttgc cttgtccaag  11340
agcaccaggc acacagagtc ttggatgagg atcaaaattg ccaacccatg gcaaagacta  11400
ttgaggcata gtaaagggat agcagggatc ctggcttttct gggggcccag ttttttgggg  11460
catcagaggc atgaggtgtt gagccactaa gctctcttcc ccaggggctg tgcccatcct  11520
caggccacat agggtccaag aaggagccct gggacgtggc aggaggtggc tcaccccagc  11580
ccttgtctcc ccagaccttc ccttctgggc tgtcatcctc atcggcttgg caggactcct  11640
```

```
gggagtcatc acatgcctga tctgcggtgt cctggtgagc aaggaagggt tgcttgtctt   11700
cttaacaatt gggttgtaag agttcttaat atattataaa accatactat actatacaca   11760
agtcctttgc tggatatatg ttttgcaaat attttctccc agttcacgga gtggctttcc   11820
tattttcttt ttataatttt attttttaatt aattgacaaa taatgaatgc atatatttag   11880
gggatacaat gtgatgcttt ggtatatgta caattatgga atgactcaat caagctaatt   11940
aatatgtccc tcacctctca tacttattat ttctttgtgg tgtgaacatt ggcaacctat   12000
actcttagca attttgaaat ctacattatt attaactata gttactatgt tatgcagatc   12060
tcaaaaactt cacaacctat atgctgatta caagatattg agagaaaaag tgattgcaaa   12120
gagtgtaaat aaaataatgt aagagggaaa aatgtaacaa aattagtcgt tagggaaatg   12180
tacacggaag tcacaatgag aggccacttt tcacaagaat ggataaaatt gaaaagattg   12240
actataacaa gtgttggtga aaatgtgaca gaactggaac tctcataaag tgaaagtgga   12300
aaatagcttg gccatttctt tgaaaattac acacacctac cgtaagacct accatcccac   12360
tactagtaat ttatctaaga gaaataaaaa catatgtcta tatgaagact tgtacacaag   12420
taaatgttca taacagcttt gtttgtaata gccaaactct gaaaacaagc ccctaatgtc   12480
cattaacaaa tatatcctga caatggaata ttattcagca acaaaaagga attattaata   12540
cattaataaa ttatacagca acatgtataa attgcaaaat agttatgcct agtgaaagaa   12600
tccagatgaa gaaaagagta catgccatat gattccctta atagacaaat tctagaaaat   12660
acaaactaat ctgtaaggac aggaatcaga tcagcggttg cctgggaatg aaaatgtgtt   12720
tgcagtggca gggaaaaagg aattgtaaaa gagcaggaag aaagtttttt tgttgttttt   12780
ttttgtttt tcttgagac agagtcttag tctatcgccc aagctggagt gcaatggcac   12840
gatctcagct cattgcaacc tctgcctctc gggttcaagc gttttcctg ccccagcctc   12900
ccaagtagct gggattacac atgcgcacca ccacactcag ctaattttg tattttagt   12960
agagacgggg ttttaccatg ttggccaggc tggtctcgaa ctcctgacct caggtgatcc   13020
acccgccttg gcctcccaaa gtgctgggat tacaggagtg agccaccatg cctggccagg   13080
acgaaagttt tggggatgat ggatggatgt tccttatgtt gattgtgtg acgattcaat   13140
aagttatgat cagaacttat caaaacattc actttaaatg tgtgcagttt attttatgtc   13200
agttatgcct cagttaagct ggacagatgt agaggaggaa gggagggaga gagggggctg   13260
agatcaggac caaaagccag agagaaagag actgagaatg agatgagaga gaaatggtat   13320
ttagacagaa gacaggcgat agatgattga tagttgacag atgattggtg gatannnnnn   13380
nnnnnnnnnn nnnnnnnnnn nnnnnnnnnn nnnnnnnnnn nnnnnnnnnn nnnnnnnnnn   13440
nnnnnnnnnn nnnnnnnnnn nnnnnnnnnn nnnnnnnnnn nnnnnnnnnn nnnnnnnnnn   13500
aggaggttta acaaaacgc aattatgttg aaatgacaat gattgtggat ataaaggtag   13560
atagaaatag atatttgtga agataatggt tagataaaaa tgataggtaa cagatattga   13620
tagatcttga taagtagatg ataaatacat gattgatgga tgacaggtga ttgatagatg   13680
atttgatgga ttataaatag gagatgattg agaggtgaga gataattgat ggttatttga   13740
ttggtagata attgattgac aggttgataa atattgatag ctagatgata gataaataga   13800
tcattggtag atatgtgata tattgataaa gaaattcaga ggcaaaagga gagagaaatg   13860
aaggggatat cggagggga aaatttttt taaaccgaga gtgaaacaag gagacagaag   13920
aaagaaagt ggtgaaaaga ggaaaagaac tgagggagaa attaaatgaa acaatgaagg   13980
gagacagagg aagcataagg cctctggctt tggccatatt ctcacccctg tggtctcctc   14040
```

```
tccctggacg gctgaccagt ccattctcac gcctcctcct caccctcata ggtgaccacc    14100
cgccggcgga agaaggaagg agaatacaac gtccagcaac agtgcccagg ctactaccag    14160
tcacacctag acctggagga tctgcaatga ctggaacttg ccggtgcctg gggtgccttt    14220 ccccagcca gggtccaaag aagcttggct ggggcagaaa taaaccatat tggtcgg       14277
```

```
<210> SEQ ID NO 4
<211> LENGTH: 66765
<212> TYPE: DNA
<213> ORGANISM: Homo sapiens
<220> FEATURE:
<221> NAME/KEY: misc_feature
<222> LOCATION: (38757)..(38757)
<223> OTHER INFORMATION: n is a, c, g, or t
<220> FEATURE:
<221> NAME/KEY: misc_feature
<222> LOCATION: (38775)..(38775)
<223> OTHER INFORMATION: n is a, c, g, or t
<220> FEATURE:
<221> NAME/KEY: misc_feature
<222> LOCATION: (38778)..(38778)
<223> OTHER INFORMATION: n is a, c, g, or t
<220> FEATURE:
<221> NAME/KEY: misc_feature
<222> LOCATION: (38835)..(38835)
<223> OTHER INFORMATION: n is a, c, g, or t
<220> FEATURE:
<221> NAME/KEY: misc_feature
<222> LOCATION: (38838)..(38838)
<223> OTHER INFORMATION: n is a, c, g, or t
<220> FEATURE:
<221> NAME/KEY: misc_feature
<222> LOCATION: (38859)..(38859)
<223> OTHER INFORMATION: n is a, c, g, or t
<220> FEATURE:
<221> NAME/KEY: misc_feature
<222> LOCATION: (38868)..(38868)
<223> OTHER INFORMATION: n is a, c, g, or t
<220> FEATURE:
<221> NAME/KEY: misc_feature
<222> LOCATION: (38883)..(38883)
<223> OTHER INFORMATION: n is a, c, g, or t
<220> FEATURE:
<221> NAME/KEY: misc_feature
<222> LOCATION: (38892)..(38892)
<223> OTHER INFORMATION: n is a, c, g, or t
<220> FEATURE:
<221> NAME/KEY: misc_feature
<222> LOCATION: (41833)..(41833)
<223> OTHER INFORMATION: n is a, c, g, or t
<220> FEATURE:
<221> NAME/KEY: misc_feature
<222> LOCATION: (41838)..(41838)
<223> OTHER INFORMATION: n is a, c, g, or t
<220> FEATURE:
<221> NAME/KEY: misc_feature
<222> LOCATION: (41843)..(41843)
<223> OTHER INFORMATION: n is a, c, g, or t
<220> FEATURE:
<221> NAME/KEY: misc_feature
<222> LOCATION: (41847)..(41847)
<223> OTHER INFORMATION: n is a, c, g, or t
<220> FEATURE:
<221> NAME/KEY: misc_feature
<222> LOCATION: (41859)..(41859)
<223> OTHER INFORMATION: n is a, c, g, or t
<220> FEATURE:
<221> NAME/KEY: misc_feature
<222> LOCATION: (41865)..(41865)
<223> OTHER INFORMATION: n is a, c, g, or t
<220> FEATURE:
<221> NAME/KEY: misc_feature
<222> LOCATION: (41874)..(41876)
<223> OTHER INFORMATION: n is a, c, g, or t
<220> FEATURE:
```

```
<221> NAME/KEY: misc_feature
<222> LOCATION: (41881)..(41883)
<223> OTHER INFORMATION: n is a, c, g, or t
<220> FEATURE:
<221> NAME/KEY: misc_feature
<222> LOCATION: (41892)..(41892)
<223> OTHER INFORMATION: n is a, c, g, or t
<220> FEATURE:
<221> NAME/KEY: misc_feature
<222> LOCATION: (41911)..(41911)
<223> OTHER INFORMATION: n is a, c, g, or t
<220> FEATURE:
<221> NAME/KEY: misc_feature
<222> LOCATION: (41942)..(41942)
<223> OTHER INFORMATION: n is a, c, g, or t
<220> FEATURE:
<221> NAME/KEY: misc_feature
<222> LOCATION: (41945)..(41945)
<223> OTHER INFORMATION: n is a, c, g, or t
<220> FEATURE:
<221> NAME/KEY: misc_feature
<222> LOCATION: (41951)..(41951)
<223> OTHER INFORMATION: n is a, c, g, or t
<220> FEATURE:
<221> NAME/KEY: misc_feature
<222> LOCATION: (41986)..(41986)
<223> OTHER INFORMATION: n is a, c, g, or t
<220> FEATURE:
<221> NAME/KEY: misc_feature
<222> LOCATION: (41989)..(41989)
<223> OTHER INFORMATION: n is a, c, g, or t
<220> FEATURE:
<221> NAME/KEY: misc_feature
<222> LOCATION: (41991)..(41991)
<223> OTHER INFORMATION: n is a, c, g, or t
<220> FEATURE:
<221> NAME/KEY: misc_feature
<222> LOCATION: (41994)..(41994)
<223> OTHER INFORMATION: n is a, c, g, or t
<220> FEATURE:
<221> NAME/KEY: misc_feature
<222> LOCATION: (42000)..(42000)
<223> OTHER INFORMATION: n is a, c, g, or t
<220> FEATURE:
<221> NAME/KEY: misc_feature
<222> LOCATION: (42016)..(42016)
<223> OTHER INFORMATION: n is a, c, g, or t
<220> FEATURE:
<221> NAME/KEY: misc_feature
<222> LOCATION: (42022)..(42022)
<223> OTHER INFORMATION: n is a, c, g, or t
<220> FEATURE:
<221> NAME/KEY: misc_feature
<222> LOCATION: (42026)..(42026)
<223> OTHER INFORMATION: n is a, c, g, or t
<220> FEATURE:
<221> NAME/KEY: misc_feature
<222> LOCATION: (43909)..(43909)
<223> OTHER INFORMATION: n is a, c, g, or t
<220> FEATURE:
<221> NAME/KEY: misc_feature
<222> LOCATION: (43911)..(43912)
<223> OTHER INFORMATION: n is a, c, g, or t
<220> FEATURE:
<221> NAME/KEY: misc_feature
<222> LOCATION: (43916)..(43916)
<223> OTHER INFORMATION: n is a, c, g, or t
<220> FEATURE:
<221> NAME/KEY: misc_feature
<222> LOCATION: (43927)..(43927)
<223> OTHER INFORMATION: n is a, c, g, or t
<220> FEATURE:
<221> NAME/KEY: misc_feature
<222> LOCATION: (43929)..(43929)
<223> OTHER INFORMATION: n is a, c, g, or t
<220> FEATURE:
<221> NAME/KEY: misc_feature
<222> LOCATION: (43932)..(43932)
<223> OTHER INFORMATION: n is a, c, g, or t
```

-continued

```
<220> FEATURE:
<221> NAME/KEY: misc_feature
<222> LOCATION: (43939)..(43939)
<223> OTHER INFORMATION: n is a, c, g, or t
<220> FEATURE:
<221> NAME/KEY: misc_feature
<222> LOCATION: (43947)..(43947)
<223> OTHER INFORMATION: n is a, c, g, or t
<220> FEATURE:
<221> NAME/KEY: misc_feature
<222> LOCATION: (43965)..(43965)
<223> OTHER INFORMATION: n is a, c, g, or t
<220> FEATURE:
<221> NAME/KEY: misc_feature
<222> LOCATION: (43968)..(43968)
<223> OTHER INFORMATION: n is a, c, g, or t
<220> FEATURE:
<221> NAME/KEY: misc_feature
<222> LOCATION: (43970)..(43970)
<223> OTHER INFORMATION: n is a, c, g, or t
<220> FEATURE:
<221> NAME/KEY: misc_feature
<222> LOCATION: (43974)..(43975)
<223> OTHER INFORMATION: n is a, c, g, or t
<220> FEATURE:
<221> NAME/KEY: misc_feature
<222> LOCATION: (43982)..(43983)
<223> OTHER INFORMATION: n is a, c, g, or t
<220> FEATURE:
<221> NAME/KEY: misc_feature
<222> LOCATION: (43985)..(43985)
<223> OTHER INFORMATION: n is a, c, g, or t
<220> FEATURE:
<221> NAME/KEY: misc_feature
<222> LOCATION: (43989)..(43989)
<223> OTHER INFORMATION: n is a, c, g, or t
<220> FEATURE:
<221> NAME/KEY: misc_feature
<222> LOCATION: (43992)..(43992)
<223> OTHER INFORMATION: n is a, c, g, or t
<220> FEATURE:
<221> NAME/KEY: misc_feature
<222> LOCATION: (44013)..(44013)
<223> OTHER INFORMATION: n is a, c, g, or t
<220> FEATURE:
<221> NAME/KEY: misc_feature
<222> LOCATION: (44377)..(44377)
<223> OTHER INFORMATION: n is a, c, g, or t
<220> FEATURE:
<221> NAME/KEY: misc_feature
<222> LOCATION: (44379)..(44380)
<223> OTHER INFORMATION: n is a, c, g, or t
<220> FEATURE:
<221> NAME/KEY: misc_feature
<222> LOCATION: (44384)..(44384)
<223> OTHER INFORMATION: n is a, c, g, or t
<220> FEATURE:
<221> NAME/KEY: misc_feature
<222> LOCATION: (44395)..(44395)
<223> OTHER INFORMATION: n is a, c, g, or t
<220> FEATURE:
<221> NAME/KEY: misc_feature
<222> LOCATION: (44397)..(44397)
<223> OTHER INFORMATION: n is a, c, g, or t
<220> FEATURE:
<221> NAME/KEY: misc_feature
<222> LOCATION: (44400)..(44400)
<223> OTHER INFORMATION: n is a, c, g, or t
<220> FEATURE:
<221> NAME/KEY: misc_feature
<222> LOCATION: (44407)..(44407)
<223> OTHER INFORMATION: n is a, c, g, or t
<220> FEATURE:
<221> NAME/KEY: misc_feature
<222> LOCATION: (44415)..(44415)
<223> OTHER INFORMATION: n is a, c, g, or t
<220> FEATURE:
<221> NAME/KEY: misc_feature
<222> LOCATION: (44433)..(44433)
```

-continued

```
<223> OTHER INFORMATION: n is a, c, g, or t
<220> FEATURE:
<221> NAME/KEY: misc_feature
<222> LOCATION: (44436)..(44436)
<223> OTHER INFORMATION: n is a, c, g, or t
<220> FEATURE:
<221> NAME/KEY: misc_feature
<222> LOCATION: (44438)..(44438)
<223> OTHER INFORMATION: n is a, c, g, or t
<220> FEATURE:
<221> NAME/KEY: misc_feature
<222> LOCATION: (44442)..(44443)
<223> OTHER INFORMATION: n is a, c, g, or t
<220> FEATURE:
<221> NAME/KEY: misc_feature
<222> LOCATION: (44450)..(44451)
<223> OTHER INFORMATION: n is a, c, g, or t
<220> FEATURE:
<221> NAME/KEY: misc_feature
<222> LOCATION: (44453)..(44453)
<223> OTHER INFORMATION: n is a, c, g, or t
<220> FEATURE:
<221> NAME/KEY: misc_feature
<222> LOCATION: (44457)..(44457)
<223> OTHER INFORMATION: n is a, c, g, or t
<220> FEATURE:
<221> NAME/KEY: misc_feature
<222> LOCATION: (44460)..(44460)
<223> OTHER INFORMATION: n is a, c, g, or t
<220> FEATURE:
<221> NAME/KEY: misc_feature
<222> LOCATION: (44481)..(44481)
<223> OTHER INFORMATION: n is a, c, g, or t
<220> FEATURE:
<221> NAME/KEY: misc_feature
<222> LOCATION: (47185)..(47185)
<223> OTHER INFORMATION: n is a, c, g, or t
<220> FEATURE:
<221> NAME/KEY: misc_feature
<222> LOCATION: (47187)..(47188)
<223> OTHER INFORMATION: n is a, c, g, or t
<220> FEATURE:
<221> NAME/KEY: misc_feature
<222> LOCATION: (47192)..(47192)
<223> OTHER INFORMATION: n is a, c, g, or t
<220> FEATURE:
<221> NAME/KEY: misc_feature
<222> LOCATION: (47203)..(47203)
<223> OTHER INFORMATION: n is a, c, g, or t
<220> FEATURE:
<221> NAME/KEY: misc_feature
<222> LOCATION: (47205)..(47205)
<223> OTHER INFORMATION: n is a, c, g, or t
<220> FEATURE:
<221> NAME/KEY: misc_feature
<222> LOCATION: (47208)..(47208)
<223> OTHER INFORMATION: n is a, c, g, or t
<220> FEATURE:
<221> NAME/KEY: misc_feature
<222> LOCATION: (47215)..(47215)
<223> OTHER INFORMATION: n is a, c, g, or t
<220> FEATURE:
<221> NAME/KEY: misc_feature
<222> LOCATION: (47223)..(47223)
<223> OTHER INFORMATION: n is a, c, g, or t
<220> FEATURE:
<221> NAME/KEY: misc_feature
<222> LOCATION: (47241)..(47241)
<223> OTHER INFORMATION: n is a, c, g, or t
<220> FEATURE:
<221> NAME/KEY: misc_feature
<222> LOCATION: (47244)..(47244)
<223> OTHER INFORMATION: n is a, c, g, or t
<220> FEATURE:
<221> NAME/KEY: misc_feature
<222> LOCATION: (47246)..(47246)
<223> OTHER INFORMATION: n is a, c, g, or t
<220> FEATURE:
<221> NAME/KEY: misc_feature
```

-continued

```
<222> LOCATION: (47250)..(47251)
<223> OTHER INFORMATION: n is a, c, g, or t
<220> FEATURE:
<221> NAME/KEY: misc_feature
<222> LOCATION: (47258)..(47259)
<223> OTHER INFORMATION: n is a, c, g, or t
<220> FEATURE:
<221> NAME/KEY: misc_feature
<222> LOCATION: (47261)..(47261)
<223> OTHER INFORMATION: n is a, c, g, or t
<220> FEATURE:
<221> NAME/KEY: misc_feature
<222> LOCATION: (47265)..(47265)
<223> OTHER INFORMATION: n is a, c, g, or t
<220> FEATURE:
<221> NAME/KEY: misc_feature
<222> LOCATION: (47268)..(47268)
<223> OTHER INFORMATION: n is a, c, g, or t
<220> FEATURE:
<221> NAME/KEY: misc_feature
<222> LOCATION: (47289)..(47289)
<223> OTHER INFORMATION: n is a, c, g, or t
<220> FEATURE:
<221> NAME/KEY: misc_feature
<222> LOCATION: (48118)..(48118)
<223> OTHER INFORMATION: n is a, c, g, or t
<220> FEATURE:
<221> NAME/KEY: misc_feature
<222> LOCATION: (48120)..(48121)
<223> OTHER INFORMATION: n is a, c, g, or t
<220> FEATURE:
<221> NAME/KEY: misc_feature
<222> LOCATION: (48125)..(48125)
<223> OTHER INFORMATION: n is a, c, g, or t
<220> FEATURE:
<221> NAME/KEY: misc_feature
<222> LOCATION: (48136)..(48136)
<223> OTHER INFORMATION: n is a, c, g, or t
<220> FEATURE:
<221> NAME/KEY: misc_feature
<222> LOCATION: (48138)..(48138)
<223> OTHER INFORMATION: n is a, c, g, or t
<220> FEATURE:
<221> NAME/KEY: misc_feature
<222> LOCATION: (48141)..(48141)
<223> OTHER INFORMATION: n is a, c, g, or t
<220> FEATURE:
<221> NAME/KEY: misc_feature
<222> LOCATION: (48148)..(48148)
<223> OTHER INFORMATION: n is a, c, g, or t
<220> FEATURE:
<221> NAME/KEY: misc_feature
<222> LOCATION: (48156)..(48156)
<223> OTHER INFORMATION: n is a, c, g, or t
<220> FEATURE:
<221> NAME/KEY: misc_feature
<222> LOCATION: (48174)..(48174)
<223> OTHER INFORMATION: n is a, c, g, or t
<220> FEATURE:
<221> NAME/KEY: misc_feature
<222> LOCATION: (48177)..(48177)
<223> OTHER INFORMATION: n is a, c, g, or t
<220> FEATURE:
<221> NAME/KEY: misc_feature
<222> LOCATION: (48179)..(48179)
<223> OTHER INFORMATION: n is a, c, g, or t
<220> FEATURE:
<221> NAME/KEY: misc_feature
<222> LOCATION: (48183)..(48184)
<223> OTHER INFORMATION: n is a, c, g, or t
<220> FEATURE:
<221> NAME/KEY: misc_feature
<222> LOCATION: (48191)..(48192)
<223> OTHER INFORMATION: n is a, c, g, or t
<220> FEATURE:
<221> NAME/KEY: misc_feature
<222> LOCATION: (48194)..(48194)
<223> OTHER INFORMATION: n is a, c, g, or t
<220> FEATURE:
```

-continued

```
<221> NAME/KEY: misc_feature
<222> LOCATION: (48198)..(48198)
<223> OTHER INFORMATION: n is a, c, g, or t
<220> FEATURE:
<221> NAME/KEY: misc_feature
<222> LOCATION: (48201)..(48201)
<223> OTHER INFORMATION: n is a, c, g, or t
<220> FEATURE:
<221> NAME/KEY: misc_feature
<222> LOCATION: (48222)..(48222)
<223> OTHER INFORMATION: n is a, c, g, or t
<220> FEATURE:
<221> NAME/KEY: misc_feature
<222> LOCATION: (48226)..(48226)
<223> OTHER INFORMATION: n is a, c, g, or t
<220> FEATURE:
<221> NAME/KEY: misc_feature
<222> LOCATION: (48228)..(48228)
<223> OTHER INFORMATION: n is a, c, g, or t
<220> FEATURE:
<221> NAME/KEY: misc_feature
<222> LOCATION: (48231)..(48231)
<223> OTHER INFORMATION: n is a, c, g, or t
<220> FEATURE:
<221> NAME/KEY: misc_feature
<222> LOCATION: (48246)..(48249)
<223> OTHER INFORMATION: n is a, c, g, or t
<220> FEATURE:
<221> NAME/KEY: misc_feature
<222> LOCATION: (48253)..(48253)
<223> OTHER INFORMATION: n is a, c, g, or t
<220> FEATURE:
<221> NAME/KEY: misc_feature
<222> LOCATION: (48255)..(48255)
<223> OTHER INFORMATION: n is a, c, g, or t
<220> FEATURE:
<221> NAME/KEY: misc_feature
<222> LOCATION: (48265)..(48265)
<223> OTHER INFORMATION: n is a, c, g, or t
<220> FEATURE:
<221> NAME/KEY: misc_feature
<222> LOCATION: (48273)..(48273)
<223> OTHER INFORMATION: n is a, c, g, or t
<220> FEATURE:
<221> NAME/KEY: misc_feature
<222> LOCATION: (48278)..(48278)
<223> OTHER INFORMATION: n is a, c, g, or t
<220> FEATURE:
<221> NAME/KEY: misc_feature
<222> LOCATION: (48305)..(48306)
<223> OTHER INFORMATION: n is a, c, g, or t
<220> FEATURE:
<221> NAME/KEY: misc_feature
<222> LOCATION: (48313)..(48313)
<223> OTHER INFORMATION: n is a, c, g, or t
<220> FEATURE:
<221> NAME/KEY: misc_feature
<222> LOCATION: (48315)..(48315)
<223> OTHER INFORMATION: n is a, c, g, or t
<220> FEATURE:
<221> NAME/KEY: misc_feature
<222> LOCATION: (48322)..(48322)
<223> OTHER INFORMATION: n is a, c, g, or t
<220> FEATURE:
<221> NAME/KEY: misc_feature
<222> LOCATION: (48327)..(48327)
<223> OTHER INFORMATION: n is a, c, g, or t
<220> FEATURE:
<221> NAME/KEY: misc_feature
<222> LOCATION: (48340)..(48340)
<223> OTHER INFORMATION: n is a, c, g, or t
<220> FEATURE:
<221> NAME/KEY: misc_feature
<222> LOCATION: (48356)..(48356)
<223> OTHER INFORMATION: n is a, c, g, or t
<220> FEATURE:
<221> NAME/KEY: misc_feature
<222> LOCATION: (48362)..(48363)
<223> OTHER INFORMATION: n is a, c, g, or t
```

-continued

```
<220> FEATURE:
<221> NAME/KEY: misc_feature
<222> LOCATION: (48365)..(48365)
<223> OTHER INFORMATION: n is a, c, g, or t
<220> FEATURE:
<221> NAME/KEY: misc_feature
<222> LOCATION: (48367)..(48367)
<223> OTHER INFORMATION: n is a, c, g, or t
<220> FEATURE:
<221> NAME/KEY: misc_feature
<222> LOCATION: (48369)..(48369)
<223> OTHER INFORMATION: n is a, c, g, or t
<220> FEATURE:
<221> NAME/KEY: misc_feature
<222> LOCATION: (48378)..(48378)
<223> OTHER INFORMATION: n is a, c, g, or t
<220> FEATURE:
<221> NAME/KEY: misc_feature
<222> LOCATION: (48388)..(48388)
<223> OTHER INFORMATION: n is a, c, g, or t
<220> FEATURE:
<221> NAME/KEY: misc_feature
<222> LOCATION: (48393)..(48393)
<223> OTHER INFORMATION: n is a, c, g, or t
<220> FEATURE:
<221> NAME/KEY: misc_feature
<222> LOCATION: (48398)..(48398)
<223> OTHER INFORMATION: n is a, c, g, or t
<220> FEATURE:
<221> NAME/KEY: misc_feature
<222> LOCATION: (48402)..(48402)
<223> OTHER INFORMATION: n is a, c, g, or t
<220> FEATURE:
<221> NAME/KEY: misc_feature
<222> LOCATION: (48414)..(48414)
<223> OTHER INFORMATION: n is a, c, g, or t
<220> FEATURE:
<221> NAME/KEY: misc_feature
<222> LOCATION: (48420)..(48420)
<223> OTHER INFORMATION: n is a, c, g, or t
<220> FEATURE:
<221> NAME/KEY: misc_feature
<222> LOCATION: (48429)..(48431)
<223> OTHER INFORMATION: n is a, c, g, or t
<220> FEATURE:
<221> NAME/KEY: misc_feature
<222> LOCATION: (48436)..(48438)
<223> OTHER INFORMATION: n is a, c, g, or t
<220> FEATURE:
<221> NAME/KEY: misc_feature
<222> LOCATION: (48447)..(48447)
<223> OTHER INFORMATION: n is a, c, g, or t
<220> FEATURE:
<221> NAME/KEY: misc_feature
<222> LOCATION: (48466)..(48466)
<223> OTHER INFORMATION: n is a, c, g, or t
<220> FEATURE:
<221> NAME/KEY: misc_feature
<222> LOCATION: (49006)..(49006)
<223> OTHER INFORMATION: n is a, c, g, or t
<220> FEATURE:
<221> NAME/KEY: misc_feature
<222> LOCATION: (49009)..(49009)
<223> OTHER INFORMATION: n is a, c, g, or t
<220> FEATURE:
<221> NAME/KEY: misc_feature
<222> LOCATION: (49011)..(49011)
<223> OTHER INFORMATION: n is a, c, g, or t
<220> FEATURE:
<221> NAME/KEY: misc_feature
<222> LOCATION: (49014)..(49014)
<223> OTHER INFORMATION: n is a, c, g, or t
<220> FEATURE:
<221> NAME/KEY: misc_feature
<222> LOCATION: (49020)..(49020)
<223> OTHER INFORMATION: n is a, c, g, or t
<220> FEATURE:
<221> NAME/KEY: misc_feature
<222> LOCATION: (49036)..(49036)
```

-continued

```
<223> OTHER INFORMATION: n is a, c, g, or t
<220> FEATURE:
<221> NAME/KEY: misc_feature
<222> LOCATION: (49042)..(49042)
<223> OTHER INFORMATION: n is a, c, g, or t
<220> FEATURE:
<221> NAME/KEY: misc_feature
<222> LOCATION: (49046)..(49046)
<223> OTHER INFORMATION: n is a, c, g, or t
<220> FEATURE:
<221> NAME/KEY: misc_feature
<222> LOCATION: (49321)..(49321)
<223> OTHER INFORMATION: n is a, c, g, or t
<220> FEATURE:
<221> NAME/KEY: misc_feature
<222> LOCATION: (49326)..(49326)
<223> OTHER INFORMATION: n is a, c, g, or t
<220> FEATURE:
<221> NAME/KEY: misc_feature
<222> LOCATION: (49331)..(49331)
<223> OTHER INFORMATION: n is a, c, g, or t
<220> FEATURE:
<221> NAME/KEY: misc_feature
<222> LOCATION: (49335)..(49335)
<223> OTHER INFORMATION: n is a, c, g, or t
<220> FEATURE:
<221> NAME/KEY: misc_feature
<222> LOCATION: (49347)..(49347)
<223> OTHER INFORMATION: n is a, c, g, or t
<220> FEATURE:
<221> NAME/KEY: misc_feature
<222> LOCATION: (49353)..(49353)
<223> OTHER INFORMATION: n is a, c, g, or t
<220> FEATURE:
<221> NAME/KEY: misc_feature
<222> LOCATION: (49362)..(49364)
<223> OTHER INFORMATION: n is a, c, g, or t
<220> FEATURE:
<221> NAME/KEY: misc_feature
<222> LOCATION: (49369)..(49371)
<223> OTHER INFORMATION: n is a, c, g, or t
<220> FEATURE:
<221> NAME/KEY: misc_feature
<222> LOCATION: (49380)..(49380)
<223> OTHER INFORMATION: n is a, c, g, or t
<220> FEATURE:
<221> NAME/KEY: misc_feature
<222> LOCATION: (49399)..(49399)
<223> OTHER INFORMATION: n is a, c, g, or t
<220> FEATURE:
<221> NAME/KEY: misc_feature
<222> LOCATION: (49430)..(49430)
<223> OTHER INFORMATION: n is a, c, g, or t
<220> FEATURE:
<221> NAME/KEY: misc_feature
<222> LOCATION: (49433)..(49433)
<223> OTHER INFORMATION: n is a, c, g, or t
<220> FEATURE:
<221> NAME/KEY: misc_feature
<222> LOCATION: (49439)..(49439)
<223> OTHER INFORMATION: n is a, c, g, or t
<220> FEATURE:
<221> NAME/KEY: misc_feature
<222> LOCATION: (49474)..(49474)
<223> OTHER INFORMATION: n is a, c, g, or t
<220> FEATURE:
<221> NAME/KEY: misc_feature
<222> LOCATION: (49477)..(49477)
<223> OTHER INFORMATION: n is a, c, g, or t
<220> FEATURE:
<221> NAME/KEY: misc_feature
<222> LOCATION: (49479)..(49479)
<223> OTHER INFORMATION: n is a, c, g, or t
<220> FEATURE:
<221> NAME/KEY: misc_feature
<222> LOCATION: (49482)..(49482)
<223> OTHER INFORMATION: n is a, c, g, or t
<220> FEATURE:
<221> NAME/KEY: misc_feature
```

```
<222> LOCATION: (49488)..(49488)
<223> OTHER INFORMATION: n is a, c, g, or t
<220> FEATURE:
<221> NAME/KEY: misc_feature
<222> LOCATION: (49504)..(49504)
<223> OTHER INFORMATION: n is a, c, g, or t
<220> FEATURE:
<221> NAME/KEY: misc_feature
<222> LOCATION: (49510)..(49510)
<223> OTHER INFORMATION: n is a, c, g, or t
<220> FEATURE:
<221> NAME/KEY: misc_feature
<222> LOCATION: (49514)..(49514)
<223> OTHER INFORMATION: n is a, c, g, or t
<220> FEATURE:
<221> NAME/KEY: misc_feature
<222> LOCATION: (49519)..(49519)
<223> OTHER INFORMATION: n is a, c, g, or t
<220> FEATURE:
<221> NAME/KEY: misc_feature
<222> LOCATION: (49521)..(49522)
<223> OTHER INFORMATION: n is a, c, g, or t
<220> FEATURE:
<221> NAME/KEY: misc_feature
<222> LOCATION: (49526)..(49526)
<223> OTHER INFORMATION: n is a, c, g, or t
<220> FEATURE:
<221> NAME/KEY: misc_feature
<222> LOCATION: (49537)..(49537)
<223> OTHER INFORMATION: n is a, c, g, or t
<220> FEATURE:
<221> NAME/KEY: misc_feature
<222> LOCATION: (49539)..(49539)
<223> OTHER INFORMATION: n is a, c, g, or t
<220> FEATURE:
<221> NAME/KEY: misc_feature
<222> LOCATION: (49542)..(49542)
<223> OTHER INFORMATION: n is a, c, g, or t
<220> FEATURE:
<221> NAME/KEY: misc_feature
<222> LOCATION: (49549)..(49549)
<223> OTHER INFORMATION: n is a, c, g, or t
<220> FEATURE:
<221> NAME/KEY: misc_feature
<222> LOCATION: (49557)..(49557)
<223> OTHER INFORMATION: n is a, c, g, or t
<220> FEATURE:
<221> NAME/KEY: misc_feature
<222> LOCATION: (49575)..(49575)
<223> OTHER INFORMATION: n is a, c, g, or t
<220> FEATURE:
<221> NAME/KEY: misc_feature
<222> LOCATION: (49578)..(49578)
<223> OTHER INFORMATION: n is a, c, g, or t
<220> FEATURE:
<221> NAME/KEY: misc_feature
<222> LOCATION: (49580)..(49580)
<223> OTHER INFORMATION: n is a, c, g, or t
<220> FEATURE:
<221> NAME/KEY: misc_feature
<222> LOCATION: (49584)..(49585)
<223> OTHER INFORMATION: n is a, c, g, or t
<220> FEATURE:
<221> NAME/KEY: misc_feature
<222> LOCATION: (49592)..(49593)
<223> OTHER INFORMATION: n is a, c, g, or t
<220> FEATURE:
<221> NAME/KEY: misc_feature
<222> LOCATION: (49595)..(49595)
<223> OTHER INFORMATION: n is a, c, g, or t
<220> FEATURE:
<221> NAME/KEY: misc_feature
<222> LOCATION: (49599)..(49599)
<223> OTHER INFORMATION: n is a, c, g, or t
<220> FEATURE:
<221> NAME/KEY: misc_feature
<222> LOCATION: (49602)..(49602)
<223> OTHER INFORMATION: n is a, c, g, or t
<220> FEATURE:
```

-continued

```
<221> NAME/KEY: misc_feature
<222> LOCATION: (49623)..(49623)
<223> OTHER INFORMATION: n is a, c, g, or t
<220> FEATURE:
<221> NAME/KEY: misc_feature
<222> LOCATION: (50725)..(50725)
<223> OTHER INFORMATION: n is a, c, g, or t
<220> FEATURE:
<221> NAME/KEY: misc_feature
<222> LOCATION: (50730)..(50730)
<223> OTHER INFORMATION: n is a, c, g, or t
<220> FEATURE:
<221> NAME/KEY: misc_feature
<222> LOCATION: (50735)..(50735)
<223> OTHER INFORMATION: n is a, c, g, or t
<220> FEATURE:
<221> NAME/KEY: misc_feature
<222> LOCATION: (50739)..(50739)
<223> OTHER INFORMATION: n is a, c, g, or t
<220> FEATURE:
<221> NAME/KEY: misc_feature
<222> LOCATION: (50751)..(50751)
<223> OTHER INFORMATION: n is a, c, g, or t
<220> FEATURE:
<221> NAME/KEY: misc_feature
<222> LOCATION: (50757)..(50757)
<223> OTHER INFORMATION: n is a, c, g, or t
<220> FEATURE:
<221> NAME/KEY: misc_feature
<222> LOCATION: (50766)..(50768)
<223> OTHER INFORMATION: n is a, c, g, or t
<220> FEATURE:
<221> NAME/KEY: misc_feature
<222> LOCATION: (50773)..(50775)
<223> OTHER INFORMATION: n is a, c, g, or t
<220> FEATURE:
<221> NAME/KEY: misc_feature
<222> LOCATION: (50784)..(50784)
<223> OTHER INFORMATION: n is a, c, g, or t
<220> FEATURE:
<221> NAME/KEY: misc_feature
<222> LOCATION: (50803)..(50803)
<223> OTHER INFORMATION: n is a, c, g, or t
<220> FEATURE:
<221> NAME/KEY: misc_feature
<222> LOCATION: (50834)..(50834)
<223> OTHER INFORMATION: n is a, c, g, or t
<220> FEATURE:
<221> NAME/KEY: misc_feature
<222> LOCATION: (50837)..(50837)
<223> OTHER INFORMATION: n is a, c, g, or t
<220> FEATURE:
<221> NAME/KEY: misc_feature
<222> LOCATION: (50843)..(50843)
<223> OTHER INFORMATION: n is a, c, g, or t
<220> FEATURE:
<221> NAME/KEY: misc_feature
<222> LOCATION: (50878)..(50878)
<223> OTHER INFORMATION: n is a, c, g, or t
<220> FEATURE:
<221> NAME/KEY: misc_feature
<222> LOCATION: (50881)..(50881)
<223> OTHER INFORMATION: n is a, c, g, or t
<220> FEATURE:
<221> NAME/KEY: misc_feature
<222> LOCATION: (50883)..(50883)
<223> OTHER INFORMATION: n is a, c, g, or t
<220> FEATURE:
<221> NAME/KEY: misc_feature
<222> LOCATION: (50886)..(50886)
<223> OTHER INFORMATION: n is a, c, g, or t
<220> FEATURE:
<221> NAME/KEY: misc_feature
<222> LOCATION: (50892)..(50892)
<223> OTHER INFORMATION: n is a, c, g, or t
<220> FEATURE:
<221> NAME/KEY: misc_feature
<222> LOCATION: (50908)..(50908)
<223> OTHER INFORMATION: n is a, c, g, or t
```

-continued

```
<220> FEATURE:
<221> NAME/KEY: misc_feature
<222> LOCATION: (50914)..(50914)
<223> OTHER INFORMATION: n is a, c, g, or t
<220> FEATURE:
<221> NAME/KEY: misc_feature
<222> LOCATION: (50918)..(50918)
<223> OTHER INFORMATION: n is a, c, g, or t
<220> FEATURE:
<221> NAME/KEY: misc_feature
<222> LOCATION: (50923)..(50923)
<223> OTHER INFORMATION: n is a, c, g, or t
<220> FEATURE:
<221> NAME/KEY: misc_feature
<222> LOCATION: (50925)..(50926)
<223> OTHER INFORMATION: n is a, c, g, or t
<220> FEATURE:
<221> NAME/KEY: misc_feature
<222> LOCATION: (50930)..(50930)
<223> OTHER INFORMATION: n is a, c, g, or t
<220> FEATURE:
<221> NAME/KEY: misc_feature
<222> LOCATION: (50941)..(50941)
<223> OTHER INFORMATION: n is a, c, g, or t
<220> FEATURE:
<221> NAME/KEY: misc_feature
<222> LOCATION: (50943)..(50943)
<223> OTHER INFORMATION: n is a, c, g, or t
<220> FEATURE:
<221> NAME/KEY: misc_feature
<222> LOCATION: (50946)..(50946)
<223> OTHER INFORMATION: n is a, c, g, or t
<220> FEATURE:
<221> NAME/KEY: misc_feature
<222> LOCATION: (50953)..(50953)
<223> OTHER INFORMATION: n is a, c, g, or t
<220> FEATURE:
<221> NAME/KEY: misc_feature
<222> LOCATION: (50961)..(50961)
<223> OTHER INFORMATION: n is a, c, g, or t
<220> FEATURE:
<221> NAME/KEY: misc_feature
<222> LOCATION: (50979)..(50979)
<223> OTHER INFORMATION: n is a, c, g, or t
<220> FEATURE:
<221> NAME/KEY: misc_feature
<222> LOCATION: (50982)..(50982)
<223> OTHER INFORMATION: n is a, c, g, or t
<220> FEATURE:
<221> NAME/KEY: misc_feature
<222> LOCATION: (50984)..(50984)
<223> OTHER INFORMATION: n is a, c, g, or t
<220> FEATURE:
<221> NAME/KEY: misc_feature
<222> LOCATION: (50988)..(50989)
<223> OTHER INFORMATION: n is a, c, g, or t
<220> FEATURE:
<221> NAME/KEY: misc_feature
<222> LOCATION: (50996)..(50997)
<223> OTHER INFORMATION: n is a, c, g, or t
<220> FEATURE:
<221> NAME/KEY: misc_feature
<222> LOCATION: (50999)..(50999)
<223> OTHER INFORMATION: n is a, c, g, or t
<220> FEATURE:
<221> NAME/KEY: misc_feature
<222> LOCATION: (51003)..(51003)
<223> OTHER INFORMATION: n is a, c, g, or t
<220> FEATURE:
<221> NAME/KEY: misc_feature
<222> LOCATION: (51006)..(51006)
<223> OTHER INFORMATION: n is a, c, g, or t
<220> FEATURE:
<221> NAME/KEY: misc_feature
<222> LOCATION: (51027)..(51027)
<223> OTHER INFORMATION: n is a, c, g, or t
<220> FEATURE:
<221> NAME/KEY: misc_feature
<222> LOCATION: (52597)..(52597)
```

```
<223> OTHER INFORMATION: n is a, c, g, or t
<220> FEATURE:
<221> NAME/KEY: misc_feature
<222> LOCATION: (52602)..(52602)
<223> OTHER INFORMATION: n is a, c, g, or t
<220> FEATURE:
<221> NAME/KEY: misc_feature
<222> LOCATION: (52607)..(52607)
<223> OTHER INFORMATION: n is a, c, g, or t
<220> FEATURE:
<221> NAME/KEY: misc_feature
<222> LOCATION: (52611)..(52611)
<223> OTHER INFORMATION: n is a, c, g, or t
<220> FEATURE:
<221> NAME/KEY: misc_feature
<222> LOCATION: (52623)..(52623)
<223> OTHER INFORMATION: n is a, c, g, or t
<220> FEATURE:
<221> NAME/KEY: misc_feature
<222> LOCATION: (52629)..(52629)
<223> OTHER INFORMATION: n is a, c, g, or t
<220> FEATURE:
<221> NAME/KEY: misc_feature
<222> LOCATION: (52638)..(52640)
<223> OTHER INFORMATION: n is a, c, g, or t
<220> FEATURE:
<221> NAME/KEY: misc_feature
<222> LOCATION: (52645)..(52647)
<223> OTHER INFORMATION: n is a, c, g, or t
<220> FEATURE:
<221> NAME/KEY: misc_feature
<222> LOCATION: (52656)..(52656)
<223> OTHER INFORMATION: n is a, c, g, or t
<220> FEATURE:
<221> NAME/KEY: misc_feature
<222> LOCATION: (52675)..(52675)
<223> OTHER INFORMATION: n is a, c, g, or t
<220> FEATURE:
<221> NAME/KEY: misc_feature
<222> LOCATION: (52706)..(52706)
<223> OTHER INFORMATION: n is a, c, g, or t
<220> FEATURE:
<221> NAME/KEY: misc_feature
<222> LOCATION: (52709)..(52709)
<223> OTHER INFORMATION: n is a, c, g, or t
<220> FEATURE:
<221> NAME/KEY: misc_feature
<222> LOCATION: (52715)..(52715)
<223> OTHER INFORMATION: n is a, c, g, or t
<220> FEATURE:
<221> NAME/KEY: misc_feature
<222> LOCATION: (52750)..(52750)
<223> OTHER INFORMATION: n is a, c, g, or t
<220> FEATURE:
<221> NAME/KEY: misc_feature
<222> LOCATION: (52753)..(52753)
<223> OTHER INFORMATION: n is a, c, g, or t
<220> FEATURE:
<221> NAME/KEY: misc_feature
<222> LOCATION: (52755)..(52755)
<223> OTHER INFORMATION: n is a, c, g, or t
<220> FEATURE:
<221> NAME/KEY: misc_feature
<222> LOCATION: (52758)..(52758)
<223> OTHER INFORMATION: n is a, c, g, or t
<220> FEATURE:
<221> NAME/KEY: misc_feature
<222> LOCATION: (52764)..(52764)
<223> OTHER INFORMATION: n is a, c, g, or t
<220> FEATURE:
<221> NAME/KEY: misc_feature
<222> LOCATION: (52780)..(52780)
<223> OTHER INFORMATION: n is a, c, g, or t
<220> FEATURE:
<221> NAME/KEY: misc_feature
<222> LOCATION: (52786)..(52786)
<223> OTHER INFORMATION: n is a, c, g, or t
<220> FEATURE:
<221> NAME/KEY: misc_feature
```

```
<222> LOCATION: (52790)..(52790)
<223> OTHER INFORMATION: n is a, c, g, or t
<220> FEATURE:
<221> NAME/KEY: misc_feature
<222> LOCATION: (52795)..(52795)
<223> OTHER INFORMATION: n is a, c, g, or t
<220> FEATURE:
<221> NAME/KEY: misc_feature
<222> LOCATION: (52797)..(52798)
<223> OTHER INFORMATION: n is a, c, g, or t
<220> FEATURE:
<221> NAME/KEY: misc_feature
<222> LOCATION: (52802)..(52802)
<223> OTHER INFORMATION: n is a, c, g, or t
<220> FEATURE:
<221> NAME/KEY: misc_feature
<222> LOCATION: (52813)..(52813)
<223> OTHER INFORMATION: n is a, c, g, or t
<220> FEATURE:
<221> NAME/KEY: misc_feature
<222> LOCATION: (52815)..(52815)
<223> OTHER INFORMATION: n is a, c, g, or t
<220> FEATURE:
<221> NAME/KEY: misc_feature
<222> LOCATION: (52818)..(52818)
<223> OTHER INFORMATION: n is a, c, g, or t
<220> FEATURE:
<221> NAME/KEY: misc_feature
<222> LOCATION: (52825)..(52825)
<223> OTHER INFORMATION: n is a, c, g, or t
<220> FEATURE:
<221> NAME/KEY: misc_feature
<222> LOCATION: (52833)..(52833)
<223> OTHER INFORMATION: n is a, c, g, or t
<220> FEATURE:
<221> NAME/KEY: misc_feature
<222> LOCATION: (52851)..(52851)
<223> OTHER INFORMATION: n is a, c, g, or t
<220> FEATURE:
<221> NAME/KEY: misc_feature
<222> LOCATION: (52854)..(52854)
<223> OTHER INFORMATION: n is a, c, g, or t
<220> FEATURE:
<221> NAME/KEY: misc_feature
<222> LOCATION: (52856)..(52856)
<223> OTHER INFORMATION: n is a, c, g, or t
<220> FEATURE:
<221> NAME/KEY: misc_feature
<222> LOCATION: (52860)..(52861)
<223> OTHER INFORMATION: n is a, c, g, or t
<220> FEATURE:
<221> NAME/KEY: misc_feature
<222> LOCATION: (52868)..(52869)
<223> OTHER INFORMATION: n is a, c, g, or t
<220> FEATURE:
<221> NAME/KEY: misc_feature
<222> LOCATION: (52871)..(52871)
<223> OTHER INFORMATION: n is a, c, g, or t
<220> FEATURE:
<221> NAME/KEY: misc_feature
<222> LOCATION: (52875)..(52875)
<223> OTHER INFORMATION: n is a, c, g, or t
<220> FEATURE:
<221> NAME/KEY: misc_feature
<222> LOCATION: (52878)..(52878)
<223> OTHER INFORMATION: n is a, c, g, or t
<220> FEATURE:
<221> NAME/KEY: misc_feature
<222> LOCATION: (52899)..(52899)
<223> OTHER INFORMATION: n is a, c, g, or t
<220> FEATURE:
<221> NAME/KEY: misc_feature
<222> LOCATION: (52903)..(52903)
<223> OTHER INFORMATION: n is a, c, g, or t
<220> FEATURE:
<221> NAME/KEY: misc_feature
<222> LOCATION: (52905)..(52905)
<223> OTHER INFORMATION: n is a, c, g, or t
<220> FEATURE:
```

-continued

```
<221> NAME/KEY: misc_feature
<222> LOCATION: (52908)..(52908)
<223> OTHER INFORMATION: n is a, c, g, or t
<220> FEATURE:
<221> NAME/KEY: misc_feature
<222> LOCATION: (52923)..(52926)
<223> OTHER INFORMATION: n is a, c, g, or t
<220> FEATURE:
<221> NAME/KEY: misc_feature
<222> LOCATION: (52930)..(52930)
<223> OTHER INFORMATION: n is a, c, g, or t
<220> FEATURE:
<221> NAME/KEY: misc_feature
<222> LOCATION: (52932)..(52932)
<223> OTHER INFORMATION: n is a, c, g, or t
<220> FEATURE:
<221> NAME/KEY: misc_feature
<222> LOCATION: (52942)..(52942)
<223> OTHER INFORMATION: n is a, c, g, or t
<220> FEATURE:
<221> NAME/KEY: misc_feature
<222> LOCATION: (52950)..(52950)
<223> OTHER INFORMATION: n is a, c, g, or t
<220> FEATURE:
<221> NAME/KEY: misc_feature
<222> LOCATION: (52955)..(52955)
<223> OTHER INFORMATION: n is a, c, g, or t
<220> FEATURE:
<221> NAME/KEY: misc_feature
<222> LOCATION: (52982)..(52983)
<223> OTHER INFORMATION: n is a, c, g, or t
<220> FEATURE:
<221> NAME/KEY: misc_feature
<222> LOCATION: (52990)..(52990)
<223> OTHER INFORMATION: n is a, c, g, or t
<220> FEATURE:
<221> NAME/KEY: misc_feature
<222> LOCATION: (52992)..(52992)
<223> OTHER INFORMATION: n is a, c, g, or t
<220> FEATURE:
<221> NAME/KEY: misc_feature
<222> LOCATION: (52999)..(52999)
<223> OTHER INFORMATION: n is a, c, g, or t
<220> FEATURE:
<221> NAME/KEY: misc_feature
<222> LOCATION: (53004)..(53004)
<223> OTHER INFORMATION: n is a, c, g, or t
<220> FEATURE:
<221> NAME/KEY: misc_feature
<222> LOCATION: (53017)..(53017)
<223> OTHER INFORMATION: n is a, c, g, or t
<220> FEATURE:
<221> NAME/KEY: misc_feature
<222> LOCATION: (53033)..(53033)
<223> OTHER INFORMATION: n is a, c, g, or t
<220> FEATURE:
<221> NAME/KEY: misc_feature
<222> LOCATION: (53039)..(53040)
<223> OTHER INFORMATION: n is a, c, g, or t
<220> FEATURE:
<221> NAME/KEY: misc_feature
<222> LOCATION: (53042)..(53042)
<223> OTHER INFORMATION: n is a, c, g, or t
<220> FEATURE:
<221> NAME/KEY: misc_feature
<222> LOCATION: (53044)..(53044)
<223> OTHER INFORMATION: n is a, c, g, or t
<220> FEATURE:
<221> NAME/KEY: misc_feature
<222> LOCATION: (53046)..(53046)
<223> OTHER INFORMATION: n is a, c, g, or t
<220> FEATURE:
<221> NAME/KEY: misc_feature
<222> LOCATION: (53055)..(53055)
<223> OTHER INFORMATION: n is a, c, g, or t
<220> FEATURE:
<221> NAME/KEY: misc_feature
<222> LOCATION: (53065)..(53065)
<223> OTHER INFORMATION: n is a, c, g, or t
```

-continued

```
<220> FEATURE:
<221> NAME/KEY: misc_feature
<222> LOCATION: (53070)..(53070)
<223> OTHER INFORMATION: n is a, c, g, or t
<220> FEATURE:
<221> NAME/KEY: misc_feature
<222> LOCATION: (53075)..(53075)
<223> OTHER INFORMATION: n is a, c, g, or t
<220> FEATURE:
<221> NAME/KEY: misc_feature
<222> LOCATION: (53079)..(53079)
<223> OTHER INFORMATION: n is a, c, g, or t
<220> FEATURE:
<221> NAME/KEY: misc_feature
<222> LOCATION: (53091)..(53091)
<223> OTHER INFORMATION: n is a, c, g, or t
<220> FEATURE:
<221> NAME/KEY: misc_feature
<222> LOCATION: (53097)..(53097)
<223> OTHER INFORMATION: n is a, c, g, or t
<220> FEATURE:
<221> NAME/KEY: misc_feature
<222> LOCATION: (53533)..(53533)
<223> OTHER INFORMATION: n is a, c, g, or t
<220> FEATURE:
<221> NAME/KEY: misc_feature
<222> LOCATION: (53538)..(53538)
<223> OTHER INFORMATION: n is a, c, g, or t
<220> FEATURE:
<221> NAME/KEY: misc_feature
<222> LOCATION: (53543)..(53543)
<223> OTHER INFORMATION: n is a, c, g, or t
<220> FEATURE:
<221> NAME/KEY: misc_feature
<222> LOCATION: (53547)..(53547)
<223> OTHER INFORMATION: n is a, c, g, or t
<220> FEATURE:
<221> NAME/KEY: misc_feature
<222> LOCATION: (53559)..(53559)
<223> OTHER INFORMATION: n is a, c, g, or t
<220> FEATURE:
<221> NAME/KEY: misc_feature
<222> LOCATION: (53565)..(53565)
<223> OTHER INFORMATION: n is a, c, g, or t
<220> FEATURE:
<221> NAME/KEY: misc_feature
<222> LOCATION: (53574)..(53576)
<223> OTHER INFORMATION: n is a, c, g, or t
<220> FEATURE:
<221> NAME/KEY: misc_feature
<222> LOCATION: (53581)..(53583)
<223> OTHER INFORMATION: n is a, c, g, or t
<220> FEATURE:
<221> NAME/KEY: misc_feature
<222> LOCATION: (53592)..(53592)
<223> OTHER INFORMATION: n is a, c, g, or t
<220> FEATURE:
<221> NAME/KEY: misc_feature
<222> LOCATION: (53611)..(53611)
<223> OTHER INFORMATION: n is a, c, g, or t
<220> FEATURE:
<221> NAME/KEY: misc_feature
<222> LOCATION: (53642)..(53642)
<223> OTHER INFORMATION: n is a, c, g, or t
<220> FEATURE:
<221> NAME/KEY: misc_feature
<222> LOCATION: (53645)..(53645)
<223> OTHER INFORMATION: n is a, c, g, or t
<220> FEATURE:
<221> NAME/KEY: misc_feature
<222> LOCATION: (53651)..(53651)
<223> OTHER INFORMATION: n is a, c, g, or t
<220> FEATURE:
<221> NAME/KEY: misc_feature
<222> LOCATION: (53686)..(53686)
<223> OTHER INFORMATION: n is a, c, g, or t
<220> FEATURE:
<221> NAME/KEY: misc_feature
<222> LOCATION: (53689)..(53689)
```

```
<223> OTHER INFORMATION: n is a, c, g, or t
<220> FEATURE:
<221> NAME/KEY: misc_feature
<222> LOCATION: (53691)..(53691)
<223> OTHER INFORMATION: n is a, c, g, or t
<220> FEATURE:
<221> NAME/KEY: misc_feature
<222> LOCATION: (53694)..(53694)
<223> OTHER INFORMATION: n is a, c, g, or t
<220> FEATURE:
<221> NAME/KEY: misc_feature
<222> LOCATION: (53700)..(53700)
<223> OTHER INFORMATION: n is a, c, g, or t
<220> FEATURE:
<221> NAME/KEY: misc_feature
<222> LOCATION: (53716)..(53716)
<223> OTHER INFORMATION: n is a, c, g, or t
<220> FEATURE:
<221> NAME/KEY: misc_feature
<222> LOCATION: (53722)..(53722)
<223> OTHER INFORMATION: n is a, c, g, or t
<220> FEATURE:
<221> NAME/KEY: misc_feature
<222> LOCATION: (53726)..(53726)
<223> OTHER INFORMATION: n is a, c, g, or t
<220> FEATURE:
<221> NAME/KEY: misc_feature
<222> LOCATION: (53731)..(53731)
<223> OTHER INFORMATION: n is a, c, g, or t
<220> FEATURE:
<221> NAME/KEY: misc_feature
<222> LOCATION: (53733)..(53734)
<223> OTHER INFORMATION: n is a, c, g, or t
<220> FEATURE:
<221> NAME/KEY: misc_feature
<222> LOCATION: (53738)..(53738)
<223> OTHER INFORMATION: n is a, c, g, or t
<220> FEATURE:
<221> NAME/KEY: misc_feature
<222> LOCATION: (53749)..(53749)
<223> OTHER INFORMATION: n is a, c, g, or t
<220> FEATURE:
<221> NAME/KEY: misc_feature
<222> LOCATION: (53751)..(53751)
<223> OTHER INFORMATION: n is a, c, g, or t
<220> FEATURE:
<221> NAME/KEY: misc_feature
<222> LOCATION: (53754)..(53754)
<223> OTHER INFORMATION: n is a, c, g, or t
<220> FEATURE:
<221> NAME/KEY: misc_feature
<222> LOCATION: (53761)..(53761)
<223> OTHER INFORMATION: n is a, c, g, or t
<220> FEATURE:
<221> NAME/KEY: misc_feature
<222> LOCATION: (53769)..(53769)
<223> OTHER INFORMATION: n is a, c, g, or t
<220> FEATURE:
<221> NAME/KEY: misc_feature
<222> LOCATION: (53787)..(53787)
<223> OTHER INFORMATION: n is a, c, g, or t
<220> FEATURE:
<221> NAME/KEY: misc_feature
<222> LOCATION: (53790)..(53790)
<223> OTHER INFORMATION: n is a, c, g, or t
<220> FEATURE:
<221> NAME/KEY: misc_feature
<222> LOCATION: (53792)..(53792)
<223> OTHER INFORMATION: n is a, c, g, or t
<220> FEATURE:
<221> NAME/KEY: misc_feature
<222> LOCATION: (53796)..(53797)
<223> OTHER INFORMATION: n is a, c, g, or t
<220> FEATURE:
<221> NAME/KEY: misc_feature
<222> LOCATION: (53804)..(53805)
<223> OTHER INFORMATION: n is a, c, g, or t
<220> FEATURE:
<221> NAME/KEY: misc_feature
```

-continued

```
<222> LOCATION: (53807)..(53807)
<223> OTHER INFORMATION: n is a, c, g, or t
<220> FEATURE:
<221> NAME/KEY: misc_feature
<222> LOCATION: (53811)..(53811)
<223> OTHER INFORMATION: n is a, c, g, or t
<220> FEATURE:
<221> NAME/KEY: misc_feature
<222> LOCATION: (53814)..(53814)
<223> OTHER INFORMATION: n is a, c, g, or t
<220> FEATURE:
<221> NAME/KEY: misc_feature
<222> LOCATION: (53835)..(53835)
<223> OTHER INFORMATION: n is a, c, g, or t
<220> FEATURE:
<221> NAME/KEY: misc_feature
<222> LOCATION: (53839)..(53839)
<223> OTHER INFORMATION: n is a, c, g, or t
<220> FEATURE:
<221> NAME/KEY: misc_feature
<222> LOCATION: (53841)..(53841)
<223> OTHER INFORMATION: n is a, c, g, or t
<220> FEATURE:
<221> NAME/KEY: misc_feature
<222> LOCATION: (53844)..(53844)
<223> OTHER INFORMATION: n is a, c, g, or t
<220> FEATURE:
<221> NAME/KEY: misc_feature
<222> LOCATION: (53859)..(53862)
<223> OTHER INFORMATION: n is a, c, g, or t
<220> FEATURE:
<221> NAME/KEY: misc_feature
<222> LOCATION: (53866)..(53866)
<223> OTHER INFORMATION: n is a, c, g, or t
<220> FEATURE:
<221> NAME/KEY: misc_feature
<222> LOCATION: (53868)..(53868)
<223> OTHER INFORMATION: n is a, c, g, or t
<220> FEATURE:
<221> NAME/KEY: misc_feature
<222> LOCATION: (53878)..(53878)
<223> OTHER INFORMATION: n is a, c, g, or t
<220> FEATURE:
<221> NAME/KEY: misc_feature
<222> LOCATION: (53886)..(53886)
<223> OTHER INFORMATION: n is a, c, g, or t
<220> FEATURE:
<221> NAME/KEY: misc_feature
<222> LOCATION: (53891)..(53891)
<223> OTHER INFORMATION: n is a, c, g, or t
<220> FEATURE:
<221> NAME/KEY: misc_feature
<222> LOCATION: (53918)..(53919)
<223> OTHER INFORMATION: n is a, c, g, or t
<220> FEATURE:
<221> NAME/KEY: misc_feature
<222> LOCATION: (53926)..(53926)
<223> OTHER INFORMATION: n is a, c, g, or t
<220> FEATURE:
<221> NAME/KEY: misc_feature
<222> LOCATION: (53928)..(53928)
<223> OTHER INFORMATION: n is a, c, g, or t
<220> FEATURE:
<221> NAME/KEY: misc_feature
<222> LOCATION: (53935)..(53935)
<223> OTHER INFORMATION: n is a, c, g, or t
<220> FEATURE:
<221> NAME/KEY: misc_feature
<222> LOCATION: (53940)..(53940)
<223> OTHER INFORMATION: n is a, c, g, or t
<220> FEATURE:
<221> NAME/KEY: misc_feature
<222> LOCATION: (53953)..(53953)
<223> OTHER INFORMATION: n is a, c, g, or t
<220> FEATURE:
<221> NAME/KEY: misc_feature
<222> LOCATION: (53969)..(53969)
<223> OTHER INFORMATION: n is a, c, g, or t
<220> FEATURE:
```

```
<221> NAME/KEY: misc_feature
<222> LOCATION: (53975)..(53976)
<223> OTHER INFORMATION: n is a, c, g, or t
<220> FEATURE:
<221> NAME/KEY: misc_feature
<222> LOCATION: (53978)..(53978)
<223> OTHER INFORMATION: n is a, c, g, or t
<220> FEATURE:
<221> NAME/KEY: misc_feature
<222> LOCATION: (53980)..(53980)
<223> OTHER INFORMATION: n is a, c, g, or t
<220> FEATURE:
<221> NAME/KEY: misc_feature
<222> LOCATION: (53982)..(53982)
<223> OTHER INFORMATION: n is a, c, g, or t
<220> FEATURE:
<221> NAME/KEY: misc_feature
<222> LOCATION: (53991)..(53991)
<223> OTHER INFORMATION: n is a, c, g, or t
<220> FEATURE:
<221> NAME/KEY: misc_feature
<222> LOCATION: (54001)..(54001)
<223> OTHER INFORMATION: n is a, c, g, or t
<220> FEATURE:
<221> NAME/KEY: misc_feature
<222> LOCATION: (54006)..(54006)
<223> OTHER INFORMATION: n is a, c, g, or t
<220> FEATURE:
<221> NAME/KEY: misc_feature
<222> LOCATION: (54011)..(54011)
<223> OTHER INFORMATION: n is a, c, g, or t
<220> FEATURE:
<221> NAME/KEY: misc_feature
<222> LOCATION: (54015)..(54015)
<223> OTHER INFORMATION: n is a, c, g, or t
<220> FEATURE:
<221> NAME/KEY: misc_feature
<222> LOCATION: (54027)..(54027)
<223> OTHER INFORMATION: n is a, c, g, or t
<220> FEATURE:
<221> NAME/KEY: misc_feature
<222> LOCATION: (54033)..(54033)
<223> OTHER INFORMATION: n is a, c, g, or t
<220> FEATURE:
<221> NAME/KEY: misc_feature
<222> LOCATION: (54042)..(54044)
<223> OTHER INFORMATION: n is a, c, g, or t
<220> FEATURE:
<221> NAME/KEY: misc_feature
<222> LOCATION: (54049)..(54051)
<223> OTHER INFORMATION: n is a, c, g, or t
<220> FEATURE:
<221> NAME/KEY: misc_feature
<222> LOCATION: (54060)..(54060)
<223> OTHER INFORMATION: n is a, c, g, or t
<220> FEATURE:
<221> NAME/KEY: misc_feature
<222> LOCATION: (54079)..(54079)
<223> OTHER INFORMATION: n is a, c, g, or t
<220> FEATURE:
<221> NAME/KEY: misc_feature
<222> LOCATION: (54469)..(54469)
<223> OTHER INFORMATION: n is a, c, g, or t
<220> FEATURE:
<221> NAME/KEY: misc_feature
<222> LOCATION: (54474)..(54474)
<223> OTHER INFORMATION: n is a, c, g, or t
<220> FEATURE:
<221> NAME/KEY: misc_feature
<222> LOCATION: (54479)..(54479)
<223> OTHER INFORMATION: n is a, c, g, or t
<220> FEATURE:
<221> NAME/KEY: misc_feature
<222> LOCATION: (54483)..(54483)
<223> OTHER INFORMATION: n is a, c, g, or t
<220> FEATURE:
<221> NAME/KEY: misc_feature
<222> LOCATION: (54495)..(54495)
<223> OTHER INFORMATION: n is a, c, g, or t
```

-continued

```
<220> FEATURE:
<221> NAME/KEY: misc_feature
<222> LOCATION: (54501)..(54501)
<223> OTHER INFORMATION: n is a, c, g, or t
<220> FEATURE:
<221> NAME/KEY: misc_feature
<222> LOCATION: (54510)..(54512)
<223> OTHER INFORMATION: n is a, c, g, or t
<220> FEATURE:
<221> NAME/KEY: misc_feature
<222> LOCATION: (54517)..(54519)
<223> OTHER INFORMATION: n is a, c, g, or t
<220> FEATURE:
<221> NAME/KEY: misc_feature
<222> LOCATION: (54528)..(54528)
<223> OTHER INFORMATION: n is a, c, g, or t
<220> FEATURE:
<221> NAME/KEY: misc_feature
<222> LOCATION: (54547)..(54547)
<223> OTHER INFORMATION: n is a, c, g, or t
<220> FEATURE:
<221> NAME/KEY: misc_feature
<222> LOCATION: (54578)..(54578)
<223> OTHER INFORMATION: n is a, c, g, or t
<220> FEATURE:
<221> NAME/KEY: misc_feature
<222> LOCATION: (54581)..(54581)
<223> OTHER INFORMATION: n is a, c, g, or t
<220> FEATURE:
<221> NAME/KEY: misc_feature
<222> LOCATION: (54587)..(54587)
<223> OTHER INFORMATION: n is a, c, g, or t
<220> FEATURE:
<221> NAME/KEY: misc_feature
<222> LOCATION: (54622)..(54622)
<223> OTHER INFORMATION: n is a, c, g, or t
<220> FEATURE:
<221> NAME/KEY: misc_feature
<222> LOCATION: (54625)..(54625)
<223> OTHER INFORMATION: n is a, c, g, or t
<220> FEATURE:
<221> NAME/KEY: misc_feature
<222> LOCATION: (54627)..(54627)
<223> OTHER INFORMATION: n is a, c, g, or t
<220> FEATURE:
<221> NAME/KEY: misc_feature
<222> LOCATION: (54630)..(54630)
<223> OTHER INFORMATION: n is a, c, g, or t
<220> FEATURE:
<221> NAME/KEY: misc_feature
<222> LOCATION: (54636)..(54636)
<223> OTHER INFORMATION: n is a, c, g, or t
<220> FEATURE:
<221> NAME/KEY: misc_feature
<222> LOCATION: (54652)..(54652)
<223> OTHER INFORMATION: n is a, c, g, or t
<220> FEATURE:
<221> NAME/KEY: misc_feature
<222> LOCATION: (54658)..(54658)
<223> OTHER INFORMATION: n is a, c, g, or t
<220> FEATURE:
<221> NAME/KEY: misc_feature
<222> LOCATION: (54662)..(54662)
<223> OTHER INFORMATION: n is a, c, g, or t
<220> FEATURE:
<221> NAME/KEY: misc_feature
<222> LOCATION: (54667)..(54667)
<223> OTHER INFORMATION: n is a, c, g, or t
<220> FEATURE:
<221> NAME/KEY: misc_feature
<222> LOCATION: (54669)..(54670)
<223> OTHER INFORMATION: n is a, c, g, or t
<220> FEATURE:
<221> NAME/KEY: misc_feature
<222> LOCATION: (54674)..(54674)
<223> OTHER INFORMATION: n is a, c, g, or t
<220> FEATURE:
<221> NAME/KEY: misc_feature
<222> LOCATION: (54685)..(54685)
```

-continued

```
<223> OTHER INFORMATION: n is a, c, g, or t
<220> FEATURE:
<221> NAME/KEY: misc_feature
<222> LOCATION: (54687)..(54687)
<223> OTHER INFORMATION: n is a, c, g, or t
<220> FEATURE:
<221> NAME/KEY: misc_feature
<222> LOCATION: (54690)..(54690)
<223> OTHER INFORMATION: n is a, c, g, or t
<220> FEATURE:
<221> NAME/KEY: misc_feature
<222> LOCATION: (54697)..(54697)
<223> OTHER INFORMATION: n is a, c, g, or t
<220> FEATURE:
<221> NAME/KEY: misc_feature
<222> LOCATION: (54705)..(54705)
<223> OTHER INFORMATION: n is a, c, g, or t
<220> FEATURE:
<221> NAME/KEY: misc_feature
<222> LOCATION: (54723)..(54723)
<223> OTHER INFORMATION: n is a, c, g, or t
<220> FEATURE:
<221> NAME/KEY: misc_feature
<222> LOCATION: (54726)..(54726)
<223> OTHER INFORMATION: n is a, c, g, or t
<220> FEATURE:
<221> NAME/KEY: misc_feature
<222> LOCATION: (54728)..(54728)
<223> OTHER INFORMATION: n is a, c, g, or t
<220> FEATURE:
<221> NAME/KEY: misc_feature
<222> LOCATION: (54732)..(54733)
<223> OTHER INFORMATION: n is a, c, g, or t
<220> FEATURE:
<221> NAME/KEY: misc_feature
<222> LOCATION: (54740)..(54741)
<223> OTHER INFORMATION: n is a, c, g, or t
<220> FEATURE:
<221> NAME/KEY: misc_feature
<222> LOCATION: (54743)..(54743)
<223> OTHER INFORMATION: n is a, c, g, or t
<220> FEATURE:
<221> NAME/KEY: misc_feature
<222> LOCATION: (54747)..(54747)
<223> OTHER INFORMATION: n is a, c, g, or t
<220> FEATURE:
<221> NAME/KEY: misc_feature
<222> LOCATION: (54750)..(54750)
<223> OTHER INFORMATION: n is a, c, g, or t
<220> FEATURE:
<221> NAME/KEY: misc_feature
<222> LOCATION: (54771)..(54771)
<223> OTHER INFORMATION: n is a, c, g, or t
<220> FEATURE:
<221> NAME/KEY: misc_feature
<222> LOCATION: (54775)..(54775)
<223> OTHER INFORMATION: n is a, c, g, or t
<220> FEATURE:
<221> NAME/KEY: misc_feature
<222> LOCATION: (54777)..(54777)
<223> OTHER INFORMATION: n is a, c, g, or t
<220> FEATURE:
<221> NAME/KEY: misc_feature
<222> LOCATION: (54780)..(54780)
<223> OTHER INFORMATION: n is a, c, g, or t
<220> FEATURE:
<221> NAME/KEY: misc_feature
<222> LOCATION: (54795)..(54798)
<223> OTHER INFORMATION: n is a, c, g, or t
<220> FEATURE:
<221> NAME/KEY: misc_feature
<222> LOCATION: (54802)..(54802)
<223> OTHER INFORMATION: n is a, c, g, or t
<220> FEATURE:
<221> NAME/KEY: misc_feature
<222> LOCATION: (54804)..(54804)
<223> OTHER INFORMATION: n is a, c, g, or t
<220> FEATURE:
<221> NAME/KEY: misc_feature
```

-continued

```
<222> LOCATION: (54814)..(54814)
<223> OTHER INFORMATION: n is a, c, g, or t
<220> FEATURE:
<221> NAME/KEY: misc_feature
<222> LOCATION: (54822)..(54822)
<223> OTHER INFORMATION: n is a, c, g, or t
<220> FEATURE:
<221> NAME/KEY: misc_feature
<222> LOCATION: (54827)..(54827)
<223> OTHER INFORMATION: n is a, c, g, or t
<220> FEATURE:
<221> NAME/KEY: misc_feature
<222> LOCATION: (54854)..(54855)
<223> OTHER INFORMATION: n is a, c, g, or t
<220> FEATURE:
<221> NAME/KEY: misc_feature
<222> LOCATION: (54862)..(54862)
<223> OTHER INFORMATION: n is a, c, g, or t
<220> FEATURE:
<221> NAME/KEY: misc_feature
<222> LOCATION: (54864)..(54864)
<223> OTHER INFORMATION: n is a, c, g, or t
<220> FEATURE:
<221> NAME/KEY: misc_feature
<222> LOCATION: (54871)..(54871)
<223> OTHER INFORMATION: n is a, c, g, or t
<220> FEATURE:
<221> NAME/KEY: misc_feature
<222> LOCATION: (54876)..(54876)
<223> OTHER INFORMATION: n is a, c, g, or t
<220> FEATURE:
<221> NAME/KEY: misc_feature
<222> LOCATION: (54889)..(54889)
<223> OTHER INFORMATION: n is a, c, g, or t
<220> FEATURE:
<221> NAME/KEY: misc_feature
<222> LOCATION: (54905)..(54905)
<223> OTHER INFORMATION: n is a, c, g, or t
<220> FEATURE:
<221> NAME/KEY: misc_feature
<222> LOCATION: (54911)..(54912)
<223> OTHER INFORMATION: n is a, c, g, or t
<220> FEATURE:
<221> NAME/KEY: misc_feature
<222> LOCATION: (54914)..(54914)
<223> OTHER INFORMATION: n is a, c, g, or t
<220> FEATURE:
<221> NAME/KEY: misc_feature
<222> LOCATION: (54916)..(54916)
<223> OTHER INFORMATION: n is a, c, g, or t
<220> FEATURE:
<221> NAME/KEY: misc_feature
<222> LOCATION: (54918)..(54918)
<223> OTHER INFORMATION: n is a, c, g, or t
<220> FEATURE:
<221> NAME/KEY: misc_feature
<222> LOCATION: (54927)..(54927)
<223> OTHER INFORMATION: n is a, c, g, or t
<220> FEATURE:
<221> NAME/KEY: misc_feature
<222> LOCATION: (54937)..(54937)
<223> OTHER INFORMATION: n is a, c, g, or t
<220> FEATURE:
<221> NAME/KEY: misc_feature
<222> LOCATION: (54942)..(54942)
<223> OTHER INFORMATION: n is a, c, g, or t
<220> FEATURE:
<221> NAME/KEY: misc_feature
<222> LOCATION: (54947)..(54947)
<223> OTHER INFORMATION: n is a, c, g, or t
<220> FEATURE:
<221> NAME/KEY: misc_feature
<222> LOCATION: (54951)..(54951)
<223> OTHER INFORMATION: n is a, c, g, or t
<220> FEATURE:
<221> NAME/KEY: misc_feature
<222> LOCATION: (54963)..(54963)
<223> OTHER INFORMATION: n is a, c, g, or t
<220> FEATURE:
```

-continued

```
<221> NAME/KEY: misc_feature
<222> LOCATION: (54969)..(54969)
<223> OTHER INFORMATION: n is a, c, g, or t
<220> FEATURE:
<221> NAME/KEY: misc_feature
<222> LOCATION: (54978)..(54980)
<223> OTHER INFORMATION: n is a, c, g, or t
<220> FEATURE:
<221> NAME/KEY: misc_feature
<222> LOCATION: (54985)..(54987)
<223> OTHER INFORMATION: n is a, c, g, or t
<220> FEATURE:
<221> NAME/KEY: misc_feature
<222> LOCATION: (54996)..(54996)
<223> OTHER INFORMATION: n is a, c, g, or t
<220> FEATURE:
<221> NAME/KEY: misc_feature
<222> LOCATION: (55015)..(55015)
<223> OTHER INFORMATION: n is a, c, g, or t
<220> FEATURE:
<221> NAME/KEY: misc_feature
<222> LOCATION: (55405)..(55405)
<223> OTHER INFORMATION: n is a, c, g, or t
<220> FEATURE:
<221> NAME/KEY: misc_feature
<222> LOCATION: (55410)..(55410)
<223> OTHER INFORMATION: n is a, c, g, or t
<220> FEATURE:
<221> NAME/KEY: misc_feature
<222> LOCATION: (55415)..(55415)
<223> OTHER INFORMATION: n is a, c, g, or t
<220> FEATURE:
<221> NAME/KEY: misc_feature
<222> LOCATION: (55419)..(55419)
<223> OTHER INFORMATION: n is a, c, g, or t
<220> FEATURE:
<221> NAME/KEY: misc_feature
<222> LOCATION: (55431)..(55431)
<223> OTHER INFORMATION: n is a, c, g, or t
<220> FEATURE:
<221> NAME/KEY: misc_feature
<222> LOCATION: (55437)..(55437)
<223> OTHER INFORMATION: n is a, c, g, or t
<220> FEATURE:
<221> NAME/KEY: misc_feature
<222> LOCATION: (55446)..(55448)
<223> OTHER INFORMATION: n is a, c, g, or t
<220> FEATURE:
<221> NAME/KEY: misc_feature
<222> LOCATION: (55453)..(55455)
<223> OTHER INFORMATION: n is a, c, g, or t
<220> FEATURE:
<221> NAME/KEY: misc_feature
<222> LOCATION: (55464)..(55464)
<223> OTHER INFORMATION: n is a, c, g, or t
<220> FEATURE:
<221> NAME/KEY: misc_feature
<222> LOCATION: (55483)..(55483)
<223> OTHER INFORMATION: n is a, c, g, or t
<220> FEATURE:
<221> NAME/KEY: misc_feature
<222> LOCATION: (55514)..(55514)
<223> OTHER INFORMATION: n is a, c, g, or t
<220> FEATURE:
<221> NAME/KEY: misc_feature
<222> LOCATION: (55517)..(55517)
<223> OTHER INFORMATION: n is a, c, g, or t
<220> FEATURE:
<221> NAME/KEY: misc_feature
<222> LOCATION: (55523)..(55523)
<223> OTHER INFORMATION: n is a, c, g, or t
<220> FEATURE:
<221> NAME/KEY: misc_feature
<222> LOCATION: (55558)..(55558)
<223> OTHER INFORMATION: n is a, c, g, or t
<220> FEATURE:
<221> NAME/KEY: misc_feature
<222> LOCATION: (55561)..(55561)
<223> OTHER INFORMATION: n is a, c, g, or t
```

-continued

```
<220> FEATURE:
<221> NAME/KEY: misc_feature
<222> LOCATION: (55563)..(55563)
<223> OTHER INFORMATION: n is a, c, g, or t
<220> FEATURE:
<221> NAME/KEY: misc_feature
<222> LOCATION: (55566)..(55566)
<223> OTHER INFORMATION: n is a, c, g, or t
<220> FEATURE:
<221> NAME/KEY: misc_feature
<222> LOCATION: (55572)..(55572)
<223> OTHER INFORMATION: n is a, c, g, or t
<220> FEATURE:
<221> NAME/KEY: misc_feature
<222> LOCATION: (55588)..(55588)
<223> OTHER INFORMATION: n is a, c, g, or t
<220> FEATURE:
<221> NAME/KEY: misc_feature
<222> LOCATION: (55594)..(55594)
<223> OTHER INFORMATION: n is a, c, g, or t
<220> FEATURE:
<221> NAME/KEY: misc_feature
<222> LOCATION: (55598)..(55598)
<223> OTHER INFORMATION: n is a, c, g, or t
<220> FEATURE:
<221> NAME/KEY: misc_feature
<222> LOCATION: (55603)..(55603)
<223> OTHER INFORMATION: n is a, c, g, or t
<220> FEATURE:
<221> NAME/KEY: misc_feature
<222> LOCATION: (55605)..(55606)
<223> OTHER INFORMATION: n is a, c, g, or t
<220> FEATURE:
<221> NAME/KEY: misc_feature
<222> LOCATION: (55610)..(55610)
<223> OTHER INFORMATION: n is a, c, g, or t
<220> FEATURE:
<221> NAME/KEY: misc_feature
<222> LOCATION: (55621)..(55621)
<223> OTHER INFORMATION: n is a, c, g, or t
<220> FEATURE:
<221> NAME/KEY: misc_feature
<222> LOCATION: (55623)..(55623)
<223> OTHER INFORMATION: n is a, c, g, or t
<220> FEATURE:
<221> NAME/KEY: misc_feature
<222> LOCATION: (55626)..(55626)
<223> OTHER INFORMATION: n is a, c, g, or t
<220> FEATURE:
<221> NAME/KEY: misc_feature
<222> LOCATION: (55633)..(55633)
<223> OTHER INFORMATION: n is a, c, g, or t
<220> FEATURE:
<221> NAME/KEY: misc_feature
<222> LOCATION: (55641)..(55641)
<223> OTHER INFORMATION: n is a, c, g, or t
<220> FEATURE:
<221> NAME/KEY: misc_feature
<222> LOCATION: (55659)..(55659)
<223> OTHER INFORMATION: n is a, c, g, or t
<220> FEATURE:
<221> NAME/KEY: misc_feature
<222> LOCATION: (55662)..(55662)
<223> OTHER INFORMATION: n is a, c, g, or t
<220> FEATURE:
<221> NAME/KEY: misc_feature
<222> LOCATION: (55664)..(55664)
<223> OTHER INFORMATION: n is a, c, g, or t
<220> FEATURE:
<221> NAME/KEY: misc_feature
<222> LOCATION: (55668)..(55669)
<223> OTHER INFORMATION: n is a, c, g, or t
<220> FEATURE:
<221> NAME/KEY: misc_feature
<222> LOCATION: (55676)..(55677)
<223> OTHER INFORMATION: n is a, c, g, or t
<220> FEATURE:
<221> NAME/KEY: misc_feature
<222> LOCATION: (55679)..(55679)
```

```
<223> OTHER INFORMATION: n is a, c, g, or t
<220> FEATURE:
<221> NAME/KEY: misc_feature
<222> LOCATION: (55683)..(55683)
<223> OTHER INFORMATION: n is a, c, g, or t
<220> FEATURE:
<221> NAME/KEY: misc_feature
<222> LOCATION: (55686)..(55686)
<223> OTHER INFORMATION: n is a, c, g, or t
<220> FEATURE:
<221> NAME/KEY: misc_feature
<222> LOCATION: (55707)..(55707)
<223> OTHER INFORMATION: n is a, c, g, or t
<220> FEATURE:
<221> NAME/KEY: misc_feature
<222> LOCATION: (55711)..(55711)
<223> OTHER INFORMATION: n is a, c, g, or t
<220> FEATURE:
<221> NAME/KEY: misc_feature
<222> LOCATION: (55713)..(55713)
<223> OTHER INFORMATION: n is a, c, g, or t
<220> FEATURE:
<221> NAME/KEY: misc_feature
<222> LOCATION: (55716)..(55716)
<223> OTHER INFORMATION: n is a, c, g, or t
<220> FEATURE:
<221> NAME/KEY: misc_feature
<222> LOCATION: (55731)..(55734)
<223> OTHER INFORMATION: n is a, c, g, or t
<220> FEATURE:
<221> NAME/KEY: misc_feature
<222> LOCATION: (55738)..(55738)
<223> OTHER INFORMATION: n is a, c, g, or t
<220> FEATURE:
<221> NAME/KEY: misc_feature
<222> LOCATION: (55740)..(55740)
<223> OTHER INFORMATION: n is a, c, g, or t
<220> FEATURE:
<221> NAME/KEY: misc_feature
<222> LOCATION: (55750)..(55750)
<223> OTHER INFORMATION: n is a, c, g, or t
<220> FEATURE:
<221> NAME/KEY: misc_feature
<222> LOCATION: (55758)..(55758)
<223> OTHER INFORMATION: n is a, c, g, or t
<220> FEATURE:
<221> NAME/KEY: misc_feature
<222> LOCATION: (55763)..(55763)
<223> OTHER INFORMATION: n is a, c, g, or t
<220> FEATURE:
<221> NAME/KEY: misc_feature
<222> LOCATION: (55790)..(55791)
<223> OTHER INFORMATION: n is a, c, g, or t
<220> FEATURE:
<221> NAME/KEY: misc_feature
<222> LOCATION: (55798)..(55798)
<223> OTHER INFORMATION: n is a, c, g, or t
<220> FEATURE:
<221> NAME/KEY: misc_feature
<222> LOCATION: (55800)..(55800)
<223> OTHER INFORMATION: n is a, c, g, or t
<220> FEATURE:
<221> NAME/KEY: misc_feature
<222> LOCATION: (55807)..(55807)
<223> OTHER INFORMATION: n is a, c, g, or t
<220> FEATURE:
<221> NAME/KEY: misc_feature
<222> LOCATION: (55812)..(55812)
<223> OTHER INFORMATION: n is a, c, g, or t
<220> FEATURE:
<221> NAME/KEY: misc_feature
<222> LOCATION: (55825)..(55825)
<223> OTHER INFORMATION: n is a, c, g, or t
<220> FEATURE:
<221> NAME/KEY: misc_feature
<222> LOCATION: (55841)..(55841)
<223> OTHER INFORMATION: n is a, c, g, or t
<220> FEATURE:
<221> NAME/KEY: misc_feature
```

```
<222> LOCATION: (55847)..(55848)
<223> OTHER INFORMATION: n is a, c, g, or t
<220> FEATURE:
<221> NAME/KEY: misc_feature
<222> LOCATION: (55850)..(55850)
<223> OTHER INFORMATION: n is a, c, g, or t
<220> FEATURE:
<221> NAME/KEY: misc_feature
<222> LOCATION: (55852)..(55852)
<223> OTHER INFORMATION: n is a, c, g, or t
<220> FEATURE:
<221> NAME/KEY: misc_feature
<222> LOCATION: (55854)..(55854)
<223> OTHER INFORMATION: n is a, c, g, or t
<220> FEATURE:
<221> NAME/KEY: misc_feature
<222> LOCATION: (55863)..(55863)
<223> OTHER INFORMATION: n is a, c, g, or t
<220> FEATURE:
<221> NAME/KEY: misc_feature
<222> LOCATION: (55873)..(55873)
<223> OTHER INFORMATION: n is a, c, g, or t
<220> FEATURE:
<221> NAME/KEY: misc_feature
<222> LOCATION: (55878)..(55878)
<223> OTHER INFORMATION: n is a, c, g, or t
<220> FEATURE:
<221> NAME/KEY: misc_feature
<222> LOCATION: (55883)..(55883)
<223> OTHER INFORMATION: n is a, c, g, or t
<220> FEATURE:
<221> NAME/KEY: misc_feature
<222> LOCATION: (55887)..(55887)
<223> OTHER INFORMATION: n is a, c, g, or t
<220> FEATURE:
<221> NAME/KEY: misc_feature
<222> LOCATION: (55899)..(55899)
<223> OTHER INFORMATION: n is a, c, g, or t
<220> FEATURE:
<221> NAME/KEY: misc_feature
<222> LOCATION: (55905)..(55905)
<223> OTHER INFORMATION: n is a, c, g, or t
<220> FEATURE:
<221> NAME/KEY: misc_feature
<222> LOCATION: (55914)..(55916)
<223> OTHER INFORMATION: n is a, c, g, or t
<220> FEATURE:
<221> NAME/KEY: misc_feature
<222> LOCATION: (55921)..(55923)
<223> OTHER INFORMATION: n is a, c, g, or t
<220> FEATURE:
<221> NAME/KEY: misc_feature
<222> LOCATION: (55932)..(55932)
<223> OTHER INFORMATION: n is a, c, g, or t
<220> FEATURE:
<221> NAME/KEY: misc_feature
<222> LOCATION: (55951)..(55951)
<223> OTHER INFORMATION: n is a, c, g, or t
<220> FEATURE:
<221> NAME/KEY: misc_feature
<222> LOCATION: (56341)..(56341)
<223> OTHER INFORMATION: n is a, c, g, or t
<220> FEATURE:
<221> NAME/KEY: misc_feature
<222> LOCATION: (56346)..(56346)
<223> OTHER INFORMATION: n is a, c, g, or t
<220> FEATURE:
<221> NAME/KEY: misc_feature
<222> LOCATION: (56351)..(56351)
<223> OTHER INFORMATION: n is a, c, g, or t
<220> FEATURE:
<221> NAME/KEY: misc_feature
<222> LOCATION: (56355)..(56355)
<223> OTHER INFORMATION: n is a, c, g, or t
<220> FEATURE:
<221> NAME/KEY: misc_feature
<222> LOCATION: (56367)..(56367)
<223> OTHER INFORMATION: n is a, c, g, or t
<220> FEATURE:
```

-continued

```
<221> NAME/KEY: misc_feature
<222> LOCATION: (56373)..(56373)
<223> OTHER INFORMATION: n is a, c, g, or t
<220> FEATURE:
<221> NAME/KEY: misc_feature
<222> LOCATION: (56382)..(56384)
<223> OTHER INFORMATION: n is a, c, g, or t
<220> FEATURE:
<221> NAME/KEY: misc_feature
<222> LOCATION: (56389)..(56391)
<223> OTHER INFORMATION: n is a, c, g, or t
<220> FEATURE:
<221> NAME/KEY: misc_feature
<222> LOCATION: (56400)..(56400)
<223> OTHER INFORMATION: n is a, c, g, or t
<220> FEATURE:
<221> NAME/KEY: misc_feature
<222> LOCATION: (56419)..(56419)
<223> OTHER INFORMATION: n is a, c, g, or t
<220> FEATURE:
<221> NAME/KEY: misc_feature
<222> LOCATION: (56450)..(56450)
<223> OTHER INFORMATION: n is a, c, g, or t
<220> FEATURE:
<221> NAME/KEY: misc_feature
<222> LOCATION: (56453)..(56453)
<223> OTHER INFORMATION: n is a, c, g, or t
<220> FEATURE:
<221> NAME/KEY: misc_feature
<222> LOCATION: (56459)..(56459)
<223> OTHER INFORMATION: n is a, c, g, or t
<220> FEATURE:
<221> NAME/KEY: misc_feature
<222> LOCATION: (56494)..(56494)
<223> OTHER INFORMATION: n is a, c, g, or t
<220> FEATURE:
<221> NAME/KEY: misc_feature
<222> LOCATION: (56497)..(56497)
<223> OTHER INFORMATION: n is a, c, g, or t
<220> FEATURE:
<221> NAME/KEY: misc_feature
<222> LOCATION: (56499)..(56499)
<223> OTHER INFORMATION: n is a, c, g, or t
<220> FEATURE:
<221> NAME/KEY: misc_feature
<222> LOCATION: (56502)..(56502)
<223> OTHER INFORMATION: n is a, c, g, or t
<220> FEATURE:
<221> NAME/KEY: misc_feature
<222> LOCATION: (56508)..(56508)
<223> OTHER INFORMATION: n is a, c, g, or t
<220> FEATURE:
<221> NAME/KEY: misc_feature
<222> LOCATION: (56524)..(56524)
<223> OTHER INFORMATION: n is a, c, g, or t
<220> FEATURE:
<221> NAME/KEY: misc_feature
<222> LOCATION: (56530)..(56530)
<223> OTHER INFORMATION: n is a, c, g, or t
<220> FEATURE:
<221> NAME/KEY: misc_feature
<222> LOCATION: (56534)..(56534)
<223> OTHER INFORMATION: n is a, c, g, or t
<220> FEATURE:
<221> NAME/KEY: misc_feature
<222> LOCATION: (56539)..(56539)
<223> OTHER INFORMATION: n is a, c, g, or t
<220> FEATURE:
<221> NAME/KEY: misc_feature
<222> LOCATION: (56541)..(56542)
<223> OTHER INFORMATION: n is a, c, g, or t
<220> FEATURE:
<221> NAME/KEY: misc_feature
<222> LOCATION: (56546)..(56546)
<223> OTHER INFORMATION: n is a, c, g, or t
<220> FEATURE:
<221> NAME/KEY: misc_feature
<222> LOCATION: (56557)..(56557)
<223> OTHER INFORMATION: n is a, c, g, or t
```

-continued

```
<220> FEATURE:
<221> NAME/KEY: misc_feature
<222> LOCATION: (56559)..(56559)
<223> OTHER INFORMATION: n is a, c, g, or t
<220> FEATURE:
<221> NAME/KEY: misc_feature
<222> LOCATION: (56562)..(56562)
<223> OTHER INFORMATION: n is a, c, g, or t
<220> FEATURE:
<221> NAME/KEY: misc_feature
<222> LOCATION: (56569)..(56569)
<223> OTHER INFORMATION: n is a, c, g, or t
<220> FEATURE:
<221> NAME/KEY: misc_feature
<222> LOCATION: (56577)..(56577)
<223> OTHER INFORMATION: n is a, c, g, or t
<220> FEATURE:
<221> NAME/KEY: misc_feature
<222> LOCATION: (56595)..(56595)
<223> OTHER INFORMATION: n is a, c, g, or t
<220> FEATURE:
<221> NAME/KEY: misc_feature
<222> LOCATION: (56598)..(56598)
<223> OTHER INFORMATION: n is a, c, g, or t
<220> FEATURE:
<221> NAME/KEY: misc_feature
<222> LOCATION: (56600)..(56600)
<223> OTHER INFORMATION: n is a, c, g, or t
<220> FEATURE:
<221> NAME/KEY: misc_feature
<222> LOCATION: (56604)..(56605)
<223> OTHER INFORMATION: n is a, c, g, or t
<220> FEATURE:
<221> NAME/KEY: misc_feature
<222> LOCATION: (56612)..(56613)
<223> OTHER INFORMATION: n is a, c, g, or t
<220> FEATURE:
<221> NAME/KEY: misc_feature
<222> LOCATION: (56615)..(56615)
<223> OTHER INFORMATION: n is a, c, g, or t
<220> FEATURE:
<221> NAME/KEY: misc_feature
<222> LOCATION: (56619)..(56619)
<223> OTHER INFORMATION: n is a, c, g, or t
<220> FEATURE:
<221> NAME/KEY: misc_feature
<222> LOCATION: (56622)..(56622)
<223> OTHER INFORMATION: n is a, c, g, or t
<220> FEATURE:
<221> NAME/KEY: misc_feature
<222> LOCATION: (56643)..(56643)
<223> OTHER INFORMATION: n is a, c, g, or t
<220> FEATURE:
<221> NAME/KEY: misc_feature
<222> LOCATION: (56647)..(56647)
<223> OTHER INFORMATION: n is a, c, g, or t
<220> FEATURE:
<221> NAME/KEY: misc_feature
<222> LOCATION: (56649)..(56649)
<223> OTHER INFORMATION: n is a, c, g, or t
<220> FEATURE:
<221> NAME/KEY: misc_feature
<222> LOCATION: (56652)..(56652)
<223> OTHER INFORMATION: n is a, c, g, or t
<220> FEATURE:
<221> NAME/KEY: misc_feature
<222> LOCATION: (56667)..(56670)
<223> OTHER INFORMATION: n is a, c, g, or t
<220> FEATURE:
<221> NAME/KEY: misc_feature
<222> LOCATION: (56674)..(56674)
<223> OTHER INFORMATION: n is a, c, g, or t
<220> FEATURE:
<221> NAME/KEY: misc_feature
<222> LOCATION: (56676)..(56676)
<223> OTHER INFORMATION: n is a, c, g, or t
<220> FEATURE:
<221> NAME/KEY: misc_feature
<222> LOCATION: (56686)..(56686)
```

-continued

```
<223> OTHER INFORMATION: n is a, c, g, or t
<220> FEATURE:
<221> NAME/KEY: misc_feature
<222> LOCATION: (56694)..(56694)
<223> OTHER INFORMATION: n is a, c, g, or t
<220> FEATURE:
<221> NAME/KEY: misc_feature
<222> LOCATION: (56699)..(56699)
<223> OTHER INFORMATION: n is a, c, g, or t
<220> FEATURE:
<221> NAME/KEY: misc_feature
<222> LOCATION: (56726)..(56727)
<223> OTHER INFORMATION: n is a, c, g, or t
<220> FEATURE:
<221> NAME/KEY: misc_feature
<222> LOCATION: (56734)..(56734)
<223> OTHER INFORMATION: n is a, c, g, or t
<220> FEATURE:
<221> NAME/KEY: misc_feature
<222> LOCATION: (56736)..(56736)
<223> OTHER INFORMATION: n is a, c, g, or t
<220> FEATURE:
<221> NAME/KEY: misc_feature
<222> LOCATION: (56743)..(56743)
<223> OTHER INFORMATION: n is a, c, g, or t
<220> FEATURE:
<221> NAME/KEY: misc_feature
<222> LOCATION: (56748)..(56748)
<223> OTHER INFORMATION: n is a, c, g, or t
<220> FEATURE:
<221> NAME/KEY: misc_feature
<222> LOCATION: (56761)..(56761)
<223> OTHER INFORMATION: n is a, c, g, or t
<220> FEATURE:
<221> NAME/KEY: misc_feature
<222> LOCATION: (56777)..(56777)
<223> OTHER INFORMATION: n is a, c, g, or t
<220> FEATURE:
<221> NAME/KEY: misc_feature
<222> LOCATION: (56783)..(56784)
<223> OTHER INFORMATION: n is a, c, g, or t
<220> FEATURE:
<221> NAME/KEY: misc_feature
<222> LOCATION: (56786)..(56786)
<223> OTHER INFORMATION: n is a, c, g, or t
<220> FEATURE:
<221> NAME/KEY: misc_feature
<222> LOCATION: (56788)..(56788)
<223> OTHER INFORMATION: n is a, c, g, or t
<220> FEATURE:
<221> NAME/KEY: misc_feature
<222> LOCATION: (56790)..(56790)
<223> OTHER INFORMATION: n is a, c, g, or t
<220> FEATURE:
<221> NAME/KEY: misc_feature
<222> LOCATION: (56799)..(56799)
<223> OTHER INFORMATION: n is a, c, g, or t
<220> FEATURE:
<221> NAME/KEY: misc_feature
<222> LOCATION: (56809)..(56809)
<223> OTHER INFORMATION: n is a, c, g, or t
<220> FEATURE:
<221> NAME/KEY: misc_feature
<222> LOCATION: (56814)..(56814)
<223> OTHER INFORMATION: n is a, c, g, or t
<220> FEATURE:
<221> NAME/KEY: misc_feature
<222> LOCATION: (56819)..(56819)
<223> OTHER INFORMATION: n is a, c, g, or t
<220> FEATURE:
<221> NAME/KEY: misc_feature
<222> LOCATION: (56823)..(56823)
<223> OTHER INFORMATION: n is a, c, g, or t
<220> FEATURE:
<221> NAME/KEY: misc_feature
<222> LOCATION: (56835)..(56835)
<223> OTHER INFORMATION: n is a, c, g, or t
<220> FEATURE:
<221> NAME/KEY: misc_feature
```

-continued

```
<222> LOCATION: (56841)..(56841)
<223> OTHER INFORMATION: n is a, c, g, or t
<220> FEATURE:
<221> NAME/KEY: misc_feature
<222> LOCATION: (56850)..(56852)
<223> OTHER INFORMATION: n is a, c, g, or t
<220> FEATURE:
<221> NAME/KEY: misc_feature
<222> LOCATION: (56857)..(56859)
<223> OTHER INFORMATION: n is a, c, g, or t
<220> FEATURE:
<221> NAME/KEY: misc_feature
<222> LOCATION: (56868)..(56868)
<223> OTHER INFORMATION: n is a, c, g, or t
<220> FEATURE:
<221> NAME/KEY: misc_feature
<222> LOCATION: (56887)..(56887)
<223> OTHER INFORMATION: n is a, c, g, or t
<220> FEATURE:
<221> NAME/KEY: misc_feature
<222> LOCATION: (57475)..(57475)
<223> OTHER INFORMATION: n is a, c, g, or t
<220> FEATURE:
<221> NAME/KEY: misc_feature
<222> LOCATION: (57477)..(57478)
<223> OTHER INFORMATION: n is a, c, g, or t
<220> FEATURE:
<221> NAME/KEY: misc_feature
<222> LOCATION: (57482)..(57482)
<223> OTHER INFORMATION: n is a, c, g, or t
<220> FEATURE:
<221> NAME/KEY: misc_feature
<222> LOCATION: (57493)..(57493)
<223> OTHER INFORMATION: n is a, c, g, or t
<220> FEATURE:
<221> NAME/KEY: misc_feature
<222> LOCATION: (57495)..(57495)
<223> OTHER INFORMATION: n is a, c, g, or t
<220> FEATURE:
<221> NAME/KEY: misc_feature
<222> LOCATION: (57498)..(57498)
<223> OTHER INFORMATION: n is a, c, g, or t
<220> FEATURE:
<221> NAME/KEY: misc_feature
<222> LOCATION: (57505)..(57505)
<223> OTHER INFORMATION: n is a, c, g, or t
<220> FEATURE:
<221> NAME/KEY: misc_feature
<222> LOCATION: (57513)..(57513)
<223> OTHER INFORMATION: n is a, c, g, or t
<220> FEATURE:
<221> NAME/KEY: misc_feature
<222> LOCATION: (57531)..(57531)
<223> OTHER INFORMATION: n is a, c, g, or t
<220> FEATURE:
<221> NAME/KEY: misc_feature
<222> LOCATION: (57534)..(57534)
<223> OTHER INFORMATION: n is a, c, g, or t
<220> FEATURE:
<221> NAME/KEY: misc_feature
<222> LOCATION: (57536)..(57536)
<223> OTHER INFORMATION: n is a, c, g, or t
<220> FEATURE:
<221> NAME/KEY: misc_feature
<222> LOCATION: (57540)..(57541)
<223> OTHER INFORMATION: n is a, c, g, or t
<220> FEATURE:
<221> NAME/KEY: misc_feature
<222> LOCATION: (57548)..(57549)
<223> OTHER INFORMATION: n is a, c, g, or t
<220> FEATURE:
<221> NAME/KEY: misc_feature
<222> LOCATION: (57551)..(57551)
<223> OTHER INFORMATION: n is a, c, g, or t
<220> FEATURE:
<221> NAME/KEY: misc_feature
<222> LOCATION: (57555)..(57555)
<223> OTHER INFORMATION: n is a, c, g, or t
<220> FEATURE:
```

```
<221> NAME/KEY: misc_feature
<222> LOCATION: (57558)..(57558)
<223> OTHER INFORMATION: n is a, c, g, or t
<220> FEATURE:
<221> NAME/KEY: misc_feature
<222> LOCATION: (57579)..(57579)
<223> OTHER INFORMATION: n is a, c, g, or t
<220> FEATURE:
<221> NAME/KEY: misc_feature
<222> LOCATION: (57583)..(57583)
<223> OTHER INFORMATION: n is a, c, g, or t
<220> FEATURE:
<221> NAME/KEY: misc_feature
<222> LOCATION: (57585)..(57585)
<223> OTHER INFORMATION: n is a, c, g, or t
<220> FEATURE:
<221> NAME/KEY: misc_feature
<222> LOCATION: (57588)..(57588)
<223> OTHER INFORMATION: n is a, c, g, or t
<220> FEATURE:
<221> NAME/KEY: misc_feature
<222> LOCATION: (57603)..(57606)
<223> OTHER INFORMATION: n is a, c, g, or t
<220> FEATURE:
<221> NAME/KEY: misc_feature
<222> LOCATION: (57610)..(57610)
<223> OTHER INFORMATION: n is a, c, g, or t
<220> FEATURE:
<221> NAME/KEY: misc_feature
<222> LOCATION: (57612)..(57612)
<223> OTHER INFORMATION: n is a, c, g, or t
<220> FEATURE:
<221> NAME/KEY: misc_feature
<222> LOCATION: (57622)..(57622)
<223> OTHER INFORMATION: n is a, c, g, or t
<220> FEATURE:
<221> NAME/KEY: misc_feature
<222> LOCATION: (57630)..(57630)
<223> OTHER INFORMATION: n is a, c, g, or t
<220> FEATURE:
<221> NAME/KEY: misc_feature
<222> LOCATION: (57635)..(57635)
<223> OTHER INFORMATION: n is a, c, g, or t
<220> FEATURE:
<221> NAME/KEY: misc_feature
<222> LOCATION: (57662)..(57663)
<223> OTHER INFORMATION: n is a, c, g, or t
<220> FEATURE:
<221> NAME/KEY: misc_feature
<222> LOCATION: (57670)..(57670)
<223> OTHER INFORMATION: n is a, c, g, or t
<220> FEATURE:
<221> NAME/KEY: misc_feature
<222> LOCATION: (57672)..(57672)
<223> OTHER INFORMATION: n is a, c, g, or t
<220> FEATURE:
<221> NAME/KEY: misc_feature
<222> LOCATION: (57679)..(57679)
<223> OTHER INFORMATION: n is a, c, g, or t
<220> FEATURE:
<221> NAME/KEY: misc_feature
<222> LOCATION: (57684)..(57684)
<223> OTHER INFORMATION: n is a, c, g, or t
<220> FEATURE:
<221> NAME/KEY: misc_feature
<222> LOCATION: (57697)..(57697)
<223> OTHER INFORMATION: n is a, c, g, or t
<220> FEATURE:
<221> NAME/KEY: misc_feature
<222> LOCATION: (57713)..(57713)
<223> OTHER INFORMATION: n is a, c, g, or t
<220> FEATURE:
<221> NAME/KEY: misc_feature
<222> LOCATION: (57719)..(57720)
<223> OTHER INFORMATION: n is a, c, g, or t
<220> FEATURE:
<221> NAME/KEY: misc_feature
<222> LOCATION: (57722)..(57722)
<223> OTHER INFORMATION: n is a, c, g, or t
```

-continued

```
<220> FEATURE:
<221> NAME/KEY: misc_feature
<222> LOCATION: (57724)..(57724)
<223> OTHER INFORMATION: n is a, c, g, or t
<220> FEATURE:
<221> NAME/KEY: misc_feature
<222> LOCATION: (57726)..(57726)
<223> OTHER INFORMATION: n is a, c, g, or t
<220> FEATURE:
<221> NAME/KEY: misc_feature
<222> LOCATION: (57735)..(57735)
<223> OTHER INFORMATION: n is a, c, g, or t
<220> FEATURE:
<221> NAME/KEY: misc_feature
<222> LOCATION: (57745)..(57745)
<223> OTHER INFORMATION: n is a, c, g, or t
<220> FEATURE:
<221> NAME/KEY: misc_feature
<222> LOCATION: (57750)..(57750)
<223> OTHER INFORMATION: n is a, c, g, or t
<220> FEATURE:
<221> NAME/KEY: misc_feature
<222> LOCATION: (57755)..(57755)
<223> OTHER INFORMATION: n is a, c, g, or t
<220> FEATURE:
<221> NAME/KEY: misc_feature
<222> LOCATION: (57759)..(57759)
<223> OTHER INFORMATION: n is a, c, g, or t
<220> FEATURE:
<221> NAME/KEY: misc_feature
<222> LOCATION: (57771)..(57771)
<223> OTHER INFORMATION: n is a, c, g, or t
<220> FEATURE:
<221> NAME/KEY: misc_feature
<222> LOCATION: (57777)..(57777)
<223> OTHER INFORMATION: n is a, c, g, or t
<220> FEATURE:
<221> NAME/KEY: misc_feature
<222> LOCATION: (57786)..(57788)
<223> OTHER INFORMATION: n is a, c, g, or t
<220> FEATURE:
<221> NAME/KEY: misc_feature
<222> LOCATION: (57793)..(57795)
<223> OTHER INFORMATION: n is a, c, g, or t
<220> FEATURE:
<221> NAME/KEY: misc_feature
<222> LOCATION: (57804)..(57804)
<223> OTHER INFORMATION: n is a, c, g, or t
<220> FEATURE:
<221> NAME/KEY: misc_feature
<222> LOCATION: (57823)..(57823)
<223> OTHER INFORMATION: n is a, c, g, or t
<220> FEATURE:
<221> NAME/KEY: misc_feature
<222> LOCATION: (58213)..(58213)
<223> OTHER INFORMATION: n is a, c, g, or t
<220> FEATURE:
<221> NAME/KEY: misc_feature
<222> LOCATION: (58218)..(58218)
<223> OTHER INFORMATION: n is a, c, g, or t
<220> FEATURE:
<221> NAME/KEY: misc_feature
<222> LOCATION: (58223)..(58223)
<223> OTHER INFORMATION: n is a, c, g, or t
<220> FEATURE:
<221> NAME/KEY: misc_feature
<222> LOCATION: (58227)..(58227)
<223> OTHER INFORMATION: n is a, c, g, or t
<220> FEATURE:
<221> NAME/KEY: misc_feature
<222> LOCATION: (58239)..(58239)
<223> OTHER INFORMATION: n is a, c, g, or t
<220> FEATURE:
<221> NAME/KEY: misc_feature
<222> LOCATION: (58245)..(58245)
<223> OTHER INFORMATION: n is a, c, g, or t
<220> FEATURE:
<221> NAME/KEY: misc_feature
<222> LOCATION: (58254)..(58256)
```

-continued

```
<223> OTHER INFORMATION: n is a, c, g, or t
<220> FEATURE:
<221> NAME/KEY: misc_feature
<222> LOCATION: (58261)..(58263)
<223> OTHER INFORMATION: n is a, c, g, or t
<220> FEATURE:
<221> NAME/KEY: misc_feature
<222> LOCATION: (58272)..(58272)
<223> OTHER INFORMATION: n is a, c, g, or t
<220> FEATURE:
<221> NAME/KEY: misc_feature
<222> LOCATION: (58291)..(58291)
<223> OTHER INFORMATION: n is a, c, g, or t
<220> FEATURE:
<221> NAME/KEY: misc_feature
<222> LOCATION: (58322)..(58322)
<223> OTHER INFORMATION: n is a, c, g, or t
<220> FEATURE:
<221> NAME/KEY: misc_feature
<222> LOCATION: (58325)..(58325)
<223> OTHER INFORMATION: n is a, c, g, or t
<220> FEATURE:
<221> NAME/KEY: misc_feature
<222> LOCATION: (58331)..(58331)
<223> OTHER INFORMATION: n is a, c, g, or t
<220> FEATURE:
<221> NAME/KEY: misc_feature
<222> LOCATION: (58366)..(58366)
<223> OTHER INFORMATION: n is a, c, g, or t
<220> FEATURE:
<221> NAME/KEY: misc_feature
<222> LOCATION: (58369)..(58369)
<223> OTHER INFORMATION: n is a, c, g, or t
<220> FEATURE:
<221> NAME/KEY: misc_feature
<222> LOCATION: (58371)..(58371)
<223> OTHER INFORMATION: n is a, c, g, or t
<220> FEATURE:
<221> NAME/KEY: misc_feature
<222> LOCATION: (58374)..(58374)
<223> OTHER INFORMATION: n is a, c, g, or t
<220> FEATURE:
<221> NAME/KEY: misc_feature
<222> LOCATION: (58380)..(58380)
<223> OTHER INFORMATION: n is a, c, g, or t
<220> FEATURE:
<221> NAME/KEY: misc_feature
<222> LOCATION: (58396)..(58396)
<223> OTHER INFORMATION: n is a, c, g, or t
<220> FEATURE:
<221> NAME/KEY: misc_feature
<222> LOCATION: (58402)..(58402)
<223> OTHER INFORMATION: n is a, c, g, or t
<220> FEATURE:
<221> NAME/KEY: misc_feature
<222> LOCATION: (58406)..(58406)
<223> OTHER INFORMATION: n is a, c, g, or t
<220> FEATURE:
<221> NAME/KEY: misc_feature
<222> LOCATION: (58411)..(58411)
<223> OTHER INFORMATION: n is a, c, g, or t
<220> FEATURE:
<221> NAME/KEY: misc_feature
<222> LOCATION: (58413)..(58414)
<223> OTHER INFORMATION: n is a, c, g, or t
<220> FEATURE:
<221> NAME/KEY: misc_feature
<222> LOCATION: (58418)..(58418)
<223> OTHER INFORMATION: n is a, c, g, or t
<220> FEATURE:
<221> NAME/KEY: misc_feature
<222> LOCATION: (58429)..(58429)
<223> OTHER INFORMATION: n is a, c, g, or t
<220> FEATURE:
<221> NAME/KEY: misc_feature
<222> LOCATION: (58431)..(58431)
<223> OTHER INFORMATION: n is a, c, g, or t
<220> FEATURE:
<221> NAME/KEY: misc_feature
```

-continued

```
<222> LOCATION: (58434)..(58434)
<223> OTHER INFORMATION: n is a, c, g, or t
<220> FEATURE:
<221> NAME/KEY: misc_feature
<222> LOCATION: (58441)..(58441)
<223> OTHER INFORMATION: n is a, c, g, or t
<220> FEATURE:
<221> NAME/KEY: misc_feature
<222> LOCATION: (58449)..(58449)
<223> OTHER INFORMATION: n is a, c, g, or t
<220> FEATURE:
<221> NAME/KEY: misc_feature
<222> LOCATION: (58467)..(58467)
<223> OTHER INFORMATION: n is a, c, g, or t
<220> FEATURE:
<221> NAME/KEY: misc_feature
<222> LOCATION: (58470)..(58470)
<223> OTHER INFORMATION: n is a, c, g, or t
<220> FEATURE:
<221> NAME/KEY: misc_feature
<222> LOCATION: (58472)..(58472)
<223> OTHER INFORMATION: n is a, c, g, or t
<220> FEATURE:
<221> NAME/KEY: misc_feature
<222> LOCATION: (58476)..(58477)
<223> OTHER INFORMATION: n is a, c, g, or t
<220> FEATURE:
<221> NAME/KEY: misc_feature
<222> LOCATION: (58484)..(58485)
<223> OTHER INFORMATION: n is a, c, g, or t
<220> FEATURE:
<221> NAME/KEY: misc_feature
<222> LOCATION: (58487)..(58487)
<223> OTHER INFORMATION: n is a, c, g, or t
<220> FEATURE:
<221> NAME/KEY: misc_feature
<222> LOCATION: (58491)..(58491)
<223> OTHER INFORMATION: n is a, c, g, or t
<220> FEATURE:
<221> NAME/KEY: misc_feature
<222> LOCATION: (58494)..(58494)
<223> OTHER INFORMATION: n is a, c, g, or t
<220> FEATURE:
<221> NAME/KEY: misc_feature
<222> LOCATION: (58515)..(58515)
<223> OTHER INFORMATION: n is a, c, g, or t
<220> FEATURE:
<221> NAME/KEY: misc_feature
<222> LOCATION: (58519)..(58519)
<223> OTHER INFORMATION: n is a, c, g, or t
<220> FEATURE:
<221> NAME/KEY: misc_feature
<222> LOCATION: (58521)..(58521)
<223> OTHER INFORMATION: n is a, c, g, or t
<220> FEATURE:
<221> NAME/KEY: misc_feature
<222> LOCATION: (58524)..(58524)
<223> OTHER INFORMATION: n is a, c, g, or t
<220> FEATURE:
<221> NAME/KEY: misc_feature
<222> LOCATION: (58539)..(58542)
<223> OTHER INFORMATION: n is a, c, g, or t
<220> FEATURE:
<221> NAME/KEY: misc_feature
<222> LOCATION: (58546)..(58546)
<223> OTHER INFORMATION: n is a, c, g, or t
<220> FEATURE:
<221> NAME/KEY: misc_feature
<222> LOCATION: (58548)..(58548)
<223> OTHER INFORMATION: n is a, c, g, or t
<220> FEATURE:
<221> NAME/KEY: misc_feature
<222> LOCATION: (58558)..(58558)
<223> OTHER INFORMATION: n is a, c, g, or t
<220> FEATURE:
<221> NAME/KEY: misc_feature
<222> LOCATION: (58566)..(58566)
<223> OTHER INFORMATION: n is a, c, g, or t
<220> FEATURE:
```

-continued

```
<221> NAME/KEY: misc_feature
<222> LOCATION: (58571)..(58571)
<223> OTHER INFORMATION: n is a, c, g, or t
<220> FEATURE:
<221> NAME/KEY: misc_feature
<222> LOCATION: (58598)..(58599)
<223> OTHER INFORMATION: n is a, c, g, or t
<220> FEATURE:
<221> NAME/KEY: misc_feature
<222> LOCATION: (58606)..(58606)
<223> OTHER INFORMATION: n is a, c, g, or t
<220> FEATURE:
<221> NAME/KEY: misc_feature
<222> LOCATION: (58608)..(58608)
<223> OTHER INFORMATION: n is a, c, g, or t
<220> FEATURE:
<221> NAME/KEY: misc_feature
<222> LOCATION: (58615)..(58615)
<223> OTHER INFORMATION: n is a, c, g, or t
<220> FEATURE:
<221> NAME/KEY: misc_feature
<222> LOCATION: (58620)..(58620)
<223> OTHER INFORMATION: n is a, c, g, or t
<220> FEATURE:
<221> NAME/KEY: misc_feature
<222> LOCATION: (58633)..(58633)
<223> OTHER INFORMATION: n is a, c, g, or t
<220> FEATURE:
<221> NAME/KEY: misc_feature
<222> LOCATION: (58649)..(58649)
<223> OTHER INFORMATION: n is a, c, g, or t
<220> FEATURE:
<221> NAME/KEY: misc_feature
<222> LOCATION: (58655)..(58656)
<223> OTHER INFORMATION: n is a, c, g, or t
<220> FEATURE:
<221> NAME/KEY: misc_feature
<222> LOCATION: (58658)..(58658)
<223> OTHER INFORMATION: n is a, c, g, or t
<220> FEATURE:
<221> NAME/KEY: misc_feature
<222> LOCATION: (58660)..(58660)
<223> OTHER INFORMATION: n is a, c, g, or t
<220> FEATURE:
<221> NAME/KEY: misc_feature
<222> LOCATION: (58662)..(58662)
<223> OTHER INFORMATION: n is a, c, g, or t
<220> FEATURE:
<221> NAME/KEY: misc_feature
<222> LOCATION: (58671)..(58671)
<223> OTHER INFORMATION: n is a, c, g, or t
<220> FEATURE:
<221> NAME/KEY: misc_feature
<222> LOCATION: (58681)..(58681)
<223> OTHER INFORMATION: n is a, c, g, or t
<220> FEATURE:
<221> NAME/KEY: misc_feature
<222> LOCATION: (58686)..(58686)
<223> OTHER INFORMATION: n is a, c, g, or t
<220> FEATURE:
<221> NAME/KEY: misc_feature
<222> LOCATION: (58691)..(58691)
<223> OTHER INFORMATION: n is a, c, g, or t
<220> FEATURE:
<221> NAME/KEY: misc_feature
<222> LOCATION: (58695)..(58695)
<223> OTHER INFORMATION: n is a, c, g, or t
<220> FEATURE:
<221> NAME/KEY: misc_feature
<222> LOCATION: (58707)..(58707)
<223> OTHER INFORMATION: n is a, c, g, or t
<220> FEATURE:
<221> NAME/KEY: misc_feature
<222> LOCATION: (58713)..(58713)
<223> OTHER INFORMATION: n is a, c, g, or t
<220> FEATURE:
<221> NAME/KEY: misc_feature
<222> LOCATION: (58722)..(58724)
<223> OTHER INFORMATION: n is a, c, g, or t
```

```
<220> FEATURE:
<221> NAME/KEY: misc_feature
<222> LOCATION: (58729)..(58731)
<223> OTHER INFORMATION: n is a, c, g, or t
<220> FEATURE:
<221> NAME/KEY: misc_feature
<222> LOCATION: (58740)..(58740)
<223> OTHER INFORMATION: n is a, c, g, or t
<220> FEATURE:
<221> NAME/KEY: misc_feature
<222> LOCATION: (58759)..(58759)
<223> OTHER INFORMATION: n is a, c, g, or t
<220> FEATURE:
<221> NAME/KEY: misc_feature
<222> LOCATION: (59149)..(59149)
<223> OTHER INFORMATION: n is a, c, g, or t
<220> FEATURE:
<221> NAME/KEY: misc_feature
<222> LOCATION: (59154)..(59154)
<223> OTHER INFORMATION: n is a, c, g, or t
<220> FEATURE:
<221> NAME/KEY: misc_feature
<222> LOCATION: (59159)..(59159)
<223> OTHER INFORMATION: n is a, c, g, or t
<220> FEATURE:
<221> NAME/KEY: misc_feature
<222> LOCATION: (59163)..(59163)
<223> OTHER INFORMATION: n is a, c, g, or t
<220> FEATURE:
<221> NAME/KEY: misc_feature
<222> LOCATION: (59175)..(59175)
<223> OTHER INFORMATION: n is a, c, g, or t
<220> FEATURE:
<221> NAME/KEY: misc_feature
<222> LOCATION: (59181)..(59181)
<223> OTHER INFORMATION: n is a, c, g, or t
<220> FEATURE:
<221> NAME/KEY: misc_feature
<222> LOCATION: (59190)..(59192)
<223> OTHER INFORMATION: n is a, c, g, or t
<220> FEATURE:
<221> NAME/KEY: misc_feature
<222> LOCATION: (59197)..(59199)
<223> OTHER INFORMATION: n is a, c, g, or t
<220> FEATURE:
<221> NAME/KEY: misc_feature
<222> LOCATION: (59208)..(59208)
<223> OTHER INFORMATION: n is a, c, g, or t
<220> FEATURE:
<221> NAME/KEY: misc_feature
<222> LOCATION: (59227)..(59227)
<223> OTHER INFORMATION: n is a, c, g, or t
<220> FEATURE:
<221> NAME/KEY: misc_feature
<222> LOCATION: (59258)..(59258)
<223> OTHER INFORMATION: n is a, c, g, or t
<220> FEATURE:
<221> NAME/KEY: misc_feature
<222> LOCATION: (59261)..(59261)
<223> OTHER INFORMATION: n is a, c, g, or t
<220> FEATURE:
<221> NAME/KEY: misc_feature
<222> LOCATION: (59267)..(59267)
<223> OTHER INFORMATION: n is a, c, g, or t
<220> FEATURE:
<221> NAME/KEY: misc_feature
<222> LOCATION: (59302)..(59302)
<223> OTHER INFORMATION: n is a, c, g, or t
<220> FEATURE:
<221> NAME/KEY: misc_feature
<222> LOCATION: (59305)..(59305)
<223> OTHER INFORMATION: n is a, c, g, or t
<220> FEATURE:
<221> NAME/KEY: misc_feature
<222> LOCATION: (59307)..(59307)
<223> OTHER INFORMATION: n is a, c, g, or t
<220> FEATURE:
<221> NAME/KEY: misc_feature
<222> LOCATION: (59310)..(59310)
```

-continued

```
<223> OTHER INFORMATION: n is a, c, g, or t
<220> FEATURE:
<221> NAME/KEY: misc_feature
<222> LOCATION: (59316)..(59316)
<223> OTHER INFORMATION: n is a, c, g, or t
<220> FEATURE:
<221> NAME/KEY: misc_feature
<222> LOCATION: (59332)..(59332)
<223> OTHER INFORMATION: n is a, c, g, or t
<220> FEATURE:
<221> NAME/KEY: misc_feature
<222> LOCATION: (59338)..(59338)
<223> OTHER INFORMATION: n is a, c, g, or t
<220> FEATURE:
<221> NAME/KEY: misc_feature
<222> LOCATION: (59342)..(59342)
<223> OTHER INFORMATION: n is a, c, g, or t
<220> FEATURE:
<221> NAME/KEY: misc_feature
<222> LOCATION: (59347)..(59347)
<223> OTHER INFORMATION: n is a, c, g, or t
<220> FEATURE:
<221> NAME/KEY: misc_feature
<222> LOCATION: (59349)..(59350)
<223> OTHER INFORMATION: n is a, c, g, or t
<220> FEATURE:
<221> NAME/KEY: misc_feature
<222> LOCATION: (59354)..(59354)
<223> OTHER INFORMATION: n is a, c, g, or t
<220> FEATURE:
<221> NAME/KEY: misc_feature
<222> LOCATION: (59365)..(59365)
<223> OTHER INFORMATION: n is a, c, g, or t
<220> FEATURE:
<221> NAME/KEY: misc_feature
<222> LOCATION: (59367)..(59367)
<223> OTHER INFORMATION: n is a, c, g, or t
<220> FEATURE:
<221> NAME/KEY: misc_feature
<222> LOCATION: (59370)..(59370)
<223> OTHER INFORMATION: n is a, c, g, or t
<220> FEATURE:
<221> NAME/KEY: misc_feature
<222> LOCATION: (59377)..(59377)
<223> OTHER INFORMATION: n is a, c, g, or t
<220> FEATURE:
<221> NAME/KEY: misc_feature
<222> LOCATION: (59385)..(59385)
<223> OTHER INFORMATION: n is a, c, g, or t
<220> FEATURE:
<221> NAME/KEY: misc_feature
<222> LOCATION: (59403)..(59403)
<223> OTHER INFORMATION: n is a, c, g, or t
<220> FEATURE:
<221> NAME/KEY: misc_feature
<222> LOCATION: (59406)..(59406)
<223> OTHER INFORMATION: n is a, c, g, or t
<220> FEATURE:
<221> NAME/KEY: misc_feature
<222> LOCATION: (59408)..(59408)
<223> OTHER INFORMATION: n is a, c, g, or t
<220> FEATURE:
<221> NAME/KEY: misc_feature
<222> LOCATION: (59412)..(59413)
<223> OTHER INFORMATION: n is a, c, g, or t
<220> FEATURE:
<221> NAME/KEY: misc_feature
<222> LOCATION: (59420)..(59421)
<223> OTHER INFORMATION: n is a, c, g, or t
<220> FEATURE:
<221> NAME/KEY: misc_feature
<222> LOCATION: (59423)..(59423)
<223> OTHER INFORMATION: n is a, c, g, or t
<220> FEATURE:
<221> NAME/KEY: misc_feature
<222> LOCATION: (59427)..(59427)
<223> OTHER INFORMATION: n is a, c, g, or t
<220> FEATURE:
<221> NAME/KEY: misc_feature
```

```
<222> LOCATION: (59430)..(59430)
<223> OTHER INFORMATION: n is a, c, g, or t
<220> FEATURE:
<221> NAME/KEY: misc_feature
<222> LOCATION: (59451)..(59451)
<223> OTHER INFORMATION: n is a, c, g, or t
<220> FEATURE:
<221> NAME/KEY: misc_feature
<222> LOCATION: (59455)..(59455)
<223> OTHER INFORMATION: n is a, c, g, or t
<220> FEATURE:
<221> NAME/KEY: misc_feature
<222> LOCATION: (59457)..(59457)
<223> OTHER INFORMATION: n is a, c, g, or t
<220> FEATURE:
<221> NAME/KEY: misc_feature
<222> LOCATION: (59460)..(59460)
<223> OTHER INFORMATION: n is a, c, g, or t
<220> FEATURE:
<221> NAME/KEY: misc_feature
<222> LOCATION: (59475)..(59478)
<223> OTHER INFORMATION: n is a, c, g, or t
<220> FEATURE:
<221> NAME/KEY: misc_feature
<222> LOCATION: (59482)..(59482)
<223> OTHER INFORMATION: n is a, c, g, or t
<220> FEATURE:
<221> NAME/KEY: misc_feature
<222> LOCATION: (59484)..(59484)
<223> OTHER INFORMATION: n is a, c, g, or t
<220> FEATURE:
<221> NAME/KEY: misc_feature
<222> LOCATION: (59494)..(59494)
<223> OTHER INFORMATION: n is a, c, g, or t
<220> FEATURE:
<221> NAME/KEY: misc_feature
<222> LOCATION: (59502)..(59502)
<223> OTHER INFORMATION: n is a, c, g, or t
<220> FEATURE:
<221> NAME/KEY: misc_feature
<222> LOCATION: (59507)..(59507)
<223> OTHER INFORMATION: n is a, c, g, or t
<220> FEATURE:
<221> NAME/KEY: misc_feature
<222> LOCATION: (59534)..(59535)
<223> OTHER INFORMATION: n is a, c, g, or t
<220> FEATURE:
<221> NAME/KEY: misc_feature
<222> LOCATION: (59542)..(59542)
<223> OTHER INFORMATION: n is a, c, g, or t
<220> FEATURE:
<221> NAME/KEY: misc_feature
<222> LOCATION: (59544)..(59544)
<223> OTHER INFORMATION: n is a, c, g, or t
<220> FEATURE:
<221> NAME/KEY: misc_feature
<222> LOCATION: (59551)..(59551)
<223> OTHER INFORMATION: n is a, c, g, or t
<220> FEATURE:
<221> NAME/KEY: misc_feature
<222> LOCATION: (59556)..(59556)
<223> OTHER INFORMATION: n is a, c, g, or t
<220> FEATURE:
<221> NAME/KEY: misc_feature
<222> LOCATION: (59569)..(59569)
<223> OTHER INFORMATION: n is a, c, g, or t
<220> FEATURE:
<221> NAME/KEY: misc_feature
<222> LOCATION: (59585)..(59585)
<223> OTHER INFORMATION: n is a, c, g, or t
<220> FEATURE:
<221> NAME/KEY: misc_feature
<222> LOCATION: (59591)..(59592)
<223> OTHER INFORMATION: n is a, c, g, or t
<220> FEATURE:
<221> NAME/KEY: misc_feature
<222> LOCATION: (59594)..(59594)
<223> OTHER INFORMATION: n is a, c, g, or t
<220> FEATURE:
```

```
<221> NAME/KEY: misc_feature
<222> LOCATION: (59596)..(59596)
<223> OTHER INFORMATION: n is a, c, g, or t
<220> FEATURE:
<221> NAME/KEY: misc_feature
<222> LOCATION: (59598)..(59598)
<223> OTHER INFORMATION: n is a, c, g, or t
<220> FEATURE:
<221> NAME/KEY: misc_feature
<222> LOCATION: (59607)..(59607)
<223> OTHER INFORMATION: n is a, c, g, or t
<220> FEATURE:
<221> NAME/KEY: misc_feature
<222> LOCATION: (59617)..(59617)
<223> OTHER INFORMATION: n is a, c, g, or t
<220> FEATURE:
<221> NAME/KEY: misc_feature
<222> LOCATION: (59622)..(59622)
<223> OTHER INFORMATION: n is a, c, g, or t
<220> FEATURE:
<221> NAME/KEY: misc_feature
<222> LOCATION: (59627)..(59627)
<223> OTHER INFORMATION: n is a, c, g, or t
<220> FEATURE:
<221> NAME/KEY: misc_feature
<222> LOCATION: (59631)..(59631)
<223> OTHER INFORMATION: n is a, c, g, or t
<220> FEATURE:
<221> NAME/KEY: misc_feature
<222> LOCATION: (59643)..(59643)
<223> OTHER INFORMATION: n is a, c, g, or t
<220> FEATURE:
<221> NAME/KEY: misc_feature
<222> LOCATION: (59649)..(59649)
<223> OTHER INFORMATION: n is a, c, g, or t
<220> FEATURE:
<221> NAME/KEY: misc_feature
<222> LOCATION: (59658)..(59660)
<223> OTHER INFORMATION: n is a, c, g, or t
<220> FEATURE:
<221> NAME/KEY: misc_feature
<222> LOCATION: (59665)..(59667)
<223> OTHER INFORMATION: n is a, c, g, or t
<220> FEATURE:
<221> NAME/KEY: misc_feature
<222> LOCATION: (59676)..(59676)
<223> OTHER INFORMATION: n is a, c, g, or t
<220> FEATURE:
<221> NAME/KEY: misc_feature
<222> LOCATION: (59695)..(59695)
<223> OTHER INFORMATION: n is a, c, g, or t
<220> FEATURE:
<221> NAME/KEY: misc_feature
<222> LOCATION: (60082)..(60082)
<223> OTHER INFORMATION: n is a, c, g, or t
<220> FEATURE:
<221> NAME/KEY: misc_feature
<222> LOCATION: (60087)..(60087)
<223> OTHER INFORMATION: n is a, c, g, or t
<220> FEATURE:
<221> NAME/KEY: misc_feature
<222> LOCATION: (60092)..(60092)
<223> OTHER INFORMATION: n is a, c, g, or t
<220> FEATURE:
<221> NAME/KEY: misc_feature
<222> LOCATION: (60096)..(60096)
<223> OTHER INFORMATION: n is a, c, g, or t
<220> FEATURE:
<221> NAME/KEY: misc_feature
<222> LOCATION: (60108)..(60108)
<223> OTHER INFORMATION: n is a, c, g, or t
<220> FEATURE:
<221> NAME/KEY: misc_feature
<222> LOCATION: (60114)..(60114)
<223> OTHER INFORMATION: n is a, c, g, or t
<220> FEATURE:
<221> NAME/KEY: misc_feature
<222> LOCATION: (60123)..(60125)
<223> OTHER INFORMATION: n is a, c, g, or t
```

```
<220> FEATURE:
<221> NAME/KEY: misc_feature
<222> LOCATION: (60130)..(60132)
<223> OTHER INFORMATION: n is a, c, g, or t
<220> FEATURE:
<221> NAME/KEY: misc_feature
<222> LOCATION: (60141)..(60141)
<223> OTHER INFORMATION: n is a, c, g, or t
<220> FEATURE:
<221> NAME/KEY: misc_feature
<222> LOCATION: (60160)..(60160)
<223> OTHER INFORMATION: n is a, c, g, or t
<220> FEATURE:
<221> NAME/KEY: misc_feature
<222> LOCATION: (60191)..(60191)
<223> OTHER INFORMATION: n is a, c, g, or t
<220> FEATURE:
<221> NAME/KEY: misc_feature
<222> LOCATION: (60194)..(60194)
<223> OTHER INFORMATION: n is a, c, g, or t
<220> FEATURE:
<221> NAME/KEY: misc_feature
<222> LOCATION: (60200)..(60200)
<223> OTHER INFORMATION: n is a, c, g, or t
<220> FEATURE:
<221> NAME/KEY: misc_feature
<222> LOCATION: (60235)..(60235)
<223> OTHER INFORMATION: n is a, c, g, or t
<220> FEATURE:
<221> NAME/KEY: misc_feature
<222> LOCATION: (60238)..(60238)
<223> OTHER INFORMATION: n is a, c, g, or t
<220> FEATURE:
<221> NAME/KEY: misc_feature
<222> LOCATION: (60240)..(60240)
<223> OTHER INFORMATION: n is a, c, g, or t
<220> FEATURE:
<221> NAME/KEY: misc_feature
<222> LOCATION: (60243)..(60243)
<223> OTHER INFORMATION: n is a, c, g, or t
<220> FEATURE:
<221> NAME/KEY: misc_feature
<222> LOCATION: (60249)..(60249)
<223> OTHER INFORMATION: n is a, c, g, or t
<220> FEATURE:
<221> NAME/KEY: misc_feature
<222> LOCATION: (60265)..(60265)
<223> OTHER INFORMATION: n is a, c, g, or t
<220> FEATURE:
<221> NAME/KEY: misc_feature
<222> LOCATION: (60271)..(60271)
<223> OTHER INFORMATION: n is a, c, g, or t
<220> FEATURE:
<221> NAME/KEY: misc_feature
<222> LOCATION: (60275)..(60275)
<223> OTHER INFORMATION: n is a, c, g, or t
<220> FEATURE:
<221> NAME/KEY: misc_feature
<222> LOCATION: (60280)..(60280)
<223> OTHER INFORMATION: n is a, c, g, or t
<220> FEATURE:
<221> NAME/KEY: misc_feature
<222> LOCATION: (60282)..(60283)
<223> OTHER INFORMATION: n is a, c, g, or t
<220> FEATURE:
<221> NAME/KEY: misc_feature
<222> LOCATION: (60287)..(60287)
<223> OTHER INFORMATION: n is a, c, g, or t
<220> FEATURE:
<221> NAME/KEY: misc_feature
<222> LOCATION: (60298)..(60298)
<223> OTHER INFORMATION: n is a, c, g, or t
<220> FEATURE:
<221> NAME/KEY: misc_feature
<222> LOCATION: (60300)..(60300)
<223> OTHER INFORMATION: n is a, c, g, or t
<220> FEATURE:
<221> NAME/KEY: misc_feature
<222> LOCATION: (60303)..(60303)
```

```
<223> OTHER INFORMATION: n is a, c, g, or t
<220> FEATURE:
<221> NAME/KEY: misc_feature
<222> LOCATION: (60310)..(60310)
<223> OTHER INFORMATION: n is a, c, g, or t
<220> FEATURE:
<221> NAME/KEY: misc_feature
<222> LOCATION: (60318)..(60318)
<223> OTHER INFORMATION: n is a, c, g, or t
<220> FEATURE:
<221> NAME/KEY: misc_feature
<222> LOCATION: (60336)..(60336)
<223> OTHER INFORMATION: n is a, c, g, or t
<220> FEATURE:
<221> NAME/KEY: misc_feature
<222> LOCATION: (60339)..(60339)
<223> OTHER INFORMATION: n is a, c, g, or t
<220> FEATURE:
<221> NAME/KEY: misc_feature
<222> LOCATION: (60341)..(60341)
<223> OTHER INFORMATION: n is a, c, g, or t
<220> FEATURE:
<221> NAME/KEY: misc_feature
<222> LOCATION: (60345)..(60346)
<223> OTHER INFORMATION: n is a, c, g, or t
<220> FEATURE:
<221> NAME/KEY: misc_feature
<222> LOCATION: (60353)..(60354)
<223> OTHER INFORMATION: n is a, c, g, or t
<220> FEATURE:
<221> NAME/KEY: misc_feature
<222> LOCATION: (60356)..(60356)
<223> OTHER INFORMATION: n is a, c, g, or t
<220> FEATURE:
<221> NAME/KEY: misc_feature
<222> LOCATION: (60360)..(60360)
<223> OTHER INFORMATION: n is a, c, g, or t
<220> FEATURE:
<221> NAME/KEY: misc_feature
<222> LOCATION: (60363)..(60363)
<223> OTHER INFORMATION: n is a, c, g, or t
<220> FEATURE:
<221> NAME/KEY: misc_feature
<222> LOCATION: (60384)..(60384)
<223> OTHER INFORMATION: n is a, c, g, or t
<220> FEATURE:
<221> NAME/KEY: misc_feature
<222> LOCATION: (60388)..(60388)
<223> OTHER INFORMATION: n is a, c, g, or t
<220> FEATURE:
<221> NAME/KEY: misc_feature
<222> LOCATION: (60390)..(60390)
<223> OTHER INFORMATION: n is a, c, g, or t
<220> FEATURE:
<221> NAME/KEY: misc_feature
<222> LOCATION: (60393)..(60393)
<223> OTHER INFORMATION: n is a, c, g, or t
<220> FEATURE:
<221> NAME/KEY: misc_feature
<222> LOCATION: (60408)..(60411)
<223> OTHER INFORMATION: n is a, c, g, or t
<220> FEATURE:
<221> NAME/KEY: misc_feature
<222> LOCATION: (60415)..(60415)
<223> OTHER INFORMATION: n is a, c, g, or t
<220> FEATURE:
<221> NAME/KEY: misc_feature
<222> LOCATION: (60417)..(60417)
<223> OTHER INFORMATION: n is a, c, g, or t
<220> FEATURE:
<221> NAME/KEY: misc_feature
<222> LOCATION: (60427)..(60427)
<223> OTHER INFORMATION: n is a, c, g, or t
<220> FEATURE:
<221> NAME/KEY: misc_feature
<222> LOCATION: (60435)..(60435)
<223> OTHER INFORMATION: n is a, c, g, or t
<220> FEATURE:
<221> NAME/KEY: misc_feature
```

-continued

```
<222> LOCATION: (60440)..(60440)
<223> OTHER INFORMATION: n is a, c, g, or t
<220> FEATURE:
<221> NAME/KEY: misc_feature
<222> LOCATION: (60467)..(60468)
<223> OTHER INFORMATION: n is a, c, g, or t
<220> FEATURE:
<221> NAME/KEY: misc_feature
<222> LOCATION: (60475)..(60475)
<223> OTHER INFORMATION: n is a, c, g, or t
<220> FEATURE:
<221> NAME/KEY: misc_feature
<222> LOCATION: (60477)..(60477)
<223> OTHER INFORMATION: n is a, c, g, or t
<220> FEATURE:
<221> NAME/KEY: misc_feature
<222> LOCATION: (60484)..(60484)
<223> OTHER INFORMATION: n is a, c, g, or t
<220> FEATURE:
<221> NAME/KEY: misc_feature
<222> LOCATION: (60489)..(60489)
<223> OTHER INFORMATION: n is a, c, g, or t
<220> FEATURE:
<221> NAME/KEY: misc_feature
<222> LOCATION: (60502)..(60502)
<223> OTHER INFORMATION: n is a, c, g, or t
<220> FEATURE:
<221> NAME/KEY: misc_feature
<222> LOCATION: (60518)..(60518)
<223> OTHER INFORMATION: n is a, c, g, or t
<220> FEATURE:
<221> NAME/KEY: misc_feature
<222> LOCATION: (60524)..(60525)
<223> OTHER INFORMATION: n is a, c, g, or t
<220> FEATURE:
<221> NAME/KEY: misc_feature
<222> LOCATION: (60527)..(60527)
<223> OTHER INFORMATION: n is a, c, g, or t
<220> FEATURE:
<221> NAME/KEY: misc_feature
<222> LOCATION: (60529)..(60529)
<223> OTHER INFORMATION: n is a, c, g, or t
<220> FEATURE:
<221> NAME/KEY: misc_feature
<222> LOCATION: (60531)..(60531)
<223> OTHER INFORMATION: n is a, c, g, or t
<220> FEATURE:
<221> NAME/KEY: misc_feature
<222> LOCATION: (60540)..(60540)
<223> OTHER INFORMATION: n is a, c, g, or t
<220> FEATURE:
<221> NAME/KEY: misc_feature
<222> LOCATION: (60550)..(60550)
<223> OTHER INFORMATION: n is a, c, g, or t
<220> FEATURE:
<221> NAME/KEY: misc_feature
<222> LOCATION: (60555)..(60555)
<223> OTHER INFORMATION: n is a, c, g, or t
<220> FEATURE:
<221> NAME/KEY: misc_feature
<222> LOCATION: (60560)..(60560)
<223> OTHER INFORMATION: n is a, c, g, or t
<220> FEATURE:
<221> NAME/KEY: misc_feature
<222> LOCATION: (60564)..(60564)
<223> OTHER INFORMATION: n is a, c, g, or t
<220> FEATURE:
<221> NAME/KEY: misc_feature
<222> LOCATION: (60576)..(60576)
<223> OTHER INFORMATION: n is a, c, g, or t
<220> FEATURE:
<221> NAME/KEY: misc_feature
<222> LOCATION: (60582)..(60582)
<223> OTHER INFORMATION: n is a, c, g, or t
<220> FEATURE:
<221> NAME/KEY: misc_feature
<222> LOCATION: (60591)..(60593)
<223> OTHER INFORMATION: n is a, c, g, or t
<220> FEATURE:
```

-continued

```
<221> NAME/KEY: misc_feature
<222> LOCATION: (60598)..(60600)
<223> OTHER INFORMATION: n is a, c, g, or t
<220> FEATURE:
<221> NAME/KEY: misc_feature
<222> LOCATION: (60609)..(60609)
<223> OTHER INFORMATION: n is a, c, g, or t
<220> FEATURE:
<221> NAME/KEY: misc_feature
<222> LOCATION: (60628)..(60628)
<223> OTHER INFORMATION: n is a, c, g, or t
<220> FEATURE:
<221> NAME/KEY: misc_feature
<222> LOCATION: (61018)..(61018)
<223> OTHER INFORMATION: n is a, c, g, or t
<220> FEATURE:
<221> NAME/KEY: misc_feature
<222> LOCATION: (61023)..(61023)
<223> OTHER INFORMATION: n is a, c, g, or t
<220> FEATURE:
<221> NAME/KEY: misc_feature
<222> LOCATION: (61028)..(61028)
<223> OTHER INFORMATION: n is a, c, g, or t
<220> FEATURE:
<221> NAME/KEY: misc_feature
<222> LOCATION: (61032)..(61032)
<223> OTHER INFORMATION: n is a, c, g, or t
<220> FEATURE:
<221> NAME/KEY: misc_feature
<222> LOCATION: (61044)..(61044)
<223> OTHER INFORMATION: n is a, c, g, or t
<220> FEATURE:
<221> NAME/KEY: misc_feature
<222> LOCATION: (61050)..(61050)
<223> OTHER INFORMATION: n is a, c, g, or t
<220> FEATURE:
<221> NAME/KEY: misc_feature
<222> LOCATION: (61059)..(61061)
<223> OTHER INFORMATION: n is a, c, g, or t
<220> FEATURE:
<221> NAME/KEY: misc_feature
<222> LOCATION: (61066)..(61068)
<223> OTHER INFORMATION: n is a, c, g, or t
<220> FEATURE:
<221> NAME/KEY: misc_feature
<222> LOCATION: (61077)..(61077)
<223> OTHER INFORMATION: n is a, c, g, or t
<220> FEATURE:
<221> NAME/KEY: misc_feature
<222> LOCATION: (61096)..(61096)
<223> OTHER INFORMATION: n is a, c, g, or t
<220> FEATURE:
<221> NAME/KEY: misc_feature
<222> LOCATION: (61127)..(61127)
<223> OTHER INFORMATION: n is a, c, g, or t
<220> FEATURE:
<221> NAME/KEY: misc_feature
<222> LOCATION: (61130)..(61130)
<223> OTHER INFORMATION: n is a, c, g, or t
<220> FEATURE:
<221> NAME/KEY: misc_feature
<222> LOCATION: (61136)..(61136)
<223> OTHER INFORMATION: n is a, c, g, or t
<220> FEATURE:
<221> NAME/KEY: misc_feature
<222> LOCATION: (61171)..(61171)
<223> OTHER INFORMATION: n is a, c, g, or t
<220> FEATURE:
<221> NAME/KEY: misc_feature
<222> LOCATION: (61174)..(61174)
<223> OTHER INFORMATION: n is a, c, g, or t
<220> FEATURE:
<221> NAME/KEY: misc_feature
<222> LOCATION: (61176)..(61176)
<223> OTHER INFORMATION: n is a, c, g, or t
<220> FEATURE:
<221> NAME/KEY: misc_feature
<222> LOCATION: (61179)..(61179)
<223> OTHER INFORMATION: n is a, c, g, or t
```

-continued

```
<220> FEATURE:
<221> NAME/KEY: misc_feature
<222> LOCATION: (61185)..(61185)
<223> OTHER INFORMATION: n is a, c, g, or t
<220> FEATURE:
<221> NAME/KEY: misc_feature
<222> LOCATION: (61201)..(61201)
<223> OTHER INFORMATION: n is a, c, g, or t
<220> FEATURE:
<221> NAME/KEY: misc_feature
<222> LOCATION: (61207)..(61207)
<223> OTHER INFORMATION: n is a, c, g, or t
<220> FEATURE:
<221> NAME/KEY: misc_feature
<222> LOCATION: (61211)..(61211)
<223> OTHER INFORMATION: n is a, c, g, or t
<220> FEATURE:
<221> NAME/KEY: misc_feature
<222> LOCATION: (62620)..(62620)
<223> OTHER INFORMATION: n is a, c, g, or t
<220> FEATURE:
<221> NAME/KEY: misc_feature
<222> LOCATION: (62622)..(62623)
<223> OTHER INFORMATION: n is a, c, g, or t
<220> FEATURE:
<221> NAME/KEY: misc_feature
<222> LOCATION: (62627)..(62627)
<223> OTHER INFORMATION: n is a, c, g, or t
<220> FEATURE:
<221> NAME/KEY: misc_feature
<222> LOCATION: (62638)..(62638)
<223> OTHER INFORMATION: n is a, c, g, or t
<220> FEATURE:
<221> NAME/KEY: misc_feature
<222> LOCATION: (62640)..(62640)
<223> OTHER INFORMATION: n is a, c, g, or t
<220> FEATURE:
<221> NAME/KEY: misc_feature
<222> LOCATION: (62643)..(62643)
<223> OTHER INFORMATION: n is a, c, g, or t
<220> FEATURE:
<221> NAME/KEY: misc_feature
<222> LOCATION: (62650)..(62650)
<223> OTHER INFORMATION: n is a, c, g, or t
<220> FEATURE:
<221> NAME/KEY: misc_feature
<222> LOCATION: (62658)..(62658)
<223> OTHER INFORMATION: n is a, c, g, or t
<220> FEATURE:
<221> NAME/KEY: misc_feature
<222> LOCATION: (62676)..(62676)
<223> OTHER INFORMATION: n is a, c, g, or t
<220> FEATURE:
<221> NAME/KEY: misc_feature
<222> LOCATION: (62679)..(62679)
<223> OTHER INFORMATION: n is a, c, g, or t
<220> FEATURE:
<221> NAME/KEY: misc_feature
<222> LOCATION: (62681)..(62681)
<223> OTHER INFORMATION: n is a, c, g, or t
<220> FEATURE:
<221> NAME/KEY: misc_feature
<222> LOCATION: (62685)..(62686)
<223> OTHER INFORMATION: n is a, c, g, or t
<220> FEATURE:
<221> NAME/KEY: misc_feature
<222> LOCATION: (62693)..(62694)
<223> OTHER INFORMATION: n is a, c, g, or t
<220> FEATURE:
<221> NAME/KEY: misc_feature
<222> LOCATION: (62696)..(62696)
<223> OTHER INFORMATION: n is a, c, g, or t
<220> FEATURE:
<221> NAME/KEY: misc_feature
<222> LOCATION: (62700)..(62700)
<223> OTHER INFORMATION: n is a, c, g, or t
<220> FEATURE:
<221> NAME/KEY: misc_feature
<222> LOCATION: (62703)..(62703)
```

<223> OTHER INFORMATION: n is a, c, g, or t
<220> FEATURE:
<221> NAME/KEY: misc_feature
<222> LOCATION: (62724)..(62724)
<223> OTHER INFORMATION: n is a, c, g, or t

<400> SEQUENCE: 4

```
aagcgttgca caattccccc aacctccata catacggcag ctcttctaga cacaggtttt      60
cccaggtcaa atgcggggac cccagccata tctcccaccc tgagaaattt tggagtttca     120
gggagctcag aagctctgca gaggccaccc tctctgaggg gattcttctt agacctccat     180
ccagaggcaa atgttgacct gtccatgctg aaaccctcag gccttcctgg gtcatcttct     240
cccacccgct ccttgatgac agggagcagg agcactaaag ccacaccaga aatggattca     300
ggactgacag gagccacctt gtcacctaag acatctacag gtgcaatcgt ggtgacagaa     360
catactctgc cctttacttc cccagataag accttggcca gtcctacatc ttcggttgtg     420
ggaagaacca cccagtcttt gggggtgatg tcctctgctc tccctgagtc aacctctaga     480
ggaatgacac actccgagca aagaaccagc ccatcgctga gtcccaggt caatggaact     540
ccctctagga actaccctgc tacaagcatg gtttcaggat tgagttcccc aaggaccagg     600
accagttcca cagaaggaaa ttttaccaaa gaagcatcta catacacact cactgtagag     660
accacaagtg gcccagtcac tgagaagtac acagtcccca ctgagacctc aacaactgaa     720
ggtgacagca cagagacccc ctgggacaca agatatattc ctgtaaaaat cacatctcca     780
atgaaaacat ttgcagattc aactgcatcc aaggaaaatg ccccagtgtc tatgactcca     840
gctgagacca cagttactga ctcacatact ccaggaagga caaacccatc atttgggaca     900
ctttattctt ccttccttga cctatcacct aaagggaccc caaattccag aggtgaaaca     960
agcctggaac tgattctatc aaccactgga tatcccttct cctctcctga acctggctct    1020
gcaggacaca gcagaataag taccagtgcg cctttgtcat catctgcttc agttctcgat    1080
aataaaatat cagagaccag catattctca ggccagagtc tcacctcccc tctgtctcct    1140
ggggtgcccg aggccagagc cagcacaatg cccaactcag ctatcccttt ttccatgaca    1200
ctaagcaatg cagaaacaag tgccgaaagg gtcagaagca caatttcctc tctgggact    1260
ccatcaatat ccacaaagca gacagcagag actatcctta ccttccatgc cttcgctgag    1320
accatggata tacccagcac ccacatagcc aagactttgg cttcagaatg gttgggaagt    1380
ccaggtaccc ttggtggcac cagcacttca gcgctgacaa ccacatctcc atctaccact    1440
ttagtctcag aggagaccaa cacccatcac tccacgagtg gaaaggaaac agaaggaact    1500
ttgaatacat ctatgactcc acttgagacc tctgctcctg gagaagagtc cgaaatgact    1560
gccaccttgg tccccactct aggttttaca actcttgaca gcaagatcag aagtccatct    1620
caggtctctt catcccaccc aacaagagag ctcagaacca caggcagcac ctctgggagg    1680
cagagttcca gcacagctgc ccacgggagc tctgacatcc tgagggcaac cacttccagc    1740
acctcaaaag catcatcatg gaccagtgaa agcacagctc agcaatttag tgaacccag    1800
cacacacagt gggtggagac aagtcctagc atgaaaacag agagaccccc agcatcaacc    1860
agtgtggcag cccctatcac cacttctgtt ccctcagtgg tctctggctt caccaccctg    1920
aagaccagct ccacaaaagg gatttggctt gaagaaacat ctgcagacac actcatcgga    1980
gaatccacag ctggcccaac cacccatcag tttgctgttc ccactgggat ttcaatgaca    2040
ggaggcagca gcaccagggg aagccagggc acaacccacc tactcaccag agccacagca    2100
tcatctgaga catccgcaga tttgactctg gccacgaacg gtgtcccagt ctccgtgtct    2160
```

```
ccagcagtga gcaagacggc tgctggctca agtcctccag gagggacaaa gccatcatat    2220
acaatggttt cttctgtcat ccctgagaca tcatctctac agtcctcagc tttcagggaa    2280
ggaaccagcc tgggactgac tccattaaac actagacatc ccttctcttc ccctgaacca    2340
gactctgcag gacacaccaa gataagcacc agcattcctc tgttgtcatc tgcttcagtt    2400
cttgaggata aagtgtcagc gaccagcaca ttctcacacc acaaagccac ctcatctatt    2460
accacaggga ctcctgaaat ctcaacaaag acaaagccca gctcagccgt tctttcctcc    2520
atgaccctaa gcaatgcagc aacaagtcct gaaagagtca gaaatgcaac ttcccctctg    2580
actcatccat ctccatcagg ggaagagaca gcagggagtg tcctcactct cagcacctct    2640
gctgagacta cagactcacc taacatccac ccaactggga cactgacttc agaatcgtca    2700
gagagtccta gcactctcag cctcccaagt gtctctggag tcaaaaccac attttcttca    2760
tctactcctt ccactcatct atttactagt ggagaagaaa cagaggaaac ttcgaatcca    2820
tctgtgtctc aacctgagac ttctgtttcc agagtaagga ccaccttggc cagcacctct    2880
gtccctaccc cagtattccc caccatggac acctggccta cacgttcagc tcagttctct    2940
tcatcccacc tagtgagtga gctcagagct acgagcagta cctcagttac aaactcaact    3000
ggttcagctc ttcctaaaat atctcacctc actgggacgg caacaatgtc acagaccaat    3060
agagacacgt taatgactc tgctgcaccc caaagcacaa cttggccaga gactagtccc    3120
agattcaaga cagggttacc ttcagcaaca accactgttt caacctctgc cacttctctc    3180
tctgctactg taatggtctc taaattcact tctccagcaa ctagttccat ggaagcaact    3240
tctatcaggg aaccatcaac aaccatcctc acaacagaga ccacgaatgg cccaggctct    3300
atggctgtgg cttctaccaa catcccaatt ggaaagggct acattactga aggaagattg    3360
gacacaagcc atctgcccat tggaaccaca gcttcctctg agacatctat ggatttttacc    3420 atggccaaag aaagtgtctc aatgtcagta tctccatctc agtccatgga tgctgctggc    3480
tcaagcactc caggaaggac aagccaattc gttgacacat tttctgatga tgtctatcat    3540
ttaacatcca gagaaattac aatacctaga gatggaacaa gctcagctct gactccacaa    3600
atgactgcaa ctcacccctcc atctcctgat cctggctctg ctagaagcac ctggcttggc    3660
atcttgtcct catctccttc ttctcctact cccaaagtca caatgagctc cacatttttca    3720 actcagagag tcaccacaag catgataatg gacacagttg aaactagtcg gtggaacatg    3780
cccaacttac cttccacgac ttccctgaca ccaagtaata ttccaacaag tggtgccata    3840
ggaaaaagca ccctggttcc cttggacact ccatctccag ccacatcatt ggaggcatca    3900 gaaggggggac ttccaaccct cagcacctac cctgaatcaa caaacacacc cagcatccac    3960
ctcggagcac acgctagttc agaaagtcca agcaccatca aacttaccat ggcttcagta    4020
gtaaaacctg gctcttacac acctctcacc ttccctcaa tagagaccca cattcatgta    4080
tcaacagcca gaatggctta ctcttctggg tcttcacctg agatgacagc tcctggagag    4140
actaacactg gtagtacctg ggaccccacc acctacatca ccactacgga tcctaaggat    4200
acaagttcag ctcaggtctc tacacccca tcagtgagga cactcagaac cacagaaaac    4260
catccaaaga cagagtccgc caccccagct gcttactctg gaagtcctaa atctcaagt    4320 tcacccaatc tcaccagtcc ggccacaaaa gcatggacca tcacagacac aactgaacac    4380
tccactcaat tacattacac aaaattggca gaaaaatcat ctggatttga gacacagtca    4440
gctccaggac ctgtctctgt agtaatccct acctccccta ccattggaag cagcacattg    4500
```

```
gaactaactt ctgatgtccc aggggaaccc ctggtccttg ctcccagtga gcagaccaca   4560
atcactctcc ccatggcaac atggctgagt accagtttga cagaggaaat ggcttcaaca   4620
gaccttgata tttcaagtcc aagttcaccc atgagtacat ttgctatttt tccacctatg   4680
tccacacctt ctcatgaact ttcaaagtca gaggcagata ccagtgccat tagaaataca   4740
gattcaacaa cgttggatca gcacctagga atcaggagtt tgggcagaac tggggactta   4800
acaactgttc ctatcacccc actgacaacc acgtggacca gtgtgattga acactcaaca   4860
caagcacagg acacccttc tgcaacgatg agtcctactc acgtgacaca gtcactcaaa    4920
gatcaaacat ctataccagc ctcagcatcc ccttcccatc ttactgaagt ctaccctgag   4980
ctcgggacac aagggagaag ctcctctgag gcaaccactt tttggaaacc atctacagac   5040
acactgtcca gagagattga gactggccca caaacattc aatccactcc acccatggac    5100
aacacaacaa cagggagcag tagtagtgga gtcaccctgg gcatagccca ccttcccata   5160
ggaacatcct ccccagctga gacatccaca aacatggcac tggaaagaag aagttctaca   5220
gccactgtct ctatggctgg gacaatggga ctccttgtta ctagtgctcc aggaagaagc   5280
atcagccagt cattaggaag agtttcctct gtcctttctg agtcaactac tgaaggagtc   5340
acagattcta gtaagggaag cagcccaagg ctgaacacac agggaaatac agctctctcc   5400
tcctctcttg aacccagcta tgctgaagga agccagatga gcacaagcat ccctctaacc   5460
tcatctccta caactcctga tgtggaattc atagggggca gcacattttg gaccaaggag   5520
gtcaccacag ttatgacctc agacatctcc aagtcttcag caaggacaga gtccagctca   5580 gctacccta tgtccacagc tttgggaagc actgaaaata caggaaaaga aaaactcaga    5640
actgcctcta tggatcttcc atctccaact ccatcaatgg aggtgacacc atggatttct   5700
ctcactctca gtaatgcccc caataccaca gattcacttg acctcagcca tggggtgcac   5760
accagctctg cagggacttt ggccactgac aggtcattga atactggtgt cactagagcc   5820
tccagattgg aaaacggctc tgatacctct tctaagtccc tgtctatggg aaacagcact   5880
cacacttcca tgactgacac agagaagagt gaagtgtctt cttcaatcca tccccgacct   5940
gagacctcag ctcctggagc agagaccact ttgacttcca ctcctggaaa cagggccata   6000
agcttaacat tgccttttc atccattcca gtggaagaag tcatttctac aggcataacc    6060
tcaggaccag acatcaactc agcacccatg acacattctc ccatcacccc accaacaatt   6120
gtatggacca gtacaggcac aattgaacag tccactcaac cactacatgc agtttcttca   6180
gaaaaagttt ctgtgcagac acagtcaact ccatatgtca actctgtggc agtgtctgct   6240 tccccctaccc atgagaattc agtctcttct ggaagcagca catcctctcc atattcctca  6300
gcctcacttg aatccttgga ttccacaatc agtaggagga atgcaatcac ttcctggcta   6360
tgggacctca ctacatctct ccccactaca acttggccaa gtactagttt atctgaggca   6420
ctgtcctcag gccattctgg ggtttcaaac ccaagttcaa ctacgactga atttccactc   6480
ttttcagctg catccacatc tgctgctaag caaagaaatc cagaaacaga gacccatggt   6540
ccccagaata cagccgcgag tactttgaac actgatgcat cctcggtcac aggtctttct   6600
gagactcctg tggggcaag tatcagctct gaagtccctc ttccaatggc cataacttct    6660
agatcagatg tttctggcct tacatctgag agtactgcta acccgagttt aggcacagcc   6720
tcttcagcag ggaccaaatt aactaggaca atatccctgc ccacttcaga gtctttggtt   6780 tccttttagaa tgaacaagga tccatggaca gtgtcaatcc ctttggggtc ccatccaact  6840
actaatacag aaacaagcat cccagtaaac agcgcaggtc cacctggctt gtccacagta   6900
```

```
gcatcagatg taattgacac accttcagat ggggctgaga gtattcccac tgtctccttt    6960 tcccccctccc ctgatactga agtgacaact atctcacatt tcccagaaaa gacaactcat   7020
tcatttagaa ccatttcatc tctcactcat gagttgactt caagagtgac acctattcct    7080
ggggattgga tgagttcagc tatgtctaca aagcccacag gagccagtcc ctccattaca    7140
ctgggagaga gaaggacaat cacctctgct gctccaacca cttcccccat agttctcact    7200
gctagtttca cagagaccag cacagtttca ctggataatg aaactacagt aaaaacctca    7260
gatatccttg acgcacggaa aacaaatgag ctcccctcag atagcagttc ttcttctgat    7320
ctgatcaaca cctccatagc ttcttcaact atggatgtca ctaaaacagc ctccatcagt    7380
cccactagca tctcaggaat gacagcaagt tcctccccat ctctcttctc ttcagataga    7440
ccccaggttc ccacatctac aacagagaca aatacagcca cctctccatc tgtttccagt    7500
aacacctatt ctcttgatgg gggctccaat gtgggtggca ctccatccac tttaccaccc    7560
tttacaatca cccaccctgt cgagacaagc tcggccctat tagcctggtc tagaccagta    7620
agaactttca gcaccatggt cagcactgac actgcctccg gagaaaatcc tacctctagc    7680
aattctgtgg tgacttctgt tccagcacca ggtacatggg ccagtgtagg cagtactact    7740
gacttacctg ccatgggctt tctcaagaca agtcctgcag gagaggcaca ctcacttcta    7800
gcatcaacta ttgaaccagc cactgccttc actccccatc tctcagcagc agtggtcact    7860
ggatccagtg ctacatcaga agccagtctt ctcactacga gtgaaagcaa agccattcat    7920
tcttcaccac agaccccaac tacacccacc tctggagcaa actgggaaac ttcagctact    7980
cctgagagcc ttttggtagt cactgagact tcagacacaa cacttacctc aaagattttg    8040
gtcacagata ccatcttgtt ttcaactgtg tccacgccac cttctaaatt tccaagtacg    8100
gggactctgt ctggagcttc cttccctact ttactcccgg acactccagc catccctctc    8160
actgccactg agccaacaag ttcattagct acatcctttg attccacccc actggtgact    8220
atagcttcgg atagtcttgg cacagtccca gagactaccc tgaccatgtc agagacctca    8280
aatggtgatg cactggttct taagacagta agtaacccag ataggagcat ccctggaatc    8340
actatccaag gagtaacaga aagtccactc catccttctt ccacttcccc ctctaagatt    8400
gttgctccac ggaatacaac ctatgaaggt tcgatcacag tggcactttc tactttgcct    8460
gcgggaacta ctggttccct tgtattcagt cagagttctg aaaactcaga gacaacggct    8520
ttggtagact catcagctgg gcttgagagg gcatctgtga tgccactaac cacaggaagc    8580
cagggtatgg ctagctctgg aggaatcaga agtgggtcca ctcactcaac tggaaccaaa    8640 acatttttctt ctctccctct gaccatgaac ccaggtgagg ttacagccat gtctgaaatc    8700
accacgaaca gactgacagc tactcaatca acagcaccca aagggatacc tgtgaagccc    8760
accagtgctg agtcaggcct cctaacacct gtctctgcct cctcaagccc atcaaaggcc    8820
tttgcctcac tgactacagc tcccccatca acttggggga tccacagtc taccttgaca    8880 tttgagtttt ctgaggtccc aagtttggat actaagtccg cttctttacc aactcctgga    8940
cagtccctga acaccattcc agactcagat gcaagcacag catcttcctc actgtccaag    9000
tctccagaaa aaaacccaag ggcaaggatg atgacttcca caaaggccat aagtgcaagc    9060
tcatttcaat caacaggttt tactgaaacc cctgagggat ctgcctcccc ttctatggca    9120
gggcatgaac ccagagtccc cacttcagga acagggacc ctagatatgc ctcagagagc    9180
atgtcttatc cagacccaag caaggcatca tcagctatga catcgacctc tcttgcatca    9240
```

```
aaactcacaa ctctcttcag cacaggtcaa gcagcaaggt ctggttctag ttcctctccc    9300
ataagcctat ccactgagaa agaaacaagc ttcctttccc ccactgcatc cacctccaga    9360
aagacttcac tatttcttgg gccttccatg gcaaggcagc ccaacatatt ggtgcatctt    9420
cagacttcag ctctgacact ttctccaaca tccactctaa atatgtccca ggaggagcct    9480
cctgagttaa cctcaagcca gaccattgca gaagaagagg gaacaacagc tgaaacacag    9540
acgttaacct tcacaccatc tgagacccca acatccttgt tacctgtctc ttctcccaca    9600
gaacccacag ccagaagaaa gagttctcca gaaacatggg caagctctat ttcagttcct    9660
gccaagacct ccttggttga aacaactgat ggaacgctag tgaccaccat aaagatgtca    9720
agccaggcag cacaaggaaa ttccacgtgg cctgccccag cagaggagac ggggaccagt    9780
ccagcaggca catccccagg aagcccagaa gtgtctacca ctctcaaaat catgagctcc    9840
aaggaaccca gcatcagccc agagatcagg tccactgtgc gaaattctcc ttggaagact    9900
ccagaaacaa ctgttcccat ggagaccaca gtggaaccag tcacccttca gtccacagcc    9960
ctaggaagtg gcagcaccag catctctcac ctgcccacag gaaccacatc accaaccaag   10020
tcaccaacag aaaatatgtt ggctacagaa agggtctccc tctccccatc cccacctgag   10080
gcttggacca acctttattc tggaactcca ggagggacca ggcagtcact ggccacaatg   10140
tcctctgtct ccctagagtc accaactgct agaagcatca cagggactgg tcagcaaagc   10200
agtccagaac tggtttcaaa gacaactgga atggaattct ctatgtggca tggctctact   10260
ggagggacca caggggacac acatgtctct ctgagcacat cttccaatat ccttgaagac   10320
cctgtaacca gcccaaactc tgtgagctca ttgacagata aatccaaaca taaaaccgag   10380
acatgggtaa gcaccacagc cattccctcc actgtcctga ataataagat aatggcagct   10440
gaacaacaga caagtcgatc tgtggatgag gcttattcat caactagttc ttggtcagat   10500
cagacatctg ggagtgacat cacccttggt gcatctcctg atgtcacaaa cacattatac   10560
atcacctcca cagcacaaac cacctcacta gtgtctctgc cctctggaga ccaaggcatt   10620
acaagcctca ccaatccctc aggaggaaaa acaagctctg cgtcatctgt cacatctcct   10680
tcaatagggc ttgagactct gagggccaat gtaagtgcag tgaaaagtga cattgccccc   10740
actgctgggc atctatctca gacttcatct cctgcggaag tgagcatcct ggacgtaacc   10800
acagctccta ctccaggtat ctccaccacc atcaccacca tgggaaccaa ctcaatctca   10860
actaccacac ccaacccaga agtgggtatg agtaccatgg acagcaccccc ggccacagag   10920
aggcgcacaa cttctacaga acaccctttc acctggtctt ccacagctgc atcagattcc   10980
tggactgtca cagacatgac ttcaaacttg aaagttgcaa gatctcctgg aacaatttcc   11040
acaatgcata caacttcatt cttagcctca agcactgaat tagactccat gtctactccc   11100
catggccgta taactgtcat tggaaccagc ctggtcactc catcctctga tgcttcagct   11160
gtaaagacag agaccagtac aagtgaaaga acattgagtc cttcagacac aactgcatct   11220
actcccatct caacttttttc tcgtgtccag aggatgagca tctcagttcc tgacatttta   11280
agtacaagtt ggactcccag tagtacagaa gcagaagatg tgcctgtttc aatggtttct   11340
acagatcatg ctagtacaaa gactgaccca aatacgcccc tgtccacttt tctgtttgat   11400
tctctgtcca ctcttgactg ggacactggg agatctctgt catcagccac agccactacc   11460
tcagctcctc agggggccac aactcccag gaactcactt tggaaaccat gatcagccca   11520
gctacctcac agttgccctt ctctataggg cacattacaa gtgcagtcac accagctgca   11580
atggcaagga gctctggagt tacttttttca agaccagatc ccacaagcaa aaaggcagag   11640
```

```
cagacttcca ctcagcttcc caccaccact tctgcacatc cagggcaggt gcccagatca   11700
gcagcaacaa ctctggatgt gatcccacac acagcaaaaa ctccagatgc aacttttcag   11760
agacaagggc agacagctct tacaacagag gcaagagcta catctgactc ctggaatgag   11820
aaagaaaaat caaccccaag tgcaccttgg atcactgaga tgatgaattc tgtctcagaa   11880
gataccatca aggaggttac cagctcctcc agtgtattaa aggaccctga atacgctgga   11940
cataaacttg gaatctggga cgacttcatc cccaagtttg gaaaagcagc ccatatgaga   12000
gagttgcccc ttctgagtcc accacaggac aaagaggcaa ttcacccttc tacaaacaca   12060
gtagagacca caggctgggt cacaagttcc gaacatgctt ctcattccac tatcccagcc   12120
cactcagcgt catccaaact cacatctcca gtggttacaa cctccaccag ggaacaagca   12180
atagtttcta tgtcaacaac cacatggcca gagtctacaa gggctagaac agagcctaat   12240
tccttcttga ctattgaact gagggacgtc agcccttaca tggacaccag ctcaaccaca   12300
caaacaagta ttatctcttc cccaggttcc actgcgatca ccaaggggcc tagaacagaa   12360
attacctcct ctaagagaat atccagctca ttccttgccc agtctatgag gtcgtcagac   12420
agcccctcag aagccatcac caggctgtct aactttcctg ccatgacaga atctggagga   12480
atgatccttg ctatgcaaac aagtccacct ggcgctacat cactaagtgc acctactttg   12540
gatacatcag ccacagcctc ctggacaggg actccactgg ctacgactca gagatttaca   12600
tactcagaga agaccactct ctttagcaaa ggtcctgagg atacatcaca gccaagccct   12660
ccctctgtgg aagaaaccag ctcttcctct tccctggtac ctatccatgc tacaacctcg   12720
ccttccaata ttttgttgac atcacaaggg cacagtccct cctctactcc acctgtgacc   12780
tcagttttct tgtctgagac ctctggcctg gggaagacca cagacatgtc gaggataagc   12840
ttggaacctg gcacaagttt acctcccaat ttgagcagta cagcaggtga ggcgttatcc   12900
acttatgaag cctccagaga tacaaaggca attcatcatt ctgcagacac agcagtgacg   12960
aatatggagg caaccagttc tgaatattct cctatcccag gccatacaaa gccatccaaa   13020
gccacatctc cattggttac ctcccacatc atgggggaca tcacttcttc cacatcagta   13080
tttggctcct ccgagaccac agagattgag acagtgtcct ctgtgaacca gggacttcag   13140
gagagaagca catcccaggt ggccagctct gctacagaga caagcactgt cattacccat   13200
gtgtctagtg gtgatgctac tactcatgtc accaagacac aagccacttt ctctagcgga   13260
acatccatct caagccctca tcagtttata acttctacca acacatttac agatgtgagc   13320 accaaccct ccacctctct gataatgaca gaatcttcag gagtgaccat caccacccaa   13380
acaggtccta ctggagctgc aacacagggt ccatatctct tggacacatc aaccatgcct   13440
tacttgacag agactccatt agctgtgact ccagatttta tgcaatcaga gaagaccact   13500
ctcataagca aggtcccaa ggatgtgacc tggacaagcc ctccctctgt ggcagaaacc   13560
agctatccct cttccctgac acctttcttg gtcacaacca tacctcctgc cacttccacg   13620
ttacaagggc aacatacatc ctctcctgtt tctgcgactt cagttcttac ctctggactg   13680
gtgaagacca cagatatgtt gaacacaagc atggaacctg tgaccaattc acctcaaaat   13740
ttgaacaatc catcaaatga gatactggcc actttggcag ccaccacaga tatagagact   13800
attcatcctt ccataaacaa agcagtgacc aatatgggga ctgccagttc agcacatgta   13860
ctgcattcca ctctcccagt cagctcagaa ccatctacag ccacatctcc aatggttcct   13920
gcctccagca tgggggacgc tcttgcttct atatcaatac ctggttctga gaccacagac   13980
```

```
attgagggag agccaacatc ctccctgact gctggacgaa aagagaacag caccctccag    14040
gagatgaact caactacaga gtcaaacatc atcctctcca atgtgtctgt gggggctatt    14100
actgaagcca caaaaatgga agtcccctct tttgatgcaa cattcatacc aactcctgct    14160
cagtcaacaa agttcccaga tattttctca gtagccagca gtagactttc aaactctcct    14220
cccatgacaa tatctaccca catgaccacc acccagacag ggtcttctgg agctacatca    14280
aagattccac ttgccttaga cacatcaacc ttggaaacct cagcagggac tccatcagtg    14340
gtgactgagg ggtttgccca ctcaaaaata accactgcaa tgaacaatga tgtcaaggac    14400
gtgtcacaga caaaccctcc ctttcaggat gaagccagct ctccctcttc tcaagcacct    14460
gtccttgtca caaccttacc ttcttctgtt gctttcacac cgcaatggca cagtacctcc    14520
tctcctgttt ctatgtcctc agttcttact tcttcactgg taaagaccgc aggcaaggtg    14580
gatacaagct tagaaacagt gaccagttca cctcaaagta tgagcaacac tttggatgac    14640
atatcggtca cttcagcagc caccacagat atagagacaa cgcatccttc cataaacaca    14700
gtagttacca atgtggggac caccggttca gcatttgaat cacattctac tgtctcagct    14760
tacccagagc catctaaagt cacatctcca aatgttacca cctccaccat ggaagacacc    14820
acaatttccc gatcaatacc taaatcctct aagactacaa gaactgagac tgagacaact    14880
tcctccctga ctcctaaact gagggagacc agcatctccc aggagatcac ctcgtccaca    14940
gagacaagca ctgttcctta caaagagctc actggtgcca ctaccgaggt atccaggaca    15000
gatgtcactt cctctagcag tacatccttc cctggccctg atcagtccac agtgtcacta    15060
gacatctcca cagaaaccaa caccaggctg tctacctccc caataatgac agaatctgca    15120
gaaataacca tcaccaccca aacaggtcct catggggcta catcacagga tacttttacc    15180
atggacccat caaatacaac cccccaggca gggatccact cagctatgac tcatggattt    15240
tcacaattgg atgtgaccac tcttatgagc agaattccac aggatgtatc atggacaagt    15300 cctcccctctg tggataaaac cagctccccc tcttcctttc tgtcctcacc tgcaatgacc    15360
acaccttccc tgatttcttc taccttacca gaggataagc tctcctctcc tatgacttca    15420
cttctcacct ctggcctagt gaagattaca gacatattac gtacacgctt ggaacctgtg    15480
accagctcac ttccaaattt cagcagcacc tcagataaga tactggccac ttctaaagac    15540
agtaaagaca caaggaaat ttttccttct ataaacacag aagagaccaa tgtgaaagcc    15600
aacaactctg gacatgaatc ccattcccct gcactggctg actcagagac acccaaagcc    15660
acaactcaaa tggttatcac caccactgtg ggagatccag ctccttccac atcaatgcca    15720
gtgcatggtt cctctgagac tacaaacatt aagagagagc caacatattt cttgactcct    15780
agactgagag agaccagtac ctctcaggag tccagctttc ccacgacac aagttttcta    15840 cttttccaaag tccccactgg tactattact gaggtctcca gtacagggt caactcttct    15900 agcaaaattt ccaccccaga ccatgataag tccacagtgc cacctgacac cttcacagga    15960
gagatcccca gggtcttcac ctcctctatt aagacaaaat ctgcagaaat gacgatcacc    16020
acccaagcaa gtcctcctga gtctgcatcg cacagtaccc ttcccttgga cacatcaacc    16080
acactttccc agggagggac tcattcaact gtgactcagg gattcccata ctcagaggtg    16140
accactctca tgggcatggg tcctgggaat gtgtcatgga tgacaactcc ccctgtggaa    16200
gaaaccagct ctgtgtcttc cctgatgtct tcacctgcca tgcatcccc ttctcctgtt    16260 tcctccacat caccacagag catccctcc tctcctcttc ctgtgactgc acttcctact    16320
tctgttctgg tgacaaccac agatgtgttg ggcacaacaa gcccagagtc tgtaaccagt    16380
```

```
tcacctccaa atttgagcag catcactcat gagagaccgg ccacttacaa agacactgca   16440
cacacagaag ccgccatgca tcattccaca aacaccgcag tgaccaatgt agggacttcc   16500
gggtctggac ataaatcaca atcctctgtc ctagctgact cagagacatc gaaagccaca   16560
cctctgatga gtaccacctc caccctgggg gacacaagtg tttccacatc aactcctaat   16620
atctctcaga ctaaccaaat tcaaacagag ccaacagcat ccctgagccc tagactgagg   16680
gagagcagca cgtctgagaa gaccagctca acaacagaga caaatactgc cttttcttat   16740
gtgcccacag gtgctattac tcaggcctcc agaacagaaa tctcctctag cagaacatcc   16800
atctcagacc ttgatcggcc cacaatagca cccgacatct ccacaggaat gatcaccagg   16860
ctcttcacct cccccatcat gacaaaatct gcagaaatga ccgtcaccac tcaaacaact   16920
actcctgggg ctacatcaca gggtatcctt ccttgggaca catcaaccac acttttccag   16980
ggagggactc attcaaccgt gtctcaggga ttcccacact cagagataac cactcttcgg   17040
agcagaaccc ctggagatgt gtcatggatg acaactcccc ctgtggaaga aaccagctct   17100
gggttttccc tgatgtcacc ttccatgaca tccccttctc ctgtttcctc cacatcacca   17160
gagagcatcc cctcctctcc tctccctgtg actgcacttc ttacttctgt tctggtgaca   17220
accaccaatg tattgggcac aacaagccca gagaccgtaa cgagttcacc tccaaattta   17280
agcagcccca cacaggagag actgaccact tacaaagaca ctgcgcacac agaagccatg   17340
catgcttcca tgcatacaaa cactgcagtg gccaacgtcg ggacctccat ttctggacat   17400
gaatcacaat cttctgtccc agctgattca cacacatcca aagccacatc tccaatgggt   17460
atcaccttcg ccatggggga tacaagtgtt tctacatcaa ctcctgcctt ctttgagact   17520
agaattcaga ctgaatcaac atcctctttg attcctggat taagggacac caggacgtct   17580
gaggagatca acactgtgac agagaccagc actgtccttt cagaagtgcc cactactact   17640
actactgagg tctccaggac agaagttatc acttccagca gaacaaccat ctcagggcct   17700
gatcattcca aaatgtcacc ctacatctcc acagaaacca tcaccaggct ctccactttt   17760
cctttttgtaa caggatccac agaaatggcc atcaccaacc aaacaggtcc tatagggact   17820
atctcacagg ctacccttac cctggacaca tcaagcacag cttcctggga agggactcac   17880
tcacctgtga ctcagagatt tccacactca gaggagacca ctactatgag cagaagtact   17940
aagggcgtgt catggcaaag ccctccctct gtggaagaaa ccagttctcc ttcttcccca   18000
gtgcctttac ctgcaataac ctcacattca tctctttatt ccgcagtatc aggaagtagc   18060
cccacttctg ctctccctgt gacttccctt ctcacctctg gcaggaggaa gaccatagac   18120
atgttggaca cacactcaga acttgtgacc agctccttac caagtgcaag tagcttctca   18180
ggtgagatac tcacttctga agcctccaca aatacagaga caattcactt ttcagagaac   18240
acagcagaaa ccaatatggg gaccaccaat tctatgcata aactacattc ctctgtctca   18300
atccactccc agccatccgg acacacacct ccaaaggtta ctggatctat gatggaggac   18360
gctattgttt ccacatcaac acctggttct cctgagacta aaaatgttga cagagactca   18420
acatcccctc tgactcctga actgaaaagag gacagcaccg ccctggtgat gaactcaact   18480
acagagtcaa acactgtttt ctccagtgtg tccctggatg ctgctactga ggtctccagg   18540
gcagaagtca cctactatga tcctacattc atgccagctt ctgctcagtc aacaaagtcc   18600
ccagacattt cacctgaagc cagcagcagt cattctaact ctcctcccct gacaatatct   18660
acacacaaga ccatcgccac acaaacaggt ccttctgggg tgacatctct tggccaactg   18720
```

```
accctggaca catcaaccat agccacctca gcaggaactc catcagccag aactcaggat   18780
tttgtagatt cagaaacaac cagtgtcatg aacaatgatc tcaatgatgt gttgaagaca   18840
agcccttrct ctgcagaaga agccaactct ctctcttctc aggcacctct ccttgtgaca   18900
acctcacctt ctcctgtaac ttccacattg caagagcaca gtacctcctc tcttgtttct   18960
gtgacctcag tacccacccc tacactggcg aagatcacag acatggacac aaacttagaa   19020
cctgtgactc gttcacctca aaatttaagg aacaccttgg ccacttcaga agccaccaca   19080
gatacacaca caatgcatcc ttctataaac acagcaatgg ccaatgtggg gaccaccagt   19140
tcaccaaatg aattctattt tactgtctca cctgactcag acccatataa agccacatcc   19200
gcagtagtta tcacttccac ctcgggggac tcaatagttt ccacatcaat gcctagatcc   19260
tctgcgatga aaaagattga gtctgagaca actttctccc tgatatttag actgagggag   19320
actagcacct cccagaaaat tggctcatcc tcagacacaa gcacggtctt tgacaaagca   19380
ttcactgctg ctactactga ggtctccaga acagaactca cctcctctag cagaacatcc   19440
atccaaggca ctgaaaagcc cacaatgtca ccggacacct ccacaagatc tgtcaccatg   19500 cttctctactt tgctggcct gacaaaatcc gaagaaagga ccattgccac ccaaacaggt   19560
cctcataggg cgacatcaca gggtacccett acctgggaca catcaatcac aacctcacag   19620
gcagggaccc actcagctat gactcatgga ttttcacaat tagattgtc cactcttacg   19680 agtagagttc ctgagtacat atcagggaca agcccaccct ctgtggaaaa aaccagctct   19740
tcctcttccc ttctgtcttt accagcaata acctcaccgt ccctgtacc tactacatta   19800 ccagaaagta ggccgtcttc tcctgttcat ctgacttcac tcccccacctc tggcctagtg   19860 aagaccacag atatgctggc atctgtggcc agtttacctc caaacttggg cagcacctca   19920
cataagatac cgactacttc agaagacatt aaagatacag agaaaatgta tccttccaca   19980
aacatagcag taaccaatgt ggggaccacc acttctgaaa aggaatctta ttcgtctgtc   20040
ccagcctact cagaaccacc caaagtcacc tctccaatgg ttacctcttt caacataagg   20100
gacaccattg tttccacatc catgcctggc tcctctgaga ttacaaggat tgagatggag   20160
tcaacattct ccgtggctca tgggctgaag ggaaccagca cctcccagga ccccatcgta   20220
tccacagaga aaagtgctgt ccttcacaag ttgaccactg gtgctactga gacctctagg   20280
acagaagttg cctcttctag aagaacatcc attccaggcc ctgatcattc cacagagtca   20340
ccagacatct ccactgaagt gatccccagc ctgcctatct cccttggcat tacagaatct   20400
tcaaatatga ccatcatcac tcgaacaggt cctcctcttg gctctacatc acagggcaca   20460
tttaccttgg acacaccaac tacatcctcc agggcaggaa cacactcgat ggcgactcag   20520
gaatttccac actcagaaat gaccactgtc atgaacaagg accctgagat tctatcatgg   20580
acaatccctc cttctataga gaaaaccagc ttctcctctt ccctgatgcc ttcaccagcc   20640
atgacttcac ctcctgtttc ctcaacatta ccaaagacca ttcacaccac tccttctcct   20700
atgacctcac tgctcacccc tagcctagtg atgaccacag acacattggg gacaagccca   20760
gaacctacaa ccagttcacc tccaaatttg agcagtacct cacatgtgat actgacaaca   20820
gatgaagaca ccacagctat agaagccatg catccttcca caagcacagc agcgactaat   20880
gtggaaacca cctgttctgg acatgggtca caatcctctg tcctaactga ctcagaaaaa   20940
accaaggcca cagctccaat ggataccacc tccaccatgg ggcatacaac tgtttccaca   21000
tcaatgtctg tttcctctga gactacaaaa attaagagag agtcaacata ttccttgact   21060
cctggactga gagagaccag catttcccaa aatgccagct tttccactga cacaagtatt   21120
```

```
gttctttcag aagtccccac tggtactact gctgaggtct ccaggacaga agtcacctcc   21180
tctggtagaa catccatccc tggcccttct cagtccacag ttttgccaga aatatccaca   21240
agaacaatga caaggctctt tgcctcgccc accatgacag aatcagcaga aatgaccatc   21300
cccactcaaa caggtccttc tgggtctacc tcacaggata cccttacctt ggacacatcc   21360
accacaaagt cccaggcaaa gactcattca actttgactc agagatttcc acactcagag   21420
atgaccactc tcatgagcag aggtcctgga gatatgtcat ggcaaagctc tccctctctg   21480
gaaaatccca gctctctccc ttccctgctg tctttacctg ccacaacctc acctcctccc   21540
atttcctcca cattaccagt gactatctcc tcctctcctc ttcctgtgac ttcacttctc   21600
acctctagcc cggtaacgac cacagacatg ttacacacaa gcccagaact tgtaaccagt   21660
tcacctccaa agctgagcca cacttcagat gagagactga ccactggcaa ggacaccaca   21720
aatacagaag ctgtgcatcc ttccacaaac acagcagcgt ccaatgtgga gattcccagc   21780
tttggacatg aatccccttc ctctgcctta gctgactcag agacatccaa agccacatca   21840
ccaatgttta ttacctccac ccaggaggat acaactgttg ccatatcaac ccctcacttc   21900
ttggagacta gcagaattca gaaagagtca atttcctccc tgagccctaa attgagggag   21960
acaggcagtt ctgtggagac aagctcagcc atagagacaa gtgctgtcct ttctgaagtg   22020
tccattggtg ctactactga gatctccagg acagaagtca cctcctctag cagaacatcc   22080
atctctggtt ctgctgagtc cacaatgttg ccagaaatat ccaccacaag aaaaatcatt   22140
aagttcccta cttcccccat cctggcagaa tcatcagaaa tgaccatcaa gacccaaaca   22200
agtcctcctg ggtctacatc agagagtacc tttacattag acacatcaac cactccctcc   22260
ttggtaataa cccattcgac tatgactcag agattgccac actcagagat aaccactctt   22320
gtgagtagag gtgctgggga tgtgccacgg cccagctctc tccctgtgga agaaacaagc   22380
cctccatctt cccagctgtc tttatctgcc atgatctcac cttctcctgt ttcttccaca   22440
ttaccagcaa gtagccactc ctcttctgct tctgtgactt cacctctcac accaggccaa   22500
gtgaagacta ctgaggtgtt ggacgcaagt gcagaacctg aaaccagttc acctccaagt   22560
ttgagcagca cctcagttga aatactggcc acctctgaag tcaccacaga tacggagaaa   22620
attcatcctt tcccaaacac ggcagtaacc aaagttggaa cttccagttc tggacatgaa   22680
tccccttcct ctgtcctacc tgactcagag acaaccaaag ccacatcggc aatgggtacc   22740
atctccatta tgggggatac aagtgttttct acattaactc ctgccttatc taacactagg   22800
aaaattcagt cagagccagc ttcctcactg accaccagat tgagggagac cagcacctct   22860
gaagagacca gcttagccac agaagcaaac actgttcttt ctaaagtgtc cactggtgct   22920
actactgagg tctccaggac agaagccatc tcctttagca gaacatccat gtcaggccct   22980
gagcagtcca caatgtcaca agacatctcc ataggaacca tccccaggat ttctgcctcc   23040
tctgtcctga cagaatctgc aaaaatgacc atcacaaccc aaacaggtcc ttcggagtct   23100
acactagaaa gtaccttaa tttgaacaca gcaaccacac cctcttgggt ggaaacccac   23160
tctatagtaa ttcagggatt tccacaccca gagatgacca cttccatggg cagaggtcct   23220
ggaggtgtgt catggcctag ccctcccttt gtgaaagaaa ccagccctcc atcctccccg   23280
ctgtctttac ctgccgtgac ctcacctcat cctgtttcca ccacattcct agcacatatc   23340 ccccctctc cccttcctgt gacttcactt ctcacctctg gccggcgac aaccacagat   23400 atcttgggta caagcacaga acctggaacc agttcatctt caagtttgag caccacctcc   23460
```

```
catgagagac tgaccactta caaagacact gcacatacag aagccgtgca tccttccaca    23520
aacacaggag ggaccaatgt ggcaaccacc agctctggat ataaatcaca gtcctctgtc    23580
ctagctgact catctccaat gtgtaccacc tccaccatgg gggatacaag tgttctcaca    23640
tcaactcctg ccttccttga gactaggagg attcagacag agctagcttc ctccctgacc    23700
cctggattga gggagtccag tggctctgaa gggaccagct caggcaccaa gatgagcact    23760
gtcctctcta aagtgcccac tggtgctact actgagatct ccaaggaaga cgtcacctcc    23820
atcccaggtc ccgctcaatc cacaatatca ccagacatct ccacaagaac cgtcagctgg    23880
ttctctacat cccctgtcat gacagaatca gcagaaataa ccatgaacac ccatacaagt    23940
cctttagggg ccacaacaca aggcaccagt actttggcca cgtcaagcac aacctctttg    24000
acaatgacac actcaactat atctcaagga ttttcacact cacagatgag cactcttatg    24060
aggaggggtc ctgaggatgt atcatggatg agccctcccc ttctggaaaa aactagacct    24120
tccttttctc tgatgtcttc accagccaca acttcacctt ctcctgtttc ctccacatta    24180
ccagagagca tctcttcctc tcctcttcct gtgacttcac tcctcacgtc tggcttggca    24240
aaaactacag atatgttgca caaaagctca gaacctgtaa ccaactcacc tgcaaatttg    24300
agcagcacct cagttgaaat actggccacc tctgaagtca ccacagatac agagaaaact    24360
catccttctt caaacagaac agtgaccgat gtggggacct ccagttctgg acatgaatcc    24420
acttcctttg tcctagctga ctcacagaca tccaaagtca catctccaat ggttattacc    24480
tccaccatgg aggatacgag tgtctccaca tcaactcctg ctttttttga gactagcaga    24540
attcagacag aaccaacatc ctccctgacc cttggactga aaagaccag cagctctgag    24600 gggaccagct tagccacaga gatgagcact gtcctttctg gagtgcccac tggtgccact    24660
gctgaagtct ccaggacaga agtcacctcc tctagcagaa catccatctc aggctttgct    24720
cagctcacag tgtcaccaga gacttccaca gaaaccatca ccagactccc tacctccagc    24780
ataatgacag aatcagcaga aatgatgatc aagacacaaa cagatcctcc tgggtctaca    24840
ccagagagta ctcatactgt ggacatatca acaacaccca actgggtaga aacccactcg    24900
actgtgactc agagattttc acactcagag atgaccactc ttgtgagcag aagccctggt    24960
gatatgttat ggcctagtca atcctctgtg aagaaaccag gctctgcctc ttccctgctg    25020
tctctgcctg ccacgacctc accttctcct gtttcctcta cattagtaga ggatttccct    25080
tccgcttctc ttcctgtgac ttctcttctc accccotggcc tggtgataac cacagacagg    25140
atgggcataa gcagagaacc tggaaccagt tccacttcaa atttgagcag cacctcccat    25200
gagagactga ccactttgga agacactgta gatacagaag acatgcagcc ttccacacac    25260
acagcagtga ccaacgtgag gacctccatt tctggacatg aatcacaatc ttctgtccta    25320
tctgactcag agacacccaa agccacatct ccaatgggta ccacctacac catgggggaa    25380
acgagtgttt ccatatccac ttctgacttc tttgagacca gcagaattca gatagaacca    25440
acatcctccc tgacttctgg attgagggag accagcagct ctgagaggat cagctcagcc    25500
acagagggaa gcactgtcct ttctgaagtg cccagtggtg ctaccactga ggtctccagg    25560
acagaagtga tatcctctag gggaacatcc atgtcagggc ctgatcagtt caccatatca    25620
ccagacatct ctactgaagc gatcaccagg ctttctactt cccccattat gacagaatca    25680
gcagaaagtg ccatcactat tgagacaggt tctcctgggg ctacatcaga gggtaccctc    25740
accttggaca cctcaacaac aaccttttgg tcagggaccc actcaactgc atctccagga    25800
ttttcacact cagagatgac cactcttatg agtagaactc ctggagatgt gccatggccg    25860
```

```
agccttccct ctgtggaaga agccagctct gtctcttcct cactgtcttc acctgccatg   25920
acctcaactt cttttttctc cgcattacca gagagcatct cctcctctcc tcatcctgtg   25980
actgcacttc tcacccttgg cccagtgaag accacagaca tgttgcgcac aagctcagaa   26040
cctgaaacca gttcacctcc aaatttgagc agcacctcag ctgaaatatt agccacgtct   26100
gaagtcacca agatagaga gaaaattcat ccctcctcaa acacacctgt agtcaatgta   26160
gggactgtga tttataaaca tctatcccct tcctctgttt tggctgactt agtgacaaca   26220
aaacccacat ctccaatggc taccacctcc actctgggga atacaagtgt ttccacatca   26280
actcctgcct tccagaaaac tatgatgaca cagccaactt cctccctgac ttctggatta   26340
agggagatca gtacctctca agagaccagc tcagcaacag agagaagtgc ttctctttct   26400
ggaatgccca ctggtgctac tactaaggtc tccagaacag aagccctctc cttaggcaga   26460
acatccaccc caggtcctgc tcaatccaca atatcaccag aaatctccac ggaaaccatc   26520
actagaattt ctactcccct caccacgaca ggatcagcag aaatgaccat caccccaaa    26580 acaggtcatt ctggggcatc ctcacaaggt acctttacct tggacacatc aagcagagcc   26640
tcctggccag gaactcactc agctgcaact cacagatctc cacactcagg gatgaccact   26700
cctatgagca gaggtcctga ggatgtgtca tggccaagcc gcccatcagt ggaaaaaact   26760
agccctccat cttccctggt gtctttatct gcagtaacct caccttcgcc actttattcc   26820
acaccatctg agagtagcca ctcatctcct ctccgggtga cttctctttt caccctgtc    26880 atgatgaaga ccacagacat gttggacaca agcttggaac ctgtgaccac ttcacctccc   26940
agtatgaata tcacctcaga tgagagtctg gccacttcta aagccaccat ggagacagag   27000
gcaattcagc tttcagaaaa cacagctgtg actcagatgg gcaccatcag cgctagacaa   27060
gaattctatt cctcttatcc aggcctccca gagccatcca aagtgacatc tccagtggtc   27120
acctcttcca ccataaaaga cattgttttct acaaccatac ctgcttcctc tgagataaca   27180
agaattgaga tggagtcaac atccaccctg accccacac caagggagac cagcacctcc   27240
caggagatcc actcagccac aaagccaagc actgttcctt acaaggcact cactagtgcc   27300
acgattgagg actccatgac acaagtcatg tcctctagca gaggacctag ccctgatcag   27360
tccacaatgt cacaagacat atccagtgaa gtgatcacca ggctctctac ctcccccatc   27420
aaggcagaat ctacagaaat gaccattacc acccaaacag gttctcctgg ggctacatca   27480
aggggtaccc ttaccttgga cacttcaaca actttatgt cagggaccca ctcaactgca   27540
tctcaaggat tttcacactc acagatgacc gctcttatga gtagaactcc tggagatgtg   27600
ccatggctaa gccatccctc tgtggaagaa gccagctctg cctctttctc actgtcttca   27660
cctgtcatga cctcatcttc tcccgtttct tccacattac cagacagcat ccactcttct   27720
tcgcttcctg tgacatcact tctcacctca gggctggtga agaccacaga gctgttgggc   27780
acaagctcag aacctgaaac cagttcaccc ccaaatttga gcagcacctc agctgaaata   27840
ctggccacca ctgaagtcac tacagataca gagaaactgg agatgaccaa tgtggtaacc   27900
tcaggttata cacatgaatc tccttcctct gtcctagctg actcagtgac aacaaaggcc   27960
acatcttcaa tgggtatcac ctaccccaca ggagatacaa atgttctcac atcaacccct   28020
gccttctctg acaccagtag gattcaaaca aagtcaaagc tctcactgac tcctgggttg   28080
atggagacca gcatctctga agagaccagc tctgccacag aaaaaagcac tgtccttttct  28140 agtgtgccca ctggtgctac tactgaggtc tccaggacag aagccatctc ttctagcaga   28200
```

```
acatccatcc caggccctgc tcaatccaca atgtcatcag acacctccat ggaaaccatc    28260
actagaattt ctaccccct cacaaggaaa gaatcaacag acatggccat cacccccaaa    28320
acaggtcctt ctggggctac ctcgcagggt acctttacct tggactcatc aagcacagcc    28380
tcctggccag gaactcactc agctacaact cagagatttc cacagtcagt ggtgacaact    28440
cctatgagca gaggtcctga ggatgtgtca tggccaagcc cgctgtctgt ggaaaaaaac    28500
agccctccat cttccctggt atcttcatct tcagtaacct caccttcgcc actttattcc    28560
acaccatctg ggagtagcca ctcctctcct gtccctgtca cttctctttt cacctctatc    28620
atgatgaagg ccacagacat gttggatgca agtttggaac ctgagaccac ttcagctccc    28680
aatatgaata tcacctcaga tgagagtctg gccacttcta aagccaccac ggagacagag    28740
gcaattcacg tttttgaaaa tacagcagcg tcccatgtgg aaaccaccag tgctacagag    28800
gaactctatt cctcttcccc aggcttctca gagccaacaa aagtgatatc tccagtggtc    28860
acctcttcct ctataagaga caacatggtt tccacaacaa tgcctggctc ctctggcatt    28920
acaaggattg agatagagtc aatgtcatct ctgacccctg gactgaggga gaccagaacc    28980
tcccaggaca tcacctcatc cacagagaca agcactgtcc tttacaagat gtcctctggt    29040
gccactcctg aggtctccag gacagaagtt atgccctcta gcagaacatc cattcctggc    29100
cctgctcagt ccacaatgtc actagacatc tccgatgaag ttgtcaccag gctgtctacc    29160
tctcccatca tgcagaatc tgcagaaata accatcacca cccaaacagg ttattctctg    29220
gctacatccc aggttaccct tcccttgggc acctcaatga cctttttgtc agggacccac    29280
tcaactatgt ctcaaggact ttcacactca gagatgacca atcttatgag caggggtcct    29340
gaaagtctgt catggacgag ccctcgcttt gtggaaacaa ctagatcttc ctcttctctg    29400
acatcattac ctctcacgac ctcactttct cctgtgtcct ccacattact agacagtagc    29460
ccctcctctc ctcttcctgt gacttcactt atcctcccag gcctggtgaa gactacagaa    29520
gtgttggata caagctcaga gcctaaaacc agttcatctc caaatttgag cagcacctca    29580
gttgaaatac cggccacctc tgaaatcatg acagatacag agaaaattca tccttcctca    29640
aacacagcgg tggccaaagt gaggacctcc agttctgttc atgaatctca ttcctctgtc    29700
ctagctgact cagaaacaac cataaccata ccttcaatgg gtatcacctc cgctgtggac    29760
gataccactg tttccacatc aaatcctgcc ttctctgaga ctaggaggat tccgacagag    29820
ccaacattct cattgactcc tggattcagg gagactagca cctctgaaga gaccacctca    29880
atcacagaaa caagtgcagt ccttttatgga gtgcccacta tgctactac tgaagtctcc    29940 atgacagaaa tcatgtcctc taatagaaca cacatccctg actctgatca gtccacgatg    30000
tctccagaca tcatcactga agtgatcacc aggctctctt cctcatccat gatgtcagaa    30060
tcaacacaaa tgaccatcac cacccaaaaa agttctcctg gggctacagc acagagtact    30120
cttaccttgg ccacaacaac agccccttg gcaaggaccc actcaactgt tcctcctaga    30180
tttttacact cagagatgac aactcttatg agtaggagtc ctgaaaatcc atcatggaag    30240
agctctccct tgtggaaaa aactagctct tcatcttctc tgttgtcctt acctgtcacg    30300
acctcacctt ctgtttcttc cacattaccg cagagtatcc cttcctcctc tttttctgtg    30360
acttcactcc tcaccccagg catggtgaag actacagaca caagcacaga acctggaacc    30420
agtttatctc caaatctgag tggcacctca gttgaaatac tggctgcctc tgaagtcacc    30480
acagatacag agaaaattca tccttcttca agcatggcag tgaccaatgt gggaaccacc    30540
agttctggac atgaactata ttcctctgtt tcaatccact cggagccatc caaggctaca    30600
```

```
tacccagtgg gtactccctc ttccatggct gaaacctcta tttccacatc aatgcctgct   30660
aattttgaga ccacaggatt tgaggctgag ccatttctc atttgacttc tggatttagg    30720
aagacaaaca tgtccctgga caccagctca gtcacaccaa caaatacacc ttcttctcct   30780
gggtccactc acctttaca gagttccaag actgatttca cctcttctgc aaaaacatca    30840
tccccagact ggcctccagc ctcacagtat actgaaattc cagtggacat aatcaccccc   30900
tttaatgctt ctccatctat tacgagtcc actgggataa cctccttccc agaatccagg    30960
tttactatgt ctgtaacaga aagtactcat catctgagta cagatttgct gccttcagct   31020
gagactattt ccactggcac agtgatgcct tctctatcag aggccatgac ttcatttgcc   31080
accactggag ttccacgagc catctcaggt tcaggtagtc cattctctag gacagagtca   31140
ggccctgggg atgctactct gtccaccatt gcagagagcc tgccttcatc cactcctgtg   31200
ccattctcct cttcaacctt cactaccact gattcttcaa ccatcccagc cctccatgag   31260
ataacttcct cttcagctac cccatataga gtggacacca gtcttgggac agagagcagc   31320
actactgaag gacgcttggt tatggtcagt actttggaca cttcaagcca accaggcagg   31380
acatcttcaa cacccatttt ggataccaga atgacagaga gcgttgagct gggaacagtg   31440
acaagtgctt atcaagttcc ttcactctca acacggttga caagaactga tggcattatg   31500
gaacacatca caaaatacc caatgaagca gcacacagag gtaccataag accagtcaaa   31560
ggccctcaga catccacttc gcctgccagt cctaaaggac tacacacagg agggacaaaa   31620
agaatggaga ccaccaccac agctttgaag accaccacca cagctttgaa gaccacttcc   31680
agagccacct tgaccaccag tgtctatact cccactttgg gaacactgac tccctcaat    31740 gcatcaaggc aaatggccag cacaatcctc acagaaatga tgatcacaac cccatatgtt   31800
ttccctgatg ttccagaaac gacatcctca ttggctacca gcctgggagc agaaaccagc   31860
acagctcttc ccaggacaac cccatctgtt ctcaatagag aatcagagac cacagcctca   31920
ctggtctctc gttctggggc agagagaagt ccggttattc aaactctaga tgtttcttct   31980
agtgagccag atacaacagc ttcatgggtt atccatcctg cagagaccat cccaactgtt   32040
tccaagacaa cccccaattt ttttccacagt gaattagaca ctgtatcttc cacagccacc   32100
agtcatgggg cagacgtcag ctcagccatt ccaacaaata tctcacctag tgaactagat   32160
gcactgaccc cactggtcac tatttcgggg acagatacta gtacaacatt cccaacactg   32220
actaagtccc cacatgaaac agagacaaga accacatggc tcactcatcc tgcagagacc   32280
agctcaacta ttcccagaac aatccccaat ttttctcatc atgaatcaga tgccacacct   32340
tcaatagcca ccagtcctgg ggcagaaacc agttcagcta ttccaattat gactgtctca   32400
cctggtgcag aagatctggt gacctcacag gtcactagtt ctgggacaga cagaaatatg   32460
actattccaa ctttgactct ttctcctggt gaaccaaaga cgatagcctc attagtcacc   32520
catcctgaag cacagacaag ttcggccatt ccaacttcaa ctatctcgcc tgctgtatca   32580
cggttggtga cctcaatggt caccagtttg gcggcaaaga caagtacaac taatcgagct   32640 ctgacaaaact cccctggtga accagctaca acagtttcat tggtcacgca tcctgcacag   32700
accagcccaa cagttccctg gacaacttcc attttttcc atagtaaatc agacaccaca    32760
ccttcaatga ccaccagtca tggggcagaa tccagttcag ctgttccaac tccaactgtt   32820
tcaactgagg taccaggagt agtgacccct ttggtcacca gttctagggc agtgatcagt   32880
acaactattc caattctgac tctttctcct ggtgaaccag agaccacacc ttcaatggcc   32940
```

```
accagtcatg gggaagaagc cagttctgct attccaactc caactgtttc acctggggta    33000
ccaggagtgg tgacctctct ggtcactagt tctagggcag tgactagtac aactattcca    33060
attctgactt tttctcttgg tgaaccagag accacacctt caatgccac cagtcatggg     33120 acagaagctg gctcagctgt tccaactgtt ttacctgagg taccaggaat ggtgacctct    33180
ctggttgcta gttctagggc agtaaccagt acaactcttc caactctgac tctttctcct    33240
ggtgaaccag agaccacacc ttcaatggcc accagtcatg gggcagaagc cagctcaact    33300
gttccaactg tttcacctga ggtaccagga gtggtgacct ctctggtcac tagttctagt    33360
ggagtaaaca gtacaagtat tccaactctg attctttctc ctggtgaact agaaaccaca    33420
ccttcaatgg ccaccagtca tggggcagaa gccagctcag ctgttccaac tccaactgtt    33480
tcacctgggg tatcaggagt ggtgacccct ctggtcacta gttccagggc agtgaccagt    33540
acaactattc caattctaac tctttcttct agtgagccag agaccacacc ttcaatggcc    33600
accagtcatg gggtagaagc cagctcagct gttctaactg tttcacctga ggtaccagga    33660
atggtgacct ctctggtcac tagttctaga gcagtaacca gtacaactat tccaactctg    33720
actatttctt ctgatgaacc agagaccaca acttcattgg tcacccattc tgaggcaaag    33780
atgatttcag ccattccaac tttagctgtc tcccctactg tacaagggct ggtgacttca    33840
ctggtcacta gttctgggtc agagaccagt gcgttttcaa atctaactgt tgcctcaagt    33900
caaccagaga ccatagactc atgggtcgct catcctggga cagaagcaag ttctgttgtt    33960
ccaactttga ctgtctccac tggtgagccg tttacaaata tctcattggt cacccatcct    34020
gcagagagta gctcaactct tcccaggaca acctcaaggt tttcccacag tgaattagac    34080
actatgcctt ctacagtcac cagtcctgag gcagaatcca gctcagccat ttcaactact    34140
atttcacctg gtataccagg tgtgctgaca tcactggtca ctagctctgg gagagacatc    34200
agtgcaactt ttccaacagt gcctgagtcc ccacatgaat cagaggcaac agcctcatgg    34260
gttactcatc ctgcagtcac cagcacaaca gttcccagga caacccctaa ttattctcat    34320
agtgaaccag acaccacacc atcaatagcc accagtcctg gggcagaagc cacttcagat    34380
tttccaacaa taactgtctc acctgatgta ccagatatgg taacctcaca ggtcactagt    34440
tctgggacag acaccagtat aactattcca actctgactc tttcttctgg tgagccagag    34500
accacaacct catttatcac ctattctgag acacacacaa gttcagccat tccaactctc    34560
cctgtctccc ctggtgcatc aaagatgctg acctcactgg tcatcagttc tgggacagac    34620
agcactacaa ctttcccaac actgacggag accccatatg aaccagagac aacagccata    34680
cagctcattc atcctgcaga gaccaacaca atggttccca agacaactcc caagttttcc    34740
catagtaagt cagacaccac actcccagta gccatcacca gtcctgggcc agaagccagt    34800
tcagctgttt caacgacaac tatctcacct gatatgtcag atctggtgac ctcactggtc    34860
cctagttctg ggacagacac cagtacaacc ttcccaacat tgagtgagac cccatatgaa    34920
ccagagacta cagtcacgtg gctcactcat cctgcagaaa ccagcacaac ggtttctggg    34980
acaattccca cttttcccca taggggatca gacactgcac cctcaatggt caccagtcct    35040
ggagtagaca cgaggtcagg tgttccaact acaaccatcc cacccagtat accagggata    35100
gtgacctcac aggtcactag ttctgcaaca gacactagta cagctattcc aactttgact    35160
ccttctcctg gtgaaccaga gaccacagcc tcatcagcta cccatcctgg gacacagact    35220
ggcttcactg ttccaattcg gactgttccc tctagtgagc cagatacaat ggcttcctgg    35280
gtcactcatc ctccacagac cagcacacct gtttccagaa caacctccag tttttcccat    35340
```

```
agtagtccag atgccacacc tgtaatggcc accagtccta ggacagaagc cagttcagct    35400
gtactgacaa caatctcacc tggtgcacca gagatggtga cttcacagat cactagttct    35460
ggggcagcaa ccagtacaac tgttccaact ttgactcatt ctcctggtat gccagagacc    35520
acagccttat tgagcaccca tcccagaaca gggacaagta aaacatttcc tgcttcaact    35580
gtgtttcctc aagtatcaga gaccacagcc tcactcacca ttagacctgg tgcagagact    35640
agcacagctc tcccaactca gacaacatcc tctctcttca ccctacttgt aactggaacc    35700
agcagagttg atctaagtcc aactgcttca cctggtgttt ctgcaaaaac agccccactt    35760
tccacccatc cagggacaga gaccagcaca atgattccaa cttcaactct ttcccttggt    35820
ttactagaga ctacaggctt actggccacc agctcttcag cagagaccag cacgagtact    35880
ctaactctga ctgtttcccc tgctgtctct gggcttccca gtgcctctat aacaactgat    35940
aagccccaaa ctgtgacctc ctggaacaca gaaacctcac catctgtaac ttcagttgga    36000
cccccagaat tttccaggac tgtcacaggc accactatga ccttgatacc atcagagatg    36060
ccaacaccac ctaaaaccag tcatggagaa ggagtgagtc caaccactat cttgagaact    36120
acaatggttg aagccactaa tttagctacc acaggttcca gtcccactgt ggccaagaca    36180
acaaccacct tcaatacact ggctggaagc ctctttactc ctctgaccac acctgggatg    36240
tccaccttgg cctctgagag tgtgacctca agaacaagtt ataaccatcg gtcctggatc    36300
tccaccacca gcagttataa ccgtcggtac tggacccctg ccaccagcac tccagtgact    36360
tctacattct ccccagggat ttccacatcc tccatcccca gctccacagc agccacagtc    36420
ccattcatgg tgccattcac cctcaacttc accatcacca acctgcagta cgaggaggac    36480
atgcggcacc ctggttccag gaagttcaac gccacagaga gagaactgca gggtctgctc    36540
aaacccttgt tcaggaatag cagtctggaa tacctctatt caggctgcag actagcctca    36600
ctcaggccag agaaggatag ctcagccatg gcagtggatg ccatctgcac acatcgccct    36660
gaccctgaag acctcggact ggacagagag cgactgtact gggagctgag caatctgaca    36720
aatggcatcc aggagctggg cccctacacc ctggaccgga acagtctcta tgtcaatggt    36780
ttcacccatc gaagctctat gcccaccacc agcactcctg gacctccac agtggatgtg    36840
ggaacctcag ggactccatc ctccagcccc agcccacgg ctgctggccc tctcctgatg    36900
ccgttcaccc tcaacttcac catcaccaac ctgcagtacg aggaggacat gcgtcgcact    36960
ggctccagga agttcaacac catggagagt gtcctgcagg gtctgctcaa gcccttgttc    37020
aagaacacca gtgttggccc tctgtactct ggctgcagat tgaccttgct caggcccgag    37080
aaagatgggg cagccactgg agtggatgcc atctgcaccc accgccttga ccccaaaagc    37140
cctggactca acaggagca gctgtactgg gagctaagca aactgaccaa tgacattgaa    37200
gagctgggcc cctacaccct ggacaggaac agtctctatg tcaatggttt cacccatcag    37260
agctctgtgt ccaccaccag cactcctggg acctccacag tggatctcag aacctcaggg    37320
actccatcct ccctctccag ccccacaatt atggctgctg ccctctcct ggtaccattc    37380
accctcaact tcaccatcac caacctgcag tatgggagg acatgggtca ccctggctcc    37440
aggaagttca acaccacaga gagggtcctg cagggtctgc ttggtccat attcaagaac    37500
accagtgttg ccctctgta ctctggctgc agactgacct ctctcaggtc tgagaaggat    37560
ggagcagcca ctggagtgga tgccatctgc atccatcatc ttgaccccaa aagccctgga    37620
ctcaacagag agcggctgta ctgggagctg agccaactga ccaatggcat caaagagctg    37680
```

```
ggcccctaca ccctggacag gaacagtctc tatgtcaatg gtttcaccca tcggacctct   37740
gtgcccacca ccagcactcc tgggacctcc acagtggacc ttggaacctc agggactcca   37800
ttctccctcc caagccccgc aactgctggc cctctcctgg tgctgttcac cctcaacttc   37860
accatcacca acctgaagta tgaggaggac atgcatcgcc ctggctccag gaagttcaac   37920
accactgaga gggtcctgca gactctgctt ggtcctatgt tcaagaacac cagtgttggc   37980
cttctgtact ctggctgcag actgaccttg ctcaggtccg agaaggatgg agcagccact   38040
ggagtggatg ccatctgcac ccaccgtctt gaccccaaaa gccctggact ggacagagag   38100
cagctatact gggagctgag ccagctgacc aatggcatca agagctgggc cctacacc    38160 ctggacagga acagtctcta tgtcaatggt ttcacccatt ggatccctgt gcccaccagc   38220
agcactcctg gacctccac agtggacctt gggtcaggga ctccatcctc cctccccagc    38280
cccacagctg ctggccctct cctggtgcca ttcaccctca acttcaccat caccaacctg   38340
cagtacgagg aggacatgca tcacccaggc tccaggaagt tcaacaccac ggagcgggtc   38400
ctgcagggtc tgcttggtcc catgttcaag aacaccagtg tcggccttct gtactctggc   38460
tgcagactga ccttgctcag gtccgagaag gatggagcag ccactggagt ggatgccatc   38520
tgcacccacc gtcttgaccc caaaagccct ggagtggaca gggagcagct atactgggag   38580
ctgagccagc tgaccaatgg catcaaagag ctgggtccct acacctgga cagaaacagt    38640 ctctatgtca atggtttcac ccatcagacc tctgcgccca acaccagcac tcctgggacc   38700
tccacagtgg accttgggac ctcagggact ccatcctccc tccccagccc tacatcngct   38760
ggccctctcc tggtnccntt caccctcaac ttcaccatca ccaacctgca gtacgaggag   38820
gacatgcggc accnggntc caggaagttc aacaccacng agagggtnct gcagggtctg    38880
ctnaagcccc tnttcaagag caccagtgtt ggccctctgt actctggctg cagactgacc   38940
ttgctcaggt ccgagaagga tggagcagcc actggagtgg atgccatctg cacccaccgt   39000
cttgacccca aaagccctgg agtggacagg gagcagctat actgggagct gagccagctg   39060
accaatggca tcaaagagct gggtccctac accctggaca gaaacagtct ctatgtcaat   39120
ggtttcaccc atcagacctc tgcgcccaac accagcactc tgggacctc cacagtggac    39180 cttgggacct cagggactcc atcctccctc cccagcccta catctgctgg ccctctcctg   39240
gtgccattca ccctcaactt caccatcacc aacctgcagt acgaggagga catgcatcac   39300
ccaggctcca ggaagttcaa caccacggag cgggtcctgc agggtctgct tggtcccatg   39360
ttcaagaaca ccagtgtcgg ccttctgtac tctggctgca gactgacctt gctcaggcct   39420
gagaagaatg ggcagccac tggaatggat gccatctgca gccaccgtct tgaccccaaa    39480
agccctggac tcaacagaga gcagctgtac tgggagctga gccagctgac catggcatc   39540 aaagagctgg gccctacac cctggacagg aacagtctct atgtcaatgg tttcacccat   39600
cggagctctg tgggccccac cagcactcct gggacctcca gtggacct tgggacctca     39660 gggactccat cctccctccc cagccccaca acagctgttc ctctcctggt gccgttcacc   39720
ctcaacttta ccatcaccaa tctgcagtat ggggaggaca tgcgtcaccc tggctccagg   39780
aagttcaaca ccacagagag ggtcctgcag ggtctgcttg gtcccttgtt caagaactcc   39840
agtgtcggcc ctctgtactc tggctgcaga ctgatctctc tcaggtctga aaggatggg    39900 gcagccactg gagtggatgc catctgcacc caccaccta accctcaaag ccctggactg    39960
gacagggagc agctgtactg gcagctgagc cagatgacca atggcatcaa agagctggc    40020 ccctacaccc tggaccggaa cagtctctac gtcaatggtt tcacccatcg gagctctggg   40080
```

```
ctcaccacca gcactccttg gacttccaca gttgaccttg gaacctcagg gactccatcc   40140
cccgtcccca gccccacaac tgctggccct tcctggtgc cattcaccct caacttcacc    40200
atcaccaacc tgcagtatga ggaggacatg catcgccctg gatctaggaa gttcaacacc   40260
acagagaggg tcctgcaggg tctgcttagt cccattttca agaactccag tgttggccct   40320
ctgtactctg gctgcagact gacctctctc aggcccgaga aggatggggc agcaactgga   40380
atggatgctg tctgcctcta ccaccctaat cccaaaagac ctggactgga cagagagcag   40440
ctgtactggg agctaagcca gctgacccac aacatcactg agctgggccc ctacagcctg   40500
gacagggaca gtctctatgt caatggtttc acccatcaga actctgtgcc caccaccagt   40560
actcctggga cctccacagt gtactgggca accactggga ctccatcctc cttccccggc   40620
cacacagagc ctggccctct cctgatacca ttcactttca actttaccat caccaacctg   40680
cattatgagg aaaacatgca acaccctggt tccaggaagt tcaacaccac ggagagggtt   40740
ctgcagggtc tgctcaagcc cttgttcaag aacaccagtg ttggccctct gtactctggc   40800
tgcagactga cctctctcag gcccgagaag gatggggcag caactggaat ggatgctgtc   40860
tgcctctacc accctaatcc caaaagacct gggctggaca gagagcagct gtactgggag   40920
ctaagccagc tgacccacaa catcactgag ctgggcccct acagcctgga cagggacagt   40980
ctctatgtca atggtttcac ccatcagaac tctgtgccca ccaccagtac tcctgggacc   41040
tccacagtgt actgggcaac cactgggact ccatcctcct tccccggcca cacagagcct   41100
ggccctctcc tgataccatt cactttcaac tttaccatca ccaacctgca ttatgaggaa   41160
aacatgcaac ccctggttc aggaagttc aacaccacgg agagggttct gcagggtctg   41220
ctcaagccct tgttcaagaa caccagtgtt ggccctctgt actctggctg cagactgacc   41280
ttgctcagac ctgagaagca tgaggcagcc actggagtgg acaccatctg tacccaccgc   41340
gttgatccca tcggacctgg actggacagg gagcggctat actgggagct gagccagctg   41400
accaacagca ttaccgaact gggaccctac accctggaca gggacagtct ctatgtcaat   41460
ggcttcaacc ctcggagctc tgtgccaacc accagcactc ctgggacctc cacagtgcac   41520
ctggcaacct ctgggactcc atcctccctg cctggccaca cagcccctgt ccctctcttg   41580
ataccattca ccctcaactt taccatcacc aacctgcatt atgaggaaaa catgcaacac   41640
cctggttcca ggaagttcaa caccacggag agggttctgc agggtctgct caagcccttg   41700
ttcaagaaca ccagtgttgg ccctctgtac tctggctgca gactgacctt gctcagacct   41760
gagaagcatg aggcagccac tggagtggac accatctgta cccaccgcgt tgatcccatc   41820
ggacctggac tgnacagnga gcngctntac tgggagctna gccanctgac caannncatc   41880
nnngagctgg gncccacac cctggacagg nacagtctct atgtcaatgg tttcacccat   41940
cnganctctg ngcccaccac cagcactcct gggacctcca cagtgnacnt nggnacctcn   42000
gggactccat cctccntccc cngccncaca tctgctggcc ctctcctggt gccattcacc   42060
ctcaacttca ccatcaccaa cctgcagtac gaggaggaca tgcatcaccc aggctccagg   42120
aagttcaaca ccacggagcg ggtcctgcag ggtctgcttg gtccatgtt caagaacacc   42180 agtgtcggcc ttctgtactc tggctgcaga ctgaccttgc tcaggcctga aagaatggg    42240 gcagccactg gaatggatgc catctgcagc caccgtcttg acccaaaaag ccctggactc   42300
gacagagagc agctgtactg ggagctgagc cagctgaccc atggcatcaa agagctgggc   42360
ccctacaccc tggacaggaa cagtctctat gtcaatggtt tcacccatcg gagctctgtg   42420
```

```
gcccccacca gcactcctgg gacctccaca gtggaccttg ggacctcagg gactccatcc   42480
tccctcccca gccccacaac agctgttcct ctcctggtgc cgttcaccct caactttacc   42540
atcaccaatc tgcagtatgg ggaggacatg cgtcaccctg gctccaggaa gttcaacacc   42600
acagagaggg tcctgcaggg tctgcttggt cccttgttca agaactccag tgtcggccct   42660
ctgtactctg gctgcagact gatctctctc aggtctgaga aggatggggc agccactgga   42720
gtggatgcca tctgcaccca ccaccttaac cctcaaagcc ctggactgga cagggagcag   42780
ctgtactggc agctgagcca gatgaccaat ggcatcaaag agctgggccc ctacacccctg   42840 gaccggaaca gtctctacgt caatggtttc acccatcgga gctctgggct caccaccagc   42900
actccttgga cttccacagt tgaccttgga acctcaggga ctccatcccc cgtcccagc    42960 cccacaactg ctggccctct cctggtgcca ttcaccctaa acttcaccat caccaacctg   43020
cagtatgagg aggacatgca tcgccctgga tctaggaagt tcaacgccac agagagggtc   43080
ctgcagggtc tgcttagtcc catattcaag aactccagtg ttggccctct gtactctggc   43140
tgcagactga cctctctcag gcccgagaag gatggggcag caactggaat ggatgctgtc   43200
tgcctctacc accctaatcc caaaagacct ggactggaca gagagcagct gtactgggag   43260
ctaagccagc tgacccacaa catcactgag ctgggcccct acagcctgga cagggacagt   43320
ctctatgtca atggtttcac ccatcagagc tctatgacga ccaccagaac tcctgatacc   43380
tccacaatgc acctggcaac ctcgagaact ccagcctccc tgtctggacc tacgaccgcc   43440
agccctctcc tggtgctatt cacaatcaac tgcaccatca ccaacctgca gtacgaggag   43500
gacatgcgtc gcactggctc caggaagttc aacaccatgg agagtgtcct gcagggtctg   43560
ctcaagccct tgttcaagaa caccagtgtt ggccctctgt actctggctg cagattgacc   43620
ttgctcaggc ccaagaaaga tggggcagcc actggagtgg atgccatctg cacccaccgc   43680
cttgacccca aaagccctgg actcaacagg gagcagctgt actgggagct aagcaaactg   43740
accaatgaca ttgaagagct gggccccctac accctggaca ggaacagtct ctatgtcaat   43800
ggtttcaccc atcagagctc tgtgtccacc accagcactc ctgggacctc cacagtggat   43860
ctcagaacct cagggactcc atcctccctc tccagcccca caattatgnc nnctgnccct   43920
ctcctgntnc cnttcaccnt caacttnacc atcaccaacc tgcantangn ggannacatg   43980
cnncncccng gntccaggaa gttcaacacc acngagaggg tcctacaggg tctgctcagg   44040
cccttgttca agaacaccag tgtcagctct ctgtactctg gttgcagact gaccttgctc   44100
aggcctgaga aggatggggc agccaccaga gtggatgctg cctgcaccta ccgccctgat   44160
cccaaaagcc ctggactgga cagagagcaa ctatactggg agctgagcca gctaacccac   44220
agcatcactg agctgggacc ctacacccctg acagggtcag tctctatgt caatggcttc   44280 aaccctcgga gctctgtgcc aaccaccagc actcctggga cctccacagt gcacctggca   44340
acctctggga ctccatcctc cctgcctggc cacacancnn ctgncccctct cctgntnccn   44400 ttcaccntca acttnaccat caccaacctg cantangngg annacatgcn ncncccnggn   44460
tccaggaagt tcaacaccac ngagagggtt ctgcagggtc tgctcaaacc cttgttcagg   44520
aatagcagtc tggaatacct ctattcaggc tgcagactag cctcactcag gccagagaag   44580
gatagctcag ccatggcagt ggatgccatc tgcacacatc gccctgaccc tgaagacctc   44640
ggactggaca gagagcgact gtactggag ctgagcaatc tgacaaatgg catccaggag   44700
ctgggccccc acaccctgga ccggaacagt ctctacgtca atggtttcac ccatcggagc   44760
tctgggctca ccaccagcac tccttggact tccacagttg accttggaac ctcagggact   44820
```

```
ccatccccg tccccagccc cacaactgct ggccctctcc tggtgccatt caccctcaac   44880
ttcaccatca ccaacctgca gtatgaggag gacatgcatc gccctggttc caggaggttc   44940
aacaccacgg agagggttct gcagggtctg ctcacgccct tgttcaagaa caccagtgtt   45000
ggccctctgt actctggctg cagactgacc ttgctcagac ctgagaagca agaggcagcc   45060
actggagtgg acaccatctg tacccaccgc gttgatccca tcggacctgg actggacaga   45120
gagcggctat actgggagct gagccagctg accaacagca tcacagagct gggaccctac   45180
accctggata gggacagtct ctatgtcaat ggcttcaacc cttggagctc tgtgccaacc   45240
accagcactc ctgggacctc cacagtgcac ctggcaacct ctgggactcc atcctccctg   45300
cctggccaca cagcccctgt ccctctcttg ataccattca ccctcaactt taccatcacc   45360
gacctgcatt atgaagaaaa catgcaacac cctggttcca ggaagttcaa caccacggag   45420
agggttctgc agggtctgct caagcccttg ttcaagagca ccagcgttgg ccctctgtac   45480
tctggctgca gactgacctt gctcagacct gagaaacatg gggcagccac tggagtggac   45540
gccatctgca ccctccgcct tgatcccact ggtcctggac tggacagaga gcggctatac   45600
tgggagctga gccagctgac caacagcgtt acagagctgg gccctacac cctggacagg   45660 gacagtctct atgtcaatgg cttcacccat cggagctctg tgccaaccac cagtattcct   45720
gggacctctg cagtgcacct ggaaacctct gggactccag cctccctccc tggccacaca   45780
gcccctggcc ctctcctggt gccattcacc ctcaacttca ctatcaccaa cctgcagtat   45840
gaggaggaca tgcgtcaccc tggttccagg aagttcagca ccacggagag agtcctgcag   45900
ggtctgctca gcccttgtt caagaacacc agtgtcagct ctctgtactc tggttgcaga   45960
ctgaccttgc tcaggcctga aaggatgggg cagccacca gagtggatgc tgtctgcacc   46020
catcgtcctg accccaaaag ccctggactg gacagagagc ggctgtactg gaagctgagc   46080
cagctgaccc acggcatcac tgagctgggc cctacacc tggacaggca gtctctat   46140 gtcaatggtt tcacccatca gagctctatg acgaccacca gaactcctga tacctccaca   46200
atgcacctgg caacctcgag aactccagcc tccctgtctg gcctacgac cgccagccct   46260 ctcctggtgc tattcacaat taacttcacc atcactaacc tgcggtatga ggagaacatg   46320 catcacctg gctctagaaa gtttaacacc acggagagag tccttcaggg tctgctcagg   46380
cctgtgttca agaacaccag tgttggccct ctgtactctg gctgcagact gaccacgctc   46440
aggcccaaga aggatggggc agccaccaaa gtggatgcca tctgcaccta ccgccctgat   46500
cccaaaagcc ctggactgga cagagagcag ctatactggg agctgagcca gctaacccac   46560
agcatcactg agctgggccc ctacacccag gacagggaca gtctctatgt caatggcttc   46620
acccatcgga gctctgtgcc aaccaccagt attcctggga cctctgcagt gcacctggaa   46680
acctctggga ctccagcctc cctccctggc cacacagccc ctggccctct cctggtgcca   46740 ttcacccca acttcactat caccaacctg cagtatgagg aggacatgcg tcaccctggt   46800
tccaggaagt tcaacaccac ggagagagtc ctgcagggtc tgctcaagcc cttgttcaag   46860
agcaccagtg ttggccctct gtactctggc tgcagactga ccttgctcag gcctgaaaaa   46920
cgtggggcag ccaccggcgt ggacaccatc tgcactcacc gccttgaccc tctaaaccca   46980
ggactggaca gagagcagct atactgggag ctgagcaaac tgacccgtgg catcatcgag   47040 ctgggccct acctcctgga cagaggcagt ctctatgtca atggtttcac ccatcggacc   47100
tctgtgccca ccaccagcac tcctgggacc tccacagtgg accttggaac ctcagggact   47160
```

```
ccattctccc tcccaagccc cgcancnnct gnccctctcc tgntnccntt caccntcaac   47220
ttnaccatca ccaacctgca ntangnggan nacatgcnnc ncccnggntc caggaagttc   47280
aacaccacng agagggtcct gcagactctg cttggtccta tgttcaagaa caccagtgtt   47340
ggccttctgt actctggctg cagactgacc ttgctcaggt ccgagaagga tggagcagcc   47400
actggagtgg atgccatctg cacccaccgt ctttgacccca aaagccctgg agtggacagg   47460
gagcaactat actgggagct gagccagctg accaatggca ttaaagaact gggcccctac   47520
accctggaca ggaacagtct ctatgtcaat gggttcaccc attggatccc tgtgcccacc   47580
agcagcactc ctgggacctc cacagtggac cttgggtcag ggactccatc ctccctcccc   47640
agccccacaa ctgctggccc tctcctggtg ccgttcaccc tcaacttcac catcaccaac   47700
ctgaagtacg aggaggacat gcattgccct ggctccagga agttcaacac cacagagaga   47760
gtcctgcaga gtctgcttgg tcccatgttc aagaacacca gtgttggccc tctgtactct   47820
ggctgcagac tgaccttgct caggtccgag aaggatggag cagccactgg agtggatgcc   47880
atctgcaccc accgtcttga ccccaaaagc cctggagtgg acaggagca gctatactgg   47940
gagctgagcc agctgaccaa tggcatcaaa gagctgggtc cctacaccct ggacagaaac   48000
agtctctatg tcaatggttt cacccatcag acctctgcgc caacaccag cactcctggg   48060
acctccacag tggaccttgg gacctcaggg actccatcct ccctcccag ccctacancn   48120
nctgnccctc tcctgntncc nttcaccntc aacttnacca tcaccaacct gcantangng   48180
gannacatgc nncnccngg ntccaggaag ttcaacacca cngagngngt nctgcagggt   48240
ctgctnnnnc ccntnttcaa gaacnccagt gtnggccntc tgtactctgg ctgcagactg   48300
acctnnctca ggncngagaa gnatggngca gccactggan tggatgccat ctgcanccac   48360
cnncntnanc ccaaaagncc tggactgnac agngagcngc tntactggga gctnagccan   48420
ctgaccaann ncatcnnnga gctgggnccc tacaccctgg acaggnacag tctctatgtc   48480
aatggtttca cccattggat ccctgtgccc accagcagca ctcctgggac ctccacagtg   48540
gaccttgggt cagggactcc atcctccctc ccagccccaa ctgctggccc ctctcctg   48600
gtgccgttca ccctcaactt caccatcacc aacctgaagt acgaggagga catgcattgc   48660
cctggctcca ggaagttcaa caccacagag agtcctgca gagtctgct tggtcccatg   48720
ttcaagaaca ccagtgttgg ccctctgtac tctggctgca gactgacctc gctcaggtcc   48780
gagaaggatg gagcagccac tggagtggat gccatctgca cccaccgtgt tgaccccaaa   48840
agccctggag tggacaggga gcagctatac tgggagctga gccagctgac caatggcatc   48900
aaagagctgg gtccctacac cctggacaga aacagtctct atgtcaatgg tttcacccat   48960
cagacctctg cgcccaacac cagcactcct gggacctcca cagtgnacnt nggnaccctcn   49020
gggactccat cctccntccc cngccncaca tctgctggcc ctctcctggt gccattcacc   49080
ctcaacttca ccatcaccaa cctgcagtac gaggaggaca tgcatcaccc aggctccagg   49140
aagttcaaca ccacggagcg ggtcctgcag ggtctgcttg gtcccatgtt caagaacacc   49200
agtgtcggcc ttctgtactc tggctgcaga ctgaccttgc tcaggcctga agaatggg   49260
gcaaccactg gaatggatgc catctgcacc accgtcttg accccaaaag ccctggactg   49320
nacagngagc ngctntactg ggagctnagc canctgacca annncatcnn ngagctgggn   49380
ccctacaccc tggacaggna cagtctctat gtcaatggtt tcacccatcn ganctctgng   49440
cccaccacca gcactcctgg gacctccaca gtgnacntng gnacctcggg gactccatcc   49500
tccntcccn gccncacanc nnctgnccct ctcctgntnc cnttcaccnt caacttnacc   49560
```

```
atcaccaacc tgcantangn ggannacatg cnncncccng gntccaggaa gttcaacacc    49620
acngagaggg ttctgcaggg tctgctcaaa cccttgttca ggaatagcag tctggaatac    49680
ctctattcag gctgcagact agcctcactc aggccagaga aggatagctc agccatggca    49740
gtggatgcca tctgcacaca tcgccctgac cctgaagacc tcggactgga cagagagcga    49800
ctgtactggg agctgagcaa tctgacaaat ggcatccagg agctgggccc ctacaccctg    49860
gaccggaaca gtctctatgt caatggtttc acccatcgaa gctctatgcc caccaccagc    49920
actcctggga cctccacagt ggatgtggga acctcaggga ctccatcctc cagccccagc    49980
cccacgactg ctggccctct cctgatacca ttcaccctca acttcaccat caccaacctg    50040
cagtatgggg aggacatggg tcaccctggc tccaggaagt tcaacaccac agagagggtc    50100
ctgcagggtc tgcttggtcc catattcaag aacaccagtg ttggccctct gtactctggc    50160
tgcagactga cctctctcag gtctgagaag gatggagcag ccactggagt ggatgccatc    50220
tgcatccatc atcttgaccc caaaagccct ggactcaaca gagagcggct gtactgggag    50280
ctgagccaac tgaccaatgg catcaaagag ctgggcccct acaccctgga caggaacagt    50340
ctctatgtca atggtttcac ccatcggacc tctgtgccca ccaccagcac tcctgggacc    50400
tccacagtgg accttggaac ctcagggact ccattctccc tcccaagccc cgcaactgct    50460
ggccctctcc tggtgctgtt caccctcaac ttcaccatca ccaacctgaa gtatgaggag    50520
gacatgcatc gccctggctc caggaagttc aacaccactg agagggtcct gcagactctg    50580
cttggtccta tgttcaagaa caccagtgtt ggccttctgt actctggctg cagactgacc    50640
ttgctcaggt ccgagaagga tggagcagcc actgagtgg atgccatctg cacccaccgt    50700
cttgacccca aaagccctgg actgacagn gagcngctnt actgggagct nagccanctg    50760
accaannnca tcnnngagct gggnccctac acctggaca ggnacagtct ctatgtcaat    50820
ggtttcaccc atcnganctc tgngcccacc accagcactc ctgggacctc cacagtgnac    50880
ntnggnacct cnggactcc atcctccntc cccngccnca cancnnctgn ccctctcctg    50940
ntnccnttca ccntcaactt naccatcacc aacctgcant angngganna catgcnncnc    51000
ccnggntcca ggaagttcaa caccacngag agagtccttc agggtctgct caggcctgtg    51060
ttcaagaaca ccagtgttgg ccctctgtac tctggctgca gactgacctt gctcaggccc    51120
aagaaggatg gggcagccac caaagtggat gccatctgca cctaccgccc tgatcccaaa    51180
agccctggac tggacagaga gcagctatac tgggagctga ccagctaac ccacagcatc    51240 actgagctgg gccctacac ccaggacagg gacagtctct atgtcaatgg cttcacccat    51300
cggagctctg tgccaaccac cagtattcct gggacctctg cagtgcacct ggaaaccact    51360
gggactccat cctccttccc cggccacaca gagcctggcc ctctcctgat accattcact    51420
ttcaacttta ccatcaccaa cctgcgttat gaggaaaaca tgcaacaccc tggttccagg    51480
aagttcaaca ccacggagag ggttctgcag ggtctgctca cgcccttgtt caagaacacc    51540
agtgttggcc ctctgtactc tggctgcaga ctgaccttgc tcagacctga aagcaggag    51600 gcagccactg gagtggacac catctgtacc caccgcgttg atcccatcgg acctggactg    51660
gacagagagc ggctatactg ggagctgagc agctgacca acagcatcac agagctggga    51720
ccctacaccc tggataggga cagtctctat gtcgatggct tcaacccttg gagctctgtg    51780
ccaaccacca gcactcctgg gacctccaca gtgcacctgg caacctctgg gactccatcc    51840
cccctgcctg gccacacagc ccctgtccct ctcttgatac cattcaccct caactttacc    51900
```

```
atcaccgacc tgcattatga agaaaacatg caacaccctg gttccaggaa gttcaacacc    51960
acggagaggg ttctgcaggg tctgctcaag cccttgttca agagcaccag cgttggccct    52020
ctgtactctg gctgcagact gaccttgctc agacctgaga acatggggc agccactgga     52080 gtggacgcca tctgcaccct ccgccttgat cccactggtc ctggactgga cagagagcgg    52140
ctatactggg agctgagcca gctgaccaac agcatcacag agctgggacc ctacaccctg    52200
gatagggaca gtctctatgt caatggcttc aaccttgga gctctgtgcc aaccaccagc     52260
actcctggga cctccacagt gcacctggca acctctggga ctccatcctc cctgcctggc    52320
cacacaactg ctggccctct cctggtgccg ttcaccctca acttcaccat caccaacctg    52380
aagtacgagg aggacatgca ttgcccctggc tccaggaagt tcaacaccac agagagagtc   52440
ctgcagagtc tgcatggtcc catgttcaag aacaccagtg ttggccctct gtactctggc    52500
tgcagactga ccttgctcag gtccgagaag gatggagcag ccactggagt ggatgccatc    52560
tgcacccacc gtcttgaccc caaaagccct ggactgnaca ngagcngct ntactgggag     52620 ctnagccanc tgaccaannn catcnnngag ctgggncct acaccctgga caggnacagt    52680
ctctatgtca atggtttcac ccatcnganc tctgngccca ccaccagcac tcctgggacc    52740
tccacagtgn acntnggnac ctcngggact ccatcctccn tccccngcc cacancnnct    52800 gnccctctcc tgntnccntt caccntcaac ttnaccatca ccaacctgca ntangnggan    52860
nacatgcnnc ncccnggntc caggaagttc aacaccacng agngngtnct gcagggtctg   52920
ctnnnncccn tnttcaagaa cnccagtgtn ggccntctgt actctggctg cagactgacc    52980
tnnctcaggn cngagaagna tggngcagcc actggantgg atgccatctg canccaccnn   53040
cntnanccca aaagncctgg actgnacagn gagcngctnt actgggagct nagccanctg    53100
accaacagca tcacagagct gggaccctac accctggata gggacagtct ctatgtcaat    53160
ggtttcaccc atcgaagctc tatgcccacc accagtattc ctgggacctc tgcagtgcac    53220
ctggaaacct ctgggactcc agcctccctc cctggccaca cagcccctgg ccctctcctg    53280
gtgccattca ccctcaactt cactatcacc aacctgcagt atgaggagga catgcgtcac    53340
cctggttcca ggaagttcaa caccacggag agagtcctgc agggtctgct caagcccttg    53400
ttcaagagca ccagtgttgg ccctctgtac tctggctgca gactgacctt gctcaggcct    53460
gaaaaacgtg gggcagccac cggcgtggac catctgca ctcaccgcct tgaccctcta      53520
aaccctggac tgnacagnga gcngctntac tgggagctna gccanctgac caannncatc    53580
nnngagctgg gncctacac cctggacagg nacagtctct atgtcaatgg tttcaccccat    53640 cnganctctg ngcccaccac cagcactcct gggacctcca cagtgnacnt nggnacctcn    53700
gggactccat cctccntccc cngcncaca ncnnctgncc ctctcctgnt nccnttcacc     53760
ntcaacttna ccatcaccaa cctgcantan ngggannaca tgcnncnccc nggntccagg    53820
aagttcaaca ccacngagng ngtnctgcag ggtctgctnn nncccntntt caagaacncc    53880
agtgtnggcc ntctgtactc tggctgcaga ctgacctnnc tcaggncnga agnatggn     53940 gcagccactg gantggatgc catctgcanc caccnncntn ancccaaaag ncctggactg    54000
nacagngagc ngctntactg ggagctnagc canctgacca annncatcnn ngagctgggn   54060
ccctacaccc tggacaggna cagtctctat gtcaatggtt ttcacccctcg agctctgtg    54120 ccaaccacca gcactcctgg gacctccaca gtgcacctgg caacctctgg gactccatcc    54180
tccctgcctg gccacacagc ccctgtccct ctcttgatac cattcaccct caactttacc    54240
atcaccaacc tgcattatga agaaaacatg caacaccctg gttccaggaa gttcaacacc    54300
```

```
acggagcggg tcctgcaggg tctgcttggt cccatgttca agaacacaag tgtcggcctt    54360
ctgtactctg gctgcagact gaccttgctc aggcctgaga agaatggggc agccactgga    54420
atggatgcca tctgcagcca ccgtcttgac cccaaaagcc ctggactgna cagngagcng    54480
ctntactggg agctnagcca nctgaccaan nncatcnnng agctgggncc ctacaccctg    54540
gacaggnaca gtctctatgt caatggtttc acccatcnga nctctgngcc caccaccagc    54600
actcctggga cctccacagt gnacntnggn acctcnggga ctccatcctc cntccccngc    54660
cncacancnn ctgnccctct cctgntnccn ttcaccntca acttnaccat caccaacctg    54720
cantangngg annacatgcn ncncccnggn tccaggaagt tcaacaccac ngagngngtn    54780
ctgcagggtc tgctnnnncc cntnttcaag aacnccagtg tnggccntct gtactctggc    54840
tgcagactga cctnnctcag gncngagaag natggngcag ccactggant ggatgccatc    54900
tgcanccacc nncntnancc caaaagncct ggactgnaca gngagcngct ntactgggag    54960
ctnagccanc tgaccaannn catcnnngag ctgggnccct acaccctgga caggnacagt    55020
ctctatgtca atggtttcac ccatcagaac tctgtgccca ccaccagtac tcctgggacc    55080
tccacagtgt actgggcaac cactgggact ccatcctcct tccccggcca cacagagcct    55140
ggccctctcc tgataccatt cactttcaac tttaccatca ccaacctgca ttatgaggaa    55200
aacatgcaac ccctggttc caggaagttc aacaccacgg agagggtct gcagggtctg    55260 ctcacgccct tgttcaagaa caccagtgtt ggccctctgt actctggctg cagactgacc    55320
ttgctcagac ctgagaagca ggaggcagcc actggagtgg acaccatctg tacccaccgc    55380
gttgatccca tcggacctgg actgnacagn gagcngctnt actgggagct nagccanctg    55440
accaannnca tcnnngagct gggnccctac accctggaca ggnacagtct ctatgtcaat    55500
ggtttcaccc atcnganctc tgngcccacc accagcactc ctgggacctc cacagtgnac    55560
ntnggnacct cngggactcc atcctccntc cccngccnca cancnnctgn ccctctcctg    55620
ntnccnttca ccntcaactt naccatcacc aacctgcant angngganna catgcnncnc    55680 ccggntcca ggaagttcaa caccacngag ngngtnctgc agggtctgct nnnnccntn    55740 ttcaagaacn ccagtgtngg ccntctgtac tctggctgca gactgacctn nctcaggncn    55800
gagaagnatg gngcagccac tggantggat gccatctgca nccacnncn tnancccaaa    55860 agncctggac tgnacagnga gcngctntac tgggagctna gccanctgac caannncatc    55920
nnngagctgg gnccctacac cctggacagg nacagtctct atgtcaatgg tttcacccat    55980
cggagctctg tgccaaccac cagcagtcct ggaccca cagtgcacct ggcaacctct    56040
gggactccat cctccctgcc tggccacaca gccctgtcc ctctcttgat accattcacc    56100
ctcaacttta ccatcaccaa cctgcattat gaagaaaaca tgcaaccc tggttccagg    56160 aagttcaaca ccacggagag ggttctgcag gtctgctca gcccttgtt caagagcacc    56220 agtgttggcc ctctgtactc tggctgcaga ctgaccttgc tcagacctga gaacatggg    56280 gcagccactg gagtggacgc catctgcacc ctccgccttg atcccactgg tcctggactg    56340
nacagngagc ngctntactg ggagctnagc canctgacca anncatcnn ngagctgggn    56400 ccctacaccc tggacaggna cagtctctat gtcaatggtt tcacccatcn ganctctgng    56460
cccaccacca gcactcctgg gacctccaca gtgnacntng gnacctcngg gactccatcc    56520
tccntccccn gccncacanc nnctgnccct ctcctgntnc cnttcaccnt caacttnacc    56580
atcaccaacc tgcantangn ggannacatg cnncncccng gntccaggaa gttcaacacc    56640
```

```
acngagngng tnctgcaggg tctgctnnnn cccntnttca agaacnccag tgtnggccnt    56700
ctgtactctg gctgcagact gacctnnctc aggncngaga agnatggngc agccactgga    56760
ntggatgcca tctgcancca ccnncntnan cccaaaagnc ctggactgna cagngagcng    56820
ctntactggg agctnagcca nctgaccaan nncatcnnng agctgggncc ctacaccctg    56880
gacaggnaca gtctctatgt caatggtttc acccatcgga cctctgtgcc caccaccagc    56940
actcctggga cctccacagt gcacctggca acctctggga ctccatcctc cctgcctggc    57000
cacacagccc ctgtccctct cttgatacca ttcaccctca actttaccat caccaacctg    57060
cagtatgagg aggacatgca tcgccctgga tctaggaagt tcaacaccac agagagggtc    57120
ctgcagggtc tgcttagtcc cattttcaag aactccagtg ttggccctct gtactctggc    57180
tgcagactga cctctctcag gcccgagaag gatgggcag caactggaat ggatgctgtc    57240
tgcctctacc accctaatcc caaaagacct gggctggaca gagagcagct gtactgcgag    57300
ctaagccagc tgacccacaa catcactgag ctgggcccct acagcctgga cagggacagt    57360
ctctatgtca atggtttcac ccatcagaac tctgtgccca ccaccagtac tcctgggacc    57420
tccacagtgt actgggcaac cactgggact ccatcctcct tccccggcca cacancnnct    57480
gnccctctcc tgntnccntt caccntcaac ttnaccatca ccaacctgca ntangnggan    57540
nacatgcnnc nccnggntc caggaagttc aacaccacng agngngtnct gcagggtctg    57600 ctnnnnccc tnttcaagaa cnccagtgtn ggccntctgt actctggctg cagactgacc    57660
tnnctcaggn cngagaagna tggncagcc actggantgg atgccatctg canccaccnn    57720
cntnanccca aaagncctgg actgnacagn gagcngctnt actgggagct nagccanctg    57780
accaannnca tcnnngagct gggncnctac acctggaca ggnacagtct ctatgtcaat    57840
ggtttcaccc attggagctc tgggctcacc accagcactc cttggacttc cacagttgac    57900
cttggaacct caggactcc atccccgtc ccagcccca caactgctgg ccctctcctg    57960
gtgccattca ccctaaactt caccatcacc aacctgcagt atgaggagga catgcatcgc    58020
cctggatcta ggaagttcaa cgccacagag agggtcctgc agggtctgct tagtcccata    58080
ttcaagaaca ccagtgttgg ccctctgtac tctggctgca gactgacctt gctcagacct    58140
gagaagcagg aggcagccac tggagtggac accatctgta cccaccgcgt tgatcccatc    58200
ggacctggac tgnacagnga gcngctntac tgggagctna gccanctgac caannncatc    58260
nnngagctgg gncctacac cctggacagg nacagtctct atgtcaatgg tttcacccat    58320
cnganctctg ngcccaccac cagcactcct gggacctcca cagtgnacnt nggnacctcn    58380
gggactccat cctccntccc cngccncaca ncnnctgncc ctctcctgnt nccnttcacc    58440
ntcaacttna ccatcaccaa cctgcantan gnggannaca tgcnncnccc nggntccagg    58500
aagttcaaca ccacngagng ngtnctgcag ggtctgctnn nccntnttt caagaacncc    58560 agtgtnggcc ntctgtactc tggctgcaga ctgacctnnc tcaggncnga aagnatggn    58620 gcagccactg gantggatgc catctgcanc caccnncntn ancccaaaag ncctggactg    58680
nacagngagc ngctntactg ggagctnagc canctgacca annncatcnn ngagctgggn    58740
ccctacaccc tggacaggna cagtctctat gtcaatggtt tcacccatcg agctttggg    58800 ctcaccacca gcactccttg gacttccaca gttgaccttg aacctcagg actccatcc    58860 cccgtcccca gccccacaac tgctggccct cctggtgc cattcaccct aaacttcacc    58920
atcaccaacc tgcagtatga ggaggacatg catcgccctg gctccaggaa gttcaacacc    58980
acggagaggg tccttcaggg tctgcttacg cccttgttca ggaacaccag tgtcagctct    59040
```

```
ctgtactctg gttgcagact gaccttgctc aggcctgaga aggatggggc agccaccaga   59100
gtggatgctg tctgcaccca tcgtcctgac cccaaaagcc ctggactgna cagngagcng   59160
ctntactggg agctnagcca nctgaccaan nncatcnnng agctgggncc ctacaccctg   59220
gacaggnaca gtctctatgt caatggtttc acccatcnga nctctgngcc caccaccagc   59280
actcctggga cctccacagt gnacntnggn acctcnggga ctccatcctc cntccccngc   59340
cncacancnn ctgnccctct cctgntnccn ttcacntca acttnaccat caccaacctg   59400
cantangngg annacatgcn ncncccnggn tccaggaagt tcaacaccac ngagngngtn   59460
ctgcagggtc tgctnnnncc cntnttcaag aacnccagtg tnggccntct gtactctggc   59520
tgcagactga cctnnctcag gncngagaag natggngcag ccactggant ggatgccatc   59580
tgcanccacc nncntnancc caaaagncct ggactgnaca gngagcngct ntactgggag   59640
ctnagccanc tgaccaannn catcnnngag ctgggnccct acaccctgga caggnacagt   59700
ctctatgtca atggtttcac ccattggatc cctgtgccca ccagcagcac tcctgggacc   59760
tccacagtgg accttgggtc agggactcca tcctccctcc ccagccccac aactgctggc   59820
cctctcctgg taccattcac cctcaacttc accatcacca acctgcagta tggggaggac   59880
atgggtcacc ctggctccag gaagttcaac accacagaga gggtcctgca gggtctgctt   59940
ggtcccatat tcaagaacac cagtgttggc cctctgtact ctggctgcag actgacctct   60000
ctcaggtccg agaaggatgg agcagccact ggagtggatg ccatctgcat ccatcatctt   60060
gaccccaaaa gccctggact gnacagngag cngctntact gggagctnag ccanctgacc   60120
aannncatcn nngagctggg ncctacacc ctggacaggn acagtctcta tgtcaatggt   60180
ttcacccatc nganctctgn gcccaccacc agcactcctg ggacctccac agtgnacntn   60240
ggnacctcng ggactccatc ctccntcccc ngccncacan cnnctgnccc tctcctgntn   60300
ccnttcaccn tcaacttnac catcaccaac ctgcantang nggannacat gcnncnccn   60360
ggntccagga agttcaacac cacngagngn gtnctgcagg gtctgctnnn ncccntnttc   60420
aagaacncca gtgtnggccn tctgtactct ggctgcagac tgacctnnct caggncngag   60480
aagnatgggn cagccactgg antggatgcc atctgcancc accnncntna ncccaaaagn   60540
cctggactgn acagngagcn gctntactgg gagctnagcc anctgaccaa nnncatcnnn   60600
gagctgggnc cctacaccct ggacaggnac agtctctatg tcaatggttt cacccatcag   60660
acctttgcgc caacaccag cactcctggg acctccacag tggaccttgg gacctcaggg   60720
actccatcct ccctccccag ccctacatct gctggccctc tcctggtgcc attcaccctc   60780
aacttcacca tcaccaacct gcagtacgag gaggacatgc atcacccagg ctccaggaag   60840
ttcaacacca cggagcgggt cctgcagggt ctgcttggtc ccatgttcaa gaacaccagt   60900
gtcggccttc tgtactctgg ctgcagactg accttgctca ggcctgagaa gaatggggca   60960
gccaccagag tggatgctgt ctgcacccat cgtcctgacc ccaaaagccc tggactgnac   61020
agngagcngc tntactggga gctnagccan ctgaccaann ncatcnnnga gctgggnccc   61080
tacaccctgg acaggnacag tctctatgtc aatggtttca cccatcngan ctctgngccc   61140
accaccagca ctcctgggac ctccacagtg nacntnggna cctcgggac tccatcctcc   61200
ntccccngcc ncacagcccc tgtccctctc ttgataccat tcaccctcaa ctttaccatc   61260
accaacctgc attatgaaga aaacatgcaa caccctggtt ccaggaagtt caacaccacg   61320
gagagggttc tgcagggtct gctcaagccc ttgttcaaga gcaccagcgt tggccctctg   61380
```

```
tactctggct gcagactgac cttgctcaga cctgagaaac atggggcagc cactggagtg    61440
gacgccatct gcaccctccg ccttgatccc actggtcctg gactggacag agagcggcta    61500
tactgggagc tgagccagct gaccaacagc gttacagagc tgggcccta  caccctggac     61560 agggacagtc tctatgtcaa tggcttcacc cagcggagc  ctgtgccaac caccagtatt    61620
cctgggacct ctgcagtgca cctggaaacc tctgggactc cagcctccct ccctggccac    61680
acagcccctg ccctctcct  ggtgccattc accctcaact tcactatcac caacctgcag    61740
tatgaggtgg acatgcgtca ccctggttcc aggaagttca acaccacgga gagagtcctg    61800
cagggtctgc tcaagccctt gttcaagagc accagtgttg ccctctgta  ctctggctgc    61860 agactgacct tgctcaggcc tgaaaaacgt ggggcagcca ccggcgtgga caccatctgc    61920
actcaccgcc ttgaccctct aaaccctgga ctggacagag agcagctata ctgggagctg    61980
agcaaactga cccgtggcat catcgagctg ggcccctacc tcctggacag aggcagtctc    62040
tatgtcaatg gtttcaccca tcggaacttt gtgcccatca ccagcactcc tgggacctcc    62100
acagtacacc taggaacctc tgaaactcca tcctccctac ctagacccat agtgcctggc    62160
cctctcctgg tgccattcac cctcaacttc accatcacca acttgcagta tgaggaggcc    62220
atgcgacacc ctggctccag gaagttcaat accacgagag gggtcctaca gggtctgctc    62280
aggcccttgt tcaagaatac cagtatcggc cctctgtact ccagctgcag actgaccttg    62340
ctcaggccag agaaggacaa ggcagccacc agagtggatg ccatctgtac ccaccaccct    62400
gaccctcaaa gccctggact gaacagagag cagctgtact gggagctgag ccagctgacc    62460
cacggcatca ctgagctggg ccctacacc  ctggacaggg acagtctcta tgtcgatggt    62520
ttcactcatt ggagcccat  accgaccacc agcactcctg gacctccat  agtgaacctg    62580 ggaacctctg gatcccacc  ttccctccct gaaactacan cnnctgnccc tctcctgntn    62640
ccnttcaccn tcaacttnac catcaccaac ctgcantang nggannacat gcnncnccn     62700 ggntccagga agttcaacac cacngagagg gttctgcagg gtctgctcaa gcccttgttc    62760
aagagcacca gtgttggccc tctgtattct ggctgcagac tgaccttgct caggcctgag    62820
aaggacggag tagccaccag agtggacgcc atctgcaccc accgccctga ccccaaaatc    62880
cctgggctag acagacagca gctatactgg gagctgagcc agctgaccca cagcatcact    62940
gagctgggac cctacaccct ggatagggac agtctctatg tcaatggttt cacccagcgg    63000
agctctgtgc ccaccaccag cactcctggg actttcacag tacagccgga aacctctgag    63060
actccatcat ccctccctgg ccccacagcc actggccctg tcctgctgcc attcaccctc    63120
aattttacca tcactaacct gcagtatgag gaggacatgc atcgccctgg ctccaggaag    63180
ttcaacacca cggagagggt ccttcagggt ctgcttatgc ccttgttcaa gaacaccagt    63240
gtcagctctc tgtactctgg ttgcagactg accttgctca ggcctgagaa ggatggggca    63300
gccaccagag tggatgctgt ctgcacccat cgtcctgacc ccaaaagccc tggactggac    63360
agagagcggc tgtactggaa gctgagccag ctgacccacg catcactga  gctgggcccc    63420 tacaccctgg acaggcacag tctctatgtc aatggtttca cccatcagag ctctatgacg    63480
accaccagaa ctcctgatac ctccacaatg cacctggcaa cctcgagaac tccagcctcc    63540
ctgtctggac ctacgaccgc cagccctctc ctggtgctat tcacaattaa cttcaccatc    63600
actaacctgc ggtatgagga gaacatgcat caccctggct ctagaaagtt taacaccacg    63660
gagagagtcc ttcagggtct gctcaggcct gtgttcaaga acaccagtgt tggccctctg    63720
tactctggct gcagactgac cttgctcagg cccaagaagg atggggcagc caccaaagtg    63780
```

```
gatgccatct gcacctaccg ccctgatccc aaaagccctg gactggacag agagcagcta   63840
tactgggagc tgagccagct aacccacagc atcactgagc tgggcccta caccctggac   63900 agggacagtc tctatgtcaa tggtttcaca cagcggagct ctgtgccac cactagcatt   63960 cctgggaccc ccacagtgga cctgggaaca tctgggactc cagtttctaa acctggtccc   64020
tcggctgcca gccctctcct ggtgctattc actctcaact tcaccatcac caacctgcgg   64080
tatgaggaga acatgcagca ccctggctcc aggaagttca acaccacgga gagggtcctt   64140
cagggcctgc tcaggtccct gttcaagagc accagtgttg ccctctgta ctctggctgc   64200 agactgactt tgctcaggcc tgaaaaggat gggacagcca ctggagtgga tgccatctgc   64260
acccaccacc ctgaccccaa aagccctagg ctggacagag agcagctgta ttgggagctg   64320
agccagctga cccacaatat cactgagctg ggccactatg ccctggacaa cgacagcctc   64380
tttgtcaatg gtttcactca tcggagctct gtgtccacca ccagcactcc tgggaccccc   64440
acagtgtatc tgggagcatc taagactcca gcctcgatat ttgggccttc agctgccagc   64500
catctcctga tactattcac cctcaacttc accatcacta acctgcggta tgaggagaac   64560
atgtggcctg gctccaggaa gttcaacact acagagaggg tccttcaggg cctgctaagg   64620
cccttgttca agaacaccag tgttggccct ctgtactctg gctccaggct gaccttgctc   64680
aggccagaga agatgggga agccaccgga gtggatgcca tctgcaccca ccgcctgac   64740 cccacaggcc ctgggctgga cagagagcag ctgtatttgg agctgagcca gctgaccac   64800 agcatcactg agctgggccc ctacacactg gacagggaca gtctctatgt caatggtttc   64860
acccatcgga gctctgtacc caccaccagc accggggtgg tcagcgagga gccattcaca   64920
ctgaacttca ccatcaacaa cctgcgctac atggcggaca tgggccaacc cggctccctc   64980
aagttcaaca tcacagacaa cgtcatgaag cacctgctca gtcctttgtt ccagaggagc   65040
agcctgggtg cacggtacac aggctgcagg gtcatcgcac taaggtctgt gaagaacggt   65100
gctgagacac gggtggacct cctctgcacc tacctgcagc ccctcagcgg cccaggtctg   65160
cctatcaagc aggtgttcca tgagctgagc cagcagaccc atggcatcac ccggctgggc   65220
ccctactctc tggacaaaga cagcctctac cttaacggtt acaatgaacc tggtctagat   65280
gagcctccta caactcccaa gccagccacc acattcctgc ctcctctgtc agaagccaca   65340
acagccatgg ggtaccacct gaagaccctc acactcaact tcaccatctc caatctccag   65400
tattcaccag atatgggcaa gggctcagct acattcaact ccaccgaggg ggtccttcag   65460
cacctgctca gacccttgtt ccagaagagc agcatgggcc ccttctactt gggttgcaa   65520 ctgatctccc tcaggcctga gaaggatggg gcagccactg gtgtggacac cacctgcacc   65580
taccaccctg accctgtggg ccccgggctg gacatacagc agctttactg ggagctgagt   65640
cagctgaccc atggtgtcac ccaactgggc ttctatgtcc tggacaggga tagcctcttc   65700
atcaatggct atgcacccca gaatttatca atccggggcg agtaccagat aaatttccac   65760
attgtcaact ggaacctcag taatccagac cccacatcct cagagtacat caccctgctg   65820
agggacatcc aggacaaggt caccacactc tacaaaggca gtcaactaca tgacacattc   65880
cgcttctgcc tggtcaccaa cttgacgatg gactccgtgt tggtcactgt caaggcattg   65940
ttctcctcca atttggaccc cagcctggtg gagcaagtct ttctagataa gaccctgaat   66000
gcctcattcc attggctggg ctccacctac cagttggtgg acatccatgt gacagaaatg   66060
gagtcatcag tttatcaacc aacaagcagc tccagcaccc agcacttcta cctgaatttc   66120
```

-continued

```
accatcacca acctaccata ttcccaggac aaagcccagc caggcaccac caattaccag    66180
aggaacaaaa ggaatattga ggatgcgctc aaccaactct tccgaaacag cagcatcaag    66240
agttattttt ctgactgtca agtttcaaca ttcaggtctg tccccaacag gcaccacacc    66300
ggggtggact ccctgtgtaa cttctcgcca ctggctcgga gagtagacag agttgccatc    66360
tatgaggaat ttctgcggat gacccggaat ggtacccagc tgcagaactt cacgctggac    66420
aggagcagtg tccttgtgga tgggtattct cccaacagaa atgagcgctt aactgggaat    66480
tctgaccttc ccttctgggc tgtcatcctc atcggcttgg caggactcct gggactcatc    66540
acatgcctga tctgcggtgt cctggtgacc acccgccggc ggaagaagga aggagaatac    66600
aacgtccagc aacagtgccc aggctactac cagtcacacc tagacctgga ggatctgcaa    66660
tgactggaac ttgccggtgc ctggggtgcc tttcccccag ccagggtcca aagaagcttg    66720
gctggggcag aaataaacca tattggtcgg aaaaaaaaaa aaaaa                    66765
```

```
<210> SEQ ID NO 5
<211> LENGTH: 22152
<212> TYPE: PRT
<213> ORGANISM: Homo sapiens
<220> FEATURE:
<221> NAME/KEY: misc_feature
<222> LOCATION: (13880)..(13880)
<223> OTHER INFORMATION: Xaa can be any naturally occurring amino acid
<220> FEATURE:
<221> NAME/KEY: misc_feature
<222> LOCATION: (13887)..(13887)
<223> OTHER INFORMATION: Xaa can be any naturally occurring amino acid
<220> FEATURE:
<221> NAME/KEY: misc_feature
<222> LOCATION: (13890)..(13891)
<223> OTHER INFORMATION: Xaa can be any naturally occurring amino acid
<220> FEATURE:
<221> NAME/KEY: misc_feature
<222> LOCATION: (13893)..(13893)
<223> OTHER INFORMATION: Xaa can be any naturally occurring amino acid
<220> FEATURE:
<221> NAME/KEY: misc_feature
<222> LOCATION: (13899)..(13899)
<223> OTHER INFORMATION: Xaa can be any naturally occurring amino acid
<220> FEATURE:
<221> NAME/KEY: misc_feature
<222> LOCATION: (13903)..(13903)
<223> OTHER INFORMATION: Xaa can be any naturally occurring amino acid
<220> FEATURE:
<221> NAME/KEY: misc_feature
<222> LOCATION: (13911)..(13918)
<223> OTHER INFORMATION: Xaa can be any naturally occurring amino acid
<220> FEATURE:
<221> NAME/KEY: misc_feature
<222> LOCATION: (13926)..(13926)
<223> OTHER INFORMATION: Xaa can be any naturally occurring amino acid
<220> FEATURE:
<221> NAME/KEY: misc_feature
<222> LOCATION: (13928)..(13928)
<223> OTHER INFORMATION: Xaa can be any naturally occurring amino acid
<220> FEATURE:
<221> NAME/KEY: misc_feature
<222> LOCATION: (13930)..(13930)
<223> OTHER INFORMATION: Xaa can be any naturally occurring amino acid
<220> FEATURE:
<221> NAME/KEY: misc_feature
<222> LOCATION: (13936)..(13938)
<223> OTHER INFORMATION: Xaa can be any naturally occurring amino acid
<220> FEATURE:
<221> NAME/KEY: misc_feature
<222> LOCATION: (13940)..(13941)
<223> OTHER INFORMATION: Xaa can be any naturally occurring amino acid
<220> FEATURE:
<221> NAME/KEY: misc_feature
<222> LOCATION: (14569)..(14571)
<223> OTHER INFORMATION: Xaa can be any naturally occurring amino acid
```

```
<220> FEATURE:
<221> NAME/KEY: misc_feature
<222> LOCATION: (14575)..(14575)
<223> OTHER INFORMATION: Xaa can be any naturally occurring amino acid
<220> FEATURE:
<221> NAME/KEY: misc_feature
<222> LOCATION: (14587)..(14587)
<223> OTHER INFORMATION: Xaa can be any naturally occurring amino acid
<220> FEATURE:
<221> NAME/KEY: misc_feature
<222> LOCATION: (14591)..(14591)
<223> OTHER INFORMATION: Xaa can be any naturally occurring amino acid
<220> FEATURE:
<221> NAME/KEY: misc_feature
<222> LOCATION: (14593)..(14594)
<223> OTHER INFORMATION: Xaa can be any naturally occurring amino acid
<220> FEATURE:
<221> NAME/KEY: misc_feature
<222> LOCATION: (14725)..(14727)
<223> OTHER INFORMATION: Xaa can be any naturally occurring amino acid
<220> FEATURE:
<221> NAME/KEY: misc_feature
<222> LOCATION: (14731)..(14731)
<223> OTHER INFORMATION: Xaa can be any naturally occurring amino acid
<220> FEATURE:
<221> NAME/KEY: misc_feature
<222> LOCATION: (14743)..(14743)
<223> OTHER INFORMATION: Xaa can be any naturally occurring amino acid
<220> FEATURE:
<221> NAME/KEY: misc_feature
<222> LOCATION: (14747)..(14747)
<223> OTHER INFORMATION: Xaa can be any naturally occurring amino acid
<220> FEATURE:
<221> NAME/KEY: misc_feature
<222> LOCATION: (14749)..(14750)
<223> OTHER INFORMATION: Xaa can be any naturally occurring amino acid
<220> FEATURE:
<221> NAME/KEY: misc_feature
<222> LOCATION: (15661)..(15663)
<223> OTHER INFORMATION: Xaa can be any naturally occurring amino acid
<220> FEATURE:
<221> NAME/KEY: misc_feature
<222> LOCATION: (15667)..(15667)
<223> OTHER INFORMATION: Xaa can be any naturally occurring amino acid
<220> FEATURE:
<221> NAME/KEY: misc_feature
<222> LOCATION: (15679)..(15679)
<223> OTHER INFORMATION: Xaa can be any naturally occurring amino acid
<220> FEATURE:
<221> NAME/KEY: misc_feature
<222> LOCATION: (15683)..(15683)
<223> OTHER INFORMATION: Xaa can be any naturally occurring amino acid
<220> FEATURE:
<221> NAME/KEY: misc_feature
<222> LOCATION: (15685)..(15686)
<223> OTHER INFORMATION: Xaa can be any naturally occurring amino acid
<220> FEATURE:
<221> NAME/KEY: misc_feature
<222> LOCATION: (15972)..(15974)
<223> OTHER INFORMATION: Xaa can be any naturally occurring amino acid
<220> FEATURE:
<221> NAME/KEY: misc_feature
<222> LOCATION: (15978)..(15978)
<223> OTHER INFORMATION: Xaa can be any naturally occurring amino acid
<220> FEATURE:
<221> NAME/KEY: misc_feature
<222> LOCATION: (15990)..(15990)
<223> OTHER INFORMATION: Xaa can be any naturally occurring amino acid
<220> FEATURE:
<221> NAME/KEY: misc_feature
<222> LOCATION: (15994)..(15994)
<223> OTHER INFORMATION: Xaa can be any naturally occurring amino acid
<220> FEATURE:
<221> NAME/KEY: misc_feature
<222> LOCATION: (15996)..(15997)
<223> OTHER INFORMATION: Xaa can be any naturally occurring amino acid
<220> FEATURE:
<221> NAME/KEY: misc_feature
<222> LOCATION: (16015)..(16015)
```

```
<223> OTHER INFORMATION: Xaa can be any naturally occurring amino acid
<220> FEATURE:
<221> NAME/KEY: misc_feature
<222> LOCATION: (16017)..(16017)
<223> OTHER INFORMATION: Xaa can be any naturally occurring amino acid
<220> FEATURE:
<221> NAME/KEY: misc_feature
<222> LOCATION: (16020)..(16020)
<223> OTHER INFORMATION: Xaa can be any naturally occurring amino acid
<220> FEATURE:
<221> NAME/KEY: misc_feature
<222> LOCATION: (16025)..(16025)
<223> OTHER INFORMATION: Xaa can be any naturally occurring amino acid
<220> FEATURE:
<221> NAME/KEY: misc_feature
<222> LOCATION: (16037)..(16037)
<223> OTHER INFORMATION: Xaa can be any naturally occurring amino acid
<220> FEATURE:
<221> NAME/KEY: misc_feature
<222> LOCATION: (16040)..(16041)
<223> OTHER INFORMATION: Xaa can be any naturally occurring amino acid
<220> FEATURE:
<221> NAME/KEY: misc_feature
<222> LOCATION: (16045)..(16045)
<223> OTHER INFORMATION: Xaa can be any naturally occurring amino acid
<220> FEATURE:
<221> NAME/KEY: misc_feature
<222> LOCATION: (16048)..(16049)
<223> OTHER INFORMATION: Xaa can be any naturally occurring amino acid
<220> FEATURE:
<221> NAME/KEY: misc_feature
<222> LOCATION: (16051)..(16054)
<223> OTHER INFORMATION: Xaa can be any naturally occurring amino acid
<220> FEATURE:
<221> NAME/KEY: misc_feature
<222> LOCATION: (16057)..(16058)
<223> OTHER INFORMATION: Xaa can be any naturally occurring amino acid
<220> FEATURE:
<221> NAME/KEY: misc_feature
<222> LOCATION: (16065)..(16065)
<223> OTHER INFORMATION: Xaa can be any naturally occurring amino acid
<220> FEATURE:
<221> NAME/KEY: misc_feature
<222> LOCATION: (16072)..(16072)
<223> OTHER INFORMATION: Xaa can be any naturally occurring amino acid
<220> FEATURE:
<221> NAME/KEY: misc_feature
<222> LOCATION: (16075)..(16076)
<223> OTHER INFORMATION: Xaa can be any naturally occurring amino acid
<220> FEATURE:
<221> NAME/KEY: misc_feature
<222> LOCATION: (16078)..(16078)
<223> OTHER INFORMATION: Xaa can be any naturally occurring amino acid
<220> FEATURE:
<221> NAME/KEY: misc_feature
<222> LOCATION: (16084)..(16084)
<223> OTHER INFORMATION: Xaa can be any naturally occurring amino acid
<220> FEATURE:
<221> NAME/KEY: misc_feature
<222> LOCATION: (16088)..(16088)
<223> OTHER INFORMATION: Xaa can be any naturally occurring amino acid
<220> FEATURE:
<221> NAME/KEY: misc_feature
<222> LOCATION: (16376)..(16376)
<223> OTHER INFORMATION: Xaa can be any naturally occurring amino acid
<220> FEATURE:
<221> NAME/KEY: misc_feature
<222> LOCATION: (16383)..(16383)
<223> OTHER INFORMATION: Xaa can be any naturally occurring amino acid
<220> FEATURE:
<221> NAME/KEY: misc_feature
<222> LOCATION: (16386)..(16387)
<223> OTHER INFORMATION: Xaa can be any naturally occurring amino acid
<220> FEATURE:
<221> NAME/KEY: misc_feature
<222> LOCATION: (16389)..(16389)
<223> OTHER INFORMATION: Xaa can be any naturally occurring amino acid
<220> FEATURE:
<221> NAME/KEY: misc_feature
```

```
<222> LOCATION: (16395)..(16395)
<223> OTHER INFORMATION: Xaa can be any naturally occurring amino acid
<220> FEATURE:
<221> NAME/KEY: misc_feature
<222> LOCATION: (16399)..(16399)
<223> OTHER INFORMATION: Xaa can be any naturally occurring amino acid
<220> FEATURE:
<221> NAME/KEY: misc_feature
<222> LOCATION: (16407)..(16414)
<223> OTHER INFORMATION: Xaa can be any naturally occurring amino acid
<220> FEATURE:
<221> NAME/KEY: misc_feature
<222> LOCATION: (16422)..(16422)
<223> OTHER INFORMATION: Xaa can be any naturally occurring amino acid
<220> FEATURE:
<221> NAME/KEY: misc_feature
<222> LOCATION: (16424)..(16424)
<223> OTHER INFORMATION: Xaa can be any naturally occurring amino acid
<220> FEATURE:
<221> NAME/KEY: misc_feature
<222> LOCATION: (16426)..(16426)
<223> OTHER INFORMATION: Xaa can be any naturally occurring amino acid
<220> FEATURE:
<221> NAME/KEY: misc_feature
<222> LOCATION: (16432)..(16434)
<223> OTHER INFORMATION: Xaa can be any naturally occurring amino acid
<220> FEATURE:
<221> NAME/KEY: misc_feature
<222> LOCATION: (16436)..(16437)
<223> OTHER INFORMATION: Xaa can be any naturally occurring amino acid
<220> FEATURE:
<221> NAME/KEY: misc_feature
<222> LOCATION: (16439)..(16441)
<223> OTHER INFORMATION: Xaa can be any naturally occurring amino acid
<220> FEATURE:
<221> NAME/KEY: misc_feature
<222> LOCATION: (16445)..(16445)
<223> OTHER INFORMATION: Xaa can be any naturally occurring amino acid
<220> FEATURE:
<221> NAME/KEY: misc_feature
<222> LOCATION: (16457)..(16457)
<223> OTHER INFORMATION: Xaa can be any naturally occurring amino acid
<220> FEATURE:
<221> NAME/KEY: misc_feature
<222> LOCATION: (16461)..(16461)
<223> OTHER INFORMATION: Xaa can be any naturally occurring amino acid
<220> FEATURE:
<221> NAME/KEY: misc_feature
<222> LOCATION: (16463)..(16464)
<223> OTHER INFORMATION: Xaa can be any naturally occurring amino acid
<220> FEATURE:
<221> NAME/KEY: misc_feature
<222> LOCATION: (16844)..(16844)
<223> OTHER INFORMATION: Xaa can be any naturally occurring amino acid
<220> FEATURE:
<221> NAME/KEY: misc_feature
<222> LOCATION: (16851)..(16851)
<223> OTHER INFORMATION: Xaa can be any naturally occurring amino acid
<220> FEATURE:
<221> NAME/KEY: misc_feature
<222> LOCATION: (16854)..(16855)
<223> OTHER INFORMATION: Xaa can be any naturally occurring amino acid
<220> FEATURE:
<221> NAME/KEY: misc_feature
<222> LOCATION: (16857)..(16857)
<223> OTHER INFORMATION: Xaa can be any naturally occurring amino acid
<220> FEATURE:
<221> NAME/KEY: misc_feature
<222> LOCATION: (16863)..(16863)
<223> OTHER INFORMATION: Xaa can be any naturally occurring amino acid
<220> FEATURE:
<221> NAME/KEY: misc_feature
<222> LOCATION: (16867)..(16867)
<223> OTHER INFORMATION: Xaa can be any naturally occurring amino acid
<220> FEATURE:
<221> NAME/KEY: misc_feature
<222> LOCATION: (16875)..(16882)
<223> OTHER INFORMATION: Xaa can be any naturally occurring amino acid
<220> FEATURE:
```

```
<221> NAME/KEY: misc_feature
<222> LOCATION: (16890)..(16890)
<223> OTHER INFORMATION: Xaa can be any naturally occurring amino acid
<220> FEATURE:
<221> NAME/KEY: misc_feature
<222> LOCATION: (16892)..(16892)
<223> OTHER INFORMATION: Xaa can be any naturally occurring amino acid
<220> FEATURE:
<221> NAME/KEY: misc_feature
<222> LOCATION: (16894)..(16894)
<223> OTHER INFORMATION: Xaa can be any naturally occurring amino acid
<220> FEATURE:
<221> NAME/KEY: misc_feature
<222> LOCATION: (16900)..(16902)
<223> OTHER INFORMATION: Xaa can be any naturally occurring amino acid
<220> FEATURE:
<221> NAME/KEY: misc_feature
<222> LOCATION: (16904)..(16905)
<223> OTHER INFORMATION: Xaa can be any naturally occurring amino acid
<220> FEATURE:
<221> NAME/KEY: misc_feature
<222> LOCATION: (16907)..(16909)
<223> OTHER INFORMATION: Xaa can be any naturally occurring amino acid
<220> FEATURE:
<221> NAME/KEY: misc_feature
<222> LOCATION: (16913)..(16913)
<223> OTHER INFORMATION: Xaa can be any naturally occurring amino acid
<220> FEATURE:
<221> NAME/KEY: misc_feature
<222> LOCATION: (16925)..(16925)
<223> OTHER INFORMATION: Xaa can be any naturally occurring amino acid
<220> FEATURE:
<221> NAME/KEY: misc_feature
<222> LOCATION: (16929)..(16929)
<223> OTHER INFORMATION: Xaa can be any naturally occurring amino acid
<220> FEATURE:
<221> NAME/KEY: misc_feature
<222> LOCATION: (16931)..(16932)
<223> OTHER INFORMATION: Xaa can be any naturally occurring amino acid
<220> FEATURE:
<221> NAME/KEY: misc_feature
<222> LOCATION: (17468)..(17468)
<223> OTHER INFORMATION: Xaa can be any naturally occurring amino acid
<220> FEATURE:
<221> NAME/KEY: misc_feature
<222> LOCATION: (17475)..(17475)
<223> OTHER INFORMATION: Xaa can be any naturally occurring amino acid
<220> FEATURE:
<221> NAME/KEY: misc_feature
<222> LOCATION: (17478)..(17479)
<223> OTHER INFORMATION: Xaa can be any naturally occurring amino acid
<220> FEATURE:
<221> NAME/KEY: misc_feature
<222> LOCATION: (17481)..(17481)
<223> OTHER INFORMATION: Xaa can be any naturally occurring amino acid
<220> FEATURE:
<221> NAME/KEY: misc_feature
<222> LOCATION: (17487)..(17487)
<223> OTHER INFORMATION: Xaa can be any naturally occurring amino acid
<220> FEATURE:
<221> NAME/KEY: misc_feature
<222> LOCATION: (17491)..(17491)
<223> OTHER INFORMATION: Xaa can be any naturally occurring amino acid
<220> FEATURE:
<221> NAME/KEY: misc_feature
<222> LOCATION: (17499)..(17506)
<223> OTHER INFORMATION: Xaa can be any naturally occurring amino acid
<220> FEATURE:
<221> NAME/KEY: misc_feature
<222> LOCATION: (17514)..(17514)
<223> OTHER INFORMATION: Xaa can be any naturally occurring amino acid
<220> FEATURE:
<221> NAME/KEY: misc_feature
<222> LOCATION: (17516)..(17516)
<223> OTHER INFORMATION: Xaa can be any naturally occurring amino acid
<220> FEATURE:
<221> NAME/KEY: misc_feature
<222> LOCATION: (17518)..(17518)
<223> OTHER INFORMATION: Xaa can be any naturally occurring amino acid
```

-continued

```
<220> FEATURE:
<221> NAME/KEY: misc_feature
<222> LOCATION: (17524)..(17526)
<223> OTHER INFORMATION: Xaa can be any naturally occurring amino acid
<220> FEATURE:
<221> NAME/KEY: misc_feature
<222> LOCATION: (17528)..(17529)
<223> OTHER INFORMATION: Xaa can be any naturally occurring amino acid
<220> FEATURE:
<221> NAME/KEY: misc_feature
<222> LOCATION: (17531)..(17533)
<223> OTHER INFORMATION: Xaa can be any naturally occurring amino acid
<220> FEATURE:
<221> NAME/KEY: misc_feature
<222> LOCATION: (17537)..(17537)
<223> OTHER INFORMATION: Xaa can be any naturally occurring amino acid
<220> FEATURE:
<221> NAME/KEY: misc_feature
<222> LOCATION: (17549)..(17549)
<223> OTHER INFORMATION: Xaa can be any naturally occurring amino acid
<220> FEATURE:
<221> NAME/KEY: misc_feature
<222> LOCATION: (17553)..(17553)
<223> OTHER INFORMATION: Xaa can be any naturally occurring amino acid
<220> FEATURE:
<221> NAME/KEY: misc_feature
<222> LOCATION: (17555)..(17556)
<223> OTHER INFORMATION: Xaa can be any naturally occurring amino acid
<220> FEATURE:
<221> NAME/KEY: misc_feature
<222> LOCATION: (17574)..(17574)
<223> OTHER INFORMATION: Xaa can be any naturally occurring amino acid
<220> FEATURE:
<221> NAME/KEY: misc_feature
<222> LOCATION: (17576)..(17576)
<223> OTHER INFORMATION: Xaa can be any naturally occurring amino acid
<220> FEATURE:
<221> NAME/KEY: misc_feature
<222> LOCATION: (17579)..(17579)
<223> OTHER INFORMATION: Xaa can be any naturally occurring amino acid
<220> FEATURE:
<221> NAME/KEY: misc_feature
<222> LOCATION: (17584)..(17584)
<223> OTHER INFORMATION: Xaa can be any naturally occurring amino acid
<220> FEATURE:
<221> NAME/KEY: misc_feature
<222> LOCATION: (17596)..(17596)
<223> OTHER INFORMATION: Xaa can be any naturally occurring amino acid
<220> FEATURE:
<221> NAME/KEY: misc_feature
<222> LOCATION: (17599)..(17600)
<223> OTHER INFORMATION: Xaa can be any naturally occurring amino acid
<220> FEATURE:
<221> NAME/KEY: misc_feature
<222> LOCATION: (17604)..(17604)
<223> OTHER INFORMATION: Xaa can be any naturally occurring amino acid
<220> FEATURE:
<221> NAME/KEY: misc_feature
<222> LOCATION: (17607)..(17608)
<223> OTHER INFORMATION: Xaa can be any naturally occurring amino acid
<220> FEATURE:
<221> NAME/KEY: misc_feature
<222> LOCATION: (17610)..(17613)
<223> OTHER INFORMATION: Xaa can be any naturally occurring amino acid
<220> FEATURE:
<221> NAME/KEY: misc_feature
<222> LOCATION: (17616)..(17617)
<223> OTHER INFORMATION: Xaa can be any naturally occurring amino acid
<220> FEATURE:
<221> NAME/KEY: misc_feature
<222> LOCATION: (17624)..(17624)
<223> OTHER INFORMATION: Xaa can be any naturally occurring amino acid
<220> FEATURE:
<221> NAME/KEY: misc_feature
<222> LOCATION: (17631)..(17631)
<223> OTHER INFORMATION: Xaa can be any naturally occurring amino acid
<220> FEATURE:
<221> NAME/KEY: misc_feature
<222> LOCATION: (17780)..(17780)
```

```
<223> OTHER INFORMATION: Xaa can be any naturally occurring amino acid
<220> FEATURE:
<221> NAME/KEY: misc_feature
<222> LOCATION: (17787)..(17787)
<223> OTHER INFORMATION: Xaa can be any naturally occurring amino acid
<220> FEATURE:
<221> NAME/KEY: misc_feature
<222> LOCATION: (17790)..(17791)
<223> OTHER INFORMATION: Xaa can be any naturally occurring amino acid
<220> FEATURE:
<221> NAME/KEY: misc_feature
<222> LOCATION: (17793)..(17793)
<223> OTHER INFORMATION: Xaa can be any naturally occurring amino acid
<220> FEATURE:
<221> NAME/KEY: misc_feature
<222> LOCATION: (17799)..(17799)
<223> OTHER INFORMATION: Xaa can be any naturally occurring amino acid
<220> FEATURE:
<221> NAME/KEY: misc_feature
<222> LOCATION: (17803)..(17803)
<223> OTHER INFORMATION: Xaa can be any naturally occurring amino acid
<220> FEATURE:
<221> NAME/KEY: misc_feature
<222> LOCATION: (17811)..(17818)
<223> OTHER INFORMATION: Xaa can be any naturally occurring amino acid
<220> FEATURE:
<221> NAME/KEY: misc_feature
<222> LOCATION: (17826)..(17826)
<223> OTHER INFORMATION: Xaa can be any naturally occurring amino acid
<220> FEATURE:
<221> NAME/KEY: misc_feature
<222> LOCATION: (17828)..(17828)
<223> OTHER INFORMATION: Xaa can be any naturally occurring amino acid
<220> FEATURE:
<221> NAME/KEY: misc_feature
<222> LOCATION: (17830)..(17830)
<223> OTHER INFORMATION: Xaa can be any naturally occurring amino acid
<220> FEATURE:
<221> NAME/KEY: misc_feature
<222> LOCATION: (17836)..(17838)
<223> OTHER INFORMATION: Xaa can be any naturally occurring amino acid
<220> FEATURE:
<221> NAME/KEY: misc_feature
<222> LOCATION: (17840)..(17841)
<223> OTHER INFORMATION: Xaa can be any naturally occurring amino acid
<220> FEATURE:
<221> NAME/KEY: misc_feature
<222> LOCATION: (17843)..(17845)
<223> OTHER INFORMATION: Xaa can be any naturally occurring amino acid
<220> FEATURE:
<221> NAME/KEY: misc_feature
<222> LOCATION: (17849)..(17849)
<223> OTHER INFORMATION: Xaa can be any naturally occurring amino acid
<220> FEATURE:
<221> NAME/KEY: misc_feature
<222> LOCATION: (17861)..(17861)
<223> OTHER INFORMATION: Xaa can be any naturally occurring amino acid
<220> FEATURE:
<221> NAME/KEY: misc_feature
<222> LOCATION: (17865)..(17865)
<223> OTHER INFORMATION: Xaa can be any naturally occurring amino acid
<220> FEATURE:
<221> NAME/KEY: misc_feature
<222> LOCATION: (17867)..(17868)
<223> OTHER INFORMATION: Xaa can be any naturally occurring amino acid
<220> FEATURE:
<221> NAME/KEY: misc_feature
<222> LOCATION: (17886)..(17886)
<223> OTHER INFORMATION: Xaa can be any naturally occurring amino acid
<220> FEATURE:
<221> NAME/KEY: misc_feature
<222> LOCATION: (17888)..(17888)
<223> OTHER INFORMATION: Xaa can be any naturally occurring amino acid
<220> FEATURE:
<221> NAME/KEY: misc_feature
<222> LOCATION: (17891)..(17891)
<223> OTHER INFORMATION: Xaa can be any naturally occurring amino acid
<220> FEATURE:
<221> NAME/KEY: misc_feature
```

```
<222> LOCATION: (17896)..(17896)
<223> OTHER INFORMATION: Xaa can be any naturally occurring amino acid
<220> FEATURE:
<221> NAME/KEY: misc_feature
<222> LOCATION: (17908)..(17908)
<223> OTHER INFORMATION: Xaa can be any naturally occurring amino acid
<220> FEATURE:
<221> NAME/KEY: misc_feature
<222> LOCATION: (17911)..(17912)
<223> OTHER INFORMATION: Xaa can be any naturally occurring amino acid
<220> FEATURE:
<221> NAME/KEY: misc_feature
<222> LOCATION: (17916)..(17916)
<223> OTHER INFORMATION: Xaa can be any naturally occurring amino acid
<220> FEATURE:
<221> NAME/KEY: misc_feature
<222> LOCATION: (17919)..(17920)
<223> OTHER INFORMATION: Xaa can be any naturally occurring amino acid
<220> FEATURE:
<221> NAME/KEY: misc_feature
<222> LOCATION: (17922)..(17925)
<223> OTHER INFORMATION: Xaa can be any naturally occurring amino acid
<220> FEATURE:
<221> NAME/KEY: misc_feature
<222> LOCATION: (17928)..(17929)
<223> OTHER INFORMATION: Xaa can be any naturally occurring amino acid
<220> FEATURE:
<221> NAME/KEY: misc_feature
<222> LOCATION: (17936)..(17936)
<223> OTHER INFORMATION: Xaa can be any naturally occurring amino acid
<220> FEATURE:
<221> NAME/KEY: misc_feature
<222> LOCATION: (17943)..(17943)
<223> OTHER INFORMATION: Xaa can be any naturally occurring amino acid
<220> FEATURE:
<221> NAME/KEY: misc_feature
<222> LOCATION: (17946)..(17947)
<223> OTHER INFORMATION: Xaa can be any naturally occurring amino acid
<220> FEATURE:
<221> NAME/KEY: misc_feature
<222> LOCATION: (17949)..(17949)
<223> OTHER INFORMATION: Xaa can be any naturally occurring amino acid
<220> FEATURE:
<221> NAME/KEY: misc_feature
<222> LOCATION: (17955)..(17955)
<223> OTHER INFORMATION: Xaa can be any naturally occurring amino acid
<220> FEATURE:
<221> NAME/KEY: misc_feature
<222> LOCATION: (17959)..(17959)
<223> OTHER INFORMATION: Xaa can be any naturally occurring amino acid
<220> FEATURE:
<221> NAME/KEY: misc_feature
<222> LOCATION: (18092)..(18092)
<223> OTHER INFORMATION: Xaa can be any naturally occurring amino acid
<220> FEATURE:
<221> NAME/KEY: misc_feature
<222> LOCATION: (18099)..(18099)
<223> OTHER INFORMATION: Xaa can be any naturally occurring amino acid
<220> FEATURE:
<221> NAME/KEY: misc_feature
<222> LOCATION: (18102)..(18103)
<223> OTHER INFORMATION: Xaa can be any naturally occurring amino acid
<220> FEATURE:
<221> NAME/KEY: misc_feature
<222> LOCATION: (18105)..(18105)
<223> OTHER INFORMATION: Xaa can be any naturally occurring amino acid
<220> FEATURE:
<221> NAME/KEY: misc_feature
<222> LOCATION: (18111)..(18111)
<223> OTHER INFORMATION: Xaa can be any naturally occurring amino acid
<220> FEATURE:
<221> NAME/KEY: misc_feature
<222> LOCATION: (18115)..(18115)
<223> OTHER INFORMATION: Xaa can be any naturally occurring amino acid
<220> FEATURE:
<221> NAME/KEY: misc_feature
<222> LOCATION: (18123)..(18130)
<223> OTHER INFORMATION: Xaa can be any naturally occurring amino acid
<220> FEATURE:
```

```
<221> NAME/KEY: misc_feature
<222> LOCATION: (18138)..(18138)
<223> OTHER INFORMATION: Xaa can be any naturally occurring amino acid
<220> FEATURE:
<221> NAME/KEY: misc_feature
<222> LOCATION: (18140)..(18140)
<223> OTHER INFORMATION: Xaa can be any naturally occurring amino acid
<220> FEATURE:
<221> NAME/KEY: misc_feature
<222> LOCATION: (18142)..(18142)
<223> OTHER INFORMATION: Xaa can be any naturally occurring amino acid
<220> FEATURE:
<221> NAME/KEY: misc_feature
<222> LOCATION: (18148)..(18150)
<223> OTHER INFORMATION: Xaa can be any naturally occurring amino acid
<220> FEATURE:
<221> NAME/KEY: misc_feature
<222> LOCATION: (18152)..(18153)
<223> OTHER INFORMATION: Xaa can be any naturally occurring amino acid
<220> FEATURE:
<221> NAME/KEY: misc_feature
<222> LOCATION: (18155)..(18157)
<223> OTHER INFORMATION: Xaa can be any naturally occurring amino acid
<220> FEATURE:
<221> NAME/KEY: misc_feature
<222> LOCATION: (18161)..(18161)
<223> OTHER INFORMATION: Xaa can be any naturally occurring amino acid
<220> FEATURE:
<221> NAME/KEY: misc_feature
<222> LOCATION: (18173)..(18173)
<223> OTHER INFORMATION: Xaa can be any naturally occurring amino acid
<220> FEATURE:
<221> NAME/KEY: misc_feature
<222> LOCATION: (18177)..(18177)
<223> OTHER INFORMATION: Xaa can be any naturally occurring amino acid
<220> FEATURE:
<221> NAME/KEY: misc_feature
<222> LOCATION: (18179)..(18180)
<223> OTHER INFORMATION: Xaa can be any naturally occurring amino acid
<220> FEATURE:
<221> NAME/KEY: misc_feature
<222> LOCATION: (18198)..(18198)
<223> OTHER INFORMATION: Xaa can be any naturally occurring amino acid
<220> FEATURE:
<221> NAME/KEY: misc_feature
<222> LOCATION: (18200)..(18200)
<223> OTHER INFORMATION: Xaa can be any naturally occurring amino acid
<220> FEATURE:
<221> NAME/KEY: misc_feature
<222> LOCATION: (18203)..(18203)
<223> OTHER INFORMATION: Xaa can be any naturally occurring amino acid
<220> FEATURE:
<221> NAME/KEY: misc_feature
<222> LOCATION: (18208)..(18208)
<223> OTHER INFORMATION: Xaa can be any naturally occurring amino acid
<220> FEATURE:
<221> NAME/KEY: misc_feature
<222> LOCATION: (18220)..(18220)
<223> OTHER INFORMATION: Xaa can be any naturally occurring amino acid
<220> FEATURE:
<221> NAME/KEY: misc_feature
<222> LOCATION: (18223)..(18224)
<223> OTHER INFORMATION: Xaa can be any naturally occurring amino acid
<220> FEATURE:
<221> NAME/KEY: misc_feature
<222> LOCATION: (18228)..(18228)
<223> OTHER INFORMATION: Xaa can be any naturally occurring amino acid
<220> FEATURE:
<221> NAME/KEY: misc_feature
<222> LOCATION: (18231)..(18232)
<223> OTHER INFORMATION: Xaa can be any naturally occurring amino acid
<220> FEATURE:
<221> NAME/KEY: misc_feature
<222> LOCATION: (18234)..(18237)
<223> OTHER INFORMATION: Xaa can be any naturally occurring amino acid
<220> FEATURE:
<221> NAME/KEY: misc_feature
<222> LOCATION: (18240)..(18241)
<223> OTHER INFORMATION: Xaa can be any naturally occurring amino acid
```

```
<220> FEATURE:
<221> NAME/KEY: misc_feature
<222> LOCATION: (18248)..(18248)
<223> OTHER INFORMATION: Xaa can be any naturally occurring amino acid
<220> FEATURE:
<221> NAME/KEY: misc_feature
<222> LOCATION: (18255)..(18255)
<223> OTHER INFORMATION: Xaa can be any naturally occurring amino acid
<220> FEATURE:
<221> NAME/KEY: misc_feature
<222> LOCATION: (18258)..(18259)
<223> OTHER INFORMATION: Xaa can be any naturally occurring amino acid
<220> FEATURE:
<221> NAME/KEY: misc_feature
<222> LOCATION: (18261)..(18261)
<223> OTHER INFORMATION: Xaa can be any naturally occurring amino acid
<220> FEATURE:
<221> NAME/KEY: misc_feature
<222> LOCATION: (18267)..(18267)
<223> OTHER INFORMATION: Xaa can be any naturally occurring amino acid
<220> FEATURE:
<221> NAME/KEY: misc_feature
<222> LOCATION: (18271)..(18271)
<223> OTHER INFORMATION: Xaa can be any naturally occurring amino acid
<220> FEATURE:
<221> NAME/KEY: misc_feature
<222> LOCATION: (18404)..(18404)
<223> OTHER INFORMATION: Xaa can be any naturally occurring amino acid
<220> FEATURE:
<221> NAME/KEY: misc_feature
<222> LOCATION: (18411)..(18411)
<223> OTHER INFORMATION: Xaa can be any naturally occurring amino acid
<220> FEATURE:
<221> NAME/KEY: misc_feature
<222> LOCATION: (18414)..(18415)
<223> OTHER INFORMATION: Xaa can be any naturally occurring amino acid
<220> FEATURE:
<221> NAME/KEY: misc_feature
<222> LOCATION: (18417)..(18417)
<223> OTHER INFORMATION: Xaa can be any naturally occurring amino acid
<220> FEATURE:
<221> NAME/KEY: misc_feature
<222> LOCATION: (18423)..(18423)
<223> OTHER INFORMATION: Xaa can be any naturally occurring amino acid
<220> FEATURE:
<221> NAME/KEY: misc_feature
<222> LOCATION: (18427)..(18427)
<223> OTHER INFORMATION: Xaa can be any naturally occurring amino acid
<220> FEATURE:
<221> NAME/KEY: misc_feature
<222> LOCATION: (18435)..(18442)
<223> OTHER INFORMATION: Xaa can be any naturally occurring amino acid
<220> FEATURE:
<221> NAME/KEY: misc_feature
<222> LOCATION: (18450)..(18450)
<223> OTHER INFORMATION: Xaa can be any naturally occurring amino acid
<220> FEATURE:
<221> NAME/KEY: misc_feature
<222> LOCATION: (18452)..(18452)
<223> OTHER INFORMATION: Xaa can be any naturally occurring amino acid
<220> FEATURE:
<221> NAME/KEY: misc_feature
<222> LOCATION: (18454)..(18454)
<223> OTHER INFORMATION: Xaa can be any naturally occurring amino acid
<220> FEATURE:
<221> NAME/KEY: misc_feature
<222> LOCATION: (18460)..(18462)
<223> OTHER INFORMATION: Xaa can be any naturally occurring amino acid
<220> FEATURE:
<221> NAME/KEY: misc_feature
<222> LOCATION: (18464)..(18465)
<223> OTHER INFORMATION: Xaa can be any naturally occurring amino acid
<220> FEATURE:
<221> NAME/KEY: misc_feature
<222> LOCATION: (18467)..(18469)
<223> OTHER INFORMATION: Xaa can be any naturally occurring amino acid
<220> FEATURE:
<221> NAME/KEY: misc_feature
<222> LOCATION: (18473)..(18473)
```

```
<223> OTHER INFORMATION: Xaa can be any naturally occurring amino acid
<220> FEATURE:
<221> NAME/KEY: misc_feature
<222> LOCATION: (18485)..(18485)
<223> OTHER INFORMATION: Xaa can be any naturally occurring amino acid
<220> FEATURE:
<221> NAME/KEY: misc_feature
<222> LOCATION: (18489)..(18489)
<223> OTHER INFORMATION: Xaa can be any naturally occurring amino acid
<220> FEATURE:
<221> NAME/KEY: misc_feature
<222> LOCATION: (18491)..(18492)
<223> OTHER INFORMATION: Xaa can be any naturally occurring amino acid
<220> FEATURE:
<221> NAME/KEY: misc_feature
<222> LOCATION: (18510)..(18510)
<223> OTHER INFORMATION: Xaa can be any naturally occurring amino acid
<220> FEATURE:
<221> NAME/KEY: misc_feature
<222> LOCATION: (18512)..(18512)
<223> OTHER INFORMATION: Xaa can be any naturally occurring amino acid
<220> FEATURE:
<221> NAME/KEY: misc_feature
<222> LOCATION: (18515)..(18515)
<223> OTHER INFORMATION: Xaa can be any naturally occurring amino acid
<220> FEATURE:
<221> NAME/KEY: misc_feature
<222> LOCATION: (18520)..(18520)
<223> OTHER INFORMATION: Xaa can be any naturally occurring amino acid
<220> FEATURE:
<221> NAME/KEY: misc_feature
<222> LOCATION: (18532)..(18532)
<223> OTHER INFORMATION: Xaa can be any naturally occurring amino acid
<220> FEATURE:
<221> NAME/KEY: misc_feature
<222> LOCATION: (18535)..(18536)
<223> OTHER INFORMATION: Xaa can be any naturally occurring amino acid
<220> FEATURE:
<221> NAME/KEY: misc_feature
<222> LOCATION: (18540)..(18540)
<223> OTHER INFORMATION: Xaa can be any naturally occurring amino acid
<220> FEATURE:
<221> NAME/KEY: misc_feature
<222> LOCATION: (18543)..(18544)
<223> OTHER INFORMATION: Xaa can be any naturally occurring amino acid
<220> FEATURE:
<221> NAME/KEY: misc_feature
<222> LOCATION: (18546)..(18549)
<223> OTHER INFORMATION: Xaa can be any naturally occurring amino acid
<220> FEATURE:
<221> NAME/KEY: misc_feature
<222> LOCATION: (18552)..(18553)
<223> OTHER INFORMATION: Xaa can be any naturally occurring amino acid
<220> FEATURE:
<221> NAME/KEY: misc_feature
<222> LOCATION: (18560)..(18560)
<223> OTHER INFORMATION: Xaa can be any naturally occurring amino acid
<220> FEATURE:
<221> NAME/KEY: misc_feature
<222> LOCATION: (18567)..(18567)
<223> OTHER INFORMATION: Xaa can be any naturally occurring amino acid
<220> FEATURE:
<221> NAME/KEY: misc_feature
<222> LOCATION: (18570)..(18571)
<223> OTHER INFORMATION: Xaa can be any naturally occurring amino acid
<220> FEATURE:
<221> NAME/KEY: misc_feature
<222> LOCATION: (18573)..(18573)
<223> OTHER INFORMATION: Xaa can be any naturally occurring amino acid
<220> FEATURE:
<221> NAME/KEY: misc_feature
<222> LOCATION: (18579)..(18579)
<223> OTHER INFORMATION: Xaa can be any naturally occurring amino acid
<220> FEATURE:
<221> NAME/KEY: misc_feature
<222> LOCATION: (18583)..(18583)
<223> OTHER INFORMATION: Xaa can be any naturally occurring amino acid
<220> FEATURE:
<221> NAME/KEY: misc_feature
```

```
<222> LOCATION: (18716)..(18716)
<223> OTHER INFORMATION: Xaa can be any naturally occurring amino acid
<220> FEATURE:
<221> NAME/KEY: misc_feature
<222> LOCATION: (18723)..(18723)
<223> OTHER INFORMATION: Xaa can be any naturally occurring amino acid
<220> FEATURE:
<221> NAME/KEY: misc_feature
<222> LOCATION: (18726)..(18727)
<223> OTHER INFORMATION: Xaa can be any naturally occurring amino acid
<220> FEATURE:
<221> NAME/KEY: misc_feature
<222> LOCATION: (18729)..(18729)
<223> OTHER INFORMATION: Xaa can be any naturally occurring amino acid
<220> FEATURE:
<221> NAME/KEY: misc_feature
<222> LOCATION: (18735)..(18735)
<223> OTHER INFORMATION: Xaa can be any naturally occurring amino acid
<220> FEATURE:
<221> NAME/KEY: misc_feature
<222> LOCATION: (18739)..(18739)
<223> OTHER INFORMATION: Xaa can be any naturally occurring amino acid
<220> FEATURE:
<221> NAME/KEY: misc_feature
<222> LOCATION: (18747)..(18754)
<223> OTHER INFORMATION: Xaa can be any naturally occurring amino acid
<220> FEATURE:
<221> NAME/KEY: misc_feature
<222> LOCATION: (18762)..(18762)
<223> OTHER INFORMATION: Xaa can be any naturally occurring amino acid
<220> FEATURE:
<221> NAME/KEY: misc_feature
<222> LOCATION: (18764)..(18764)
<223> OTHER INFORMATION: Xaa can be any naturally occurring amino acid
<220> FEATURE:
<221> NAME/KEY: misc_feature
<222> LOCATION: (18766)..(18766)
<223> OTHER INFORMATION: Xaa can be any naturally occurring amino acid
<220> FEATURE:
<221> NAME/KEY: misc_feature
<222> LOCATION: (18772)..(18774)
<223> OTHER INFORMATION: Xaa can be any naturally occurring amino acid
<220> FEATURE:
<221> NAME/KEY: misc_feature
<222> LOCATION: (18776)..(18777)
<223> OTHER INFORMATION: Xaa can be any naturally occurring amino acid
<220> FEATURE:
<221> NAME/KEY: misc_feature
<222> LOCATION: (18779)..(18781)
<223> OTHER INFORMATION: Xaa can be any naturally occurring amino acid
<220> FEATURE:
<221> NAME/KEY: misc_feature
<222> LOCATION: (18785)..(18785)
<223> OTHER INFORMATION: Xaa can be any naturally occurring amino acid
<220> FEATURE:
<221> NAME/KEY: misc_feature
<222> LOCATION: (18797)..(18797)
<223> OTHER INFORMATION: Xaa can be any naturally occurring amino acid
<220> FEATURE:
<221> NAME/KEY: misc_feature
<222> LOCATION: (18801)..(18801)
<223> OTHER INFORMATION: Xaa can be any naturally occurring amino acid
<220> FEATURE:
<221> NAME/KEY: misc_feature
<222> LOCATION: (18803)..(18804)
<223> OTHER INFORMATION: Xaa can be any naturally occurring amino acid
<220> FEATURE:
<221> NAME/KEY: misc_feature
<222> LOCATION: (18822)..(18822)
<223> OTHER INFORMATION: Xaa can be any naturally occurring amino acid
<220> FEATURE:
<221> NAME/KEY: misc_feature
<222> LOCATION: (18824)..(18824)
<223> OTHER INFORMATION: Xaa can be any naturally occurring amino acid
<220> FEATURE:
<221> NAME/KEY: misc_feature
<222> LOCATION: (18827)..(18827)
<223> OTHER INFORMATION: Xaa can be any naturally occurring amino acid
<220> FEATURE:
```

```
<221> NAME/KEY: misc_feature
<222> LOCATION: (18832)..(18832)
<223> OTHER INFORMATION: Xaa can be any naturally occurring amino acid
<220> FEATURE:
<221> NAME/KEY: misc_feature
<222> LOCATION: (18844)..(18844)
<223> OTHER INFORMATION: Xaa can be any naturally occurring amino acid
<220> FEATURE:
<221> NAME/KEY: misc_feature
<222> LOCATION: (18847)..(18848)
<223> OTHER INFORMATION: Xaa can be any naturally occurring amino acid
<220> FEATURE:
<221> NAME/KEY: misc_feature
<222> LOCATION: (18852)..(18852)
<223> OTHER INFORMATION: Xaa can be any naturally occurring amino acid
<220> FEATURE:
<221> NAME/KEY: misc_feature
<222> LOCATION: (18855)..(18856)
<223> OTHER INFORMATION: Xaa can be any naturally occurring amino acid
<220> FEATURE:
<221> NAME/KEY: misc_feature
<222> LOCATION: (18858)..(18861)
<223> OTHER INFORMATION: Xaa can be any naturally occurring amino acid
<220> FEATURE:
<221> NAME/KEY: misc_feature
<222> LOCATION: (18864)..(18865)
<223> OTHER INFORMATION: Xaa can be any naturally occurring amino acid
<220> FEATURE:
<221> NAME/KEY: misc_feature
<222> LOCATION: (18872)..(18872)
<223> OTHER INFORMATION: Xaa can be any naturally occurring amino acid
<220> FEATURE:
<221> NAME/KEY: misc_feature
<222> LOCATION: (18879)..(18879)
<223> OTHER INFORMATION: Xaa can be any naturally occurring amino acid
<220> FEATURE:
<221> NAME/KEY: misc_feature
<222> LOCATION: (18882)..(18883)
<223> OTHER INFORMATION: Xaa can be any naturally occurring amino acid
<220> FEATURE:
<221> NAME/KEY: misc_feature
<222> LOCATION: (18885)..(18885)
<223> OTHER INFORMATION: Xaa can be any naturally occurring amino acid
<220> FEATURE:
<221> NAME/KEY: misc_feature
<222> LOCATION: (18891)..(18891)
<223> OTHER INFORMATION: Xaa can be any naturally occurring amino acid
<220> FEATURE:
<221> NAME/KEY: misc_feature
<222> LOCATION: (18895)..(18895)
<223> OTHER INFORMATION: Xaa can be any naturally occurring amino acid
<220> FEATURE:
<221> NAME/KEY: misc_feature
<222> LOCATION: (19091)..(19093)
<223> OTHER INFORMATION: Xaa can be any naturally occurring amino acid
<220> FEATURE:
<221> NAME/KEY: misc_feature
<222> LOCATION: (19097)..(19097)
<223> OTHER INFORMATION: Xaa can be any naturally occurring amino acid
<220> FEATURE:
<221> NAME/KEY: misc_feature
<222> LOCATION: (19109)..(19109)
<223> OTHER INFORMATION: Xaa can be any naturally occurring amino acid
<220> FEATURE:
<221> NAME/KEY: misc_feature
<222> LOCATION: (19113)..(19113)
<223> OTHER INFORMATION: Xaa can be any naturally occurring amino acid
<220> FEATURE:
<221> NAME/KEY: misc_feature
<222> LOCATION: (19115)..(19116)
<223> OTHER INFORMATION: Xaa can be any naturally occurring amino acid
<220> FEATURE:
<221> NAME/KEY: misc_feature
<222> LOCATION: (19134)..(19134)
<223> OTHER INFORMATION: Xaa can be any naturally occurring amino acid
<220> FEATURE:
<221> NAME/KEY: misc_feature
<222> LOCATION: (19136)..(19136)
<223> OTHER INFORMATION: Xaa can be any naturally occurring amino acid
```

```
<220> FEATURE:
<221> NAME/KEY: misc_feature
<222> LOCATION: (19139)..(19139)
<223> OTHER INFORMATION: Xaa can be any naturally occurring amino acid
<220> FEATURE:
<221> NAME/KEY: misc_feature
<222> LOCATION: (19144)..(19144)
<223> OTHER INFORMATION: Xaa can be any naturally occurring amino acid
<220> FEATURE:
<221> NAME/KEY: misc_feature
<222> LOCATION: (19156)..(19156)
<223> OTHER INFORMATION: Xaa can be any naturally occurring amino acid
<220> FEATURE:
<221> NAME/KEY: misc_feature
<222> LOCATION: (19159)..(19160)
<223> OTHER INFORMATION: Xaa can be any naturally occurring amino acid
<220> FEATURE:
<221> NAME/KEY: misc_feature
<222> LOCATION: (19164)..(19164)
<223> OTHER INFORMATION: Xaa can be any naturally occurring amino acid
<220> FEATURE:
<221> NAME/KEY: misc_feature
<222> LOCATION: (19167)..(19168)
<223> OTHER INFORMATION: Xaa can be any naturally occurring amino acid
<220> FEATURE:
<221> NAME/KEY: misc_feature
<222> LOCATION: (19170)..(19173)
<223> OTHER INFORMATION: Xaa can be any naturally occurring amino acid
<220> FEATURE:
<221> NAME/KEY: misc_feature
<222> LOCATION: (19176)..(19177)
<223> OTHER INFORMATION: Xaa can be any naturally occurring amino acid
<220> FEATURE:
<221> NAME/KEY: misc_feature
<222> LOCATION: (19184)..(19184)
<223> OTHER INFORMATION: Xaa can be any naturally occurring amino acid
<220> FEATURE:
<221> NAME/KEY: misc_feature
<222> LOCATION: (19191)..(19191)
<223> OTHER INFORMATION: Xaa can be any naturally occurring amino acid
<220> FEATURE:
<221> NAME/KEY: misc_feature
<222> LOCATION: (19194)..(19195)
<223> OTHER INFORMATION: Xaa can be any naturally occurring amino acid
<220> FEATURE:
<221> NAME/KEY: misc_feature
<222> LOCATION: (19197)..(19197)
<223> OTHER INFORMATION: Xaa can be any naturally occurring amino acid
<220> FEATURE:
<221> NAME/KEY: misc_feature
<222> LOCATION: (19203)..(19203)
<223> OTHER INFORMATION: Xaa can be any naturally occurring amino acid
<220> FEATURE:
<221> NAME/KEY: misc_feature
<222> LOCATION: (19207)..(19207)
<223> OTHER INFORMATION: Xaa can be any naturally occurring amino acid
<220> FEATURE:
<221> NAME/KEY: misc_feature
<222> LOCATION: (19340)..(19340)
<223> OTHER INFORMATION: Xaa can be any naturally occurring amino acid
<220> FEATURE:
<221> NAME/KEY: misc_feature
<222> LOCATION: (19347)..(19347)
<223> OTHER INFORMATION: Xaa can be any naturally occurring amino acid
<220> FEATURE:
<221> NAME/KEY: misc_feature
<222> LOCATION: (19350)..(19351)
<223> OTHER INFORMATION: Xaa can be any naturally occurring amino acid
<220> FEATURE:
<221> NAME/KEY: misc_feature
<222> LOCATION: (19353)..(19353)
<223> OTHER INFORMATION: Xaa can be any naturally occurring amino acid
<220> FEATURE:
<221> NAME/KEY: misc_feature
<222> LOCATION: (19359)..(19359)
<223> OTHER INFORMATION: Xaa can be any naturally occurring amino acid
<220> FEATURE:
<221> NAME/KEY: misc_feature
<222> LOCATION: (19363)..(19363)
```

-continued

```
<223> OTHER INFORMATION: Xaa can be any naturally occurring amino acid
<220> FEATURE:
<221> NAME/KEY: misc_feature
<222> LOCATION: (19371)..(19378)
<223> OTHER INFORMATION: Xaa can be any naturally occurring amino acid
<220> FEATURE:
<221> NAME/KEY: misc_feature
<222> LOCATION: (19386)..(19386)
<223> OTHER INFORMATION: Xaa can be any naturally occurring amino acid
<220> FEATURE:
<221> NAME/KEY: misc_feature
<222> LOCATION: (19388)..(19388)
<223> OTHER INFORMATION: Xaa can be any naturally occurring amino acid
<220> FEATURE:
<221> NAME/KEY: misc_feature
<222> LOCATION: (19390)..(19390)
<223> OTHER INFORMATION: Xaa can be any naturally occurring amino acid
<220> FEATURE:
<221> NAME/KEY: misc_feature
<222> LOCATION: (19396)..(19398)
<223> OTHER INFORMATION: Xaa can be any naturally occurring amino acid
<220> FEATURE:
<221> NAME/KEY: misc_feature
<222> LOCATION: (19400)..(19401)
<223> OTHER INFORMATION: Xaa can be any naturally occurring amino acid
<220> FEATURE:
<221> NAME/KEY: misc_feature
<222> LOCATION: (19403)..(19405)
<223> OTHER INFORMATION: Xaa can be any naturally occurring amino acid
<220> FEATURE:
<221> NAME/KEY: misc_feature
<222> LOCATION: (19409)..(19409)
<223> OTHER INFORMATION: Xaa can be any naturally occurring amino acid
<220> FEATURE:
<221> NAME/KEY: misc_feature
<222> LOCATION: (19421)..(19421)
<223> OTHER INFORMATION: Xaa can be any naturally occurring amino acid
<220> FEATURE:
<221> NAME/KEY: misc_feature
<222> LOCATION: (19425)..(19425)
<223> OTHER INFORMATION: Xaa can be any naturally occurring amino acid
<220> FEATURE:
<221> NAME/KEY: misc_feature
<222> LOCATION: (19427)..(19428)
<223> OTHER INFORMATION: Xaa can be any naturally occurring amino acid
<220> FEATURE:
<221> NAME/KEY: misc_feature
<222> LOCATION: (19446)..(19446)
<223> OTHER INFORMATION: Xaa can be any naturally occurring amino acid
<220> FEATURE:
<221> NAME/KEY: misc_feature
<222> LOCATION: (19448)..(19448)
<223> OTHER INFORMATION: Xaa can be any naturally occurring amino acid
<220> FEATURE:
<221> NAME/KEY: misc_feature
<222> LOCATION: (19451)..(19451)
<223> OTHER INFORMATION: Xaa can be any naturally occurring amino acid
<220> FEATURE:
<221> NAME/KEY: misc_feature
<222> LOCATION: (19456)..(19456)
<223> OTHER INFORMATION: Xaa can be any naturally occurring amino acid
<220> FEATURE:
<221> NAME/KEY: misc_feature
<222> LOCATION: (19468)..(19468)
<223> OTHER INFORMATION: Xaa can be any naturally occurring amino acid
<220> FEATURE:
<221> NAME/KEY: misc_feature
<222> LOCATION: (19471)..(19472)
<223> OTHER INFORMATION: Xaa can be any naturally occurring amino acid
<220> FEATURE:
<221> NAME/KEY: misc_feature
<222> LOCATION: (19476)..(19476)
<223> OTHER INFORMATION: Xaa can be any naturally occurring amino acid
<220> FEATURE:
<221> NAME/KEY: misc_feature
<222> LOCATION: (19479)..(19480)
<223> OTHER INFORMATION: Xaa can be any naturally occurring amino acid
<220> FEATURE:
<221> NAME/KEY: misc_feature
```

-continued

```
<222> LOCATION: (19482)..(19485)
<223> OTHER INFORMATION: Xaa can be any naturally occurring amino acid
<220> FEATURE:
<221> NAME/KEY: misc_feature
<222> LOCATION: (19488)..(19489)
<223> OTHER INFORMATION: Xaa can be any naturally occurring amino acid
<220> FEATURE:
<221> NAME/KEY: misc_feature
<222> LOCATION: (19496)..(19496)
<223> OTHER INFORMATION: Xaa can be any naturally occurring amino acid
<220> FEATURE:
<221> NAME/KEY: misc_feature
<222> LOCATION: (19503)..(19503)
<223> OTHER INFORMATION: Xaa can be any naturally occurring amino acid
<220> FEATURE:
<221> NAME/KEY: misc_feature
<222> LOCATION: (19506)..(19507)
<223> OTHER INFORMATION: Xaa can be any naturally occurring amino acid
<220> FEATURE:
<221> NAME/KEY: misc_feature
<222> LOCATION: (19509)..(19509)
<223> OTHER INFORMATION: Xaa can be any naturally occurring amino acid
<220> FEATURE:
<221> NAME/KEY: misc_feature
<222> LOCATION: (19515)..(19515)
<223> OTHER INFORMATION: Xaa can be any naturally occurring amino acid
<220> FEATURE:
<221> NAME/KEY: misc_feature
<222> LOCATION: (19519)..(19519)
<223> OTHER INFORMATION: Xaa can be any naturally occurring amino acid
<220> FEATURE:
<221> NAME/KEY: misc_feature
<222> LOCATION: (19652)..(19652)
<223> OTHER INFORMATION: Xaa can be any naturally occurring amino acid
<220> FEATURE:
<221> NAME/KEY: misc_feature
<222> LOCATION: (19659)..(19659)
<223> OTHER INFORMATION: Xaa can be any naturally occurring amino acid
<220> FEATURE:
<221> NAME/KEY: misc_feature
<222> LOCATION: (19662)..(19663)
<223> OTHER INFORMATION: Xaa can be any naturally occurring amino acid
<220> FEATURE:
<221> NAME/KEY: misc_feature
<222> LOCATION: (19665)..(19665)
<223> OTHER INFORMATION: Xaa can be any naturally occurring amino acid
<220> FEATURE:
<221> NAME/KEY: misc_feature
<222> LOCATION: (19671)..(19671)
<223> OTHER INFORMATION: Xaa can be any naturally occurring amino acid
<220> FEATURE:
<221> NAME/KEY: misc_feature
<222> LOCATION: (19675)..(19675)
<223> OTHER INFORMATION: Xaa can be any naturally occurring amino acid
<220> FEATURE:
<221> NAME/KEY: misc_feature
<222> LOCATION: (19683)..(19690)
<223> OTHER INFORMATION: Xaa can be any naturally occurring amino acid
<220> FEATURE:
<221> NAME/KEY: misc_feature
<222> LOCATION: (19698)..(19698)
<223> OTHER INFORMATION: Xaa can be any naturally occurring amino acid
<220> FEATURE:
<221> NAME/KEY: misc_feature
<222> LOCATION: (19700)..(19700)
<223> OTHER INFORMATION: Xaa can be any naturally occurring amino acid
<220> FEATURE:
<221> NAME/KEY: misc_feature
<222> LOCATION: (19702)..(19702)
<223> OTHER INFORMATION: Xaa can be any naturally occurring amino acid
<220> FEATURE:
<221> NAME/KEY: misc_feature
<222> LOCATION: (19708)..(19710)
<223> OTHER INFORMATION: Xaa can be any naturally occurring amino acid
<220> FEATURE:
<221> NAME/KEY: misc_feature
<222> LOCATION: (19712)..(19713)
<223> OTHER INFORMATION: Xaa can be any naturally occurring amino acid
<220> FEATURE:
```

```
<221> NAME/KEY: misc_feature
<222> LOCATION: (19715)..(19717)
<223> OTHER INFORMATION: Xaa can be any naturally occurring amino acid
<220> FEATURE:
<221> NAME/KEY: misc_feature
<222> LOCATION: (19721)..(19721)
<223> OTHER INFORMATION: Xaa can be any naturally occurring amino acid
<220> FEATURE:
<221> NAME/KEY: misc_feature
<222> LOCATION: (19733)..(19733)
<223> OTHER INFORMATION: Xaa can be any naturally occurring amino acid
<220> FEATURE:
<221> NAME/KEY: misc_feature
<222> LOCATION: (19737)..(19737)
<223> OTHER INFORMATION: Xaa can be any naturally occurring amino acid
<220> FEATURE:
<221> NAME/KEY: misc_feature
<222> LOCATION: (19739)..(19740)
<223> OTHER INFORMATION: Xaa can be any naturally occurring amino acid
<220> FEATURE:
<221> NAME/KEY: misc_feature
<222> LOCATION: (19758)..(19758)
<223> OTHER INFORMATION: Xaa can be any naturally occurring amino acid
<220> FEATURE:
<221> NAME/KEY: misc_feature
<222> LOCATION: (19760)..(19760)
<223> OTHER INFORMATION: Xaa can be any naturally occurring amino acid
<220> FEATURE:
<221> NAME/KEY: misc_feature
<222> LOCATION: (19763)..(19763)
<223> OTHER INFORMATION: Xaa can be any naturally occurring amino acid
<220> FEATURE:
<221> NAME/KEY: misc_feature
<222> LOCATION: (19768)..(19768)
<223> OTHER INFORMATION: Xaa can be any naturally occurring amino acid
<220> FEATURE:
<221> NAME/KEY: misc_feature
<222> LOCATION: (19780)..(19780)
<223> OTHER INFORMATION: Xaa can be any naturally occurring amino acid
<220> FEATURE:
<221> NAME/KEY: misc_feature
<222> LOCATION: (19783)..(19784)
<223> OTHER INFORMATION: Xaa can be any naturally occurring amino acid
<220> FEATURE:
<221> NAME/KEY: misc_feature
<222> LOCATION: (19788)..(19788)
<223> OTHER INFORMATION: Xaa can be any naturally occurring amino acid
<220> FEATURE:
<221> NAME/KEY: misc_feature
<222> LOCATION: (19791)..(19792)
<223> OTHER INFORMATION: Xaa can be any naturally occurring amino acid
<220> FEATURE:
<221> NAME/KEY: misc_feature
<222> LOCATION: (19794)..(19797)
<223> OTHER INFORMATION: Xaa can be any naturally occurring amino acid
<220> FEATURE:
<221> NAME/KEY: misc_feature
<222> LOCATION: (19800)..(19801)
<223> OTHER INFORMATION: Xaa can be any naturally occurring amino acid
<220> FEATURE:
<221> NAME/KEY: misc_feature
<222> LOCATION: (19808)..(19808)
<223> OTHER INFORMATION: Xaa can be any naturally occurring amino acid
<220> FEATURE:
<221> NAME/KEY: misc_feature
<222> LOCATION: (19815)..(19815)
<223> OTHER INFORMATION: Xaa can be any naturally occurring amino acid
<220> FEATURE:
<221> NAME/KEY: misc_feature
<222> LOCATION: (19818)..(19819)
<223> OTHER INFORMATION: Xaa can be any naturally occurring amino acid
<220> FEATURE:
<221> NAME/KEY: misc_feature
<222> LOCATION: (19821)..(19821)
<223> OTHER INFORMATION: Xaa can be any naturally occurring amino acid
<220> FEATURE:
<221> NAME/KEY: misc_feature
<222> LOCATION: (19827)..(19827)
<223> OTHER INFORMATION: Xaa can be any naturally occurring amino acid
```

```
<220> FEATURE:
<221> NAME/KEY: misc_feature
<222> LOCATION: (19831)..(19831)
<223> OTHER INFORMATION: Xaa can be any naturally occurring amino acid
<220> FEATURE:
<221> NAME/KEY: misc_feature
<222> LOCATION: (19963)..(19963)
<223> OTHER INFORMATION: Xaa can be any naturally occurring amino acid
<220> FEATURE:
<221> NAME/KEY: misc_feature
<222> LOCATION: (19970)..(19970)
<223> OTHER INFORMATION: Xaa can be any naturally occurring amino acid
<220> FEATURE:
<221> NAME/KEY: misc_feature
<222> LOCATION: (19973)..(19974)
<223> OTHER INFORMATION: Xaa can be any naturally occurring amino acid
<220> FEATURE:
<221> NAME/KEY: misc_feature
<222> LOCATION: (19976)..(19976)
<223> OTHER INFORMATION: Xaa can be any naturally occurring amino acid
<220> FEATURE:
<221> NAME/KEY: misc_feature
<222> LOCATION: (19982)..(19982)
<223> OTHER INFORMATION: Xaa can be any naturally occurring amino acid
<220> FEATURE:
<221> NAME/KEY: misc_feature
<222> LOCATION: (19986)..(19986)
<223> OTHER INFORMATION: Xaa can be any naturally occurring amino acid
<220> FEATURE:
<221> NAME/KEY: misc_feature
<222> LOCATION: (19994)..(20001)
<223> OTHER INFORMATION: Xaa can be any naturally occurring amino acid
<220> FEATURE:
<221> NAME/KEY: misc_feature
<222> LOCATION: (20009)..(20009)
<223> OTHER INFORMATION: Xaa can be any naturally occurring amino acid
<220> FEATURE:
<221> NAME/KEY: misc_feature
<222> LOCATION: (20011)..(20011)
<223> OTHER INFORMATION: Xaa can be any naturally occurring amino acid
<220> FEATURE:
<221> NAME/KEY: misc_feature
<222> LOCATION: (20013)..(20013)
<223> OTHER INFORMATION: Xaa can be any naturally occurring amino acid
<220> FEATURE:
<221> NAME/KEY: misc_feature
<222> LOCATION: (20019)..(20021)
<223> OTHER INFORMATION: Xaa can be any naturally occurring amino acid
<220> FEATURE:
<221> NAME/KEY: misc_feature
<222> LOCATION: (20023)..(20024)
<223> OTHER INFORMATION: Xaa can be any naturally occurring amino acid
<220> FEATURE:
<221> NAME/KEY: misc_feature
<222> LOCATION: (20026)..(20028)
<223> OTHER INFORMATION: Xaa can be any naturally occurring amino acid
<220> FEATURE:
<221> NAME/KEY: misc_feature
<222> LOCATION: (20032)..(20032)
<223> OTHER INFORMATION: Xaa can be any naturally occurring amino acid
<220> FEATURE:
<221> NAME/KEY: misc_feature
<222> LOCATION: (20044)..(20044)
<223> OTHER INFORMATION: Xaa can be any naturally occurring amino acid
<220> FEATURE:
<221> NAME/KEY: misc_feature
<222> LOCATION: (20048)..(20048)
<223> OTHER INFORMATION: Xaa can be any naturally occurring amino acid
<220> FEATURE:
<221> NAME/KEY: misc_feature
<222> LOCATION: (20050)..(20051)
<223> OTHER INFORMATION: Xaa can be any naturally occurring amino acid
<220> FEATURE:
<221> NAME/KEY: misc_feature
<222> LOCATION: (20069)..(20069)
<223> OTHER INFORMATION: Xaa can be any naturally occurring amino acid
<220> FEATURE:
<221> NAME/KEY: misc_feature
<222> LOCATION: (20071)..(20071)
```

-continued

```
<223> OTHER INFORMATION: Xaa can be any naturally occurring amino acid
<220> FEATURE:
<221> NAME/KEY: misc_feature
<222> LOCATION: (20074)..(20074)
<223> OTHER INFORMATION: Xaa can be any naturally occurring amino acid
<220> FEATURE:
<221> NAME/KEY: misc_feature
<222> LOCATION: (20079)..(20079)
<223> OTHER INFORMATION: Xaa can be any naturally occurring amino acid
<220> FEATURE:
<221> NAME/KEY: misc_feature
<222> LOCATION: (20091)..(20091)
<223> OTHER INFORMATION: Xaa can be any naturally occurring amino acid
<220> FEATURE:
<221> NAME/KEY: misc_feature
<222> LOCATION: (20094)..(20095)
<223> OTHER INFORMATION: Xaa can be any naturally occurring amino acid
<220> FEATURE:
<221> NAME/KEY: misc_feature
<222> LOCATION: (20099)..(20099)
<223> OTHER INFORMATION: Xaa can be any naturally occurring amino acid
<220> FEATURE:
<221> NAME/KEY: misc_feature
<222> LOCATION: (20102)..(20103)
<223> OTHER INFORMATION: Xaa can be any naturally occurring amino acid
<220> FEATURE:
<221> NAME/KEY: misc_feature
<222> LOCATION: (20105)..(20108)
<223> OTHER INFORMATION: Xaa can be any naturally occurring amino acid
<220> FEATURE:
<221> NAME/KEY: misc_feature
<222> LOCATION: (20111)..(20112)
<223> OTHER INFORMATION: Xaa can be any naturally occurring amino acid
<220> FEATURE:
<221> NAME/KEY: misc_feature
<222> LOCATION: (20119)..(20119)
<223> OTHER INFORMATION: Xaa can be any naturally occurring amino acid
<220> FEATURE:
<221> NAME/KEY: misc_feature
<222> LOCATION: (20126)..(20126)
<223> OTHER INFORMATION: Xaa can be any naturally occurring amino acid
<220> FEATURE:
<221> NAME/KEY: misc_feature
<222> LOCATION: (20129)..(20130)
<223> OTHER INFORMATION: Xaa can be any naturally occurring amino acid
<220> FEATURE:
<221> NAME/KEY: misc_feature
<222> LOCATION: (20132)..(20132)
<223> OTHER INFORMATION: Xaa can be any naturally occurring amino acid
<220> FEATURE:
<221> NAME/KEY: misc_feature
<222> LOCATION: (20138)..(20138)
<223> OTHER INFORMATION: Xaa can be any naturally occurring amino acid
<220> FEATURE:
<221> NAME/KEY: misc_feature
<222> LOCATION: (20142)..(20142)
<223> OTHER INFORMATION: Xaa can be any naturally occurring amino acid
<220> FEATURE:
<221> NAME/KEY: misc_feature
<222> LOCATION: (20275)..(20275)
<223> OTHER INFORMATION: Xaa can be any naturally occurring amino acid
<220> FEATURE:
<221> NAME/KEY: misc_feature
<222> LOCATION: (20282)..(20282)
<223> OTHER INFORMATION: Xaa can be any naturally occurring amino acid
<220> FEATURE:
<221> NAME/KEY: misc_feature
<222> LOCATION: (20285)..(20286)
<223> OTHER INFORMATION: Xaa can be any naturally occurring amino acid
<220> FEATURE:
<221> NAME/KEY: misc_feature
<222> LOCATION: (20288)..(20288)
<223> OTHER INFORMATION: Xaa can be any naturally occurring amino acid
<220> FEATURE:
<221> NAME/KEY: misc_feature
<222> LOCATION: (20294)..(20294)
<223> OTHER INFORMATION: Xaa can be any naturally occurring amino acid
<220> FEATURE:
<221> NAME/KEY: misc_feature
```

```
<222> LOCATION: (20298)..(20298)
<223> OTHER INFORMATION: Xaa can be any naturally occurring amino acid
<220> FEATURE:
<221> NAME/KEY: misc_feature
<222> LOCATION: (20306)..(20313)
<223> OTHER INFORMATION: Xaa can be any naturally occurring amino acid
<220> FEATURE:
<221> NAME/KEY: misc_feature
<222> LOCATION: (20321)..(20321)
<223> OTHER INFORMATION: Xaa can be any naturally occurring amino acid
<220> FEATURE:
<221> NAME/KEY: misc_feature
<222> LOCATION: (20323)..(20323)
<223> OTHER INFORMATION: Xaa can be any naturally occurring amino acid
<220> FEATURE:
<221> NAME/KEY: misc_feature
<222> LOCATION: (20325)..(20325)
<223> OTHER INFORMATION: Xaa can be any naturally occurring amino acid
<220> FEATURE:
<221> NAME/KEY: misc_feature
<222> LOCATION: (20331)..(20333)
<223> OTHER INFORMATION: Xaa can be any naturally occurring amino acid
<220> FEATURE:
<221> NAME/KEY: misc_feature
<222> LOCATION: (20335)..(20336)
<223> OTHER INFORMATION: Xaa can be any naturally occurring amino acid
<220> FEATURE:
<221> NAME/KEY: misc_feature
<222> LOCATION: (20806)..(20808)
<223> OTHER INFORMATION: Xaa can be any naturally occurring amino acid
<220> FEATURE:
<221> NAME/KEY: misc_feature
<222> LOCATION: (20812)..(20812)
<223> OTHER INFORMATION: Xaa can be any naturally occurring amino acid
<220> FEATURE:
<221> NAME/KEY: misc_feature
<222> LOCATION: (20824)..(20824)
<223> OTHER INFORMATION: Xaa can be any naturally occurring amino acid
<220> FEATURE:
<221> NAME/KEY: misc_feature
<222> LOCATION: (20828)..(20828)
<223> OTHER INFORMATION: Xaa can be any naturally occurring amino acid
<220> FEATURE:
<221> NAME/KEY: misc_feature
<222> LOCATION: (20830)..(20831)
<223> OTHER INFORMATION: Xaa can be any naturally occurring amino acid

<400> SEQUENCE: 5

Met Leu Lys Pro Ser Gly Leu Pro Gly Ser Ser Pro Thr Arg Ser
1               5                   10                  15

Leu Met Thr Gly Ser Arg Ser Thr Lys Ala Thr Pro Glu Met Asp Ser
            20                  25                  30

Gly Leu Thr Gly Ala Thr Leu Ser Pro Lys Thr Ser Thr Gly Ala Ile
        35                  40                  45

Val Val Thr Glu His Thr Leu Pro Phe Thr Ser Pro Asp Lys Thr Leu
    50                  55                  60

Ala Ser Pro Thr Ser Ser Val Val Gly Arg Thr Thr Gln Ser Leu Gly
65                  70                  75                  80

Val Met Ser Ser Ala Leu Pro Glu Ser Thr Ser Arg Gly Met Thr His
                85                  90                  95

Ser Glu Gln Arg Thr Ser Pro Ser Leu Ser Pro Gln Val Asn Gly Thr
            100                 105                 110

Pro Ser Arg Asn Tyr Pro Ala Thr Ser Met Val Ser Gly Leu Ser Ser
        115                 120                 125

Pro Arg Thr Arg Thr Ser Ser Thr Glu Gly Asn Phe Thr Lys Glu Ala
    130                 135                 140

Ser Thr Tyr Thr Leu Thr Val Glu Thr Thr Ser Gly Pro Val Thr Glu
145                 150                 155                 160
```

-continued

```
Lys Tyr Thr Val Pro Thr Glu Thr Ser Thr Thr Glu Gly Asp Ser Thr
                165                 170                 175
Glu Thr Pro Trp Asp Thr Arg Tyr Ile Pro Val Lys Ile Thr Ser Pro
            180                 185                 190
Met Lys Thr Phe Ala Asp Ser Thr Ala Ser Lys Glu Asn Ala Pro Val
        195                 200                 205
Ser Met Thr Pro Ala Glu Thr Thr Val Thr Asp Ser His Thr Pro Gly
    210                 215                 220
Arg Thr Asn Pro Ser Phe Gly Thr Leu Tyr Ser Ser Phe Leu Asp Leu
225                 230                 235                 240
Ser Pro Lys Gly Thr Pro Asn Ser Arg Gly Glu Thr Ser Leu Glu Leu
                245                 250                 255
Ile Leu Ser Thr Thr Gly Tyr Pro Phe Ser Ser Pro Glu Pro Gly Ser
            260                 265                 270
Ala Gly His Ser Arg Ile Ser Thr Ser Ala Pro Leu Ser Ser Ser Ala
        275                 280                 285
Ser Val Leu Asp Asn Lys Ile Ser Glu Thr Ser Ile Phe Ser Gly Gln
    290                 295                 300
Ser Leu Thr Ser Pro Leu Ser Pro Gly Val Pro Glu Ala Arg Ala Ser
305                 310                 315                 320
Thr Met Pro Asn Ser Ala Ile Pro Phe Ser Met Thr Leu Ser Asn Ala
                325                 330                 335
Glu Thr Ser Ala Glu Arg Val Arg Ser Thr Ile Ser Ser Leu Gly Thr
            340                 345                 350
Pro Ser Ile Ser Thr Lys Gln Thr Ala Glu Thr Ile Leu Thr Phe His
        355                 360                 365
Ala Phe Ala Glu Thr Met Asp Ile Pro Ser Thr His Ile Ala Lys Thr
    370                 375                 380
Leu Ala Ser Glu Trp Leu Gly Ser Pro Gly Thr Leu Gly Gly Thr Ser
385                 390                 395                 400
Thr Ser Ala Leu Thr Thr Thr Ser Pro Ser Thr Thr Leu Val Ser Glu
                405                 410                 415
Glu Thr Asn Thr His His Ser Thr Ser Gly Lys Glu Thr Glu Gly Thr
            420                 425                 430
Leu Asn Thr Ser Met Thr Pro Leu Glu Thr Ser Ala Pro Gly Glu Glu
        435                 440                 445
Ser Glu Met Thr Ala Thr Leu Val Pro Thr Leu Gly Phe Thr Thr Leu
    450                 455                 460
Asp Ser Lys Ile Arg Ser Pro Ser Gln Val Ser Ser His Pro Thr
465                 470                 475                 480
Arg Glu Leu Arg Thr Thr Gly Ser Thr Ser Gly Arg Gln Ser Ser Ser
                485                 490                 495
Thr Ala Ala His Gly Ser Ser Asp Ile Leu Arg Ala Thr Thr Ser Ser
            500                 505                 510
Thr Ser Lys Ala Ser Ser Trp Thr Ser Glu Ser Thr Ala Gln Gln Phe
        515                 520                 525
Ser Glu Pro Gln His Thr Gln Trp Val Glu Thr Ser Pro Ser Met Lys
    530                 535                 540
Thr Glu Arg Pro Pro Ala Ser Thr Ser Val Ala Ala Pro Ile Thr Thr
545                 550                 555                 560
Ser Val Pro Ser Val Val Ser Gly Phe Thr Thr Leu Lys Thr Ser Ser
                565                 570                 575
Thr Lys Gly Ile Trp Leu Glu Glu Thr Ser Ala Asp Thr Leu Ile Gly
```

```
                580                 585                 590
Glu Ser Thr Ala Gly Pro Thr Thr His Gln Phe Ala Val Pro Thr Gly
            595                 600                 605
Ile Ser Met Thr Gly Gly Ser Ser Thr Arg Gly Ser Gln Gly Thr Thr
        610                 615                 620
His Leu Leu Thr Arg Ala Thr Ala Ser Ser Glu Thr Ser Ala Asp Leu
625                 630                 635                 640
Thr Leu Ala Thr Asn Gly Val Pro Val Ser Val Ser Pro Ala Val Ser
                645                 650                 655
Lys Thr Ala Ala Gly Ser Ser Pro Pro Gly Gly Thr Lys Pro Ser Tyr
            660                 665                 670
Thr Met Val Ser Ser Val Ile Pro Glu Thr Ser Ser Leu Gln Ser Ser
        675                 680                 685
Ala Phe Arg Glu Gly Thr Ser Leu Gly Leu Thr Pro Leu Asn Thr Arg
        690                 695                 700
His Pro Phe Ser Ser Pro Glu Pro Asp Ser Ala Gly His Thr Lys Ile
705                 710                 715                 720
Ser Thr Ser Ile Pro Leu Leu Ser Ser Ala Ser Val Leu Glu Asp Lys
                725                 730                 735
Val Ser Ala Thr Ser Thr Phe Ser His His Lys Ala Thr Ser Ser Ile
            740                 745                 750
Thr Thr Gly Thr Pro Glu Ile Ser Thr Lys Thr Lys Pro Ser Ser Ala
        755                 760                 765
Val Leu Ser Ser Met Thr Leu Ser Asn Ala Ala Thr Ser Pro Glu Arg
        770                 775                 780
Val Arg Asn Ala Thr Ser Pro Leu Thr His Pro Ser Pro Ser Gly Glu
785                 790                 795                 800
Glu Thr Ala Gly Ser Val Leu Thr Leu Ser Thr Ser Ala Glu Thr Thr
                805                 810                 815
Asp Ser Pro Asn Ile His Pro Thr Gly Thr Leu Thr Ser Glu Ser Ser
            820                 825                 830
Glu Ser Pro Ser Thr Leu Ser Leu Pro Ser Val Ser Gly Val Lys Thr
        835                 840                 845
Thr Phe Ser Ser Ser Thr Pro Ser Thr His Leu Phe Thr Ser Gly Glu
        850                 855                 860
Glu Thr Glu Glu Thr Ser Asn Pro Ser Val Ser Gln Pro Glu Thr Ser
865                 870                 875                 880
Val Ser Arg Val Arg Thr Thr Leu Ala Ser Thr Ser Val Pro Thr Pro
                885                 890                 895
Val Phe Pro Thr Met Asp Thr Trp Pro Thr Arg Ser Ala Gln Phe Ser
            900                 905                 910
Ser Ser His Leu Val Ser Glu Leu Arg Ala Thr Ser Ser Thr Ser Val
        915                 920                 925
Thr Asn Ser Thr Gly Ser Ala Leu Pro Lys Ile Ser His Leu Thr Gly
        930                 935                 940
Thr Ala Thr Met Ser Gln Thr Asn Arg Asp Thr Phe Asn Asp Ser Ala
945                 950                 955                 960
Ala Pro Gln Ser Thr Thr Trp Pro Glu Thr Ser Pro Arg Phe Lys Thr
                965                 970                 975
Gly Leu Pro Ser Ala Thr Thr Val Ser Thr Ser Ala Thr Ser Leu
            980                 985                 990
Ser Ala Thr Val Met Val Ser Lys Phe Thr Ser Pro Ala Thr Ser Ser
        995                 1000                1005
```

-continued

```
Met Glu Ala Thr Ser Ile Arg Glu Pro Ser Thr Thr Ile Leu Thr
    1010                1015                1020

Thr Glu Thr Thr Asn Gly Pro Gly Ser Met Ala Val Ala Ser Thr
    1025                1030                1035

Asn Ile Pro Ile Gly Lys Gly Tyr Ile Thr Glu Gly Arg Leu Asp
    1040                1045                1050

Thr Ser His Leu Pro Ile Gly Thr Thr Ala Ser Ser Glu Thr Ser
    1055                1060                1065

Met Asp Phe Thr Met Ala Lys Glu Ser Val Ser Met Ser Val Ser
    1070                1075                1080

Pro Ser Gln Ser Met Asp Ala Ala Gly Ser Ser Thr Pro Gly Arg
    1085                1090                1095

Thr Ser Gln Phe Val Asp Thr Phe Ser Asp Asp Val Tyr His Leu
    1100                1105                1110

Thr Ser Arg Glu Ile Thr Ile Pro Arg Asp Gly Thr Ser Ser Ala
    1115                1120                1125

Leu Thr Pro Gln Met Thr Ala Thr His Pro Pro Ser Pro Asp Pro
    1130                1135                1140

Gly Ser Ala Arg Ser Thr Trp Leu Gly Ile Leu Ser Ser Ser Pro
    1145                1150                1155

Ser Ser Pro Thr Pro Lys Val Thr Met Ser Ser Thr Phe Ser Thr
    1160                1165                1170

Gln Arg Val Thr Thr Ser Met Ile Met Asp Thr Val Glu Thr Ser
    1175                1180                1185

Arg Trp Asn Met Pro Asn Leu Pro Ser Thr Thr Ser Leu Thr Pro
    1190                1195                1200

Ser Asn Ile Pro Thr Ser Gly Ala Ile Gly Lys Ser Thr Leu Val
    1205                1210                1215

Pro Leu Asp Thr Pro Ser Pro Ala Thr Ser Leu Glu Ala Ser Glu
    1220                1225                1230

Gly Gly Leu Pro Thr Leu Ser Thr Tyr Pro Glu Ser Thr Asn Thr
    1235                1240                1245

Pro Ser Ile His Leu Gly Ala His Ala Ser Ser Glu Ser Pro Ser
    1250                1255                1260

Thr Ile Asn Leu Thr Met Ala Ser Val Val Lys Pro Gly Ser Tyr
    1265                1270                1275

Thr Pro Leu Thr Phe Pro Ser Ile Glu Thr His Ile His Val Ser
    1280                1285                1290

Thr Ala Arg Met Ala Tyr Ser Ser Gly Ser Ser Pro Glu Met Thr
    1295                1300                1305

Ala Pro Gly Glu Thr Asn Thr Gly Ser Thr Trp Asp Pro Thr Thr
    1310                1315                1320

Tyr Ile Thr Thr Thr Asp Pro Lys Asp Thr Ser Ser Ala Gln Val
    1325                1330                1335

Ser Thr Pro His Ser Val Arg Thr Leu Arg Thr Thr Glu Asn His
    1340                1345                1350

Pro Lys Thr Glu Ser Ala Thr Pro Ala Ala Tyr Ser Gly Ser Pro
    1355                1360                1365

Lys Ile Ser Ser Ser Pro Asn Leu Thr Ser Pro Ala Thr Lys Ala
    1370                1375                1380

Trp Thr Ile Thr Asp Thr Thr Glu His Ser Thr Gln Leu His Tyr
    1385                1390                1395
```

```
Thr Lys Leu Ala Glu Lys Ser Ser Gly Phe Glu Thr Gln Ser Ala
    1400            1405                1410
Pro Gly Pro Val Ser Val Val Ile Pro Thr Ser Pro Thr Ile Gly
    1415            1420                1425
Ser Ser Thr Leu Glu Leu Ser Asp Val Pro Gly Glu Pro Leu
    1430            1435                1440
Val Leu Ala Pro Ser Glu Gln Thr Thr Ile Thr Leu Pro Met Ala
    1445            1450                1455
Thr Trp Leu Ser Thr Ser Leu Thr Glu Glu Met Ala Ser Thr Asp
    1460            1465                1470
Leu Asp Ile Ser Ser Pro Ser Pro Met Ser Thr Phe Ala Ile
    1475            1480                1485
Phe Pro Pro Met Ser Thr Pro Ser His Glu Leu Ser Lys Ser Glu
    1490            1495                1500
Ala Asp Thr Ser Ala Ile Arg Asn Thr Asp Ser Thr Thr Leu Asp
    1505            1510                1515
Gln His Leu Gly Ile Arg Ser Leu Gly Arg Thr Gly Asp Leu Thr
    1520            1525                1530
Thr Val Pro Ile Thr Pro Leu Thr Thr Thr Trp Thr Ser Val Ile
    1535            1540                1545
Glu His Ser Thr Gln Ala Gln Asp Thr Leu Ser Ala Thr Met Ser
    1550            1555                1560
Pro Thr His Val Thr Gln Ser Leu Lys Asp Gln Thr Ser Ile Pro
    1565            1570                1575
Ala Ser Ala Ser Pro Ser His Leu Thr Glu Val Tyr Pro Glu Leu
    1580            1585                1590
Gly Thr Gln Gly Arg Ser Ser Glu Ala Thr Thr Phe Trp Lys
    1595            1600                1605
Pro Ser Thr Asp Thr Leu Ser Arg Glu Ile Glu Thr Gly Pro Thr
    1610            1615                1620
Asn Ile Gln Ser Thr Pro Pro Met Asp Asn Thr Thr Thr Gly Ser
    1625            1630                1635
Ser Ser Ser Gly Val Thr Leu Gly Ile Ala His Leu Pro Ile Gly
    1640            1645                1650
Thr Ser Ser Pro Ala Glu Thr Ser Thr Asn Met Ala Leu Glu Arg
    1655            1660                1665
Arg Ser Ser Thr Ala Thr Val Ser Met Ala Gly Thr Met Gly Leu
    1670            1675                1680
Leu Val Thr Ser Ala Pro Gly Arg Ser Ile Ser Gln Ser Leu Gly
    1685            1690                1695
Arg Val Ser Ser Val Leu Ser Glu Ser Thr Thr Glu Gly Val Thr
    1700            1705                1710
Asp Ser Ser Lys Gly Ser Ser Pro Arg Leu Asn Thr Gln Gly Asn
    1715            1720                1725
Thr Ala Leu Ser Ser Ser Leu Glu Pro Ser Tyr Ala Glu Gly Ser
    1730            1735                1740
Gln Met Ser Thr Ser Ile Pro Leu Thr Ser Ser Pro Thr Thr Pro
    1745            1750                1755
Asp Val Glu Phe Ile Gly Gly Ser Thr Phe Trp Thr Lys Glu Val
    1760            1765                1770
Thr Thr Val Met Thr Ser Asp Ile Ser Lys Ser Ser Ala Arg Thr
    1775            1780                1785
Glu Ser Ser Ser Ala Thr Leu Met Ser Thr Ala Leu Gly Ser Thr
```

-continued

```
                1790                1795                1800
Glu Asn Thr Gly Lys Glu Lys Leu Arg Thr Ala Ser Met Asp Leu
    1805                1810                1815
Pro Ser Pro Thr Pro Ser Met Glu Val Thr Pro Trp Ile Ser Leu
    1820                1825                1830
Thr Leu Ser Asn Ala Pro Asn Thr Thr Asp Ser Leu Asp Leu Ser
    1835                1840                1845
His Gly Val His Thr Ser Ser Ala Gly Thr Leu Ala Thr Asp Arg
    1850                1855                1860
Ser Leu Asn Thr Gly Val Thr Arg Ala Ser Arg Leu Glu Asn Gly
    1865                1870                1875
Ser Asp Thr Ser Ser Lys Ser Leu Ser Met Gly Asn Ser Thr His
    1880                1885                1890
Thr Ser Met Thr Asp Thr Glu Lys Ser Glu Val Ser Ser Ser Ile
    1895                1900                1905
His Pro Arg Pro Glu Thr Ser Ala Pro Gly Ala Glu Thr Thr Leu
    1910                1915                1920
Thr Ser Thr Pro Gly Asn Arg Ala Ile Ser Leu Thr Leu Pro Phe
    1925                1930                1935
Ser Ser Ile Pro Val Glu Glu Val Ile Ser Thr Gly Ile Thr Ser
    1940                1945                1950
Gly Pro Asp Ile Asn Ser Ala Pro Met Thr His Ser Pro Ile Thr
    1955                1960                1965
Pro Pro Thr Ile Val Trp Thr Ser Thr Gly Thr Ile Glu Gln Ser
    1970                1975                1980
Thr Gln Pro Leu His Ala Val Ser Ser Glu Lys Val Ser Val Gln
    1985                1990                1995
Thr Gln Ser Thr Pro Tyr Val Asn Ser Val Ala Val Ser Ala Ser
    2000                2005                2010
Pro Thr His Glu Asn Ser Val Ser Ser Gly Ser Ser Thr Ser Ser
    2015                2020                2025
Pro Tyr Ser Ser Ala Ser Leu Glu Ser Leu Asp Ser Thr Ile Ser
    2030                2035                2040
Arg Arg Asn Ala Ile Thr Ser Trp Leu Trp Asp Leu Thr Thr Ser
    2045                2050                2055
Leu Pro Thr Thr Thr Trp Pro Ser Thr Ser Leu Ser Glu Ala Leu
    2060                2065                2070
Ser Ser Gly His Ser Gly Val Ser Asn Pro Ser Ser Thr Thr Thr
    2075                2080                2085
Glu Phe Pro Leu Phe Ser Ala Ala Ser Thr Ser Ala Ala Lys Gln
    2090                2095                2100
Arg Asn Pro Glu Thr Glu Thr His Gly Pro Gln Asn Thr Ala Ala
    2105                2110                2115
Ser Thr Leu Asn Thr Asp Ala Ser Ser Val Thr Gly Leu Ser Glu
    2120                2125                2130
Thr Pro Val Gly Ala Ser Ile Ser Ser Glu Val Pro Leu Pro Met
    2135                2140                2145
Ala Ile Thr Ser Arg Ser Asp Val Ser Gly Leu Thr Ser Glu Ser
    2150                2155                2160
Thr Ala Asn Pro Ser Leu Gly Thr Ala Ser Ser Ala Gly Thr Lys
    2165                2170                2175
Leu Thr Arg Thr Ile Ser Leu Pro Thr Ser Glu Ser Leu Val Ser
    2180                2185                2190
```

-continued

```
Phe Arg Met Asn Lys Asp Pro Trp Thr Val Ser Ile Pro Leu Gly
2195                2200                2205

Ser His Pro Thr Thr Asn Thr Glu Thr Ser Ile Pro Val Asn Ser
2210                2215                2220

Ala Gly Pro Pro Gly Leu Ser Thr Val Ala Ser Asp Val Ile Asp
2225                2230                2235

Thr Pro Ser Asp Gly Ala Glu Ser Ile Pro Thr Val Ser Phe Ser
2240                2245                2250

Pro Ser Pro Asp Thr Glu Val Thr Thr Ile Ser His Phe Pro Glu
2255                2260                2265

Lys Thr Thr His Ser Phe Arg Thr Ile Ser Ser Leu Thr His Glu
2270                2275                2280

Leu Thr Ser Arg Val Thr Pro Ile Pro Gly Asp Trp Met Ser Ser
2285                2290                2295

Ala Met Ser Thr Lys Pro Thr Gly Ala Ser Pro Ser Ile Thr Leu
2300                2305                2310

Gly Glu Arg Arg Thr Ile Thr Ser Ala Ala Pro Thr Thr Ser Pro
2315                2320                2325

Ile Val Leu Thr Ala Ser Phe Thr Glu Thr Ser Thr Val Ser Leu
2330                2335                2340

Asp Asn Glu Thr Thr Val Lys Thr Ser Asp Ile Leu Asp Ala Arg
2345                2350                2355

Lys Thr Asn Glu Leu Pro Ser Asp Ser Ser Ser Ser Asp Leu
2360                2365                2370

Ile Asn Thr Ser Ile Ala Ser Ser Thr Met Asp Val Thr Lys Thr
2375                2380                2385

Ala Ser Ile Ser Pro Thr Ser Ile Ser Gly Met Thr Ala Ser Ser
2390                2395                2400

Ser Pro Ser Leu Phe Ser Ser Asp Arg Pro Gln Val Pro Thr Ser
2405                2410                2415

Thr Thr Glu Thr Asn Thr Ala Thr Ser Pro Ser Val Ser Ser Asn
2420                2425                2430

Thr Tyr Ser Leu Asp Gly Gly Ser Asn Val Gly Gly Thr Pro Ser
2435                2440                2445

Thr Leu Pro Pro Phe Thr Ile Thr His Pro Val Glu Thr Ser Ser
2450                2455                2460

Ala Leu Leu Ala Trp Ser Arg Pro Val Arg Thr Phe Ser Thr Met
2465                2470                2475

Val Ser Thr Asp Thr Ala Ser Gly Glu Asn Pro Thr Ser Ser Asn
2480                2485                2490

Ser Val Val Thr Ser Val Pro Ala Pro Gly Thr Trp Ala Ser Val
2495                2500                2505

Gly Ser Thr Thr Asp Leu Pro Ala Met Gly Phe Leu Lys Thr Ser
2510                2515                2520

Pro Ala Gly Glu Ala His Ser Leu Leu Ala Ser Thr Ile Glu Pro
2525                2530                2535

Ala Thr Ala Phe Thr Pro His Leu Ser Ala Ala Val Val Thr Gly
2540                2545                2550

Ser Ser Ala Thr Ser Glu Ala Ser Leu Leu Thr Thr Ser Glu Ser
2555                2560                2565

Lys Ala Ile His Ser Ser Pro Gln Thr Pro Thr Thr Pro Thr Ser
2570                2575                2580
```

-continued

```
Gly Ala Asn Trp Glu Thr Ser Ala Thr Pro Glu Ser Leu Leu Val
2585                2590                2595

Val Thr Glu Thr Ser Asp Thr Leu Thr Ser Lys Ile Leu Val
2600                2605                2610

Thr Asp Thr Ile Leu Phe Ser Thr Val Ser Thr Pro Pro Ser Lys
2615                2620                2625

Phe Pro Ser Thr Gly Thr Leu Ser Gly Ala Ser Phe Pro Thr Leu
2630                2635                2640

Leu Pro Asp Thr Pro Ala Ile Pro Leu Thr Ala Thr Glu Pro Thr
2645                2650                2655

Ser Ser Leu Ala Thr Ser Phe Asp Ser Thr Pro Leu Val Thr Ile
2660                2665                2670

Ala Ser Asp Ser Leu Gly Thr Val Pro Glu Thr Thr Leu Thr Met
2675                2680                2685

Ser Glu Thr Ser Asn Gly Asp Ala Leu Val Leu Lys Thr Val Ser
2690                2695                2700

Asn Pro Asp Arg Ser Ile Pro Gly Ile Thr Ile Gln Gly Val Thr
2705                2710                2715

Glu Ser Pro Leu His Pro Ser Ser Thr Ser Pro Ser Lys Ile Val
2720                2725                2730

Ala Pro Arg Asn Thr Thr Tyr Glu Gly Ser Ile Thr Val Ala Leu
2735                2740                2745

Ser Thr Leu Pro Ala Gly Thr Thr Gly Ser Leu Val Phe Ser Gln
2750                2755                2760

Ser Ser Glu Asn Ser Glu Thr Thr Ala Leu Val Asp Ser Ser Ala
2765                2770                2775

Gly Leu Glu Arg Ala Ser Val Met Pro Leu Thr Thr Gly Ser Gln
2780                2785                2790

Gly Met Ala Ser Ser Gly Gly Ile Arg Ser Gly Ser Thr His Ser
2795                2800                2805

Thr Gly Thr Lys Thr Phe Ser Ser Leu Pro Leu Thr Met Asn Pro
2810                2815                2820

Gly Glu Val Thr Ala Met Ser Glu Ile Thr Thr Asn Arg Leu Thr
2825                2830                2835

Ala Thr Gln Ser Thr Ala Pro Lys Gly Ile Pro Val Lys Pro Thr
2840                2845                2850

Ser Ala Glu Ser Gly Leu Leu Thr Pro Val Ser Ala Ser Ser Ser
2855                2860                2865

Pro Ser Lys Ala Phe Ala Ser Leu Thr Thr Ala Pro Pro Ser Thr
2870                2875                2880

Trp Gly Ile Pro Gln Ser Thr Leu Thr Phe Glu Phe Ser Glu Val
2885                2890                2895

Pro Ser Leu Asp Thr Lys Ser Ala Ser Leu Pro Thr Pro Gly Gln
2900                2905                2910

Ser Leu Asn Thr Ile Pro Asp Ser Asp Ala Ser Thr Ala Ser Ser
2915                2920                2925

Ser Leu Ser Lys Ser Pro Glu Lys Asn Pro Arg Ala Arg Met Met
2930                2935                2940

Thr Ser Thr Lys Ala Ile Ser Ala Ser Ser Phe Gln Ser Thr Gly
2945                2950                2955

Phe Thr Glu Thr Pro Glu Gly Ser Ala Ser Pro Ser Met Ala Gly
2960                2965                2970

His Glu Pro Arg Val Pro Thr Ser Gly Thr Gly Asp Pro Arg Tyr
```

```
                2975                2980                2985
Ala Ser Glu Ser Met Ser Tyr Pro Asp Pro Ser Lys Ala Ser Ser
    2990                2995                3000
Ala Met Thr Ser Thr Ser Leu Ala Ser Lys Leu Thr Thr Leu Phe
    3005                3010                3015
Ser Thr Gly Gln Ala Ala Arg Ser Gly Ser Ser Ser Pro Ile
    3020                3025                3030
Ser Leu Ser Thr Glu Lys Glu Thr Ser Phe Leu Ser Pro Thr Ala
    3035                3040                3045
Ser Thr Ser Arg Lys Thr Ser Leu Phe Leu Gly Pro Ser Met Ala
    3050                3055                3060
Arg Gln Pro Asn Ile Leu Val His Leu Gln Thr Ser Ala Leu Thr
    3065                3070                3075
Leu Ser Pro Thr Ser Thr Leu Asn Met Ser Gln Glu Glu Pro Pro
    3080                3085                3090
Glu Leu Thr Ser Ser Gln Thr Ile Ala Glu Glu Gly Thr Thr
    3095                3100                3105
Ala Glu Thr Gln Thr Leu Thr Phe Thr Pro Ser Glu Thr Pro Thr
    3110                3115                3120
Ser Leu Leu Pro Val Ser Ser Pro Thr Glu Pro Thr Ala Arg Arg
    3125                3130                3135
Lys Ser Ser Pro Glu Thr Trp Ala Ser Ser Ile Ser Val Pro Ala
    3140                3145                3150
Lys Thr Ser Leu Val Glu Thr Asp Gly Thr Leu Val Thr Thr
    3155                3160                3165
Ile Lys Met Ser Ser Gln Ala Ala Gln Gly Asn Ser Thr Trp Pro
    3170                3175                3180
Ala Pro Ala Glu Glu Thr Gly Thr Ser Pro Ala Gly Thr Ser Pro
    3185                3190                3195
Gly Ser Pro Glu Val Ser Thr Thr Leu Lys Ile Met Ser Ser Lys
    3200                3205                3210
Glu Pro Ser Ile Ser Pro Glu Ile Arg Ser Thr Val Arg Asn Ser
    3215                3220                3225
Pro Trp Lys Thr Pro Glu Thr Thr Val Pro Met Glu Thr Thr Val
    3230                3235                3240
Glu Pro Val Thr Leu Gln Ser Thr Ala Leu Gly Ser Gly Ser Thr
    3245                3250                3255
Ser Ile Ser His Leu Pro Thr Gly Thr Thr Ser Pro Thr Lys Ser
    3260                3265                3270
Pro Thr Glu Asn Met Leu Ala Thr Glu Arg Val Ser Leu Ser Pro
    3275                3280                3285
Ser Pro Pro Glu Ala Trp Thr Asn Leu Tyr Ser Gly Thr Pro Gly
    3290                3295                3300
Gly Thr Arg Gln Ser Leu Ala Thr Met Ser Ser Val Ser Leu Glu
    3305                3310                3315
Ser Pro Thr Ala Arg Ser Ile Thr Gly Thr Gly Gln Gln Ser Ser
    3320                3325                3330
Pro Glu Leu Val Ser Lys Thr Thr Gly Met Glu Phe Ser Met Trp
    3335                3340                3345
His Gly Ser Thr Gly Gly Thr Gly Asp Thr His Val Ser Leu
    3350                3355                3360
Ser Thr Ser Ser Asn Ile Leu Glu Asp Pro Val Thr Ser Pro Asn
    3365                3370                3375
```

```
Ser Val Ser Ser Leu Thr Asp Lys Ser Lys His Lys Thr Glu Thr
    3380            3385            3390

Trp Val Ser Thr Thr Ala Ile Pro Ser Thr Val Leu Asn Asn Lys
    3395            3400            3405

Ile Met Ala Ala Glu Gln Gln Thr Ser Arg Ser Val Asp Glu Ala
    3410            3415            3420

Tyr Ser Ser Thr Ser Ser Trp Ser Asp Gln Thr Ser Gly Ser Asp
    3425            3430            3435

Ile Thr Leu Gly Ala Ser Pro Asp Val Thr Asn Thr Leu Tyr Ile
    3440            3445            3450

Thr Ser Thr Ala Gln Thr Thr Ser Leu Val Ser Leu Pro Ser Gly
    3455            3460            3465

Asp Gln Gly Ile Thr Ser Leu Thr Asn Pro Ser Gly Gly Lys Thr
    3470            3475            3480

Ser Ser Ala Ser Ser Val Thr Ser Pro Ser Ile Gly Leu Glu Thr
    3485            3490            3495

Leu Arg Ala Asn Val Ser Ala Val Lys Ser Asp Ile Ala Pro Thr
    3500            3505            3510

Ala Gly His Leu Ser Gln Thr Ser Ser Pro Ala Glu Val Ser Ile
    3515            3520            3525

Leu Asp Val Thr Thr Ala Pro Thr Pro Gly Ile Ser Thr Thr Ile
    3530            3535            3540

Thr Thr Met Gly Thr Asn Ser Ile Ser Thr Thr Thr Pro Asn Pro
    3545            3550            3555

Glu Val Gly Met Ser Thr Met Asp Ser Thr Pro Ala Thr Glu Arg
    3560            3565            3570

Arg Thr Thr Ser Thr Glu His Pro Ser Thr Trp Ser Ser Thr Ala
    3575            3580            3585

Ala Ser Asp Ser Trp Thr Val Thr Asp Met Thr Ser Asn Leu Lys
    3590            3595            3600

Val Ala Arg Ser Pro Gly Thr Ile Ser Thr Met His Thr Thr Ser
    3605            3610            3615

Phe Leu Ala Ser Ser Thr Glu Leu Asp Ser Met Ser Thr Pro His
    3620            3625            3630

Gly Arg Ile Thr Val Ile Gly Thr Ser Leu Val Thr Pro Ser Ser
    3635            3640            3645

Asp Ala Ser Ala Val Lys Thr Glu Thr Ser Thr Ser Glu Arg Thr
    3650            3655            3660

Leu Ser Pro Ser Asp Thr Thr Ala Ser Thr Pro Ile Ser Thr Phe
    3665            3670            3675

Ser Arg Val Gln Arg Met Ser Ile Ser Val Pro Asp Ile Leu Ser
    3680            3685            3690

Thr Ser Trp Thr Pro Ser Ser Thr Glu Ala Glu Asp Val Pro Val
    3695            3700            3705

Ser Met Val Pro Thr Asp His Ala Ser Thr Lys Thr Asp Pro Asn
    3710            3715            3720

Thr Pro Leu Ser Thr Phe Leu Phe Asp Ser Leu Ser Thr Leu Asp
    3725            3730            3735

Trp Asp Thr Gly Arg Ser Leu Ser Ser Ala Thr Ala Thr Thr Ser
    3740            3745            3750

Ala Pro Gln Gly Ala Thr Thr Pro Gln Glu Leu Thr Leu Glu Thr
    3755            3760            3765
```

-continued

```
Met Ile Ser Pro Ala Thr Ser Gln Leu Pro Phe Ser Ile Gly His
    3770                3775                3780

Ile Thr Ser Ala Val Thr Pro Ala Ala Met Ala Arg Ser Ser Gly
    3785                3790                3795

Val Thr Phe Ser Arg Pro Asp Pro Thr Ser Lys Lys Ala Glu Gln
    3800                3805                3810

Thr Ser Thr Gln Leu Pro Thr Thr Ser Ala His Pro Gly Gln
    3815                3820                3825

Val Pro Arg Ser Ala Ala Thr Thr Leu Asp Val Ile Pro His Thr
    3830                3835                3840

Ala Lys Thr Pro Asp Ala Thr Phe Gln Arg Gln Gly Gln Thr Ala
    3845                3850                3855

Leu Thr Thr Glu Ala Arg Ala Thr Ser Asp Ser Trp Asn Glu Lys
    3860                3865                3870

Glu Lys Ser Thr Pro Ser Ala Pro Trp Ile Thr Glu Met Met Asn
    3875                3880                3885

Ser Val Ser Glu Asp Thr Ile Lys Glu Val Thr Ser Ser Ser Ser
    3890                3895                3900

Val Leu Lys Asp Pro Glu Tyr Ala Gly His Lys Leu Gly Ile Trp
    3905                3910                3915

Asp Asp Phe Ile Pro Lys Phe Gly Lys Ala Ala His Met Arg Glu
    3920                3925                3930

Leu Pro Leu Leu Ser Pro Pro Gln Asp Lys Glu Ala Ile His Pro
    3935                3940                3945

Ser Thr Asn Thr Val Glu Thr Thr Gly Trp Val Thr Ser Ser Glu
    3950                3955                3960

His Ala Ser His Ser Thr Ile Pro Ala His Ser Ala Ser Ser Lys
    3965                3970                3975

Leu Thr Ser Pro Val Val Thr Thr Ser Thr Arg Glu Gln Ala Ile
    3980                3985                3990

Val Ser Met Ser Thr Thr Thr Trp Pro Glu Ser Thr Arg Ala Arg
    3995                4000                4005

Thr Glu Pro Asn Ser Phe Leu Thr Ile Glu Leu Arg Asp Val Ser
    4010                4015                4020

Pro Tyr Met Asp Thr Ser Ser Thr Thr Gln Thr Ser Ile Ile Ser
    4025                4030                4035

Ser Pro Gly Ser Thr Ala Ile Thr Lys Gly His Arg Thr Glu Ile
    4040                4045                4050

Thr Ser Tyr Lys Arg Ile Ser Ser Ser Phe Leu Ala Gln Ser Met
    4055                4060                4065

Arg Ser Ser Asp Ser Pro Ser Glu Ala Ile Thr Arg Leu Ser Asn
    4070                4075                4080

Phe Pro Ala Met Thr Glu Ser Gly Gly Met Ile Leu Ala Met Gln
    4085                4090                4095

Thr Ser Pro Pro Gly Ala Thr Ser Ile Ser Ala Pro Thr Leu Asp
    4100                4105                4110

Thr Ser Ala Thr Ala Ser Trp Thr Gly Thr Pro Leu Ala Thr Thr
    4115                4120                4125

Gln Arg Phe Thr Tyr Ser Glu Lys Thr Thr Leu Phe Ser Lys Gly
    4130                4135                4140

Arg Glu Asp Thr Ser Gln Pro Ser Pro Pro Cys Val Glu Glu Thr
    4145                4150                4155

Ser Ser Ser Ser Ser Val Val Pro Ile His Ala Thr Thr Ser Pro
```

```
                    4160                4165                4170
Ser Asn Ile Leu Leu Thr Ser Gln Gly His Ser Pro Ser Ser Thr
    4175                4180                4185
Pro Pro Val Thr Ser Val Phe Leu Ser Glu Thr Ser Gly Leu Gly
    4190                4195                4200
Lys Thr Thr Asp Met Ser Arg Ile Ser Leu Glu Pro Gly Thr Ser
    4205                4210                4215
Leu Pro Pro Asn Leu Ser Ser Thr Ala Gly Glu Ala Leu Ser Thr
    4220                4225                4230
Tyr Glu Ala Ser Arg Asp Thr Lys Ala Ile His His Ser Ala Asp
    4235                4240                4245
Thr Ala Val Thr Asn Met Glu Ala Thr Ser Ser Glu Tyr Ser Pro
    4250                4255                4260
Ile Pro Gly His Thr Lys Pro Ser Lys Ala Thr Ser Pro Leu Val
    4265                4270                4275
Thr Ser His Ile Met Gly Asp Ile Thr Ser Ser Thr Ser Val Phe
    4280                4285                4290
Gly Ser Ser Glu Thr Thr Glu Ile Glu Thr Val Ser Ser Val Asn
    4295                4300                4305
Gln Gly Leu Gln Glu Arg Ser Thr Ser Gln Val Ala Ser Ser Ala
    4310                4315                4320
Thr Glu Thr Ser Thr Val Ile Thr His Val Ser Ser Gly Asp Ala
    4325                4330                4335
Thr Thr His Val Thr Lys Thr Gln Ala Thr Phe Ser Ser Gly Thr
    4340                4345                4350
Ser Ile Ser Ser Pro His Gln Phe Ile Thr Ser Thr Asn Thr Phe
    4355                4360                4365
Thr Asp Val Ser Thr Asn Pro Ser Thr Ser Leu Ile Met Thr Glu
    4370                4375                4380
Ser Ser Gly Val Thr Ile Thr Gln Thr Gly Pro Thr Gly Ala
    4385                4390                4395
Ala Thr Gln Gly Pro Tyr Leu Leu Asp Thr Ser Thr Met Pro Tyr
    4400                4405                4410
Leu Thr Glu Thr Pro Leu Ala Val Thr Pro Asp Phe Met Gln Ser
    4415                4420                4425
Glu Lys Thr Thr Leu Ile Ser Lys Gly Pro Lys Asp Val Thr Trp
    4430                4435                4440
Thr Ser Pro Pro Ser Val Ala Glu Thr Ser Tyr Pro Ser Ser Leu
    4445                4450                4455
Thr Pro Phe Leu Val Thr Thr Ile Pro Pro Ala Thr Ser Thr Leu
    4460                4465                4470
Gln Gly Gln His Thr Ser Ser Pro Val Ser Ala Thr Ser Val Leu
    4475                4480                4485
Thr Ser Gly Leu Val Lys Thr Thr Asp Met Leu Asn Thr Ser Met
    4490                4495                4500
Glu Pro Val Thr Asn Ser Pro Gln Asn Leu Asn Asn Pro Ser Asn
    4505                4510                4515
Glu Ile Leu Ala Thr Leu Ala Ala Thr Thr Asp Ile Glu Thr Ile
    4520                4525                4530
His Pro Ser Ile Asn Lys Ala Val Thr Asn Met Gly Thr Ala Ser
    4535                4540                4545
Ser Ala His Val Leu His Ser Thr Leu Pro Val Ser Ser Glu Pro
    4550                4555                4560
```

-continued

```
Ser Thr Ala Thr Ser Pro Met Val Pro Ala Ser Ser Met Gly Asp
    4565                4570                4575

Ala Leu Ala Ser Ile Ser Ile Pro Gly Ser Glu Thr Thr Asp Ile
    4580                4585                4590

Glu Gly Glu Pro Thr Ser Ser Leu Thr Ala Gly Arg Lys Glu Asn
    4595                4600                4605

Ser Thr Leu Gln Glu Met Asn Ser Thr Thr Glu Ser Asn Ile Ile
    4610                4615                4620

Leu Ser Asn Val Ser Val Gly Ala Ile Thr Glu Ala Thr Lys Met
    4625                4630                4635

Glu Val Pro Ser Phe Asp Ala Thr Phe Ile Pro Thr Pro Ala Gln
    4640                4645                4650

Ser Thr Lys Phe Pro Asp Ile Phe Ser Val Ala Ser Ser Arg Leu
    4655                4660                4665

Ser Asn Ser Pro Pro Met Thr Ile Ser Thr His Met Thr Thr Thr
    4670                4675                4680

Gln Thr Gly Ser Ser Gly Ala Thr Ser Lys Ile Pro Leu Ala Leu
    4685                4690                4695

Asp Thr Ser Thr Leu Glu Thr Ser Ala Gly Thr Pro Ser Val Val
    4700                4705                4710

Thr Glu Gly Phe Ala His Ser Lys Ile Thr Thr Ala Met Asn Asn
    4715                4720                4725

Asp Val Lys Asp Val Ser Gln Thr Asn Pro Pro Phe Gln Asp Glu
    4730                4735                4740

Ala Ser Ser Pro Ser Ser Gln Ala Pro Val Leu Val Thr Thr Leu
    4745                4750                4755

Pro Ser Ser Val Ala Phe Thr Pro Gln Trp His Ser Thr Ser Ser
    4760                4765                4770

Pro Val Ser Met Ser Ser Val Leu Thr Ser Ser Leu Val Lys Thr
    4775                4780                4785

Ala Gly Lys Val Asp Thr Ser Leu Glu Thr Val Thr Ser Ser Pro
    4790                4795                4800

Gln Ser Met Ser Asn Thr Leu Asp Asp Ile Ser Val Thr Ser Ala
    4805                4810                4815

Ala Thr Thr Asp Ile Glu Thr Thr His Pro Ser Ile Asn Thr Val
    4820                4825                4830

Val Thr Asn Val Gly Thr Thr Gly Ser Ala Phe Glu Ser His Ser
    4835                4840                4845

Thr Val Ser Ala Tyr Pro Glu Pro Ser Lys Val Thr Ser Pro Asn
    4850                4855                4860

Val Thr Thr Ser Thr Met Glu Asp Thr Thr Ile Ser Arg Ser Ile
    4865                4870                4875

Pro Lys Ser Ser Lys Thr Thr Arg Thr Glu Thr Glu Thr Thr Ser
    4880                4885                4890

Ser Leu Thr Pro Lys Leu Arg Glu Thr Ser Ile Ser Gln Glu Ile
    4895                4900                4905

Thr Ser Ser Thr Glu Thr Ser Thr Val Pro Tyr Lys Glu Leu Thr
    4910                4915                4920

Gly Ala Thr Thr Glu Val Ser Arg Thr Asp Val Thr Ser Ser Ser
    4925                4930                4935

Ser Thr Ser Phe Pro Gly Pro Asp Gln Ser Thr Val Ser Leu Asp
    4940                4945                4950
```

-continued

Ile Ser Thr Glu Thr Asn Thr Arg Leu Ser Thr Ser Pro Ile Met
4955             4960                 4965

Thr Glu Ser Ala Glu Ile Thr Ile Thr Thr Gln Thr Gly Pro His
4970             4975                 4980

Gly Ala Thr Ser Gln Asp Thr Phe Thr Met Asp Pro Ser Asn Thr
4985             4990                 4995

Thr Pro Gln Ala Gly Ile His Ser Ala Met Thr His Gly Phe Ser
5000             5005                 5010

Gln Leu Asp Val Thr Thr Leu Met Ser Arg Ile Pro Gln Asp Val
5015             5020                 5025

Ser Trp Thr Ser Pro Pro Ser Val Asp Lys Thr Ser Pro Ser
5030             5035                 5040

Ser Phe Leu Ser Ser Pro Ala Met Thr Thr Pro Ser Leu Ile Ser
5045             5050                 5055

Ser Thr Leu Pro Glu Asp Lys Leu Ser Ser Pro Met Thr Ser Leu
5060             5065                 5070

Leu Thr Ser Gly Leu Val Lys Ile Thr Asp Ile Leu Arg Thr Arg
5075             5080                 5085

Leu Glu Pro Val Thr Ser Ser Leu Pro Asn Phe Ser Ser Thr Ser
5090             5095                 5100

Asp Lys Ile Leu Ala Thr Ser Lys Asp Ser Lys Asp Thr Lys Glu
5105             5110                 5115

Ile Phe Pro Ser Ile Asn Thr Glu Glu Thr Asn Val Lys Ala Asn
5120             5125                 5130

Asn Ser Gly His Glu Ser His Ser Pro Ala Leu Ala Asp Ser Glu
5135             5140                 5145

Thr Pro Lys Ala Thr Thr Gln Met Val Ile Thr Thr Val Gly
5150             5155                 5160

Asp Pro Ala Pro Ser Thr Ser Met Pro Val His Gly Ser Ser Glu
5165             5170                 5175

Thr Thr Asn Ile Lys Arg Glu Pro Thr Tyr Phe Leu Thr Pro Arg
5180             5185                 5190

Leu Arg Glu Thr Ser Thr Ser Gln Glu Ser Ser Phe Pro Thr Asp
5195             5200                 5205

Thr Ser Phe Leu Leu Ser Lys Val Pro Thr Gly Thr Ile Thr Glu
5210             5215                 5220

Val Ser Ser Thr Gly Val Ile Ser Ser Ser Lys Ile Ser Thr Pro
5225             5230                 5235

Asp His Asp Lys Ser Thr Val Pro Pro Asp Thr Phe Thr Gly Glu
5240             5245                 5250

Ile Pro Arg Val Phe Thr Ser Ser Ile Lys Thr Lys Ser Ala Glu
5255             5260                 5265

Met Thr Ile Thr Thr Gln Ala Ser Pro Pro Glu Ser Ala Ser His
5270             5275                 5280

Ser Thr Leu Pro Leu Asp Ser Thr Thr Leu Ser Gln Gly Gly
5285             5290                 5295

Thr His Ser Thr Val Ser Gln Gly Phe Pro Tyr Ser Glu Val Thr
5300             5305                 5310

Thr Leu Met Gly Met Gly Pro Gly Asn Val Ser Trp Met Thr Thr
5315             5320                 5325

Pro Pro Val Glu Glu Thr Ser Ser Val Ser Ser Leu Met Ser Ser
5330             5335                 5340

Pro Ala Met Thr Ser Pro Ser Pro Val Ser Ser Thr Ser Pro Gln

```
                  5345                5350                5355

Ser Ile Pro Ser Ser Pro Leu Pro Val Thr Ala Leu Pro Thr Ser
    5360                5365                5370

Val Leu Val Thr Thr Thr Asp Val Leu Gly Thr Thr Ser Pro Glu
    5375                5380                5385

Ser Val Thr Ser Ser Pro Pro Asn Leu Ser Ser Ile Thr His Glu
    5390                5395                5400

Arg Pro Ala Thr Tyr Lys Asp Thr Ala His Thr Glu Ala Ala Met
    5405                5410                5415

His His Ser Thr Asn Thr Ala Val Thr Asn Val Gly Thr Ser Gly
    5420                5425                5430

Ser Gly His Lys Ser Gln Ser Ser Val Leu Ala Asp Ser Glu Thr
    5435                5440                5445

Ser Lys Ala Thr Pro Leu Met Ser Thr Ala Ser Thr Leu Gly Asp
    5450                5455                5460

Thr Ser Val Ser Thr Ser Thr Pro Asn Ile Ser Gln Thr Asn Gln
    5465                5470                5475

Ile Gln Thr Glu Pro Thr Ala Ser Leu Ser Pro Arg Leu Arg Glu
    5480                5485                5490

Ser Ser Thr Ser Glu Lys Thr Ser Ser Thr Thr Glu Thr Asn Thr
    5495                5500                5505

Ala Phe Ser Tyr Val Pro Thr Gly Ala Ile Thr Gln Ala Ser Arg
    5510                5515                5520

Thr Glu Ile Ser Ser Ser Arg Thr Ser Ile Ser Asp Leu Asp Arg
    5525                5530                5535

Ser Thr Ile Ala Pro Asp Ile Ser Thr Gly Met Ile Thr Arg Leu
    5540                5545                5550

Phe Thr Ser Pro Ile Met Thr Lys Ser Ala Glu Met Thr Val Thr
    5555                5560                5565

Thr Gln Thr Thr Thr Pro Gly Ala Thr Ser Gln Gly Ile Leu Pro
    5570                5575                5580

Trp Asp Thr Ser Thr Thr Leu Phe Gln Gly Gly Thr His Ser Thr
    5585                5590                5595

Val Ser Gln Gly Phe Pro His Ser Glu Ile Thr Thr Leu Arg Ser
    5600                5605                5610

Arg Thr Pro Gly Asp Val Ser Trp Met Thr Thr Pro Pro Val Glu
    5615                5620                5625

Glu Thr Ser Ser Gly Phe Ser Leu Met Ser Pro Ser Met Thr Ser
    5630                5635                5640

Pro Ser Pro Val Ser Ser Thr Ser Pro Glu Ser Ile Pro Ser Ser
    5645                5650                5655

Pro Leu Pro Val Thr Ala Leu Leu Thr Ser Val Leu Val Thr Thr
    5660                5665                5670

Thr Asn Val Leu Gly Thr Thr Ser Pro Glu Pro Val Thr Ser Ser
    5675                5680                5685

Pro Pro Asn Leu Ser Ser Pro Thr Gln Glu Arg Leu Thr Thr Tyr
    5690                5695                5700

Lys Asp Thr Ala His Thr Glu Ala Met His Ala Ser Met His Thr
    5705                5710                5715

Asn Thr Ala Val Ala Asn Val Gly Thr Ser Ile Ser Gly His Glu
    5720                5725                5730

Ser Gln Ser Ser Val Pro Ala Asp Ser His Thr Ser Lys Ala Thr
    5735                5740                5745
```

-continued

```
Ser Pro Met Gly Ile Thr Phe Ala Met Gly Asp Thr Ser Val Tyr
    5750                5755                5760

Thr Ser Thr Pro Ala Phe Phe Glu Thr Arg Ile Gln Ser Glu Ser
    5765                5770                5775

Thr Ser Ser Leu Ile Pro Gly Leu Arg Asp Thr Arg Thr Ser Glu
    5780                5785                5790

Glu Ile Asn Thr Val Thr Glu Thr Ser Thr Val Leu Ser Glu Val
    5795                5800                5805

Pro Thr Thr Thr Thr Thr Glu Val Ser Arg Thr Glu Val Ile Thr
    5810                5815                5820

Ser Ser Arg Thr Thr Ile Ser Gly Pro Asp His Ser Lys Met Ser
    5825                5830                5835

Pro Tyr Ile Ser Thr Glu Thr Ile Thr Arg Leu Ser Thr Phe Pro
    5840                5845                5850

Phe Val Thr Gly Ser Thr Glu Met Ala Ile Thr Asn Gln Thr Gly
    5855                5860                5865

Pro Ile Gly Thr Ile Ser Gln Ala Thr Leu Thr Leu Asp Thr Ser
    5870                5875                5880

Ser Thr Ala Ser Trp Glu Gly Thr His Ser Pro Val Thr Gln Arg
    5885                5890                5895

Phe Pro His Ser Glu Glu Thr Thr Thr Met Ser Arg Ser Thr Lys
    5900                5905                5910

Gly Val Ser Trp Gln Ser Pro Pro Ser Val Glu Glu Thr Ser Ser
    5915                5920                5925

Pro Ser Ser Pro Val Pro Leu Pro Ala Ile Thr Ser His Ser Ser
    5930                5935                5940

Leu Tyr Ser Ala Val Ser Gly Ser Ser Pro Thr Ser Ala Leu Pro
    5945                5950                5955

Val Thr Ser Leu Leu Thr Ser Gly Arg Arg Lys Thr Ile Asp Met
    5960                5965                5970

Leu Asp Thr His Ser Glu Leu Val Thr Ser Ser Leu Pro Ser Ala
    5975                5980                5985

Ser Ser Phe Ser Gly Glu Ile Leu Thr Ser Glu Ala Ser Thr Asn
    5990                5995                6000

Thr Glu Thr Ile His Phe Ser Glu Asn Thr Ala Glu Thr Asn Met
    6005                6010                6015

Gly Thr Thr Asn Ser Met His Lys Leu His Ser Ser Val Ser Ile
    6020                6025                6030

His Ser Gln Pro Ser Gly His Thr Pro Pro Lys Val Thr Gly Ser
    6035                6040                6045

Met Met Glu Asp Ala Ile Val Ser Thr Ser Thr Pro Gly Ser Pro
    6050                6055                6060

Glu Thr Lys Asn Val Asp Arg Asp Ser Thr Ser Pro Leu Thr Pro
    6065                6070                6075

Glu Leu Lys Glu Asp Ser Thr Ala Leu Val Met Asn Ser Thr Thr
    6080                6085                6090

Glu Ser Asn Thr Val Phe Ser Ser Val Ser Leu Asp Ala Ala Thr
    6095                6100                6105

Glu Val Ser Arg Ala Glu Val Thr Tyr Tyr Asp Pro Thr Phe Met
    6110                6115                6120

Pro Ala Ser Ala Gln Ser Thr Lys Ser Pro Asp Ile Ser Pro Glu
    6125                6130                6135
```

```
Ala Ser Ser Ser His Ser Asn Ser Pro Pro Leu Thr Ile Ser Thr
    6140                6145                6150

His Lys Thr Ile Ala Thr Gln Thr Gly Pro Ser Gly Val Thr Ser
    6155                6160                6165

Leu Gly Gln Leu Thr Leu Asp Thr Ser Thr Ile Ala Thr Ser Ala
    6170                6175                6180

Gly Thr Pro Ser Ala Arg Thr Gln Asp Phe Val Asp Ser Glu Thr
    6185                6190                6195

Thr Ser Val Met Asn Asn Asp Leu Asn Asp Val Leu Lys Thr Ser
    6200                6205                6210

Pro Phe Ser Ala Glu Glu Ala Asn Ser Leu Ser Ser Gln Ala Pro
    6215                6220                6225

Leu Leu Val Thr Thr Ser Pro Ser Pro Val Thr Ser Thr Leu Gln
    6230                6235                6240

Glu His Ser Thr Ser Ser Leu Val Ser Val Thr Ser Val Pro Thr
    6245                6250                6255

Pro Thr Leu Ala Lys Ile Thr Asp Met Asp Thr Asn Leu Glu Pro
    6260                6265                6270

Val Thr Arg Ser Pro Gln Asn Leu Arg Asn Thr Leu Ala Thr Ser
    6275                6280                6285

Glu Ala Thr Thr Asp Thr His Thr Met His Pro Ser Ile Asn Thr
    6290                6295                6300

Ala Met Ala Asn Val Gly Thr Thr Ser Ser Pro Asn Glu Phe Tyr
    6305                6310                6315

Phe Thr Val Ser Pro Asp Ser Asp Pro Tyr Lys Ala Thr Ser Ala
    6320                6325                6330

Val Val Ile Thr Ser Thr Ser Gly Asp Ser Ile Val Ser Thr Ser
    6335                6340                6345

Met Pro Arg Ser Ser Ala Met Lys Lys Ile Glu Ser Glu Thr Thr
    6350                6355                6360

Phe Ser Leu Ile Phe Arg Leu Arg Glu Thr Ser Thr Ser Gln Lys
    6365                6370                6375

Ile Gly Ser Ser Ser Asp Thr Ser Thr Val Phe Asp Lys Ala Phe
    6380                6385                6390

Thr Ala Ala Thr Thr Glu Val Ser Arg Thr Glu Leu Thr Ser Ser
    6395                6400                6405

Ser Arg Thr Ser Ile Gln Gly Thr Glu Lys Pro Thr Met Ser Pro
    6410                6415                6420

Asp Thr Ser Thr Arg Ser Val Thr Met Leu Ser Thr Phe Ala Gly
    6425                6430                6435

Leu Thr Lys Ser Glu Glu Arg Thr Ile Ala Thr Gln Thr Gly Pro
    6440                6445                6450

His Arg Ala Thr Ser Gln Gly Thr Leu Thr Trp Asp Thr Ser Ile
    6455                6460                6465

Thr Thr Ser Gln Ala Gly Thr His Ser Ala Met Thr His Gly Phe
    6470                6475                6480

Ser Gln Leu Asp Leu Ser Thr Leu Thr Ser Arg Val Pro Glu Tyr
    6485                6490                6495

Ile Ser Gly Thr Ser Pro Pro Ser Val Glu Lys Thr Ser Ser Ser
    6500                6505                6510

Ser Ser Leu Leu Ser Leu Pro Ala Ile Thr Ser Pro Ser Pro Val
    6515                6520                6525

Pro Thr Thr Leu Pro Glu Ser Arg Pro Ser Ser Pro Val His Leu
```

```
                     6530              6535              6540
Thr Ser Leu Pro Thr Ser Gly Leu Val Lys Thr Thr Asp Met Leu
    6545              6550              6555
Ala Ser Val Ala Ser Leu Pro Pro Asn Leu Gly Ser Thr Ser His
    6560              6565              6570
Lys Ile Pro Thr Thr Ser Glu Asp Ile Lys Asp Thr Glu Lys Met
    6575              6580              6585
Tyr Pro Ser Thr Asn Ile Ala Val Thr Asn Val Gly Thr Thr Thr
    6590              6595              6600
Ser Glu Lys Glu Ser Tyr Ser Val Pro Ala Tyr Ser Glu Pro
    6605              6610              6615
Pro Lys Val Thr Ser Pro Met Val Thr Ser Phe Asn Ile Arg Asp
    6620              6625              6630
Thr Ile Val Ser Thr Ser Met Pro Gly Ser Ser Glu Ile Thr Arg
    6635              6640              6645
Ile Glu Met Glu Ser Thr Phe Ser Leu Ala His Gly Leu Lys Gly
    6650              6655              6660
Thr Ser Thr Ser Gln Asp Pro Ile Val Ser Thr Glu Lys Ser Ala
    6665              6670              6675
Val Leu His Lys Leu Thr Thr Gly Ala Thr Glu Thr Ser Arg Thr
    6680              6685              6690
Glu Val Ala Ser Ser Arg Arg Thr Ser Ile Pro Gly Pro Asp His
    6695              6700              6705
Ser Thr Glu Ser Pro Asp Ile Ser Thr Glu Val Ile Pro Ser Leu
    6710              6715              6720
Pro Ile Ser Leu Gly Ile Thr Glu Ser Ser Asn Met Thr Ile Ile
    6725              6730              6735
Thr Arg Thr Gly Pro Pro Leu Gly Ser Thr Ser Gln Gly Thr Phe
    6740              6745              6750
Thr Leu Asp Thr Pro Thr Thr Ser Ser Arg Ala Gly Thr His Ser
    6755              6760              6765
Met Ala Thr Gln Glu Phe Pro His Ser Glu Met Thr Thr Val Met
    6770              6775              6780
Asn Lys Asp Pro Glu Ile Leu Ser Trp Thr Ile Pro Pro Ser Ile
    6785              6790              6795
Glu Lys Thr Ser Phe Ser Ser Ser Leu Met Pro Ser Pro Ala Met
    6800              6805              6810
Thr Ser Pro Pro Val Ser Ser Thr Leu Pro Lys Thr Ile His Thr
    6815              6820              6825
Thr Pro Ser Pro Met Thr Ser Leu Leu Thr Pro Ser Leu Val Met
    6830              6835              6840
Thr Thr Asp Thr Leu Gly Thr Ser Pro Glu Pro Thr Thr Ser Ser
    6845              6850              6855
Pro Pro Asn Leu Ser Ser Thr Ser His Val Ile Leu Thr Thr Asp
    6860              6865              6870
Glu Asp Thr Thr Ala Ile Glu Ala Met His Pro Ser Thr Ser Thr
    6875              6880              6885
Ala Ala Thr Asn Val Glu Thr Thr Cys Ser Gly His Gly Ser Gln
    6890              6895              6900
Ser Ser Val Leu Thr Asp Ser Glu Lys Thr Lys Ala Thr Ala Pro
    6905              6910              6915
Met Asp Thr Thr Ser Thr Met Gly His Thr Thr Val Ser Thr Ser
    6920              6925              6930
```

-continued

Met Ser Val Ser Ser Glu Thr Thr Lys Ile Lys Arg Glu Ser Thr
              6935                6940                6945

Tyr Ser Leu Thr Pro Gly Leu Arg Glu Thr Ser Ile Ser Gln Asn
              6950                6955                6960

Ala Ser Phe Ser Thr Asp Thr Ser Ile Val Leu Ser Glu Val Pro
              6965                6970                6975

Thr Gly Thr Thr Ala Glu Val Ser Arg Thr Glu Val Thr Ser Ser
              6980                6985                6990

Gly Arg Thr Ser Ile Pro Gly Pro Ser Gln Ser Thr Val Leu Pro
              6995                7000                7005

Glu Ile Ser Thr Arg Thr Met Thr Arg Leu Phe Ala Ser Pro Thr
              7010                7015                7020

Met Thr Glu Ser Ala Glu Met Thr Ile Pro Thr Gln Thr Gly Pro
              7025                7030                7035

Ser Gly Ser Thr Ser Gln Asp Thr Leu Thr Leu Asp Thr Ser Thr
              7040                7045                7050

Thr Lys Ser Gln Ala Lys Thr His Ser Thr Leu Thr Gln Arg Phe
              7055                7060                7065

Pro His Ser Glu Met Thr Thr Leu Met Ser Arg Gly Pro Gly Asp
              7070                7075                7080

Met Ser Trp Gln Ser Ser Pro Ser Leu Glu Asn Pro Ser Ser Leu
              7085                7090                7095

Pro Ser Leu Leu Ser Leu Pro Ala Thr Thr Ser Pro Pro Pro Ile
              7100                7105                7110

Ser Ser Thr Leu Pro Val Thr Ile Ser Ser Ser Pro Leu Pro Val
              7115                7120                7125

Thr Ser Leu Leu Thr Ser Ser Pro Val Thr Thr Thr Asp Met Leu
              7130                7135                7140

His Thr Ser Pro Glu Leu Val Thr Ser Ser Pro Pro Lys Leu Ser
              7145                7150                7155

His Thr Ser Asp Glu Arg Leu Thr Thr Gly Lys Asp Thr Thr Asn
              7160                7165                7170

Thr Glu Ala Val His Pro Ser Thr Asn Thr Ala Ala Ser Asn Val
              7175                7180                7185

Glu Ile Pro Ser Phe Gly His Glu Ser Pro Ser Ser Ala Leu Ala
              7190                7195                7200

Asp Ser Glu Thr Ser Lys Ala Thr Ser Pro Met Phe Ile Thr Ser
              7205                7210                7215

Thr Gln Glu Asp Thr Thr Val Ala Ile Ser Thr Pro His Phe Leu
              7220                7225                7230

Glu Thr Ser Arg Ile Gln Lys Glu Ser Ile Ser Ser Leu Ser Pro
              7235                7240                7245

Lys Leu Arg Glu Thr Gly Ser Ser Val Glu Thr Ser Ser Ala Ile
              7250                7255                7260

Glu Thr Ser Ala Val Leu Ser Glu Val Ser Ile Gly Ala Thr Thr
              7265                7270                7275

Glu Ile Ser Arg Thr Glu Val Thr Ser Ser Ser Arg Thr Ser Ile
              7280                7285                7290

Ser Gly Ser Ala Glu Ser Thr Met Leu Pro Glu Ile Ser Thr Thr
              7295                7300                7305

Arg Lys Ile Ile Lys Phe Pro Thr Ser Pro Ile Leu Ala Glu Ser
              7310                7315                7320

-continued

```
Ser Glu Met Thr Ile Lys Thr Gln Thr Ser Pro Pro Gly Ser Thr
    7325                7330                7335

Ser Glu Ser Thr Phe Thr Leu Asp Thr Ser Thr Thr Pro Ser Leu
    7340                7345                7350

Val Ile Thr His Ser Thr Met Thr Gln Arg Leu Pro His Ser Glu
    7355                7360                7365

Ile Thr Thr Leu Val Ser Arg Gly Ala Gly Asp Val Pro Arg Pro
    7370                7375                7380

Ser Ser Leu Pro Val Glu Glu Thr Ser Pro Pro Ser Ser Gln Leu
    7385                7390                7395

Ser Leu Ser Ala Met Ile Ser Pro Ser Pro Val Ser Ser Thr Leu
    7400                7405                7410

Pro Ala Ser Ser His Ser Ser Ser Ala Ser Val Thr Ser Pro Leu
    7415                7420                7425

Thr Pro Gly Gln Val Lys Thr Thr Glu Val Leu Asp Ala Ser Ala
    7430                7435                7440

Glu Pro Glu Thr Ser Ser Pro Pro Ser Leu Ser Ser Thr Ser Val
    7445                7450                7455

Glu Ile Leu Ala Thr Ser Glu Val Thr Thr Asp Thr Glu Lys Ile
    7460                7465                7470

His Pro Phe Pro Asn Thr Ala Val Thr Lys Val Gly Thr Ser Ser
    7475                7480                7485

Ser Gly His Glu Ser Pro Ser Ser Val Leu Pro Asp Ser Glu Thr
    7490                7495                7500

Thr Lys Ala Thr Ser Ala Met Gly Thr Ile Ser Ile Met Gly Asp
    7505                7510                7515

Thr Ser Val Ser Thr Leu Thr Pro Ala Leu Ser Asn Thr Arg Lys
    7520                7525                7530

Ile Gln Ser Glu Pro Ala Ser Ser Leu Thr Thr Arg Leu Arg Glu
    7535                7540                7545

Thr Ser Thr Ser Glu Glu Thr Ser Leu Ala Thr Glu Ala Asn Thr
    7550                7555                7560

Val Leu Ser Lys Val Ser Thr Gly Ala Thr Thr Glu Val Ser Arg
    7565                7570                7575

Thr Glu Ala Ile Ser Phe Ser Arg Thr Ser Met Ser Gly Pro Glu
    7580                7585                7590

Gln Ser Thr Met Ser Gln Asp Ile Ser Ile Gly Thr Ile Pro Arg
    7595                7600                7605

Ile Ser Ala Ser Ser Val Leu Thr Glu Ser Ala Lys Met Thr Ile
    7610                7615                7620

Thr Thr Gln Thr Gly Pro Ser Glu Ser Thr Leu Glu Ser Thr Leu
    7625                7630                7635

Asn Leu Asn Thr Ala Thr Thr Pro Ser Trp Val Glu Thr His Ser
    7640                7645                7650

Ile Val Ile Gln Gly Phe Pro His Pro Glu Met Thr Thr Ser Met
    7655                7660                7665

Gly Arg Gly Pro Gly Gly Val Ser Trp Pro Ser Pro Pro Phe Val
    7670                7675                7680

Lys Glu Thr Ser Pro Pro Ser Ser Pro Leu Ser Leu Pro Ala Val
    7685                7690                7695

Thr Ser Pro His Pro Val Ser Thr Thr Phe Leu Ala His Ile Pro
    7700                7705                7710

Pro Ser Pro Leu Pro Val Thr Ser Leu Leu Thr Ser Gly Pro Ala
```

-continued

```
            7715                7720                7725
Thr Thr Thr Asp Ile Leu Gly Thr Ser Thr Glu Pro Gly Thr Ser
            7730                7735                7740
Ser Ser Ser Ser Leu Ser Thr Thr Ser His Glu Arg Leu Thr Thr
            7745                7750                7755
Tyr Lys Asp Thr Ala His Thr Glu Ala Val His Pro Ser Thr Asn
            7760                7765                7770
Thr Gly Gly Thr Asn Val Ala Thr Thr Ser Ser Gly Tyr Lys Ser
            7775                7780                7785
Gln Ser Ser Val Leu Ala Asp Ser Ser Pro Met Cys Thr Thr Ser
            7790                7795                7800
Thr Met Gly Asp Thr Ser Val Leu Thr Ser Thr Pro Ala Phe Leu
            7805                7810                7815
Glu Thr Arg Arg Ile Gln Thr Glu Leu Ala Ser Ser Leu Thr Pro
            7820                7825                7830
Gly Leu Arg Glu Ser Ser Gly Ser Glu Gly Thr Ser Ser Gly Thr
            7835                7840                7845
Lys Met Ser Thr Val Leu Ser Lys Val Pro Thr Gly Ala Thr Thr
            7850                7855                7860
Glu Ile Ser Lys Glu Asp Val Thr Ser Ile Pro Gly Pro Ala Gln
            7865                7870                7875
Ser Thr Ile Ser Pro Asp Thr Ser Thr Arg Thr Val Ser Trp Phe
            7880                7885                7890
Ser Thr Ser Pro Val Met Thr Glu Ser Ala Glu Ile Thr Met Asn
            7895                7900                7905
Thr His Thr Ser Pro Leu Gly Ala Thr Thr Gln Gly Thr Ser Thr
            7910                7915                7920
Leu Asp Thr Ser Ser Thr Thr Ser Leu Thr Met Thr His Ser Thr
            7925                7930                7935
Ile Ser Gln Gly Phe Ser His Ser Gln Met Ser Thr Leu Met Arg
            7940                7945                7950
Arg Gly Pro Glu Asp Val Ser Trp Met Ser Pro Leu Leu Glu
            7955                7960                7965
Lys Thr Arg Pro Ser Phe Ser Leu Met Ser Ser Pro Ala Thr Thr
            7970                7975                7980
Ser Pro Ser Pro Val Ser Ser Thr Leu Pro Glu Ser Ile Ser Ser
            7985                7990                7995
Ser Pro Leu Pro Val Thr Ser Leu Leu Thr Ser Gly Leu Ala Lys
            8000                8005                8010
Thr Thr Asp Met Leu His Lys Ser Ser Glu Pro Val Thr Asn Ser
            8015                8020                8025
Pro Ala Asn Leu Ser Ser Thr Ser Val Glu Ile Leu Ala Thr Ser
            8030                8035                8040
Glu Val Thr Thr Asp Thr Glu Lys Thr His Pro Ser Ser Asn Arg
            8045                8050                8055
Thr Val Thr Asp Val Gly Thr Ser Ser Ser Gly His Glu Ser Thr
            8060                8065                8070
Ser Phe Val Leu Ala Asp Ser Gln Thr Ser Lys Val Thr Ser Pro
            8075                8080                8085
Met Val Ile Thr Ser Thr Met Glu Asp Thr Ser Val Ser Thr Ser
            8090                8095                8100
Thr Pro Gly Phe Phe Glu Thr Ser Arg Ile Gln Thr Glu Pro Thr
            8105                8110                8115
```

-continued

```
Ser Ser Leu Thr Leu Gly Leu Arg Lys Thr Ser Ser Ser Glu Gly
    8120                8125                8130

Thr Ser Leu Ala Thr Glu Met Ser Thr Val Leu Ser Gly Val Pro
    8135                8140                8145

Thr Gly Ala Thr Ala Glu Val Ser Arg Thr Glu Val Thr Ser Ser
    8150                8155                8160

Ser Arg Thr Ser Ile Ser Gly Phe Ala Gln Leu Thr Val Ser Pro
    8165                8170                8175

Glu Thr Ser Thr Glu Thr Ile Thr Arg Leu Pro Thr Ser Ser Ile
    8180                8185                8190

Met Thr Glu Ser Ala Glu Met Met Ile Lys Thr Gln Thr Asp Pro
    8195                8200                8205

Pro Gly Ser Thr Pro Glu Ser Thr His Thr Val Asp Ile Ser Thr
    8210                8215                8220

Thr Pro Asn Trp Val Glu Thr His Ser Thr Val Thr Gln Arg Phe
    8225                8230                8235

Ser His Ser Glu Met Thr Thr Leu Val Ser Arg Ser Pro Gly Asp
    8240                8245                8250

Met Leu Trp Pro Ser Gln Ser Ser Val Glu Glu Thr Ser Ser Ala
    8255                8260                8265

Ser Ser Leu Leu Ser Leu Pro Ala Thr Thr Ser Pro Ser Pro Val
    8270                8275                8280

Ser Ser Thr Leu Val Glu Asp Phe Pro Ser Ala Ser Leu Pro Val
    8285                8290                8295

Thr Ser Leu Leu Thr Pro Gly Leu Val Ile Thr Thr Asp Arg Met
    8300                8305                8310

Gly Ile Ser Arg Glu Pro Gly Thr Ser Ser Thr Ser Asn Leu Ser
    8315                8320                8325

Ser Thr Ser His Glu Arg Leu Thr Thr Leu Glu Asp Thr Val Asp
    8330                8335                8340

Thr Glu Ala Met Gln Pro Ser Thr His Thr Ala Val Thr Asn Val
    8345                8350                8355

Arg Thr Ser Ile Ser Gly His Glu Ser Gln Ser Ser Val Leu Ser
    8360                8365                8370

Asp Ser Glu Thr Pro Lys Ala Thr Ser Ser Met Gly Thr Thr Tyr
    8375                8380                8385

Thr Met Gly Glu Thr Ser Val Ser Ile Ser Thr Ser Asp Phe Phe
    8390                8395                8400

Glu Thr Ser Arg Val Gln Ile Glu Pro Thr Ser Ser Leu Thr Ser
    8405                8410                8415

Gly Leu Arg Glu Thr Ser Ser Glu Arg Ile Ser Ser Ala Thr
    8420                8425                8430

Glu Gly Ser Thr Val Leu Ser Glu Val Pro Ser Gly Ala Thr Thr
    8435                8440                8445

Glu Val Ser Arg Thr Glu Val Ile Ser Ser Arg Gly Thr Ser Met
    8450                8455                8460

Ser Gly Pro Asp Gln Phe Thr Ile Ser Pro Asp Ile Ser Thr Glu
    8465                8470                8475

Ala Ile Thr Arg Leu Ser Thr Ser Pro Ile Met Thr Glu Ser Ala
    8480                8485                8490

Glu Ser Ala Ile Thr Ile Glu Thr Gly Ser Pro Gly Ala Thr Ser
    8495                8500                8505
```

```
Glu Gly Thr Leu Thr Leu Asp Thr Ser Thr Thr Phe Trp Ser
    8510            8515            8520
Gly Thr His Ser Thr Ala Ser Pro Gly Phe Ser His Ser Glu Met
    8525            8530            8535
Thr Thr Leu Met Ser Arg Thr Pro Gly Asp Val Pro Trp Pro Ser
    8540            8545            8550
Leu Pro Ser Val Glu Glu Ala Ser Ser Val Ser Ser Leu Ser
    8555            8560            8565
Ser Pro Ala Met Thr Ser Thr Ser Phe Phe Ser Ala Leu Pro Glu
    8570            8575            8580
Ser Ile Ser Ser Ser Pro His Pro Val Thr Ala Leu Leu Thr Leu
    8585            8590            8595
Gly Pro Val Lys Thr Thr Asp Met Leu Arg Thr Ser Ser Glu Pro
    8600            8605            8610
Glu Thr Ser Ser Pro Pro Asn Leu Ser Ser Thr Ser Ala Glu Ile
    8615            8620            8625
Leu Ala Thr Ser Glu Val Thr Lys Asp Arg Glu Lys Ile His Pro
    8630            8635            8640
Ser Ser Asn Thr Pro Val Val Asn Val Gly Thr Val Ile Tyr Lys
    8645            8650            8655
His Leu Ser Pro Ser Ser Val Leu Ala Asp Leu Val Thr Thr Lys
    8660            8665            8670
Pro Thr Ser Pro Met Ala Thr Thr Ser Thr Leu Gly Asn Thr Ser
    8675            8680            8685
Val Ser Thr Ser Thr Pro Ala Phe Pro Glu Thr Met Met Thr Gln
    8690            8695            8700
Pro Thr Ser Ser Leu Thr Ser Gly Leu Arg Glu Ile Ser Thr Ser
    8705            8710            8715
Gln Glu Thr Ser Ser Ala Thr Glu Arg Ser Ala Ser Leu Ser Gly
    8720            8725            8730
Met Pro Thr Gly Ala Thr Thr Lys Val Ser Arg Thr Glu Ala Leu
    8735            8740            8745
Ser Leu Gly Arg Thr Ser Thr Pro Gly Pro Ala Gln Ser Thr Ile
    8750            8755            8760
Ser Pro Glu Ile Ser Thr Glu Thr Ile Thr Arg Ile Ser Thr Pro
    8765            8770            8775
Leu Thr Thr Thr Gly Ser Ala Glu Met Thr Ile Thr Pro Lys Thr
    8780            8785            8790
Gly His Ser Gly Ala Ser Ser Gln Gly Thr Phe Thr Leu Asp Thr
    8795            8800            8805
Ser Ser Arg Ala Ser Trp Pro Gly Thr His Ser Ala Ala Thr His
    8810            8815            8820
Arg Ser Pro His Ser Gly Met Thr Thr Pro Met Ser Arg Gly Pro
    8825            8830            8835
Glu Asp Val Ser Trp Pro Ser Arg Pro Ser Val Glu Lys Thr Ser
    8840            8845            8850
Pro Pro Ser Ser Leu Val Ser Leu Ser Ala Val Thr Ser Pro Ser
    8855            8860            8865
Pro Leu Tyr Ser Thr Pro Ser Glu Ser Ser His Ser Ser Pro Leu
    8870            8875            8880
Arg Val Thr Ser Leu Phe Thr Pro Val Met Met Lys Thr Thr Asp
    8885            8890            8895
Met Leu Asp Thr Ser Leu Glu Pro Val Thr Thr Ser Pro Pro Ser
```

-continued

```
                8900                 8905                 8910

Met Asn Ile Thr Ser Asp Glu Ser Leu Ala Thr Ser Lys Ala Thr
    8915                 8920                 8925

Met Glu Thr Glu Ala Ile Gln Leu Ser Glu Asn Thr Ala Val Thr
    8930                 8935                 8940

Gln Met Gly Thr Ile Ser Ala Arg Gln Glu Phe Tyr Ser Ser Tyr
    8945                 8950                 8955

Pro Gly Leu Pro Glu Pro Ser Lys Val Thr Ser Pro Val Val Thr
    8960                 8965                 8970

Ser Ser Thr Ile Lys Asp Ile Val Ser Thr Thr Ile Pro Ala Ser
    8975                 8980                 8985

Ser Glu Ile Thr Arg Ile Glu Met Glu Ser Thr Ser Thr Leu Thr
    8990                 8995                 9000

Pro Thr Pro Arg Glu Thr Ser Thr Ser Gln Glu Ile His Ser Ala
    9005                 9010                 9015

Thr Lys Pro Ser Thr Val Pro Tyr Lys Ala Leu Thr Ser Ala Thr
    9020                 9025                 9030

Ile Glu Asp Ser Met Thr Gln Val Met Ser Ser Ser Arg Gly Pro
    9035                 9040                 9045

Ser Pro Asp Gln Ser Thr Met Ser Gln Asp Ile Ser Thr Glu Val
    9050                 9055                 9060

Ile Thr Arg Leu Ser Thr Ser Pro Ile Lys Ala Glu Ser Thr Glu
    9065                 9070                 9075

Met Thr Ile Thr Thr Gln Thr Gly Ser Pro Gly Ala Thr Ser Arg
    9080                 9085                 9090

Gly Thr Leu Thr Leu Asp Thr Ser Thr Thr Phe Met Ser Gly Thr
    9095                 9100                 9105

His Ser Thr Ala Ser Gln Gly Phe Ser His Ser Gln Met Thr Ala
    9110                 9115                 9120

Leu Met Ser Arg Thr Pro Gly Asp Val Pro Trp Leu Ser His Pro
    9125                 9130                 9135

Ser Val Glu Glu Ala Ser Ser Ala Ser Phe Ser Leu Ser Ser Pro
    9140                 9145                 9150

Val Met Thr Ser Ser Ser Pro Val Ser Ser Thr Leu Pro Asp Ser
    9155                 9160                 9165

Ile His Ser Ser Ser Leu Pro Val Thr Ser Leu Leu Thr Ser Gly
    9170                 9175                 9180

Leu Val Lys Thr Thr Glu Leu Leu Gly Thr Ser Ser Glu Pro Glu
    9185                 9190                 9195

Thr Ser Ser Pro Pro Asn Leu Ser Ser Thr Ser Ala Glu Ile Leu
    9200                 9205                 9210

Ala Thr Thr Glu Val Thr Thr Asp Thr Glu Lys Leu Glu Met Thr
    9215                 9220                 9225

Asn Val Val Thr Ser Gly Tyr Thr His Glu Ser Pro Ser Ser Val
    9230                 9235                 9240

Leu Ala Asp Ser Val Thr Thr Lys Ala Thr Ser Ser Met Gly Ile
    9245                 9250                 9255

Thr Tyr Pro Thr Gly Asp Thr Asn Val Leu Thr Ser Thr Pro Ala
    9260                 9265                 9270

Phe Ser Asp Thr Ser Arg Ile Gln Thr Lys Ser Lys Leu Ser Leu
    9275                 9280                 9285

Thr Pro Gly Leu Met Glu Thr Ser Ile Ser Glu Glu Thr Ser Ser
    9290                 9295                 9300
```

-continued

```
Ala  Thr  Glu  Lys  Ser  Thr  Val  Leu  Ser  Ser  Val  Pro  Thr  Gly  Ala
     9305                9310                9315

Thr  Thr  Glu  Val  Ser  Arg  Thr  Glu  Ala  Ile  Ser  Ser  Ser  Arg  Thr
     9320                9325                9330

Ser  Ile  Pro  Gly  Pro  Ala  Gln  Ser  Thr  Met  Ser  Ser  Asp  Thr  Ser
     9335                9340                9345

Met  Glu  Thr  Ile  Thr  Arg  Ile  Ser  Thr  Pro  Leu  Thr  Arg  Lys  Glu
     9350                9355                9360

Ser  Thr  Asp  Met  Ala  Ile  Thr  Pro  Lys  Thr  Gly  Pro  Ser  Gly  Ala
     9365                9370                9375

Thr  Ser  Gln  Gly  Thr  Phe  Thr  Leu  Asp  Ser  Ser  Ser  Thr  Ala  Ser
     9380                9385                9390

Trp  Pro  Gly  Thr  His  Ser  Ala  Thr  Thr  Gln  Arg  Phe  Pro  Gln  Ser
     9395                9400                9405

Val  Val  Thr  Thr  Pro  Met  Ser  Arg  Gly  Pro  Glu  Asp  Val  Ser  Trp
     9410                9415                9420

Pro  Ser  Pro  Leu  Ser  Val  Glu  Lys  Asn  Ser  Pro  Ser  Ser  Leu
     9425                9430                9435

Val  Ser  Ser  Ser  Val  Thr  Ser  Pro  Ser  Pro  Leu  Tyr  Ser  Thr
     9440                9445                9450

Pro  Ser  Gly  Ser  Ser  His  Ser  Ser  Pro  Val  Pro  Thr  Ser  Leu
     9455                9460                9465

Phe  Thr  Ser  Ile  Met  Met  Lys  Ala  Thr  Asp  Met  Leu  Asp  Ala  Ser
     9470                9475                9480

Leu  Glu  Pro  Glu  Thr  Thr  Ser  Ala  Pro  Asn  Met  Asn  Ile  Thr  Ser
     9485                9490                9495

Asp  Glu  Ser  Leu  Ala  Thr  Ser  Lys  Ala  Thr  Thr  Glu  Thr  Glu  Ala
     9500                9505                9510

Ile  His  Val  Phe  Glu  Asn  Thr  Ala  Ala  Ser  His  Val  Glu  Thr  Thr
     9515                9520                9525

Ser  Ala  Thr  Glu  Glu  Leu  Tyr  Ser  Ser  Ser  Pro  Gly  Phe  Ser  Glu
     9530                9535                9540

Pro  Thr  Lys  Val  Ile  Ser  Pro  Val  Val  Thr  Ser  Ser  Ser  Ile  Arg
     9545                9550                9555

Asp  Asn  Met  Val  Ser  Thr  Thr  Met  Pro  Gly  Ser  Ser  Gly  Ile  Thr
     9560                9565                9570

Arg  Ile  Glu  Ile  Glu  Ser  Met  Ser  Ser  Leu  Thr  Pro  Gly  Leu  Arg
     9575                9580                9585

Glu  Thr  Arg  Thr  Ser  Gln  Asp  Ile  Thr  Ser  Ser  Thr  Glu  Thr  Ser
     9590                9595                9600

Thr  Val  Leu  Tyr  Lys  Met  Ser  Ser  Gly  Ala  Thr  Pro  Glu  Val  Ser
     9605                9610                9615

Arg  Thr  Glu  Val  Met  Pro  Ser  Ser  Arg  Thr  Ser  Ile  Pro  Gly  Pro
     9620                9625                9630

Ala  Gln  Ser  Thr  Met  Ser  Leu  Asp  Ile  Ser  Asp  Glu  Val  Val  Thr
     9635                9640                9645

Arg  Leu  Ser  Thr  Ser  Pro  Ile  Met  Thr  Glu  Ser  Ala  Glu  Ile  Thr
     9650                9655                9660

Ile  Thr  Thr  Gln  Thr  Gly  Tyr  Ser  Leu  Ala  Thr  Ser  Gln  Val  Thr
     9665                9670                9675

Leu  Pro  Leu  Gly  Thr  Ser  Met  Thr  Phe  Leu  Ser  Gly  Thr  His  Ser
     9680                9685                9690
```

-continued

| | | | | | | | | | | |
|---|---|---|---|---|---|---|---|---|---|---|
| Thr | Met | Ser | Gln | Gly | Leu | Ser | His | Ser | Glu | Met | Thr | Asn | Leu | Met |
| 9695 | | | | | 9700 | | | | | 9705 | | | | |
| Ser | Arg | Gly | Pro | Glu | Ser | Leu | Ser | Trp | Thr | Ser | Pro | Arg | Phe | Val |
| 9710 | | | | | 9715 | | | | | 9720 | | | | |
| Glu | Thr | Thr | Arg | Ser | Ser | Ser | Ser | Leu | Thr | Ser | Leu | Pro | Leu | Thr |
| 9725 | | | | | 9730 | | | | | 9735 | | | | |
| Thr | Ser | Leu | Ser | Pro | Val | Ser | Ser | Thr | Leu | Leu | Asp | Ser | Ser | Pro |
| 9740 | | | | | 9745 | | | | | 9750 | | | | |
| Ser | Ser | Pro | Leu | Pro | Val | Thr | Ser | Leu | Ile | Leu | Pro | Gly | Leu | Val |
| 9755 | | | | | 9760 | | | | | 9765 | | | | |
| Lys | Thr | Thr | Glu | Val | Leu | Asp | Thr | Ser | Ser | Glu | Pro | Lys | Thr | Ser |
| 9770 | | | | | 9775 | | | | | 9780 | | | | |
| Ser | Ser | Pro | Asn | Leu | Ser | Ser | Thr | Ser | Val | Glu | Ile | Pro | Ala | Thr |
| 9785 | | | | | 9790 | | | | | 9795 | | | | |
| Ser | Glu | Ile | Met | Thr | Asp | Thr | Glu | Lys | Ile | His | Pro | Ser | Ser | Asn |
| 9800 | | | | | 9805 | | | | | 9810 | | | | |
| Thr | Ala | Val | Ala | Lys | Val | Arg | Thr | Ser | Ser | Ser | Val | His | Glu | Ser |
| 9815 | | | | | 9820 | | | | | 9825 | | | | |
| His | Ser | Ser | Val | Leu | Ala | Asp | Ser | Glu | Thr | Thr | Ile | Thr | Ile | Pro |
| 9830 | | | | | 9835 | | | | | 9840 | | | | |
| Ser | Met | Gly | Ile | Thr | Ser | Ala | Val | Asp | Asp | Thr | Thr | Val | Phe | Thr |
| 9845 | | | | | 9850 | | | | | 9855 | | | | |
| Ser | Asn | Pro | Ala | Phe | Ser | Glu | Thr | Arg | Arg | Ile | Pro | Thr | Glu | Pro |
| 9860 | | | | | 9865 | | | | | 9870 | | | | |
| Thr | Phe | Ser | Leu | Thr | Pro | Gly | Phe | Arg | Glu | Thr | Ser | Thr | Ser | Glu |
| 9875 | | | | | 9880 | | | | | 9885 | | | | |
| Glu | Thr | Thr | Ser | Ile | Thr | Glu | Thr | Ser | Ala | Val | Leu | Tyr | Gly | Val |
| 9890 | | | | | 9895 | | | | | 9900 | | | | |
| Pro | Thr | Ser | Ala | Thr | Thr | Glu | Val | Ser | Met | Thr | Glu | Ile | Met | Ser |
| 9905 | | | | | 9910 | | | | | 9915 | | | | |
| Ser | Asn | Arg | Thr | His | Ile | Pro | Asp | Ser | Asp | Gln | Ser | Thr | Met | Ser |
| 9920 | | | | | 9925 | | | | | 9930 | | | | |
| Pro | Asp | Ile | Ile | Thr | Glu | Val | Ile | Thr | Arg | Leu | Ser | Ser | Ser | Ser |
| 9935 | | | | | 9940 | | | | | 9945 | | | | |
| Met | Met | Ser | Glu | Ser | Thr | Gln | Met | Thr | Ile | Thr | Thr | Gln | Lys | Ser |
| 9950 | | | | | 9955 | | | | | 9960 | | | | |
| Ser | Pro | Gly | Ala | Thr | Ala | Gln | Ser | Thr | Leu | Thr | Leu | Ala | Thr | Thr |
| 9965 | | | | | 9970 | | | | | 9975 | | | | |
| Thr | Ala | Pro | Leu | Ala | Arg | Thr | His | Ser | Thr | Val | Pro | Pro | Arg | Phe |
| 9980 | | | | | 9985 | | | | | 9990 | | | | |
| Leu | His | Ser | Glu | Met | Thr | Thr | Leu | Met | Ser | Arg | Ser | Pro | Glu | Asn |
| 9995 | | | | | 10000 | | | | | 10005 | | | | |
| Pro | Ser | Trp | Lys | Ser | Ser | Pro | Phe | Val | Glu | Lys | Thr | Ser | Ser | Ser |
| 10010 | | | | | 10015 | | | | | 10020 | | | | |
| Ser | Ser | Leu | Leu | Ser | Leu | Pro | Val | Thr | Thr | Ser | Pro | Ser | Val | Ser |
| 10025 | | | | | 10030 | | | | | 10035 | | | | |
| Ser | Thr | Leu | Pro | Gln | Ser | Ile | Pro | Ser | Ser | Ser | Phe | Ser | Val | Thr |
| 10040 | | | | | 10045 | | | | | 10050 | | | | |
| Ser | Leu | Leu | Thr | Pro | Gly | Met | Val | Lys | Thr | Thr | Asp | Thr | Ser | Thr |
| 10055 | | | | | 10060 | | | | | 10065 | | | | |
| Glu | Pro | Gly | Thr | Ser | Leu | Ser | Pro | Asn | Leu | Ser | Gly | Thr | Ser | Val |
| 10070 | | | | | 10075 | | | | | 10080 | | | | |
| Glu | Ile | Leu | Ala | Ala | Ser | Glu | Val | Thr | Thr | Asp | Thr | Glu | Lys | Ile |

```
              10085                10090                10095
His Pro Ser Ser Ser Met Ala  Val Thr Asn Val Gly  Thr Thr Ser
              10100                10105                10110
Ser Gly His Glu Leu Tyr Ser  Ser Val Ser Ile His  Ser Glu Pro
              10115                10120                10125
Ser Lys Ala Thr Tyr Pro Val  Gly Thr Pro Ser      Met Ala Glu
              10130                10135                10140
Thr Ser Ile Ser Thr Ser Met  Pro Ala Asn Phe Glu  Thr Thr Gly
              10145                10150                10155
Phe Glu Ala Glu Pro Phe Ser  His Leu Thr Ser Gly  Phe Arg Lys
              10160                10165                10170
Thr Asn Met Ser Leu Asp Thr  Ser Ser Val Thr Pro  Thr Asn Thr
              10175                10180                10185
Pro Ser Ser Pro Gly Ser Thr  His Leu Leu Gln Ser  Ser Lys Thr
              10190                10195                10200
Asp Phe Thr Ser Ser Ala Lys  Thr Ser Ser Pro Asp  Trp Pro Pro
              10205                10210                10215
Ala Ser Gln Tyr Thr Glu Ile  Pro Val Asp Ile Ile  Thr Pro Phe
              10220                10225                10230
Asn Ala Ser Pro Ser Ile Thr  Glu Ser Thr Gly Ile  Thr Ser Phe
              10235                10240                10245
Pro Glu Ser Arg Phe Thr Met  Ser Val Thr Glu Ser  Thr His His
              10250                10255                10260
Leu Ser Thr Asp Leu Leu Pro  Ser Ala Glu Thr Ile  Ser Thr Gly
              10265                10270                10275
Thr Val Met Pro Ser Leu Ser  Glu Ala Met Thr Ser  Phe Ala Thr
              10280                10285                10290
Thr Gly Val Pro Arg Ala Ile  Ser Gly Ser Gly Ser  Pro Phe Ser
              10295                10300                10305
Arg Thr Glu Ser Gly Pro Gly  Asp Ala Thr Leu Ser  Thr Ile Ala
              10310                10315                10320
Glu Ser Leu Pro Ser Ser Thr  Pro Val Pro Phe Ser  Ser Ser Thr
              10325                10330                10335
Phe Thr Thr Asp Ser Ser Thr  Thr Ile Pro Ala Leu  His Glu Ile
              10340                10345                10350
Thr Ser Ser Ser Ala Thr Pro  Tyr Arg Val Asp Thr  Ser Leu Gly
              10355                10360                10365
Thr Glu Ser Ser Thr Thr Glu  Gly Arg Leu Val Met  Val Ser Thr
              10370                10375                10380
Leu Asp Thr Ser Ser Gln Pro  Gly Arg Thr Ser Ser  Thr Pro Ile
              10385                10390                10395
Leu Asp Thr Arg Met Thr Glu  Ser Val Glu Leu Gly  Thr Val Thr
              10400                10405                10410
Ser Ala Tyr Gln Val Pro Ser  Leu Ser Thr Arg Leu  Thr Arg Thr
              10415                10420                10425
Asp Gly Ile Met Glu His Ile  Thr Lys Ile Pro Asn  Glu Ala Ala
              10430                10435                10440
His Arg Gly Thr Ile Arg Pro  Val Lys Gly Pro Gln  Thr Ser Thr
              10445                10450                10455
Ser Pro Ala Ser Pro Lys Gly  Leu His Thr Gly Gly  Thr Lys Arg
              10460                10465                10470
Met Glu Thr Thr Thr Thr Ala  Leu Lys Thr Thr Thr  Thr Ala Leu
              10475                10480                10485
```

```
Lys Thr Thr Ser Arg Ala Thr  Leu Thr Thr Ser Val  Tyr Thr Pro
    10490           10495                10500

Thr Leu Gly Thr Leu Thr Pro  Leu Asn Ala Ser Arg  Gln Met Ala
    10505           10510                10515

Ser Thr Ile Leu Thr Glu Met  Met Ile Thr Thr Pro  Tyr Val Phe
    10520           10525                10530

Pro Asp Val Pro Glu Thr Thr  Ser Ser Leu Ala Thr  Ser Leu Gly
    10535           10540                10545

Ala Glu Thr Ser Thr Ala Leu  Pro Arg Thr Thr Pro  Ser Val Leu
    10550           10555                10560

Asn Arg Glu Ser Glu Thr Thr  Ala Ser Leu Val Ser  Arg Ser Gly
    10565           10570                10575

Ala Glu Arg Ser Pro Val Ile  Gln Thr Leu Asp Val  Ser Ser Ser
    10580           10585                10590

Glu Pro Asp Thr Thr Ala Ser  Trp Val Ile His Pro  Ala Glu Thr
    10595           10600                10605

Ile Pro Thr Val Ser Lys Thr  Thr Pro Asn Phe Phe  His Ser Glu
    10610           10615                10620

Leu Asp Thr Val Ser Ser Thr  Ala Thr Ser His Gly  Ala Asp Val
    10625           10630                10635

Ser Ser Ala Ile Pro Thr Asn  Ile Ser Pro Ser Glu  Leu Asp Ala
    10640           10645                10650

Leu Thr Pro Leu Val Thr Ile  Ser Gly Thr Asp Thr  Ser Thr Thr
    10655           10660                10665

Phe Pro Thr Leu Thr Lys Ser  Pro His Glu Thr Glu  Thr Arg Thr
    10670           10675                10680

Thr Trp Leu Thr His Pro Ala  Glu Thr Ser Ser Thr  Ile Pro Arg
    10685           10690                10695

Thr Ile Pro Asn Phe Ser His  His Glu Ser Asp Ala  Thr Pro Ser
    10700           10705                10710

Ile Ala Thr Ser Pro Gly Ala  Glu Thr Ser Ser Ala  Ile Pro Ile
    10715           10720                10725

Met Thr Val Ser Pro Gly Ala  Glu Asp Leu Val Thr  Ser Gln Val
    10730           10735                10740

Thr Ser Ser Gly Thr Asp Arg  Asn Met Thr Ile Pro  Thr Leu Thr
    10745           10750                10755

Leu Ser Pro Gly Glu Pro Lys  Thr Ile Ala Ser Leu  Val Thr His
    10760           10765                10770

Pro Glu Ala Gln Thr Ser Ser  Ala Ile Pro Thr Ser  Thr Ile Ser
    10775           10780                10785

Pro Ala Val Ser Arg Leu Val  Thr Ser Met Val Thr  Ser Leu Ala
    10790           10795                10800

Ala Lys Thr Ser Thr Thr Asn  Arg Ala Leu Thr Asn  Ser Pro Gly
    10805           10810                10815

Glu Pro Ala Thr Thr Val Ser  Leu Val Thr His Pro  Ala Gln Thr
    10820           10825                10830

Ser Pro Thr Val Pro Trp Thr  Thr Ser Ile Phe Phe  His Ser Lys
    10835           10840                10845

Ser Asp Thr Thr Pro Ser Met  Thr Thr Ser His Gly  Ala Glu Ser
    10850           10855                10860

Ser Ser Ala Val Pro Thr Pro  Thr Val Ser Thr Glu  Val Pro Gly
    10865           10870                10875
```

-continued

| | | | | | | | | | | | |
|---|---|---|---|---|---|---|---|---|---|---|---|
| Val | Val | Thr | Pro | Leu | Val | Thr | Ser | Ser | Arg | Ala | Val | Ile | Ser | Thr |
| | 10880 | | | | 10885 | | | | | 10890 | | | | |
| Thr | Ile | Pro | Ile | Leu | Thr | Leu | Ser | Pro | Gly | Glu | Pro | Glu | Thr | Thr |
| | 10895 | | | | 10900 | | | | | 10905 | | | | |
| Pro | Ser | Met | Ala | Thr | Ser | His | Gly | Glu | Glu | Ala | Ser | Ser | Ala | Ile |
| | 10910 | | | | 10915 | | | | | 10920 | | | | |
| Pro | Thr | Pro | Thr | Val | Ser | Pro | Gly | Val | Pro | Gly | Val | Val | Thr | Ser |
| | 10925 | | | | 10930 | | | | | 10935 | | | | |
| Leu | Val | Thr | Ser | Ser | Arg | Ala | Val | Thr | Ser | Thr | Thr | Ile | Pro | Ile |
| | 10940 | | | | 10945 | | | | | 10950 | | | | |
| Leu | Thr | Phe | Ser | Leu | Gly | Glu | Pro | Glu | Thr | Thr | Pro | Ser | Met | Ala |
| | 10955 | | | | 10960 | | | | | 10965 | | | | |
| Thr | Ser | His | Gly | Thr | Glu | Ala | Gly | Ser | Ala | Val | Pro | Thr | Val | Leu |
| | 10970 | | | | 10975 | | | | | 10980 | | | | |
| Pro | Glu | Val | Pro | Gly | Met | Val | Thr | Ser | Leu | Val | Ala | Ser | Ser | Arg |
| | 10985 | | | | 10990 | | | | | 10995 | | | | |
| Ala | Val | Thr | Ser | Thr | Thr | Leu | Pro | Thr | Leu | Thr | Leu | Ser | Pro | Gly |
| | 11000 | | | | 11005 | | | | | 11010 | | | | |
| Glu | Pro | Glu | Thr | Thr | Pro | Ser | Met | Ala | Thr | Ser | His | Gly | Ala | Glu |
| | 11015 | | | | 11020 | | | | | 11025 | | | | |
| Ala | Ser | Ser | Thr | Val | Pro | Thr | Val | Ser | Pro | Glu | Val | Pro | Gly | Val |
| | 11030 | | | | 11035 | | | | | 11040 | | | | |
| Val | Thr | Ser | Leu | Val | Thr | Ser | Ser | Ser | Gly | Val | Asn | Ser | Thr | Ser |
| | 11045 | | | | 11050 | | | | | 11055 | | | | |
| Ile | Pro | Thr | Leu | Ile | Leu | Ser | Pro | Gly | Glu | Leu | Glu | Thr | Thr | Pro |
| | 11060 | | | | 11065 | | | | | 11070 | | | | |
| Ser | Met | Ala | Thr | Ser | His | Gly | Ala | Glu | Ala | Ser | Ser | Ala | Val | Pro |
| | 11075 | | | | 11080 | | | | | 11085 | | | | |
| Thr | Pro | Thr | Val | Ser | Pro | Gly | Val | Ser | Gly | Val | Val | Thr | Pro | Leu |
| | 11090 | | | | 11095 | | | | | 11100 | | | | |
| Val | Thr | Ser | Ser | Arg | Ala | Val | Thr | Ser | Thr | Thr | Ile | Pro | Ile | Leu |
| | 11105 | | | | 11110 | | | | | 11115 | | | | |
| Thr | Leu | Ser | Ser | Ser | Glu | Pro | Glu | Thr | Thr | Pro | Ser | Met | Ala | Thr |
| | 11120 | | | | 11125 | | | | | 11130 | | | | |
| Ser | His | Gly | Val | Glu | Ala | Ser | Ser | Ala | Val | Leu | Thr | Val | Ser | Pro |
| | 11135 | | | | 11140 | | | | | 11145 | | | | |
| Glu | Val | Pro | Gly | Met | Val | Thr | Ser | Leu | Val | Thr | Ser | Ser | Arg | Ala |
| | 11150 | | | | 11155 | | | | | 11160 | | | | |
| Val | Thr | Ser | Thr | Thr | Ile | Pro | Thr | Leu | Thr | Ile | Ser | Ser | Asp | Glu |
| | 11165 | | | | 11170 | | | | | 11175 | | | | |
| Pro | Glu | Thr | Thr | Thr | Ser | Leu | Val | Thr | His | Ser | Glu | Ala | Lys | Met |
| | 11180 | | | | 11185 | | | | | 11190 | | | | |
| Ile | Ser | Ala | Ile | Pro | Thr | Leu | Ala | Val | Ser | Pro | Thr | Val | Gln | Gly |
| | 11195 | | | | 11200 | | | | | 11205 | | | | |
| Leu | Val | Thr | Ser | Leu | Val | Thr | Ser | Ser | Gly | Ser | Glu | Thr | Ser | Ala |
| | 11210 | | | | 11215 | | | | | 11220 | | | | |
| Phe | Ser | Asn | Leu | Thr | Val | Ala | Ser | Ser | Gln | Pro | Glu | Thr | Ile | Asp |
| | 11225 | | | | 11230 | | | | | 11235 | | | | |
| Ser | Trp | Val | Ala | His | Pro | Gly | Thr | Glu | Ala | Ser | Ser | Val | Val | Pro |
| | 11240 | | | | 11245 | | | | | 11250 | | | | |
| Thr | Leu | Thr | Val | Ser | Thr | Gly | Glu | Pro | Phe | Thr | Asn | Ile | Ser | Leu |
| | 11255 | | | | 11260 | | | | | 11265 | | | | |
| Val | Thr | His | Pro | Ala | Glu | Ser | Ser | Ser | Thr | Leu | Pro | Arg | Thr | Thr |

-continued

```
            11270               11275               11280
Ser Arg Phe Ser His Ser Glu Leu Asp Thr Met Pro Ser Thr Val
            11285               11290               11295
Thr Ser Pro Glu Ala Glu Ser Ser Ala Ile Ser Thr Thr Ile
            11300               11305               11310
Ser Pro Gly Ile Pro Gly Val Leu Thr Ser Leu Val Thr Ser Ser
            11315               11320               11325
Gly Arg Asp Ile Ser Ala Thr Phe Pro Thr Val Pro Glu Ser Pro
            11330               11335               11340
His Glu Ser Glu Ala Thr Ala Ser Trp Val Thr His Pro Ala Val
            11345               11350               11355
Thr Ser Thr Thr Val Pro Arg Thr Thr Pro Asn Tyr Ser His Ser
            11360               11365               11370
Glu Pro Asp Thr Thr Pro Ser Ile Ala Thr Ser Pro Gly Ala Glu
            11375               11380               11385
Ala Thr Ser Asp Phe Pro Thr Ile Thr Val Ser Pro Asp Val Pro
            11390               11395               11400
Asp Met Val Thr Ser Gln Val Thr Ser Ser Gly Thr Asp Thr Ser
            11405               11410               11415
Ile Thr Ile Pro Thr Leu Thr Leu Ser Ser Gly Glu Pro Glu Thr
            11420               11425               11430
Thr Thr Ser Phe Ile Thr Tyr Ser Glu Thr His Thr Ser Ser Ala
            11435               11440               11445
Ile Pro Thr Leu Pro Val Ser Pro Gly Ala Ser Lys Met Leu Thr
            11450               11455               11460
Ser Leu Val Ile Ser Ser Gly Thr Asp Ser Thr Thr Thr Phe Pro
            11465               11470               11475
Thr Leu Thr Glu Thr Pro Tyr Glu Pro Glu Thr Thr Ala Ile Gln
            11480               11485               11490
Leu Ile His Pro Ala Glu Thr Asn Thr Met Val Pro Arg Thr Thr
            11495               11500               11505
Pro Lys Phe Ser His Ser Lys Ser Asp Thr Thr Leu Pro Val Ala
            11510               11515               11520
Ile Thr Ser Pro Gly Pro Glu Ala Ser Ser Ala Val Ser Thr Thr
            11525               11530               11535
Thr Ile Ser Pro Asp Met Ser Asp Leu Val Thr Ser Leu Val Pro
            11540               11545               11550
Ser Ser Gly Thr Asp Thr Ser Thr Thr Phe Pro Thr Leu Ser Glu
            11555               11560               11565
Thr Pro Tyr Glu Pro Glu Thr Thr Ala Thr Trp Leu Thr His Pro
            11570               11575               11580
Ala Glu Thr Ser Thr Thr Val Ser Gly Thr Ile Pro Asn Phe Ser
            11585               11590               11595
His Arg Gly Ser Asp Thr Ala Pro Ser Met Val Thr Ser Pro Gly
            11600               11605               11610
Val Asp Thr Arg Ser Gly Val Pro Thr Thr Thr Ile Pro Pro Ser
            11615               11620               11625
Ile Pro Gly Val Val Thr Ser Gln Val Thr Ser Ser Ala Thr Asp
            11630               11635               11640
Thr Ser Thr Ala Ile Pro Thr Leu Thr Pro Ser Pro Gly Glu Pro
            11645               11650               11655
Glu Thr Thr Ala Ser Ser Ala Thr His Pro Gly Thr Gln Thr Gly
            11660               11665               11670
```

```
Phe Thr Val Pro Ile Arg Thr Val Pro Ser Ser Glu Pro Asp Thr
    11675           11680               11685

Met Ala Ser Trp Val Thr His Pro Pro Gln Thr Ser Thr Pro Val
    11690           11695               11700

Ser Arg Thr Thr Ser Ser Phe Ser His Ser Ser Pro Asp Ala Thr
    11705           11710               11715

Pro Val Met Ala Thr Ser Pro Arg Thr Glu Ala Ser Ser Ala Val
    11720           11725               11730

Leu Thr Thr Ile Ser Pro Gly Ala Pro Glu Met Val Thr Ser Gln
    11735           11740               11745

Ile Thr Ser Ser Gly Ala Ala Thr Ser Thr Thr Val Pro Thr Leu
    11750           11755               11760

Thr His Ser Pro Gly Met Pro Glu Thr Thr Ala Leu Leu Ser Thr
    11765           11770               11775

His Pro Arg Thr Glu Thr Ser Lys Thr Phe Pro Ala Ser Thr Val
    11780           11785               11790

Phe Pro Gln Val Ser Glu Thr Thr Ala Ser Leu Thr Ile Arg Pro
    11795           11800               11805

Gly Ala Glu Thr Ser Thr Ala Leu Pro Thr Gln Thr Thr Ser Ser
    11810           11815               11820

Leu Phe Thr Leu Leu Val Thr Gly Thr Ser Arg Val Asp Leu Ser
    11825           11830               11835

Pro Thr Ala Ser Pro Gly Val Ser Ala Lys Thr Ala Pro Leu Ser
    11840           11845               11850

Thr His Pro Gly Thr Glu Thr Ser Thr Met Ile Pro Thr Ser Thr
    11855           11860               11865

Leu Ser Leu Gly Leu Leu Glu Thr Thr Gly Leu Leu Ala Thr Ser
    11870           11875               11880

Ser Ser Ala Glu Thr Ser Thr Ser Thr Leu Thr Leu Thr Val Ser
    11885           11890               11895

Pro Ala Val Ser Gly Leu Ser Ser Ala Ser Ile Thr Thr Asp Lys
    11900           11905               11910

Pro Gln Thr Val Thr Ser Trp Asn Thr Glu Thr Ser Pro Ser Val
    11915           11920               11925

Thr Ser Val Gly Pro Pro Glu Phe Ser Arg Thr Val Thr Gly Thr
    11930           11935               11940

Thr Met Thr Leu Ile Pro Ser Glu Met Pro Thr Pro Pro Lys Thr
    11945           11950               11955

Ser His Gly Glu Gly Val Ser Pro Thr Thr Ile Leu Arg Thr Thr
    11960           11965               11970

Met Val Glu Ala Thr Asn Leu Ala Thr Thr Gly Ser Ser Pro Thr
    11975           11980               11985

Val Ala Lys Thr Thr Thr Thr Phe Asn Thr Leu Ala Gly Ser Leu
    11990           11995               12000

Phe Thr Pro Leu Thr Thr Pro Gly Met Ser Thr Leu Ala Ser Glu
    12005           12010               12015

Ser Val Thr Ser Arg Thr Ser Tyr Asn His Arg Ser Trp Ile Ser
    12020           12025               12030

Thr Thr Ser Ser Tyr Asn Arg Arg Tyr Trp Thr Pro Ala Thr Ser
    12035           12040               12045

Thr Pro Val Thr Ser Thr Phe Ser Pro Gly Ile Ser Thr Ser Ser
    12050           12055               12060
```

```
Ile Pro Ser Ser Thr Ala Ala   Thr Val Pro Phe   Met Val Pro Phe
    12065           12070         12075
Thr Leu Asn Phe Thr Ile Thr   Asn Leu Gln Tyr   Glu Glu Asp Met
    12080           12085         12090
Arg His Pro Gly Ser Arg Lys   Phe Asn Ala Thr   Glu Arg Glu Leu
    12095           12100         12105
Gln Gly Leu Leu Lys Pro Leu   Phe Arg Asn Ser   Ser Leu Glu Tyr
    12110           12115         12120
Leu Tyr Ser Gly Cys Arg Leu   Ala Ser Leu Arg   Pro Glu Lys Asp
    12125           12130         12135
Ser Ser Ala Met Ala Val Asp   Ala Ile Cys Thr   His Arg Pro Asp
    12140           12145         12150
Pro Glu Asp Leu Gly Leu Asp   Arg Glu Arg Leu   Tyr Trp Glu Leu
    12155           12160         12165
Ser Asn Leu Thr Asn Gly Ile   Gln Glu Leu Gly   Pro Tyr Thr Leu
    12170           12175         12180
Asp Arg Asn Ser Leu Tyr Val   Asn Gly Phe Thr   His Arg Ser Ser
    12185           12190         12195
Met Pro Thr Thr Ser Thr Pro   Gly Thr Ser Thr   Val Asp Val Gly
    12200           12205         12210
Thr Ser Gly Thr Pro Ser Ser   Ser Pro Ser Pro   Thr Ala Ala Gly
    12215           12220         12225
Pro Leu Leu Met Pro Phe Thr   Leu Asn Phe Thr   Ile Thr Asn Leu
    12230           12235         12240
Gln Tyr Glu Glu Asp Met Arg   Arg Thr Gly Ser   Arg Lys Phe Asn
    12245           12250         12255
Thr Met Glu Ser Val Leu Gln   Gly Leu Leu Lys   Pro Leu Phe Lys
    12260           12265         12270
Asn Thr Ser Val Gly Pro Leu   Tyr Ser Gly Cys   Arg Leu Thr Leu
    12275           12280         12285
Leu Arg Pro Glu Lys Asp Gly   Ala Ala Thr Gly   Val Asp Ala Ile
    12290           12295         12300
Cys Thr His Arg Leu Asp Pro   Lys Ser Pro Gly   Leu Asn Arg Glu
    12305           12310         12315
Gln Leu Tyr Trp Glu Leu Ser   Lys Leu Thr Asn   Asp Ile Glu Glu
    12320           12325         12330
Leu Gly Pro Tyr Thr Leu Asp   Arg Asn Ser Leu   Tyr Val Asn Gly
    12335           12340         12345
Phe Thr His Gln Ser Ser Val   Ser Thr Thr Ser   Thr Pro Gly Thr
    12350           12355         12360
Ser Thr Val Asp Leu Arg Thr   Ser Gly Thr Pro   Ser Ser Leu Ser
    12365           12370         12375
Ser Pro Thr Ile Met Ala Ala   Gly Pro Leu Leu   Val Pro Phe Thr
    12380           12385         12390
Leu Asn Phe Thr Ile Thr Asn   Leu Gln Tyr Gly   Glu Asp Met Gly
    12395           12400         12405
His Pro Gly Ser Arg Lys Phe   Asn Thr Thr Glu   Arg Val Leu Gln
    12410           12415         12420
Gly Leu Leu Gly Pro Ile Phe   Lys Asn Thr Ser   Val Gly Pro Leu
    12425           12430         12435
Tyr Ser Gly Cys Arg Leu Thr   Ser Leu Arg Ser   Glu Lys Asp Gly
    12440           12445         12450
Ala Ala Thr Gly Val Asp Ala   Ile Cys Ile His   His Leu Asp Pro
```

```
                12455               12460               12465

Lys  Ser  Pro  Gly  Leu  Asn  Arg  Glu  Arg  Leu  Tyr  Trp  Glu  Leu  Ser
          12470               12475               12480

Gln  Leu  Thr  Asn  Gly  Ile  Lys  Glu  Leu  Gly  Pro  Tyr  Thr  Leu  Asp
          12485               12490               12495

Arg  Asn  Ser  Leu  Tyr  Val  Asn  Gly  Phe  Thr  His  Arg  Thr  Ser  Val
          12500               12505               12510

Pro  Thr  Ser  Ser  Thr  Pro  Gly  Thr  Ser  Thr  Val  Asp  Leu  Gly  Thr
          12515               12520               12525

Ser  Gly  Thr  Pro  Phe  Ser  Leu  Pro  Ser  Pro  Ala  Thr  Ala  Gly  Pro
          12530               12535               12540

Leu  Leu  Val  Leu  Phe  Thr  Leu  Asn  Phe  Thr  Ile  Thr  Asn  Leu  Lys
          12545               12550               12555

Tyr  Glu  Glu  Asp  Met  His  Arg  Pro  Gly  Ser  Arg  Lys  Phe  Asn  Thr
          12560               12565               12570

Thr  Glu  Arg  Val  Leu  Gln  Thr  Leu  Leu  Gly  Pro  Met  Phe  Lys  Asn
          12575               12580               12585

Thr  Ser  Val  Gly  Leu  Leu  Tyr  Ser  Gly  Cys  Arg  Leu  Thr  Leu  Leu
          12590               12595               12600

Arg  Ser  Glu  Lys  Asp  Gly  Ala  Ala  Thr  Gly  Val  Asp  Ala  Ile  Cys
          12605               12610               12615

Thr  His  Arg  Leu  Asp  Pro  Lys  Ser  Pro  Gly  Leu  Asp  Arg  Glu  Gln
          12620               12625               12630

Leu  Tyr  Trp  Glu  Leu  Ser  Gln  Leu  Thr  Asn  Gly  Ile  Lys  Glu  Leu
          12635               12640               12645

Gly  Pro  Tyr  Thr  Leu  Asp  Arg  Asn  Ser  Leu  Tyr  Val  Asn  Gly  Phe
          12650               12655               12660

Thr  His  Trp  Ile  Pro  Val  Pro  Thr  Ser  Ser  Thr  Pro  Gly  Thr  Ser
          12665               12670               12675

Thr  Val  Asp  Leu  Gly  Ser  Gly  Thr  Pro  Ser  Ser  Leu  Pro  Ser  Pro
          12680               12685               12690

Thr  Ala  Ala  Gly  Pro  Leu  Leu  Val  Pro  Phe  Thr  Leu  Asn  Phe  Thr
          12695               12700               12705

Ile  Thr  Asn  Leu  Gln  Tyr  Glu  Glu  Asp  Met  His  His  Pro  Gly  Ser
          12710               12715               12720

Arg  Lys  Phe  Asn  Thr  Thr  Glu  Arg  Val  Leu  Gln  Gly  Leu  Leu  Gly
          12725               12730               12735

Pro  Met  Phe  Lys  Asn  Thr  Ser  Val  Gly  Leu  Leu  Tyr  Ser  Gly  Cys
          12740               12745               12750

Arg  Leu  Thr  Leu  Leu  Arg  Ser  Glu  Lys  Asp  Gly  Ala  Ala  Thr  Gly
          12755               12760               12765

Val  Asp  Ala  Ile  Cys  Thr  His  Arg  Leu  Asp  Pro  Lys  Ser  Pro  Gly
          12770               12775               12780

Val  Asp  Arg  Glu  Gln  Leu  Tyr  Trp  Glu  Leu  Ser  Gln  Leu  Thr  Asn
          12785               12790               12795

Gly  Ile  Lys  Glu  Leu  Gly  Pro  Tyr  Thr  Leu  Asp  Arg  Asn  Ser  Leu
          12800               12805               12810

Tyr  Val  Asn  Gly  Phe  Thr  His  Gln  Thr  Ser  Ala  Pro  Asn  Thr  Ser
          12815               12820               12825

Thr  Pro  Gly  Thr  Ser  Thr  Val  Asp  Leu  Gly  Thr  Ser  Gly  Thr  Pro
          12830               12835               12840

Ser  Ser  Leu  Pro  Ser  Pro  Thr  Ser  Ala  Gly  Pro  Leu  Leu  Val  Pro
          12845               12850               12855
```

-continued

```
Phe Thr Leu Asn Phe Thr Ile Thr Asn Leu Gln Tyr Glu Glu Asp
    12860           12865           12870

Met Arg His Pro Gly Ser Arg Lys Phe Asn Thr Thr Glu Arg Val
    12875           12880           12885

Leu Gln Gly Leu Leu Lys Pro Leu Phe Lys Ser Thr Ser Val Gly
    12890           12895           12900

Pro Leu Tyr Ser Gly Cys Arg Leu Thr Leu Leu Arg Ser Glu Lys
    12905           12910           12915

Asp Gly Ala Ala Thr Gly Val Asp Ala Ile Cys Thr His Arg Leu
    12920           12925           12930

Asp Pro Lys Ser Pro Gly Val Asp Arg Glu Gln Leu Tyr Trp Glu
    12935           12940           12945

Leu Ser Gln Leu Thr Asn Gly Ile Lys Glu Leu Gly Pro Tyr Thr
    12950           12955           12960

Leu Asp Arg Asn Ser Leu Tyr Val Asn Gly Phe Thr His Gln Thr
    12965           12970           12975

Ser Ala Pro Asn Thr Ser Thr Pro Gly Thr Ser Thr Val Asp Leu
    12980           12985           12990

Gly Thr Ser Gly Thr Pro Ser Ser Leu Pro Ser Pro Thr Ser Ala
    12995           13000           13005

Gly Pro Leu Leu Val Pro Phe Thr Leu Asn Phe Thr Ile Thr Asn
    13010           13015           13020

Leu Gln Tyr Glu Glu Asp Met His His Pro Gly Ser Arg Lys Phe
    13025           13030           13035

Asn Thr Thr Glu Arg Val Leu Gln Gly Leu Leu Gly Pro Met Phe
    13040           13045           13050

Lys Asn Thr Ser Val Gly Leu Leu Tyr Ser Gly Cys Arg Leu Thr
    13055           13060           13065

Leu Leu Arg Pro Glu Lys Asn Gly Ala Ala Thr Gly Met Asp Ala
    13070           13075           13080

Ile Cys Ser His Arg Leu Asp Pro Lys Ser Pro Gly Leu Asn Arg
    13085           13090           13095

Glu Gln Leu Tyr Trp Glu Leu Ser Gln Leu Thr His Gly Ile Lys
    13100           13105           13110

Glu Leu Gly Pro Tyr Thr Leu Asp Arg Asn Ser Leu Tyr Val Asn
    13115           13120           13125

Gly Phe Thr His Arg Ser Ser Val Ala Pro Thr Ser Thr Pro Gly
    13130           13135           13140

Thr Ser Thr Val Asp Leu Gly Thr Ser Gly Thr Pro Ser Ser Leu
    13145           13150           13155

Pro Ser Pro Thr Thr Ala Val Pro Leu Leu Val Pro Phe Thr Leu
    13160           13165           13170

Asn Phe Thr Ile Thr Asn Leu Gln Tyr Gly Glu Asp Met Arg His
    13175           13180           13185

Pro Gly Ser Arg Lys Phe Asn Thr Thr Glu Arg Val Leu Gln Gly
    13190           13195           13200

Leu Leu Gly Pro Leu Phe Lys Asn Ser Ser Val Gly Pro Leu Tyr
    13205           13210           13215

Ser Gly Cys Arg Leu Ile Ser Leu Arg Ser Glu Lys Asp Gly Ala
    13220           13225           13230

Ala Thr Gly Val Asp Ala Ile Cys Thr His His Leu Asn Pro Gln
    13235           13240           13245
```

```
Ser Pro Gly Leu Asp Arg Glu   Gln Leu Tyr Trp   Gln Leu Ser Gln
    13250           13255             13260

Met Thr Asn Gly Ile Lys Glu   Leu Gly Pro Tyr   Thr Leu Asp Arg
    13265           13270             13275

Asn Ser Leu Tyr Val Asn Gly   Phe Thr His Arg   Ser Ser Gly Leu
    13280           13285             13290

Thr Thr Ser Thr Pro Trp Thr   Ser Thr Val Asp   Leu Gly Thr Ser
    13295           13300             13305

Gly Thr Pro Ser Pro Val Pro   Ser Pro Thr Thr   Ala Gly Pro Leu
    13310           13315             13320

Leu Val Pro Phe Thr Leu Asn   Phe Thr Ile Thr   Asn Leu Gln Tyr
    13325           13330             13335

Glu Glu Asp Met His Arg Pro   Gly Ser Arg Lys   Phe Asn Ala Thr
    13340           13345             13350

Glu Arg Val Leu Gln Gly Leu   Leu Ser Pro Ile   Phe Lys Asn Ser
    13355           13360             13365

Ser Val Gly Pro Leu Tyr Ser   Gly Cys Arg Leu   Thr Ser Leu Arg
    13370           13375             13380

Pro Glu Lys Asp Gly Ala Ala   Thr Gly Met Asp   Ala Val Cys Leu
    13385           13390             13395

Tyr His Pro Asn Pro Lys Arg   Pro Gly Leu Asp   Arg Glu Gln Leu
    13400           13405             13410

Tyr Trp Glu Leu Ser Gln Leu   Thr His Asn Ile   Thr Glu Leu Gly
    13415           13420             13425

Pro Tyr Ser Leu Asp Arg Asp   Ser Leu Tyr Val   Asn Gly Phe Thr
    13430           13435             13440

His Gln Asn Ser Val Pro Thr   Thr Ser Thr Pro   Gly Thr Ser Thr
    13445           13450             13455

Val Tyr Trp Ala Thr Thr Gly   Thr Pro Ser Ser   Phe Pro Gly His
    13460           13465             13470

Thr Glu Pro Gly Pro Leu Leu   Ile Pro Phe Thr   Phe Asn Phe Thr
    13475           13480             13485

Ile Thr Asn Leu His Tyr Glu   Glu Asn Met Gln   His Pro Gly Ser
    13490           13495             13500

Arg Lys Phe Asn Thr Thr Glu   Arg Val Leu Gln   Gly Leu Leu Lys
    13505           13510             13515

Pro Leu Phe Lys Asn Thr Ser   Val Gly Pro Leu   Tyr Ser Gly Cys
    13520           13525             13530

Arg Leu Thr Ser Leu Arg Pro   Glu Lys Asp Gly   Ala Ala Thr Gly
    13535           13540             13545

Met Asp Ala Val Cys Leu Tyr   His Pro Asn Pro   Lys Arg Pro Gly
    13550           13555             13560

Leu Asp Arg Glu Gln Leu Tyr   Cys Glu Leu Ser   Gln Leu Thr His
    13565           13570             13575

Asn Ile Thr Glu Leu Gly Pro   Tyr Ser Leu Asp   Arg Asp Ser Leu
    13580           13585             13590

Tyr Val Asn Gly Phe Thr His   Gln Asn Ser Val   Pro Thr Thr Ser
    13595           13600             13605

Thr Pro Gly Thr Ser Thr Val   Tyr Trp Ala Thr   Thr Gly Thr Pro
    13610           13615             13620

Ser Ser Phe Pro Gly His Thr   Glu Pro Gly Pro   Leu Leu Ile Pro
    13625           13630             13635

Phe Thr Phe Asn Phe Thr Ile   Thr Asn Leu His Tyr   Glu Glu Asn
```

-continued

```
          13640               13645                13650
Met Gln His Pro Gly Ser Arg  Lys Phe Asn Thr Thr  Glu Arg Val
          13655               13660                13665
Leu Gln Gly Leu Leu Lys Pro  Leu Phe Lys Asn Thr  Ser Val Gly
          13670               13675                13680
Pro Leu Tyr Ser Gly Cys Arg  Leu Thr Leu Leu Arg  Pro Glu Lys
          13685               13690                13695
His Glu Ala Ala Thr Gly Val  Asp Thr Ile Cys Thr  His Arg Val
          13700               13705                13710
Asp Pro Ile Gly Pro Gly Leu  Asp Arg Glu Arg Leu  Tyr Trp Glu
          13715               13720                13725
Leu Ser Gln Leu Thr Asn Ser  Ile Thr Glu Leu Gly  Pro Tyr Thr
          13730               13735                13740
Leu Asp Arg Asp Ser Leu Tyr  Val Asn Gly Phe Asn  Pro Arg Ser
          13745               13750                13755
Ser Val Pro Thr Thr Ser Thr  Pro Gly Thr Ser Thr  Val His Leu
          13760               13765                13770
Ala Thr Ser Gly Thr Pro Ser  Ser Leu Pro Gly His  Thr Ala Pro
          13775               13780                13785
Val Pro Leu Leu Ile Pro Phe  Thr Leu Asn Phe Thr  Ile Thr Asn
          13790               13795                13800
Leu His Tyr Glu Glu Asn Met  Gln His Pro Gly Ser  Arg Lys Phe
          13805               13810                13815
Asn Thr Thr Glu Arg Val Leu  Gln Gly Leu Leu Lys  Pro Leu Phe
          13820               13825                13830
Lys Asn Thr Ser Val Gly Pro  Leu Tyr Ser Gly Cys  Arg Leu Thr
          13835               13840                13845
Leu Leu Arg Pro Glu Lys His  Glu Ala Ala Thr Gly  Val Asp Thr
          13850               13855                13860
Ile Cys Thr His Arg Val Asp  Pro Ile Gly Pro Gly  Leu Asp Arg
          13865               13870                13875
Glu Xaa Leu Tyr Trp Glu Leu  Ser Xaa Leu Thr Xaa  Xaa Ile Xaa
          13880               13885                13890
Glu Leu Gly Pro Tyr Xaa Leu  Asp Arg Xaa Ser Leu  Tyr Val Asn
          13895               13900                13905
Gly Phe Xaa Xaa Xaa Xaa Xaa  Xaa Xaa Xaa Thr Ser  Thr Pro Gly
          13910               13915                13920
Thr Ser Xaa Val Xaa Leu Xaa  Thr Ser Gly Thr Pro  Xaa Xaa Xaa
          13925               13930                13935
Pro Xaa Xaa Thr Ser Ala Gly  Pro Leu Leu Val Pro  Phe Thr Leu
          13940               13945                13950
Asn Phe Thr Ile Thr Asn Leu  Gln Tyr Glu Glu Asp  Met His His
          13955               13960                13965
Pro Gly Ser Arg Lys Phe Asn  Thr Thr Glu Arg Val  Leu Gln Gly
          13970               13975                13980
Leu Leu Gly Pro Met Phe Lys  Asn Thr Ser Val Gly  Leu Leu Tyr
          13985               13990                13995
Ser Gly Cys Arg Leu Thr Leu  Leu Arg Pro Glu Lys  Asn Gly Ala
          14000               14005                14010
Ala Thr Gly Met Asp Ala Ile  Cys Ser His Arg Leu  Asp Pro Lys
          14015               14020                14025
Ser Pro Gly Leu Asp Arg Glu  Gln Leu Tyr Trp Glu  Leu Ser Gln
          14030               14035                14040
```

-continued

```
Leu Thr His Gly Ile Lys Glu   Leu Gly Pro Tyr Thr   Leu Asp Arg
        14045                     14050                 14055

Asn Ser Leu Tyr Val Asn Gly   Phe Thr His Arg Ser   Ser Val Ala
        14060                     14065                 14070

Pro Thr Ser Thr Pro Gly Thr   Ser Thr Val Asp Leu   Gly Thr Ser
        14075                     14080                 14085

Gly Thr Pro Ser Ser Leu Pro   Ser Pro Thr Thr Ala   Val Pro Leu
        14090                     14095                 14100

Leu Val Pro Phe Thr Leu Asn   Phe Thr Ile Thr Asn   Leu Gln Tyr
        14105                     14110                 14115

Gly Glu Asp Met Arg His Pro   Gly Ser Arg Lys Phe   Asn Thr Thr
        14120                     14125                 14130

Glu Arg Val Leu Gln Gly Leu   Leu Gly Pro Leu Phe   Lys Asn Ser
        14135                     14140                 14145

Ser Val Gly Pro Leu Tyr Ser   Gly Cys Arg Leu Ile   Ser Leu Arg
        14150                     14155                 14160

Ser Glu Lys Asp Gly Ala Ala   Thr Gly Val Asp Ala   Ile Cys Thr
        14165                     14170                 14175

His His Leu Asn Pro Gln Ser   Pro Gly Leu Asp Arg   Glu Gln Leu
        14180                     14185                 14190

Tyr Trp Gln Leu Ser Gln Met   Thr Asn Gly Ile Lys   Glu Leu Gly
        14195                     14200                 14205

Pro Tyr Thr Leu Asp Arg Asn   Ser Leu Tyr Val Asn   Gly Phe Thr
        14210                     14215                 14220

His Arg Ser Ser Gly Leu Thr   Thr Ser Thr Pro Trp   Thr Ser Thr
        14225                     14230                 14235

Val Asp Leu Gly Thr Ser Gly   Thr Pro Ser Pro Val   Pro Ser Pro
        14240                     14245                 14250

Thr Thr Ala Gly Pro Leu Leu   Val Pro Phe Thr Leu   Asn Phe Thr
        14255                     14260                 14265

Ile Thr Asn Leu Gln Tyr Glu   Glu Asp Met His Arg   Pro Gly Ser
        14270                     14275                 14280

Arg Lys Phe Asn Ala Thr Glu   Arg Val Leu Gln Gly   Leu Leu Ser
        14285                     14290                 14295

Pro Ile Phe Lys Asn Ser Ser   Val Gly Pro Leu Tyr   Ser Gly Cys
        14300                     14305                 14310

Arg Leu Thr Ser Leu Arg Pro   Glu Lys Asp Gly Ala   Ala Thr Gly
        14315                     14320                 14325

Met Asp Ala Val Cys Leu Tyr   His Pro Asn Pro Lys   Arg Pro Gly
        14330                     14335                 14340

Leu Asp Arg Glu Gln Leu Tyr   Trp Glu Leu Ser Gln   Leu Thr His
        14345                     14350                 14355

Asn Ile Thr Glu Leu Gly Pro   Tyr Ser Leu Asp Arg   Asp Ser Leu
        14360                     14365                 14370

Tyr Val Asn Gly Phe Thr His   Gln Ser Ser Met Thr   Thr Thr Arg
        14375                     14380                 14385

Thr Pro Asp Thr Ser Thr Met   His Leu Ala Thr Ser   Arg Thr Pro
        14390                     14395                 14400

Ala Ser Leu Ser Gly Pro Thr   Thr Ala Ser Pro Leu   Leu Val Leu
        14405                     14410                 14415

Phe Thr Ile Asn Cys Thr Ile   Thr Asn Leu Gln Tyr   Glu Glu Asp
        14420                     14425                 14430
```

-continued

| | | | | | | | | | | |
|---|---|---|---|---|---|---|---|---|---|---|
| Met | Arg | Arg | Thr | Gly | Ser | Arg | Lys | Phe | Asn | Thr | Met | Glu | Ser | Val |
| | 14435 | | | | 14440 | | | | | 14445 | | | | |
| Leu | Gln | Gly | Leu | Leu | Lys | Pro | Leu | Phe | Lys | Asn | Thr | Ser | Val | Gly |
| 14450 | | | | | 14455 | | | | | 14460 | | | | |
| Pro | Leu | Tyr | Ser | Gly | Cys | Arg | Leu | Thr | Leu | Leu | Arg | Pro | Lys | Lys |
| 14465 | | | | | 14470 | | | | | 14475 | | | | |
| Asp | Gly | Ala | Ala | Thr | Gly | Val | Asp | Ala | Ile | Cys | Thr | His | Arg | Leu |
| 14480 | | | | | 14485 | | | | | 14490 | | | | |
| Asp | Pro | Lys | Ser | Pro | Gly | Leu | Asn | Arg | Glu | Gln | Leu | Tyr | Trp | Glu |
| 14495 | | | | | 14500 | | | | | 14505 | | | | |
| Leu | Ser | Lys | Leu | Thr | Asn | Asp | Ile | Glu | Glu | Leu | Gly | Pro | Tyr | Thr |
| 14510 | | | | | 14515 | | | | | 14520 | | | | |
| Leu | Asp | Arg | Asn | Ser | Leu | Tyr | Val | Asn | Gly | Phe | Thr | His | Gln | Ser |
| 14525 | | | | | 14530 | | | | | 14535 | | | | |
| Ser | Val | Ser | Thr | Thr | Ser | Thr | Pro | Gly | Thr | Ser | Thr | Val | Asp | Leu |
| 14540 | | | | | 14545 | | | | | 14550 | | | | |
| Arg | Thr | Ser | Gly | Thr | Pro | Ser | Ser | Leu | Ser | Ser | Pro | Thr | Ile | Met |
| 14555 | | | | | 14560 | | | | | 14565 | | | | |
| Xaa | Xaa | Xaa | Pro | Leu | Leu | Xaa | Pro | Phe | Thr | Leu | Asn | Phe | Thr | Ile |
| 14570 | | | | | 14575 | | | | | 14580 | | | | |
| Thr | Asn | Leu | Xaa | Tyr | Glu | Glu | Xaa | Met | Xaa | Xaa | Pro | Gly | Ser | Arg |
| 14585 | | | | | 14590 | | | | | 14595 | | | | |
| Lys | Phe | Asn | Thr | Thr | Glu | Arg | Val | Leu | Gln | Gly | Leu | Leu | Arg | Pro |
| 14600 | | | | | 14605 | | | | | 14610 | | | | |
| Leu | Phe | Lys | Asn | Thr | Ser | Val | Ser | Ser | Leu | Tyr | Ser | Gly | Cys | Arg |
| 14615 | | | | | 14620 | | | | | 14625 | | | | |
| Leu | Thr | Leu | Leu | Arg | Pro | Glu | Lys | Asp | Gly | Ala | Ala | Thr | Arg | Val |
| 14630 | | | | | 14635 | | | | | 14640 | | | | |
| Asp | Ala | Ala | Cys | Thr | Tyr | Arg | Pro | Asp | Pro | Lys | Ser | Pro | Gly | Leu |
| 14645 | | | | | 14650 | | | | | 14655 | | | | |
| Asp | Arg | Glu | Gln | Leu | Tyr | Trp | Glu | Leu | Ser | Gln | Leu | Thr | His | Ser |
| 14660 | | | | | 14665 | | | | | 14670 | | | | |
| Ile | Thr | Glu | Leu | Gly | Pro | Tyr | Thr | Leu | Asp | Arg | Val | Ser | Leu | Tyr |
| 14675 | | | | | 14680 | | | | | 14685 | | | | |
| Val | Asn | Gly | Phe | Asn | Pro | Arg | Ser | Ser | Val | Pro | Thr | Thr | Ser | Thr |
| 14690 | | | | | 14695 | | | | | 14700 | | | | |
| Pro | Gly | Thr | Ser | Thr | Val | His | Leu | Ala | Thr | Ser | Gly | Thr | Pro | Ser |
| 14705 | | | | | 14710 | | | | | 14715 | | | | |
| Ser | Leu | Pro | Gly | His | Thr | Xaa | Xaa | Xaa | Pro | Leu | Leu | Xaa | Pro | Phe |
| 14720 | | | | | 14725 | | | | | 14730 | | | | |
| Thr | Leu | Asn | Phe | Thr | Ile | Thr | Asn | Leu | Xaa | Tyr | Glu | Glu | Xaa | Met |
| 14735 | | | | | 14740 | | | | | 14745 | | | | |
| Xaa | Xaa | Pro | Gly | Ser | Arg | Lys | Phe | Asn | Thr | Thr | Glu | Arg | Val | Leu |
| 14750 | | | | | 14755 | | | | | 14760 | | | | |
| Gln | Gly | Leu | Leu | Lys | Pro | Leu | Phe | Arg | Asn | Ser | Ser | Leu | Glu | Tyr |
| 14765 | | | | | 14770 | | | | | 14775 | | | | |
| Leu | Tyr | Ser | Gly | Cys | Arg | Leu | Ala | Ser | Leu | Arg | Pro | Glu | Lys | Asp |
| 14780 | | | | | 14785 | | | | | 14790 | | | | |
| Ser | Ser | Ala | Met | Ala | Val | Asp | Ala | Ile | Cys | Thr | His | Arg | Pro | Asp |
| 14795 | | | | | 14800 | | | | | 14805 | | | | |
| Pro | Glu | Asp | Leu | Gly | Leu | Asp | Arg | Glu | Arg | Leu | Tyr | Trp | Glu | Leu |
| 14810 | | | | | 14815 | | | | | 14820 | | | | |
| Ser | Asn | Leu | Thr | Asn | Gly | Ile | Gln | Glu | Leu | Gly | Pro | Tyr | Thr | Leu |

-continued

|         | 14825 |     |     |     | 14830 |     |     |     | 14835 |     |     |     |
|---------|-------|-----|-----|-----|-------|-----|-----|-----|-------|-----|-----|-----|
| Asp | Arg | Asn | Ser | Leu | Tyr | Val | Asn | Gly | Phe | Thr | His | Arg | Ser | Ser |

```
Asp Arg Asn Ser Leu Tyr Val Asn Gly Phe Thr His Arg Ser Ser
            14840               14845               14850

Phe Leu Thr Thr Ser Thr Pro Trp Thr Ser Thr Val Asp Leu Gly
            14855               14860               14865

Thr Ser Gly Thr Pro Ser Pro Val Pro Ser Pro Thr Thr Ala Gly
            14870               14875               14880

Pro Leu Leu Val Pro Phe Thr Leu Asn Phe Thr Ile Thr Asn Leu
            14885               14890               14895

Gln Tyr Glu Glu Asp Met His Arg Pro Gly Ser Arg Arg Phe Asn
            14900               14905               14910

Thr Thr Glu Arg Val Leu Gln Gly Leu Leu Thr Pro Leu Phe Lys
            14915               14920               14925

Asn Thr Ser Val Gly Pro Leu Tyr Ser Gly Cys Arg Leu Thr Leu
            14930               14935               14940

Leu Arg Pro Glu Lys Gln Glu Ala Ala Thr Gly Val Asp Thr Ile
            14945               14950               14955

Cys Thr His Arg Val Asp Pro Ile Gly Pro Gly Leu Asp Arg Glu
            14960               14965               14970

Arg Leu Tyr Trp Glu Leu Ser Gln Leu Thr Asn Ser Ile Thr Glu
            14975               14980               14985

Leu Gly Pro Tyr Thr Leu Asp Arg Asp Ser Leu Tyr Val Asn Gly
            14990               14995               15000

Phe Asn Pro Trp Ser Ser Val Pro Thr Thr Ser Thr Pro Gly Thr
            15005               15010               15015

Ser Thr Val His Leu Ala Thr Ser Gly Thr Pro Ser Ser Leu Pro
            15020               15025               15030

Gly His Thr Ala Pro Val Pro Leu Leu Ile Pro Phe Thr Leu Asn
            15035               15040               15045

Phe Thr Ile Thr Asp Leu His Tyr Glu Glu Asn Met Gln His Pro
            15050               15055               15060

Gly Ser Arg Lys Phe Asn Thr Thr Glu Arg Val Leu Gln Gly Leu
            15065               15070               15075

Leu Lys Pro Leu Phe Lys Ser Thr Ser Val Gly Pro Leu Tyr Ser
            15080               15085               15090

Gly Cys Arg Leu Thr Leu Leu Arg Pro Glu Lys His Gly Ala Ala
            15095               15100               15105

Thr Gly Val Asp Ala Ile Cys Thr Leu Arg Leu Asp Pro Thr Gly
            15110               15115               15120

Pro Gly Leu Asp Arg Glu Arg Leu Tyr Trp Glu Leu Ser Gln Leu
            15125               15130               15135

Thr Asn Ser Val Thr Glu Leu Gly Pro Tyr Thr Leu Asp Arg Asp
            15140               15145               15150

Ser Leu Tyr Val Asn Gly Phe Thr His Arg Ser Ser Val Pro Thr
            15155               15160               15165

Thr Ser Ile Pro Gly Thr Ser Ala Val His Leu Glu Thr Ser Gly
            15170               15175               15180

Thr Pro Ala Ser Leu Pro Gly His Thr Ala Pro Gly Pro Leu Leu
            15185               15190               15195

Val Pro Phe Thr Leu Asn Phe Thr Ile Thr Asn Leu Gln Tyr Glu
            15200               15205               15210

Glu Asp Met Arg His Pro Gly Ser Arg Lys Phe Ser Thr Thr Glu
            15215               15220               15225
```

```
Arg Val Leu Gln Gly Leu Leu Lys Pro Leu Phe Lys Asn Thr Ser
    15230               15235               15240

Val Ser Ser Leu Tyr Ser Gly Cys Arg Leu Thr Leu Leu Arg Pro
    15245               15250               15255

Glu Lys Asp Gly Ala Ala Thr Arg Val Asp Ala Val Cys Thr His
    15260               15265               15270

Arg Pro Asp Pro Lys Ser Pro Gly Leu Asp Arg Glu Arg Leu Tyr
    15275               15280               15285

Trp Lys Leu Ser Gln Leu Thr His Gly Ile Thr Glu Leu Gly Pro
    15290               15295               15300

Tyr Thr Leu Asp Arg His Ser Leu Tyr Val Asn Gly Phe Thr His
    15305               15310               15315

Gln Ser Ser Met Thr Thr Thr Arg Thr Pro Asp Thr Ser Thr Met
    15320               15325               15330

His Leu Ala Thr Ser Arg Thr Pro Ala Ser Leu Ser Gly Pro Thr
    15335               15340               15345

Thr Ala Ser Pro Leu Leu Val Leu Phe Thr Ile Asn Phe Thr Ile
    15350               15355               15360

Thr Asn Gln Arg Tyr Glu Glu Asn Met His His Pro Gly Ser Arg
    15365               15370               15375

Lys Phe Asn Thr Thr Glu Arg Val Leu Gln Gly Leu Leu Arg Pro
    15380               15385               15390

Val Phe Lys Asn Thr Ser Val Gly Pro Leu Tyr Ser Gly Cys Arg
    15395               15400               15405

Leu Thr Leu Leu Arg Pro Lys Lys Asp Gly Ala Ala Thr Lys Val
    15410               15415               15420

Asp Ala Ile Cys Thr Tyr Arg Pro Asp Pro Lys Ser Pro Gly Leu
    15425               15430               15435

Asp Arg Glu Gln Leu Tyr Trp Glu Leu Ser Gln Leu Thr His Ser
    15440               15445               15450

Ile Thr Glu Leu Gly Pro Tyr Thr Gln Asp Arg Asp Ser Leu Tyr
    15455               15460               15465

Val Asn Gly Phe Thr His Arg Ser Ser Val Pro Thr Thr Ser Ile
    15470               15475               15480

Pro Gly Thr Ser Ala Val His Leu Glu Thr Ser Gly Thr Pro Ala
    15485               15490               15495

Ser Leu Pro Gly His Thr Ala Pro Gly Pro Leu Leu Val Pro Phe
    15500               15505               15510

Thr Leu Asn Phe Thr Ile Thr Asn Leu Gln Tyr Glu Glu Asp Met
    15515               15520               15525

Arg His Pro Gly Ser Arg Lys Phe Asn Thr Thr Glu Arg Val Leu
    15530               15535               15540

Gln Gly Leu Leu Lys Pro Leu Phe Lys Ser Thr Ser Val Gly Pro
    15545               15550               15555

Leu Tyr Ser Gly Cys Arg Leu Thr Leu Leu Arg Pro Glu Lys Arg
    15560               15565               15570

Gly Ala Ala Thr Gly Val Asp Thr Ile Cys Thr His Arg Leu Asp
    15575               15580               15585

Pro Leu Asn Pro Gly Leu Asp Arg Glu Gln Leu Tyr Trp Glu Leu
    15590               15595               15600

Ser Lys Leu Thr Arg Gly Ile Ile Glu Leu Gly Pro Tyr Leu Leu
    15605               15610               15615
```

```
Asp Arg Gly Ser Leu Tyr Val Asn Gly Phe Thr His Arg Thr Ser
    15620           15625               15630

Val Pro Thr Thr Ser Thr Pro Gly Thr Ser Thr Val Asp Leu Gly
    15635           15640               15645

Thr Ser Gly Thr Pro Phe Ser Leu Pro Ser Pro Ala Xaa Xaa Xaa
    15650           15655               15660

Pro Leu Leu Xaa Pro Phe Thr Leu Asn Phe Thr Ile Thr Asn Leu
    15665           15670               15675

Xaa Tyr Glu Glu Xaa Met Xaa Xaa Pro Gly Ser Arg Lys Phe Asn
    15680           15685               15690

Thr Thr Glu Arg Val Leu Gln Thr Leu Leu Gly Pro Met Phe Lys
    15695           15700               15705

Asn Thr Ser Val Gly Leu Leu Tyr Ser Gly Cys Arg Leu Thr Leu
    15710           15715               15720

Leu Arg Ser Glu Lys Asp Gly Ala Ala Thr Gly Val Asp Ala Ile
    15725           15730               15735

Cys Thr His Arg Leu Asp Pro Lys Ser Pro Gly Val Asp Arg Glu
    15740           15745               15750

Gln Leu Tyr Trp Glu Leu Ser Gln Leu Thr Asn Gly Ile Lys Glu
    15755           15760               15765

Leu Gly Pro Tyr Thr Leu Asp Arg Asn Ser Leu Tyr Val Asn Gly
    15770           15775               15780

Phe Thr His Trp Ile Pro Val Pro Thr Ser Ser Thr Pro Gly Thr
    15785           15790               15795

Ser Thr Val Asp Leu Gly Ser Gly Thr Pro Ser Leu Pro Ser Ser
    15800           15805               15810

Pro Thr Thr Ala Gly Pro Leu Leu Val Pro Phe Thr Leu Asn Phe
    15815           15820               15825

Thr Ile Thr Asn Leu Lys Tyr Glu Glu Asp Met His Cys Pro Gly
    15830           15835               15840

Ser Arg Lys Phe Asn Thr Thr Glu Arg Val Leu Gln Ser Leu Leu
    15845           15850               15855

Gly Pro Met Phe Lys Asn Thr Ser Val Gly Pro Leu Tyr Ser Gly
    15860           15865               15870

Cys Arg Leu Thr Leu Leu Arg Ser Glu Lys Asp Gly Ala Ala Thr
    15875           15880               15885

Gly Val Asp Ala Ile Cys Thr His Arg Leu Asp Pro Lys Ser Pro
    15890           15895               15900

Gly Val Asp Arg Glu Gln Leu Tyr Trp Glu Leu Ser Gln Leu Thr
    15905           15910               15915

Asn Gly Ile Lys Glu Leu Gly Pro Tyr Thr Leu Asp Arg Asn Ser
    15920           15925               15930

Leu Tyr Val Asn Gly Phe Thr His Gln Thr Ser Ala Pro Asn Thr
    15935           15940               15945

Ser Thr Pro Gly Thr Ser Thr Val Asp Leu Gly Ser Gly Thr
    15950           15955               15960

Pro Ser Ser Leu Pro Ser Pro Thr Xaa Xaa Xaa Pro Leu Leu Xaa
    15965           15970               15975

Pro Phe Thr Leu Asn Phe Thr Ile Thr Asn Leu Xaa Tyr Glu Glu
    15980           15985               15990

Xaa Met Xaa Xaa Pro Gly Ser Arg Lys Phe Asn Thr Thr Glu Arg
    15995           16000               16005

Val Leu Gln Gly Leu Leu Xaa Pro Xaa Phe Lys Xaa Thr Ser Val
```

```
              16010              16015              16020
Gly Xaa Leu Tyr Ser Gly Cys Arg Leu Thr Leu Leu Arg Xaa Glu
    16025              16030              16035
Lys Xaa Xaa Ala Ala Thr Xaa Val Asp Xaa Xaa Cys Xaa Xaa Xaa
    16040              16045              16050
Xaa Asp Pro Xaa Xaa Pro Gly Leu Asp Arg Glu Xaa Leu Tyr Trp
    16055              16060              16065
Glu Leu Ser Xaa Leu Thr Xaa Xaa Ile Xaa Glu Leu Gly Pro Tyr
    16070              16075              16080
Xaa Leu Asp Arg Xaa Ser Leu Tyr Val Asn Gly Phe Thr His Trp
    16085              16090              16095
Ile Pro Val Pro Thr Ser Ser Thr Pro Gly Thr Ser Thr Val Asp
    16100              16105              16110
Leu Gly Ser Gly Thr Pro Ser Ser Leu Pro Ser Pro Thr Thr Ala
    16115              16120              16125
Gly Pro Leu Leu Val Pro Phe Thr Leu Asn Phe Thr Ile Thr Asn
    16130              16135              16140
Leu Lys Tyr Glu Glu Asp Met His Cys Pro Gly Ser Arg Lys Phe
    16145              16150              16155
Asn Thr Thr Glu Arg Val Leu Gln Ser Leu Leu Gly Pro Met Phe
    16160              16165              16170
Lys Asn Thr Ser Val Gly Pro Leu Tyr Ser Gly Cys Arg Leu Thr
    16175              16180              16185
Ser Leu Arg Ser Glu Lys Asp Gly Ala Ala Thr Gly Val Asp Ala
    16190              16195              16200
Ile Cys Thr His Arg Val Asp Pro Lys Ser Pro Gly Val Asp Arg
    16205              16210              16215
Glu Gln Leu Tyr Trp Glu Leu Ser Gln Leu Thr Asn Gly Ile Lys
    16220              16225              16230
Glu Leu Gly Pro Tyr Thr Leu Asp Arg Asn Ser Leu Tyr Val Asn
    16235              16240              16245
Gly Phe Thr His Gln Thr Ser Ala Pro Asn Thr Ser Thr Pro Gly
    16250              16255              16260
Thr Ser Thr Val Asp Leu Gly Thr Ser Gly Thr Pro Ser Ser Leu
    16265              16270              16275
Pro Ser Pro Thr Ser Ala Gly Pro Leu Leu Val Pro Phe Thr Leu
    16280              16285              16290
Asn Phe Thr Ile Thr Asn Leu Gln Tyr Glu Glu Asp Met His His
    16295              16300              16305
Pro Gly Ser Arg Lys Phe Asn Thr Thr Glu Arg Val Leu Gln Gly
    16310              16315              16320
Leu Leu Gly Pro Met Phe Lys Asn Thr Ser Val Gly Leu Leu Tyr
    16325              16330              16335
Ser Gly Cys Arg Leu Thr Leu Leu Arg Pro Glu Lys Asn Gly Ala
    16340              16345              16350
Ala Thr Gly Met Asp Ala Ile Cys Thr His Arg Leu Asp Pro Lys
    16355              16360              16365
Ser Pro Gly Leu Asp Arg Glu Xaa Leu Tyr Trp Glu Leu Ser Xaa
    16370              16375              16380
Leu Thr Xaa Xaa Ile Xaa Glu Leu Gly Pro Tyr Xaa Leu Asp Arg
    16385              16390              16395
Xaa Ser Leu Tyr Val Asn Gly Phe Xaa Xaa Xaa Xaa Xaa Xaa Xaa
    16400              16405              16410
```

-continued

Xaa Thr Ser Thr Pro Gly Thr    Ser Xaa Val Xaa Leu    Xaa Thr Ser
    16415                16420                16425

Gly Thr Pro Xaa Xaa Pro    Xaa Xaa Thr Xaa Xaa    Xaa Pro Leu
    16430            16435                16440

Leu Xaa Pro Phe Thr Leu Asn    Phe Thr Ile Thr Asn    Leu Xaa Tyr
    16445                16450                16455

Glu Glu Xaa Met Xaa Xaa Pro    Gly Ser Arg Lys Phe    Asn Thr Thr
    16460                16465                16470

Glu Arg Val Leu Gln Gly Leu    Leu Lys Pro Leu Phe    Arg Asn Ser
    16475                16480                16485

Ser Leu Glu Tyr Leu Tyr Ser    Gly Cys Arg Leu Ala    Ser Leu Arg
    16490                16495                16500

Pro Glu Lys Asp Ser Ser Ala    Met Ala Val Asp Ala    Ile Cys Thr
    16505                16510                16515

His Arg Pro Asp Pro Glu Asp    Leu Gly Leu Asp Arg    Glu Arg Leu
    16520                16525                16530

Tyr Trp Glu Leu Ser Asn Leu    Thr Asn Gly Ile Gln    Glu Leu Gly
    16535                16540                16545

Pro Tyr Thr Leu Asp Arg Asn    Ser Leu Tyr Val Asn    Gly Phe Thr
    16550                16555                16560

His Arg Ser Ser Met Pro Thr    Thr Ser Thr Pro Gly    Thr Ser Thr
    16565                16570                16575

Val Asp Val Gly Thr Ser Gly    Thr Pro Ser Ser Ser    Pro Ser Pro
    16580                16585                16590

Thr Thr Ala Gly Pro Leu Leu    Ile Pro Phe Thr Leu    Asn Phe Thr
    16595                16600                16605

Ile Thr Asn Leu Gln Tyr Gly    Glu Asp Met Gly His    Pro Gly Ser
    16610                16615                16620

Arg Lys Phe Asn Thr Thr Glu    Arg Val Leu Gln Gly    Leu Leu Gly
    16625                16630                16635

Pro Ile Phe Lys Asn Thr Ser    Val Gly Pro Leu Tyr    Ser Gly Cys
    16640                16645                16650

Arg Leu Thr Ser Leu Arg Ser    Glu Lys Asp Gly Ala    Ala Thr Gly
    16655                16660                16665

Val Asp Ala Ile Cys Ile His    His Leu Asp Pro Lys    Ser Pro Gly
    16670                16675                16680

Leu Asn Arg Glu Arg Leu Tyr    Trp Glu Leu Ser Gln    Leu Thr Asn
    16685                16690                16695

Gly Ile Lys Glu Leu Gly Pro    Tyr Thr Leu Asp Arg    Asn Ser Leu
    16700                16705                16710

Tyr Val Asn Gly Phe Thr His    Arg Thr Ser Val Pro    Thr Thr Ser
    16715                16720                16725

Thr Pro Gly Thr Ser Thr Val    Asp Leu Gly Thr Ser    Gly Thr Pro
    16730                16735                16740

Phe Ser Leu Pro Ser Pro Ala    Thr Ala Gly Pro Leu    Leu Val Leu
    16745                16750                16755

Phe Thr Leu Asn Phe Thr Ile    Thr Asn Leu Lys Tyr    Glu Glu Asp
    16760                16765                16770

Met His Arg Pro Gly Ser Arg    Lys Phe Asn Thr Thr    Glu Arg Val
    16775                16780                16785

Leu Gln Thr Leu Leu Gly Pro    Met Phe Lys Asn Thr    Ser Val Gly
    16790                16795                16800

| | | | | | | | | | | | |
|---|---|---|---|---|---|---|---|---|---|---|---|
| Leu | Leu 16805 | Tyr | Ser | Gly | Cys | Arg 16810 | Leu | Thr | Leu | Leu 16815 | Arg | Ser | Glu | Lys |
| Asp | Gly 16820 | Ala | Ala | Thr | Gly | Val 16825 | Asp | Ala | Ile | Cys 16830 | Thr | His | Arg | Leu |
| Asp | Pro 16835 | Lys | Ser | Pro | Gly | Leu 16840 | Asp | Arg | Glu | Xaa 16845 | Leu | Tyr | Trp | Glu |
| Leu | Ser 16850 | Xaa | Leu | Thr | Xaa | Xaa 16855 | Ile | Xaa | Glu | Leu 16860 | Gly | Pro | Tyr | Xaa |
| Leu | Asp 16865 | Arg | Xaa | Ser | Leu | Tyr 16870 | Val | Asn | Gly | Phe 16875 | Xaa | Xaa | Xaa | Xaa |
| Xaa | Xaa 16880 | Xaa | Xaa | Thr | Ser | Thr 16885 | Pro | Gly | Thr | Ser 16890 | Xaa | Val | Xaa | Leu |
| Xaa | Thr 16895 | Ser | Gly | Thr | Pro | Xaa 16900 | Xaa | Xaa | Pro | Xaa 16905 | Xaa | Thr | Xaa | Xaa |
| Xaa | Pro 16910 | Leu | Leu | Xaa | Pro | Phe 16915 | Thr | Leu | Asn | Phe 16920 | Thr | Ile | Thr | Asn |
| Leu | Xaa 16925 | Tyr | Glu | Glu | Xaa | Met 16930 | Xaa | Xaa | Pro | Gly 16935 | Ser | Arg | Lys | Phe |
| Asn | Thr 16940 | Thr | Glu | Arg | Val | Leu 16945 | Gln | Gly | Leu | Leu 16950 | Arg | Pro | Val | Phe |
| Lys | Asn 16955 | Thr | Ser | Val | Gly | Pro 16960 | Leu | Tyr | Ser | Gly 16965 | Cys | Arg | Leu | Thr |
| Leu | Leu 16970 | Arg | Pro | Lys | Lys | Asp 16975 | Gly | Ala | Ala | Thr 16980 | Lys | Val | Asp | Ala |
| Ile | Cys 16985 | Thr | Tyr | Arg | Pro | Asp 16990 | Pro | Lys | Ser | Pro 16995 | Gly | Leu | Asp | Arg |
| Glu | Gln 17000 | Leu | Tyr | Trp | Glu | Leu 17005 | Ser | Gln | Leu | Thr 17010 | His | Ser | Ile | Thr |
| Glu | Leu 17015 | Gly | Pro | Tyr | Thr | Gln 17020 | Asp | Arg | Asp | Ser 17025 | Leu | Tyr | Val | Asn |
| Gly | Phe 17030 | Thr | His | Arg | Ser | Ser 17035 | Val | Pro | Thr | Thr 17040 | Ser | Ile | Pro | Gly |
| Thr | Ser 17045 | Ala | Val | His | Leu | Glu 17050 | Thr | Thr | Gly | Thr 17055 | Pro | Ser | Ser | Phe |
| Pro | Gly 17060 | His | Thr | Glu | Pro | Gly 17065 | Pro | Leu | Leu | Ile 17070 | Pro | Phe | Thr | Phe |
| Asn | Phe 17075 | Thr | Ile | Thr | Asn | Leu 17080 | Arg | Tyr | Glu | Glu 17085 | Asn | Met | Gln | His |
| Pro | Gly 17090 | Ser | Arg | Lys | Phe | Asn 17095 | Thr | Thr | Glu | Arg 17100 | Val | Leu | Gln | Gly |
| Leu | Leu 17105 | Thr | Pro | Leu | Phe | Lys 17110 | Asn | Thr | Ser | Val 17115 | Gly | Pro | Leu | Tyr |
| Ser | Gly 17120 | Cys | Arg | Leu | Thr | Leu 17125 | Leu | Arg | Pro | Glu 17130 | Lys | Gln | Glu | Ala |
| Ala | Thr 17135 | Gly | Val | Asp | Thr | Ile 17140 | Cys | Thr | His | Arg 17145 | Val | Asp | Pro | Ile |
| Gly | Pro 17150 | Gly | Leu | Asp | Arg | Glu 17155 | Arg | Leu | Tyr | Trp 17160 | Glu | Leu | Ser | Gln |
| Leu | Thr 17165 | Asn | Ser | Ile | Thr | Glu 17170 | Leu | Gly | Pro | Tyr 17175 | Thr | Leu | Asp | Arg |
| Asp | Ser 17180 | Leu | Tyr | Val | Asp | Gly 17185 | Phe | Asn | Pro | Trp 17190 | Ser | Ser | Val | Pro |
| Thr | Thr | Ser | Thr | Pro | Gly | Thr | Ser | Thr | Val | His | Leu | Ala | Thr | Ser |

-continued

|  |  |  |  |  |  |  |  |  |  |
|---|---|---|---|---|---|---|---|---|---|
| | 17195 | | | 17200 | | | 17205 | | |
| Gly | Thr | Pro | Ser | Pro | Leu | Pro | Gly | His | Thr | Ala | Pro | Val | Pro | Leu |
| | 17210 | | | | 17215 | | | 17220 | | |
| Leu | Ile | Pro | Phe | Thr | Leu | Asn | Phe | Thr | Ile | Thr | Asp | Leu | His | Tyr |
| | 17225 | | | | 17230 | | | 17235 | | |
| Glu | Glu | Asn | Met | Gln | His | Pro | Gly | Ser | Arg | Lys | Phe | Asn | Thr | Thr |
| | 17240 | | | | 17245 | | | 17250 | | |
| Glu | Arg | Val | Leu | Gln | Gly | Leu | Leu | Lys | Pro | Leu | Phe | Lys | Ser | Thr |
| | 17255 | | | | 17260 | | | 17265 | | |
| Ser | Val | Gly | Pro | Leu | Tyr | Ser | Gly | Cys | Arg | Leu | Thr | Leu | Leu | Arg |
| | 17270 | | | | 17275 | | | 17280 | | |
| Pro | Glu | Lys | His | Gly | Ala | Ala | Thr | Gly | Val | Asp | Ala | Ile | Cys | Thr |
| | 17285 | | | | 17290 | | | 17295 | | |
| Leu | Arg | Leu | Asp | Pro | Thr | Gly | Pro | Gly | Leu | Asp | Arg | Glu | Arg | Leu |
| | 17300 | | | | 17305 | | | 17310 | | |
| Tyr | Trp | Glu | Leu | Ser | Gln | Leu | Thr | Asn | Ser | Ile | Thr | Glu | Leu | Gly |
| | 17315 | | | | 17320 | | | 17325 | | |
| Pro | Tyr | Thr | Leu | Asp | Arg | Asp | Ser | Leu | Tyr | Val | Asn | Gly | Phe | Asn |
| | 17330 | | | | 17335 | | | 17340 | | |
| Pro | Trp | Ser | Ser | Val | Pro | Thr | Thr | Ser | Thr | Pro | Gly | Thr | Ser | Thr |
| | 17345 | | | | 17350 | | | 17355 | | |
| Val | His | Leu | Ala | Thr | Ser | Gly | Thr | Pro | Ser | Ser | Leu | Pro | Gly | His |
| | 17360 | | | | 17365 | | | 17370 | | |
| Thr | Thr | Ala | Gly | Pro | Leu | Leu | Val | Pro | Phe | Thr | Leu | Asn | Phe | Thr |
| | 17375 | | | | 17380 | | | 17385 | | |
| Ile | Thr | Asn | Leu | Lys | Tyr | Glu | Glu | Asp | Met | His | Cys | Pro | Gly | Ser |
| | 17390 | | | | 17395 | | | 17400 | | |
| Arg | Lys | Phe | Asn | Thr | Thr | Glu | Arg | Val | Leu | Gln | Ser | Leu | His | Gly |
| | 17405 | | | | 17410 | | | 17415 | | |
| Pro | Met | Phe | Lys | Asn | Thr | Ser | Val | Gly | Pro | Leu | Tyr | Ser | Gly | Cys |
| | 17420 | | | | 17425 | | | 17430 | | |
| Arg | Leu | Thr | Leu | Leu | Arg | Ser | Glu | Lys | Asp | Gly | Ala | Ala | Thr | Gly |
| | 17435 | | | | 17440 | | | 17445 | | |
| Val | Asp | Ala | Ile | Cys | Thr | His | Arg | Leu | Asp | Pro | Lys | Ser | Pro | Gly |
| | 17450 | | | | 17455 | | | 17460 | | |
| Leu | Asp | Arg | Glu | Xaa | Leu | Tyr | Trp | Glu | Leu | Ser | Xaa | Leu | Thr | Xaa |
| | 17465 | | | | 17470 | | | 17475 | | |
| Xaa | Ile | Xaa | Glu | Leu | Gly | Pro | Tyr | Xaa | Leu | Asp | Arg | Xaa | Ser | Leu |
| | 17480 | | | | 17485 | | | 17490 | | |
| Tyr | Val | Asn | Gly | Phe | Xaa | Xaa | Xaa | Xaa | Xaa | Xaa | Xaa | Xaa | Thr | Ser |
| | 17495 | | | | 17500 | | | 17505 | | |
| Thr | Pro | Gly | Thr | Ser | Xaa | Val | Xaa | Leu | Xaa | Thr | Ser | Gly | Thr | Pro |
| | 17510 | | | | 17515 | | | 17520 | | |
| Xaa | Xaa | Xaa | Pro | Xaa | Xaa | Thr | Xaa | Xaa | Xaa | Pro | Leu | Leu | Xaa | Pro |
| | 17525 | | | | 17530 | | | 17535 | | |
| Phe | Thr | Leu | Asn | Phe | Thr | Ile | Thr | Asn | Leu | Xaa | Tyr | Glu | Glu | Xaa |
| | 17540 | | | | 17545 | | | 17550 | | |
| Met | Xaa | Xaa | Pro | Gly | Ser | Arg | Lys | Phe | Asn | Thr | Thr | Glu | Arg | Val |
| | 17555 | | | | 17560 | | | 17565 | | |
| Leu | Gln | Gly | Leu | Leu | Xaa | Pro | Xaa | Phe | Lys | Xaa | Thr | Ser | Val | Gly |
| | 17570 | | | | 17575 | | | 17580 | | |
| Xaa | Leu | Tyr | Ser | Gly | Cys | Arg | Leu | Thr | Leu | Leu | Arg | Xaa | Glu | Lys |
| | 17585 | | | | 17590 | | | 17595 | | |

-continued

Xaa Xaa Ala Ala Thr Xaa Val Asp Xaa Xaa Cys Xaa Xaa Xaa Xaa
        17600               17605               17610

Asp Pro Xaa Xaa Pro Gly Leu Asp Arg Glu Xaa Leu Tyr Trp Glu
        17615               17620               17625

Leu Ser Xaa Leu Thr Asn Ser Ile Thr Glu Leu Gly Pro Tyr Thr
        17630               17635               17640

Leu Asp Arg Asp Ser Leu Tyr Val Asn Gly Phe Thr His Arg Ser
        17645               17650               17655

Ser Met Pro Thr Thr Ser Ile Pro Gly Thr Ser Ala Val His Leu
        17660               17665               17670

Glu Thr Ser Gly Thr Pro Ala Ser Leu Pro Gly His Thr Ala Pro
        17675               17680               17685

Gly Pro Leu Leu Val Pro Phe Thr Leu Asn Phe Thr Ile Thr Asn
        17690               17695               17700

Leu Gln Tyr Glu Glu Asp Met Arg His Pro Gly Ser Arg Lys Phe
        17705               17710               17715

Asn Thr Thr Glu Arg Val Leu Gln Gly Leu Leu Lys Pro Leu Phe
        17720               17725               17730

Lys Ser Thr Ser Val Gly Pro Leu Tyr Ser Gly Cys Arg Leu Thr
        17735               17740               17745

Leu Leu Arg Pro Glu Lys Arg Gly Ala Ala Thr Gly Val Asp Thr
        17750               17755               17760

Ile Cys Thr His Arg Leu Asp Pro Leu Asn Pro Gly Leu Asp Arg
        17765               17770               17775

Glu Xaa Leu Tyr Trp Glu Leu Ser Xaa Leu Thr Xaa Xaa Ile Xaa
        17780               17785               17790

Glu Leu Gly Pro Tyr Xaa Leu Asp Arg Xaa Ser Leu Tyr Val Asn
        17795               17800               17805

Gly Phe Xaa Xaa Xaa Xaa Xaa Xaa Xaa Xaa Thr Ser Thr Pro Gly
        17810               17815               17820

Thr Ser Xaa Val Xaa Leu Xaa Thr Ser Gly Thr Pro Xaa Xaa Xaa
        17825               17830               17835

Pro Xaa Xaa Thr Xaa Xaa Xaa Pro Leu Leu Xaa Pro Phe Thr Leu
        17840               17845               17850

Asn Phe Thr Ile Thr Asn Leu Xaa Tyr Glu Glu Xaa Met Xaa Xaa
        17855               17860               17865

Pro Gly Ser Arg Lys Phe Asn Thr Thr Glu Arg Val Leu Gln Gly
        17870               17875               17880

Leu Leu Xaa Pro Xaa Phe Lys Xaa Thr Ser Val Gly Xaa Leu Tyr
        17885               17890               17895

Ser Gly Cys Arg Leu Thr Leu Arg Xaa Glu Lys Xaa Xaa Ala
        17900               17905               17910

Ala Thr Xaa Val Asp Xaa Xaa Cys Xaa Xaa Xaa Xaa Asp Pro Xaa
        17915               17920               17925

Xaa Pro Gly Leu Asp Arg Glu Xaa Leu Tyr Trp Glu Leu Ser Xaa
        17930               17935               17940

Leu Thr Xaa Xaa Ile Xaa Glu Leu Gly Pro Tyr Xaa Leu Asp Arg
        17945               17950               17955

Xaa Ser Leu Tyr Val Asn Gly Phe His Pro Arg Ser Ser Val Pro
        17960               17965               17970

Thr Thr Ser Thr Pro Gly Thr Ser Thr Val His Leu Ala Thr Ser
        17975               17980               17985

-continued

| | | | | | | | | | | | |
|---|---|---|---|---|---|---|---|---|---|---|---|
| Gly | Thr | Pro | Ser | Ser | Leu | Pro | Gly | His | Thr | Ala | Pro | Val | Pro | Leu |
| | 17990 | | | | | 17995 | | | | | 18000 | | | |
| Leu | Ile | Pro | Phe | Thr | Leu | Asn | Phe | Thr | Ile | Thr | Asn | Leu | His | Tyr |
| | 18005 | | | | | 18010 | | | | | 18015 | | | |
| Glu | Glu | Asn | Met | Gln | His | Pro | Gly | Ser | Arg | Lys | Phe | Asn | Thr | Thr |
| | 18020 | | | | | 18025 | | | | | 18030 | | | |
| Glu | Arg | Val | Leu | Gln | Gly | Leu | Leu | Gly | Pro | Met | Phe | Lys | Asn | Thr |
| | 18035 | | | | | 18040 | | | | | 18045 | | | |
| Ser | Val | Gly | Leu | Leu | Tyr | Ser | Gly | Cys | Arg | Leu | Thr | Leu | Leu | Arg |
| | 18050 | | | | | 18055 | | | | | 18060 | | | |
| Pro | Glu | Lys | Asn | Gly | Ala | Ala | Thr | Gly | Met | Asp | Ala | Ile | Cys | Ser |
| | 18065 | | | | | 18070 | | | | | 18075 | | | |
| His | Arg | Leu | Asp | Pro | Lys | Ser | Pro | Gly | Leu | Asp | Arg | Glu | Xaa | Leu |
| | 18080 | | | | | 18085 | | | | | 18090 | | | |
| Tyr | Trp | Glu | Leu | Ser | Xaa | Leu | Thr | Xaa | Xaa | Ile | Xaa | Glu | Leu | Gly |
| | 18095 | | | | | 18100 | | | | | 18105 | | | |
| Pro | Tyr | Xaa | Leu | Asp | Arg | Xaa | Ser | Leu | Tyr | Val | Asn | Gly | Phe | Xaa |
| | 18110 | | | | | 18115 | | | | | 18120 | | | |
| Xaa | Xaa | Xaa | Xaa | Xaa | Xaa | Xaa | Thr | Ser | Thr | Pro | Gly | Thr | Ser | Xaa |
| | 18125 | | | | | 18130 | | | | | 18135 | | | |
| Val | Xaa | Leu | Xaa | Thr | Ser | Gly | Thr | Pro | Xaa | Xaa | Xaa | Pro | Xaa | Xaa |
| | 18140 | | | | | 18145 | | | | | 18150 | | | |
| Thr | Xaa | Xaa | Xaa | Pro | Leu | Leu | Xaa | Pro | Phe | Thr | Leu | Asn | Phe | Thr |
| | 18155 | | | | | 18160 | | | | | 18165 | | | |
| Ile | Thr | Asn | Leu | Xaa | Tyr | Glu | Glu | Xaa | Met | Xaa | Xaa | Pro | Gly | Ser |
| | 18170 | | | | | 18175 | | | | | 18180 | | | |
| Arg | Lys | Phe | Asn | Thr | Thr | Glu | Arg | Val | Leu | Gln | Gly | Leu | Leu | Xaa |
| | 18185 | | | | | 18190 | | | | | 18195 | | | |
| Pro | Xaa | Phe | Lys | Xaa | Thr | Ser | Val | Gly | Xaa | Leu | Tyr | Ser | Gly | Cys |
| | 18200 | | | | | 18205 | | | | | 18210 | | | |
| Arg | Leu | Thr | Leu | Leu | Arg | Xaa | Glu | Lys | Xaa | Xaa | Ala | Ala | Thr | Xaa |
| | 18215 | | | | | 18220 | | | | | 18225 | | | |
| Val | Asp | Xaa | Xaa | Cys | Xaa | Xaa | Xaa | Xaa | Asp | Pro | Xaa | Xaa | Pro | Gly |
| | 18230 | | | | | 18235 | | | | | 18240 | | | |
| Leu | Asp | Arg | Glu | Xaa | Leu | Tyr | Trp | Glu | Leu | Ser | Xaa | Leu | Thr | Xaa |
| | 18245 | | | | | 18250 | | | | | 18255 | | | |
| Xaa | Ile | Xaa | Glu | Leu | Gly | Pro | Tyr | Xaa | Leu | Asp | Arg | Xaa | Ser | Leu |
| | 18260 | | | | | 18265 | | | | | 18270 | | | |
| Tyr | Val | Asn | Gly | Phe | Thr | His | Gln | Asn | Ser | Val | Pro | Thr | Thr | Ser |
| | 18275 | | | | | 18280 | | | | | 18285 | | | |
| Thr | Pro | Gly | Thr | Ser | Thr | Val | Tyr | Trp | Ala | Thr | Thr | Gly | Thr | Pro |
| | 18290 | | | | | 18295 | | | | | 18300 | | | |
| Ser | Ser | Phe | Pro | Gly | His | Thr | Glu | Pro | Gly | Pro | Leu | Leu | Ile | Pro |
| | 18305 | | | | | 18310 | | | | | 18315 | | | |
| Phe | Thr | Phe | Asn | Phe | Thr | Ile | Thr | Asn | Leu | His | Tyr | Glu | Glu | Asn |
| | 18320 | | | | | 18325 | | | | | 18330 | | | |
| Met | Gln | His | Pro | Gly | Ser | Arg | Lys | Phe | Asn | Thr | Thr | Glu | Arg | Val |
| | 18335 | | | | | 18340 | | | | | 18345 | | | |
| Leu | Gln | Gly | Leu | Leu | Thr | Pro | Leu | Phe | Lys | Asn | Thr | Ser | Val | Gly |
| | 18350 | | | | | 18355 | | | | | 18360 | | | |
| Pro | Leu | Tyr | Ser | Gly | Cys | Arg | Leu | Thr | Leu | Leu | Arg | Pro | Glu | Lys |
| | 18365 | | | | | 18370 | | | | | 18375 | | | |
| Gln | Glu | Ala | Ala | Thr | Gly | Val | Asp | Thr | Ile | Cys | Thr | His | Arg | Val |

-continued

```
          18380              18385              18390

Asp Pro  Ile Gly Pro Gly Leu  Asp Arg Glu Xaa  Leu Tyr Trp Glu
    18395              18400              18405

Leu Ser  Xaa Leu Thr Xaa Xaa  Ile Xaa Glu Leu  Gly Pro Tyr Xaa
    18410              18415              18420

Leu Asp  Arg Xaa Ser Leu Tyr  Val Asn Gly Phe  Xaa Xaa Xaa Xaa
    18425              18430              18435

Xaa Xaa  Xaa Xaa Thr Ser Thr  Pro Gly Thr Ser  Xaa Val Xaa Leu
    18440              18445              18450

Xaa Thr  Ser Gly Thr Pro Xaa  Xaa Xaa Pro Xaa  Xaa Thr Xaa Xaa
    18455              18460              18465

Xaa Pro  Leu Leu Xaa Pro Phe  Thr Leu Asn Phe  Thr Ile Thr Asn
    18470              18475              18480

Leu Xaa  Tyr Glu Glu Xaa Met  Xaa Xaa Pro Gly  Ser Arg Lys Phe
    18485              18490              18495

Asn Thr  Thr Glu Arg Val Leu  Gln Gly Leu Leu  Xaa Pro Xaa Phe
    18500              18505              18510

Lys Xaa  Thr Ser Val Gly Xaa  Leu Tyr Ser Gly  Cys Arg Leu Thr
    18515              18520              18525

Leu Leu  Arg Xaa Glu Lys Xaa  Xaa Ala Ala Thr  Xaa Val Asp Xaa
    18530              18535              18540

Xaa Cys  Xaa Xaa Xaa Xaa Asp  Pro Xaa Xaa Pro  Gly Leu Asp Arg
    18545              18550              18555

Glu Xaa  Leu Tyr Trp Glu Leu  Ser Xaa Leu Thr  Xaa Xaa Ile Xaa
    18560              18565              18570

Glu Leu  Gly Pro Tyr Xaa Leu  Asp Arg Xaa Ser  Leu Tyr Val Asn
    18575              18580              18585

Gly Phe  Thr His Arg Ser Ser  Val Pro Thr Thr  Ser Ser Pro Gly
    18590              18595              18600

Thr Ser  Thr Val His Leu Ala  Thr Ser Gly Thr  Pro Ser Ser Leu
    18605              18610              18615

Pro Gly  His Thr Ala Pro Val  Pro Leu Leu Ile  Pro Phe Thr Leu
    18620              18625              18630

Asn Phe  Thr Ile Thr Asn Leu  His Tyr Glu Glu  Asn Met Gln His
    18635              18640              18645

Pro Gly  Ser Arg Lys Phe Asn  Thr Thr Glu Arg  Val Leu Gln Gly
    18650              18655              18660

Leu Leu  Lys Pro Leu Phe Lys  Ser Thr Ser Val  Gly Pro Leu Tyr
    18665              18670              18675

Ser Gly  Cys Arg Leu Thr Leu  Leu Arg Pro Glu  Lys His Gly Ala
    18680              18685              18690

Ala Thr  Gly Val Asp Ala Ile  Cys Thr Leu Arg  Leu Asp Pro Thr
    18695              18700              18705

Gly Pro  Gly Leu Asp Arg Glu  Xaa Leu Tyr Trp  Glu Leu Ser Xaa
    18710              18715              18720

Leu Thr  Xaa Xaa Ile Xaa Glu  Leu Gly Pro Tyr  Xaa Leu Asp Arg
    18725              18730              18735

Xaa Ser  Leu Tyr Val Asn Gly  Phe Xaa Xaa Xaa  Xaa Xaa Xaa Xaa
    18740              18745              18750

Xaa Thr  Ser Thr Pro Gly Thr  Ser Xaa Val Xaa  Leu Xaa Thr Ser
    18755              18760              18765

Gly Thr  Pro Xaa Xaa Xaa Pro  Xaa Xaa Thr Xaa  Xaa Xaa Pro Leu
    18770              18775              18780
```

```
Leu Xaa Pro Phe Thr Leu Asn   Phe Thr Ile Thr Asn   Leu Xaa Tyr
    18785                 18790                 18795

Glu Glu Xaa Met Xaa Xaa Pro   Gly Ser Arg Lys Phe   Asn Thr Thr
    18800                 18805                 18810

Glu Arg Val Leu Gln Gly Leu   Leu Xaa Pro Xaa Phe   Lys Xaa Thr
    18815                 18820                 18825

Ser Val Gly Xaa Leu Tyr Ser   Gly Cys Arg Leu Thr   Leu Leu Arg
    18830                 18835                 18840

Xaa Glu Lys Xaa Xaa Ala Ala   Thr Xaa Val Asp Xaa   Xaa Cys Xaa
    18845                 18850                 18855

Xaa Xaa Xaa Asp Pro Xaa Xaa   Pro Gly Leu Asp Arg   Glu Xaa Leu
    18860                 18865                 18870

Tyr Trp Glu Leu Ser Xaa Leu   Thr Xaa Xaa Ile Xaa   Glu Leu Gly
    18875                 18880                 18885

Pro Tyr Xaa Leu Asp Arg Xaa   Ser Leu Tyr Val Asn   Gly Phe Thr
    18890                 18895                 18900

His Arg Thr Ser Val Pro Thr   Thr Ser Thr Pro Gly   Thr Ser Thr
    18905                 18910                 18915

Val His Leu Ala Thr Ser Gly   Thr Pro Ser Ser Leu   Pro Gly His
    18920                 18925                 18930

Thr Ala Pro Val Pro Leu Leu   Ile Pro Phe Thr Leu   Asn Phe Thr
    18935                 18940                 18945

Ile Thr Asn Leu Gln Tyr Glu   Glu Asp Met His Arg   Pro Gly Ser
    18950                 18955                 18960

Arg Lys Phe Asn Thr Thr Glu   Arg Val Leu Gln Gly   Leu Leu Ser
    18965                 18970                 18975

Pro Ile Phe Lys Asn Ser Ser   Val Gly Pro Leu Tyr   Ser Gly Cys
    18980                 18985                 18990

Arg Leu Thr Ser Leu Arg Pro   Glu Lys Asp Gly Ala   Ala Thr Gly
    18995                 19000                 19005

Met Asp Ala Val Cys Leu Tyr   His Pro Asn Pro Lys   Arg Pro Gly
    19010                 19015                 19020

Leu Asp Arg Glu Gln Leu Tyr   Cys Glu Leu Ser Gln   Leu Thr His
    19025                 19030                 19035

Asn Ile Thr Glu Leu Gly Pro   Tyr Ser Leu Asp Arg   Asp Ser Leu
    19040                 19045                 19050

Tyr Val Asn Gly Phe Thr His   Gln Asn Ser Val Pro   Thr Thr Ser
    19055                 19060                 19065

Thr Pro Gly Thr Ser Thr Val   Tyr Trp Ala Thr Thr   Gly Thr Pro
    19070                 19075                 19080

Ser Ser Phe Pro Gly His Thr   Xaa Xaa Xaa Pro Leu   Leu Xaa Pro
    19085                 19090                 19095

Phe Thr Leu Asn Phe Thr Ile   Thr Asn Leu Xaa Tyr   Glu Glu Xaa
    19100                 19105                 19110

Met Xaa Xaa Pro Gly Ser Arg   Lys Phe Asn Thr Thr   Glu Arg Val
    19115                 19120                 19125

Leu Gln Gly Leu Leu Xaa Pro   Xaa Phe Lys Xaa Thr   Ser Val Gly
    19130                 19135                 19140

Xaa Leu Tyr Ser Gly Cys Arg   Leu Thr Leu Leu Arg   Xaa Glu Lys
    19145                 19150                 19155

Xaa Xaa Ala Ala Thr Xaa Val   Asp Xaa Xaa Cys Xaa   Xaa Xaa Xaa
    19160                 19165                 19170
```

-continued

```
Asp Pro Xaa Xaa Pro Gly Leu Asp Arg Glu Xaa Leu Tyr Trp Glu
    19175               19180                   19185

Leu Ser Xaa Leu Thr Xaa Xaa Ile Xaa Glu Leu Gly Pro Tyr Xaa
    19190               19195                   19200

Leu Asp Arg Xaa Ser Leu Tyr Val Asn Gly Phe Thr His Trp Ser
    19205               19210                   19215

Ser Gly Leu Thr Thr Ser Thr Pro Trp Thr Ser Thr Val Asp Leu
    19220               19225                   19230

Gly Thr Ser Gly Thr Pro Ser Pro Val Pro Ser Pro Thr Thr Ala
    19235               19240                   19245

Gly Pro Leu Leu Val Pro Phe Thr Leu Asn Phe Thr Ile Thr Asn
    19250               19255                   19260

Leu Gln Tyr Glu Glu Asp Met His Arg Pro Gly Ser Arg Lys Phe
    19265               19270                   19275

Asn Ala Thr Glu Arg Val Leu Gln Gly Leu Leu Ser Pro Ile Phe
    19280               19285                   19290

Lys Asn Thr Ser Val Gly Pro Leu Tyr Ser Gly Cys Arg Leu Thr
    19295               19300                   19305

Leu Leu Arg Pro Glu Lys Gln Glu Ala Ala Thr Gly Val Asp Thr
    19310               19315                   19320

Ile Cys Thr His Arg Val Asp Pro Ile Gly Pro Gly Leu Asp Arg
    19325               19330                   19335

Glu Xaa Leu Tyr Trp Glu Leu Ser Xaa Leu Thr Xaa Xaa Ile Xaa
    19340               19345                   19350

Glu Leu Gly Pro Tyr Xaa Leu Asp Arg Xaa Ser Leu Tyr Val Asn
    19355               19360                   19365

Gly Phe Xaa Xaa Xaa Xaa Xaa Xaa Xaa Xaa Thr Ser Thr Pro Gly
    19370               19375                   19380

Thr Ser Xaa Val Xaa Leu Xaa Thr Ser Gly Thr Pro Xaa Xaa Xaa
    19385               19390                   19395

Pro Xaa Xaa Thr Xaa Xaa Xaa Pro Leu Leu Xaa Pro Phe Thr Leu
    19400               19405                   19410

Asn Phe Thr Ile Thr Asn Leu Xaa Tyr Glu Glu Xaa Met Xaa Xaa
    19415               19420                   19425

Pro Gly Ser Arg Lys Phe Asn Thr Thr Glu Arg Val Leu Gln Gly
    19430               19435                   19440

Leu Leu Xaa Pro Xaa Phe Lys Xaa Thr Ser Val Gly Xaa Leu Tyr
    19445               19450                   19455

Ser Gly Cys Arg Leu Thr Leu Arg Xaa Glu Lys Xaa Xaa Ala
    19460               19465                   19470

Ala Thr Xaa Val Asp Xaa Xaa Cys Xaa Xaa Xaa Xaa Asp Pro Xaa
    19475               19480                   19485

Xaa Pro Gly Leu Asp Arg Glu Xaa Leu Tyr Trp Glu Leu Ser Xaa
    19490               19495                   19500

Leu Thr Xaa Xaa Ile Xaa Glu Leu Gly Pro Tyr Xaa Leu Asp Arg
    19505               19510                   19515

Xaa Ser Leu Tyr Val Asn Gly Phe Thr His Arg Ser Phe Gly Leu
    19520               19525                   19530

Thr Thr Ser Thr Pro Trp Thr Ser Thr Val Asp Leu Gly Thr Ser
    19535               19540                   19545

Gly Thr Pro Ser Pro Val Pro Ser Pro Thr Thr Ala Gly Pro Leu
    19550               19555                   19560

Leu Val Pro Phe Thr Leu Asn Phe Thr Ile Thr Asn Leu Gln Tyr
```

```
            19565               19570               19575
Glu Glu  Asp Met His Arg Pro  Gly Ser Arg Lys Phe  Asn Thr Thr
         19580               19585               19590
Glu Arg  Val Leu Gln Gly Leu  Leu Thr Pro Leu Phe  Arg Asn Thr
         19595               19600               19605
Ser Val  Ser Ser Leu Tyr Ser  Gly Cys Arg Leu Thr  Leu Leu Arg
         19610               19615               19620
Pro Glu  Lys Asp Gly Ala Ala  Thr Arg Val Asp Ala  Val Cys Thr
         19625               19630               19635
His Arg  Pro Asp Pro Lys Ser  Pro Gly Leu Asp Arg  Glu Xaa Leu
         19640               19645               19650
Tyr Trp  Glu Leu Ser Xaa Leu  Thr Xaa Xaa Ile Xaa  Glu Leu Gly
         19655               19660               19665
Pro Tyr  Xaa Leu Asp Arg Xaa  Ser Leu Tyr Val Asn  Gly Phe Xaa
         19670               19675               19680
Xaa Xaa  Xaa Xaa Xaa Xaa Xaa  Thr Ser Thr Pro Gly  Thr Ser Xaa
         19685               19690               19695
Val Xaa  Leu Xaa Thr Ser Gly  Thr Pro Xaa Xaa Xaa  Pro Xaa Xaa
         19700               19705               19710
Thr Xaa  Xaa Xaa Pro Leu Leu  Xaa Pro Phe Thr Leu  Asn Phe Thr
         19715               19720               19725
Ile Thr  Asn Leu Xaa Tyr Glu  Glu Xaa Met Xaa Xaa  Pro Gly Ser
         19730               19735               19740
Arg Lys  Phe Asn Thr Thr Glu  Arg Val Leu Gln Gly  Leu Leu Xaa
         19745               19750               19755
Pro Xaa  Phe Lys Xaa Thr Ser  Val Gly Xaa Leu Tyr  Ser Gly Cys
         19760               19765               19770
Arg Leu  Thr Leu Leu Arg Xaa  Glu Lys Xaa Xaa Ala  Ala Thr Xaa
         19775               19780               19785
Val Asp  Xaa Xaa Cys Xaa Xaa  Xaa Xaa Asp Pro Xaa  Xaa Pro Gly
         19790               19795               19800
Leu Asp  Arg Glu Xaa Leu Tyr  Trp Glu Leu Ser Xaa  Leu Thr Xaa
         19805               19810               19815
Xaa Ile  Xaa Glu Leu Gly Pro  Tyr Xaa Leu Asp Arg  Xaa Ser Leu
         19820               19825               19830
Tyr Val  Asn Gly Phe Thr His  Trp Ile Pro Val Pro  Thr Ser Ser
         19835               19840               19845
Thr Pro  Gly Thr Ser Thr Val  Asp Leu Gly Ser Gly  Thr Pro Ser
         19850               19855               19860
Ser Leu  Pro Ser Pro Thr Thr  Ala Gly Pro Leu Leu  Val Pro Phe
         19865               19870               19875
Thr Leu  Asn Phe Thr Ile Thr  Asn Leu Gln Tyr Gly  Glu Asp Met
         19880               19885               19890
Gly His  Pro Gly Ser Arg Lys  Phe Asn Thr Thr Glu  Arg Val Leu
         19895               19900               19905
Gln Gly  Leu Leu Gly Pro Ile  Phe Lys Asn Thr Ser  Val Gly Pro
         19910               19915               19920
Leu Tyr  Ser Gly Cys Arg Leu  Thr Ser Leu Arg Ser  Glu Lys Asp
         19925               19930               19935
Gly Ala  Ala Thr Gly Val Asp  Ala Ile Cys Ile His  His Leu Asp
         19940               19945               19950
Pro Lys  Ser Pro Gly Leu Asp  Arg Glu Xaa Leu Tyr  Trp Glu Leu
         19955               19960               19965
```

-continued

Ser Xaa Leu Thr Xaa Xaa Ile Xaa Glu Leu Gly Pro Tyr Xaa Leu
    19970            19975                  19980

Asp Arg Xaa Ser Leu Tyr Val Asn Gly Phe Xaa Xaa Xaa Xaa Xaa
    19985            19990              19995

Xaa Xaa Xaa Thr Ser Thr Pro Gly Thr Ser Xaa Val Xaa Leu Xaa
    20000            20005              20010

Thr Ser Gly Thr Pro Xaa Xaa Xaa Pro Xaa Xaa Thr Xaa Xaa Xaa
    20015            20020              20025

Pro Leu Leu Xaa Pro Phe Thr Leu Asn Phe Thr Ile Thr Asn Leu
    20030            20035              20040

Xaa Tyr Glu Glu Xaa Met Xaa Xaa Pro Gly Ser Arg Lys Phe Asn
    20045            20050              20055

Thr Thr Glu Arg Val Leu Gln Gly Leu Leu Xaa Pro Xaa Phe Lys
    20060            20065              20070

Xaa Thr Ser Val Gly Xaa Leu Tyr Ser Gly Cys Arg Leu Thr Leu
    20075            20080              20085

Leu Arg Xaa Glu Lys Xaa Xaa Ala Ala Thr Xaa Val Asp Xaa Xaa
    20090            20095              20100

Cys Xaa Xaa Xaa Xaa Asp Pro Xaa Xaa Pro Gly Leu Asp Arg Glu
    20105            20110              20115

Xaa Leu Tyr Trp Glu Leu Ser Xaa Leu Thr Xaa Xaa Ile Xaa Glu
    20120            20125              20130

Leu Gly Pro Tyr Xaa Leu Asp Arg Xaa Ser Leu Tyr Val Asn Gly
    20135            20140              20145

Phe Thr His Gln Thr Phe Ala Pro Asn Thr Ser Thr Pro Gly Thr
    20150            20155              20160

Ser Thr Val Asp Leu Gly Thr Ser Gly Thr Pro Ser Ser Leu Pro
    20165            20170              20175

Ser Pro Thr Ser Ala Gly Pro Leu Leu Val Pro Phe Thr Leu Asn
    20180            20185              20190

Phe Thr Ile Thr Asn Leu Gln Tyr Glu Glu Asp Met His His Pro
    20195            20200              20205

Gly Ser Arg Lys Phe Asn Thr Thr Glu Arg Val Leu Gln Gly Leu
    20210            20215              20220

Leu Gly Pro Met Phe Lys Asn Thr Ser Val Gly Leu Leu Tyr Ser
    20225            20230              20235

Gly Cys Arg Leu Thr Leu Leu Arg Pro Glu Lys Asn Gly Ala Ala
    20240            20245              20250

Thr Arg Val Asp Ala Val Cys Thr His Arg Pro Asp Pro Lys Ser
    20255            20260              20265

Pro Gly Leu Asp Arg Glu Xaa Leu Tyr Trp Glu Leu Ser Xaa Leu
    20270            20275              20280

Thr Xaa Xaa Ile Xaa Glu Leu Gly Pro Tyr Xaa Leu Asp Arg Xaa
    20285            20290              20295

Ser Leu Tyr Val Asn Gly Phe Xaa Xaa Xaa Xaa Xaa Xaa Xaa Xaa
    20300            20305              20310

Thr Ser Thr Pro Gly Thr Ser Xaa Val Xaa Leu Xaa Thr Ser Gly
    20315            20320              20325

Thr Pro Xaa Xaa Xaa Pro Xaa Xaa Thr Ala Pro Val Pro Leu Leu
    20330            20335              20340

Ile Pro Phe Thr Leu Asn Phe Thr Ile Thr Asn Leu His Tyr Glu
    20345            20350              20355

```
Glu Asn Met Gln His Pro Gly Ser Arg Lys Phe Asn Thr Thr Glu
    20360             20365             20370

Arg Val Leu Gln Gly Leu Leu Arg Pro Leu Phe Lys Ser Thr Ser
    20375             20380             20385

Val Gly Pro Leu Tyr Ser Gly Cys Arg Leu Thr Leu Leu Arg Pro
    20390             20395             20400

Glu Lys His Gly Ala Ala Thr Gly Val Asp Ala Ile Cys Thr Leu
    20405             20410             20415

Arg Leu Asp Pro Thr Gly Pro Gly Leu Asp Arg Glu Arg Leu Tyr
    20420             20425             20430

Trp Glu Leu Ser Gln Leu Thr Asn Ser Val Thr Glu Leu Gly Pro
    20435             20440             20445

Tyr Thr Leu Asp Arg Asp Ser Leu Tyr Val Asn Gly Phe Thr Gln
    20450             20455             20460

Arg Ser Ser Val Pro Thr Thr Ser Ile Pro Gly Thr Ser Ala Val
    20465             20470             20475

His Leu Glu Thr Ser Gly Thr Pro Ala Ser Leu Pro Gly His Thr
    20480             20485             20490

Ala Pro Gly Pro Leu Leu Val Pro Phe Thr Leu Asn Phe Thr Ile
    20495             20500             20505

Thr Asn Leu Gln Tyr Glu Val Asp Met Arg His Pro Gly Ser Arg
    20510             20515             20520

Lys Phe Asn Thr Thr Glu Arg Val Leu Gln Gly Leu Leu Lys Pro
    20525             20530             20535

Leu Phe Lys Ser Thr Ser Val Gly Pro Leu Tyr Ser Gly Cys Arg
    20540             20545             20550

Leu Thr Leu Leu Arg Pro Glu Lys Arg Gly Ala Ala Thr Gly Val
    20555             20560             20565

Asp Thr Ile Cys Thr His Arg Leu Asp Pro Leu Asn Pro Gly Leu
    20570             20575             20580

Asp Arg Glu Gln Leu Tyr Trp Glu Leu Ser Lys Leu Thr Arg Gly
    20585             20590             20595

Ile Ile Glu Leu Gly Pro Tyr Leu Leu Asp Arg Gly Ser Leu Tyr
    20600             20605             20610

Val Asn Gly Phe Thr His Arg Asn Phe Val Pro Ile Thr Ser Thr
    20615             20620             20625

Pro Gly Thr Ser Thr Val His Leu Gly Thr Ser Glu Thr Pro Ser
    20630             20635             20640

Ser Leu Pro Arg Pro Ile Val Pro Gly Pro Leu Leu Val Pro Phe
    20645             20650             20655

Thr Leu Asn Phe Thr Ile Thr Asn Leu Gln Tyr Glu Glu Ala Met
    20660             20665             20670

Arg His Pro Gly Ser Arg Lys Phe Asn Thr Thr Glu Arg Val Leu
    20675             20680             20685

Gln Gly Leu Leu Arg Pro Leu Phe Lys Asn Thr Ser Ile Gly Pro
    20690             20695             20700

Leu Tyr Ser Ser Cys Arg Leu Thr Leu Leu Arg Pro Glu Lys Asp
    20705             20710             20715

Lys Ala Ala Thr Arg Val Asp Ala Ile Cys Thr His His Pro Asp
    20720             20725             20730

Pro Gln Ser Pro Gly Leu Asn Arg Glu Gln Leu Tyr Trp Glu Leu
    20735             20740             20745

Ser Gln Leu Thr His Gly Ile Thr Glu Leu Gly Pro Tyr Thr Leu
```

```
            20750               20755               20760
Asp Arg Asp Ser Leu Tyr Val Asp Gly Phe Thr His Trp Ser Pro
    20765               20770               20775
Ile Pro Thr Thr Ser Thr Pro Gly Thr Ser Ile Val Asn Leu Gly
    20780               20785               20790
Thr Ser Gly Ile Pro Pro Ser Leu Pro Glu Thr Thr Xaa Xaa Xaa
    20795               20800               20805
Pro Leu Leu Xaa Pro Phe Thr Leu Asn Phe Thr Ile Thr Asn Leu
    20810               20815               20820
Xaa Tyr Glu Glu Xaa Met Xaa Xaa Pro Gly Ser Arg Lys Phe Asn
    20825               20830               20835
Thr Thr Glu Arg Val Leu Gln Gly Leu Leu Lys Pro Leu Phe Lys
    20840               20845               20850
Ser Thr Ser Val Gly Pro Leu Tyr Ser Gly Cys Arg Leu Thr Leu
    20855               20860               20865
Leu Arg Pro Glu Lys Asp Gly Val Ala Thr Arg Val Asp Ala Ile
    20870               20875               20880
Cys Thr His Arg Pro Asp Pro Lys Ile Pro Gly Leu Asp Arg Gln
    20885               20890               20895
Gln Leu Tyr Trp Glu Leu Ser Gln Leu Thr His Ser Ile Thr Glu
    20900               20905               20910
Leu Gly Pro Tyr Thr Leu Asp Arg Asp Ser Leu Tyr Val Asn Gly
    20915               20920               20925
Phe Thr Gln Arg Ser Ser Val Pro Thr Thr Ser Thr Pro Gly Thr
    20930               20935               20940
Phe Thr Val Gln Pro Glu Thr Ser Glu Thr Pro Ser Ser Leu Pro
    20945               20950               20955
Gly Pro Thr Ala Thr Gly Pro Val Leu Leu Pro Phe Thr Leu Asn
    20960               20965               20970
Phe Thr Ile Thr Asn Leu Gln Tyr Glu Glu Asp Met His Arg Pro
    20975               20980               20985
Gly Ser Arg Lys Phe Asn Thr Thr Glu Arg Val Leu Gln Gly Leu
    20990               20995               21000
Leu Met Pro Leu Phe Lys Asn Thr Ser Val Ser Ser Leu Tyr Ser
    21005               21010               21015
Gly Cys Arg Leu Thr Leu Leu Arg Pro Glu Lys Asp Gly Ala Ala
    21020               21025               21030
Thr Arg Val Asp Ala Val Cys Thr His Arg Pro Asp Pro Lys Ser
    21035               21040               21045
Pro Gly Leu Asp Arg Glu Arg Leu Tyr Trp Lys Leu Ser Gln Leu
    21050               21055               21060
Thr His Gly Ile Thr Glu Leu Gly Pro Tyr Thr Leu Asp Arg His
    21065               21070               21075
Ser Leu Tyr Val Asn Gly Phe Thr His Gln Ser Ser Met Thr Thr
    21080               21085               21090
Thr Arg Thr Pro Asp Thr Ser Thr Met His Leu Ala Thr Ser Arg
    21095               21100               21105
Thr Pro Ala Ser Leu Ser Gly Pro Thr Thr Ala Ser Pro Leu Leu
    21110               21115               21120
Val Leu Phe Thr Ile Asn Phe Thr Ile Thr Asn Leu Arg Tyr Glu
    21125               21130               21135
Glu Asn Met His His Pro Gly Ser Arg Lys Phe Asn Thr Thr Glu
    21140               21145               21150
```

-continued

Arg Val Leu Gln Gly Leu Leu Arg Pro Val Phe Lys Asn Thr Ser
21155            21160                  21165

Val Gly Pro Leu Tyr Ser Gly Cys Arg Leu Thr Leu Leu Arg Pro
21170            21175                  21180

Lys Lys Asp Gly Ala Ala Thr Lys Val Asp Ala Ile Cys Thr Tyr
21185            21190                  21195

Arg Pro Asp Pro Lys Ser Pro Gly Leu Asp Arg Glu Gln Leu Tyr
21200            21205                  21210

Trp Glu Leu Ser Gln Leu Thr His Ser Ile Thr Glu Leu Gly Pro
21215            21220                  21225

Tyr Thr Gln Asp Arg Asp Ser Leu Tyr Asn Val Gly Phe Thr Gln
21230            21235                  21240

Arg Ser Ser Val Pro Thr Thr Ser Val Pro Gly Thr Pro Thr Val
21245            21250                  21255

Asp Leu Gly Thr Ser Gly Thr Pro Val Ser Lys Pro Gly Pro Ser
21260            21265                  21270

Ala Ala Ser Pro Leu Leu Val Leu Phe Thr Leu Asn Gly Thr Ile
21275            21280                  21285

Thr Asn Leu Arg Tyr Glu Glu Asn Met Gln His Pro Gly Ser Arg
21290            21295                  21300

Lys Phe Asn Thr Thr Glu Arg Val Leu Gln Gly Leu Leu Arg Ser
21305            21310                  21315

Leu Phe Lys Ser Thr Ser Val Gly Pro Leu Tyr Ser Gly Cys Arg
21320            21325                  21330

Leu Thr Leu Leu Arg Pro Glu Lys Asp Gly Thr Ala Thr Gly Val
21335            21340                  21345

Asp Ala Ile Cys Thr His His Pro Asp Pro Lys Ser Pro Arg Leu
21350            21355                  21360

Asp Arg Glu Gln Leu Tyr Trp Glu Leu Ser Gln Leu Thr His Asn
21365            21370                  21375

Ile Thr Glu Leu Gly His Tyr Ala Leu Asp Asn Asp Ser Leu Phe
21380            21385                  21390

Val Asn Gly Phe Thr His Arg Ser Ser Val Ser Thr Ser Thr
21395            21400                  21405

Pro Gly Thr Pro Thr Val Tyr Leu Gly Ala Ser Lys Thr Pro Ala
21410            21415                  21420

Ser Ile Phe Gly Pro Ser Ala Ala Ser His Leu Leu Ile Leu Phe
21425            21430                  21435

Thr Leu Asn Phe Thr Ile Thr Asn Leu Arg Tyr Glu Glu Asn Met
21440            21445                  21450

Trp Pro Gly Ser Arg Lys Phe Asn Thr Thr Glu Arg Val Leu Gln
21455            21460                  21465

Gly Leu Leu Arg Pro Leu Phe Lys Asn Thr Ser Val Gly Pro Leu
21470            21475                  21480

Tyr Ser Gly Ser Arg Leu Thr Leu Leu Arg Pro Glu Lys Asp Gly
21485            21490                  21495

Glu Ala Thr Gly Val Asp Ala Ile Cys Thr His Arg Pro Asp Pro
21500            21505                  21510

Thr Gly Pro Gly Leu Asp Arg Glu Gln Leu Tyr Leu Glu Leu Ser
21515            21520                  21525

Gln Leu Thr His Ser Ile Thr Glu Leu Gly Pro Tyr Thr Leu Asp
21530            21535                  21540

```
Arg Asp Ser Leu Tyr Val Asn  Gly Phe Thr His Arg  Ser Ser Val
    21545           21550              21555

Pro Thr Thr Ser Thr Gly Val  Val Ser Glu Glu Pro  Phe Thr Leu
    21560           21565              21570

Asn Phe Thr Ile Asn Asn Leu  Arg Tyr Met Ala Asp  Met Gly Gln
    21575           21580              21585

Pro Gly Ser Leu Lys Phe Asn  Ile Thr Asp Asn Val  Met Lys His
    21590           21595              21600

Leu Leu Ser Pro Leu Phe Gln  Arg Ser Ser Leu Gly  Ala Arg Tyr
    21605           21610              21615

Thr Gly Cys Arg Val Ile Ala  Leu Arg Ser Val Lys  Asn Gly Ala
    21620           21625              21630

Glu Thr Arg Val Asp Leu Leu  Cys Thr Tyr Leu Gln  Pro Leu Ser
    21635           21640              21645

Gly Pro Gly Leu Pro Ile Lys  Gln Val Phe His Glu  Leu Ser Gln
    21650           21655              21660

Gln Thr His Gly Ile Thr Arg  Leu Gly Pro Tyr Ser  Leu Asp Lys
    21665           21670              21675

Asp Ser Leu Tyr Leu Asn Gly  Tyr Asn Glu Pro Gly  Leu Asp Glu
    21680           21685              21690

Pro Pro Thr Thr Pro Lys Pro  Ala Thr Thr Phe Leu  Pro Pro Leu
    21695           21700              21705

Ser Glu Ala Thr Thr Ala Met  Gly Tyr His Leu Lys  Thr Leu Thr
    21710           21715              21720

Leu Asn Phe Thr Ile Ser Asn  Leu Gln Tyr Ser Pro  Asp Met Gly
    21725           21730              21735

Lys Gly Ser Ala Thr Phe Asn  Ser Thr Glu Gly Val  Leu Gln His
    21740           21745              21750

Leu Leu Arg Pro Leu Phe Gln  Lys Ser Ser Met Gly  Pro Phe Tyr
    21755           21760              21765

Leu Gly Cys Gln Leu Ile Ser  Leu Arg Pro Glu Lys  Asp Gly Ala
    21770           21775              21780

Ala Thr Gly Val Asp Thr Thr  Cys Thr Tyr His Pro  Asp Pro Val
    21785           21790              21795

Gly Pro Gly Leu Asp Ile Gln  Gln Leu Tyr Trp Glu  Leu Ser Gln
    21800           21805              21810

Leu Thr His Gly Val Thr Gln  Leu Gly Phe Tyr Val  Leu Asp Arg
    21815           21820              21825

Asp Ser Leu Phe Ile Asn Gly  Tyr Ala Pro Gln Asn  Leu Ser Ile
    21830           21835              21840

Arg Gly Glu Tyr Gln Ile Asn  Phe His Ile Val Asn  Trp Asn Leu
    21845           21850              21855

Ser Asn Pro Asp Pro Thr Ser  Ser Glu Tyr Ile Thr  Leu Leu Arg
    21860           21865              21870

Asp Ile Gln Asp Lys Val Thr  Thr Leu Tyr Lys Gly  Ser Gln Leu
    21875           21880              21885

His Asp Thr Phe Arg Phe Cys  Leu Val Thr Asn Leu  Thr Met Asp
    21890           21895              21900

Ser Val Leu Val Thr Val Lys  Ala Leu Phe Ser Ser  Asn Leu Asp
    21905           21910              21915

Pro Ser Leu Val Glu Gln Val  Phe Leu Asp Lys Thr  Leu Asn Ala
    21920           21925              21930

Ser Phe His Trp Leu Gly Ser  Thr Tyr Gln Leu Val  Asp Ile His
```

```
               21935                 21940                 21945
Val  Thr  Glu  Met  Glu  Ser  Ser  Val  Tyr  Gln  Pro  Thr  Ser  Ser  Ser
          21950                 21955                 21960

Ser  Thr  Gln  His  Phe  Tyr  Leu  Asn  Phe  Thr  Ile  Thr  Asn  Leu  Pro
          21965                 21970                 21975

Tyr  Ser  Gln  Asp  Lys  Ala  Gln  Pro  Gly  Thr  Thr  Asn  Tyr  Gln  Arg
          21980                 21985                 21990

Asn  Lys  Arg  Asn  Ile  Glu  Asp  Ala  Leu  Asn  Gln  Leu  Phe  Arg  Asn
          21995                 22000                 22005

Ser  Ser  Ile  Lys  Ser  Tyr  Phe  Ser  Asp  Cys  Gln  Val  Ser  Thr  Phe
          22010                 22015                 22020

Arg  Ser  Val  Pro  Asn  Arg  His  His  Thr  Gly  Val  Asp  Ser  Leu  Cys
          22025                 22030                 22035

Asn  Phe  Ser  Pro  Leu  Ala  Arg  Arg  Val  Asp  Arg  Val  Ala  Ile  Tyr
          22040                 22045                 22050

Glu  Glu  Phe  Leu  Arg  Met  Thr  Arg  Asn  Gly  Thr  Gln  Leu  Gln  Asn
          22055                 22060                 22065

Phe  Thr  Leu  Asp  Arg  Ser  Ser  Val  Leu  Val  Asp  Gly  Tyr  Ser  Pro
          22070                 22075                 22080

Asn  Arg  Asn  Glu  Pro  Leu  Thr  Gly  Asn  Ser  Asp  Leu  Pro  Phe  Trp
          22085                 22090                 22095

Ala  Val  Ile  Leu  Ile  Gly  Leu  Ala  Gly  Leu  Leu  Gly  Leu  Ile  Thr
          22100                 22105                 22110

Cys  Leu  Ile  Cys  Gly  Val  Leu  Val  Thr  Thr  Arg  Arg  Arg  Lys  Lys
          22115                 22120                 22125

Glu  Gly  Glu  Tyr  Asn  Val  Gln  Gln  Gln  Cys  Pro  Gly  Tyr  Tyr  Gln
          22130                 22135                 22140

Ser  His  Leu  Asp  Leu  Glu  Asp  Leu  Gln
          22145                 22150

<210> SEQ ID NO 6
<211> LENGTH: 32
<212> TYPE: DNA
<213> ORGANISM: artificial
<220> FEATURE:
<223> OTHER INFORMATION: PCR primer

<400> SEQUENCE: 6
accggatcca tgggccacac agagcctggc cc                                      32

<210> SEQ ID NO 7
<211> LENGTH: 29
<212> TYPE: DNA
<213> ORGANISM: artificial
<220> FEATURE:
<223> OTHER INFORMATION: PCR primer

<400> SEQUENCE: 7
tgtaagctta ggcagggagg atggagtcc                                          29
```